US012421450B2

(12) United States Patent
Yasukawa et al.

(10) Patent No.: US 12,421,450 B2
(45) Date of Patent: Sep. 23, 2025

(54) COMPOUNDS, MATERIALS FOR ORGANIC ELECTROLUMINESCENT DEVICES, ORGANIC ELECTROLUMINESCENT DEVICES, AND ELECTRONIC DEVICES

(71) Applicant: IDEMITSU KOSAN CO.,LTD., Tokyo (JP)

(72) Inventors: Keiichi Yasukawa, Chiyoda-ku (JP); Hiromi Nakano, Chiyoda-ku (JP); Hisato Matsumoto, Chiyoda-ku (JP); Toshinari Ogiwara, Chiyoda-ku (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 798 days.

(21) Appl. No.: 17/765,334

(22) PCT Filed: Jun. 21, 2021

(86) PCT No.: PCT/JP2021/023489

§ 371 (c)(1),
(2) Date: Mar. 30, 2022

(87) PCT Pub. No.: WO2021/261461

PCT Pub. Date: Dec. 30, 2021

(65) Prior Publication Data

US 2023/0006145 A1 Jan. 5, 2023

(30) Foreign Application Priority Data

Jun. 24, 2020 (JP) ................................ 2020-108518

(51) Int. Cl.
*C09K 11/06* (2006.01)
*C07D 495/04* (2006.01)
(Continued)

(52) U.S. Cl.
CPC ............ *C09K 11/06* (2013.01); *C07D 495/04* (2013.01); *H10K 85/6572* (2023.02);
(Continued)

(58) Field of Classification Search
None
See application file for complete search history.

(56) References Cited

U.S. PATENT DOCUMENTS 10,590,080 B2 3/2020 Tasaki et al.
2014/0175419 A1 6/2014 Nakano et al.
(Continued)

FOREIGN PATENT DOCUMENTS

CN 105209434 A 12/2015
CN 109651406 A 4/2019
(Continued)

OTHER PUBLICATIONS

Extended European Search Report issued Jun. 11, 2024, in corresponding European Patent Application No. 21828038.6, 9 pages.
(Continued)

*Primary Examiner* — Tae H Yoon
(74) *Attorney, Agent, or Firm* — Oblon, McClelland, Maier &Neustadt, L.L.P.

(57) ABSTRACT

A compound of formula (11) to (13)

(11)

(Continued)

-continued (12)

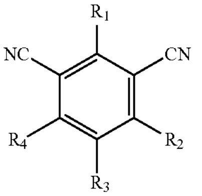

(13)

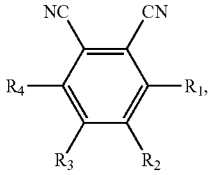

wherein $R_1$ to $R_4$ are each independently $D_1$ of a formula (1-1) etc. or $D_2$ of a formula (2-1) etc.

(1-1)

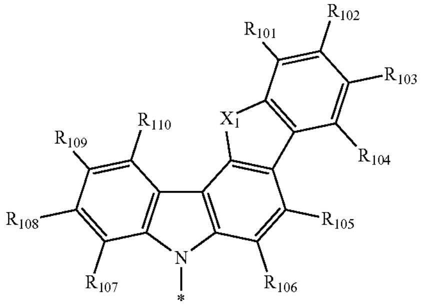

(2-1)

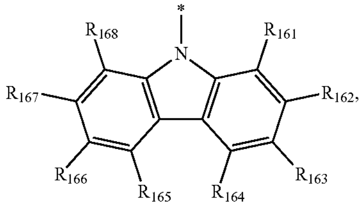

at least one of $R_1$ to $R_4$ being $D_1$, and at least one of $R_1$ to $R_4$ being $D_2$. In (1-1) and (2-1), $X_1$ is O or S, $R_{101}$ to $R_{110}$ and $R_{161}$ to $R_{168}$ are each independently H, a substituent etc. In at least one $D_1$, at least one of $R_{101}$ to $R_{110}$ is a group of a formula (110) or (120):

(110)

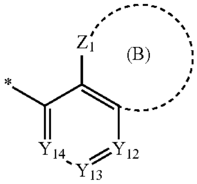

-continued (120)

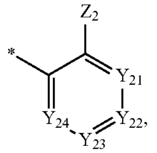

$Z_1$ is a C etc., a ring (B) is an aromatic hydrocarbon ring etc., $Y_{12}$ to $Y_{14}$ are each independently $CR_{10A}$ etc., $Y_{21}$ to $Y_{24}$ are each independently $CR_{20A}$ etc., $Z_2$ is an aryl group etc., and * is a bonding position.

44 Claims, 6 Drawing Sheets

(51) Int. Cl.

| | |
|---|---|
| ***H01L 51/00*** | (2006.01) |
| ***H10K 85/60*** | (2023.01) |
| *H10K 50/11* | (2023.01) |
| *H10K 101/20* | (2023.01) |

(52) U.S. Cl.

CPC ....... *H10K 85/6574* (2023.02); *H10K 85/658* (2023.02); *C09K 2211/1018* (2013.01); *H10K 50/11* (2023.02); *H10K 2101/20* (2023.02)

(56) References Cited

U.S. PATENT DOCUMENTS

| | | | | |
|---|---|---|---|---|
| 2014/0183486 | A1 | 7/2014 | Nakano et al. | |
| 2016/0130225 | A1 | 5/2016 | Tasaki et al. | |
| 2016/0211466 | A1 | 7/2016 | Ogiwara et al. | |
| 2017/0186974 | A1* | 6/2017 | Jung .................. | H10K 85/6572 |
| 2020/0148639 | A1 | 5/2020 | Tasaki et al. | |
| 2020/0407315 | A1 | 12/2020 | Tasaki et al. | |
| 2021/0143341 | A1 | 5/2021 | Yasukawa et al. | |
| 2021/0367163 | A1 | 11/2021 | Yasukawa et al. | |

FOREIGN PATENT DOCUMENTS

| | | | |
|---|---|---|---|
| CN | 111051283 | A | 4/2020 |
| JP | 2015-106659 | A | 6/2015 |
| JP | 2020-50650 | A | 4/2020 |
| WO | WO 2012/153780 | A1 | 11/2012 |
| WO | WO 2013/038650 | A1 | 3/2013 |
| WO | WO 2014/208698 | A1 | 12/2014 |
| WO | WO 2019/107934 | A1 | 6/2019 |
| WO | WO 2019/190235 | A1 | 10/2019 |
| WO | WO 2020/022378 | A1 | 1/2020 |
| WO | WO 2020/059862 | A1 | 3/2020 |
| WO | WO 2020/085446 | A1 | 4/2020 |

OTHER PUBLICATIONS

English translation of International Preliminary Report on Patentability and Written Opinion issued Dec. 13, 2022 in PCT/JP2021/023489, 4 pages.

International Search Report mailed on Jul. 20, 2021 in PCT/JP2021/023489 filed on Jun. 21, 2021 (2 pages).

Adachi, C., "Yuki Hando-tai no Debaisu Bussei (Device Physics of Organic Semiconductors)" published by Kodansha, Apr. 1, 2012, total 19 pages.

(56) References Cited

OTHER PUBLICATIONS

Uoyama, H. et al., "Highly efficient organic light-emitting diodes from delayed fluorescence", Nature, 2012, vol. 492, pp. 234-238.

Combined Chinese Office Action and Search Report issued Dec. 14, 2024, received Dec. 20, 2024 in Chinese Patent Application No. 202180005587.3 (with English translation of Category of Cited Documents), 14 pages.

* cited by examiner

COMPOUNDS, MATERIALS FOR ORGANIC ELECTROLUMINESCENT DEVICES, ORGANIC ELECTROLUMINESCENT DEVICES, AND ELECTRONIC DEVICES

CROSS-REFERENCE TO RELATED APPLICATIONS

The present application is the national stage of international application PCT/JP2021/023489, filed on Jun. 21, 2021, and claims the benefit of the filing date of Japanese Appl. No. 2020-108518, filed on Jun. 24, 2020.

TECHNICAL FIELD

The present invention relates to a compound, a material for an organic electroluminescence device, an organic electroluminescence device, and an electronic device.

BACKGROUND ART

When a voltage is applied to an organic electroluminescence device (hereinafter, occasionally referred to as "organic EL device"), holes are injected from an anode and electrons are injected from a cathode into an emitting layer. The injected electrons and holes are recombined in the emitting layer to form excitons. Specifically, according to the electron spin statistics theory, singlet excitons and triplet excitons are generated at a ratio of 25%:75%.

A fluorescent organic EL device using light emission from singlet excitons has been applied to a full-color display such as a mobile phone and a television set, but an internal quantum efficiency is said to be at a limit of 25%. Accordingly, studies has been made to improve a performance of the organic EL device.

For instance, it is expected to further efficiently emit the organic EL device using triplet excitons in addition to singlet excitons. In view of the above, a highly efficient fluorescent organic EL device using thermally activated delayed fluorescence (hereinafter, sometimes simply referred to as "delayed fluorescence") has been proposed and studied.

For instance, a TADF (Thermally Activated Delayed Fluorescence) mechanism has been studied. This TADF mechanism uses such a phenomenon in which inverse intersystem crossing from triplet excitons to singlet excitons thermally occurs when a material having a small energy difference (ΔST) between singlet energy level and triplet energy level is used. Thermally activated delayed fluorescence is explained in "Yuki Hando-tai no Debaisu Bussei (Device Physics of Organic Semiconductors)" (edited by ADACHI, Chihaya, published by Kodansha, issued on Apr. 1, 2012, on pages 261-268).

As a compound exhibiting thermally activated delayed fluorescence (TADF), for example, a compound in which a donor moiety and an acceptor moiety are bonded in a molecule is known.

For instance, Patent Literature 1 discloses an exemplary compound, in which, for instance, carbazole as well as benzofurocarbazole or benzothienocarbazole are substituents of dicyanobenzene.

CITATION LIST

Patent Literature(s)

Patent Literature 1: International Publication No. WO 2020/022378

SUMMARY OF THE INVENTION

Problems to be Solved by the Invention

In order to improve performance of an electronic device such as a display, an organic EL device has been required to be further improved in performance.

The performance of the organic EL device is evaluable in terms of luminous efficiency. As a factor for improving the luminous efficiency, a compound having a high photoluminescence quantum yield (PLQY) is usable.

An object of the invention is to provide a compound capable of providing a high-performance organic electroluminescence device, especially a compound having a high PLQY. Further, an object of the invention is to provide an organic-electroluminescence-device material and an organic electroluminescence device containing a compound having a high PLQY, and an electronic device including the organic electroluminescence device.

Means for Solving the Problem(s)

According to an aspect of the invention, a compound represented by one of formulae (11) to (13) below is provided.

[Formula 1]

(11)

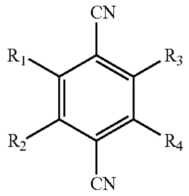

(12)

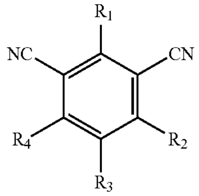

(13)

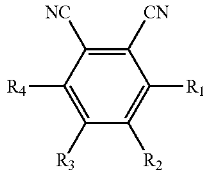

In the formulae (11) to (13):

$R_1$ to $R_4$ are each independently a group $D_1$ represented by one of formulae (1-1) to (1-6) below, or a group $D_2$ represented by one of formulae (2-1) to (2-4) below;

at least one of $R_1$ to $R_4$ is the group $D_1$;

at least one of $R_1$ to $R_4$ is the group $D_2$;

when a plurality of $D_1$ are present, the plurality of $D_1$ are mutually the same or different; and when a plurality of $D_2$ are present, the plurality of $D_2$ are mutually the same or different.

[Formula 2]
(1-1)
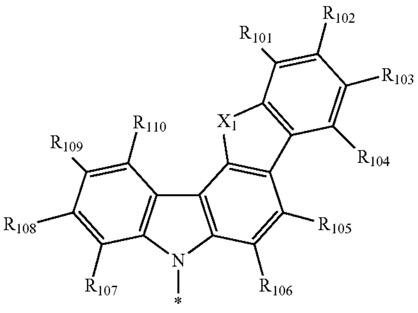
(1-2)
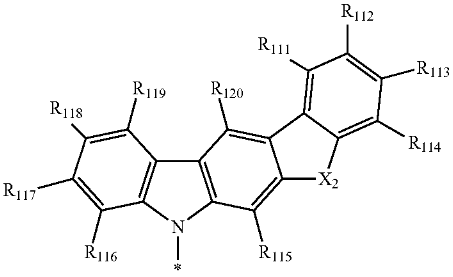
(1-3)
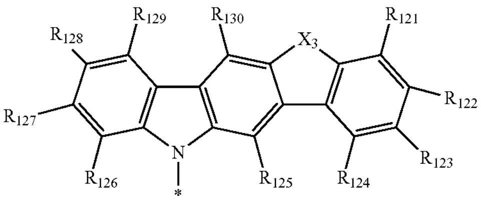
(1-4)
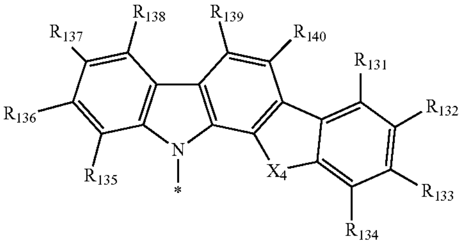
(1-5)
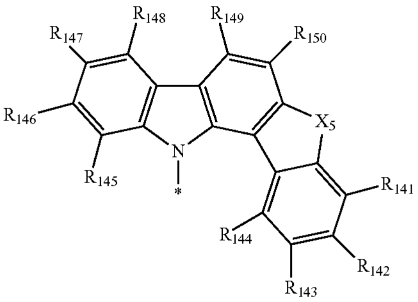
-continued
(1-6)
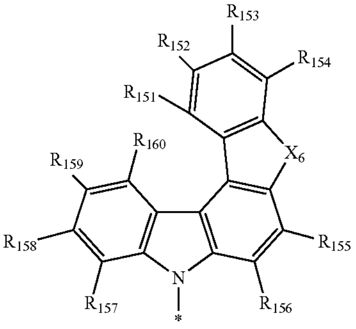
[Formula 3]
(110)
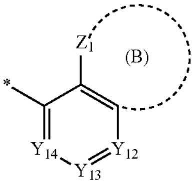
(120)
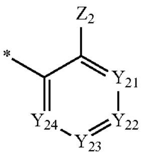
[Formula 4]
(2-1)
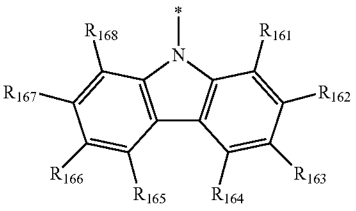
(2-2)
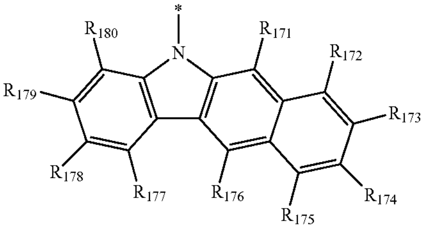
(2-3)
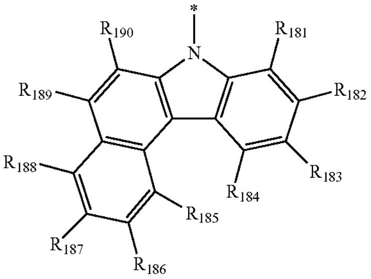

-continued (2-4)

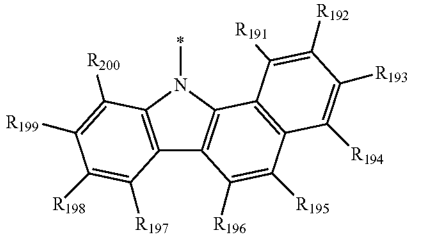

In the formulae (1-1) to (1-6):

$X_1$ to $X_6$ are each independently an oxygen atom or a sulfur atom;

$R_{101}$ to $R_{160}$ are each independently a hydrogen atom, a substituent, a group represented by the formula (110), or a group represented by the formula (120); and in at least one group $D_1$, at least one of $R_{101}$ to $R_{160}$ is a group represented by the formula (110) or a group represented by the formula (120).

In the formula (110):

$Z_1$ is an atom forming a ring (B) and is a carbon atom or a nitrogen atom;

the ring (B) including $Z_1$ is a substituted or unsubstituted aromatic hydrocarbon ring having 6 to 30 ring carbon atoms or a substituted or unsubstituted heterocyclic ring having 5 to 30 ring carbon atoms;

$Y_{12}$ to $Y_{14}$ are each independently a nitrogen atom or $CR_{10A}$; and $R_{10A}$ is each independently a hydrogen atom or a substituent, at least one combination of adjacent two or more of a plurality of $R_{10A}$ are bonded to each other to form a ring, the ring (B) is bonded to one $R_{10A}$ adjacent to the ring (B) to form a ring, or the ring (B) is bonded to at least one combination of adjacent two or more of a plurality of $R_{10A}$.

In the formula (120):

$Z_2$ is a substituted or unsubstituted aryl group having 6 to 30 ring carbon atoms or a substituted or unsubstituted heterocyclic group having 5 to 30 ring atoms;

$Y_{21}$ to $Y_{24}$ are each independently a nitrogen atom or $CR_{20A}$;

$R_{20A}$ is each independently a hydrogen atom or a substituent, or at least one combination of adjacent two or more of a plurality of $R_{20A}$ are mutually bonded to form a ring;

a plurality of $R_{10A}$ are mutually the same or different;

a plurality of $R_{20A}$ are mutually the same or different;

$R_{161}$ to $R_{168}$ and $R_{171}$ to $R_{200}$ in the formulae (2-1) to (2-4) are each independently a hydrogen atom or a substituent;

$R_{101}$ to $R_{160}$ as a substituent except for a group represented by the formula (110) and a group represented by the formula (120), $R_{10A}$ as a substituent in the formula (110), and $R_{20A}$ as a substituent in the formula (120) in the formulae (1-1) to (1-6), and $R_{161}$ to $R_{168}$ and $R_{171}$ to $R_{200}$ as a substituent in the formulae (2-1) to (2-4) are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms;

a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, a group represented by $—N(Rz)_2$, a thiol group, a substituted or unsubstituted alkylthio group having 1 to 30 carbon atoms, a substituted or unsubstituted aralkyl group having 7 to 30 ring carbon atoms, a substituted germanium group, a substituted phosphine oxide group, a nitro group, a substituted boryl group, or a substituted or unsubstituted arylthio group having 6 to 30 ring carbon atoms;

Rz is a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms; and two Rz in $—N(Rz)_2$ are mutually the same or different.

In the formulae (1-1) to (1-6), * each independently represents a bonding position to a carbon atom of the six-membered ring in the formulae (11) to (13).

In the formula (110), * represents a bonding position to a carbon atom of the six-membered ring in the formulae (1-1) to (1-6).

In the formula (120), * represents a bonding position to a carbon atom of the six-membered ring in the formulae (1-1) to (1-6).

In the formulae (2-1) to (2-4), * each independently represents a bonding position to a carbon atom of the six-membered ring in the formulae (11) to (13).

According to another aspect of the invention, an organic-electroluminescence-device material containing the compound according to the above aspect of the invention is provided.

According to still another aspect of the invention, an organic electroluminescence device includes: an anode; a cathode; and a first organic layer provided between the anode and the cathode, in which the first organic layer contains a first compound, and the first compound is the compound according to the above aspect of the invention.

According to a further aspect of the invention, an electronic device including the organic electroluminescence device according to the above aspect of the invention is provided.

According to the above aspect of the invention, a compound capable of providing a high-performance organic electroluminescence device, especially, a compound having a high PLQY can be provided. According to the above aspects of the invention, an organic-electroluminescence-device material or an organic electroluminescence device containing a compound having a high PLQY can be provided. According to the above aspect of the invention, an electronic device including the organic electroluminescence device can be provided.

BRIEF DESCRIPTION OF DRAWING(S)

An exemplary structure of the organic electroluminescence device of a third exemplary embodiment of the invention is schematically shown.

FIG. 1 schematically shows an arrangement of an organic electroluminescence device according to a third exemplary embodiment of the invention.

FIG. 2 schematically shows a device that measures transient PL.

DESCRIPTION OF EMBODIMENT(S)

First Exemplary Embodiment

Compounds

Figure 1:
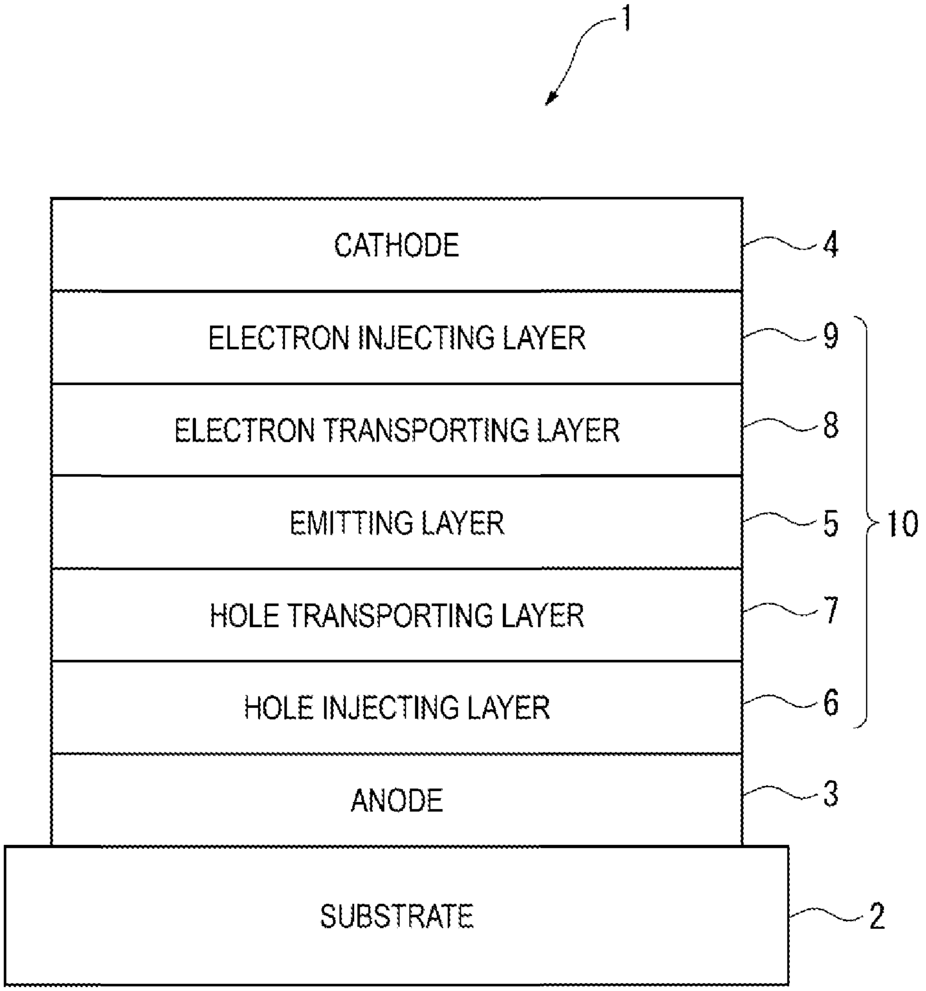

A compound according to a first exemplary embodiment is represented by one of formulae (11) to (13) below.

[Formula 5]

(11)

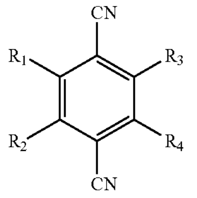

(12)

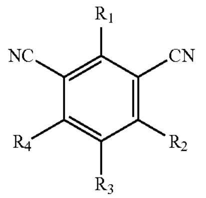

(13)

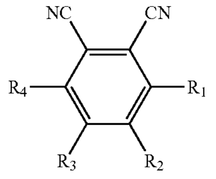

In the formulae (11) to (13):

$R_1$ to $R_4$ are each independently a group $D_1$ represented by one of formulae (1-1) to (1-6) below or a group $D_2$ represented by one of formulae (2-1) to (2-4) below;

at least one of $R_1$ to $R_4$ is the group $D_1$;

at least one of $R_1$ to $R_4$ is the group $D_2$;

when a plurality of $D_1$ are present, the plurality of $D_1$ are mutually the same or different; and when a plurality of $D_2$ are present, the plurality of $D_2$ are mutually the same or different.

[Formula 6]

(1-1)

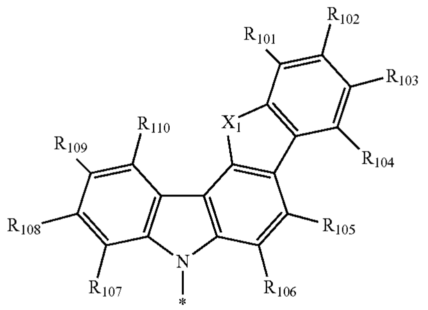

(1-2)

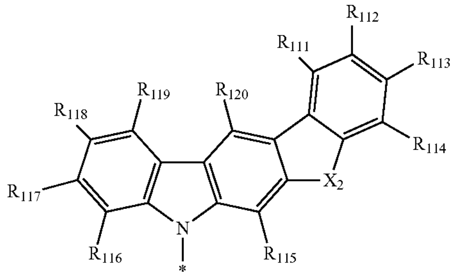

(1-3)

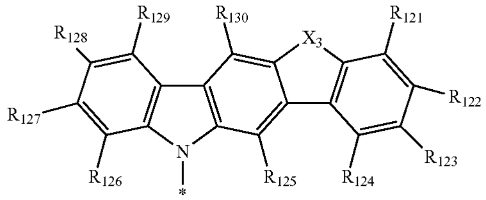

(1-4)

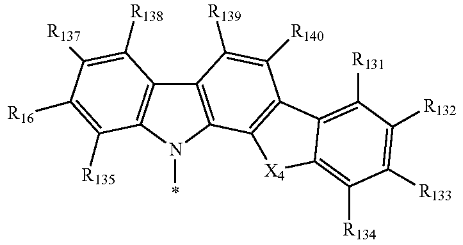

(1-5)

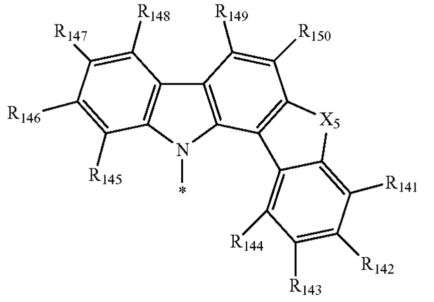

-continued (1-6)

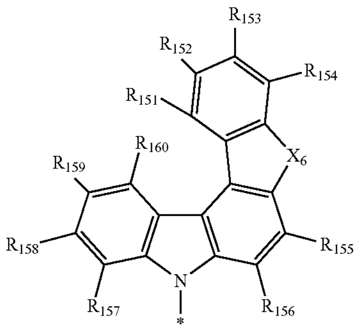

[Formula 7]

(110)

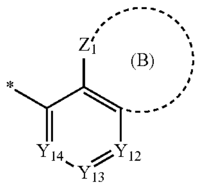

(120)

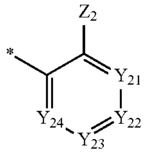

[Formula 8]

(2-1)

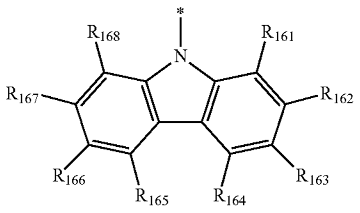

(2-2)

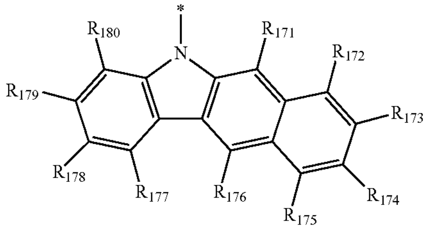

(2-3)

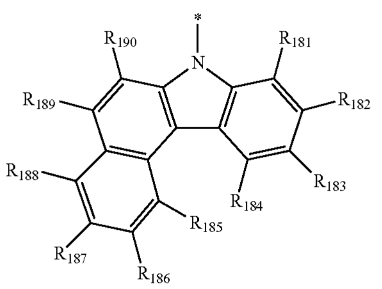

-continued (2-4)

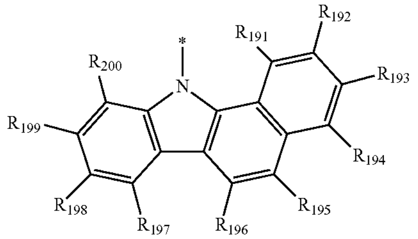

In the formulae (1-1) to (1-6):

$X_1$ to $X_6$ are each independently an oxygen atom or a sulfur atom;

$R_{101}$ to $R_{160}$ are each independently a hydrogen atom, a substituent, a group represented by the formula (110), or a group represented by the formula (120); and in at least one group $D_1$, at least one of $R_{101}$ to $R_{160}$ is a group represented by the formula (110) or a group represented by the formula (120).

In the formula (110):

$Z_1$ is an atom forming a ring (B) and is a carbon atom or a nitrogen atom;

the ring (B) including $Z_1$ is a substituted or unsubstituted aromatic hydrocarbon ring having 6 to 30 ring carbon atoms or a substituted or unsubstituted heterocyclic ring having 5 to 30 ring carbon atoms;

$Y_{12}$ to $Y_{14}$ are each independently a nitrogen atom or $CR_{10A}$; and $R_{10A}$ is each independently a hydrogen atom or a substituent, at least one combination of adjacent two or more of a plurality of $R_{10A}$ are bonded to each other to form a ring, a ring (B) is bonded to one $R_{10A}$ adjacent to the ring (B) to form a ring, or the ring (B) is bonded to at least one combination of adjacent two or more of a plurality of $R_{10A}$.

In the formula (120):

$Z_2$ is a substituted or unsubstituted aryl group having 6 to 30 ring carbon atoms or a substituted or unsubstituted heterocyclic group having 5 to 30 ring atoms;

$Y_{21}$ to $Y_{24}$ are each independently a nitrogen atom or $CR_{20A}$;

$R_{20A}$ is each independently a hydrogen atom or a substituent, or at least one combination of adjacent two or more of a plurality of $R_{20A}$ are mutually bonded to form a ring;

a plurality of $R_{10A}$ are mutually the same or different;

a plurality of $R_{20A}$ are mutually the same or different;

in the formulae (2-1) to (2-4), $R_{161}$ to $R_{168}$ and $R_{171}$ to $R_{200}$ are each independently a hydrogen atom or a substituent;

$R_{101}$ to $R_{160}$ as a substituent except for a group represented by the formula (110) and a group represented by the formula (120), $R_{10A}$ as a substituent in the formula (110), and $R_{20A}$ as a substituent in the formula (120) in the formulae (1-1) to (1-6), and $R_{161}$ to $R_{168}$ and $R_{171}$ to $R_{200}$ as a substituent in the formulae (2-1) to (2-4) are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, a group represented by —$N(Rz)_2$, a thiol group, a substituted or unsubstituted alkylthio group having 1 to 30 carbon atoms, a substituted or unsubstituted aralkyl group having 7 to 30 ring carbon atoms, a substituted germanium group, a substituted phosphine oxide group, a nitro group, a substituted boryl group, or a substituted or unsubstituted arylthio group having 6 to 30 ring carbon atoms;

Rz is a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms; and two Rz in —$N(Rz)_2$ are mutually the same or different.

In the formulae (1-1) to (1-6), * each independently represent a bonding position to a carbon atom of the six-membered ring in the formulae (11) to (13).

In the formula (110), * represents a bonding position to a carbon atom of the six-membered ring in the formulae (1-1) to (1-6).

In the formula (120), * represents a bonding position to a carbon atom of the six-membered ring in the formulae (1-1) to (1-6).

In the formulae (2-1) to (2-4), * each independently represents a bonding position to a carbon atom of the six-membered ring in the formulae (11) to (13).

The inventors have found that a compound having high PLQY can be provided by introducing a specific substituent (a group represented by the formula (110) or (120)) to each group $D_1$ represented by one of the formulae (1-1) to (1-6) and substituting dicyanobenzene, as shown in the compounds represented by the formulae (11) to (13).

The reason will be described below with reference to an instance where each group $D_1$ in the compound of the present exemplary embodiment is a group represented by one of formulae (1-4A) to (1-4C) below. The formulae (1-4A) to (1-4C) are each an example of the above-described formula (1-4).

The groups represented by the formulae (1-4A) to (1-4C) are each a group produced by introducing a specific substituent (a group represented by the formula (110) or (120)) to benzothienocarbazole.

A group represented by the formula (1-4A) is produced by bonding a phenyl group to an ortho position (**) of a benzene ring of a "benzothienocarbazole-benzene structure." In such a structure, the specific substituent (1,1'-biphenyl-2-yl group) introduced to the group $D_1$ is twisted with respect to a benzothienocarbazole plane.

The group represented by the formula (1-4B) has a carbon atom at an ortho position (**) of a benzene ring of a "benzothienocarbazole-benzene structure," the carbon atom being an atom forming a naphthalene ring. In such a structure, the specific substituent (1-naphthyl group) introduced to the group $D_1$ is twisted with respect to a benzothienocarbazole plane.

The group represented by the formula (1-4C) has a carbon atom at an ortho position (**) of a benzene ring of a "benzothienocarbazole-benzene structure," the carbon atom being an atom forming a dibenzofuran ring. In such a structure, the specific substituent (1-dibenzofuranyl group) introduced to the group $D_1$ is twisted with respect to a benzothienocarbazole plane.

It is believed that these twisted structures are caused by steric hindrance.

[Formula 9]

(1-4A)

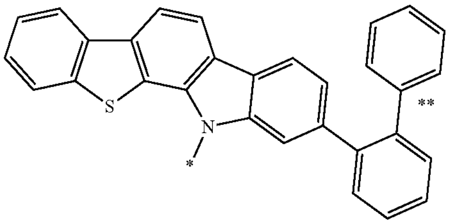

(1-4B)

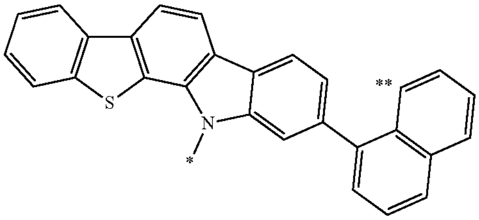

(1-4C)

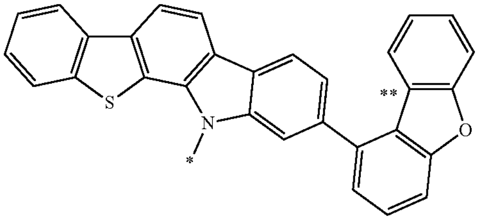

In contrast, groups represented by formulae (1-R1) to (1-R3) below are each a group produced by introducing to benzothienocarbazole a group that does not fall under the definition of the specific substituent (a group represented by the formula (110) or (120)).

Compounds including the groups represented by the formulae (1-R1) to (1-R3) correspond to later-described Comparative 4 to 6, respectively.

The group represented by the formula (1-R1) is produced by bonding a phenyl group at a meta position of a benzene ring of the "benzothienocarbazole-benzene structure." Accordingly, the group (1,1'-biphenyl-3-yl group) bonded to benzothienocarbazole has small steric hindrance and is not likely to be twisted with respect to the benzothienocarbazole plane.

The group represented by the formula (1-R2) is produced by bonding a phenyl group at a para position of a benzene ring of the "benzothienocarbazole-benzene structure." Accordingly, the group (1,1'-biphenyl-4-yl group) bonded to benzothienocarbazole has small steric hindrance and is not likely to be twisted with respect to the benzothienocarbazole plane.

The group represented by the formula (1-R3) has an oxygen atom at an ortho position of a benzene ring of a "benzothienocarbazole-benzene structure," the oxygen atom being an atom forming a dibenzofuran ring. In such a structure, since there is no hydrogen atom or substituent on an oxygen atom of the group (4-dibenzofuranyl group) bonded to benzothienocarbazole (i.e. on an oxygen atom located at the ortho position of the benzene ring), the 4-dibenzofuranyl group is unlikely to be twisted with respect to the benzothienocarbazole plane.

[Formula 10]

(1-R1)

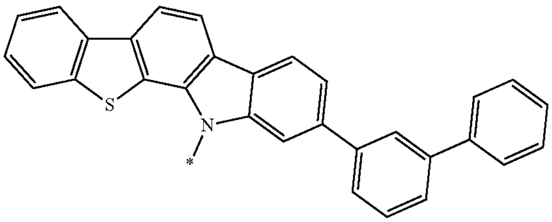

(1-R2)

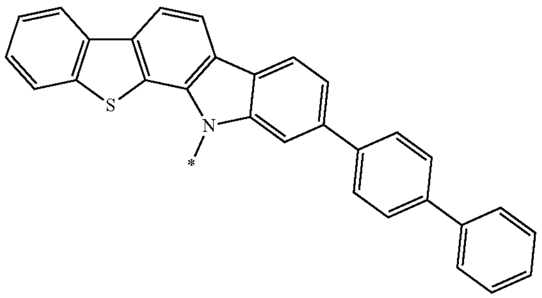

(1-R3)

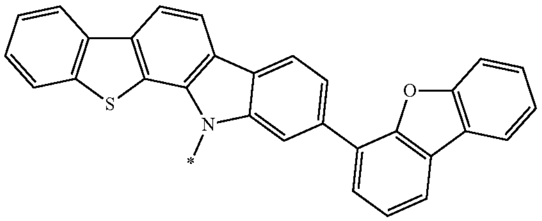

As described above, it is believed that the compound according to the present exemplary embodiment, in which the specific substituent (a group represented by the formula (110) or (120)) is introduced to the group $D_1$, has a twisted structure of the specific substituent, thereby reducing intermolecular interaction between the compounds represented by the formulae (11) to (13). Further, the intermolecular distance is likely to be enlarged by the presence of the specific substituent. As a result, concentration quenching is restrained, thereby producing a compound with high PLQY.

Accordingly, a compound capable of providing a high-performance organic EL device, especially, a compound having a high PLQY can be provided.

High performance means that at least one of luminous efficiency, device lifetime, drive voltage, luminance or the like is improved.

Examples of forms of the compound of the present exemplary embodiment, in which "in at least one group $D_1$, at least one of $R_{101}$ to $R_{160}$ is a group represented by the formula (110) or a group represented by the formula (120)," include the following forms.

Forms in which one of $R_1$ to $R_4$ is a group $D_1$ and at least one of $R_{101}$ to $R_{160}$ in the group $D_1$ is a group represented by the formula (110) or a group represented by the formula (120).

Forms in which two of $R_1$ to $R_4$ are groups $D_1$, at least one of $R_{101}$ to $R_{160}$ in one of the groups $D_1$ is a group represented by the formula (110) or a group represented by the formula (120), and at least one of $R_{101}$ to $R_{160}$ in the other one of the groups $D_1$ is a group represented by the formula (110) or a group represented by the formula (120).

Examples of forms of the formula (110), in which "the ring (B) and one $R_{10A}$ adjacent to the ring (B) are mutually bonded to form a ring," include Form 1 below.

Form 1

In the formula (110), the ring (B) is bonded to $R_{10A}$ in $Y_{12}$ (one $R_{10A}$ adjacent to the ring (B)) to form a ring (C) and the ring (C) is fused with a six-membered ring in the formula (110). In this case, a group represented by the formula (110) is represented by a formula (110-1) below. In the formula (110-1), $R_{10A}$ in $Y_{12}$ corresponds to the "one $R_{10A}$ adjacent to the ring (B)."

[Formula 11]

(110-1)

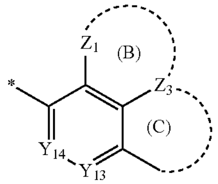

In the formula (110-1), the ring (B), $Z_1$, and $Y_{13}$ to $Y_{14}$ respectively independently represent the same as the ring (B), $Z_1$, and $Y_{13}$ to $Y_{14}$ in the formula (110). $Z_3$, which is an atom forming the ring (B) and the ring (C), represents a carbon atom, nitrogen atom, silicon atom, or germanium atom. The ring (C) is a substituted or unsubstituted aromatic hydrocarbon ring having 6 to 30 ring carbon atoms or a substituted or unsubstituted heterocyclic ring having 5 or 30 ring carbon atoms. In the formula (110-1), the ring (B) and the ring (C) share $Z_3$. * represents a bonding position to a carbon atom of a six-membered ring in the formulae (1-1) to (1-6).

Examples of the group represented by the formula (110-1) include a group represented by a formula (110-1A) and a group represented by a formula (110-1B) below.

[Formula 12]

(110-1A)

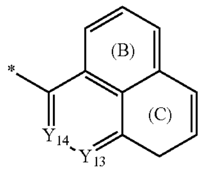

(110-1B)

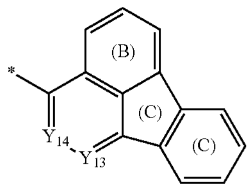

In the formulae (110-1A) and (110-11B), $Y_{13}$ to $Y_{14}$ respectively independently represent the same as $Y_{13}$ to $Y_{14}$ in the formula (110) and (B) and (C) correspond to the rings (B) and (C) in the formula (110-1).

$Z_1$ and $Z_3$ in the formula (110-1) are each a carbon atom in the formulae (110-1A) and (110-1B). Each * represents a bonding position to a carbon atom of the six-membered ring in the formulae (1-1) to (1-6).

Examples of forms of the formula (110), in which "the ring (B) and at least one combination of adjacent two or more of a plurality of $R_{10A}$ are mutually bonded to form a ring," include Form 2 below.

Form 2

In the formula (110), the ring (B) is bonded to $R_{10A}$ in $Y_{12}$ to form a ring (C), $R_{10A}$ in $Y_{12}$ is bonded to $R_{10A}$ in $Y_{13}$ to form a ring (D), and the ring (C) and the ring (D) are fused with a six-membered ring in the formula (110). In this case, a group represented by the formula (110) is represented by a formula (110-2) below. In the formula (110-2) below, $R_{10A}$ in $Y_{12}$ and $R_{10A}$ in $Y_{13}$ correspond to "a combination of adjacent ones of a plurality of $R_{10A}$ (three $R_{10A}$ in $Y_{12}$ to $Y_{14}$)."

[Formula 13]

(110-2)

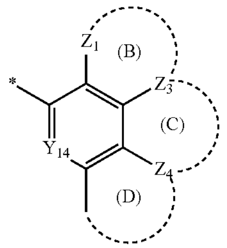

In the formula (110-2), the ring (B), ring (C), $Z_1$, $Z_3$, and $Y_{14}$ respectively independently represent the same as the ring (B), ring (C), $Z_1$, $Z_3$, and $Y_{14}$ in the formula (110-1), the ring (D) represents the same as the ring (C) in the formula (110-1), and $Z_4$ represents the same as $Z_3$ in the formula (110-1). The ring (B) and ring (C) share $Z_3$. The ring (C) and ring (D) share $Z_4$.

In the formula (110-2), the ring (B), $R_{10A}$ in $Y_{12}$ and $R_{10A}$ in $Y_{13}$ are mutually bonded to form the ring (B), ring (C), and ring (D).

* represents a bonding position to a carbon atom of the six-membered ring in the formulae (1-1) to (1-6).

In the compound of the present exemplary embodiment:

it is preferable that, when there are a plurality of groups represented by the formula (1-1) (groups $D_1$) as the groups for $R_1$ to $R_4$, the plurality of groups represented by the formula (1-1) are mutually identical groups including substituent(s) thereof;

it is preferable that, when there are a plurality of groups represented by the formula (1-2) (groups $D_1$) as the groups for $R_1$ to $R_4$, the plurality of groups represented by the formula (1-2) are mutually identical groups including substituent(s) thereof;

it is preferable that, when there are a plurality of groups represented by the formula (1-3) (groups $D_1$) as the groups for $R_1$ to $R_4$, the plurality of groups represented by the formula (1-3) are mutually identical groups including substituent(s) thereof;

it is preferable that, when there are a plurality of groups represented by the formula (1-4) (groups $D_1$) as the groups for $R_1$ to $R_4$, the plurality of groups represented by the formula (1-4) are mutually identical groups including substituent(s) thereof;

it is preferable that, when there are a plurality of groups represented by the formula (1-5) (groups $D_1$) as the groups for $R_1$ to $R_4$, the plurality of groups represented by the formula (1-5) are mutually identical groups including substituent(s) thereof; and it is preferable that, when there are a plurality of groups represented by the formula (1-6) (groups $D_1$) as the groups for $R_1$ to $R_4$, the plurality of groups represented by the formula (1-6) are mutually identical groups including substituent(s) thereof.

In the compound of the present exemplary embodiment, it is preferable that, when two group $D_1$ are selected as the groups for $R_1$ to $R_4$, the selected two groups $D_1$ are represented by one of formulae (1-1) to (1-6) and are mutually identical groups including the substituent(s) thereof.

For instance, when two groups represented by the formula (1-1) (groups $D_1$) are selected as the groups for $R_1$ and $R_2$, the two groups represented by the formula (1-1) (groups of $R_1$ and $R_2$) are preferably mutually identical groups including substituent(s) thereof.

In the compound of the present exemplary embodiment, it is preferable that, when three groups $D_1$ are selected as the groups for $R_1$ to $R_4$, all of the selected three groups $D_1$ are represented by one of the formulae (1-1) to (1-6) and are mutually identical groups including the substituent(s) thereof.

For instance, when three groups represented by the formula (1-1) (groups $D_1$) are selected as the groups for $R_1$ to $R_3$, the three groups represented by the formula (1-1) (groups of $R_1$ to $R_3$) are preferably mutually identical groups including substituent(s) thereof.

In the compound of the present exemplary embodiment, it is preferable that, when two of $R_1$ to $R_4$ are selected from the groups (groups $D_1$) represented by the formulae (1-1) to (1-6) and remaining two of $R_1$ to $R_4$ are selected from the groups (groups $D_2$) represented by the formulae (2-1) to (2-4), both of the two groups represented by the formulae (1-1) to (1-6) are represented by one of the formulae (1-1) to (1-6) and are mutually identical groups including substituent(s) thereof.

Further, it is preferable that, when three of $R_1$ to $R_4$ are selected from the groups (groups $D_1$) represented by the formulae (1-1) to (1-6) and remaining one of $R_1$ to $R_4$ is selected from the groups (groups $D_2$) represented by the formulae (2-1) to (2-4), all of the three groups represented by the formulae (1-1) to (1-6) are represented by one of the formulae (1-1) to (1-6) and are mutually identical groups including substituent(s) thereof.

For instance, it is preferable that, when three groups represented by the formula (1-1) (groups $D_1$) are selected as the groups for $R_1$ to $R_4$, the selected three groups are represented by the formula (1-1) and are mutually identical groups including substituent(s) thereof.

In the compound of the present exemplary embodiment:

it is preferable that, when there are a plurality of groups represented by the formula (2-1) (groups $D_2$) as the groups for $R_1$ to $R_4$, the plurality of groups represented by the formula (2-1) are mutually identical groups including substituent(s) thereof;

it is preferable that, when there are a plurality of groups represented by the formula (2-2) (groups $D_2$) as the groups for $R_1$ to $R_4$, the plurality of groups represented by the formula (2-2) are mutually identical groups including substituent(s) thereof;

it is preferable that, when there are a plurality of groups represented by the formula (2-3) (groups $D_2$) as the groups for $R_1$ to $R_4$, the plurality of groups represented by the formula (2-3) are mutually identical groups including substituent(s) thereof; and it is preferable that, when there are a plurality of groups represented by the formula (2-4) (groups $D_2$) as the groups for $R_1$ to $R_4$, the plurality of groups represented by the formula (2-4) are mutually identical groups including substituent(s) thereof.

In the compound of the present exemplary embodiment, it is preferable that, when two groups $D_2$ are selected as the groups for $R_1$ to $R_4$, all of the selected two groups $D_2$ are represented by one of the formulae (2-1) to (2-4) and are mutually identical groups including the substituent(s) thereof.

For instance, it is preferable that, when two groups represented by the formula (2-1) (groups $D_2$) are selected as the groups for $R_1$ and $R_2$, the two groups represented by the formula (2-1) (groups of $R_1$ and $R_2$) are mutually identical groups including substituent(s) thereof.

In the compound of the present exemplary embodiment, it is preferable that, when three groups $D_2$ are selected as the groups for $R_1$ to $R_4$, all of the selected three groups $D_2$ are represented by one of the formulae (2-1) to (2-4) and are mutually identical groups including the substituent(s) thereof.

For instance, it is preferable that, when three groups represented by the formula (2-1) (groups $D_2$) are selected as the groups for $R_1$ to $R_3$, the three groups represented by the formula (2-1) (groups of $R_1$ to $R_3$) are mutually identical groups including substituent(s) thereof.

In the compound of the present exemplary embodiment, it is preferable that, when two of $R_1$ to $R_4$ are selected from the groups (groups $D_2$) represented by the formulae (2-1) to (2-4) and remaining two of $R_1$ to $R_4$ are selected from the groups (groups $D_1$) represented by the formulae (1-1) to (1-6), both of the two groups represented by the formulae (2-1) to (2-4) are represented by one of the formulae (2-1) to (2-4) and are mutually identical groups including substituent(s) thereof.

Further, it is preferable that, when three of $R_1$ to $R_4$ are selected from the groups (groups $D_2$) represented by the formulae (2-1) to (2-4) and remaining one of $R_1$ to $R_4$ is selected from the groups (groups $D_1$) represented by the formulae (1-1) to (1-6), all of the three groups represented by the formulae (2-1) to (2-4) are represented by one of the formulae (2-1) to (2-4) and are mutually identical groups including substituent(s) thereof.

For instance, when three groups represented by the formula (2-1) (groups $D_2$) are selected as the groups for $R_1$ to $R_4$, it is preferable that the selected three groups are represented by the formula (2-1) and are mutually identical groups including substituent(s) thereof.

The compound according to the present exemplary embodiment is preferably a compound represented by one of formulae (1001) to (1023) below.

[Formula 14]

(1001)

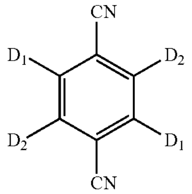

-continued (1002)

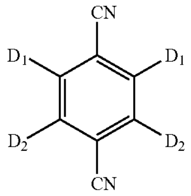

(1003)

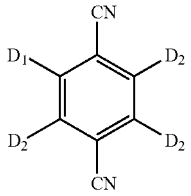

(1004)

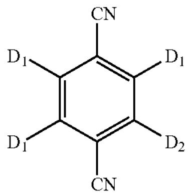

(1005)

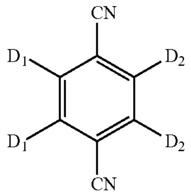

(1006)

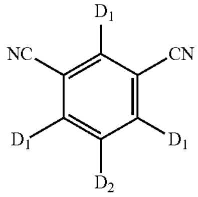

[Formula 15]

(1007)

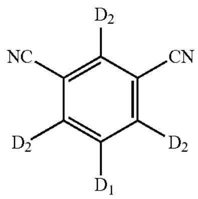

(1008)

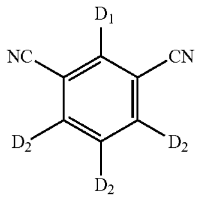

-continued
(1009)
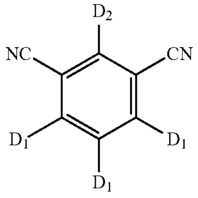
(1010)
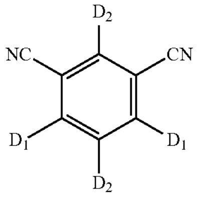
(1011)
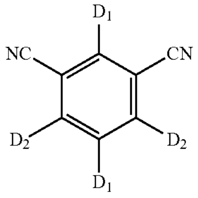
(1012)
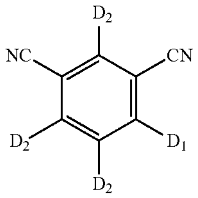
(1013)
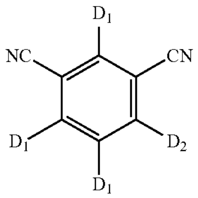
(1014)
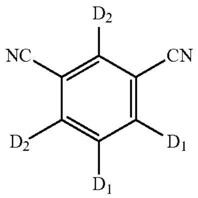
(1015)
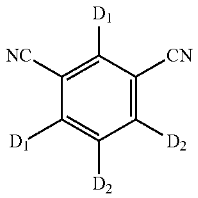
-continued
[Formula 16]
(1016)
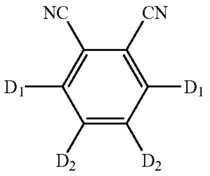
(1017)
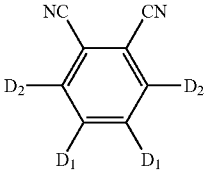
(1018)
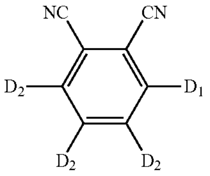
(1019)
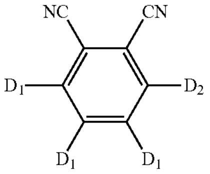
(1020)
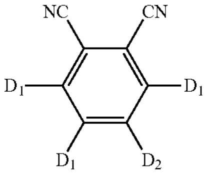
(1021)
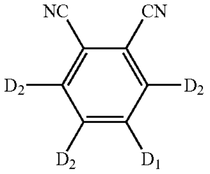
(1022)
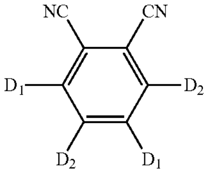
(1023)
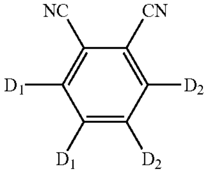
In the formulae (1001) to (1023), $D_1$ each independently represents the same as the group $D_1$ represented by one of the formulae (1-1) to (1-6) and $D_2$ each independently represents the same as the group $D_2$ represented by one of the formulae (2-1) to (2-4).

In the compound according to the present exemplary embodiment, the group $D_2$ is preferably a group represented by the formula (2-1).

In the compound according to the present exemplary embodiment, the group $D_1$ is preferably a group represented by the formula (1-4) or (1-5).

In the compound according to the present exemplary embodiment, it is preferable that, when one of $R_1$ to $R_4$ is the group $D_1$, only one of $R_{101}$ to $R_{160}$ in the group $D_1$ is a group represented by the formula (110) or a group represented by the formula (120).

In the compound according to the present exemplary embodiment, it is preferable that, when two of $R_1$ to $R_4$ are the group $D_1$, only one of $R_{101}$ to $R_{160}$ in each of the groups $D_1$ is a group represented by the formula (110) or a group represented by the formula (120).

In the compound according to the present exemplary embodiment, it is preferable that, when three of $R_1$ to $R_4$ are the group $D_1$, only one of $R_{101}$ to $R_{160}$ in each of the groups $D_1$ is a group represented by the formula (110) or a group represented by the formula (120).

In the compound of the present exemplary embodiment, it is more preferable that:

only one of $R_{107}$ to $R_{110}$ in the formula (1-1) is a group represented by the formula (110) or a group represented by the formula (120);

only one of $R_{116}$ to $R_{119}$ in the formula (1-2) is a group represented by the formula (110) or a group represented by the formula (120);

only one of $R_{126}$ to $R_{129}$ in the formula (1-3) is a group represented by the formula (110) or a group represented by the formula (120);

only one of $R_{135}$ to $R_{138}$ in the formula (1-4) is a group represented by the formula (110) or a group represented by the formula (120);

only one of $R_{145}$ to $R_{148}$ in the formula (1-5) is a group represented by the formula (110) or a group represented by the formula (120); or only one of $R_{157}$ to $R_{160}$ in the formula (1-6) is a group represented by the formula (110) or a group represented by the formula (120).

In the compound according to the present exemplary embodiment, it is preferable that:

only one of $R_{108}$ to $R_{110}$ in the formula (1-1) is a group represented by the formula (110) or a group represented by the formula (120);

only one of $R_{117}$ to $R_{119}$ in the formula (1-2) is a group represented by the formula (110) or a group represented by the formula (120);

only one of $R_{127}$ to $R_{129}$ in the formula (1-3) is a group represented by the formula (110) or a group represented by the formula (120);

only one of $R_{136}$ to $R_{138}$ in the formula (1-4) is a group represented by the formula (110) or a group represented by the formula (120);

only one of $R_{146}$ to $R_{148}$ in the formula (1-5) is a group represented by the formula (110) or a group represented by the formula (120); or only one of $R_{157}$ to $R_{160}$ in the formula (1-6) is a group represented by the formula (110) or a group represented by the formula (120).

In the compound according to the present exemplary embodiment, it is preferable that only one of $R_1$ to $R_4$ is the group $D_1$.

In other words, the compound according to the present exemplary embodiment is preferably represented by one of formulae (1003), (1007), (1008), (1012), (1018), and (1021) below.

[Formula 17]

(1003)

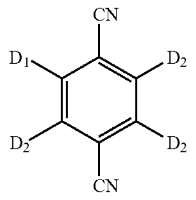

(1007)

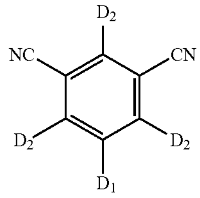

(1008)

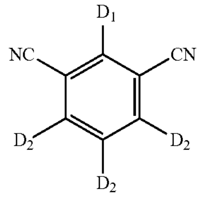

(1012)

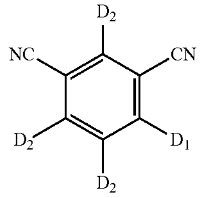

(1018)

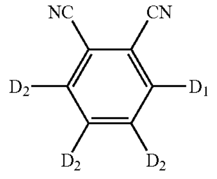

(1021)

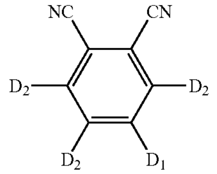

In the formulae (1003), (1007), (1008), (1012), (1018), and (1021), $D_1$ each independently represents the same as the group $D_1$ represented by one of the formulae (1-1) to (1-6) and $D_2$ each independently represents the same as the group $D_2$ represented by one of the formulae (2-1) to (2-4).

The compound according to the present exemplary embodiment is preferably a compound represented by any one of formulae (1003A), (1007A), (1008A), (1012A), (1018A), and (1021A) below.

[Formula 18]
(1003A)
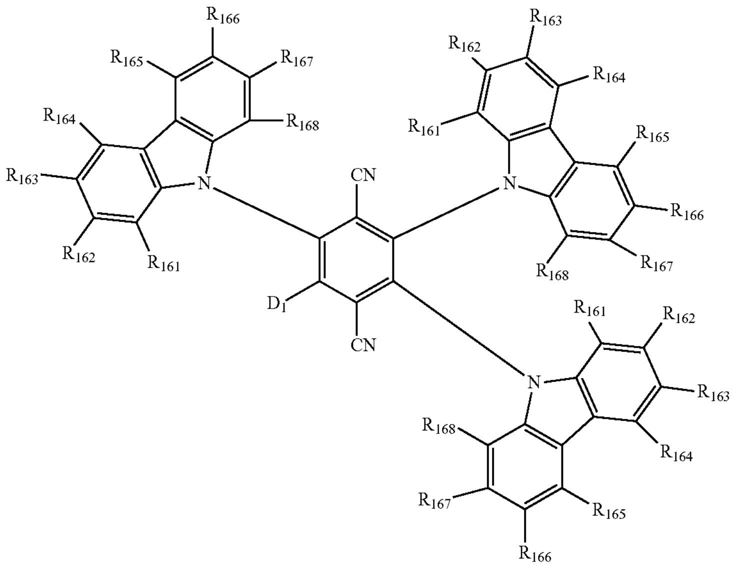
(1007A)
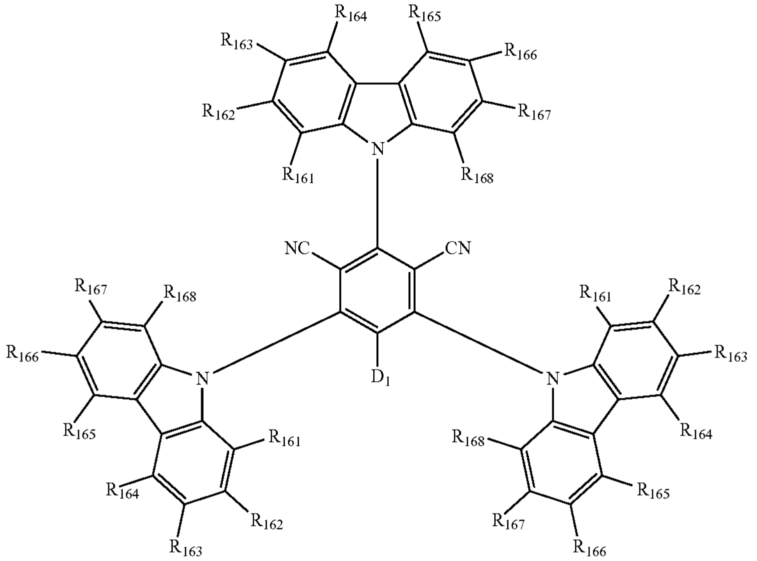
(1008A)
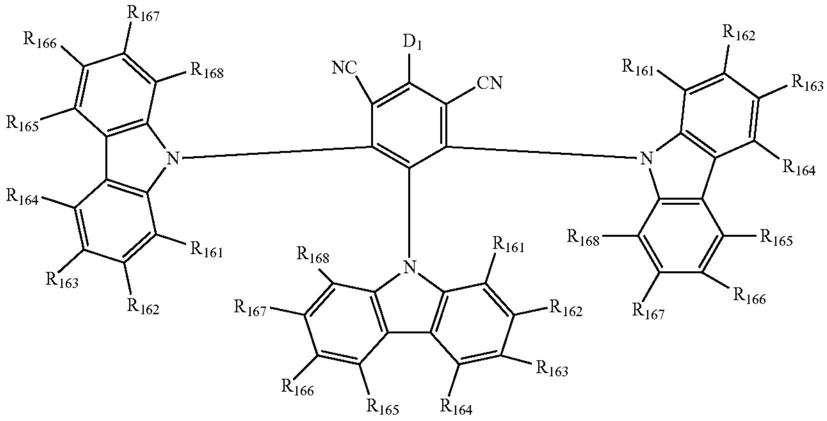

-continued
(1012A)
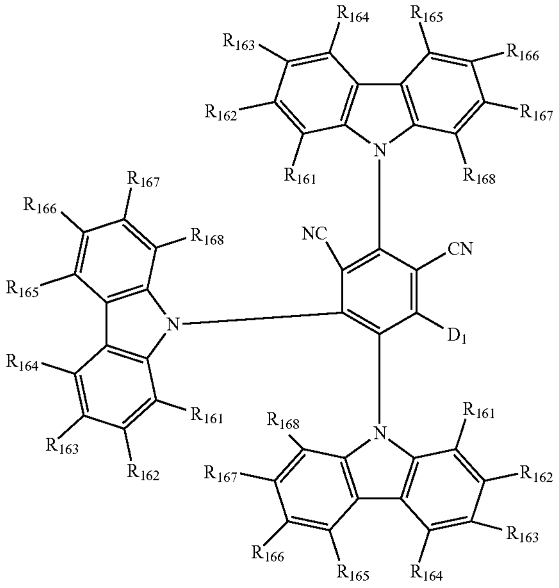
[Formula 19]
(1018A)
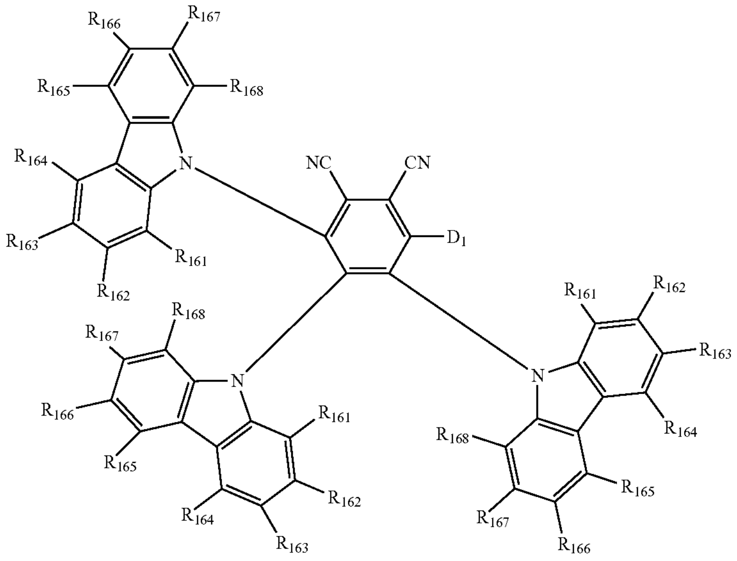

-continued (1021A)

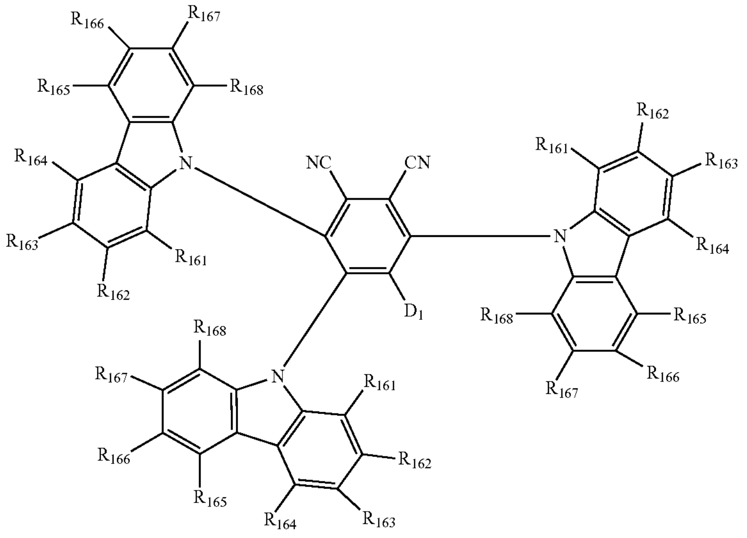

In the formulae (1003A), (1007A), (1008A), (1012A), (1018A), and (1021A), $D_1$ each independently represents the same as the group $D_1$ represented by one of the formulae (1-1) to (1-6) and $R_{161}$ to $R_{168}$ each independently represent the same as the group $R_{161}$ to $R_{168}$ in the formulae (2-1) to (2-4).

In the compound according to the present exemplary embodiment, it is preferable that only two of $R_1$ to $R_4$ are the group $D_1$.

In other words, the compound according to the present exemplary embodiment is preferably represented by one of formulae (1001), (1002), (1005), (1010), (0111), (1014) to (1017), (1022), and (1023) below.

[Formula 20]

(1001)

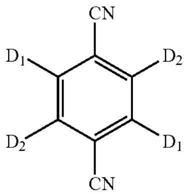

(1002)

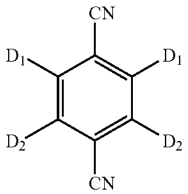

(1005)

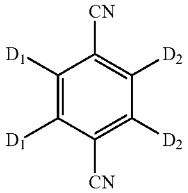

-continued (1010)

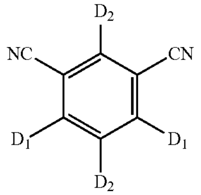

(1011)

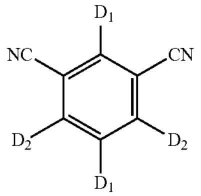

(1014)

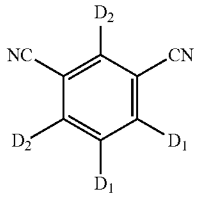

(1015)

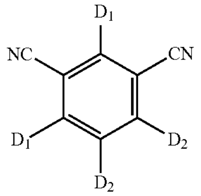

(1016)

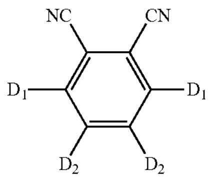

-continued (1017)

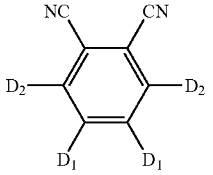

(1022)

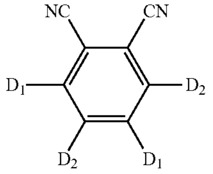

(1023)

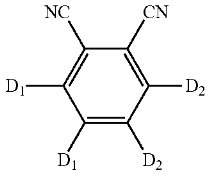

In the formulae (1001), (1002), (1005), (1010), (1011), (1014) to (1017), (1022), and (1023), $D_1$ each independently represents the same as the group $D_1$ represented by one of the formulae (1-1) to (1-6) and $D_2$ each independently represents the same as the group $D_2$ represented by one of the formulae (2-1) to (2-4).

In the compound according to the present exemplary embodiment, it is preferable that, in at least one group $D_1$, at least one of $R_{101}$ to $R_{160}$ is a group represented by the formula (110).

In the compound of the present exemplary embodiment, it is preferable that, when one of $R_1$ to $R_4$ is the group $D_1$, only one of $R_{101}$ to $R_{160}$ in the group $D_1$ is a group represented by the formula (110).

In the compound of the present exemplary embodiment, it is preferable that, when two of $R_1$ to $R_4$ are the group $D_1$, only one of $R_{101}$ to $R_{160}$ in each group $D_1$ is a group represented by the formula (110).

In the compound of the present exemplary embodiment, it is preferable that, when three of $R_1$ to $R_4$ are the group $D_1$, only one of $R_{101}$ to $R_{160}$ in each group $D_1$ is a group represented by the formula (110).

In the compound of the present exemplary embodiment, it is preferable that $Z_1$ in the formula (110) is a carbon atom.

In the compound of the present exemplary embodiment, it is preferable that a group represented by the formula (110) is a group represented by any one of formulae (111) to (117) below.

[Formula 21]

(111)

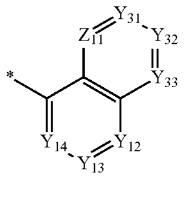

-continued (112)

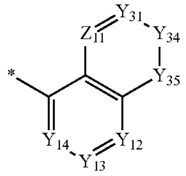

(113)

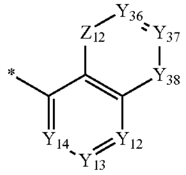

(114)

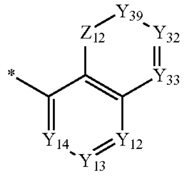

In the formula (111):

$Y_{12}$ to $Y_{14}$ are each independently a nitrogen atom or $CR_{10A}$;

$Z_{11}$ and $Y_{31}$ to $Y_{33}$ are each independently a nitrogen atom or $CR_{30A}$;

$R_{10A}$ and $R_{30A}$ are each independently a hydrogen atom or a substituent, or at least one combination of adjacent two or more groups selected from the group consisting of one or more of $R_{30A}$ and one or more of $R_{10A}$ are mutually bonded to form a ring; and $R_{10A}$ as a substituent and $R_{30A}$ as a substituent each independently represent the same as $R_{10A}$ as a substituent in the formula (110).

In the formula (112):

$Y_{12}$ to $Y_{14}$ are each independently a nitrogen atom or $CR_{10A}$;

$Z_{11}$ and $Y_{31}$ are each independently a nitrogen atom or $CR_{30A}$;

$Y_{34}$ and $Y_{35}$ are each independently $NR_{30B}$, an oxygen atom, a sulfur atom, or $CR_{30C}R_{30D}$;

$R_{10A}$, $R_{30A}$, $R_{30B}$, $R_{30C}$, and $R_{30D}$ are each independently a hydrogen atom or a substituent, or at least one combination of adjacent two or more groups selected from the group consisting of one or more of $R_{10A}$, one or more of $R_{30A}$, one or more of $R_{30B}$, one or more of $R_{30C}$, and one or more of $R_{30D}$ are mutually bonded to form a ring; and $R_{10A}$ as a substituent and $R_{30A}$, $R_{30B}$, $R_{30C}$, and $R_{30D}$ as substituents each independently represent the same as $R_{10A}$ as a substituent in the formula (110).

In the formula (113):

$Y_{12}$ to $Y_{14}$ are each independently a nitrogen atom or $CR_{10A}$;

$Z_{12}$ is $NR_{30B}$ or $CR_{30C}R_{30D}$;

$Y_{38}$ is $NR_{30B}$, an oxygen atom, a sulfur atom, or $CR_{30C}R_{30D}$;

$Y_{36}$ and $Y_{37}$ are each independently a nitrogen atom or $CR_{30A}$;

$R_{10A}$, $R_{30A}$, $R_{30B}$, $R_{30C}$, and $R_{30D}$ are each independently a hydrogen atom or a substituent, or at least one combination of adjacent two or more groups selected from the group consisting of one or more of $R_{10A}$, one or more of $R_{30A}$, one or more of $R_{30B}$, one or more of $R_{30C}$, and one or more of $R_{30D}$ are mutually bonded to form a ring; and $R_{10A}$ as a substituent and $R_{30A}$, $R_{30B}$, $R_{30C}$, and $R_{30D}$ as substituents each independently represent the same as $R_{10A}$ as a substituent in the formula (110).

In the formula (114):

$Y_{12}$ to $Y_{14}$ are each independently a nitrogen atom or $CR_{10A}$;

$Z_{12}$ is $NR_{30B}$ or $CR_{30C}R_{30D}$;

$Y_{39}$ is $NR_{30B}$, an oxygen atom, a sulfur atom, or $CR_{30C}R_{30D}$;

$Y_{32}$ and $Y_{33}$ are each independently a nitrogen atom or $CR_{30A}$;

$R_{10A}$, $R_{30A}$, $R_{30B}$, $R_{30C}$, and $R_{30D}$ are each independently a hydrogen atom or a substituent, or at least one combination of adjacent two or more groups selected from the group consisting of one or more of $R_{10A}$, one or more of $R_{30A}$, one or more of $R_{30B}$, one or more of $R_{30C}$, and one or more of $R_{30D}$ are mutually bonded to form a ring; and $R_{10A}$ as a substituent and $R_{30A}$, $R_{30B}$, $R_{30C}$, and $R_{30D}$ as substituents each independently represent the same as $R_{10A}$ as a substituent in the formula (110).

In the formulae (111) to (114), in the definition of the "combination of adjacent two or more (of . . . )", it is assumed that not only the combinations of $Z_{11}$ and $Y_{31}$, $Y_{31}$ and $Y_{32}$, $Y_{32}$ and $Y_{33}$, $Y_{12}$ and $Y_{13}$, and $Y_{13}$ and $Y_{14}$, but also $Y_{12}$ and $Y_{33}$ are adjacent to each other in the case of the formula (111). Similarly, $Y_{12}$ and $Y_{35}$ are assumed to be adjacent to each other in the formula (112), $Y_{12}$ and $Y_{38}$ are assumed to be adjacent to each other in the formula (113), and $Y_{12}$ and $Y_{33}$ are assumed to be adjacent to each other in the formula (114).

[Formula 22]

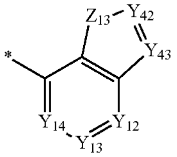

(115)

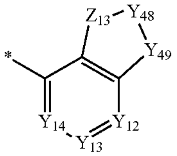

(116)

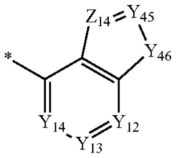

(117)

In the formula (115):

$Y_{12}$ to $Y_{14}$ are each independently a nitrogen atom or $CR_{10A}$;

$Z_{13}$ is $NR_{30B}$ or $CR_{30C}R_{30D}$;

$Y_{42}$ and $Y_{43}$ are each independently a nitrogen atom or $CR_{30A}$;

$R_{10A}$, $R_{30A}$, $R_{30B}$, $R_{30C}$, and $R_{30D}$ are each independently a hydrogen atom or a substituent, or at least one combination of adjacent two or more groups selected from the group consisting of one or more of $R_{10A}$, one or more of $R_{30A}$, one or more of $R_{30B}$, one or more of $R_{30C}$, and one or more of $R_{30D}$ are mutually bonded to form a ring; and $R_{10A}$ as a substituent and $R_{30A}$, $R_{30B}$, $R_{30C}$, and $R_{30D}$ as substituents each independently represent the same as $R_{10A}$ as a substituent in the formula (110).

In the formula (116):

$Y_{12}$ to $Y_{14}$ are each independently a nitrogen atom or $CR_{10A}$;

$Z_{13}$ is $NR_{30B}$ or $CR_{30C}R_{30D}$;

$Y_{48}$ and $Y_{49}$ are each independently $NR_{30B}$, an oxygen atom, a sulfur atom, or $CR_{30C}R_{30D}$;

$R_{10A}$, $R_{30B}$, $R_{30C}$, and $R_{30D}$ are each independently a hydrogen atom or a substituent, or at least one combination of adjacent two or more groups selected from the group consisting of one or more of $R_{10A}$, one or more of $R_{30B}$, one or more of $R_{30C}$, and one or more of $R_{30D}$ are mutually bonded to form a ring; and $R_{10A}$ as a substituent and $R_{30B}$, $R_{30C}$, and $R_{30D}$ as substituents each independently represent the same as $R_{10A}$ as a substituent in the formula (110).

In the formula (117):

$Y_{12}$ to $Y_{14}$ are each independently a nitrogen atom or $CR_{10A}$;

$Z_{14}$ and $Y_{45}$ are each independently a nitrogen atom or $CR_{30A}$;

$Y_{46}$ is $NR_{30B}$, an oxygen atom, a sulfur atom, or $CR_{30C}R_{30D}$;

$R_{10A}$, $R_{30A}$, $R_{30B}$, $R_{30C}$, and $R_{30D}$ are each independently a hydrogen atom or a substituent, or at least one combination of adjacent two or more groups selected from the group consisting of one or more of $R_{10A}$, one or more of $R_{30A}$, one or more of $R_{30B}$, one or more of $R_{30C}$, and one or more of $R_{30D}$ are mutually bonded to form a ring; and $R_{10A}$ as a substituent and $R_{30A}$, $R_{30B}$, $R_{30C}$, and $R_{30D}$ as substituents each independently represent the same as $R_{10A}$ as a substituent in the formula (110). In the formulae (111) to (117), when a plurality of $R_{10A}$ are present, the plurality of $R_{10A}$ are mutually the same or different, when a plurality of $R_{30A}$ are present, the plurality of $R_{30A}$ are mutually the same or different, when a plurality of $R_{30B}$ are present, the plurality of $R_{30B}$ are mutually the same or different, when a plurality of $R_{30C}$ are present, the plurality of $R_{30C}$ are mutually the same or different, and when a plurality of $R_{30D}$ are present, the plurality of $R_{30D}$ are mutually the same or different.

In the formulae (115) to (117), in the definition of the "combination of adjacent two or more (of . . . )", it is assumed that not only the combinations of $Z_{13}$ and $Y_{42}$, $Y_{42}$ and $Y_{43}$, $Y_{12}$ and $Y_{13}$, and $Y_{13}$ and $Y_{14}$, but also $Y_{12}$ and $Y_{43}$ are adjacent to each other in the case of the formula (115). Similarly, $Y_{12}$ and $Y_{49}$ are assumed to be adjacent to each other in the formula (116) and $Y_{12}$ and $Y_{46}$ are assumed to be adjacent to each other in the formula (117).

In the compound of the present exemplary embodiment, it is preferable that a group represented by the formula (110) is a group represented by any one of the formulae (111), (115), and (117).

In the compound of the present exemplary embodiment, it is preferable that $Y_{12}$ to $Y_{14}$ in the formula (110) are each $CR_{10A}$.

In the compound of the present exemplary embodiment, it is preferable that $Y_{21}$ to $Y_{24}$ in the formula (120) are each $CR_{20A}$.
In the compound of the present exemplary embodiment, it is preferable that a group represented by the formula (110) is a group represented by any one of formulae (b1) to (b14) below.
[Formula 23]
(b1)
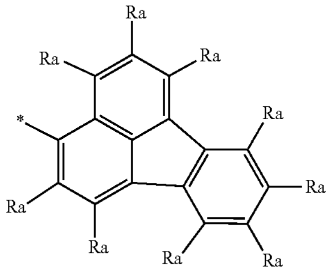
(b2)
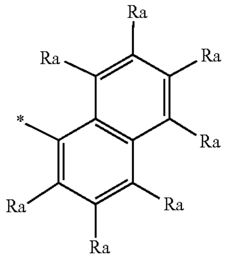
(b3)
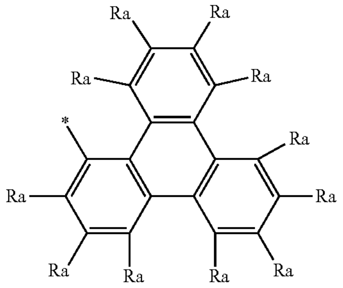
(b4)
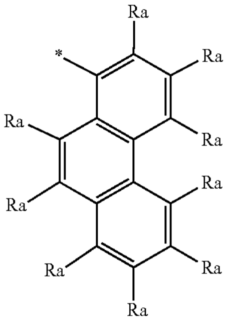
-continued
(b5)
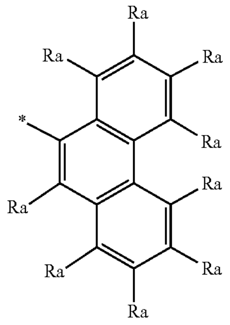
(b6)
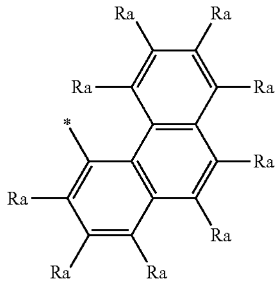
[Formula 24]
(b7)
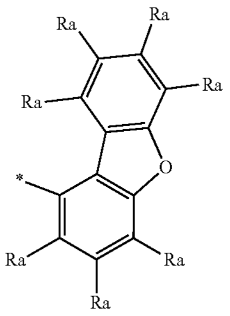
(b8)
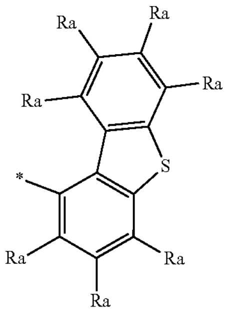
(b9)
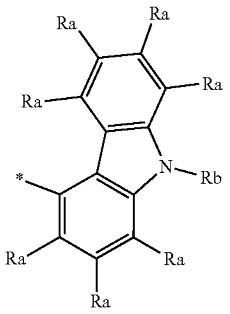

-continued (b10)

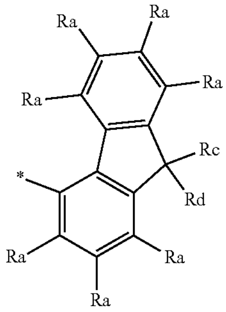

(b11)

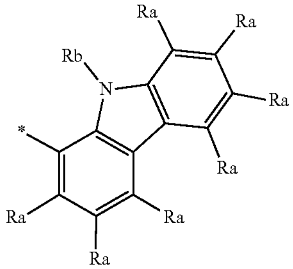

(b12)

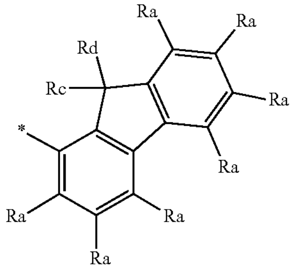

(b13)

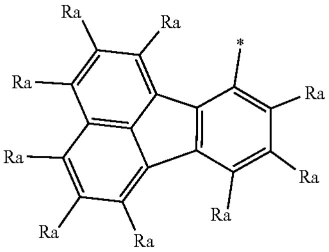

(b14)

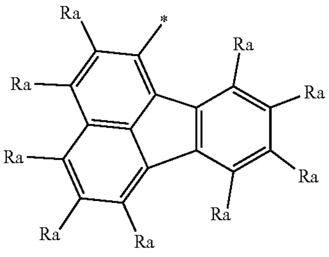

In the formulae (b1) to (b14):

Ra is a hydrogen atom or a substituent, or at least one combination of adjacent ones of Ra are mutually bonded to form a ring;

a plurality of Ra are mutually the same or different;

Rb is a hydrogen atom or a substituent;

Rc and Rd are each independently a hydrogen atom or a substituent, or a combination of Rc and Rd are mutually bonded to form a ring; and Ra, Rb, Rc, and Rd as substituents represent the same as $R_{104}$ as a substituent in the formula (110).

In the formulae (b1) to (b14), Ra is preferably a hydrogen atom, a substituted or unsubstituted aryl group having 6 to 30 ring carbon atoms, or a substituted or unsubstituted alkyl group having 1 to 30 carbon atoms, more preferably a hydrogen atom.

In the formulae (b10) and (b12), it is preferable that Rc and Rd are each independently a substituted or unsubstituted aryl group having 6 to 30 ring carbon atoms or a substituted or unsubstituted alkyl group having 1 to 30 carbon atoms, or a combination of Rc and Rd are mutually bonded to form a ring.

In the formulae (b9) and (b11), Rb is preferably a substituted or unsubstituted aryl group having 6 to 30 ring carbon atoms, a substituted or unsubstituted alkyl group having 1 to 30 carbon atoms, or a substituted or unsubstituted heterocyclic group having 5 to 30 ring atoms.

In the formulae (b1) to (b14), it is preferable that at least one combination of adjacent ones of Ra are not mutually bonded to form a ring.

In the formulae (b1) to (b14), it is preferable that the combination of Rc and Rd are not mutually bonded to form a ring.

In the compound of the present exemplary embodiment, a group represented by the formula (110) is preferably a substituted or unsubstituted naphthyl group, substituted or unsubstituted phenanthryl group, substituted or unsubstituted chrysenyl group, substituted or unsubstituted benzophenanthryl group, substituted or unsubstituted benzochrysenyl group, substituted or unsubstituted triphenylenyl group, substituted or unsubstituted fluorenyl group, substituted or unsubstituted benzofluorenyl group, substituted or unsubstituted dibenzofluorenyl group, substituted or unsubstituted fluoranthenyl group, substituted or unsubstituted dibenzofuranyl group, substituted or unsubstituted dibenzothienyl group, or substituted or unsubstituted carbazolyl group.

In the compound of the present exemplary embodiment, it is preferable that, in at least one group $D_1$, at least one of $R_{101}$ to $R_{160}$ is a group represented by the formula (120).

In the compound of the present exemplary embodiment, it is preferable that, when one of $R_1$ to $R_4$ is the group $D_1$, only one of $R_{101}$ to $R_{160}$ in the group $D_1$ is a group represented by the formula (120).

In the compound of the present exemplary embodiment, it is preferable that, when two of $R_1$ to $R_4$ are the group $D_1$, only one of $R_{101}$ to $R_{160}$ in each of the groups $D_1$ is a group represented by the formula (120).

In the compound of the present exemplary embodiment, it is preferable that, when three of $R_1$ to $R_4$ are the group $D_1$, only one of $R_{101}$ to $R_{160}$ in each of the groups $D_1$ is a group represented by the formula (120).

In the compound of the present exemplary embodiment, $Z_2$ in the formula (120) is preferably a substituted or unsubstituted phenyl group, substituted or unsubstituted naphthyl group, substituted or unsubstituted anthryl group, substituted or unsubstituted phenanthryl group, substituted or unsubstituted pyrenyl group, substituted or unsubstituted chrysenyl group, substituted or unsubstituted benzophenanthryl group, substituted or unsubstituted benzochrysenyl group, substituted or unsubstituted benzanthryl group, substituted or unsubstituted triphenylenyl group, substituted or unsubstituted fluorenyl group, substituted or unsubstituted 9,9-dimethylfluorenyl group, substituted or unsubstituted benzofluorenyl group, substituted or unsubstituted dibenzofluorenyl group, substituted or unsubstituted biphenyl group, substituted or unsubstituted terphenyl group, substituted or unsubstituted quarterphenyl group, substituted or unsubstituted fluoranthenyl group, substituted or unsubstituted dibenzofuranyl group, substituted or unsubstituted dibenzothienyl group, substituted or unsubstituted carbazolyl group, substituted or unsubstituted pyridyl group, substituted or unsubstituted pyrimidinyl group, or substituted or unsubstituted triazinyl group.

In the compound of the present exemplary embodiment, it is preferable that $Z_2$ in the formula (120) is a group represented by any one of formulae (Z21) to (Z31) below.

[Formula 25]

(Z-21)

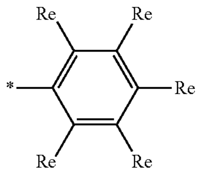

(Z-22)

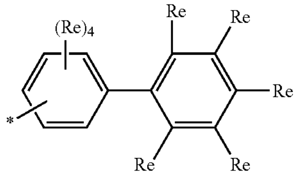

(Z-23)

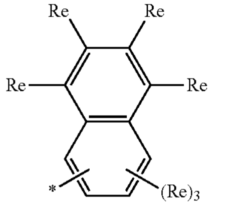

(Z-24)

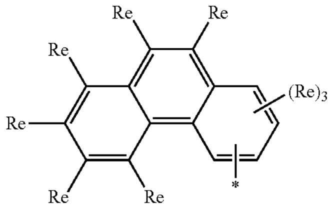

(Z-25)

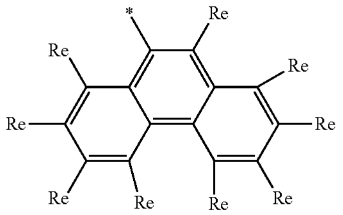

[Formula 26]

(Z-26)

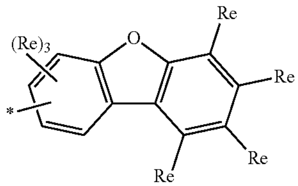

-continued (Z-27)

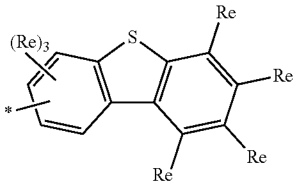

(Z-28)

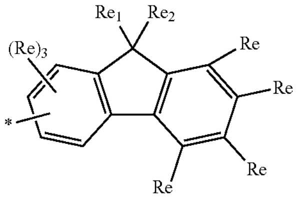

(Z-29)

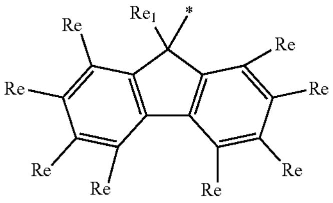

(Z-30)

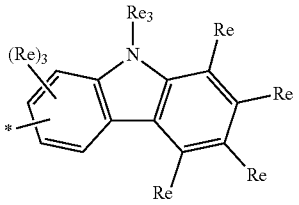

(Z-31)

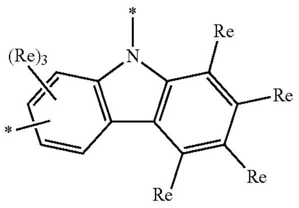

In the formulae (Z-21) to (Z-31):

Re is a hydrogen atom or a substituent, or at least one combination of adjacent ones of Re are bonded to each other to form a ring, and a plurality of Re are mutually the same or different;

$Re_1$ and $Re_2$ are each independently a hydrogen atom or a substituent, or a combination of $Re_1$ and $Re_2$ are mutually bonded to form a ring;

$Re_3$ is a hydrogen atom or a substituent; and

Re, $Re_1$, $Re_2$, and $Re_3$ as substituents represent the same as $R_{20A}$ as a substituent in the formula (120). * each independently represents a bonding position to a carbon atom of the six-membered ring in the formula (120).

In the formulae (Z-21) to (Z-31), Re is preferably a hydrogen atom, a substituted or unsubstituted aryl group having 6 to 30 ring carbon atoms, or a substituted or unsubstituted alkyl group having 1 to 30 carbon atoms, more preferably a hydrogen atom.

In the formulae (Z-28) to (Z-29), it is preferable that $Re_1$ and $Re_2$ are each independently a substituted or unsubstituted aryl group having 6 to 30 ring carbon atoms, a substituted or unsubstituted alkyl group having 1 to 30 carbon atoms, or a combination of $Re_1$ and $Re_2$ are mutually bonded to form a ring.

In the formula (Z-30), $Re_3$ is preferably a substituted or unsubstituted aryl group having 6 to 30 ring carbon atoms, substituted or unsubstituted alkyl group having 1 to 30 carbon atoms, or substituted or unsubstituted heterocyclic group having 5 to 30 ring atoms.

In the compound of the present exemplary embodiment, it is preferable that a group represented by the formula (120) is a group represented by any one of formulae (c1) to (c8) below.

[Formula 27]

(c1)

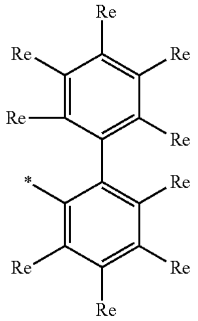

(c2)

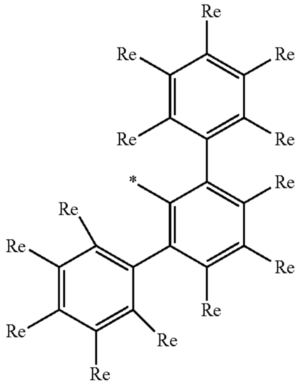

(c3)

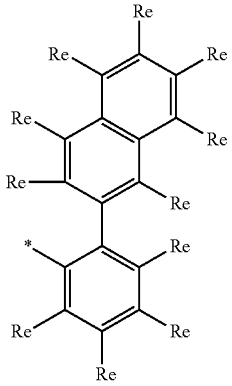

-continued (c4)

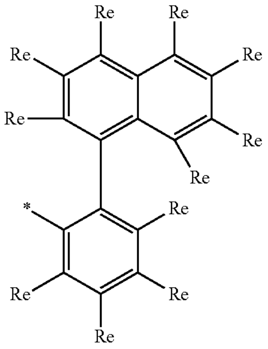

(c5)

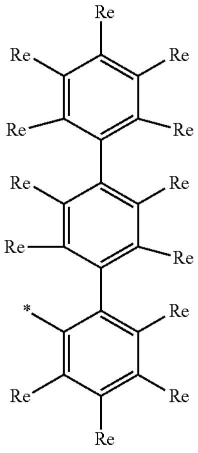

(c6)

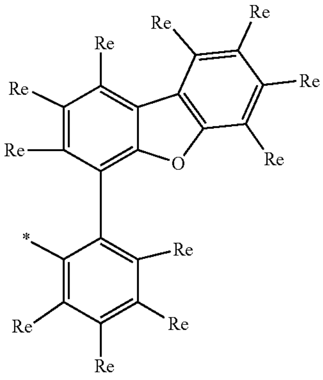

(c7)

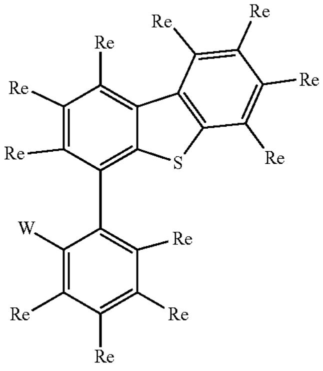

-continued (c8)

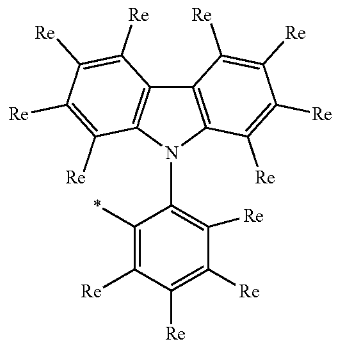

In the formulae (c1) to (c8),

Re is a hydrogen atom or a substituent;

a plurality of Re are mutually the same or different; and

Re as a substituent represents the same as $R_{20A}$ as a substituent in the formula (120).

In the formulae (c1) to (c8), Re is preferably a hydrogen atom, a substituted or unsubstituted aryl group having 6 to 30 ring carbon atoms, or a substituted or unsubstituted alkyl group having 1 to 30 carbon atoms, more preferably a hydrogen atom.

In the compound according to the present exemplary embodiment, $X_1$ to $X_6$ in the group $D_1$ are each preferably an oxygen atom.

In the compound according to the present exemplary embodiment, $X_1$ to $X_6$ in the group $D_1$ are each preferably a sulfur atom.

The compound of the present exemplary embodiment is preferably a compound represented by the formula (11).

The compound of the present exemplary embodiment is preferably a compound represented by the formula (12).

The compound of the present exemplary embodiment is preferably a compound represented by the formula (13).

In the compound of the present exemplary embodiment, $R_{101}$ to $R_{160}$, $R_{161}$ to $R_{168}$, $R_{171}$ to $R_{200}$, $R_{10A}$, and $R_{20A}$ are each independently preferably a hydrogen atom, halogen atom, cyano group, unsubstituted aryl group having 6 to 30 ring carbon atoms, unsubstituted heterocyclic group having 5 to 30 ring atoms, unsubstituted alkyl group having 1 to 30 carbon atoms, unsubstituted alkyl halide group having 1 to 30, unsubstituted alkenyl group having 2 to 30 carbon atoms, unsubstituted alkynyl group having 2 to 30 carbon atoms, unsubstituted alkylsilyl group having 3 to 30 carbon atoms, unsubstituted arylsilyl group having 6 to 60 ring carbon atoms, unsubstituted arylphosphoryl group having 6 to 60 ring carbon atoms, hydroxy group, unsubstituted alkoxy group having 1 to 30 carbon atoms, unsubstituted aryloxy group having 6 to 30 ring carbon atoms, group represented by —N(Rz)$_2$, thiol group, unsubstituted alkylthio group having 1 to 30 carbon atoms, unsubstituted aralkyl group having 7 to 30 ring carbon atoms, substituted germanium group, substituted phosphine oxide group, nitro group, substituted boryl group, or unsubstituted arylthio group having 6 to 30 ring carbon atoms.

In the compound of the present exemplary embodiment, Rz in —N(Rz)$_2$ is preferably an unsubstituted aryl group having 6 to 30 ring carbon atoms, an unsubstituted heterocyclic group having 5 to 30 ring atoms, or an unsubstituted alkyl group having 1 to 30 carbon atoms.

In the compound of the present exemplary embodiment, it is preferable that $R_{101}$ to $R_{160}$, $R_{161}$ to $R_{168}$, $R_{171}$ to $R_{200}$, $R_{10A}$, and $R_{20A}$ are each independently a hydrogen atom, a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 30 carbon atoms, a substituted or unsubstituted alkylsilyl group having 3 to 6 carbon atoms, a substituted or unsubstituted alkoxy group having 1 to 6 carbon atoms, a substituted or unsubstituted aryloxy group having 6 to 14 ring carbon atoms, a group represented by —N(Rz)$_2$, a substituted or unsubstituted alkylthio group having 1 to 6 carbon atoms, or a substituted or unsubstituted arylthio group having 6 to 14 ring carbon atoms.

In the compound of the present exemplary embodiment, it is preferable that $R_{101}$ to $R_{160}$, $R_{161}$ to $R_{168}$, $R_{171}$ to $R_{200}$, $R_{10A}$, and $R_{20A}$ are each independently a hydrogen atom, a halogen atom, an unsubstituted aryl group having 6 to 14 ring carbon atoms, an unsubstituted heterocyclic group having 5 to 14 ring atoms, an unsubstituted alkyl group having 1 to 6 carbon atoms, an unsubstituted alkyl halide group having 1 to 30 carbon atoms, an unsubstituted alkylsilyl group having 3 to 6 carbon atoms, an unsubstituted alkoxy group having 1 to 6 carbon atoms, an unsubstituted aryloxy group having 6 to 14 ring carbon atoms, an unsubstituted alkylamino group having 2 to 12 carbon atoms, an unsubstituted alkylthio group having 1 to 6 carbon atoms, or an unsubstituted arylthio group having 6 to 14 ring carbon atoms.

In the compound of the present exemplary embodiment, $R_{101}$ to $R_{160}$, $R_{161}$ to $R_{168}$, $R_{171}$ to $R_{200}$, $R_{10A}$, and $R_{20A}$ are preferably each independently a hydrogen atom, an unsubstituted aryl group having 6 to 14 ring carbon atoms, an unsubstituted heterocyclic group having 5 to 14 ring atoms, or an unsubstituted alkyl group having 1 to 6 carbon atoms.

In the compound of the present exemplary embodiment, it is preferable that $R_{10A}$ and $R_{20A}$ are each a hydrogen atom, the ring (B) is an unsubstituted aromatic hydrocarbon ring having 6 to 30 ring carbon atoms or an unsubstituted heterocyclic ring having 5 to 30 ring atoms, and $Z_2$ is an unsubstituted aryl group having 6 to 30 ring carbon atoms or an unsubstituted heterocyclic group having 5 to 30 ring atoms.

In the compound of the present exemplary embodiment, it is also preferable that one or more hydrogen atoms in a molecule are each a deuterium atom.

In the compound according to the present exemplary embodiment, it is also preferable that one or more $R_{101}$ to $R_{160}$ in the group $D_1$ are each a hydrogen atom and all of the hydrogen atom(s) are deuterium atoms.

In the compound according to the present exemplary embodiment, it is also preferable that one or more $R_{101}$ to $R_{160}$ in the group $D_1$ are each a hydrogen atom and all of the hydrogen atom(s) are protium atoms.

In the compound of the present exemplary embodiment, it is also preferable that $R_{101}$ to $R_{160}$ in the group $D_1$ except for a group represented by the formula (110) and a group represented by the formula (120) are hydrogen atoms and the hydrogen atoms are deuterium atoms.

In the compound of the present exemplary embodiment, it is preferable that, when at least one of $R_{101}$ to $R_{160}$ in the group $D_1$ are each a substituent (including a group represented by the formula (110) and a group represented by the formula (120)) and the substituent has at least one hydrogen atom, all of the hydrogen atom(s) are protium atoms, at least one of the hydrogen atom(s) is a deuterium atom, or all of the hydrogen atom(s) are deuterium atoms.

In the compound according to the present exemplary embodiment, it is also preferable that one or more of $R_{161}$ to $R_{168}$ and $R_{171}$ to $R_{200}$ in the group $D_2$ is a hydrogen atom and all of the hydrogen atom(s) are deuterium atoms.

In the compound according to the present exemplary embodiment, it is also preferable that one or more $R_{161}$ to $R_{168}$ and $R_{171}$ to $R_{200}$ in the group $D_2$ is a hydrogen atom and all of the hydrogen atom(s) are protium atoms.

In the compound according to the present exemplary embodiment, it is also preferable that $R_{161}$ to $R_{168}$ and $R_{171}$ to $R_{200}$ in the group $D_2$ are hydrogen atoms and the hydrogen atoms are deuterium atoms.

In the compound of the present exemplary embodiment, it is preferable that, when at least one of $R_{161}$ to $R_{168}$ and $R_{171}$ to $R_{200}$ in the group $D_2$ is a substituent and the substituent has one or more hydrogen atoms, all of the hydrogen atom(s) are protium atoms, at least one of the hydrogen atom(s) is a deuterium atom, or all of the hydrogen atom(s) are deuterium atoms.

In the compound of the present exemplary embodiment, it is preferable that $R_{101}$ to $R_{160}$ except for a group represented by the formula (110) and a group represented by the formula (120) are each a hydrogen atom and $R_{161}$ to $R_{168}$ and $R_{171}$ to $R_{200}$ are each a hydrogen atom.

In the compound of the present exemplary embodiment, it is preferable that $R_{101}$ to $R_{160}$ except for a group represented by the formula (110) and a group represented by the formula (120) are hydrogen atom(s), the hydrogen atom(s) are each a deuterium atom, $R_{161}$ to $R_{168}$ and $R_{171}$ to $R_{200}$ are hydrogen atoms, and the hydrogen atoms are deuterium atoms.

In the compound of the present exemplary embodiment (the compound represented by one of the formulae (11) to (13)), a substituent for "substituted or unsubstituted" is each independently preferably a halogen atom, a cyano group, an unsubstituted aryl group having 6 to 30 ring carbon atoms, an unsubstituted heterocyclic group having 5 to 30 ring atoms, an unsubstituted alkyl group having 1 to 30 carbon atoms, an unsubstituted alkyl halide group having 1 to 30 carbon atoms, an unsubstituted alkenyl group having 2 to 30 carbon atoms, an unsubstituted alkynyl group having 2 to 30 carbon atoms, an unsubstituted alkylsilyl group having 3 to 30 carbon atoms, an unsubstituted arylsilyl group having 6 to 60 ring carbon atoms, an unsubstituted arylphosphoryl group having 6 to 60 ring carbon atoms, a hydroxy group, an unsubstituted alkoxy group having 1 to 30 carbon atoms, an unsubstituted aryloxy group having 6 to 30 ring carbon atoms, a group represented by —$N(Rz)_2$, a thiol group, an unsubstituted alkylthio group having 1 to 30 carbon atoms, an unsubstituted aralkyl group having 7 to 30 ring carbon atoms, a substituted germanium group, a substituted phosphine oxide group, a nitro group, a substituted boryl group, or an unsubstituted arylthio group having 6 to 30 ring carbon atoms;

Rz is an unsubstituted aryl group having 6 to 30 ring carbon atoms, an unsubstituted heterocyclic group having 5 to 30 ring atoms, or an unsubstituted alkyl group having 1 to 30 carbon atoms.

Two Rz in the —$N(Rz)_2$ are the same or different.

Manufacturing Method of Compound According to the Present Exemplary Embodiment The compound of the present exemplary embodiment can be manufactured by, for instance, a method described in later-described Examples. The compound of the present exemplary embodiment can be manufactured by reactions described in later-described Examples and using known alternative reactions or raw materials suitable for the desired substances.

Specific Examples of Compound of the Present Exemplary Embodiment

Examples of the compound of the present exemplary embodiment include the following compounds. It should however be noted that the invention is not limited to these specific examples of the compound.

[Formula 28]

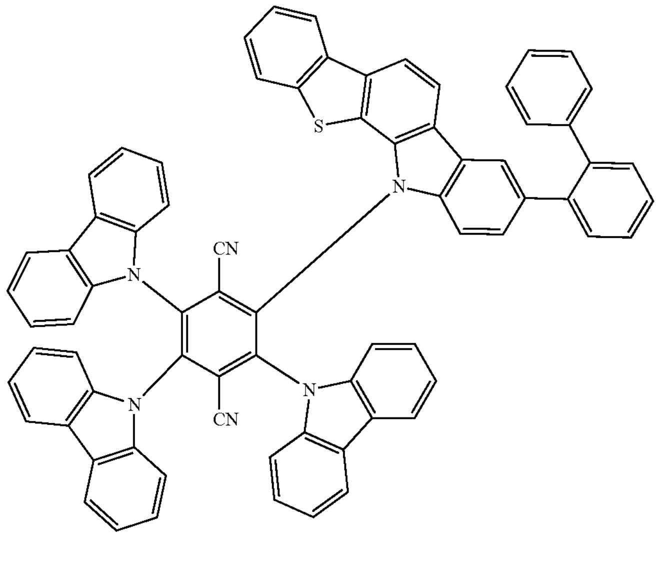

-continued
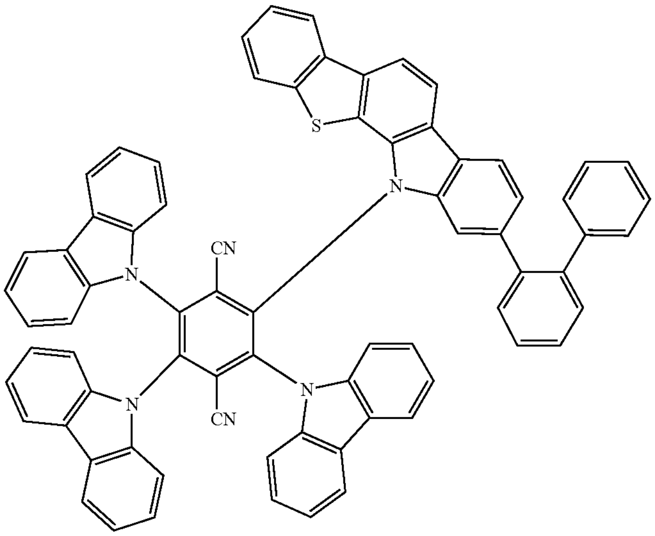
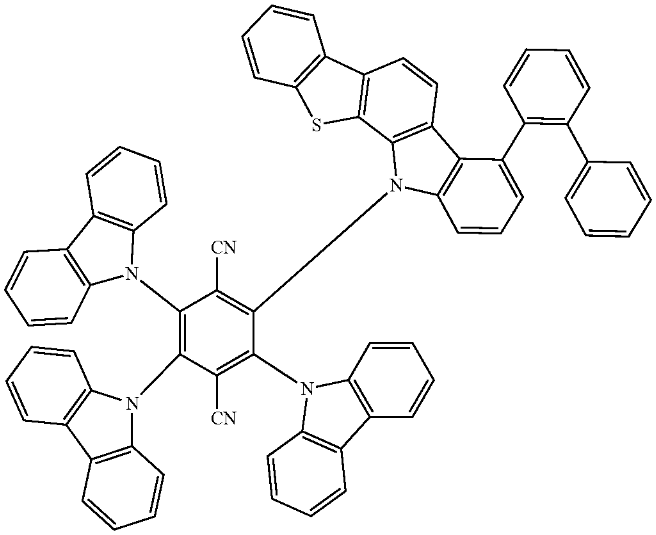
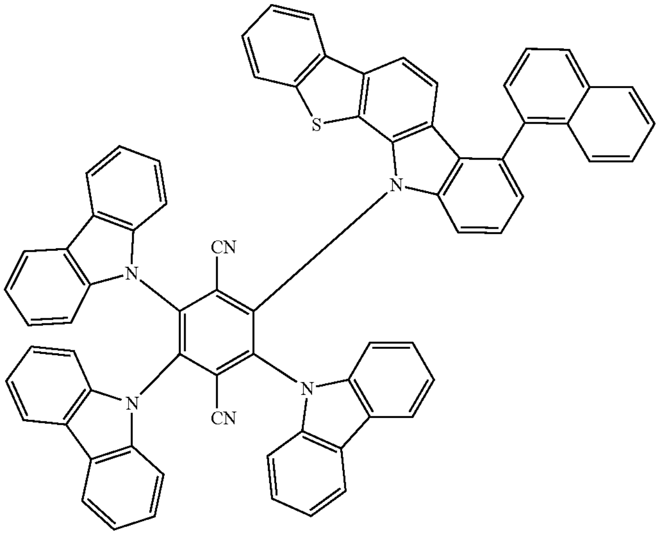

-continued
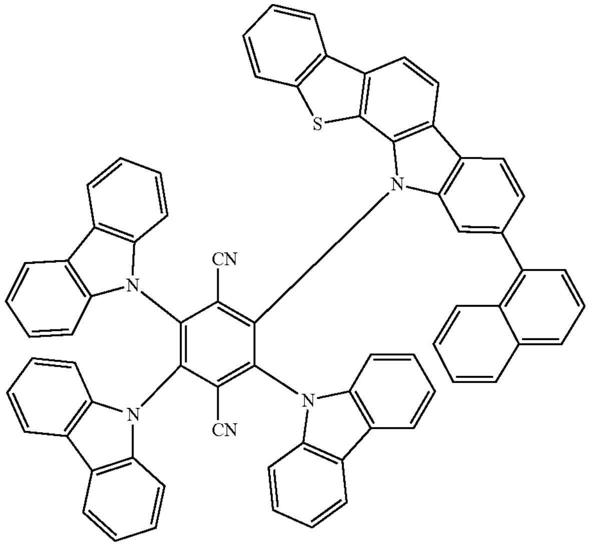
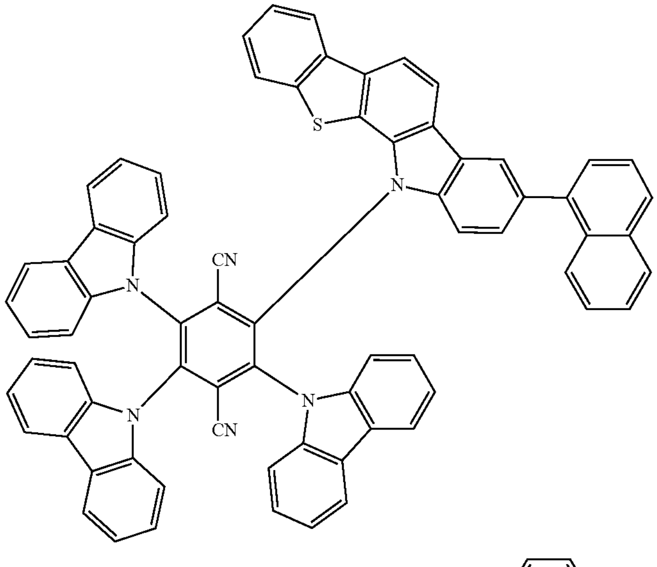
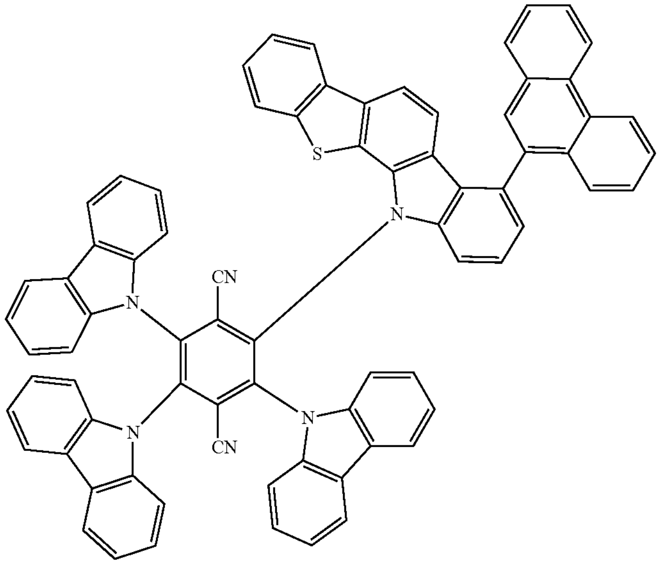

-continued
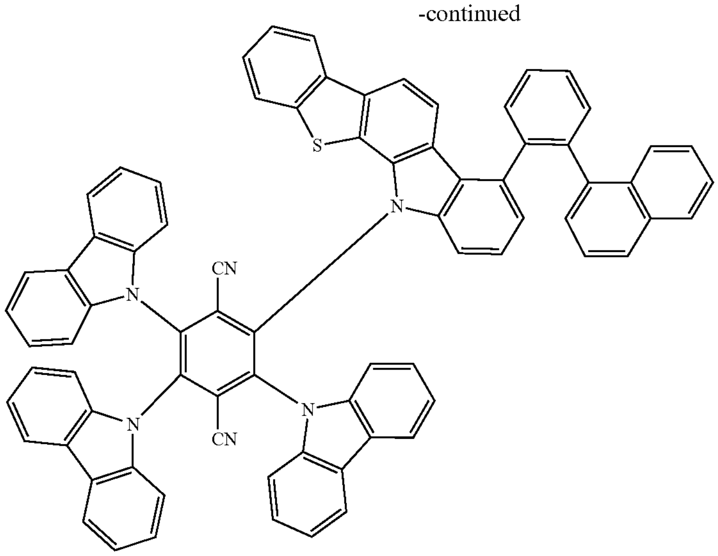
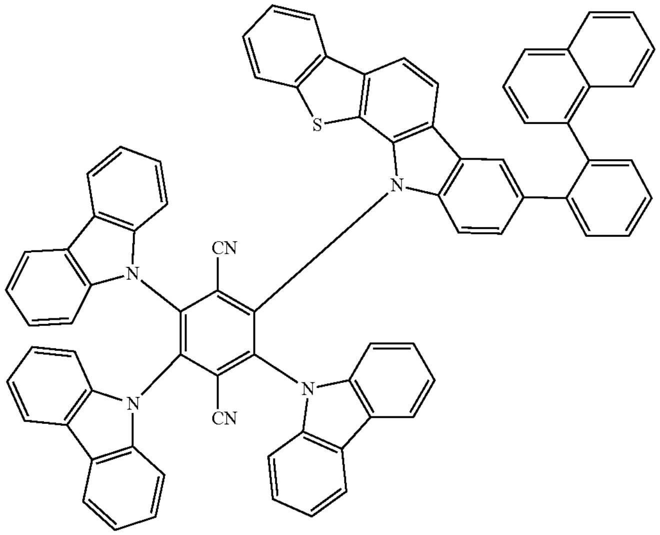
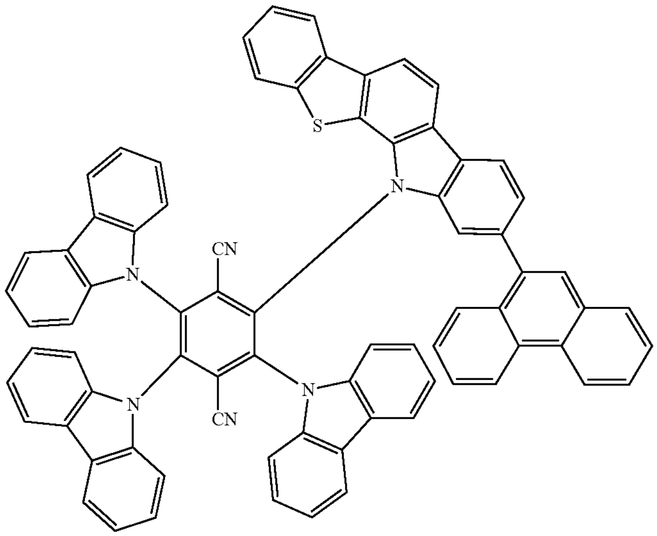

-continued
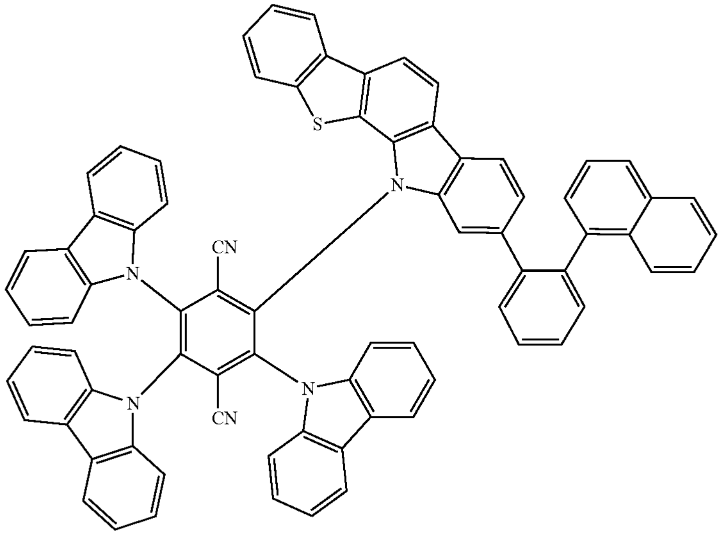
[Formula 29]
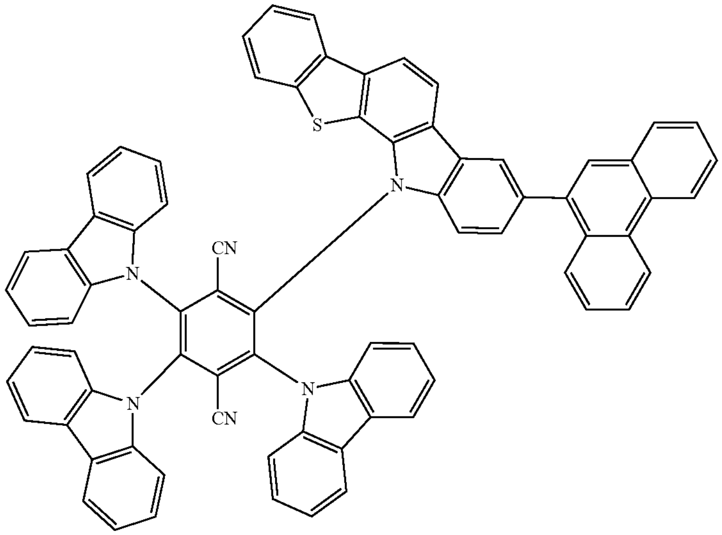
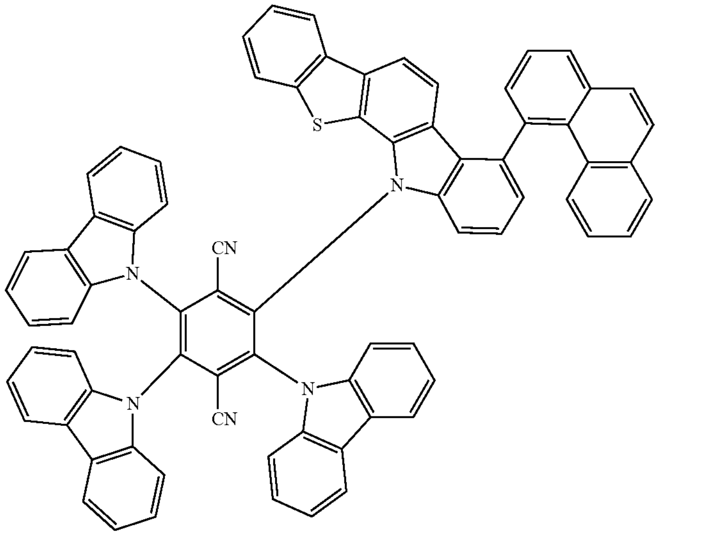

-continued
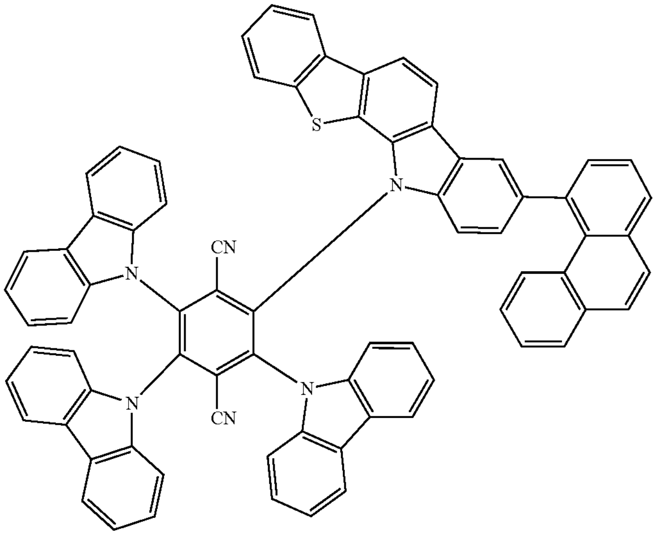
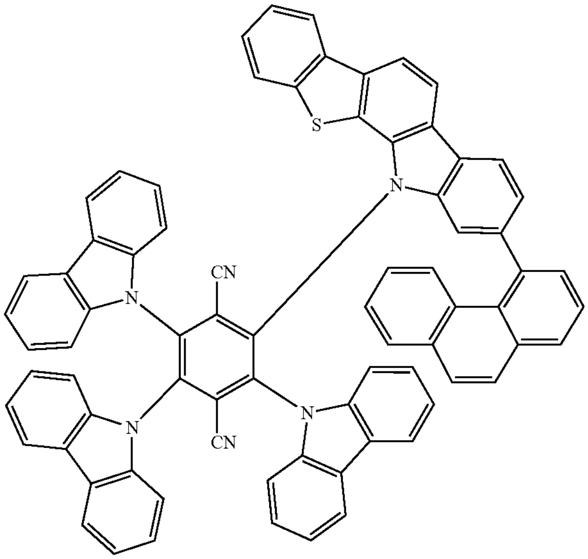
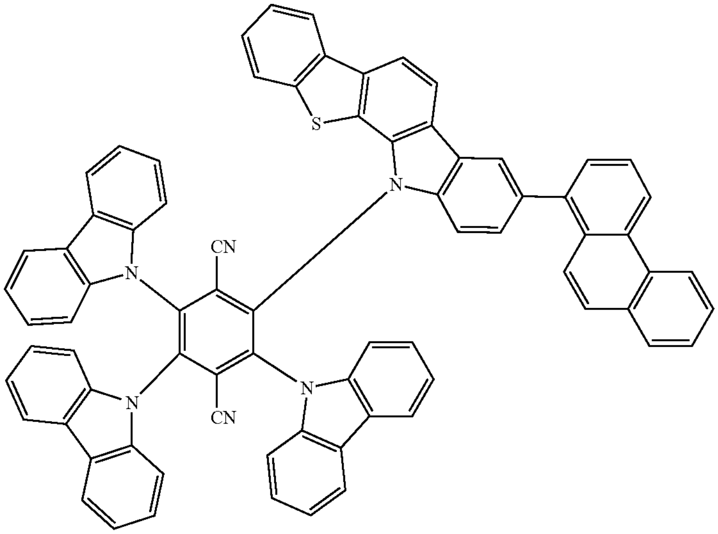

-continued
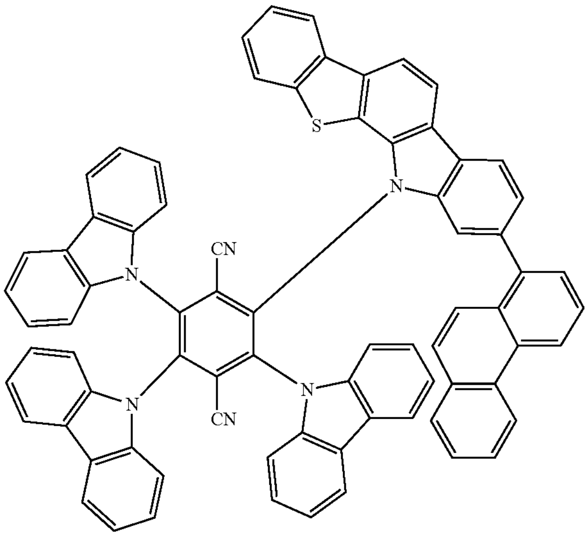
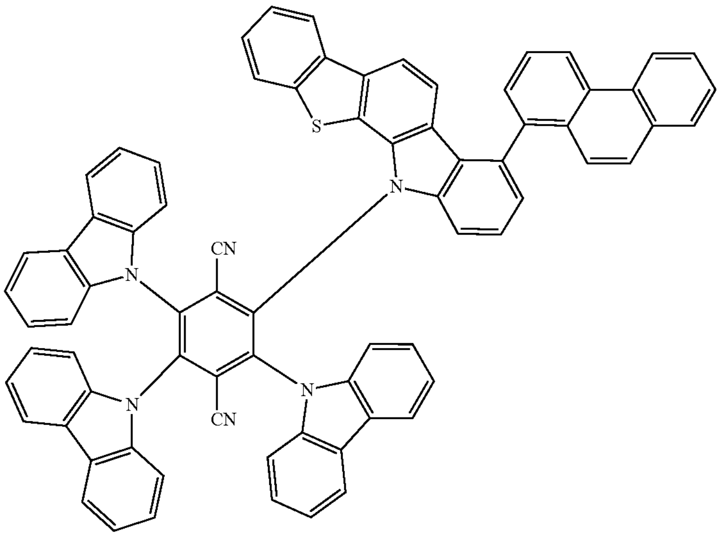
[Formula 30]
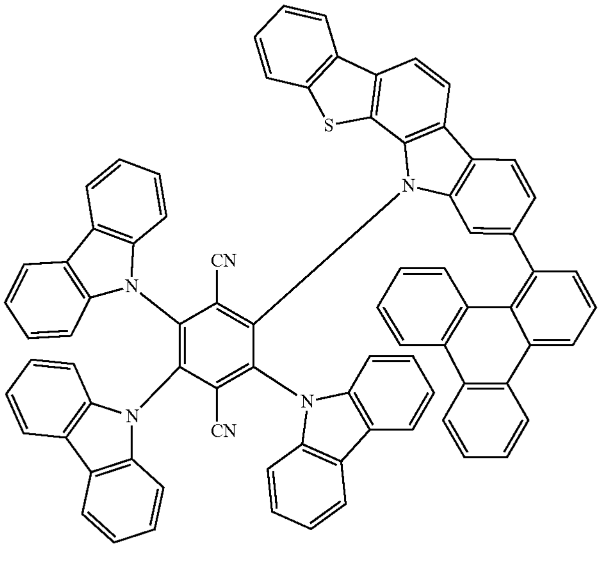

-continued
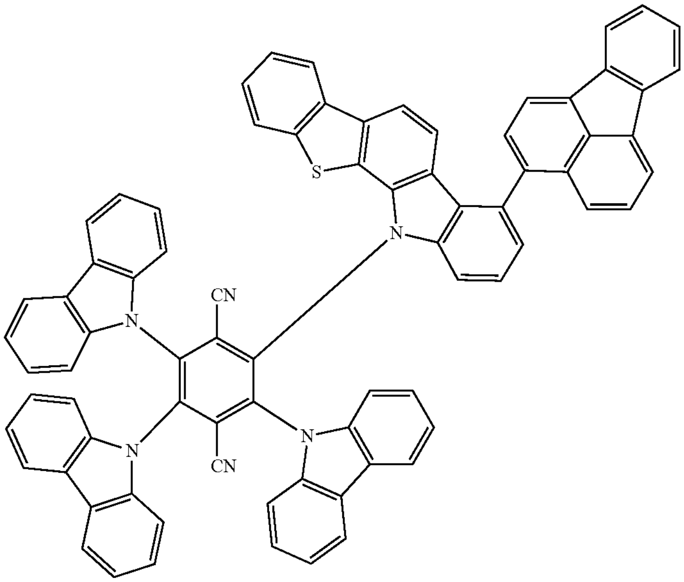
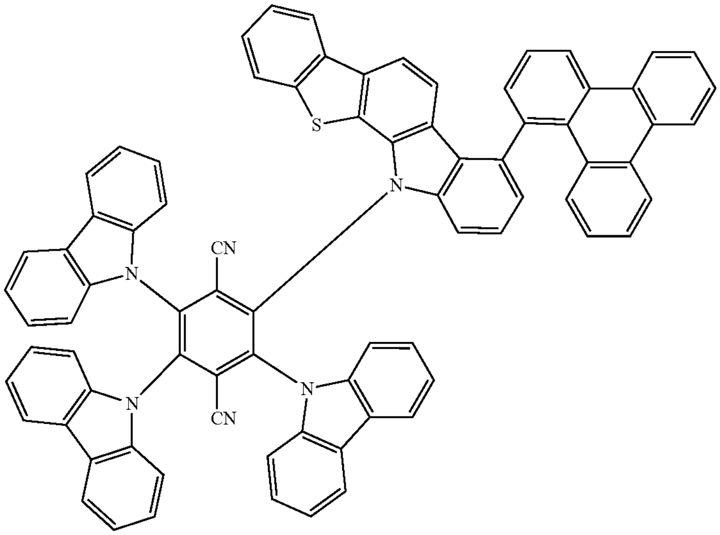
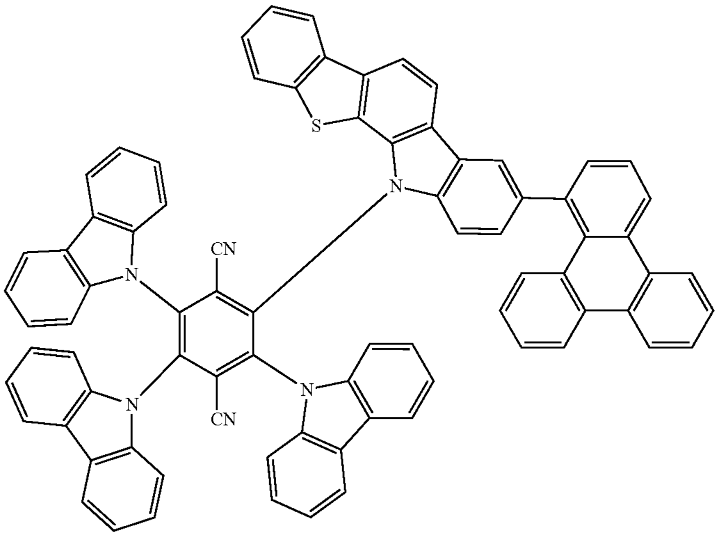

-continued
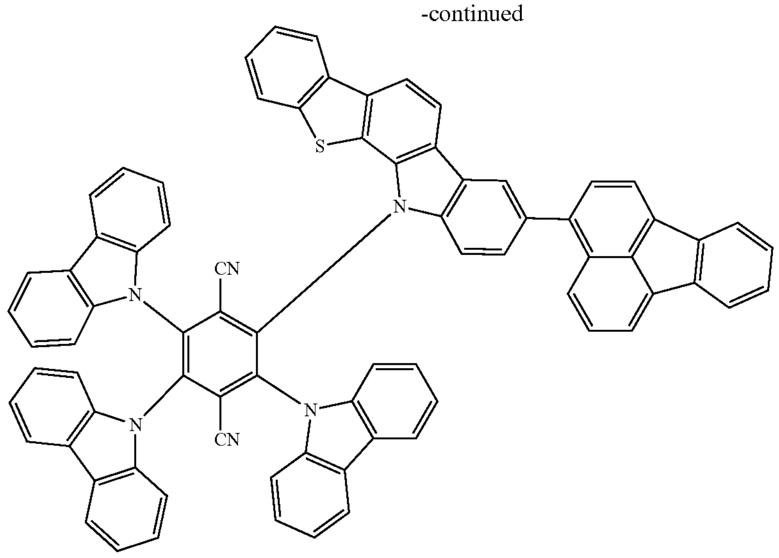
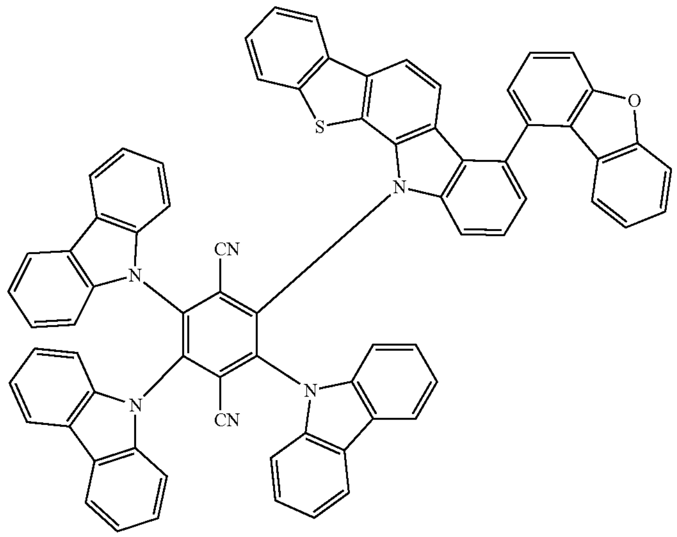
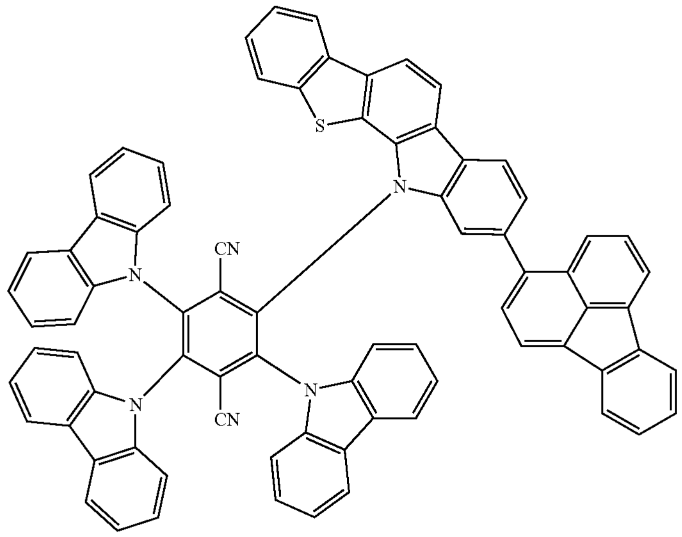

-continued
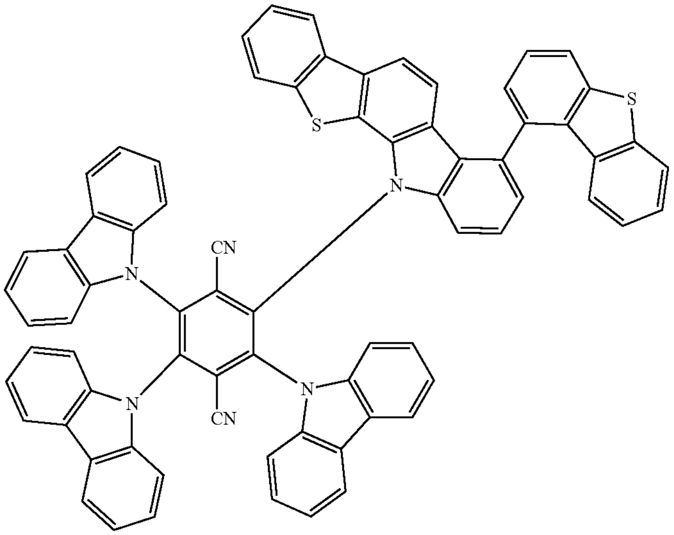
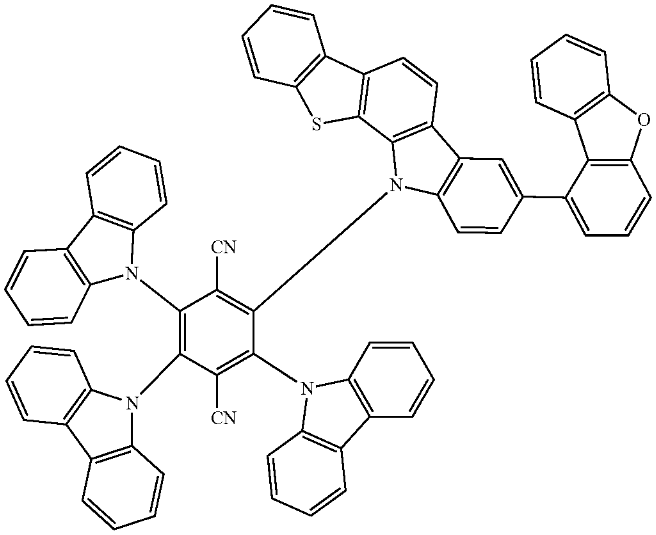
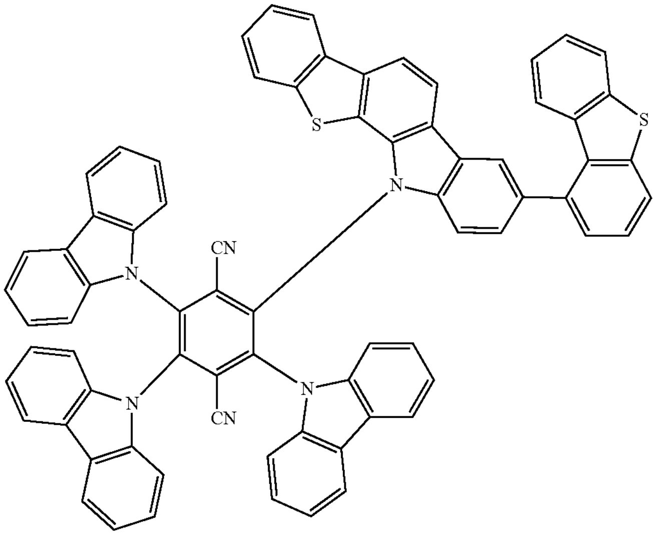

-continued
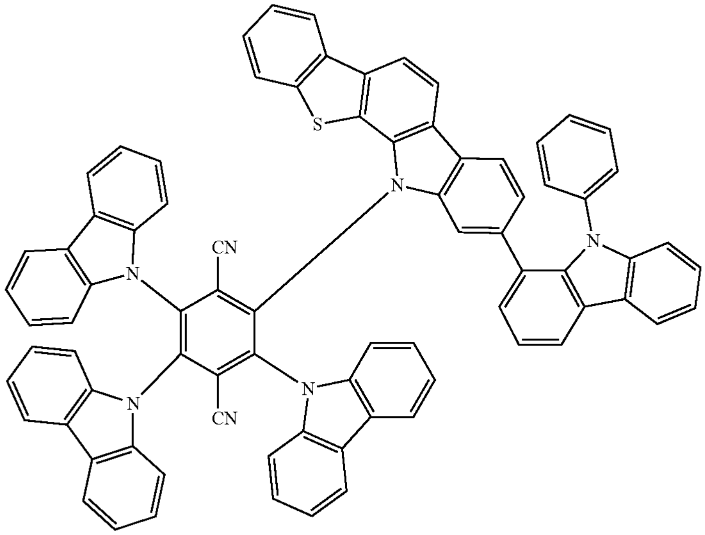
[Formula 31]
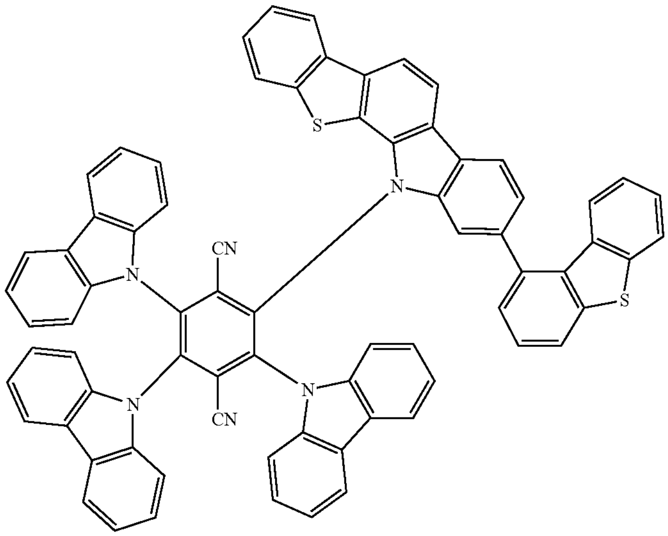
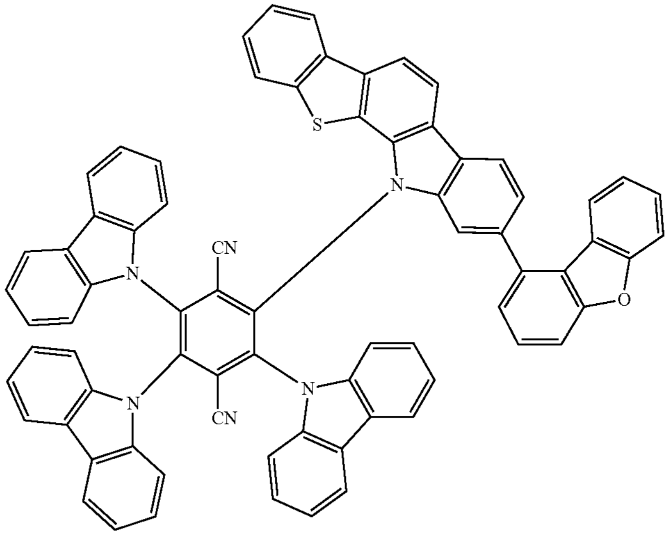

-continued
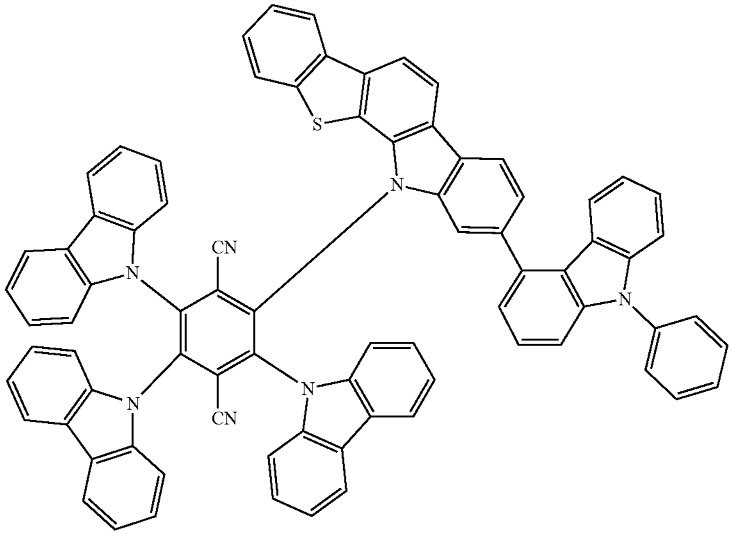
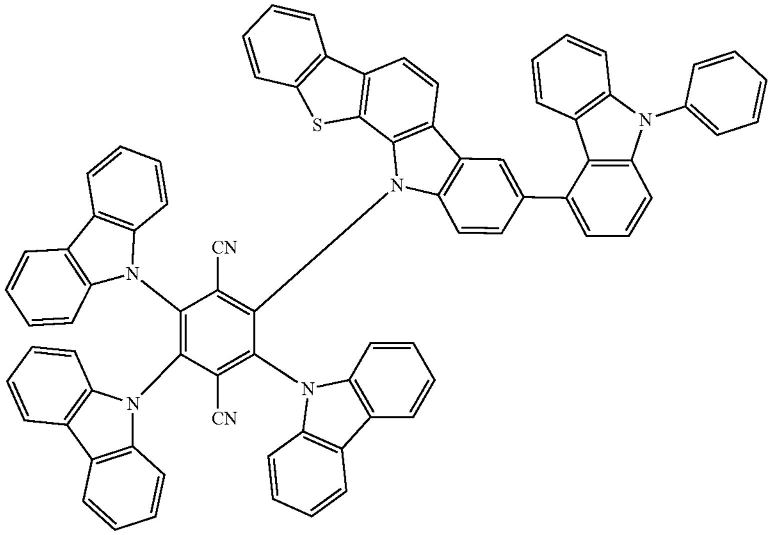
[Formula 32]
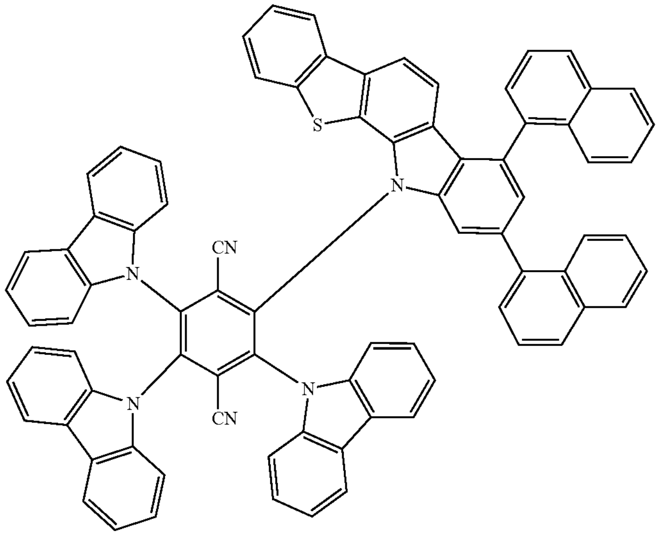

-continued
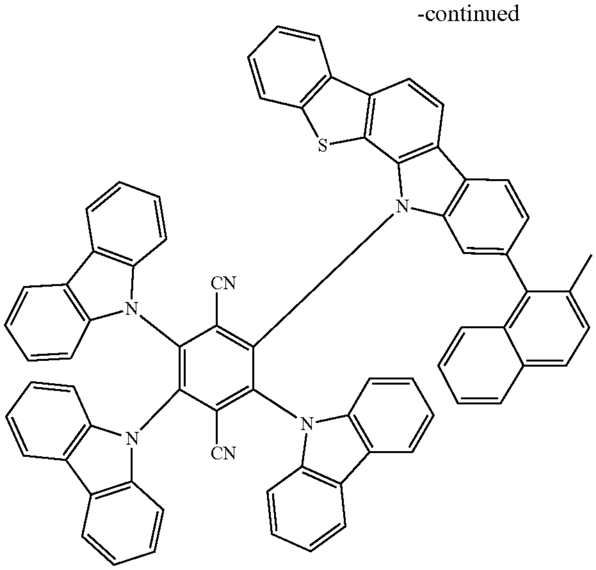
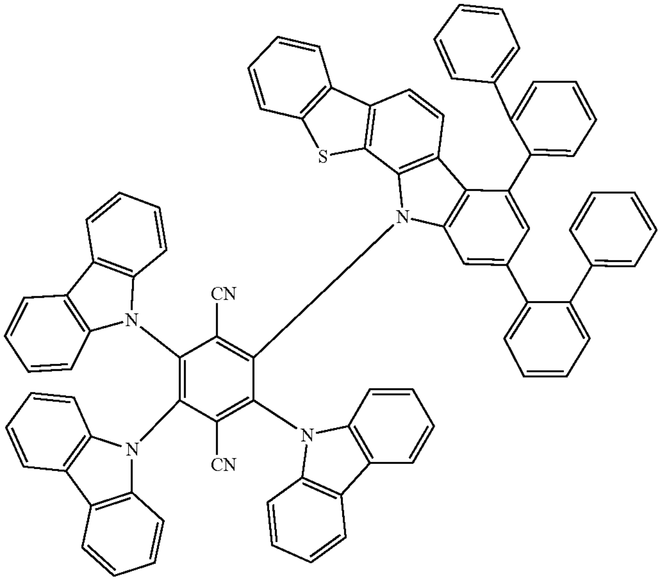
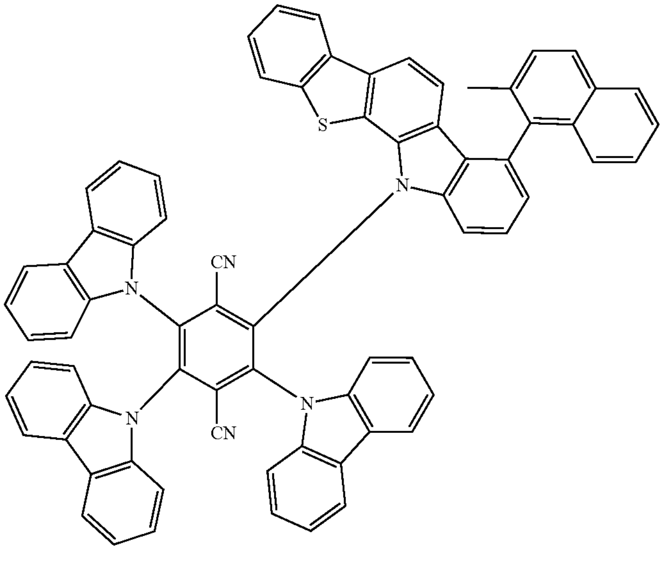

-continued
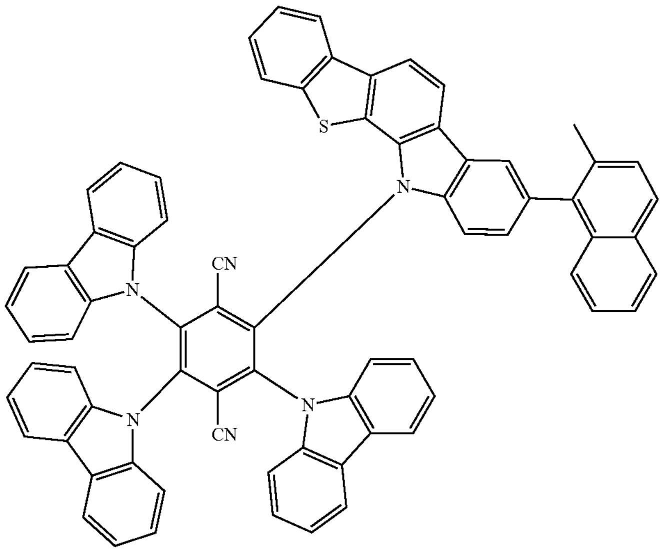
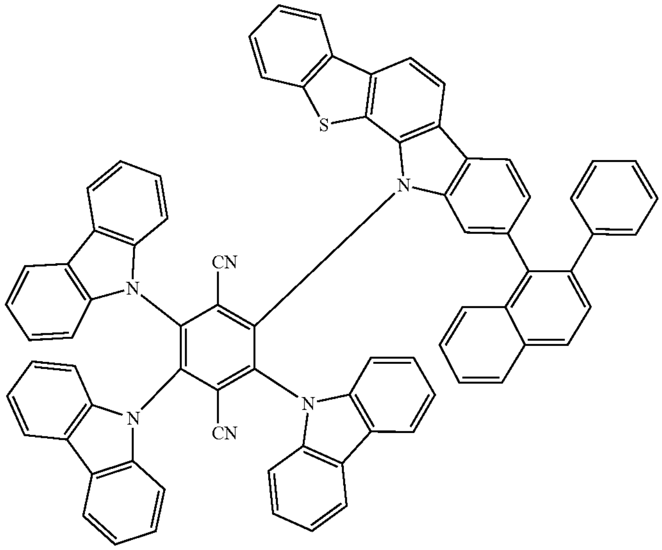
[Formula 33]
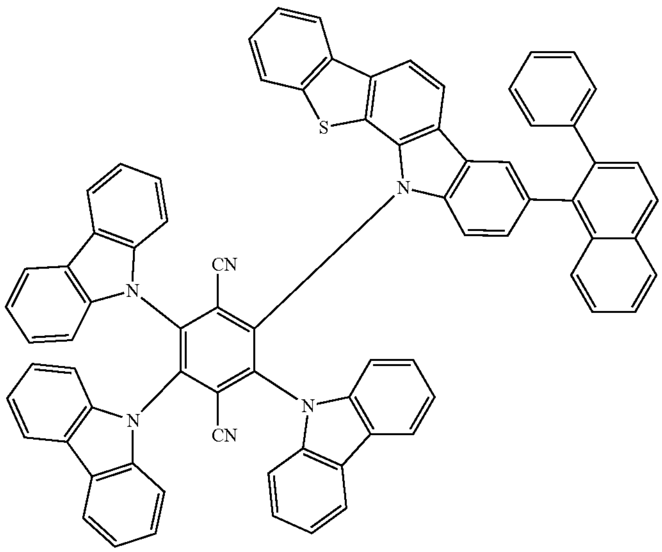

-continued
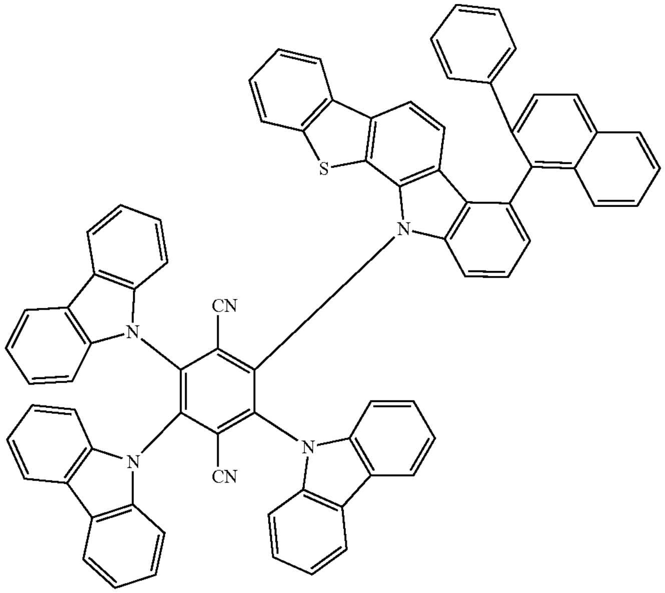
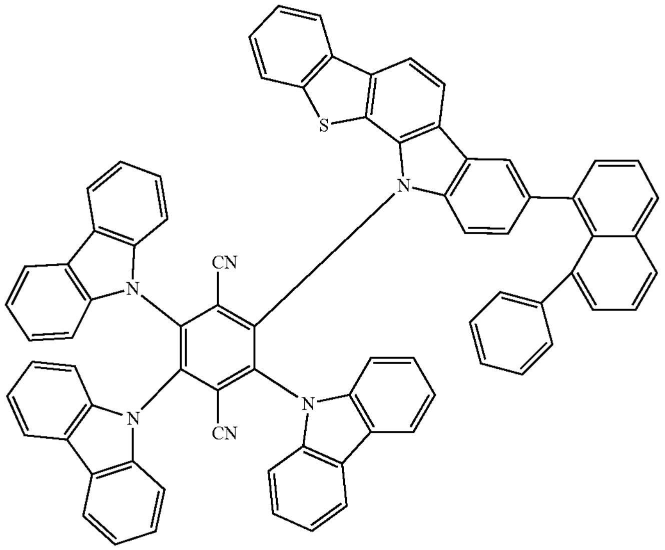
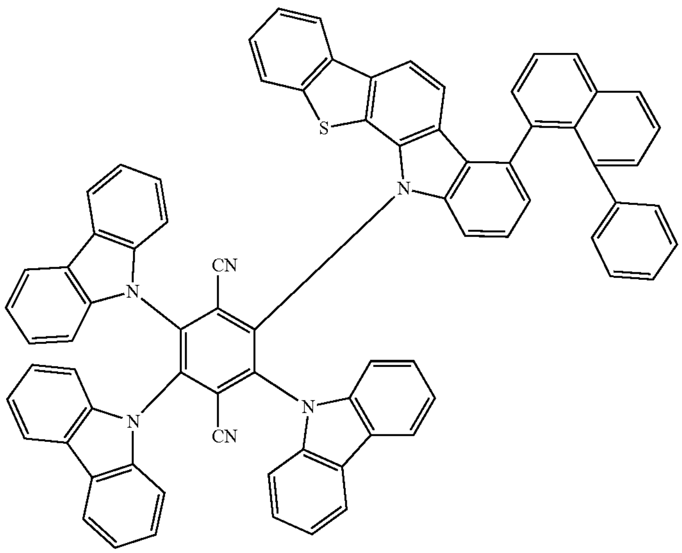

-continued
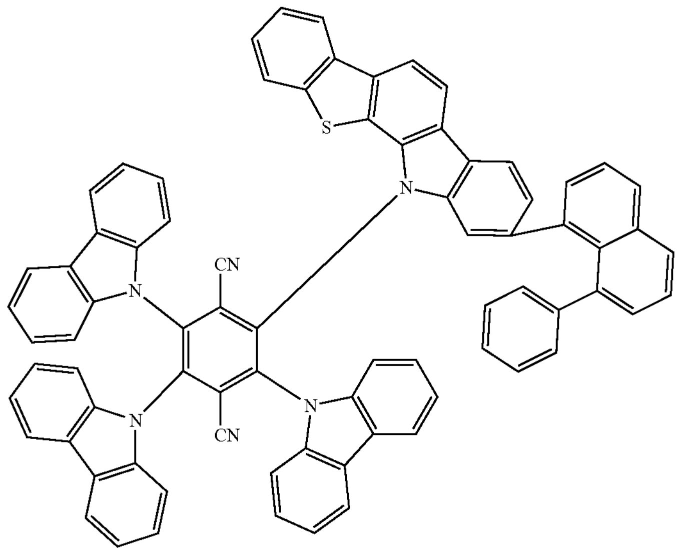
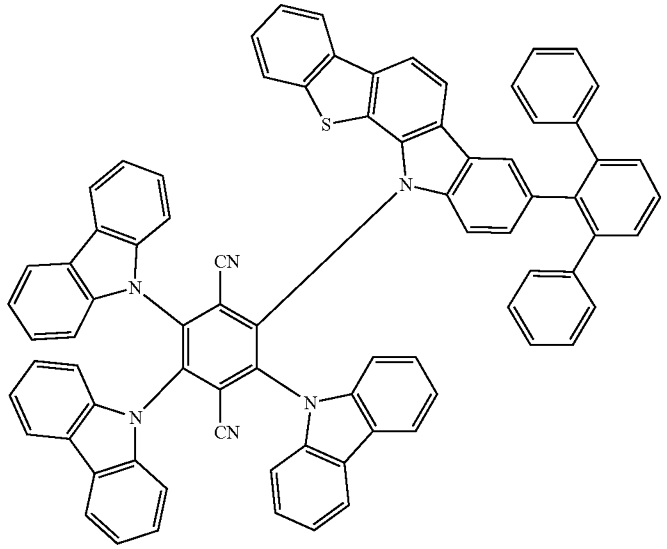
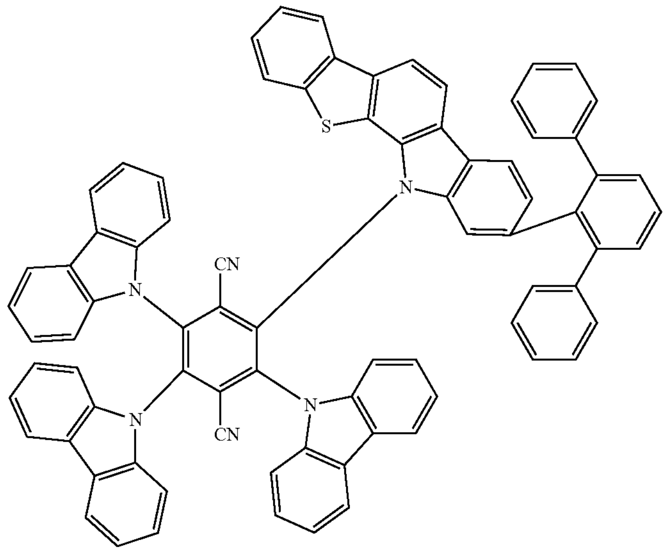

-continued
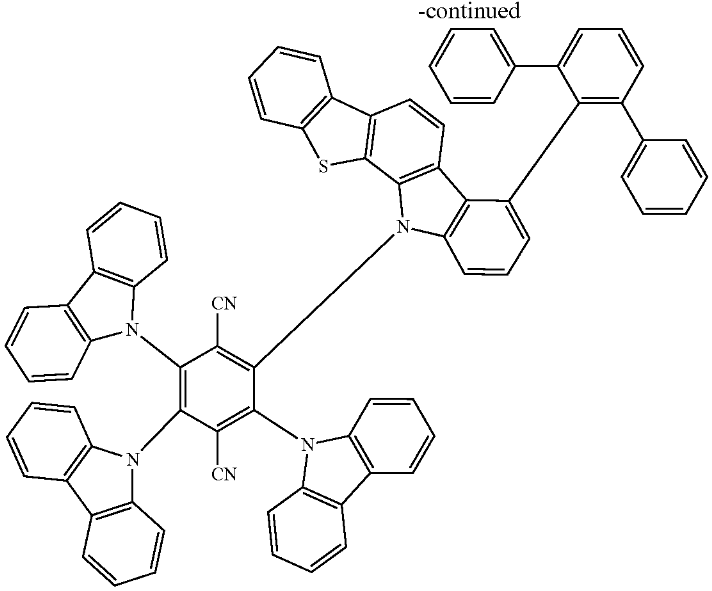
[Formula 34]
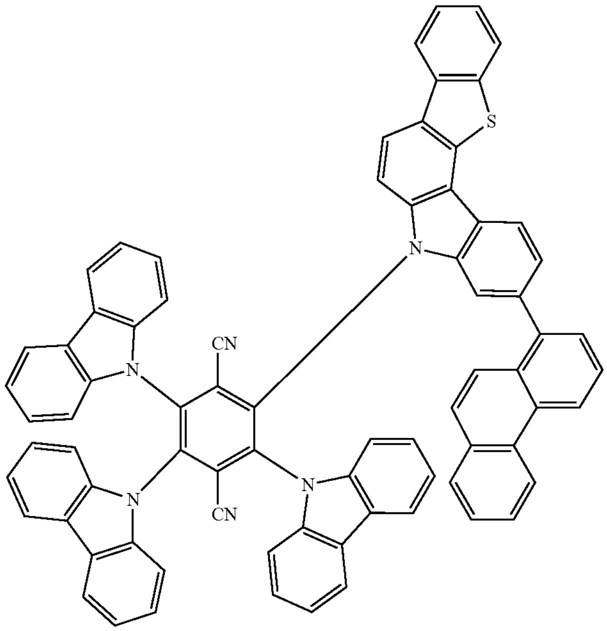

-continued
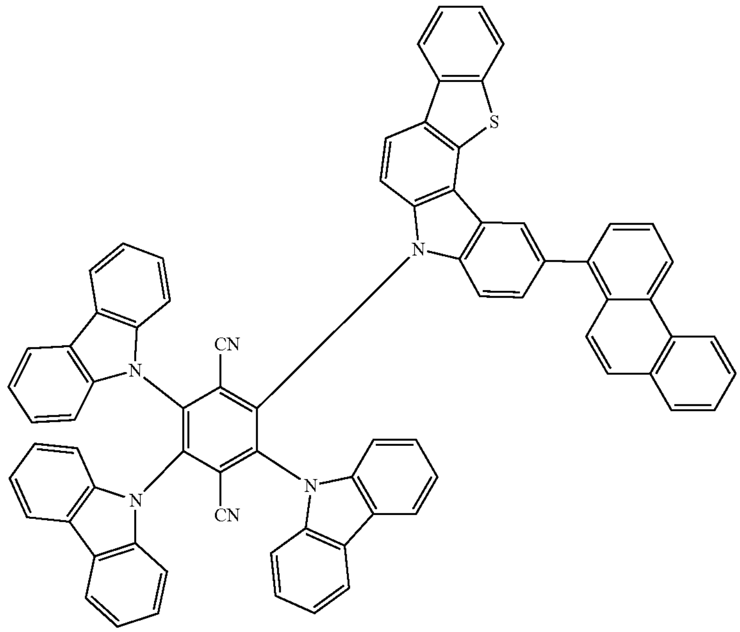
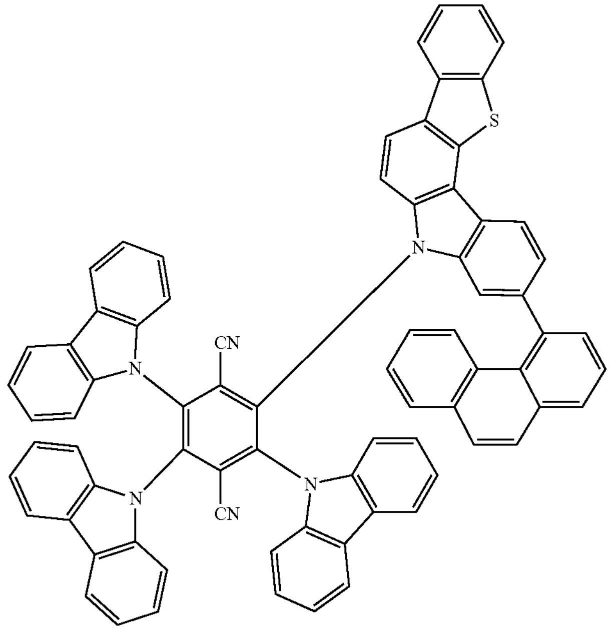

-continued
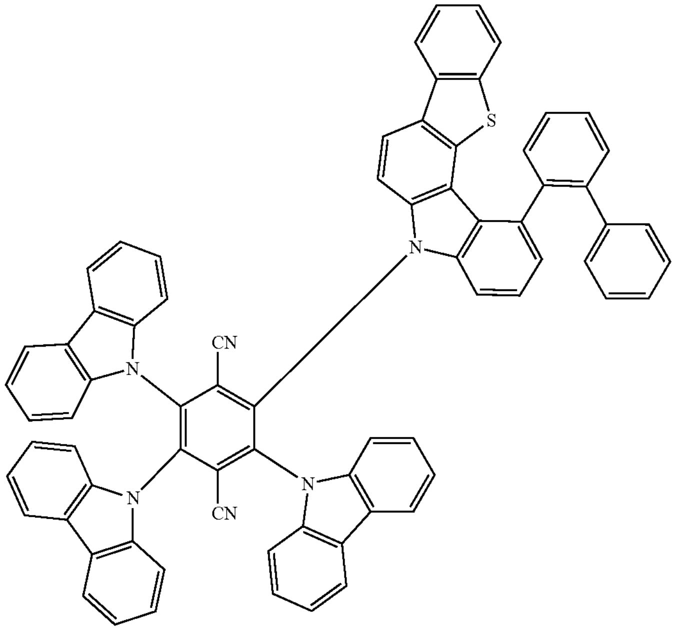
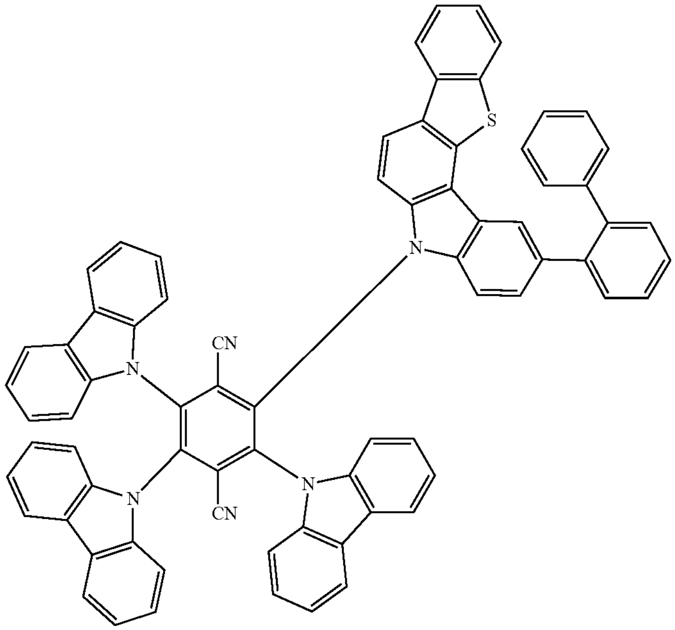

-continued
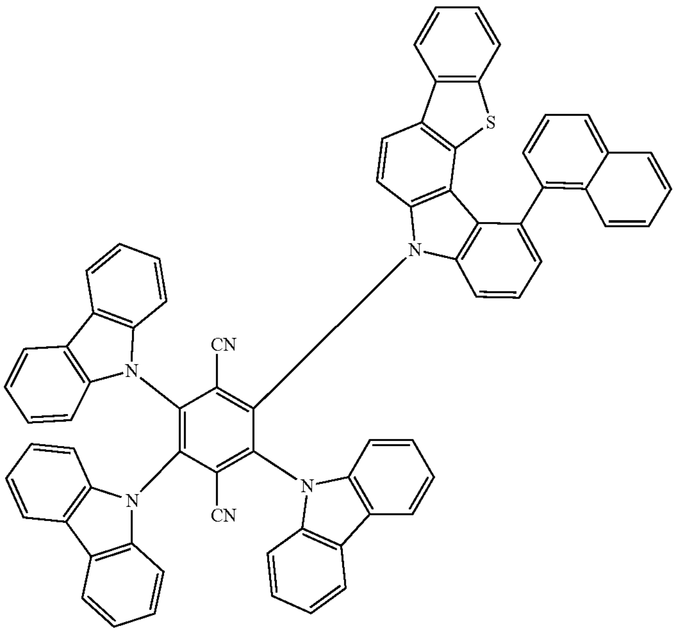
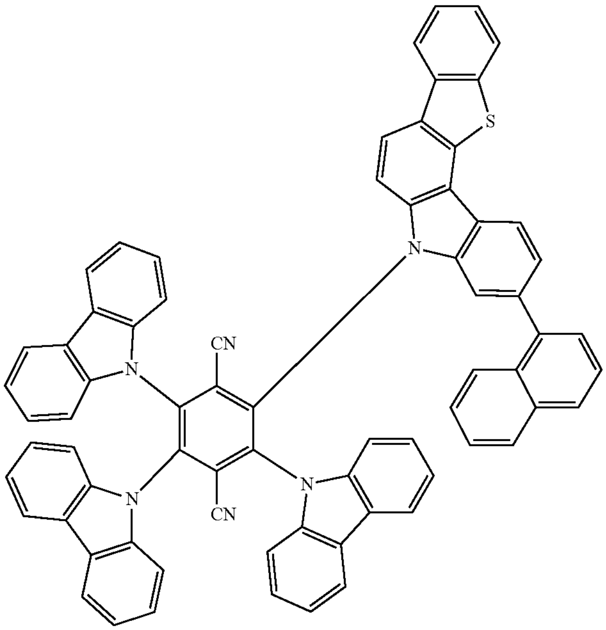

-continued
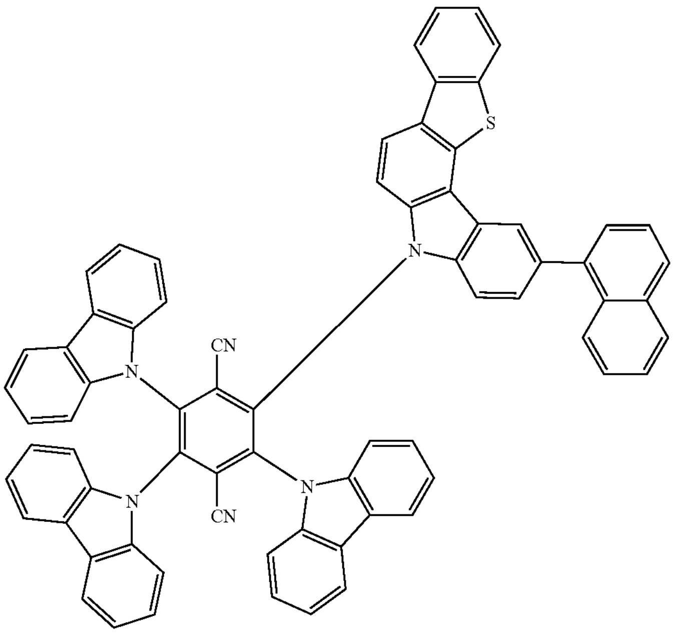
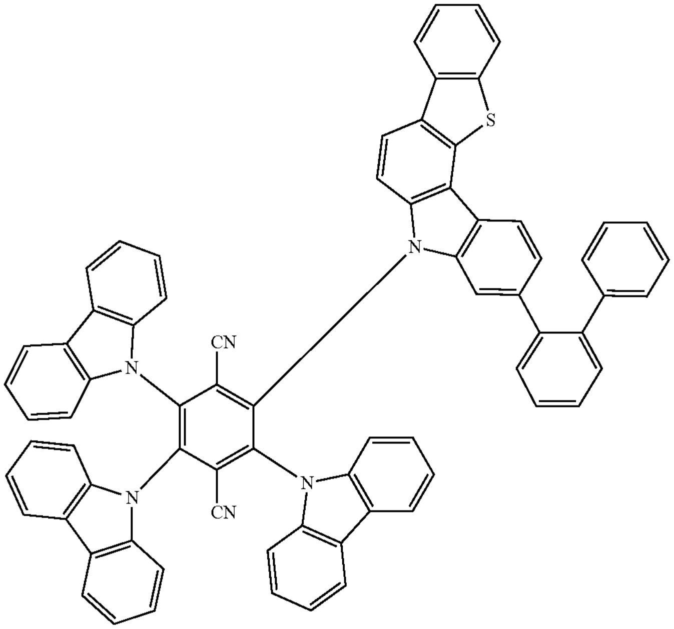

-continued
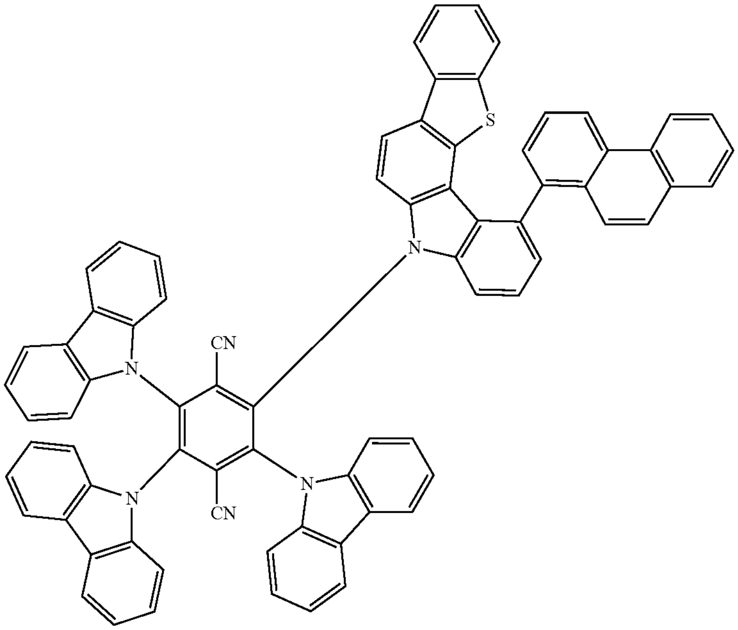
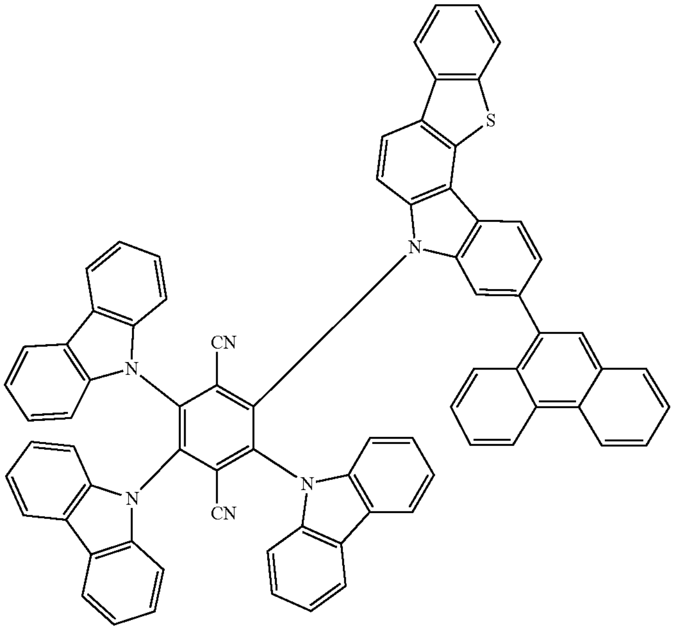

-continued
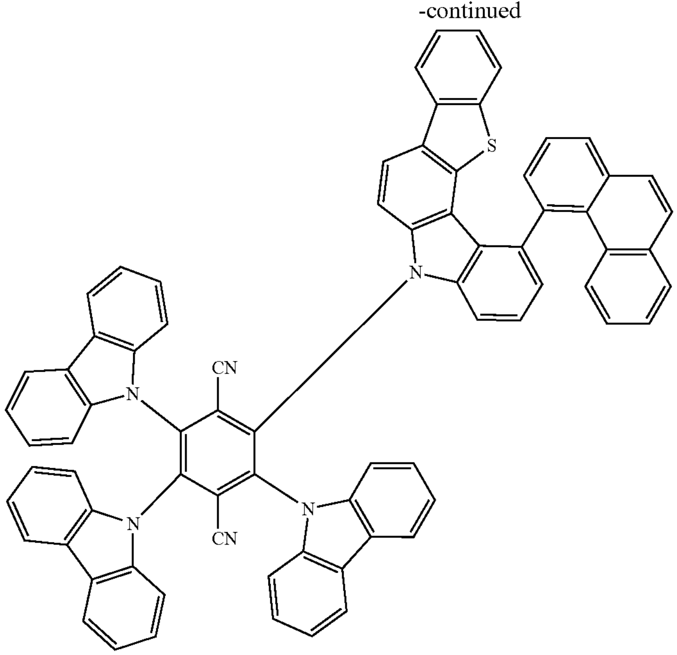
[Formula 35]
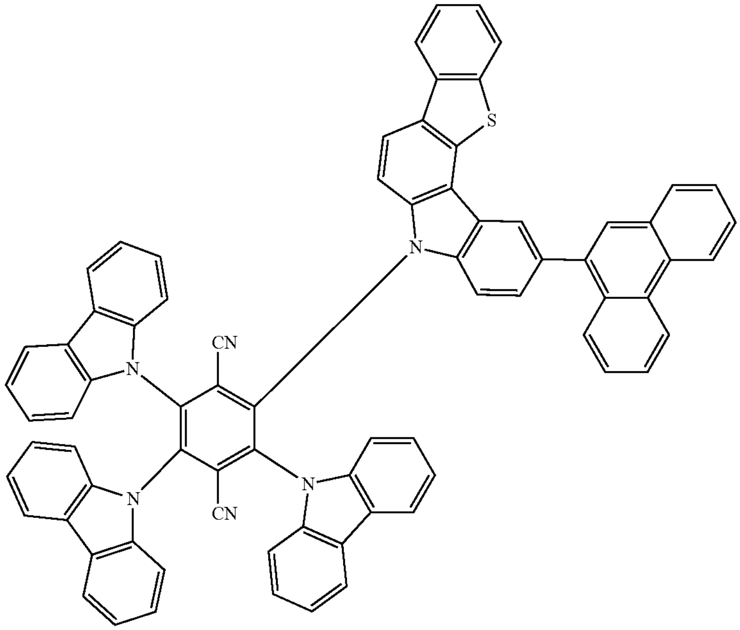

-continued
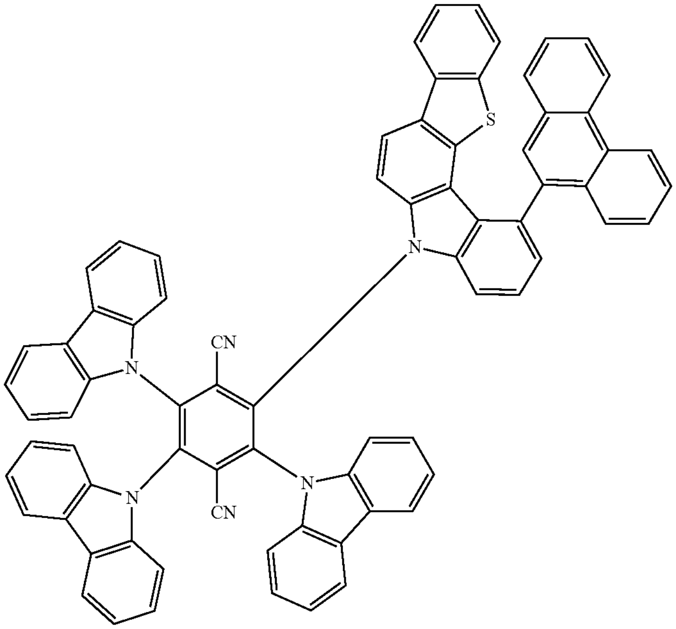
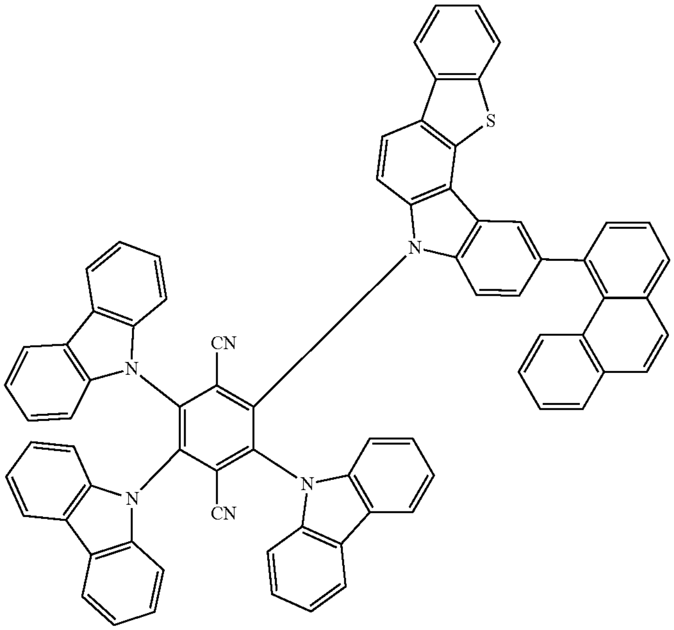

-continued
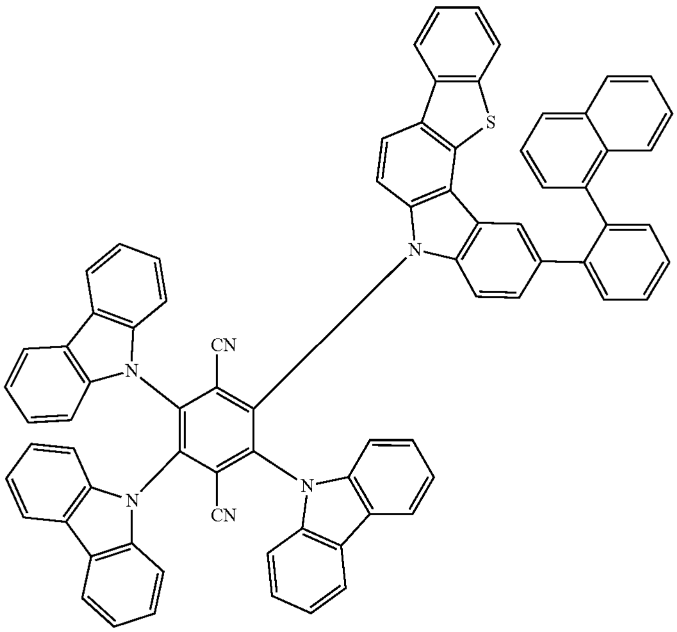
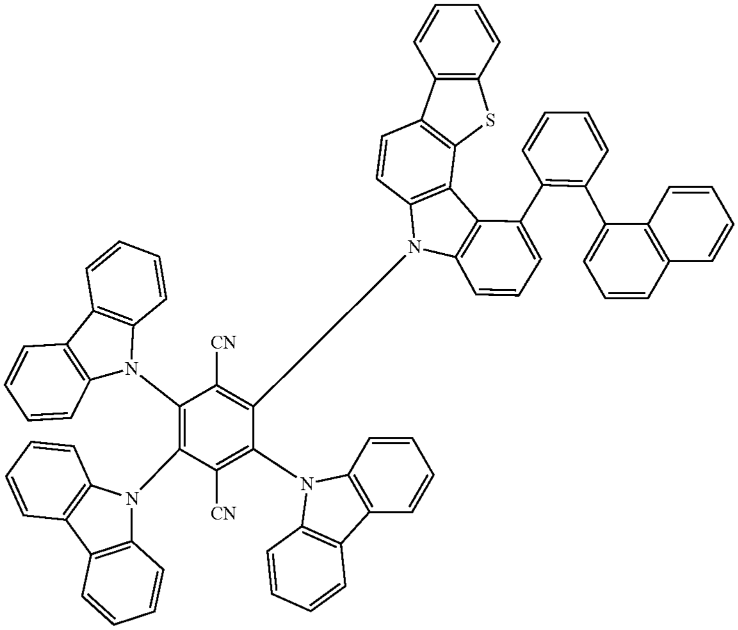

-continued
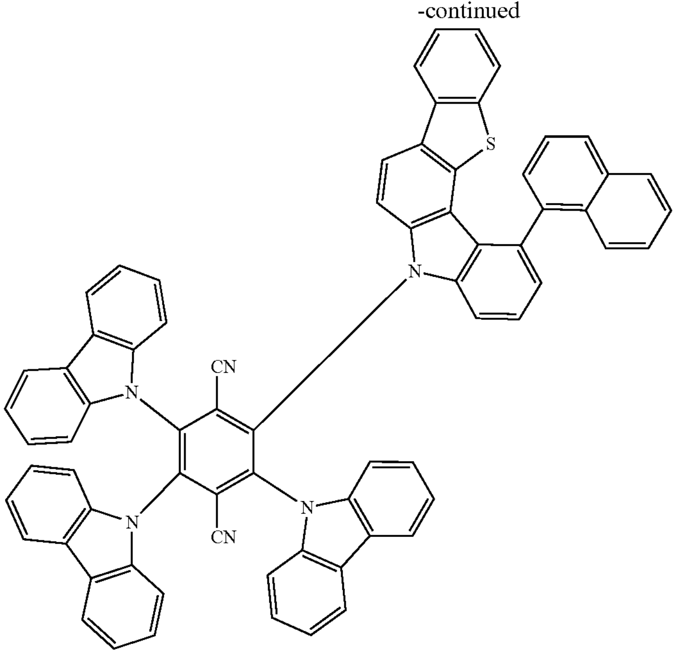
[Formula 36]
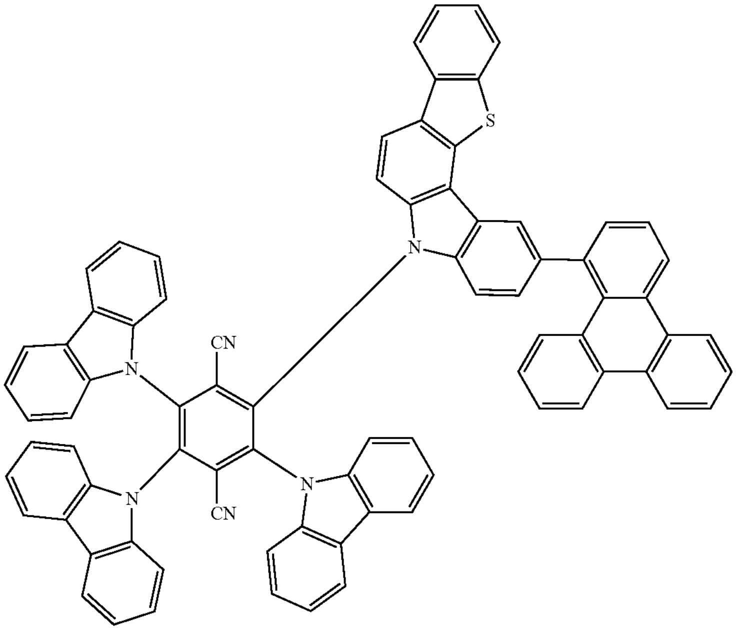

-continued
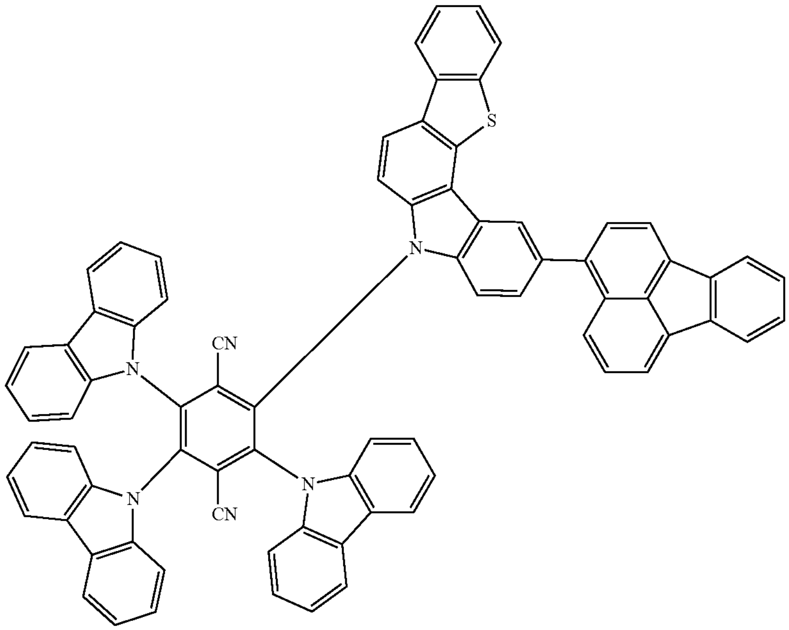
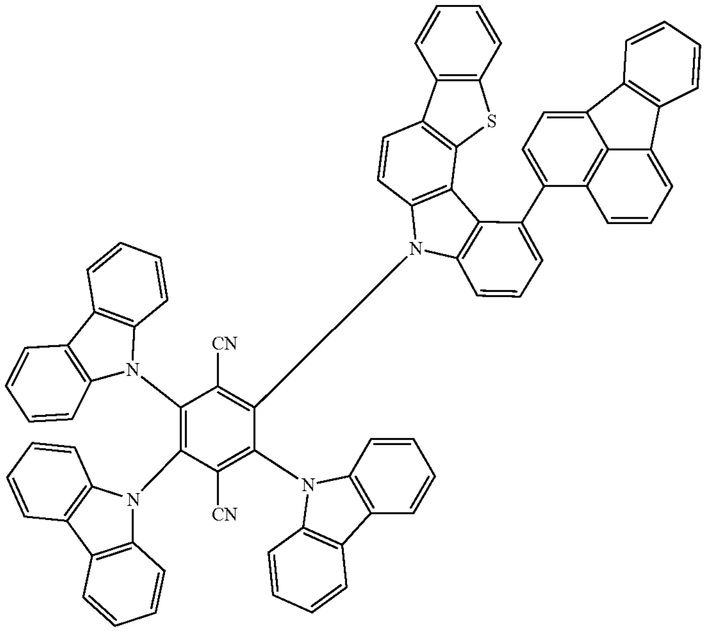

-continued
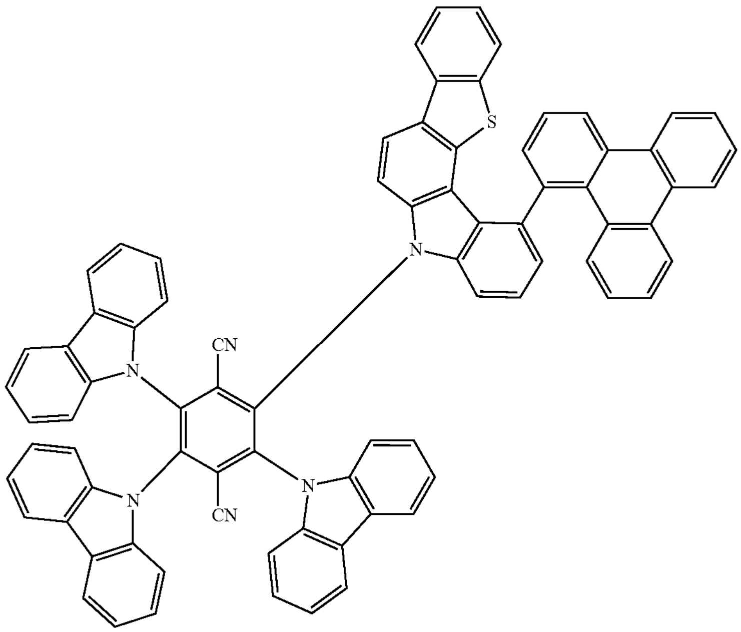
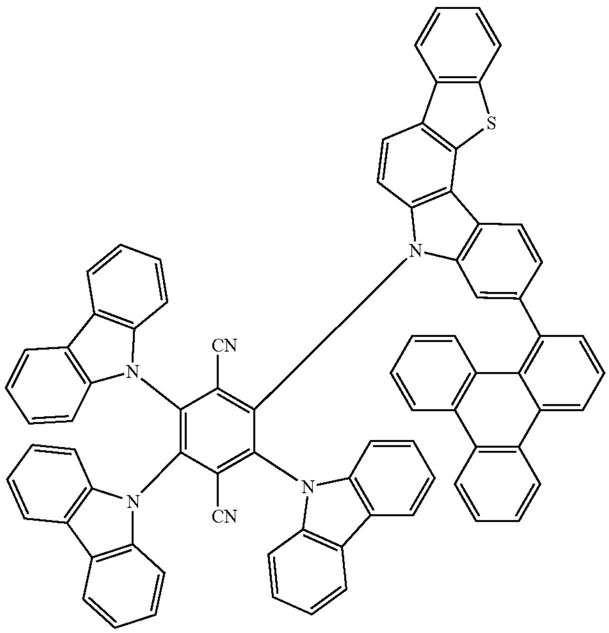

-continued
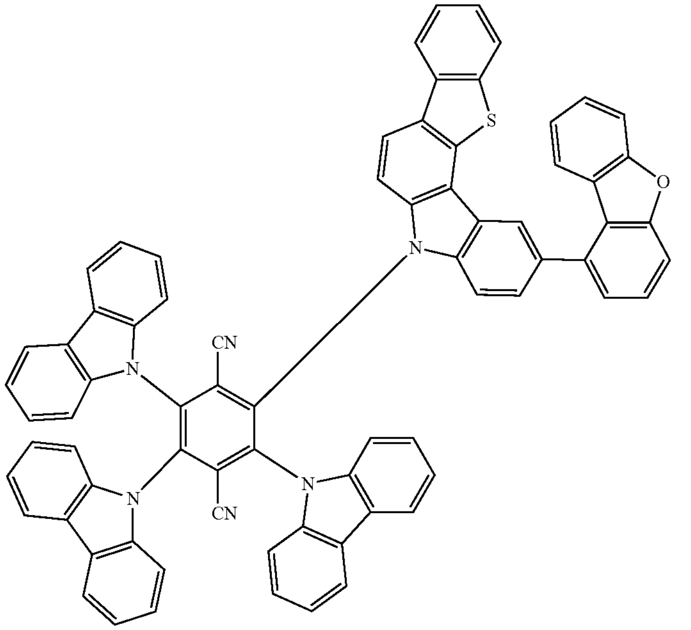
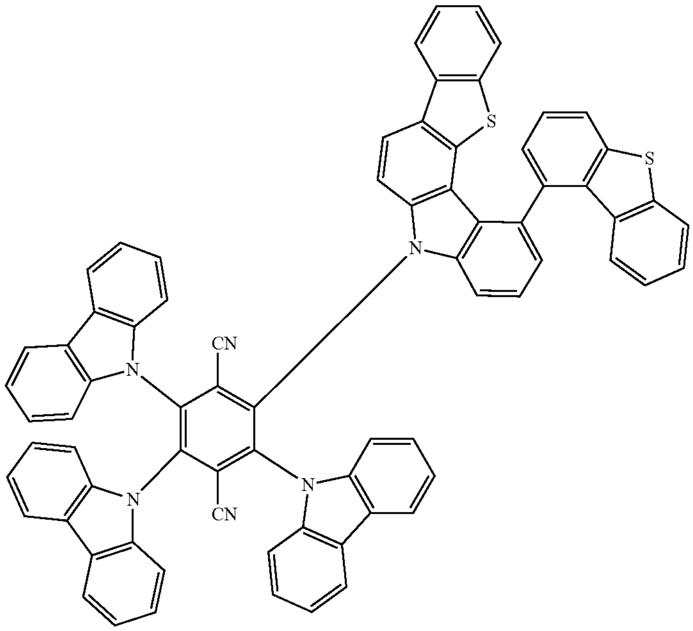

-continued
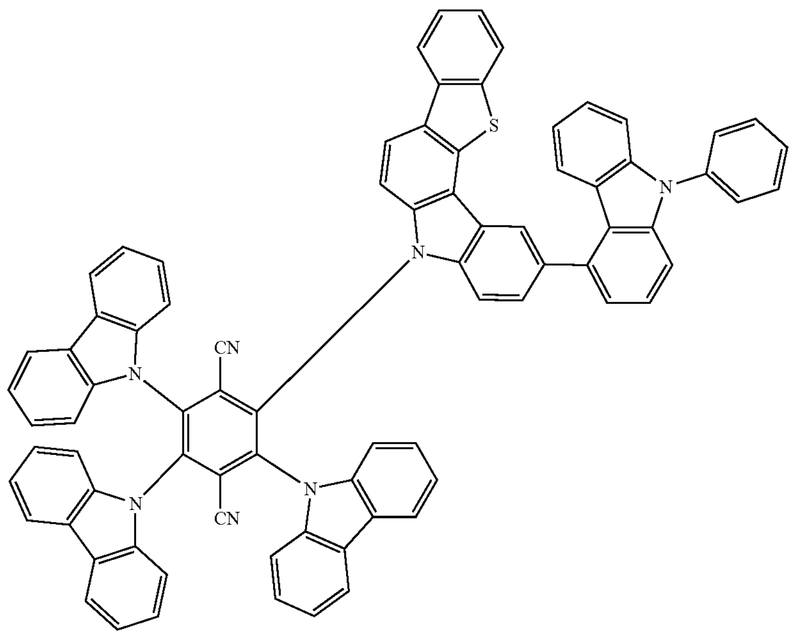
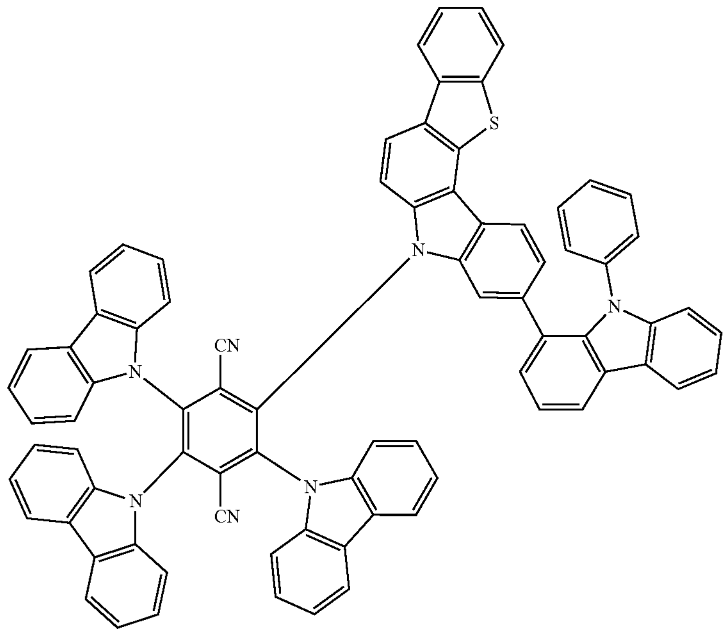

-continued
[Formula 37]
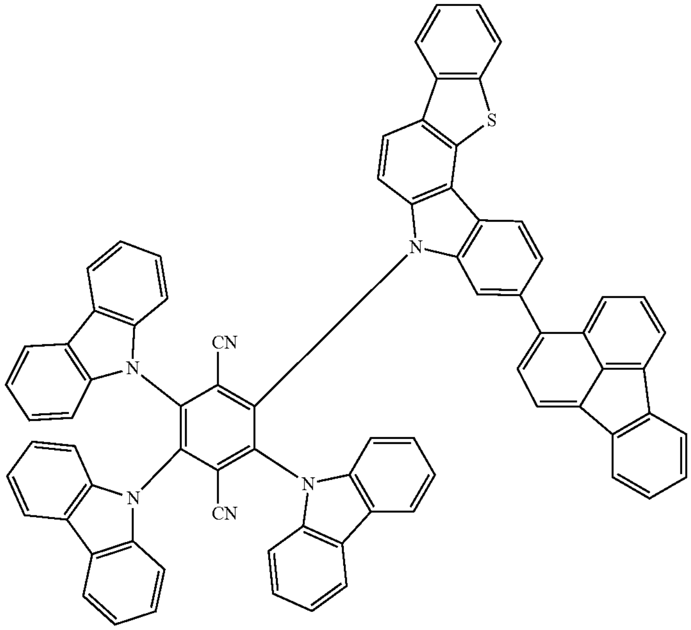
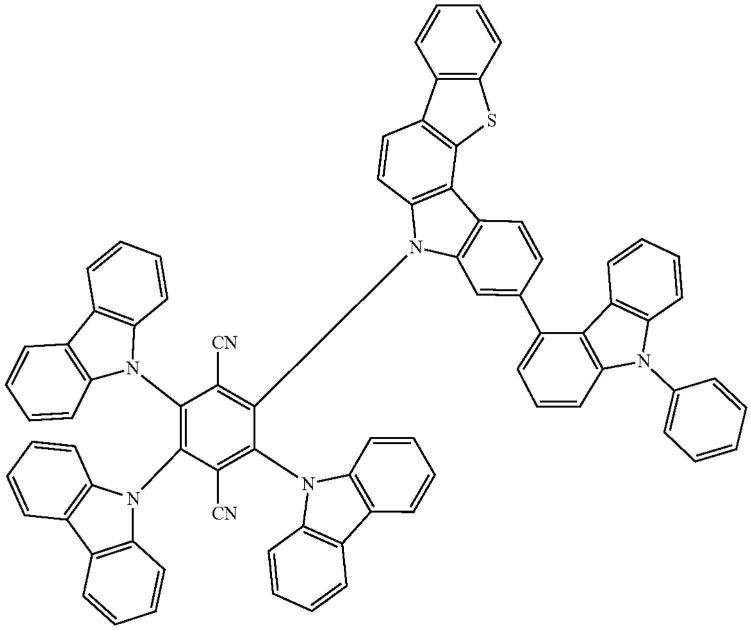

-continued
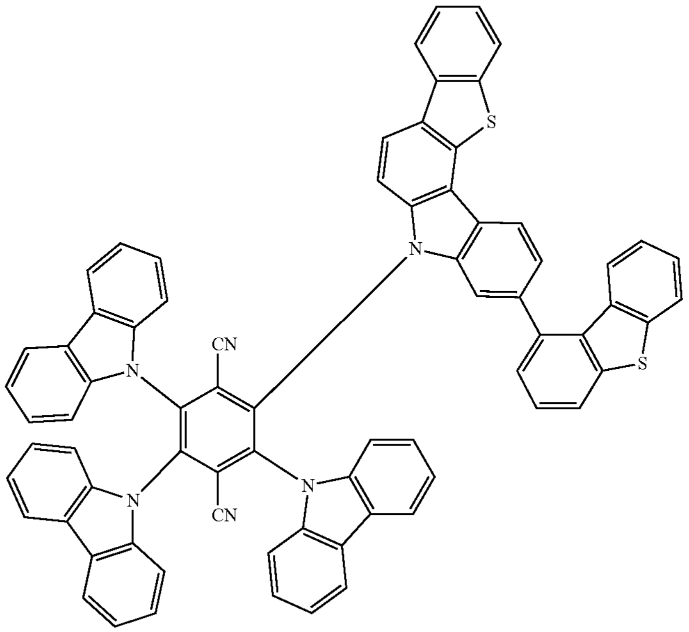
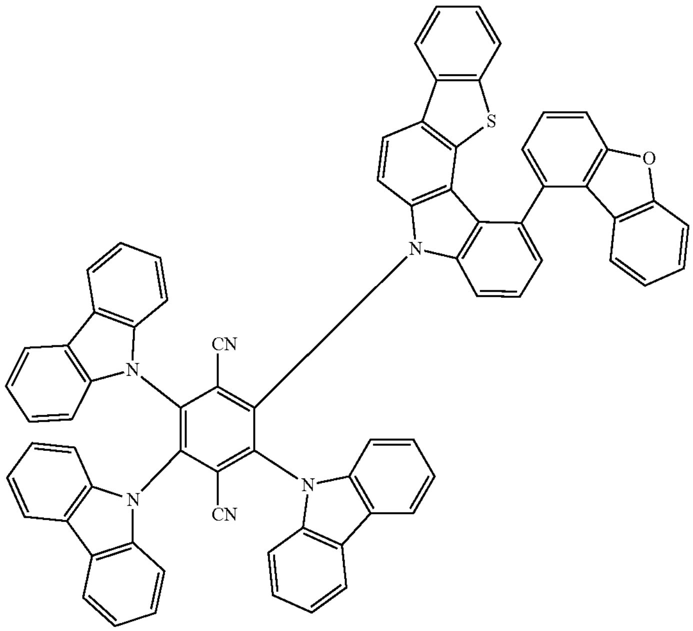

-continued
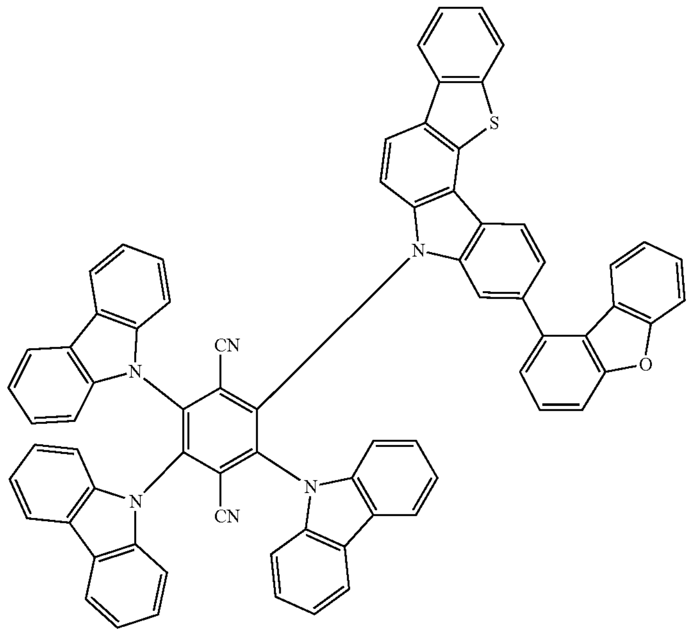
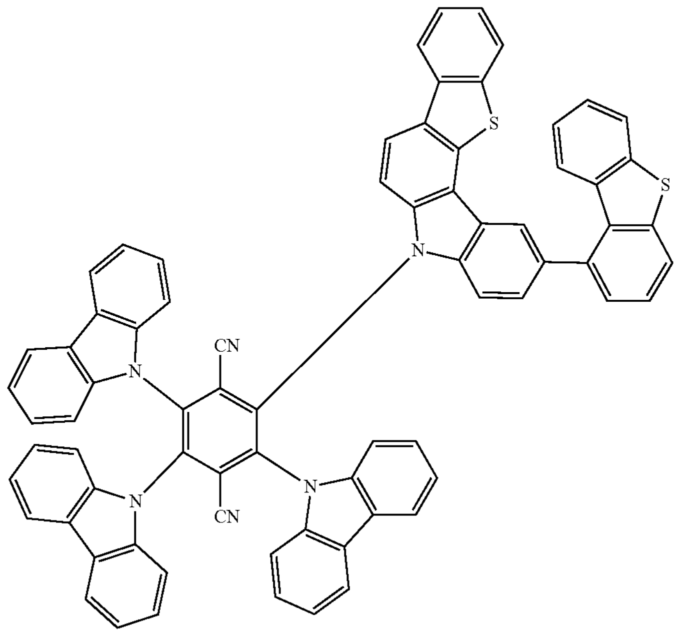

-continued
[Formula 38]
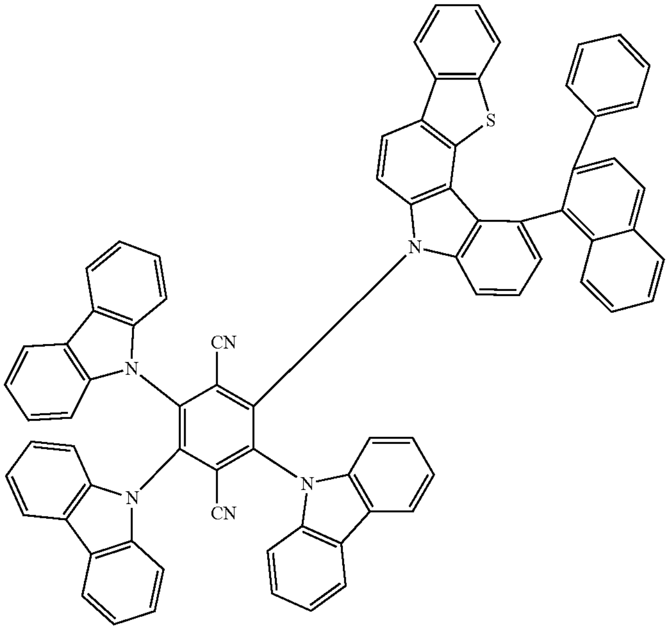
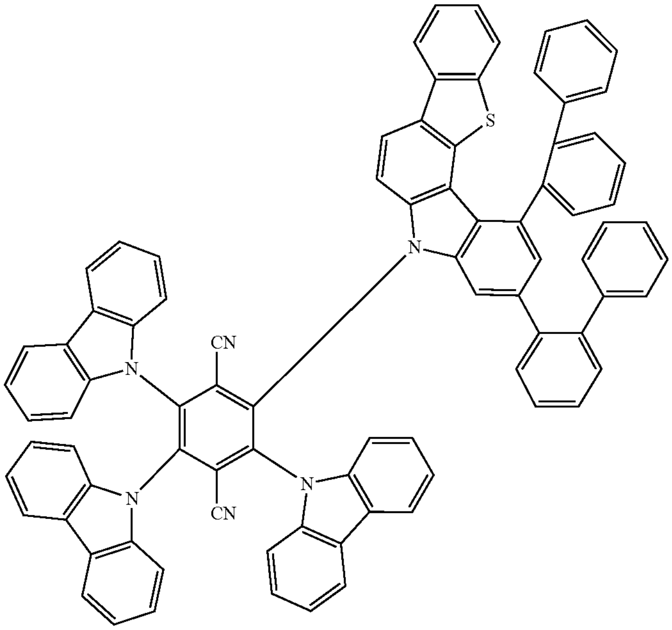

-continued
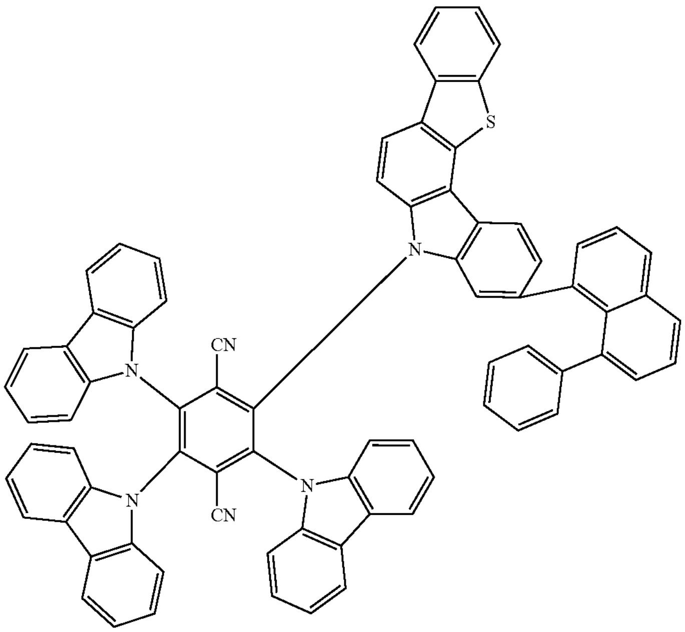
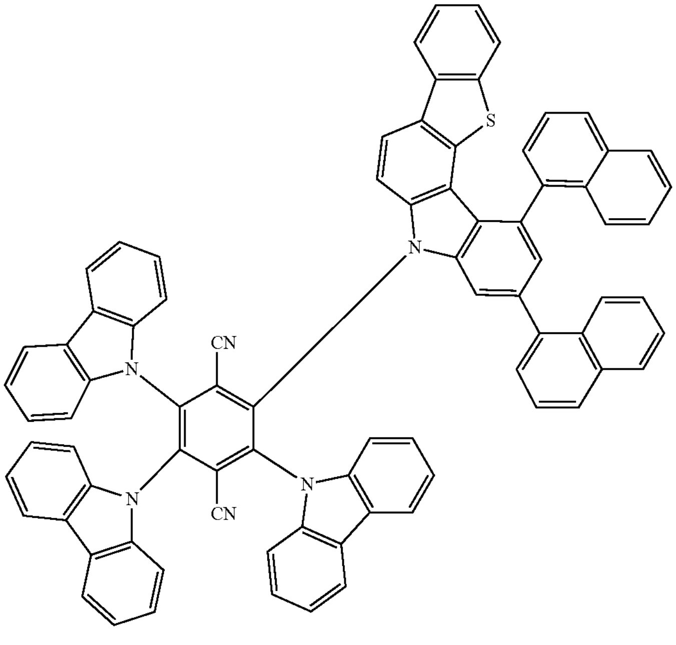

-continued
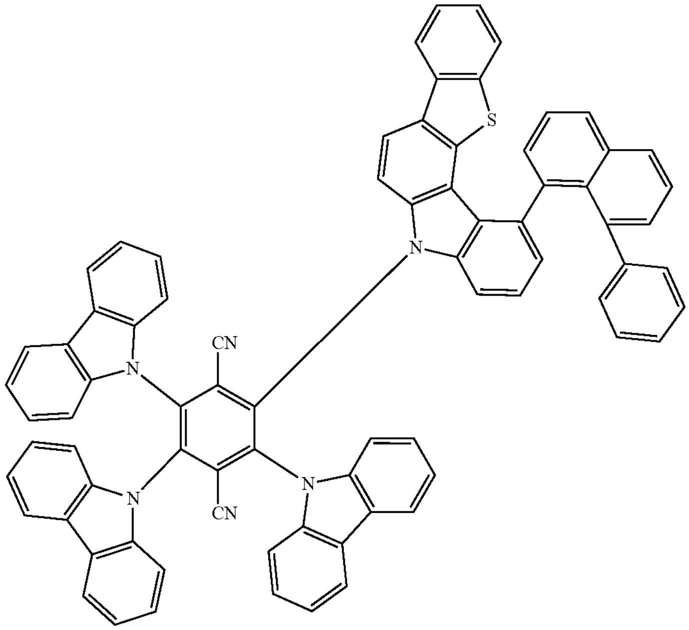
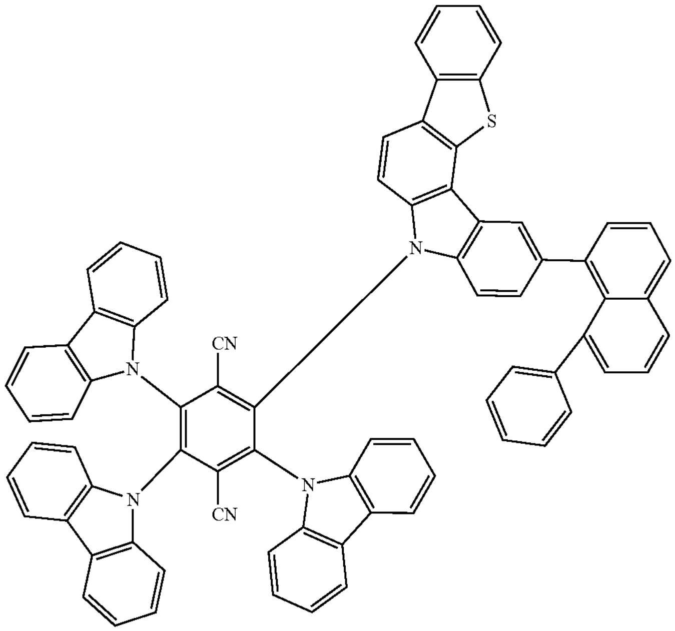

-continued
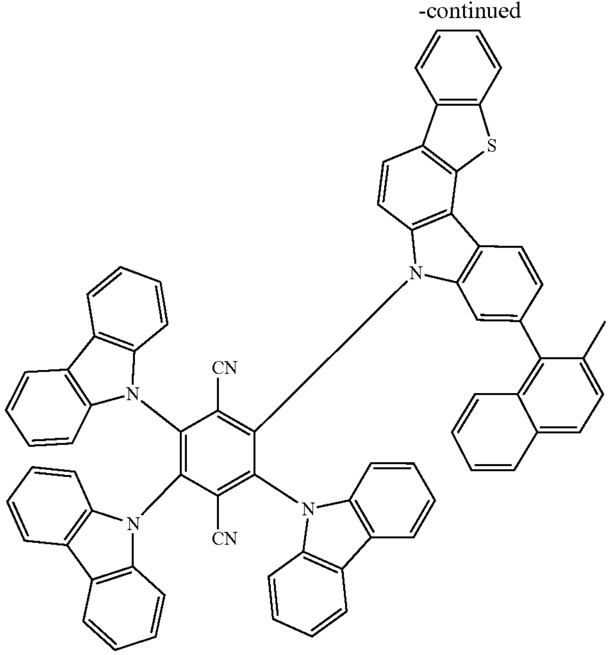
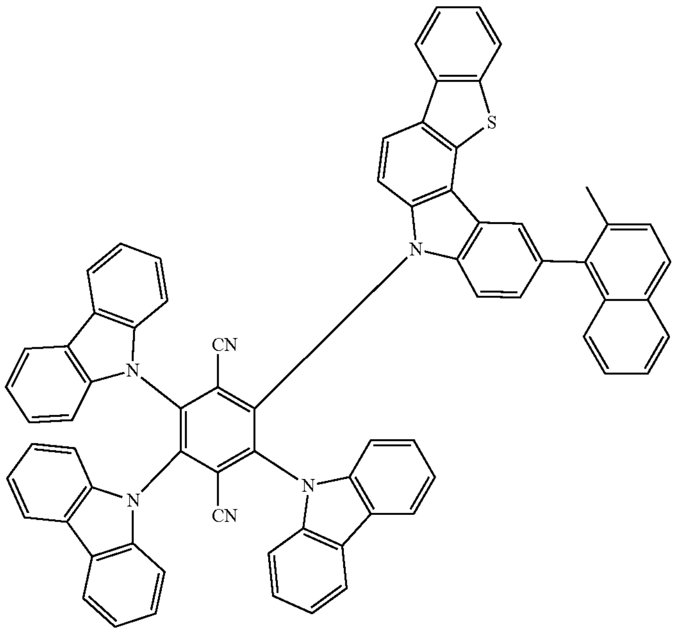

-continued
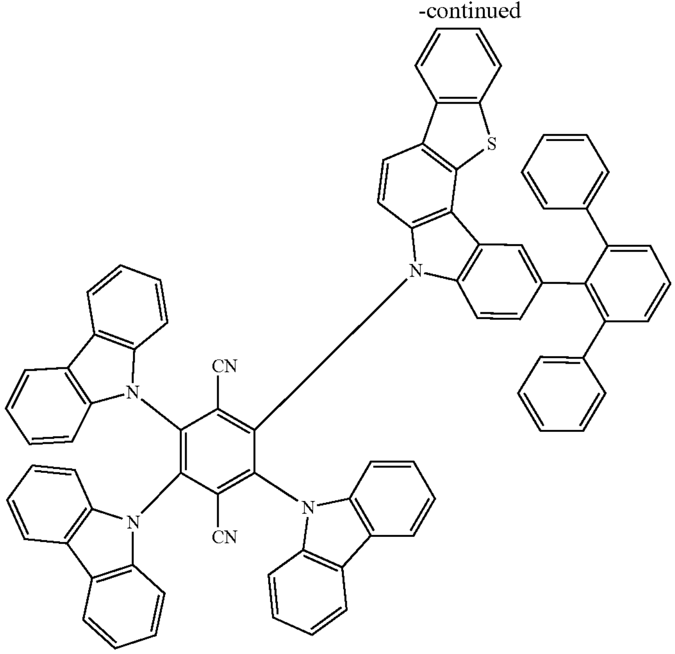
[Formula 39]
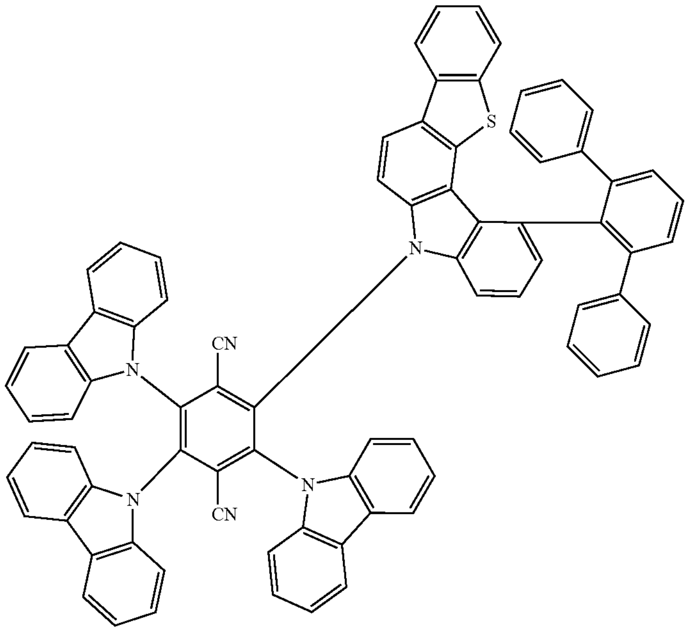

-continued
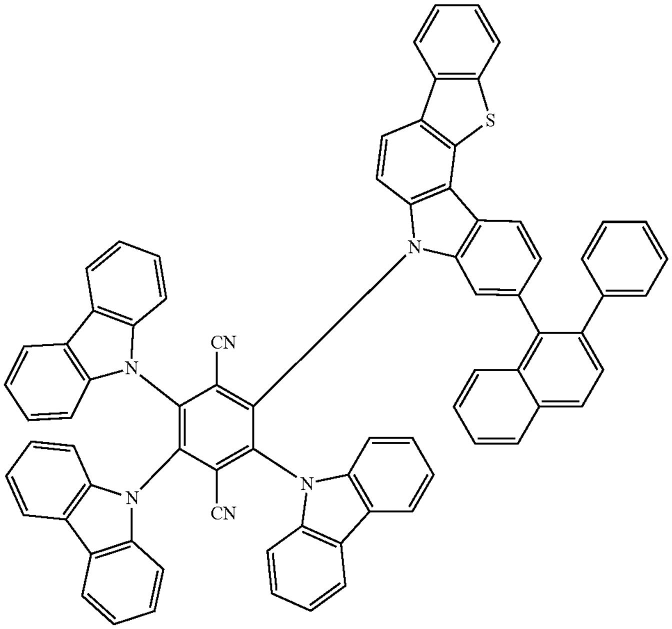
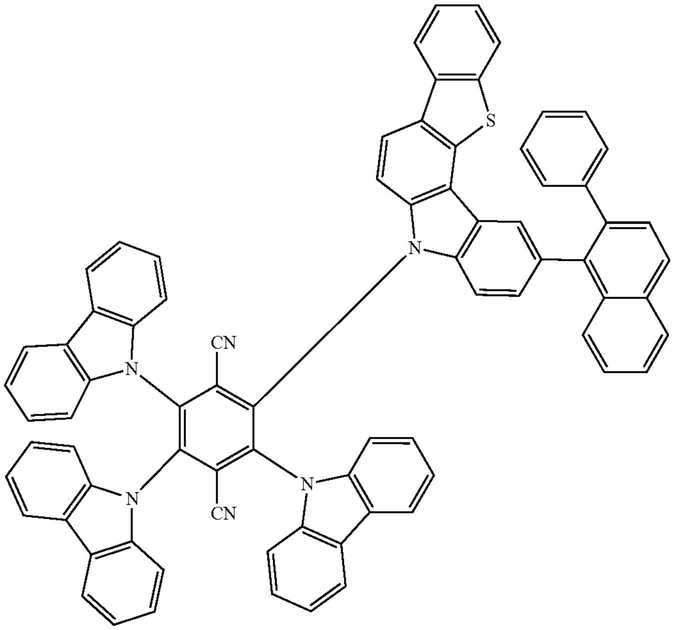

-continued
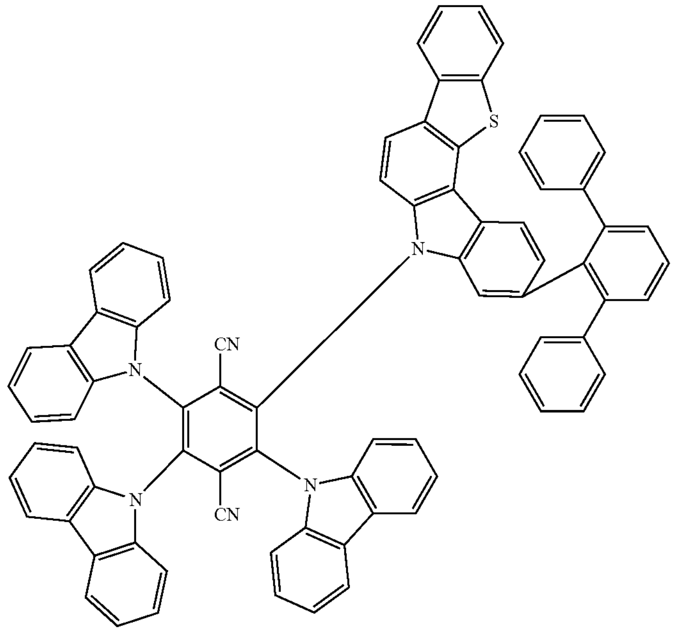
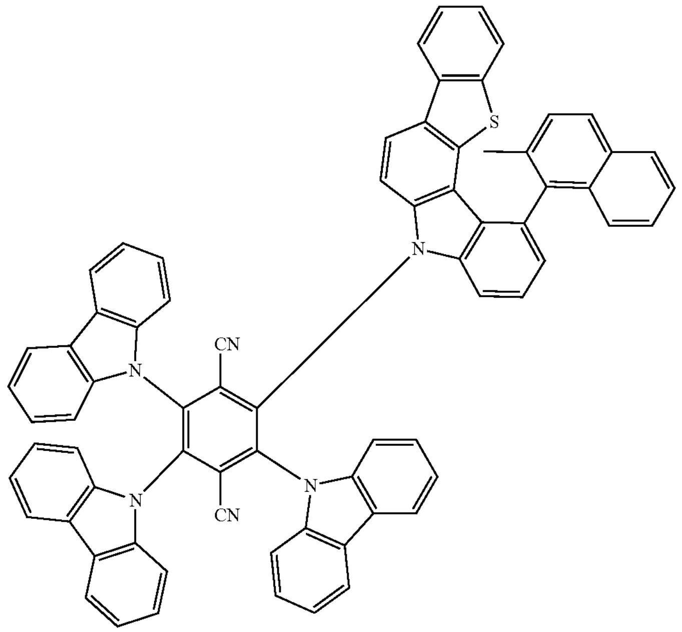

-continued
[Formula 40]
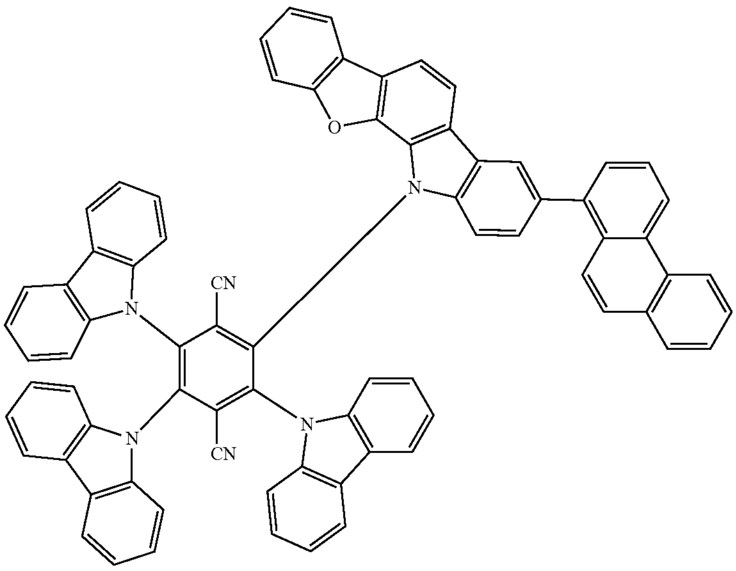
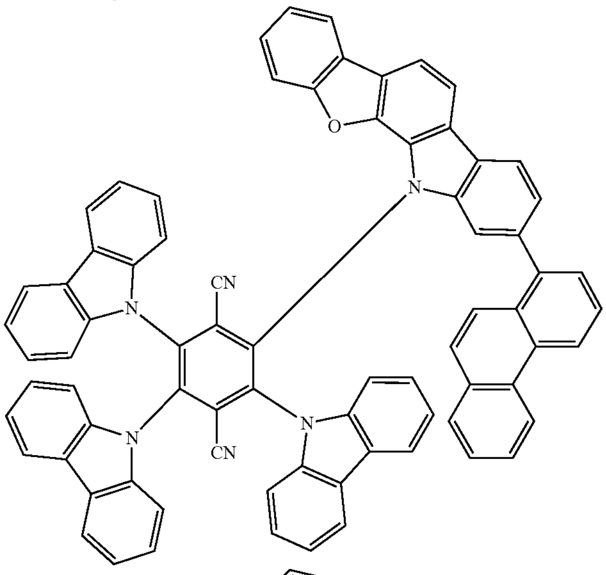
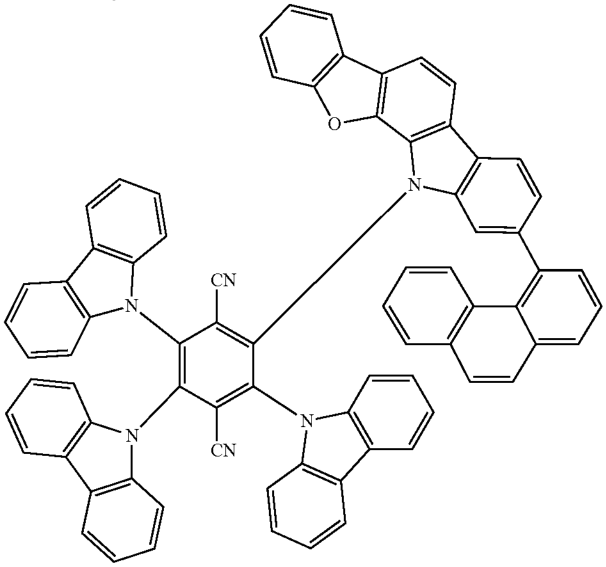

-continued
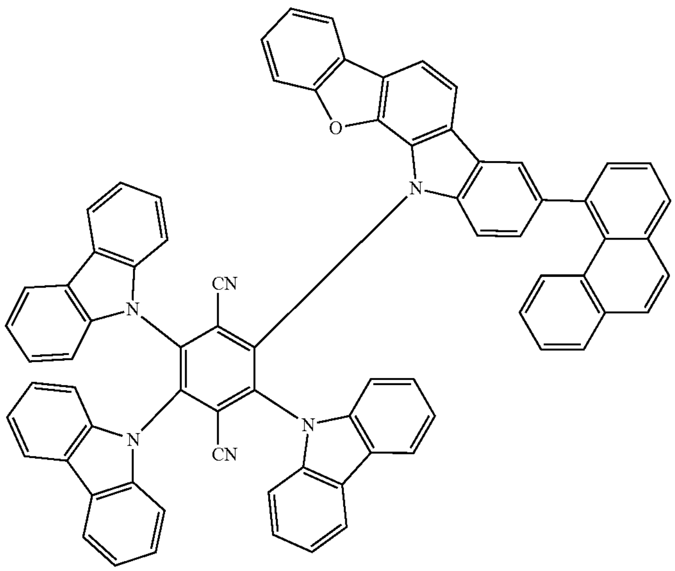
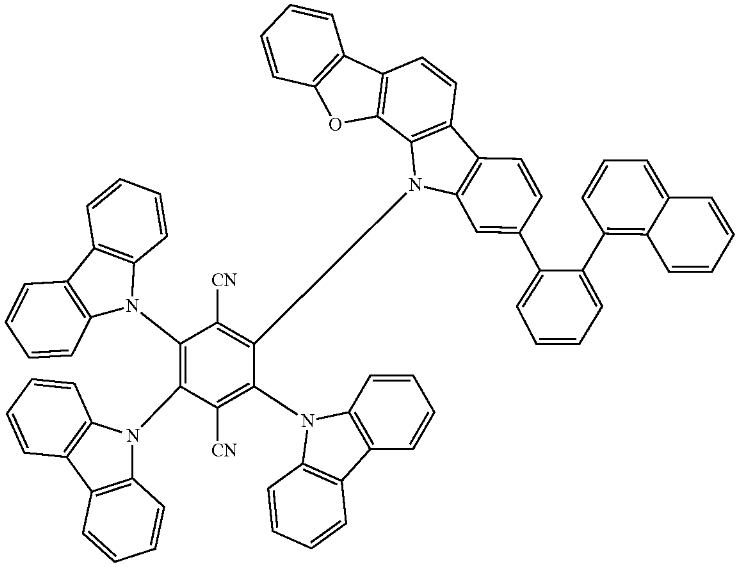
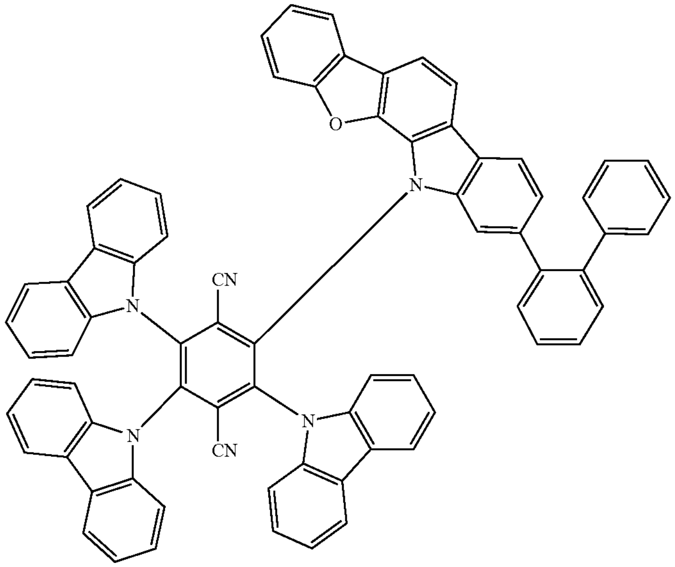

-continued
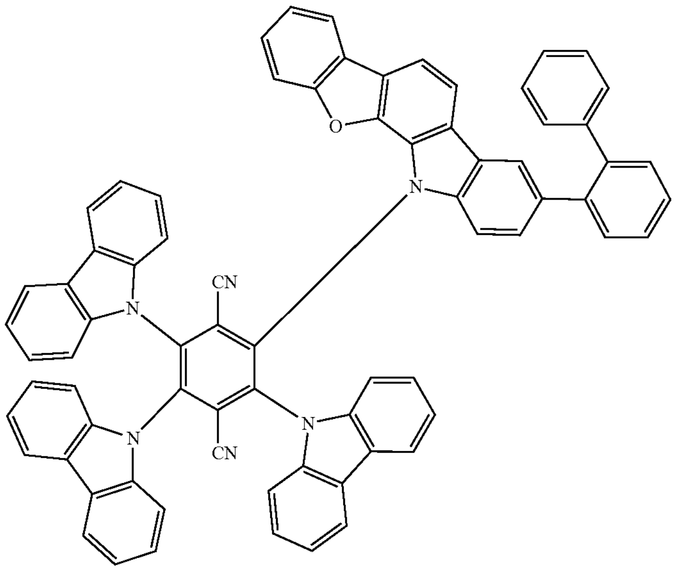
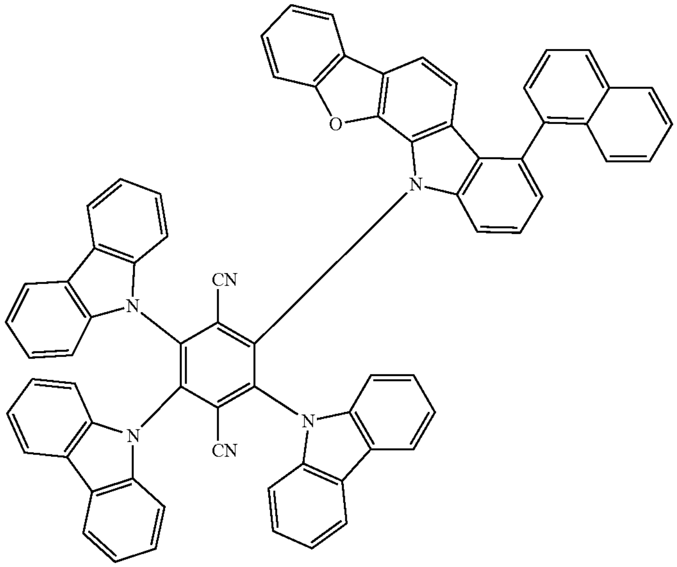
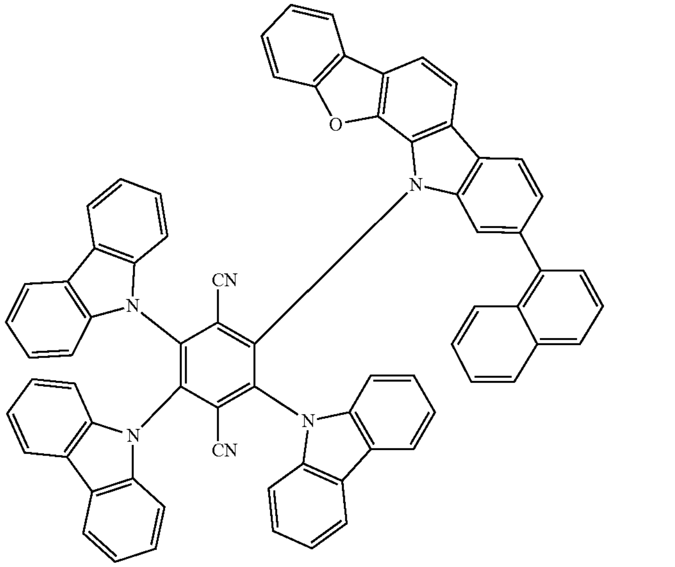

-continued
[Formula 41]
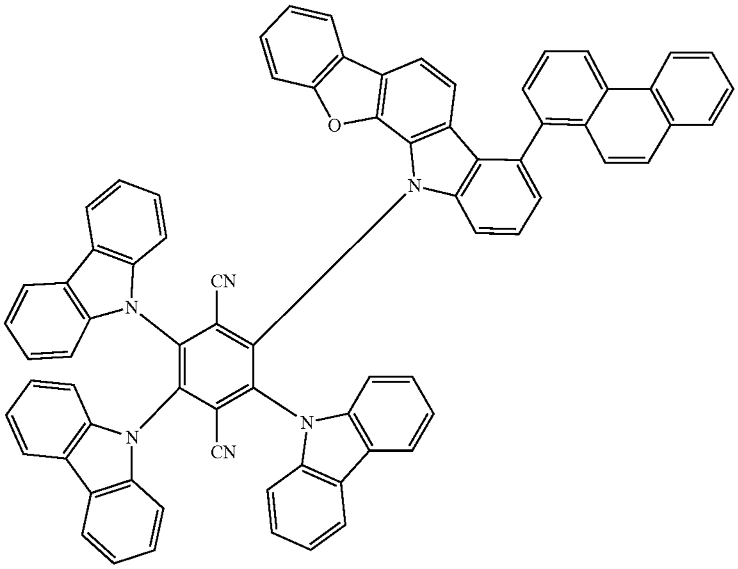
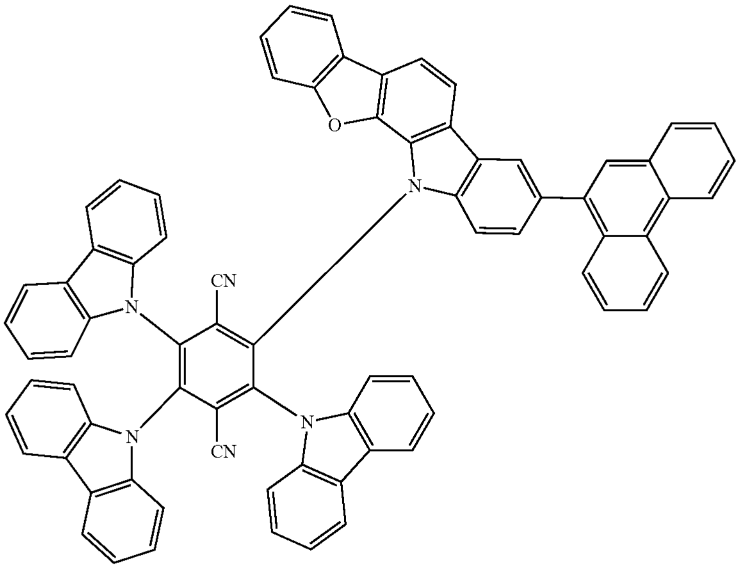

-continued
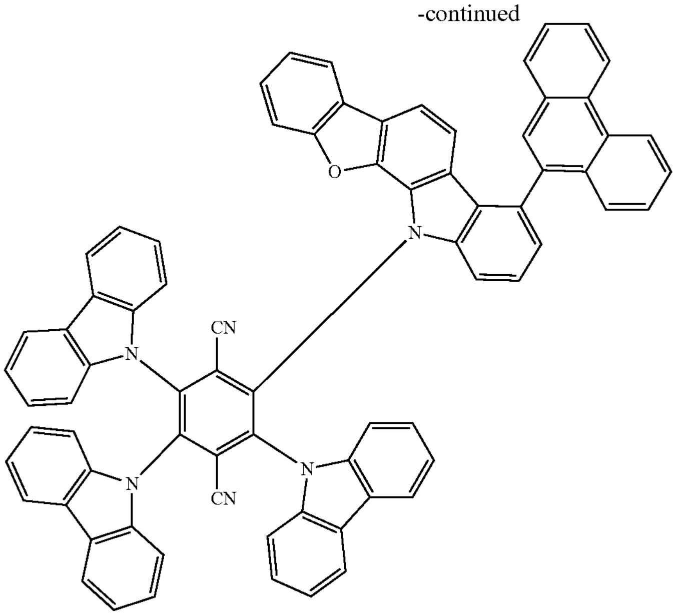
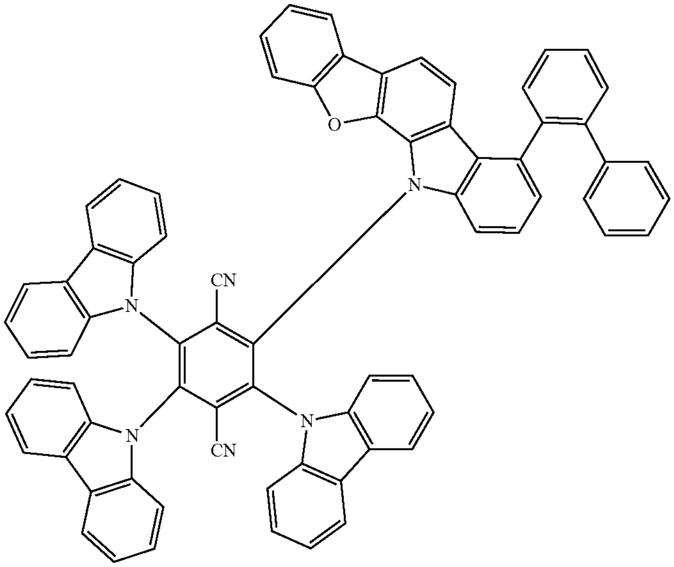
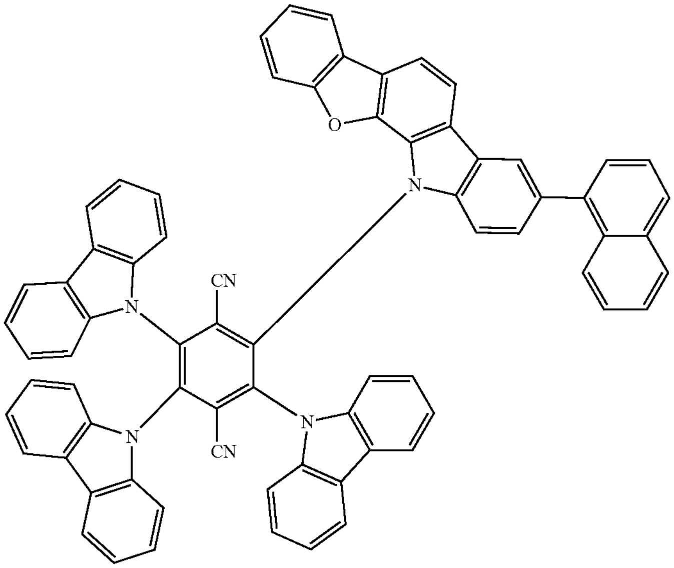

-continued
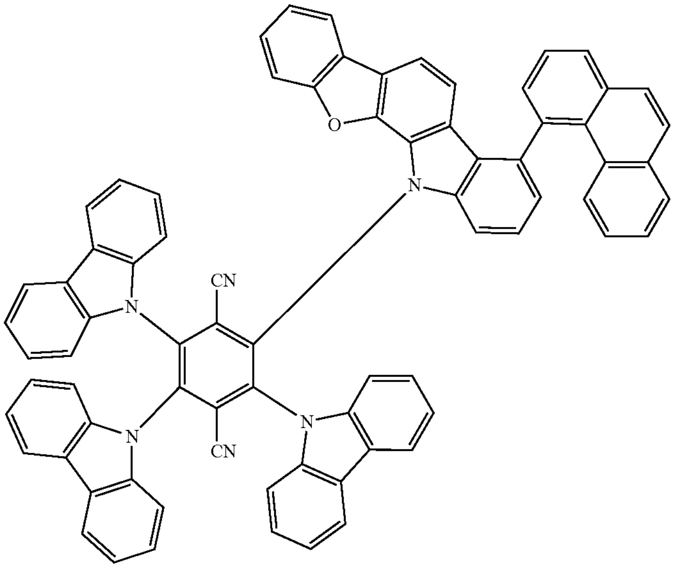
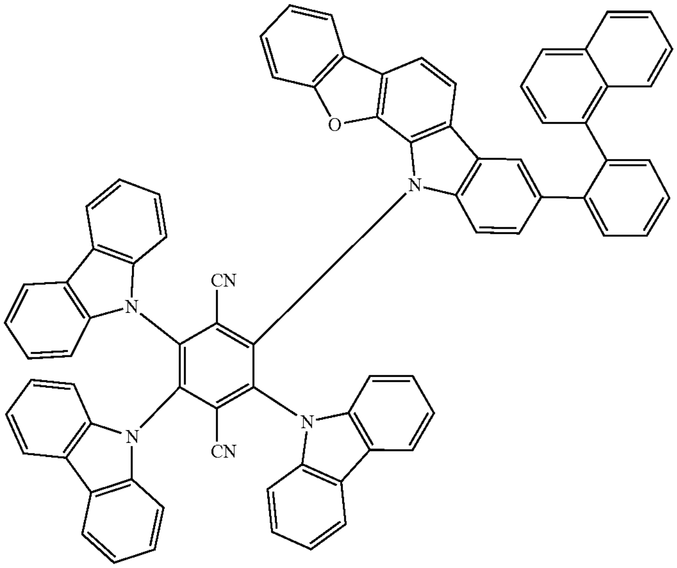
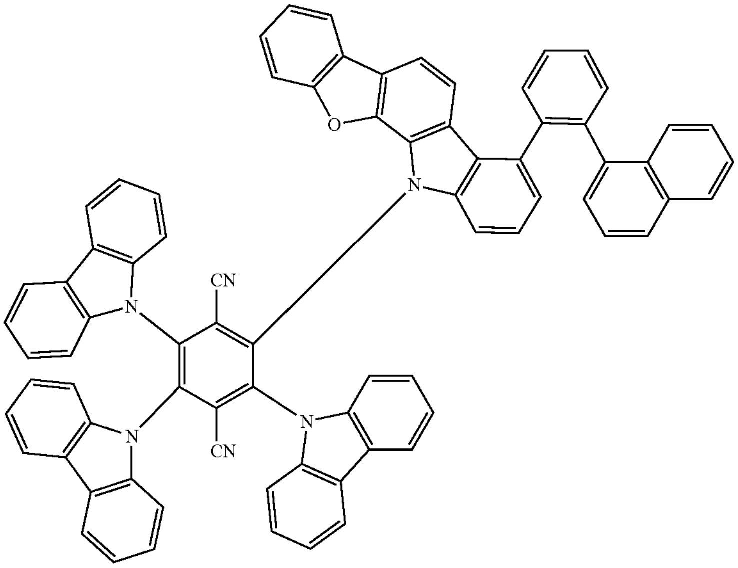

-continued
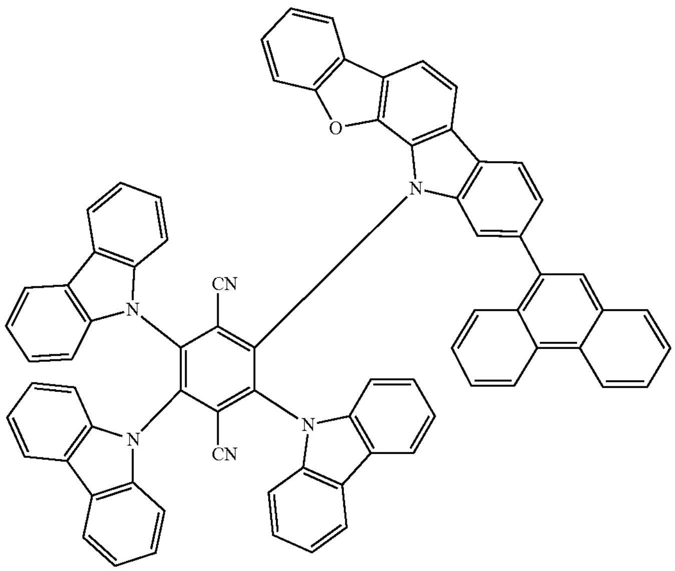
[Formula 42]
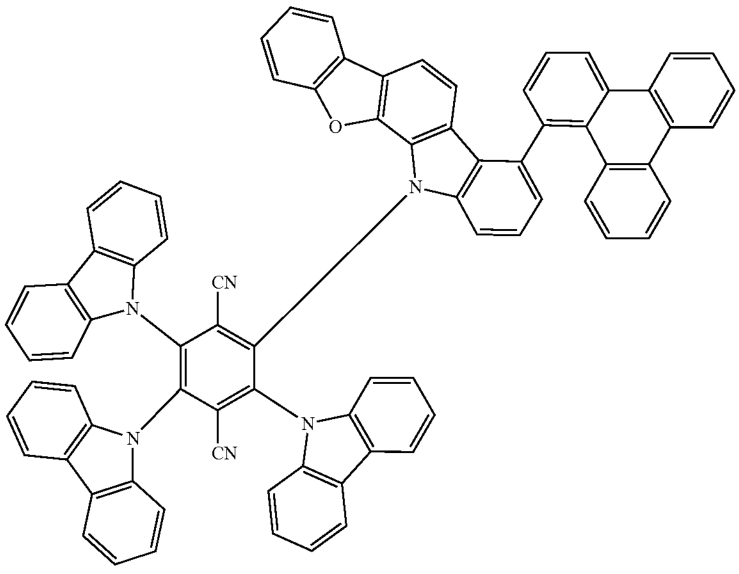

-continued
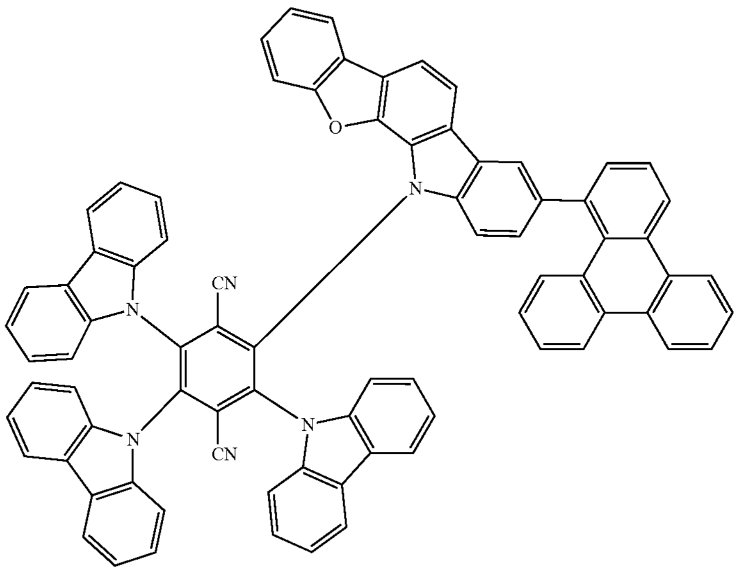
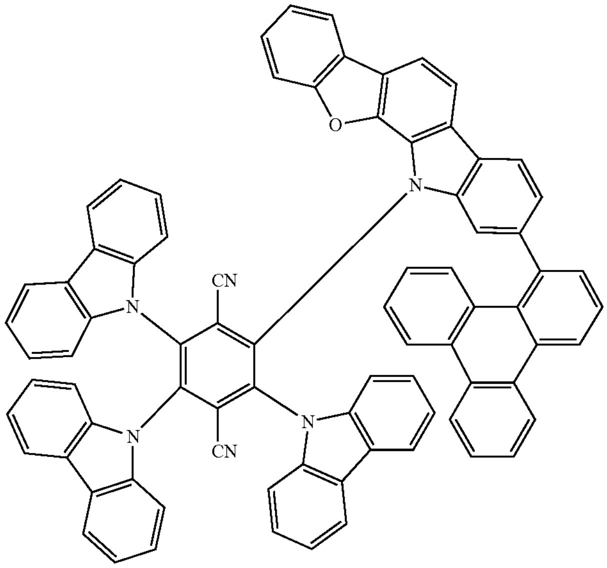
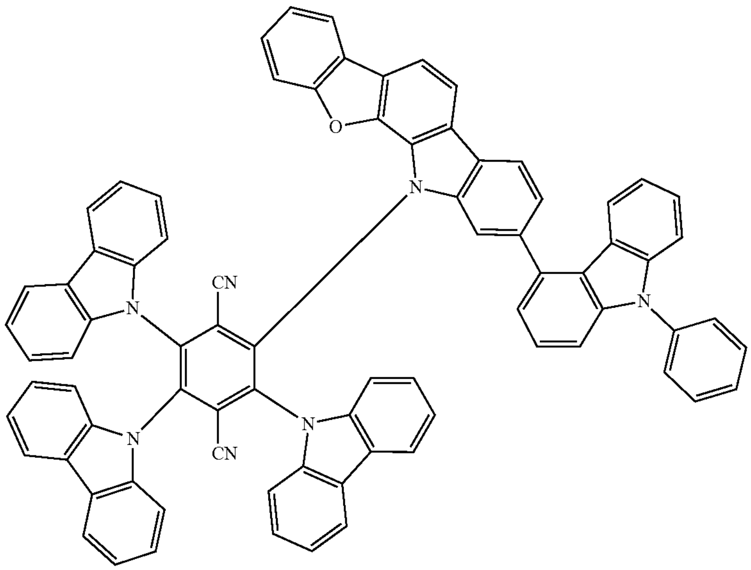

-continued
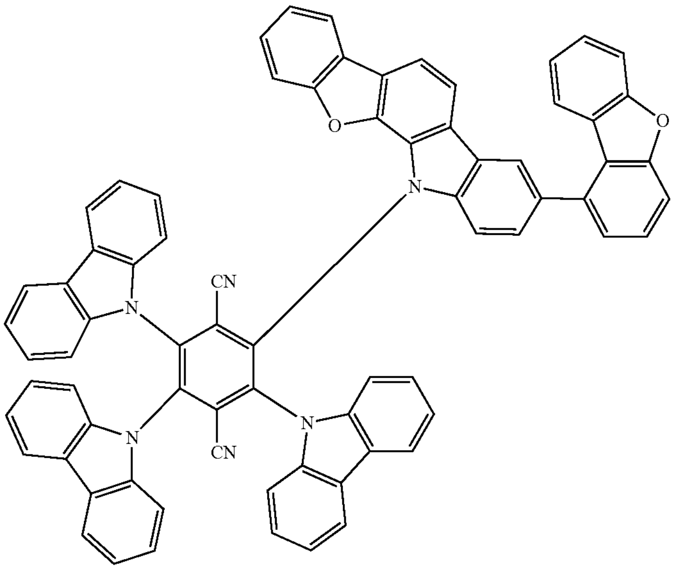
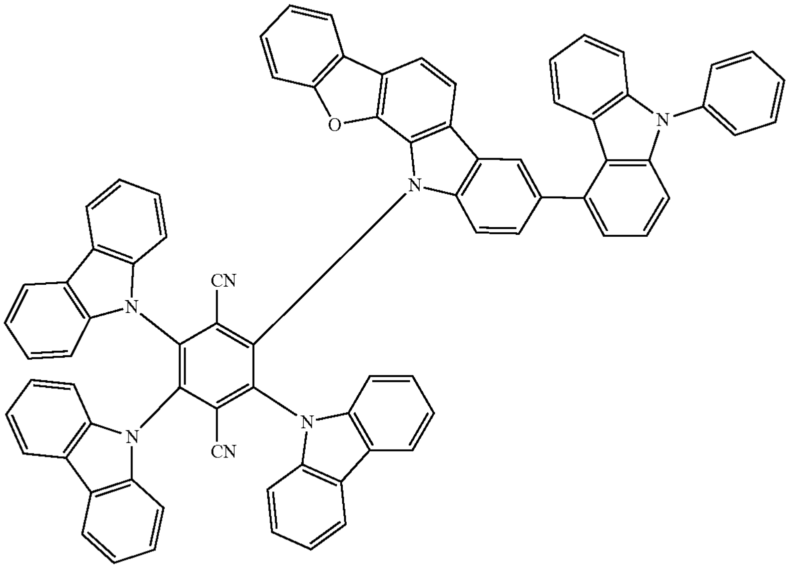
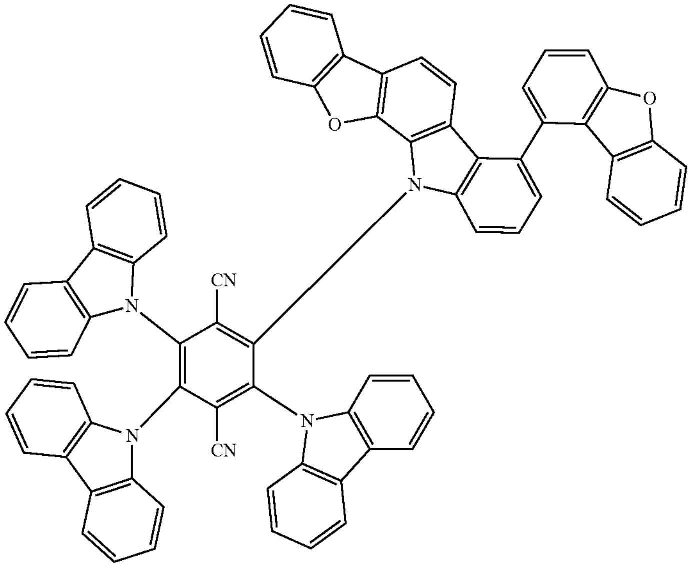

-continued
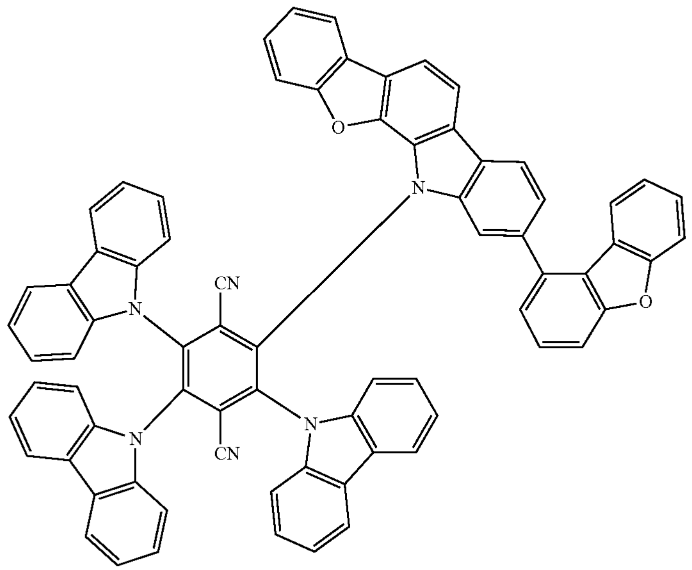
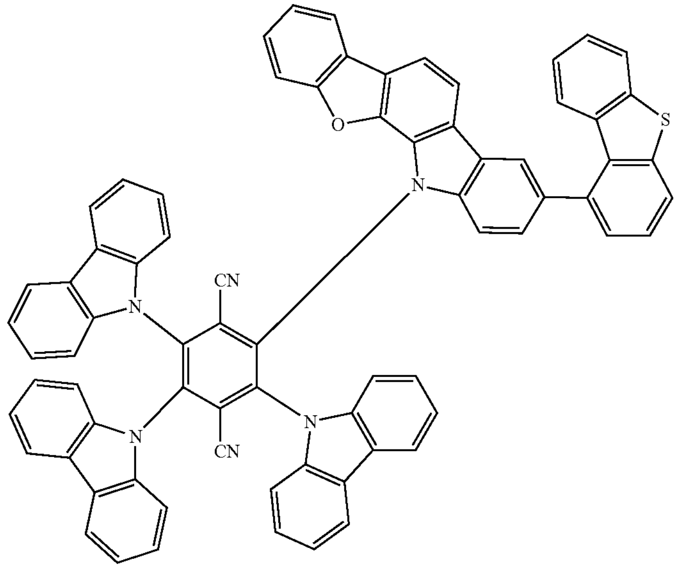
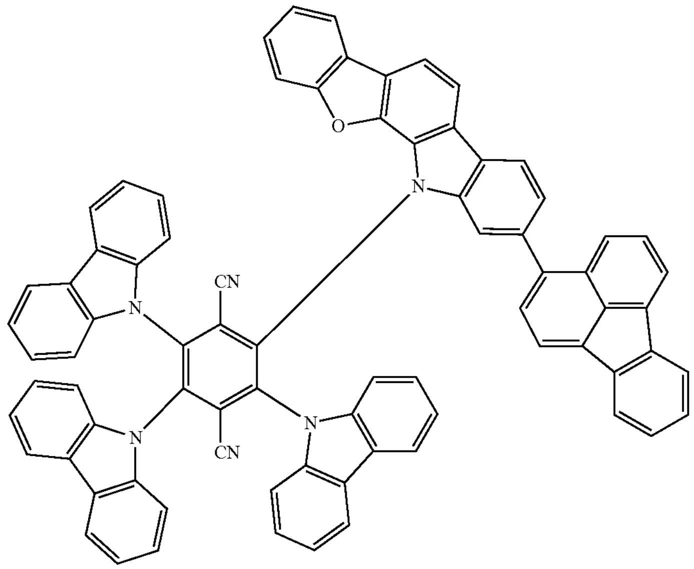

-continued
[Formula 43]
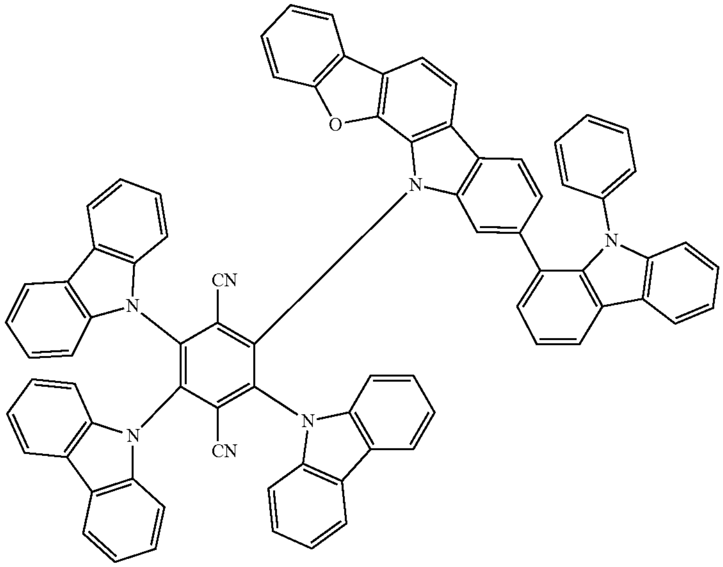
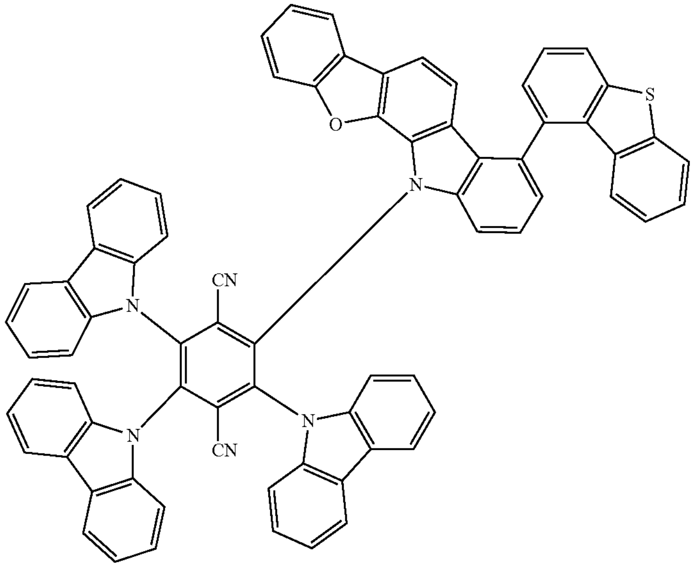

-continued
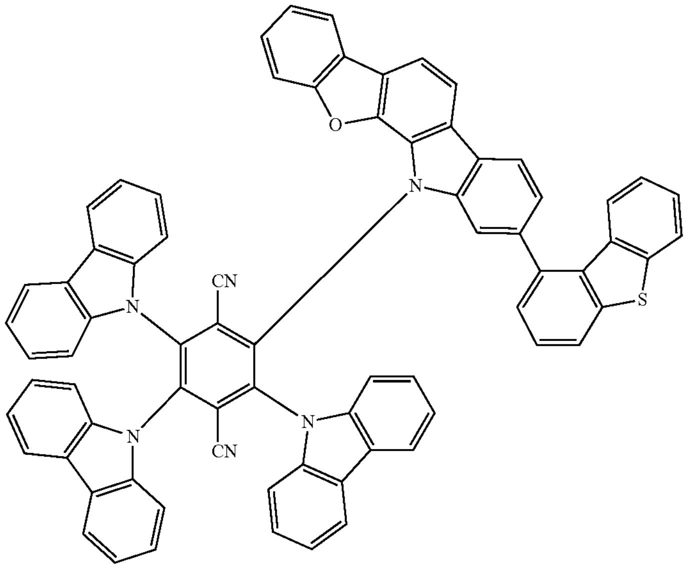
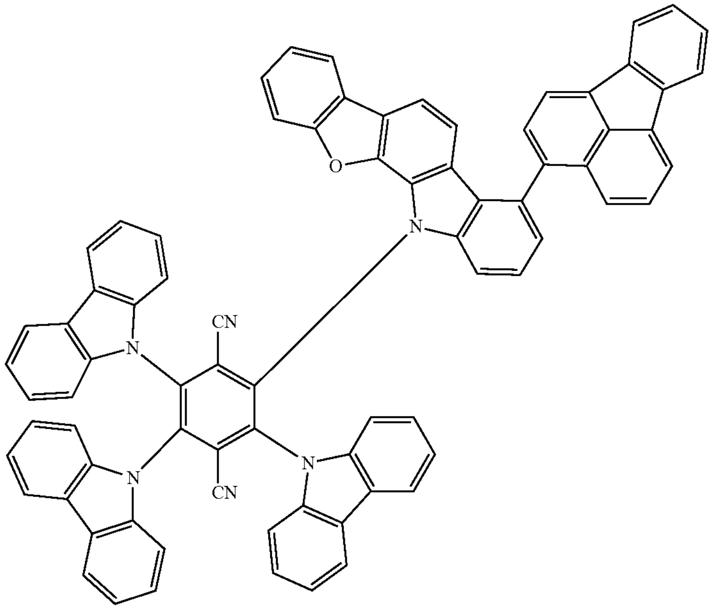

-continued
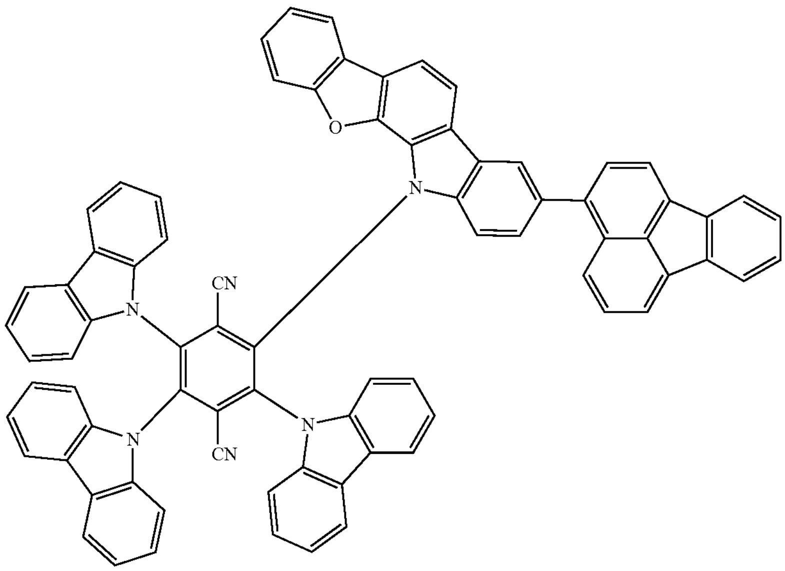
[Formula 44]
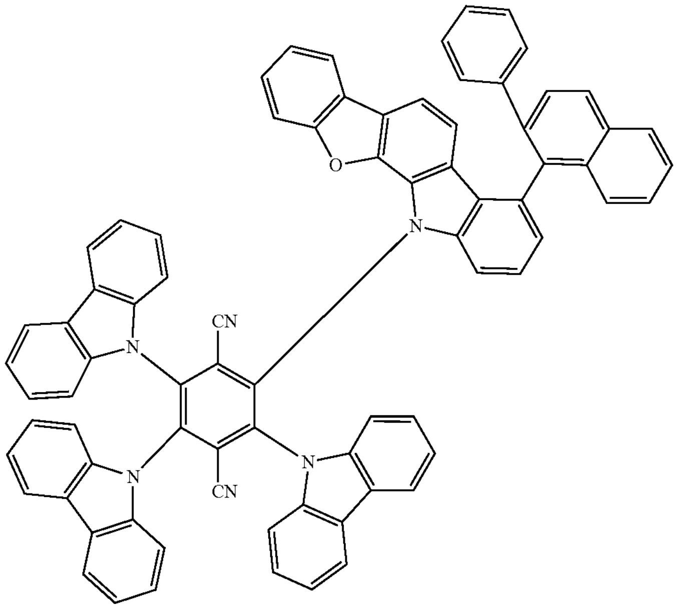

-continued
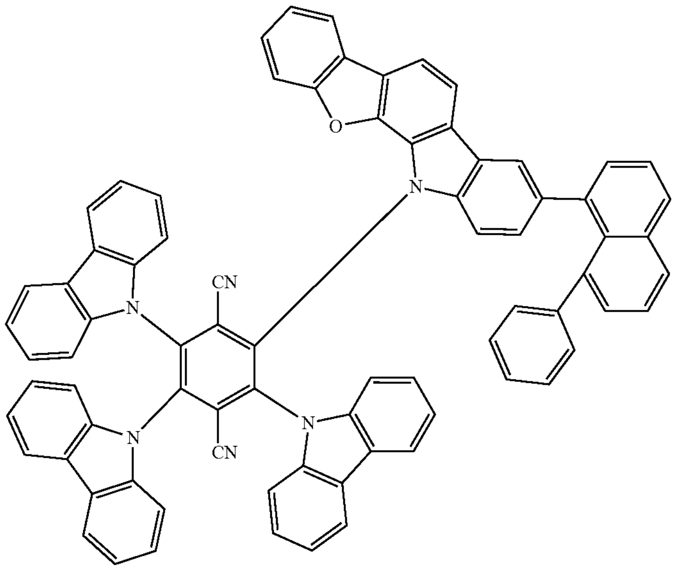
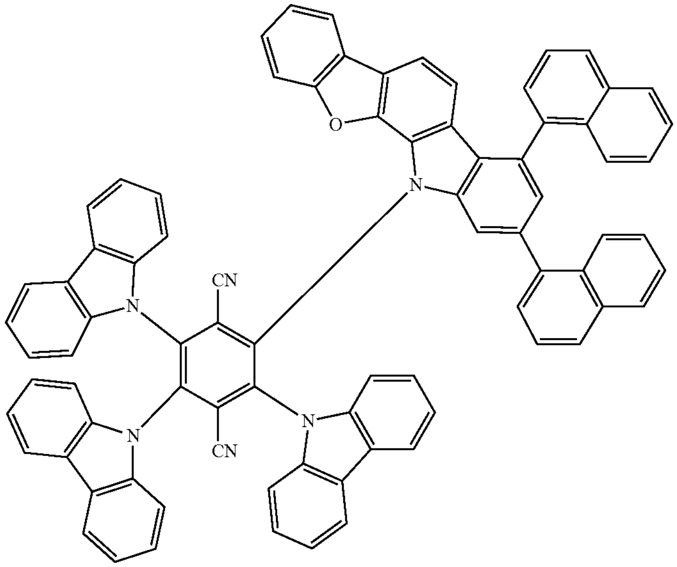
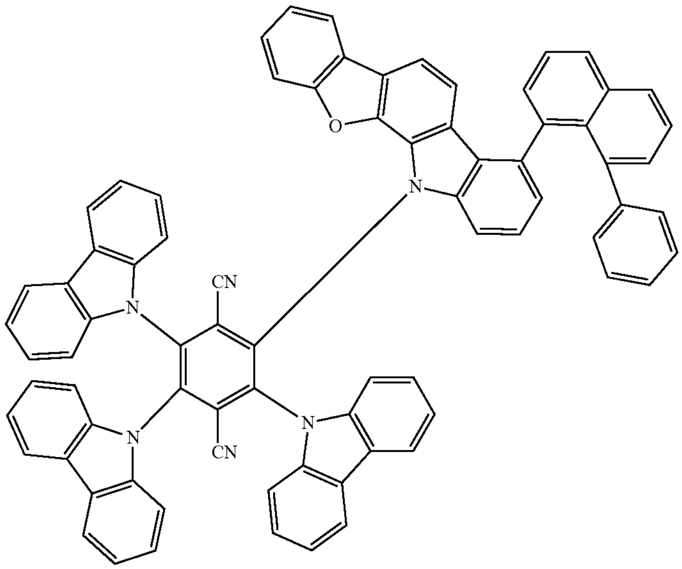

-continued
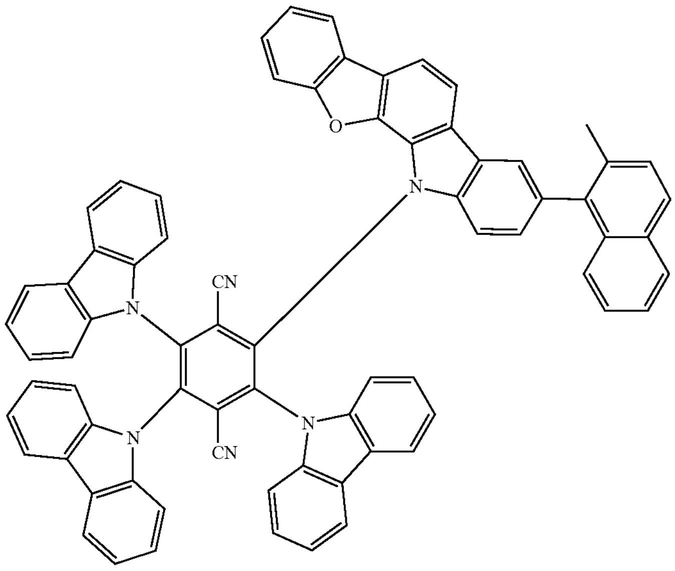
[Formula 45]
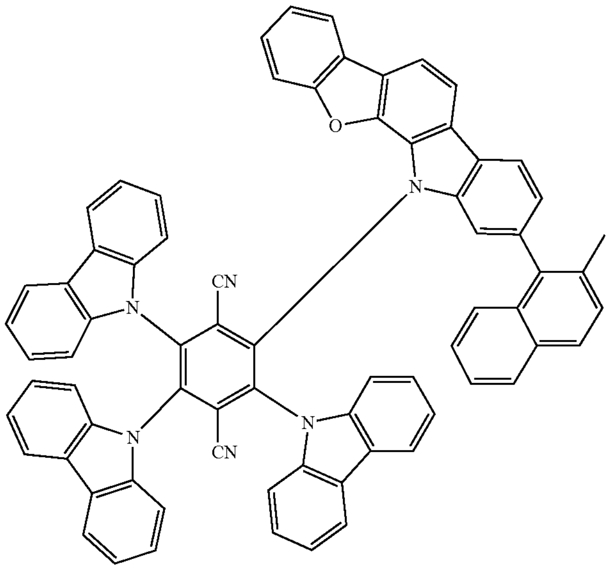

-continued
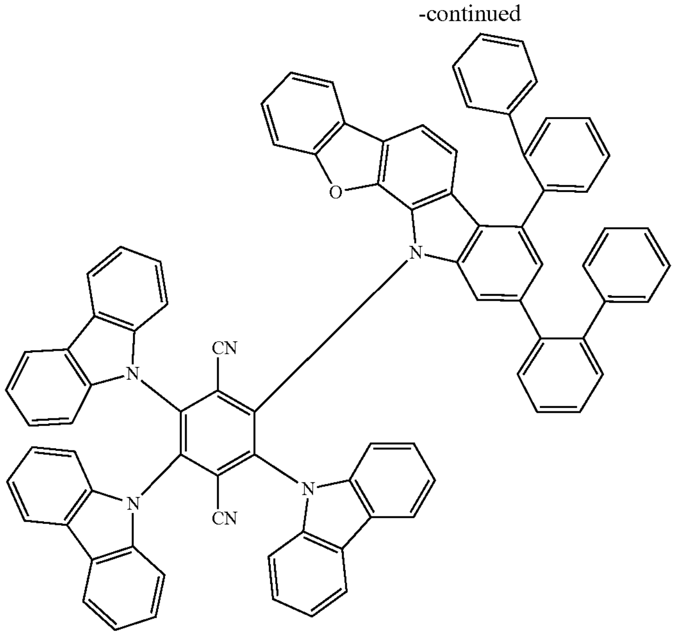
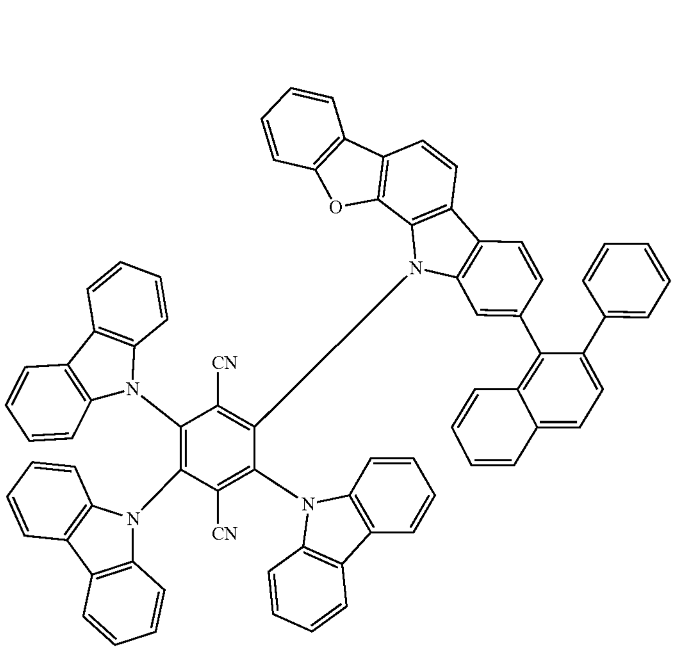

-continued
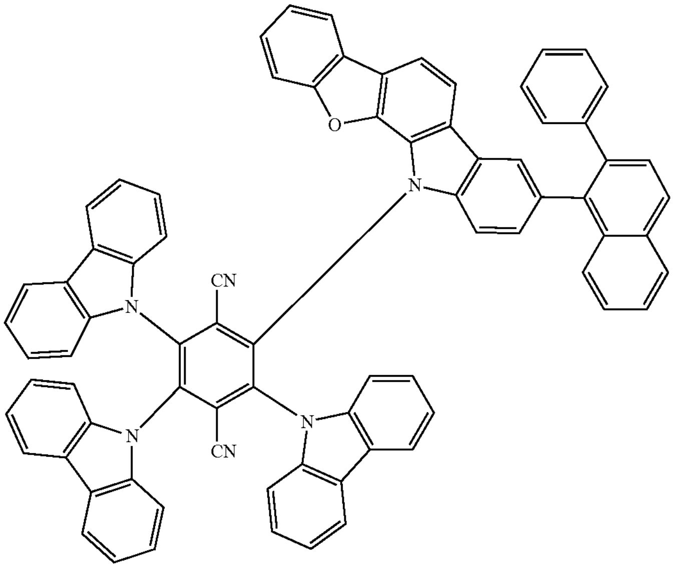
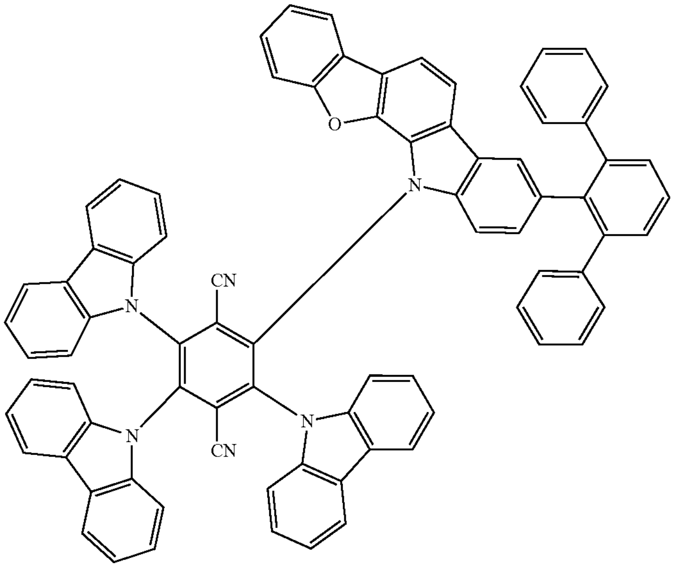
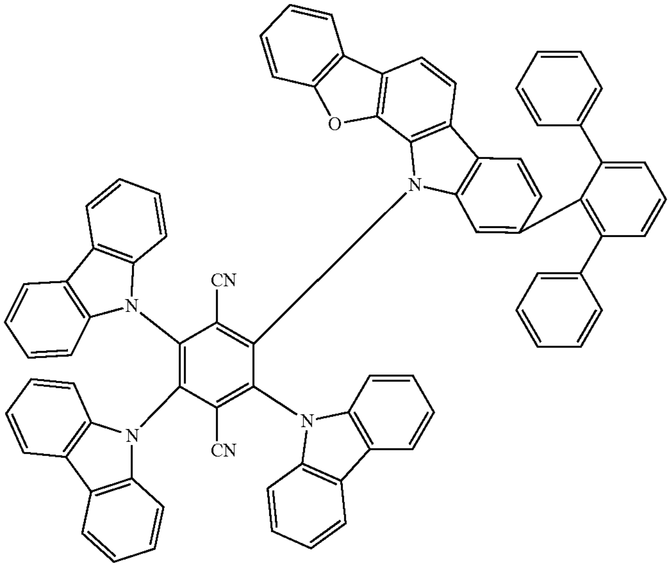

-continued
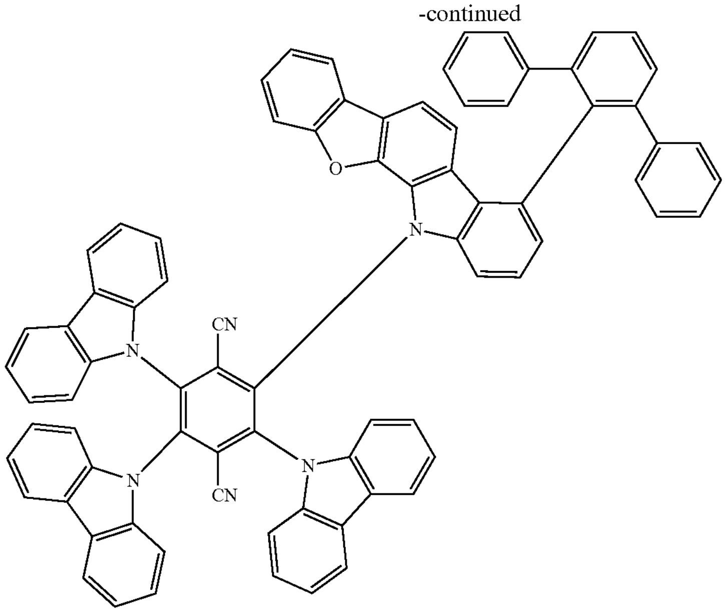
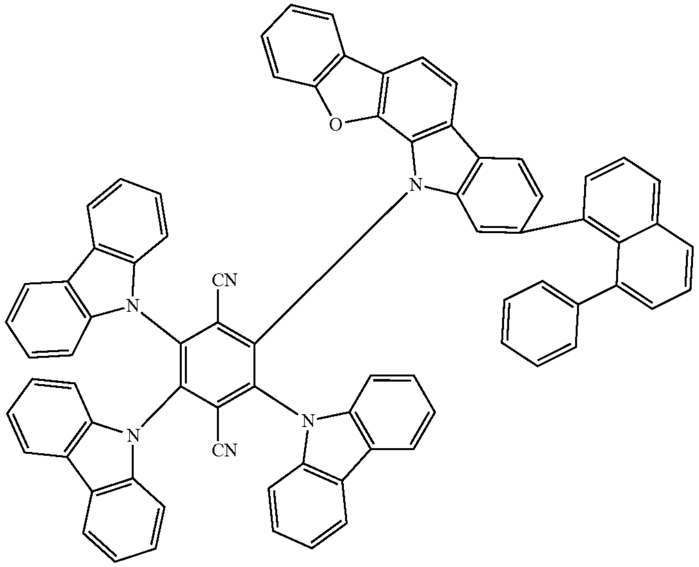
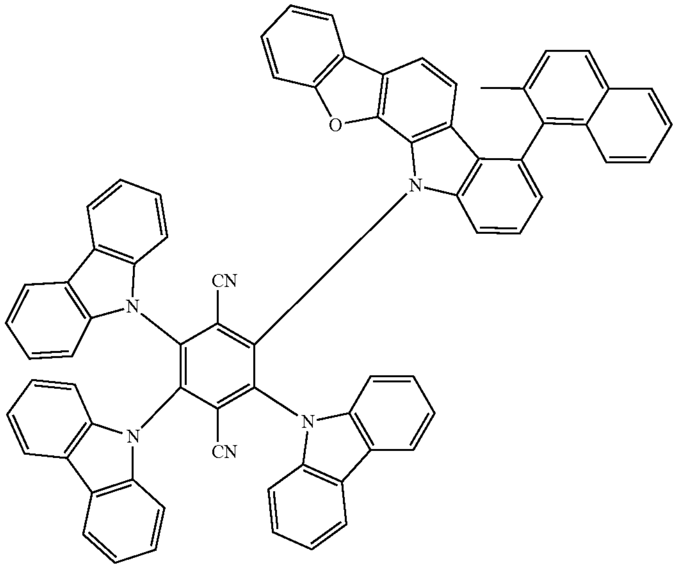

-continued
[Formula 46]
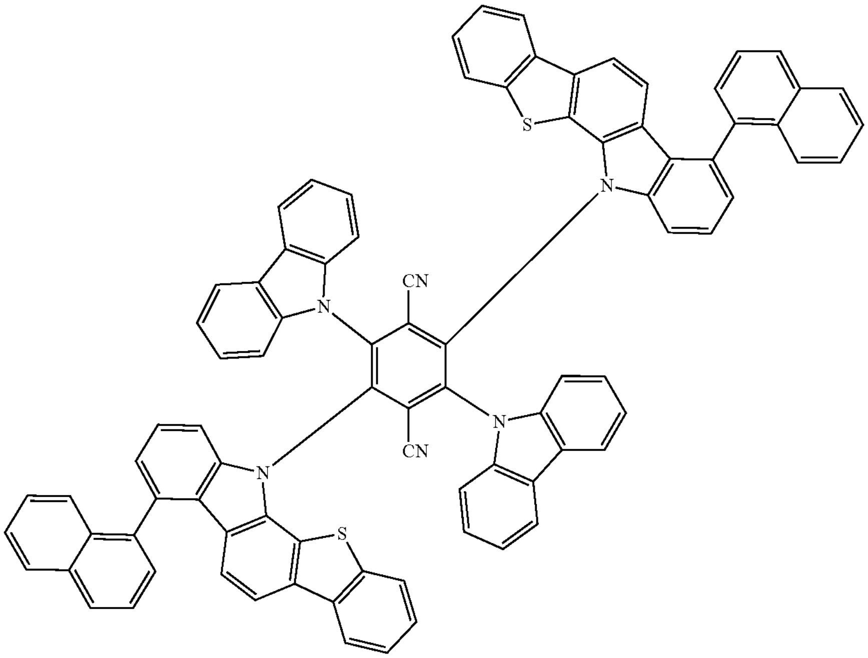
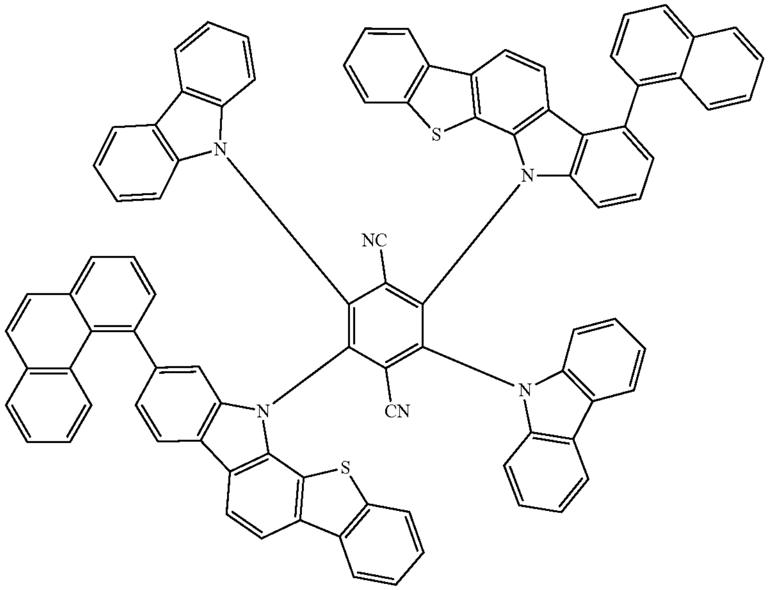

-continued
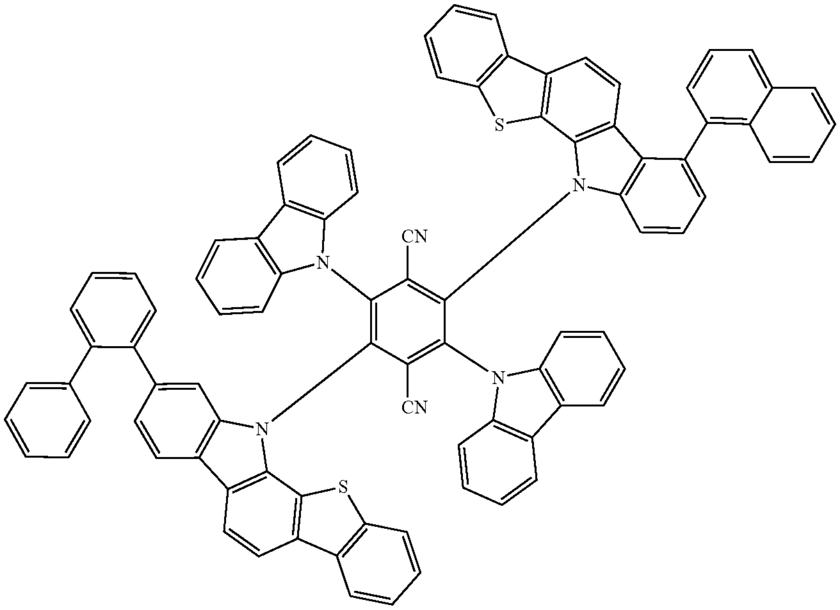
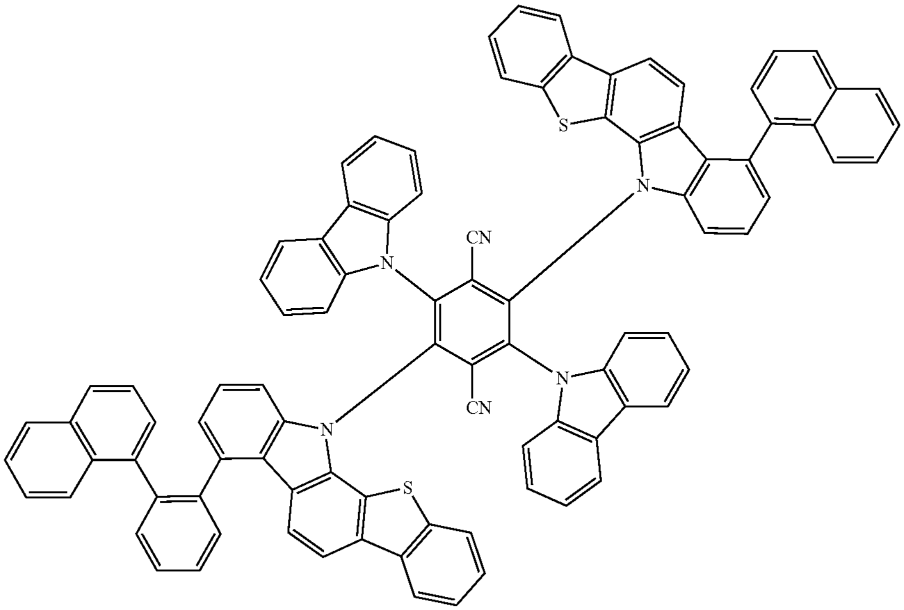

-continued
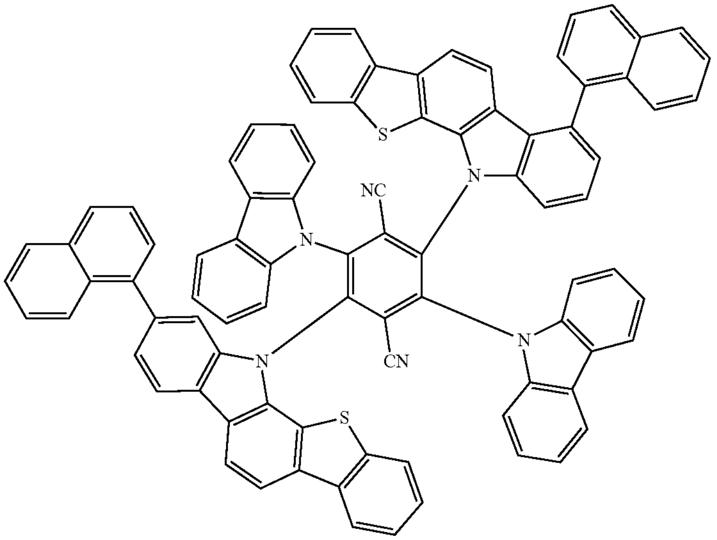
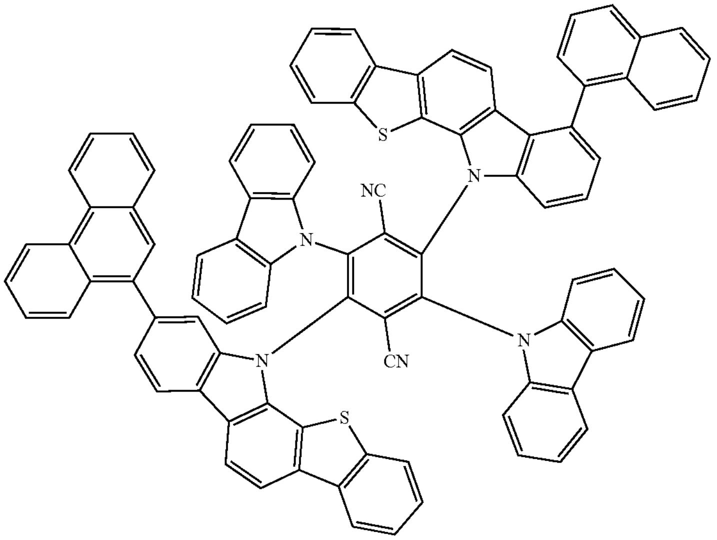
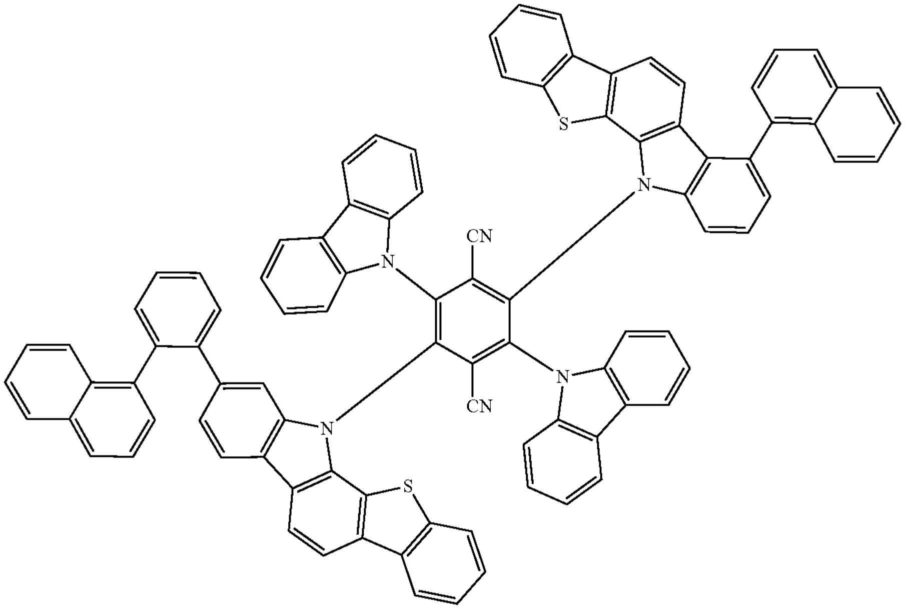

-continued
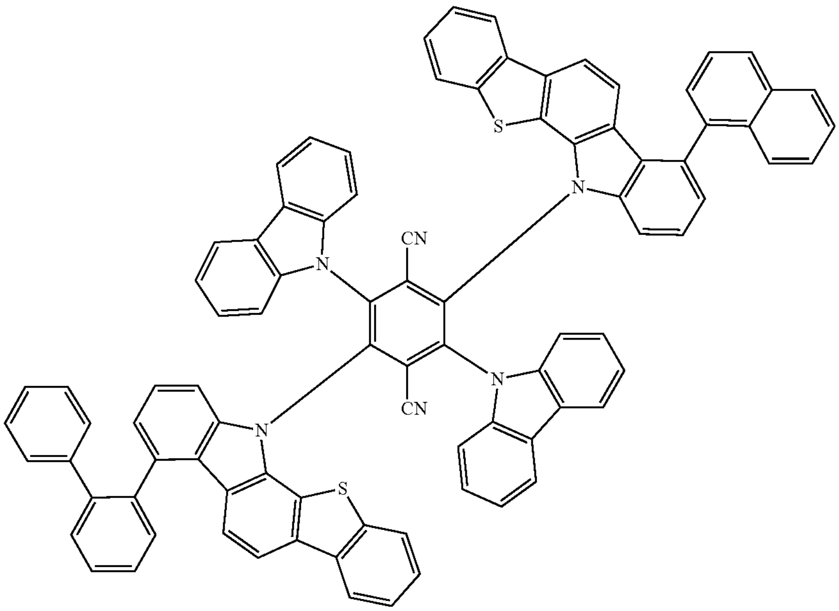
[Formula 47]
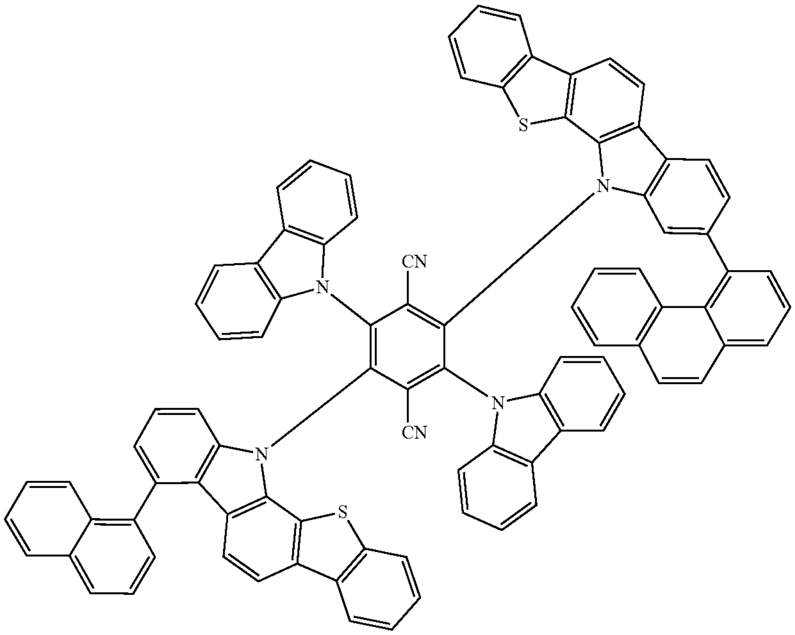

-continued
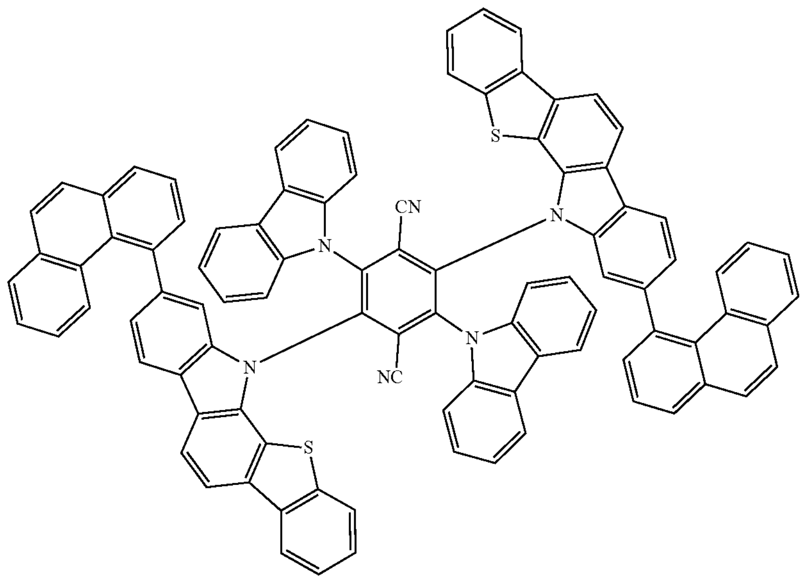
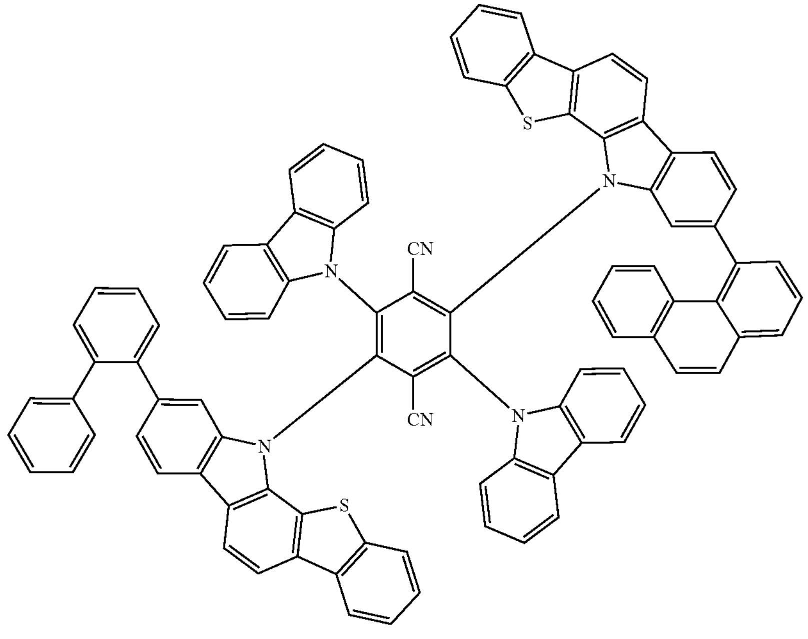

-continued
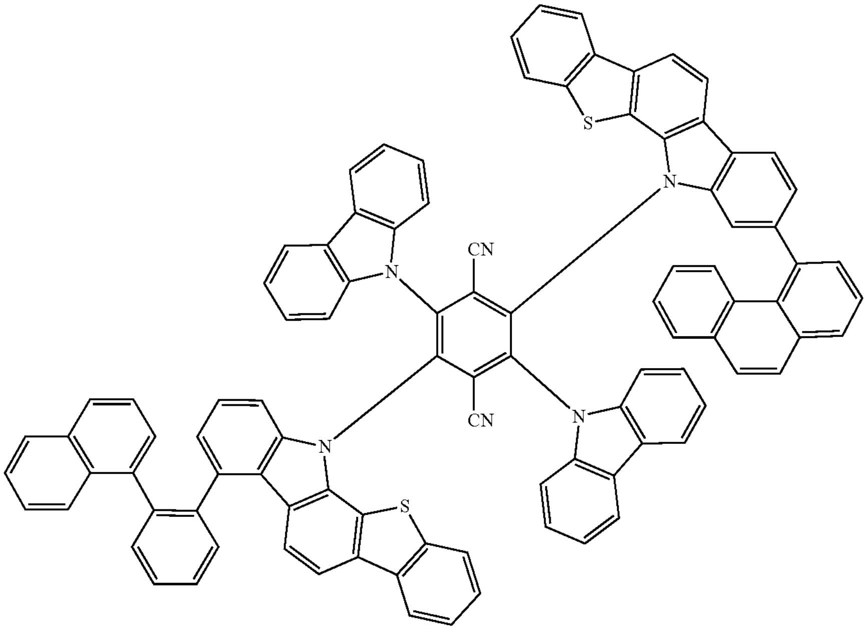
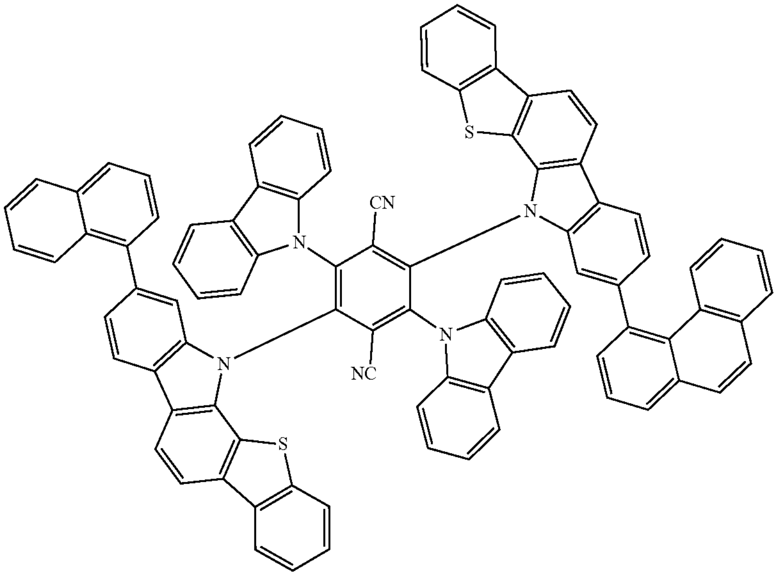

-continued
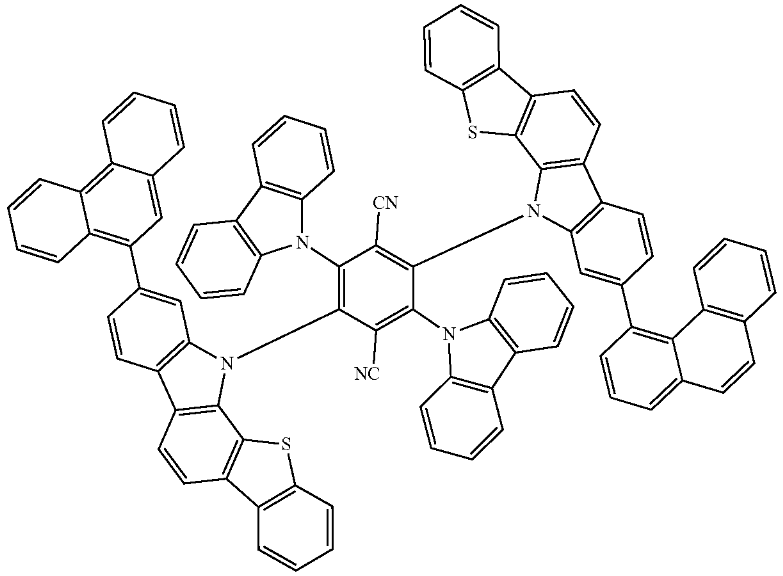
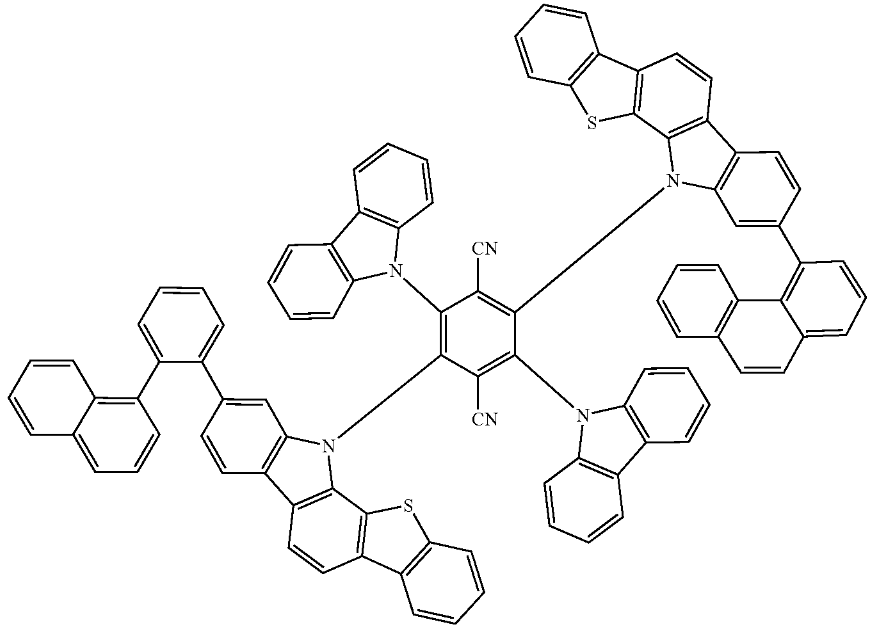

-continued
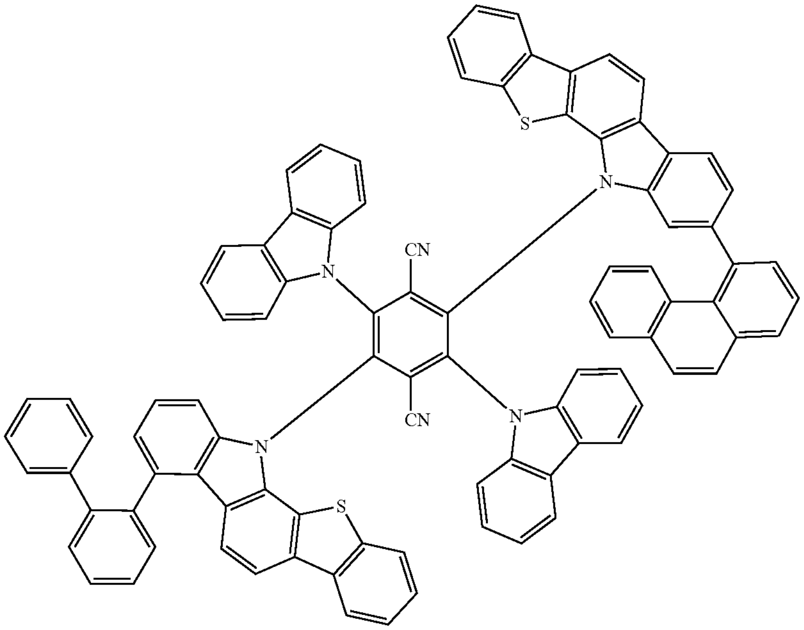
[Formula 48]
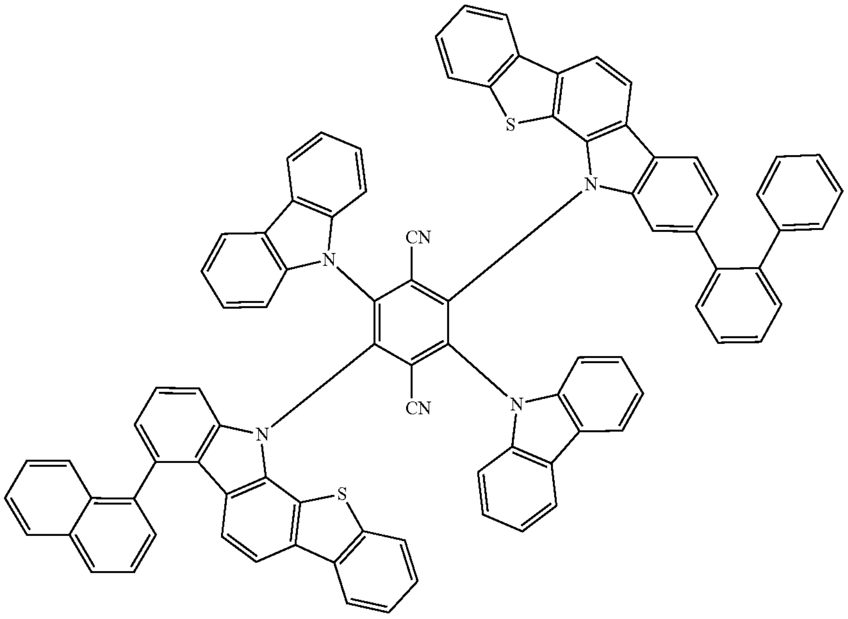

-continued
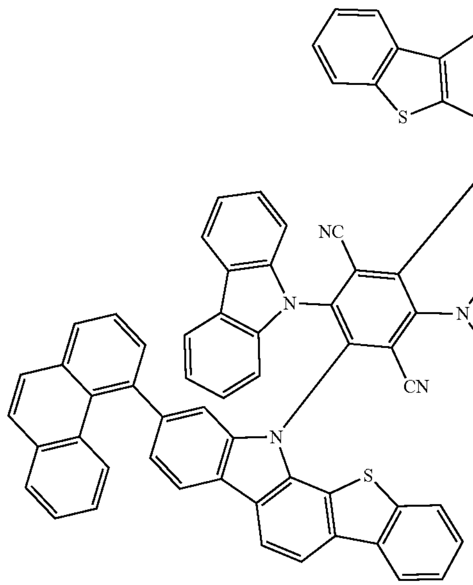
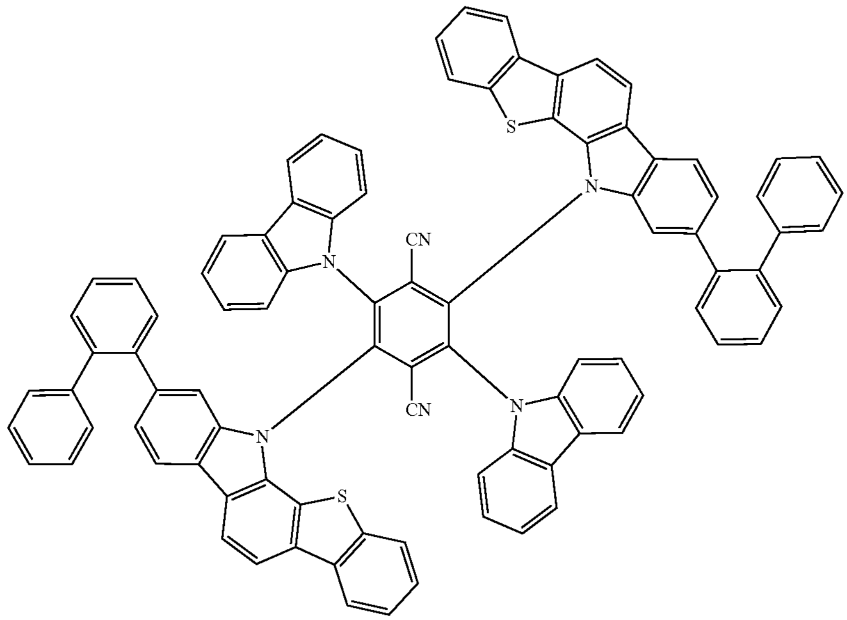

-continued
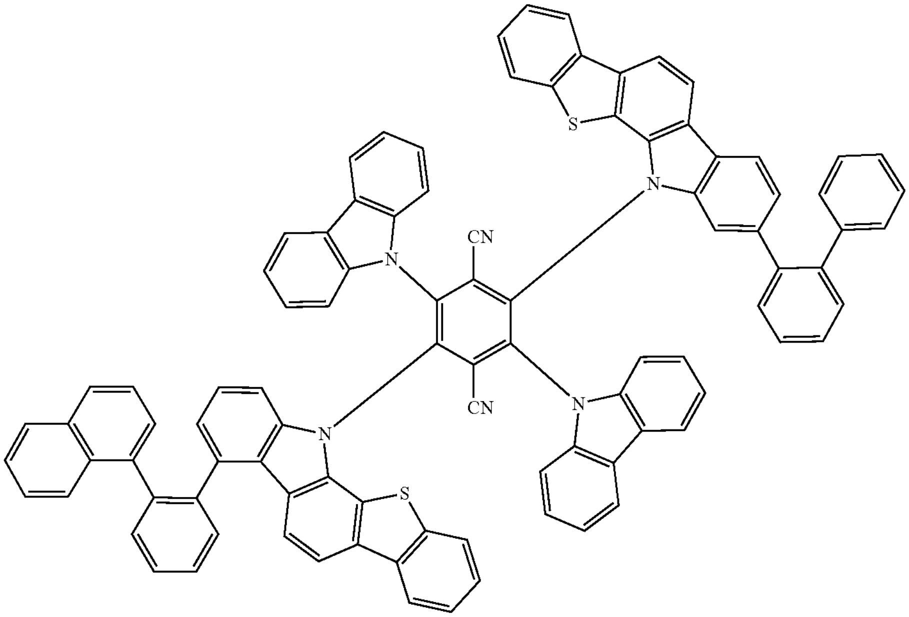
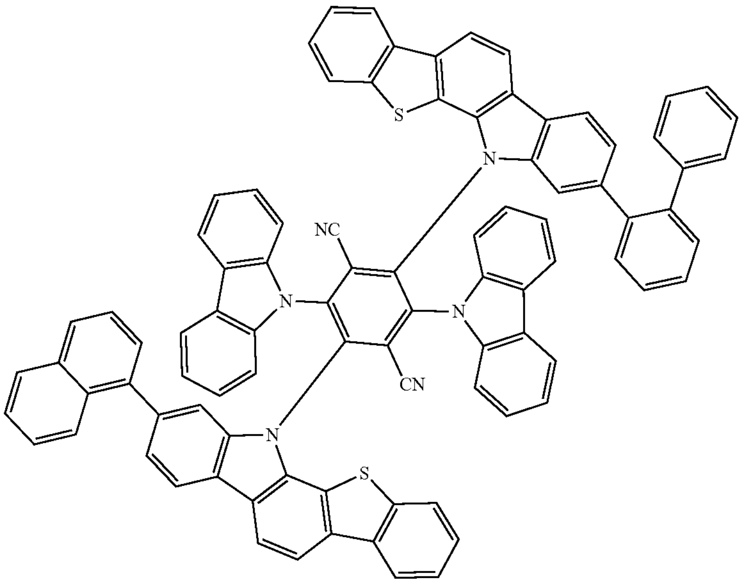

-continued
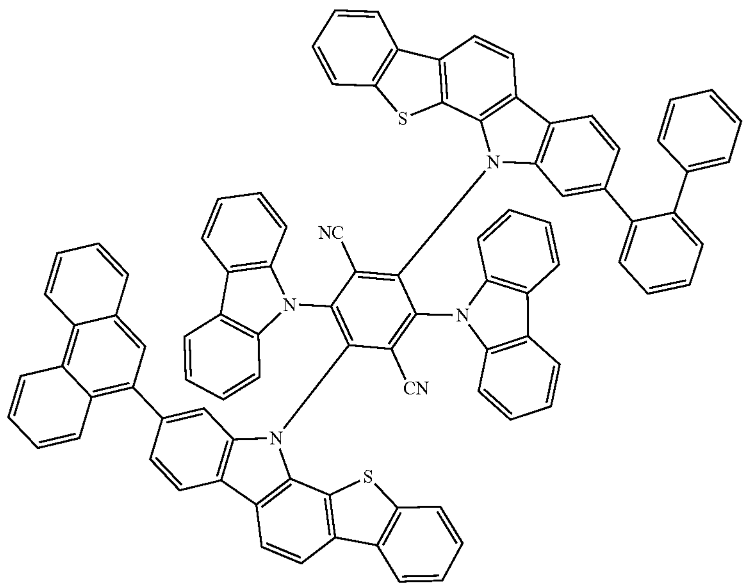
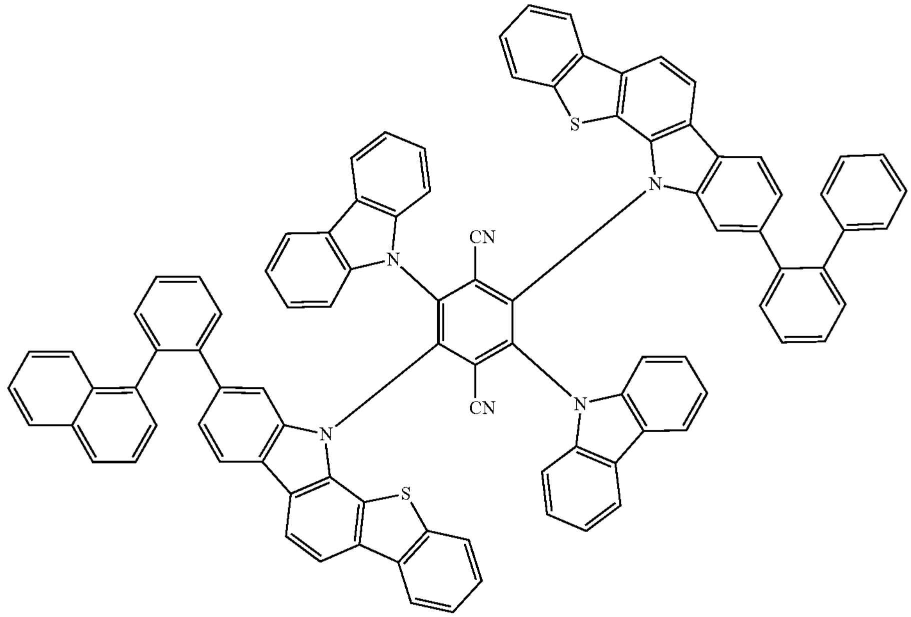

-continued
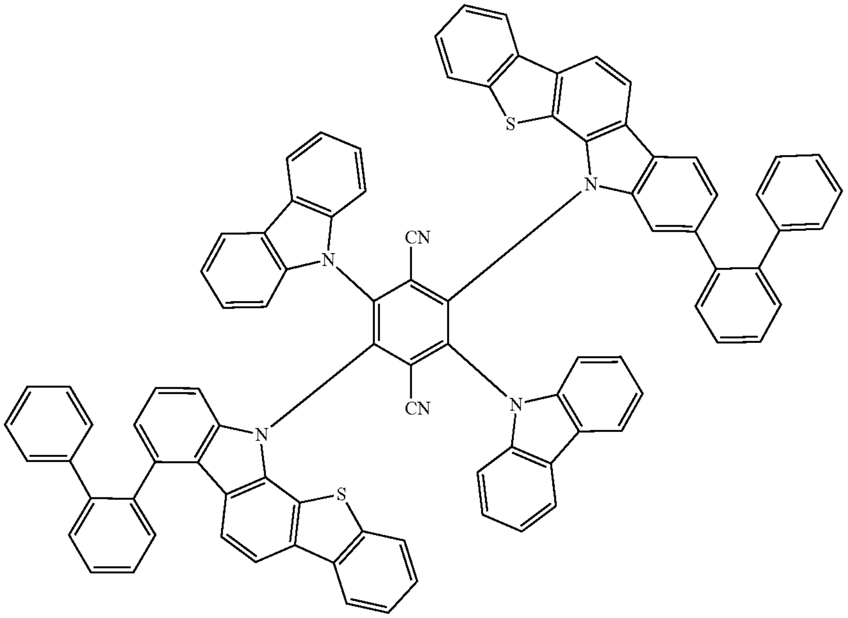
[Formula 49]
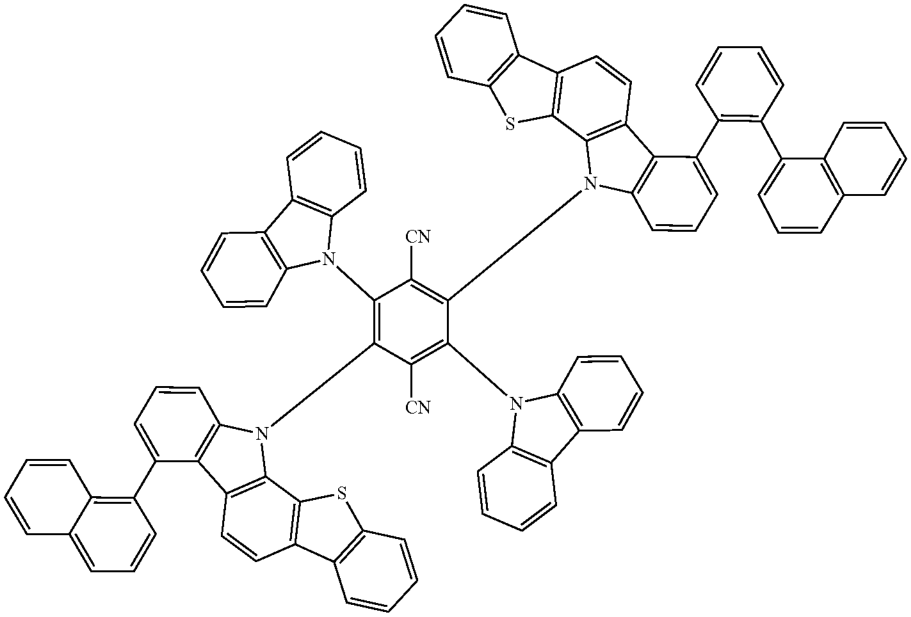

-continued
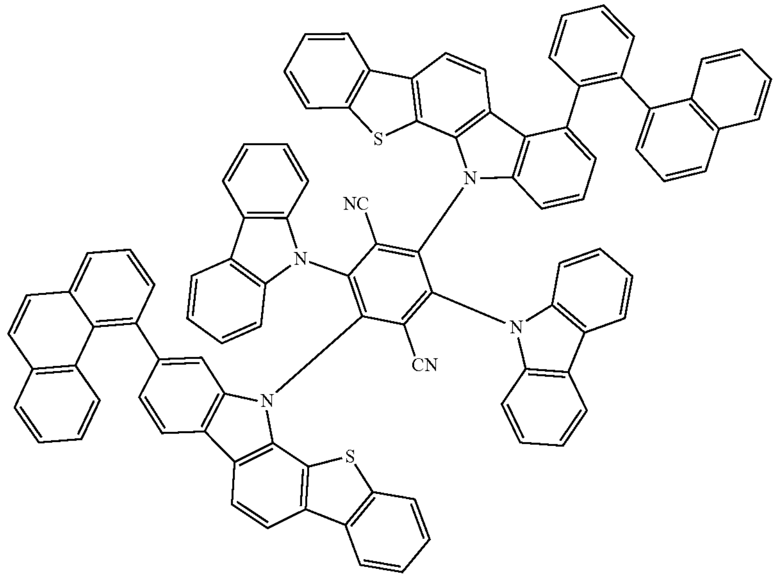
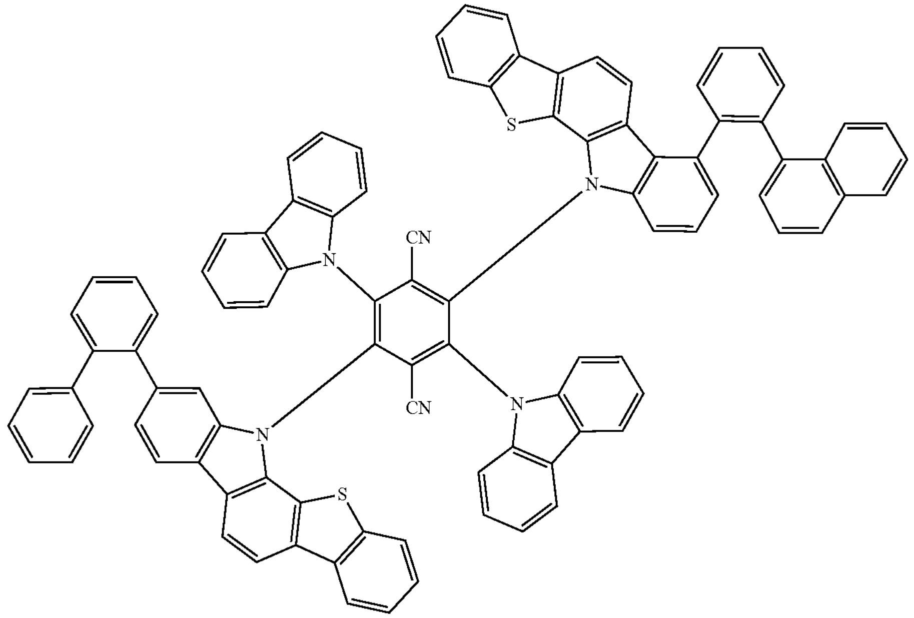

-continued
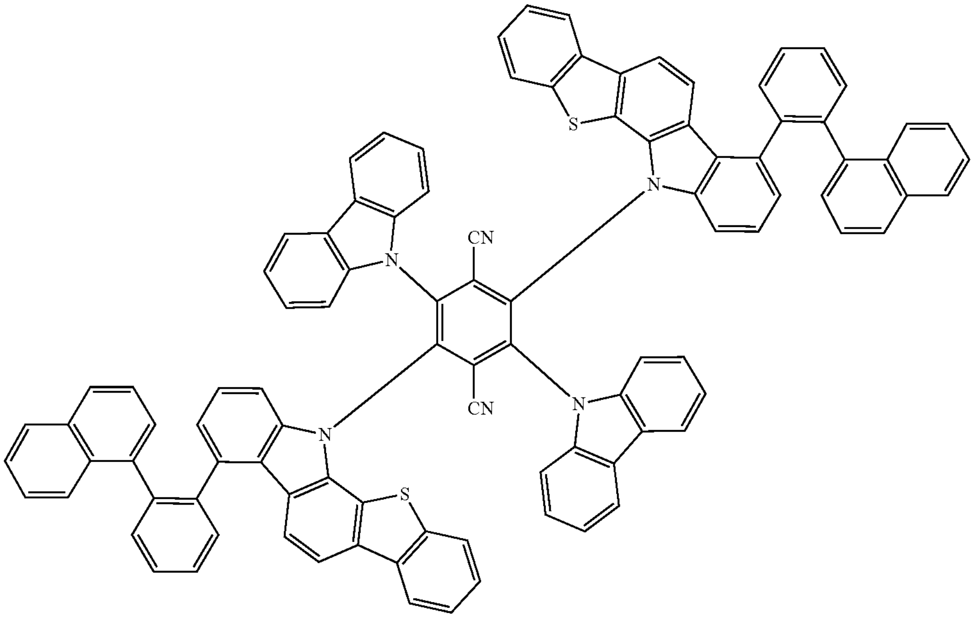
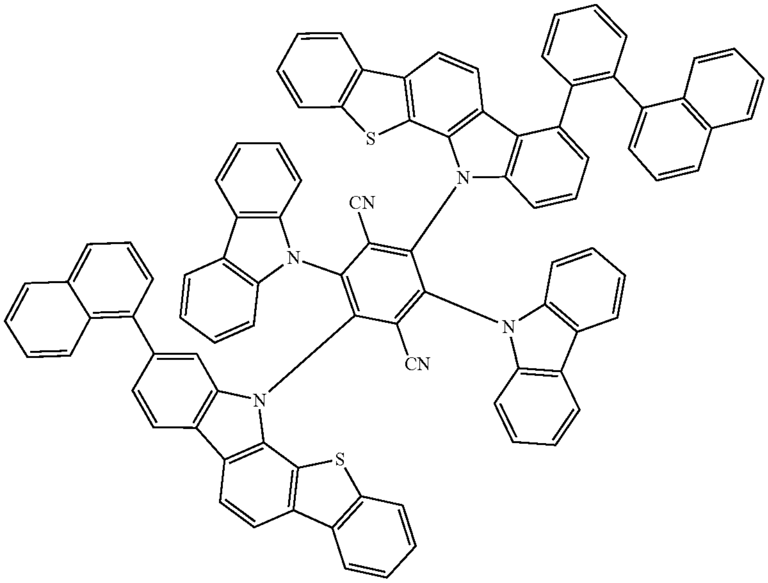

-continued
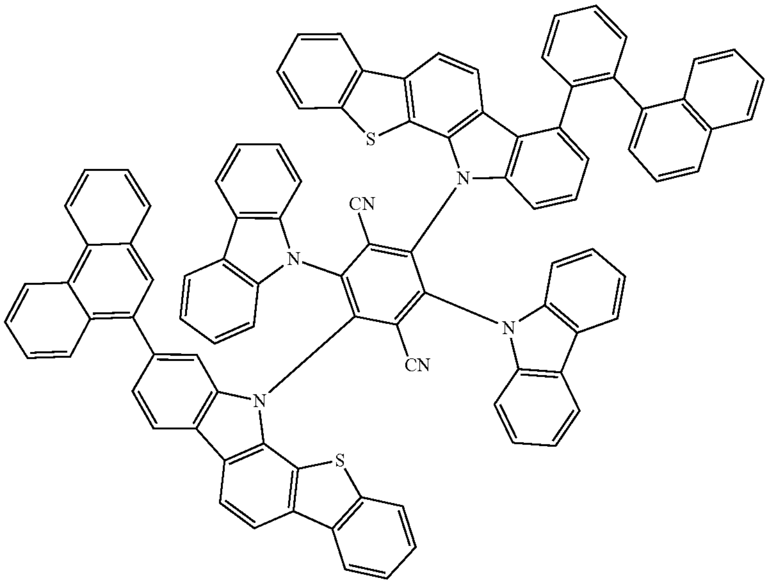
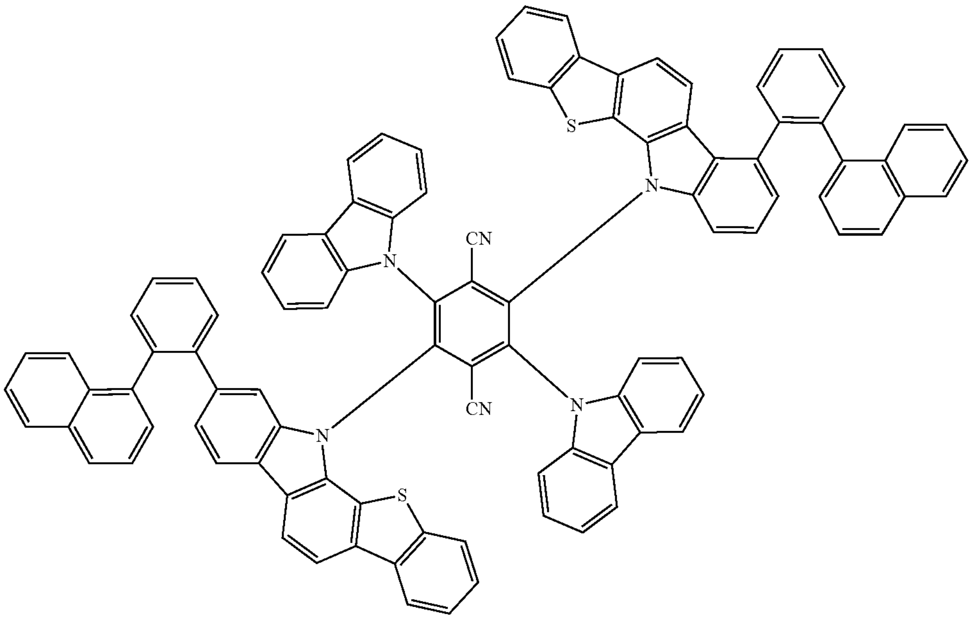

-continued
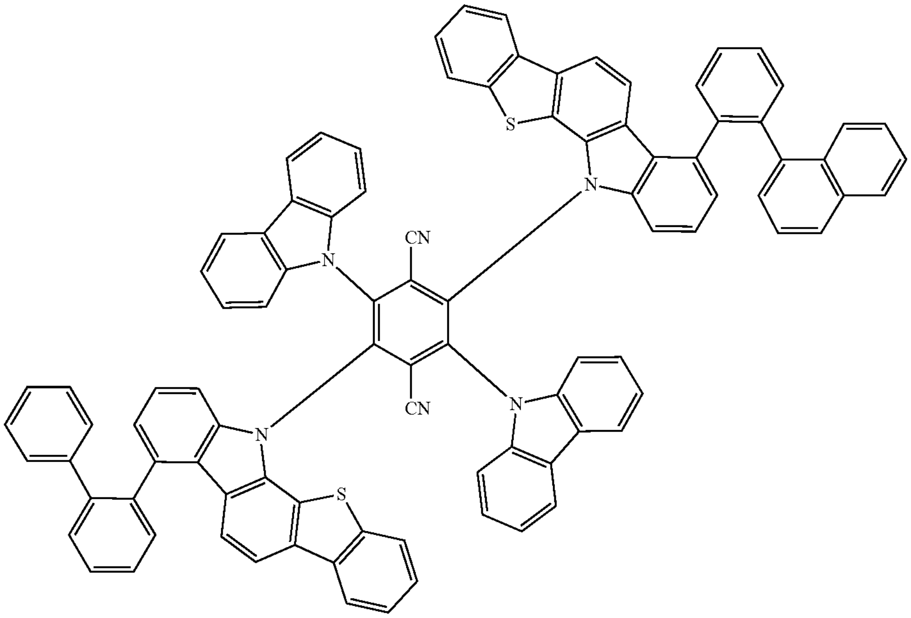
[Formula 50]
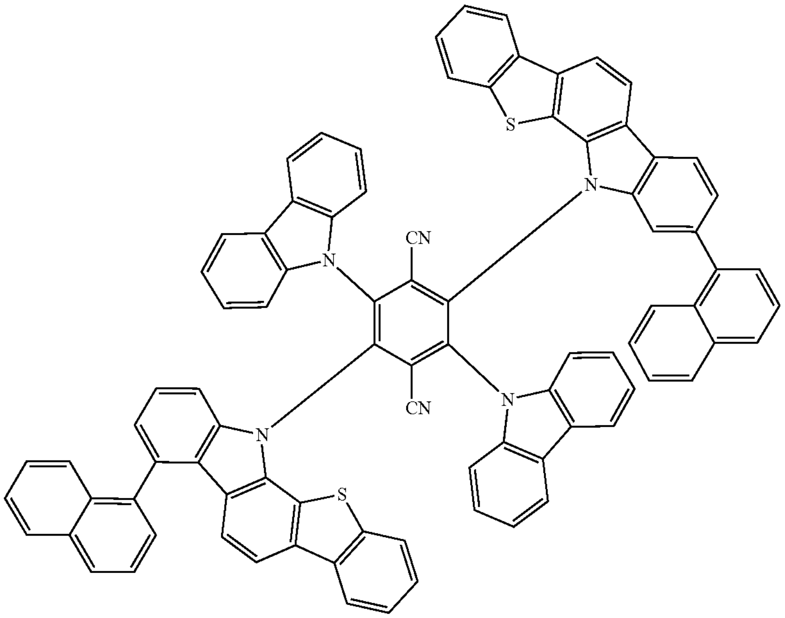

-continued
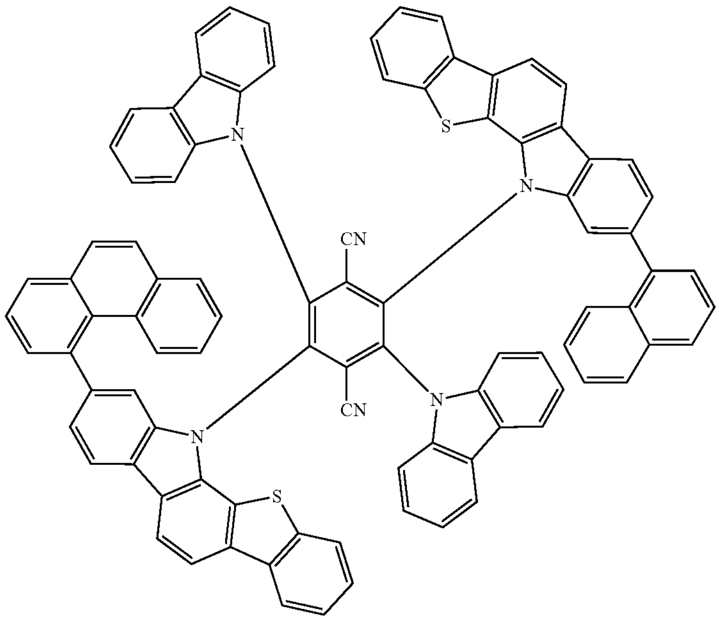
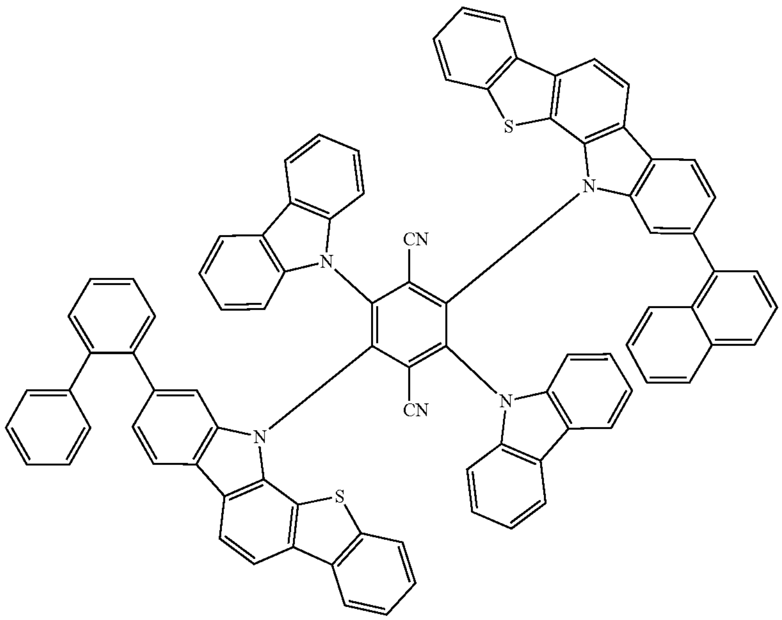

-continued
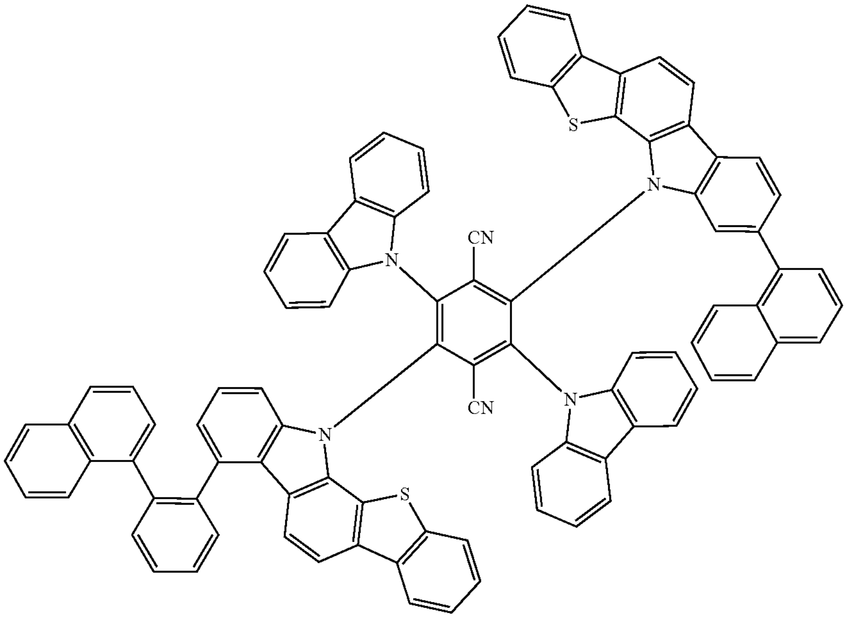
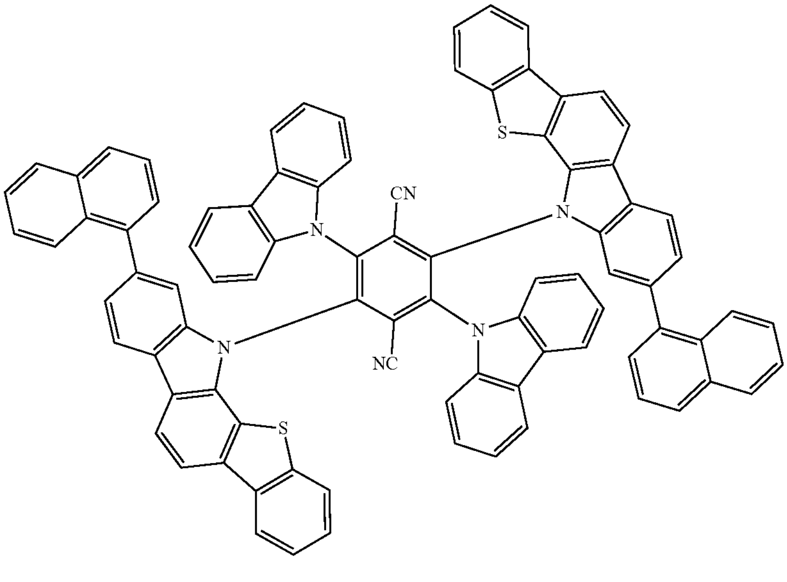

-continued
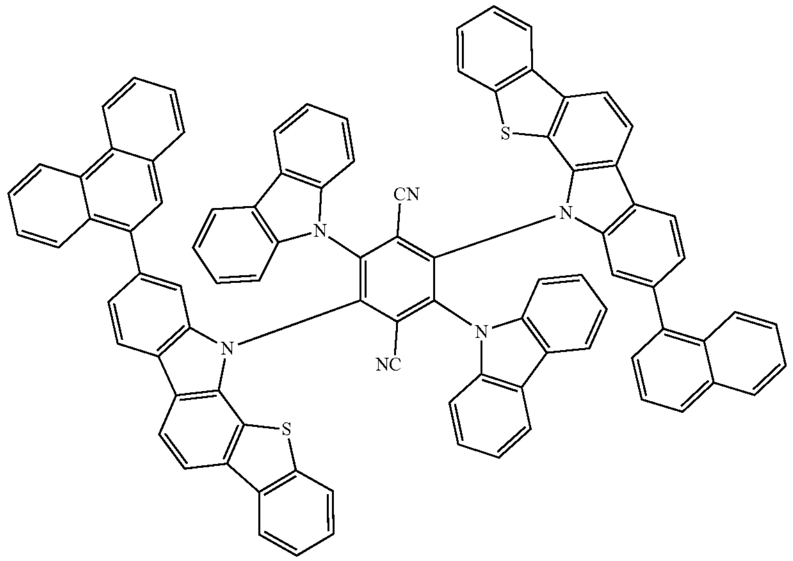
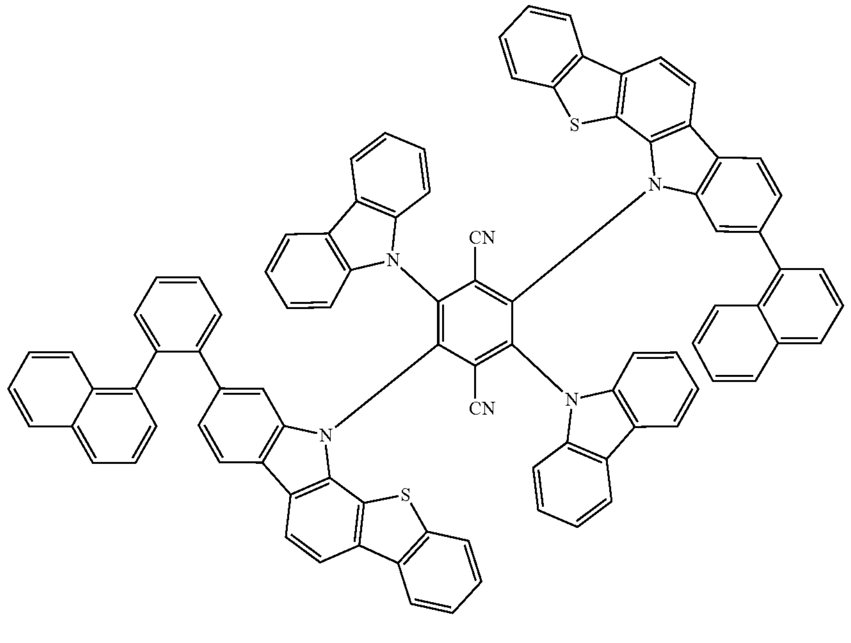

-continued
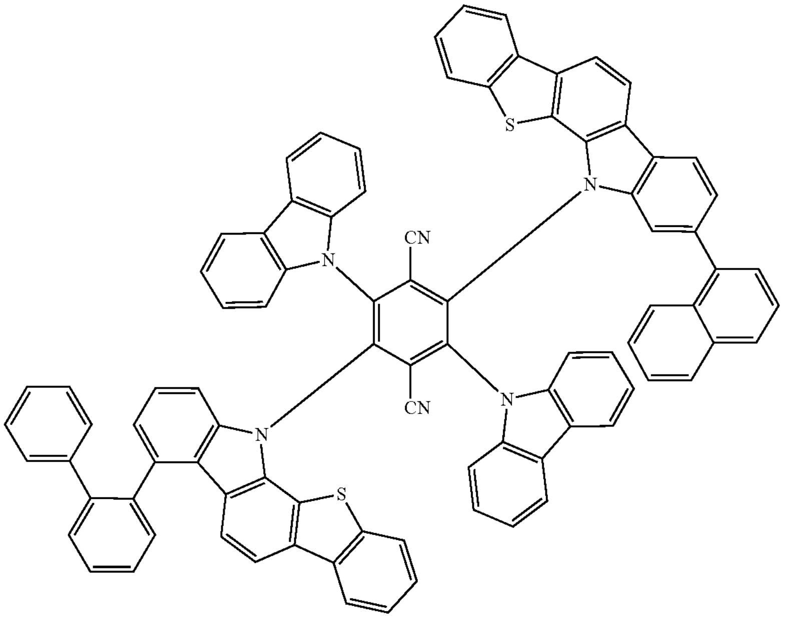
[Formula 51]
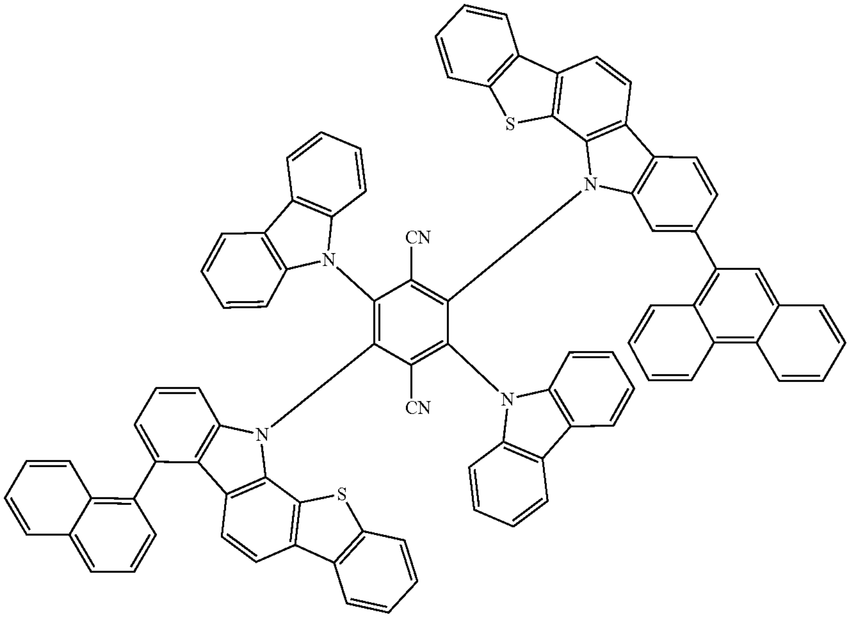

-continued
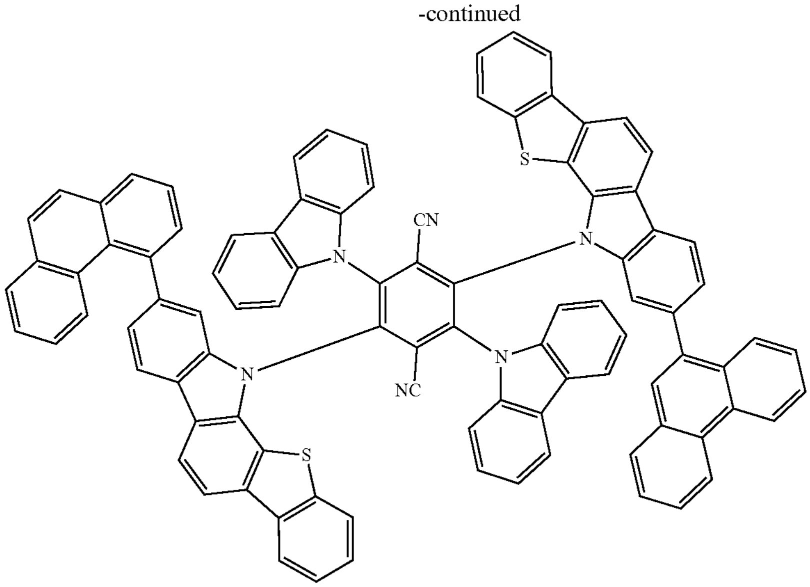
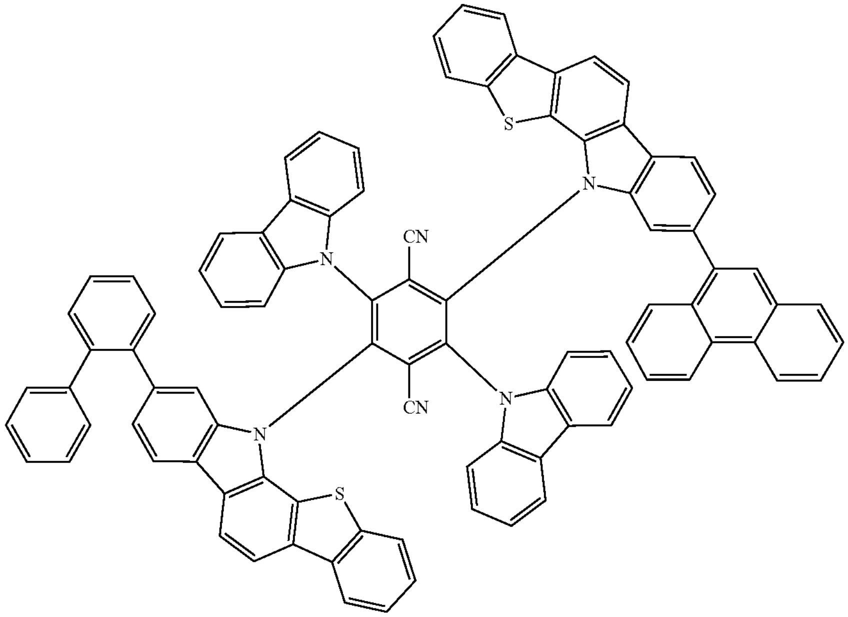

-continued
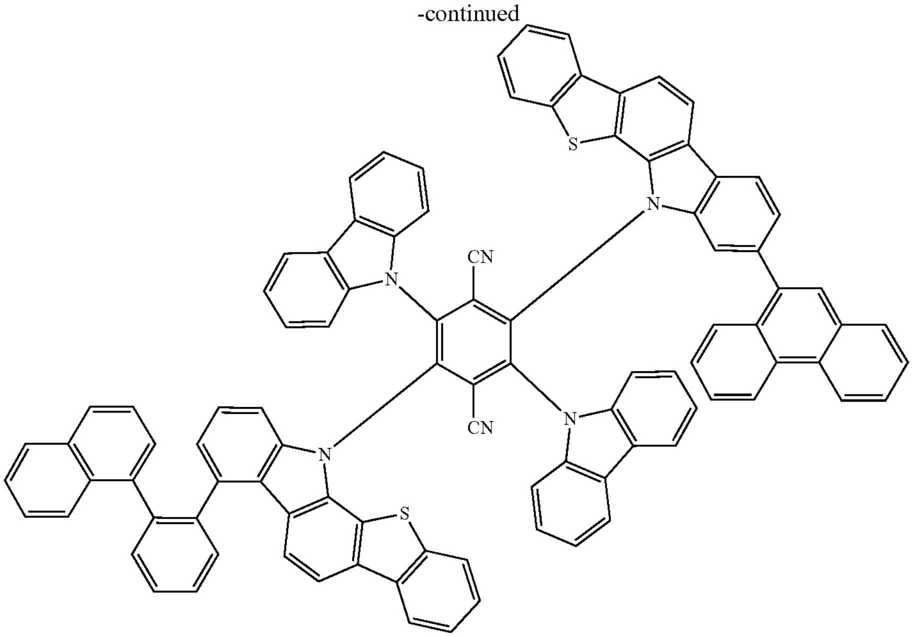
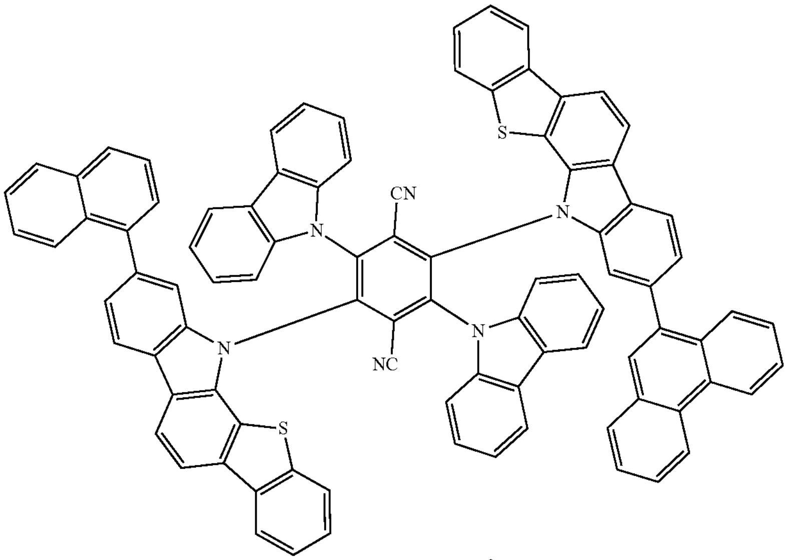
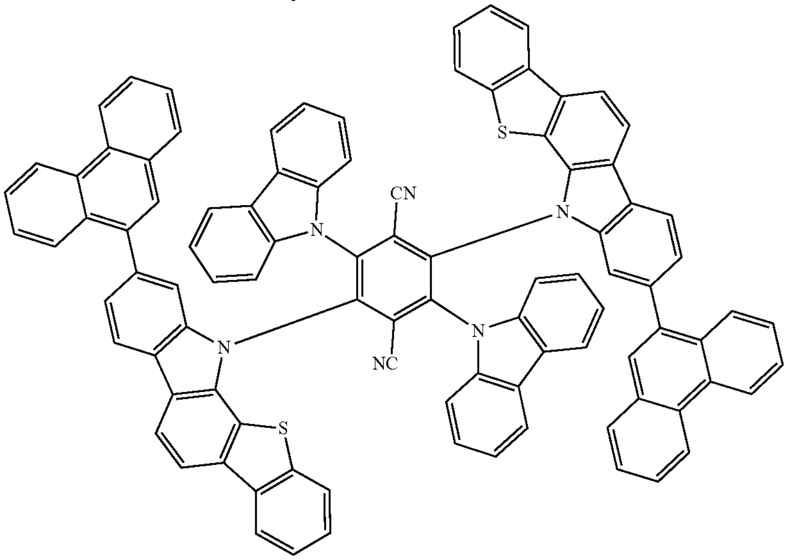

-continued
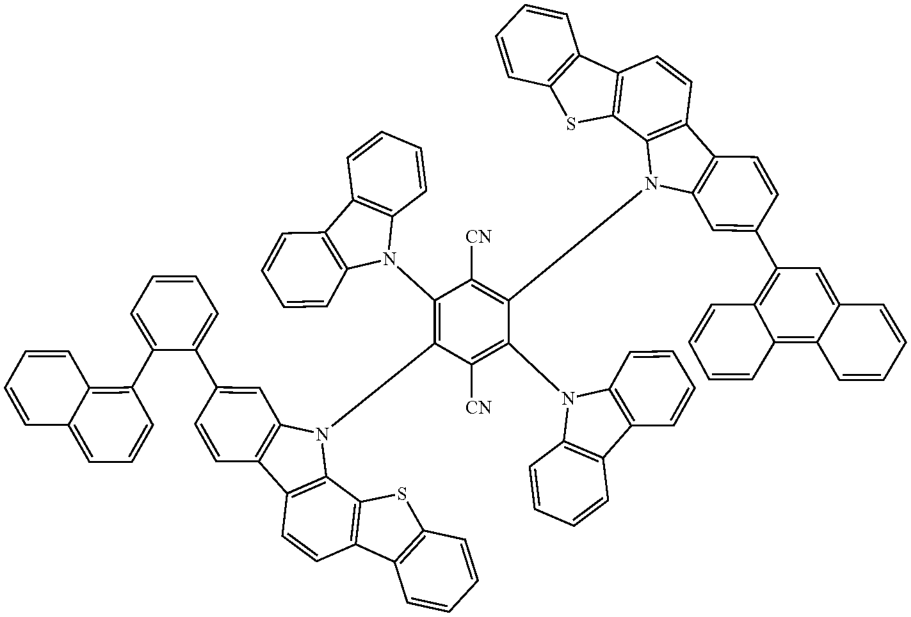
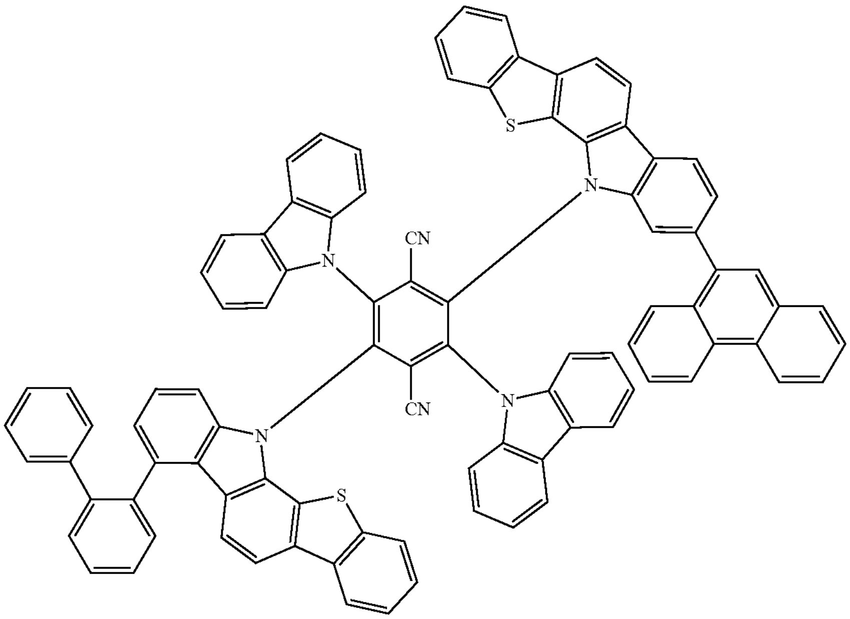

-continued
[Formula 52]
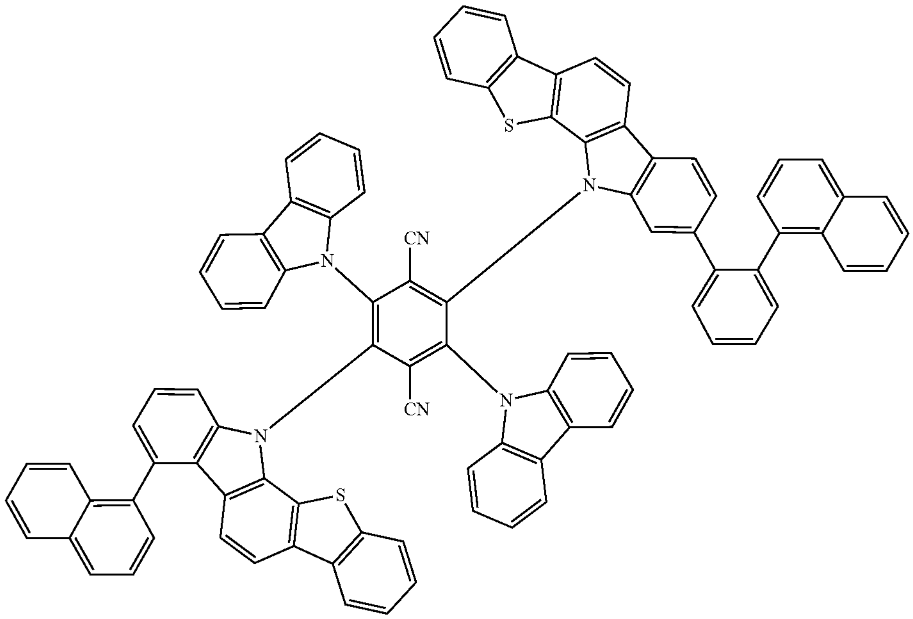
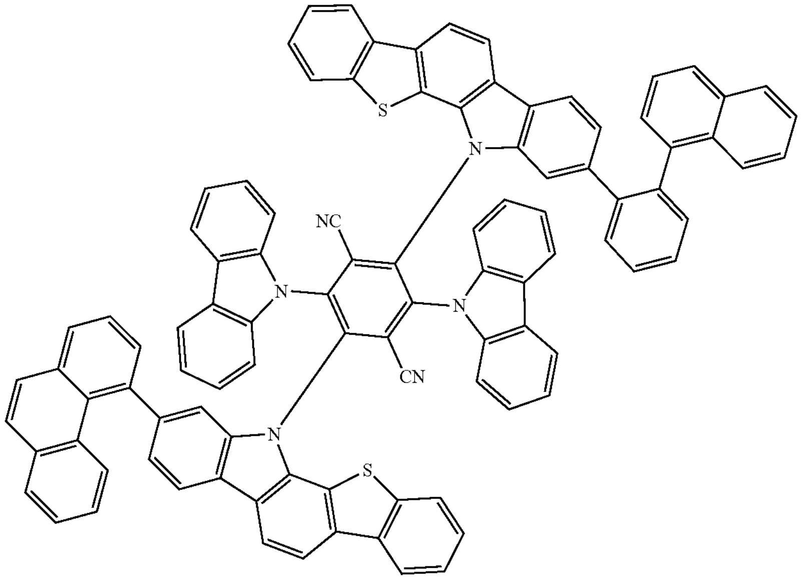

-continued
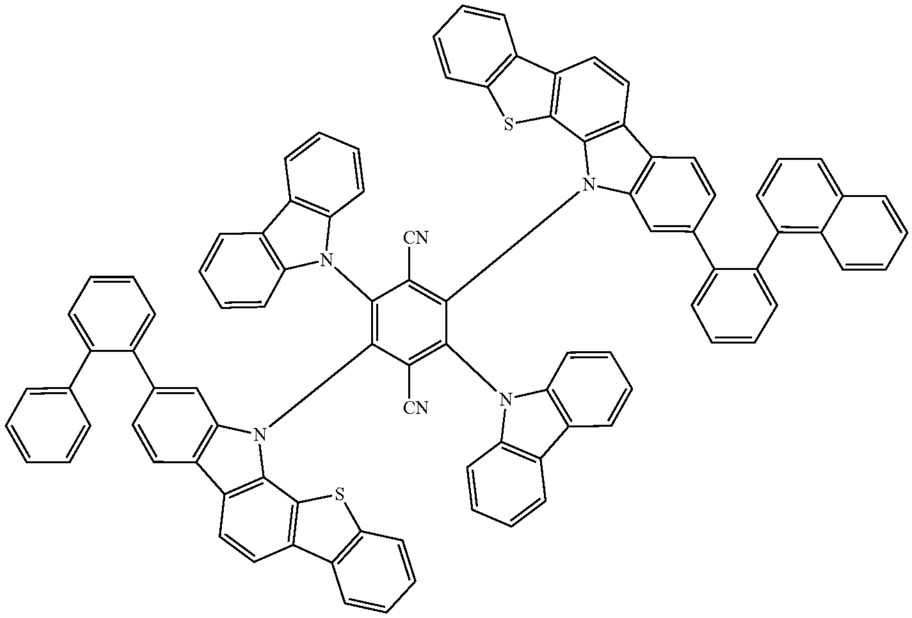
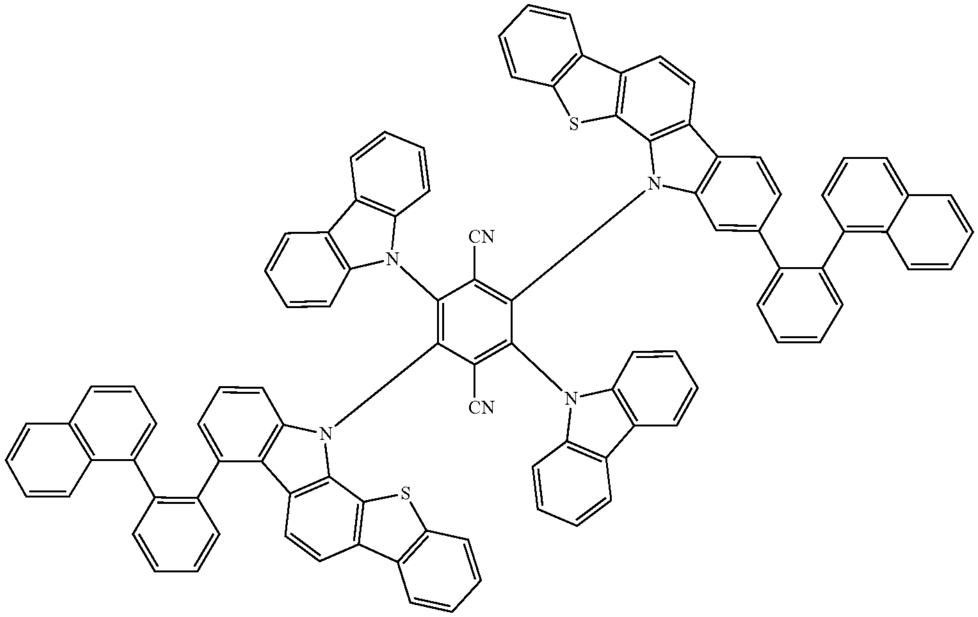

-continued
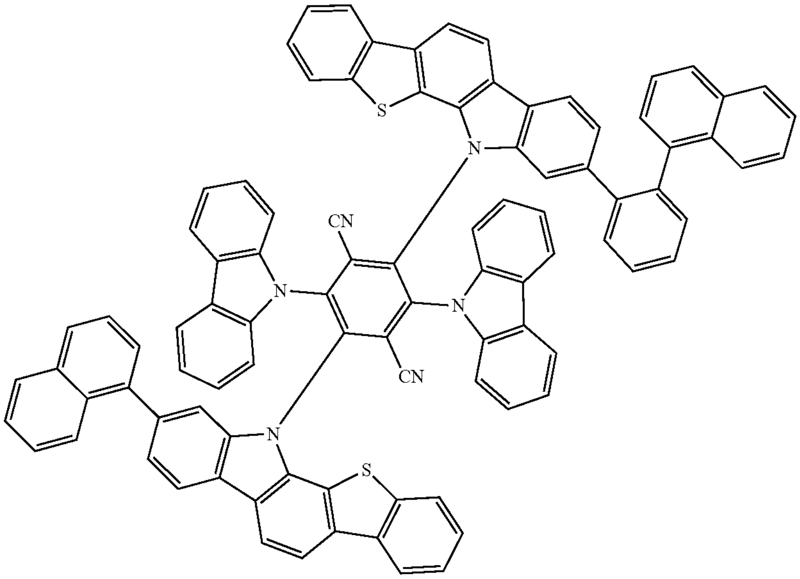
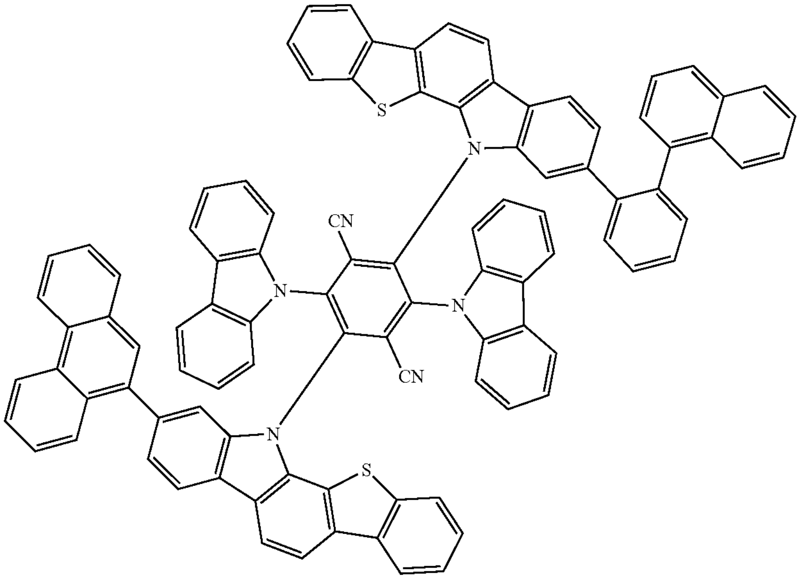
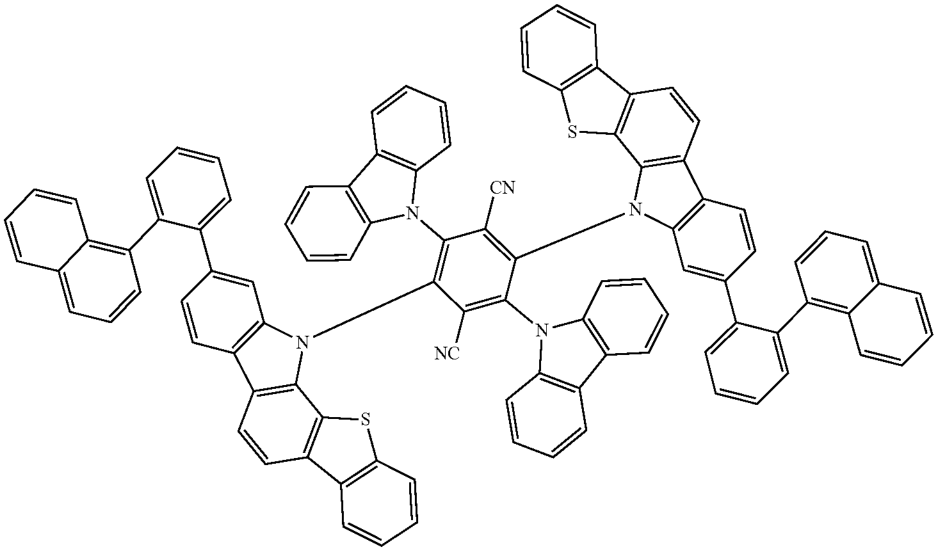

-continued
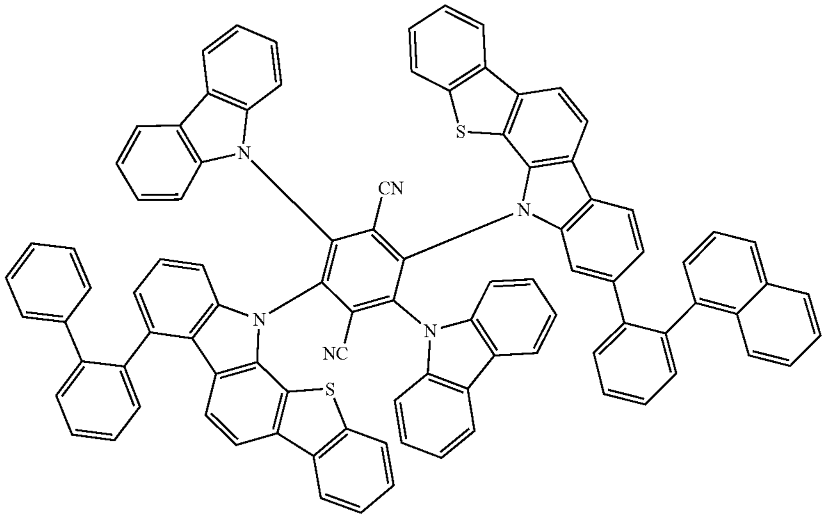
[Formula 53]
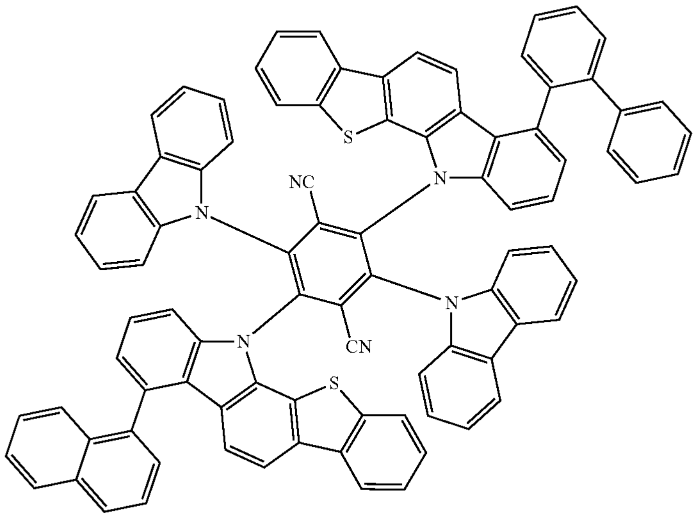
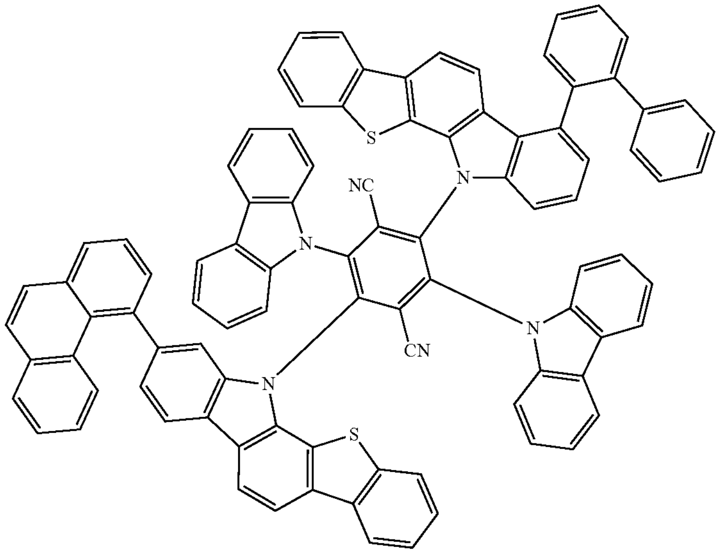

-continued
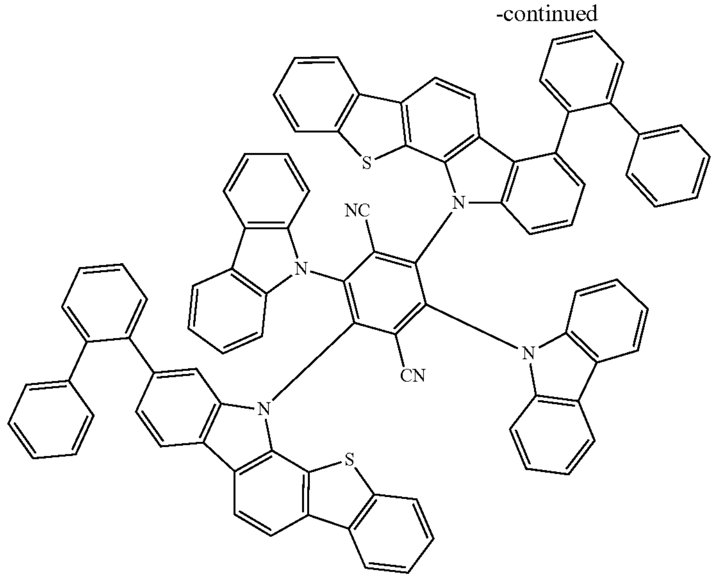
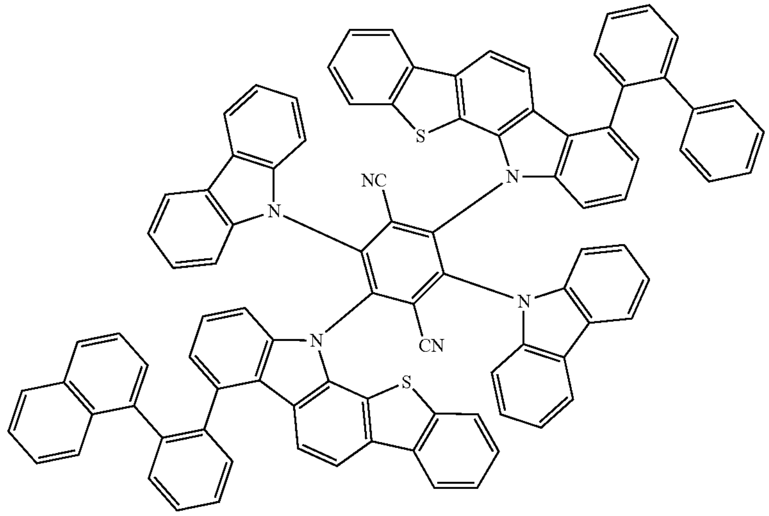
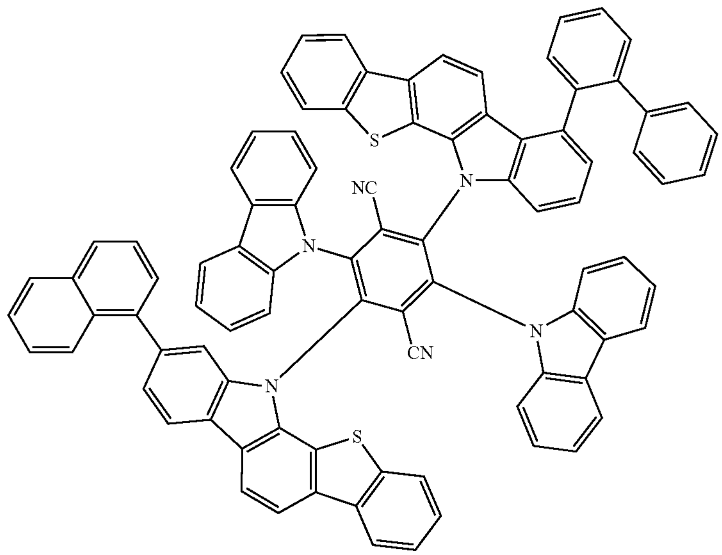

-continued
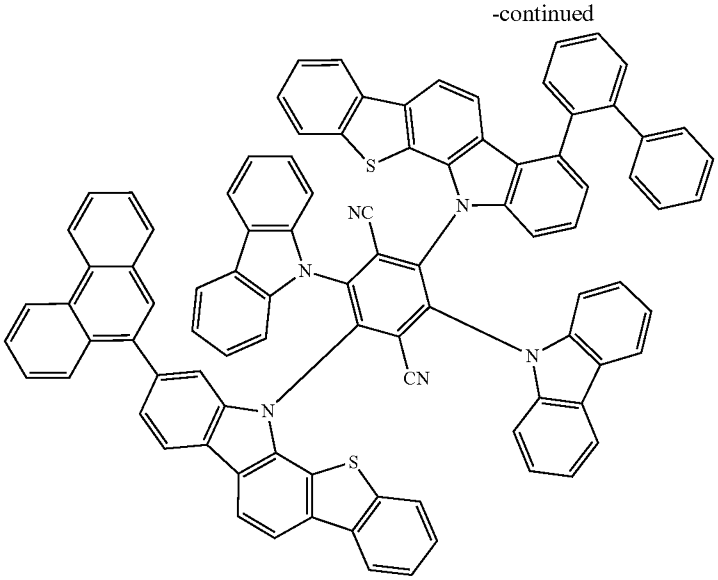
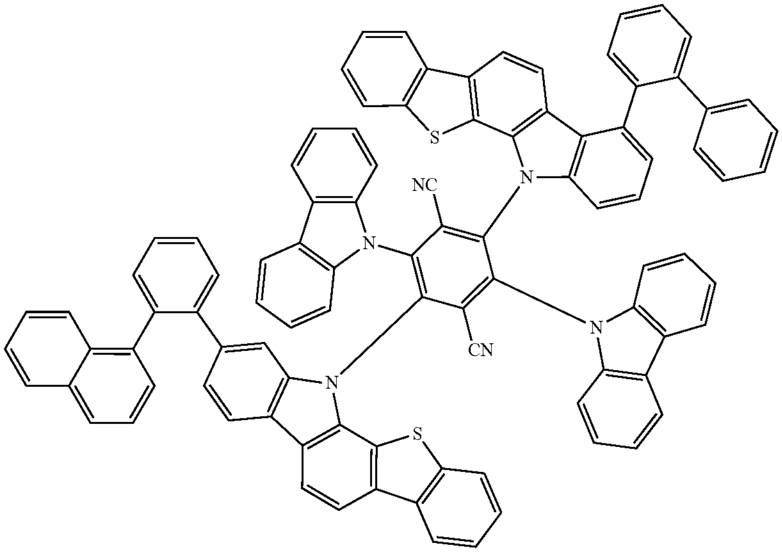
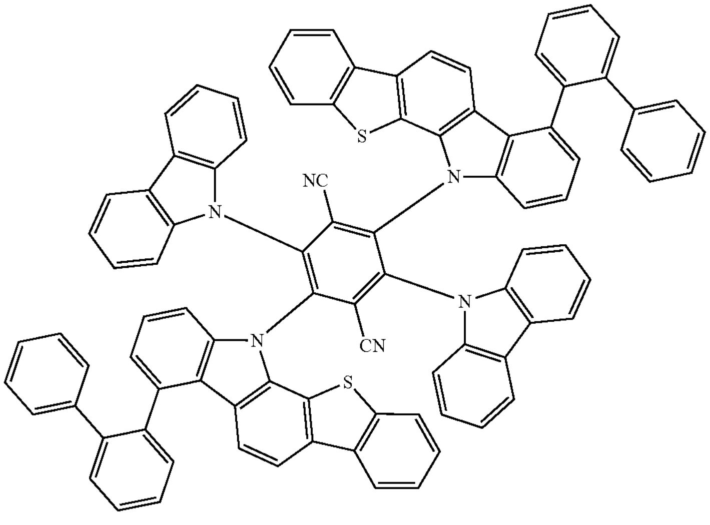

-continued
[Formula 54]
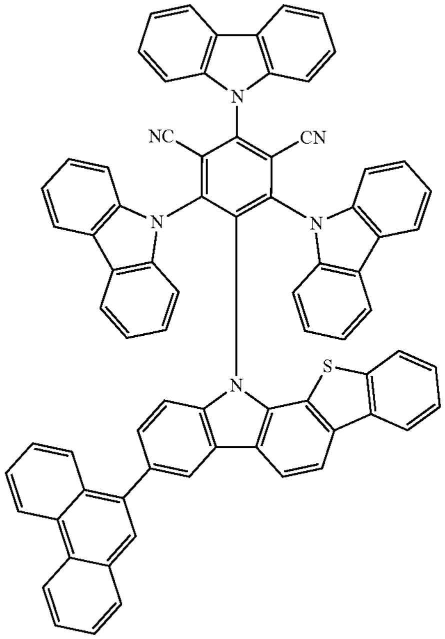
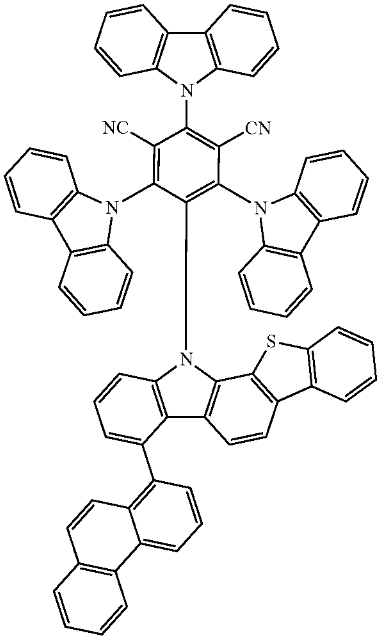
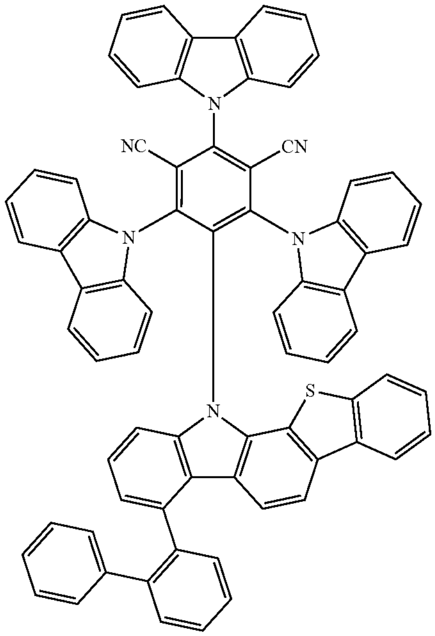
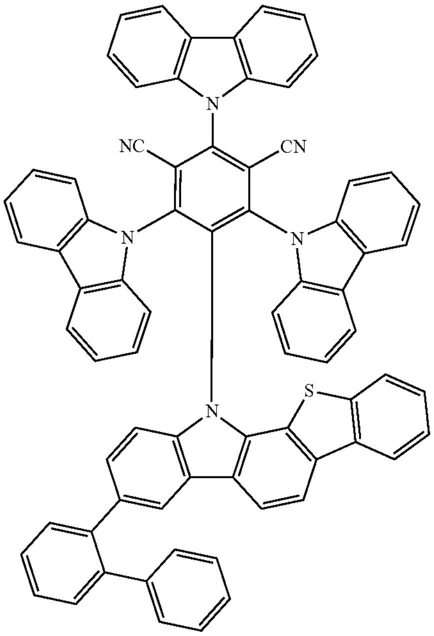

-continued
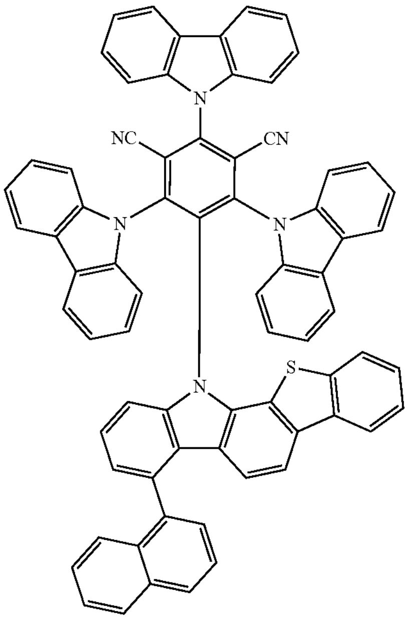
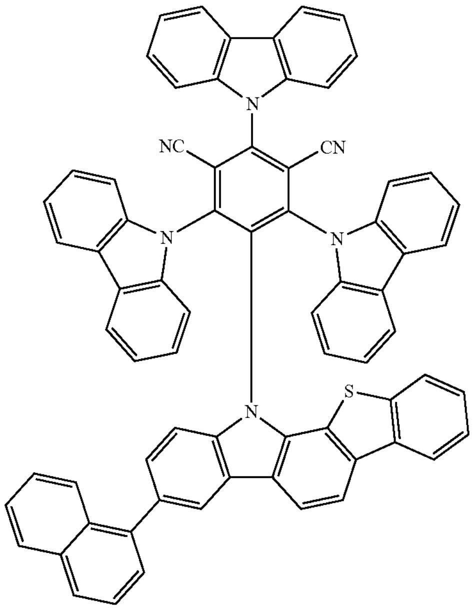
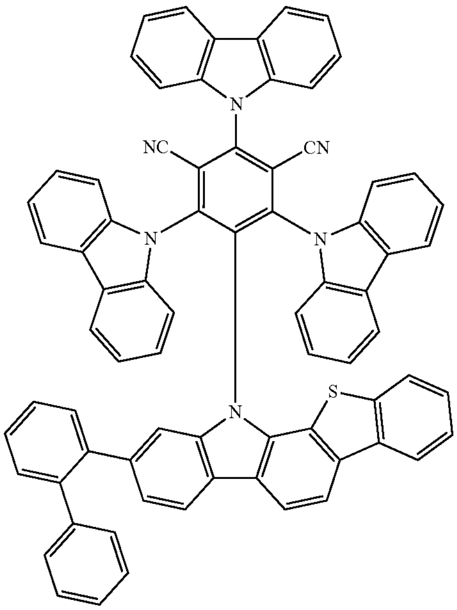
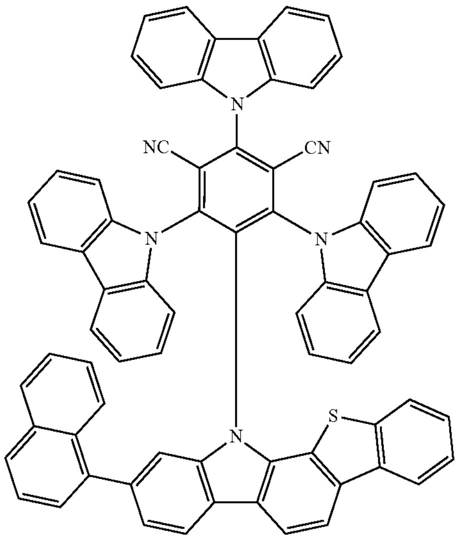

-continued
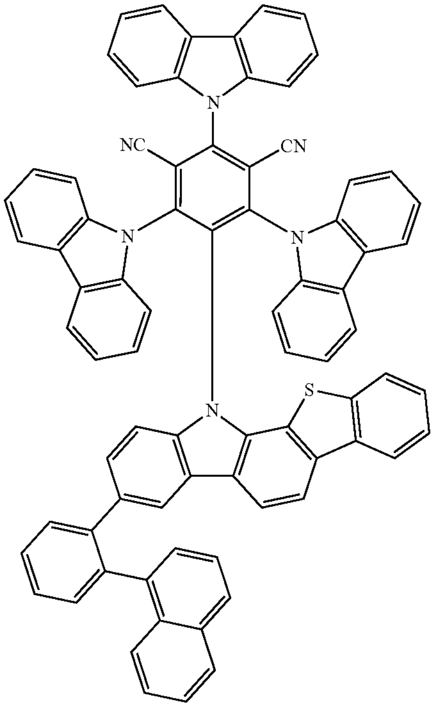
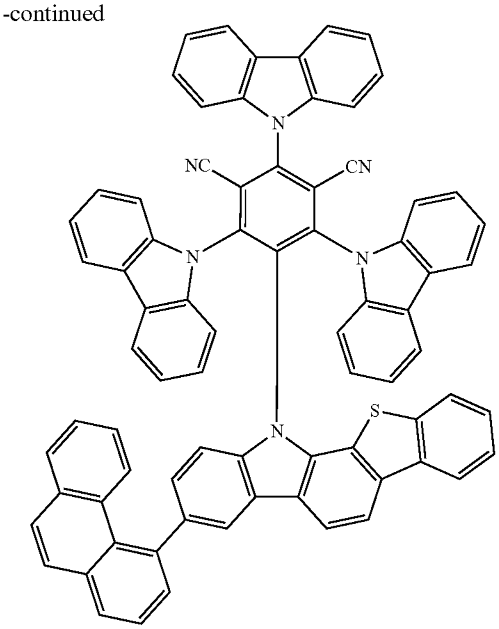
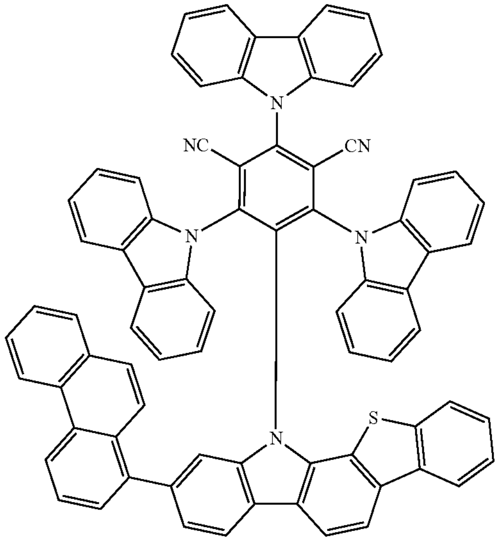
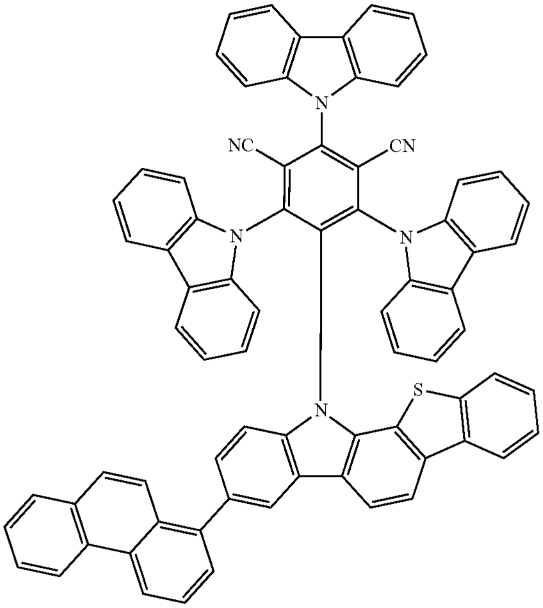

-continued
[Formula 55]
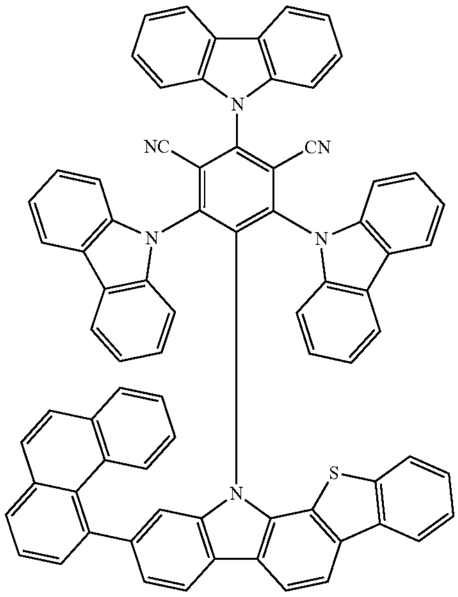
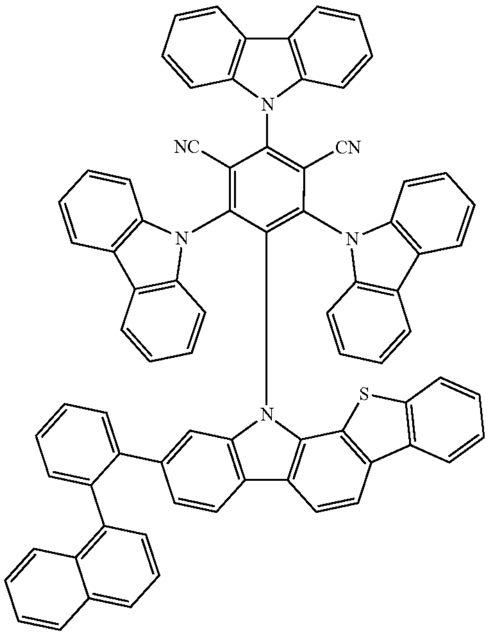
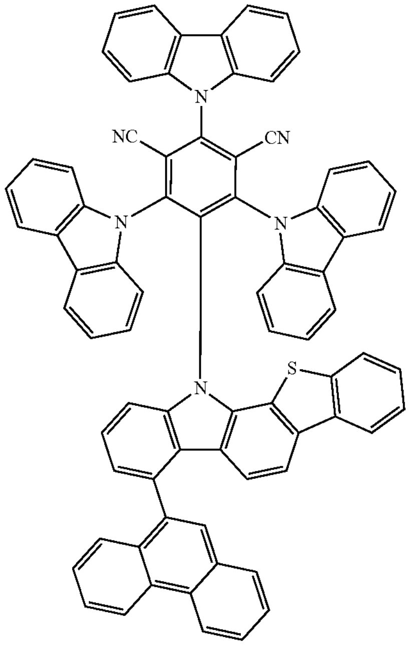
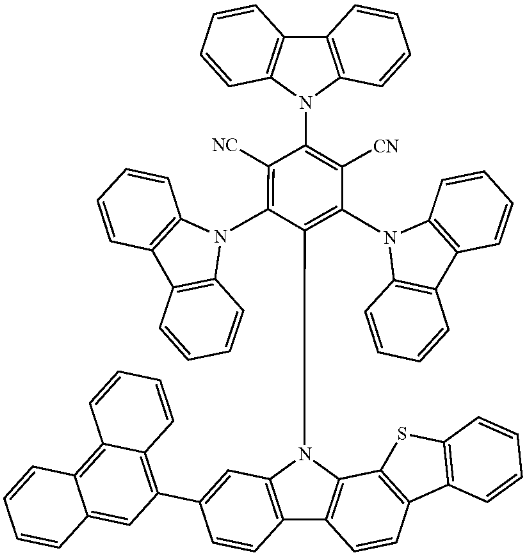

-continued
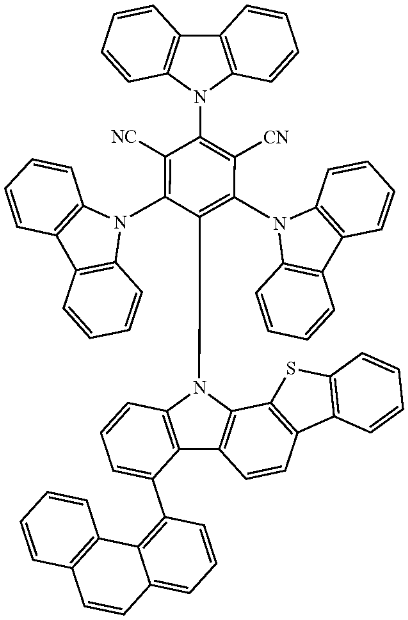
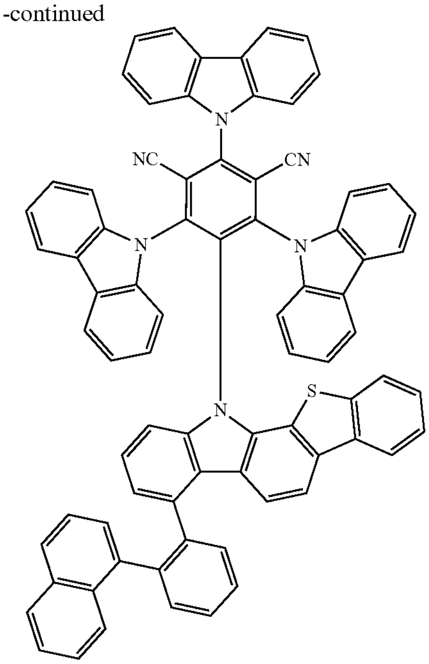
[Formula 56]
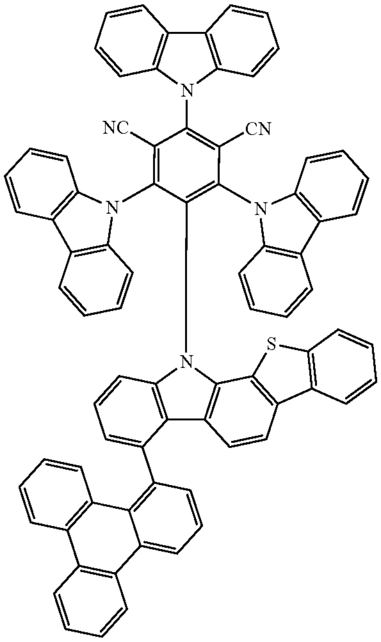
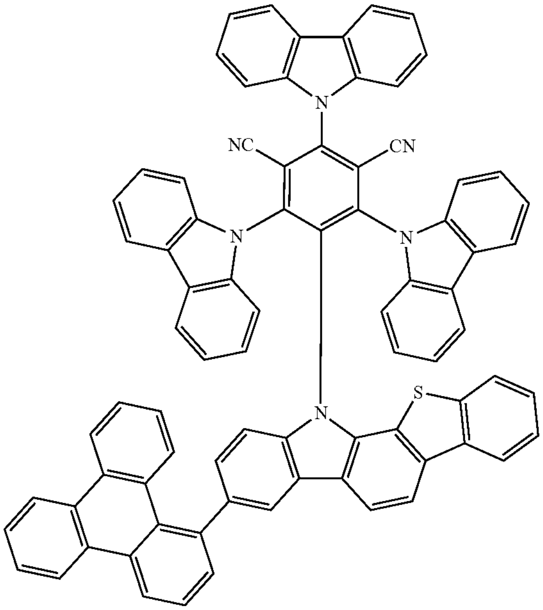

-continued
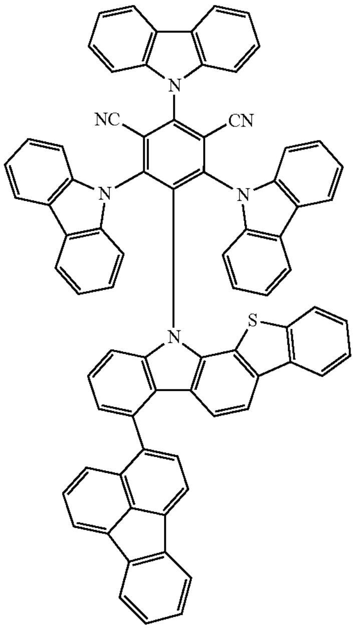
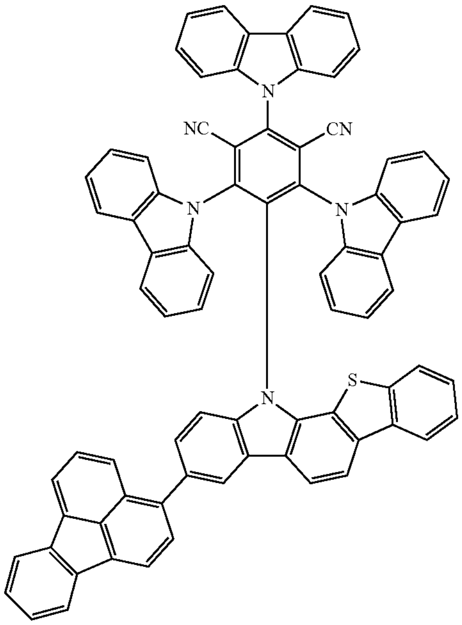
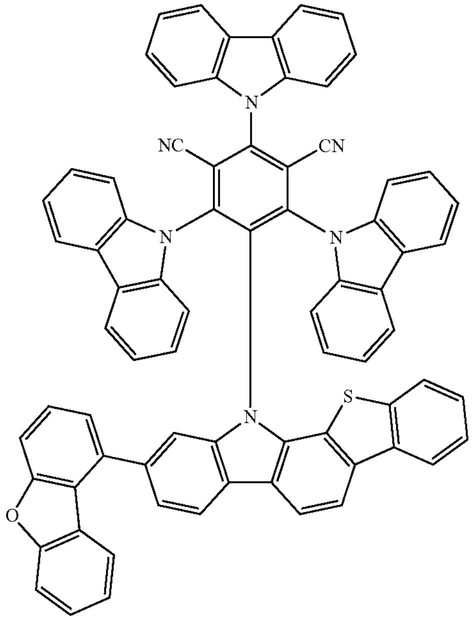
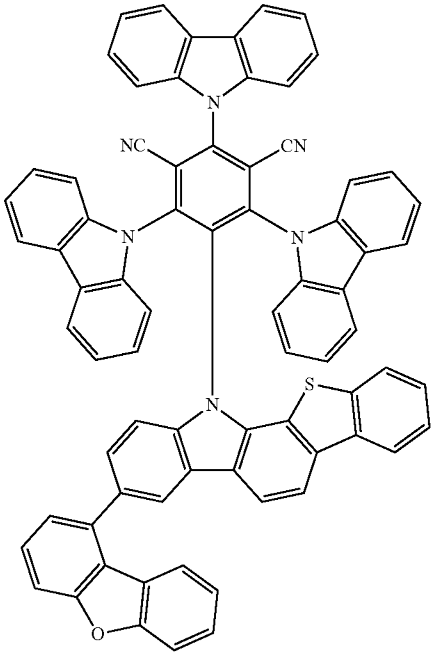

-continued
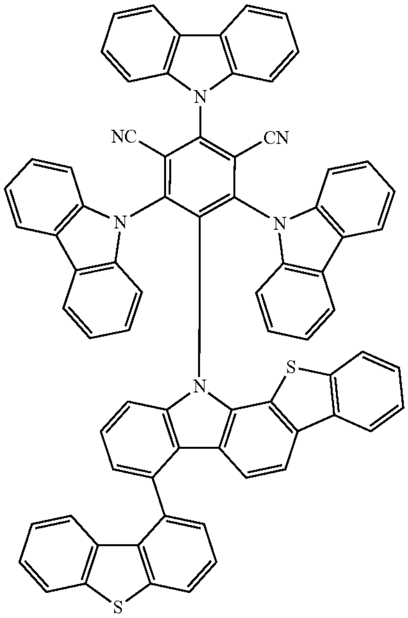
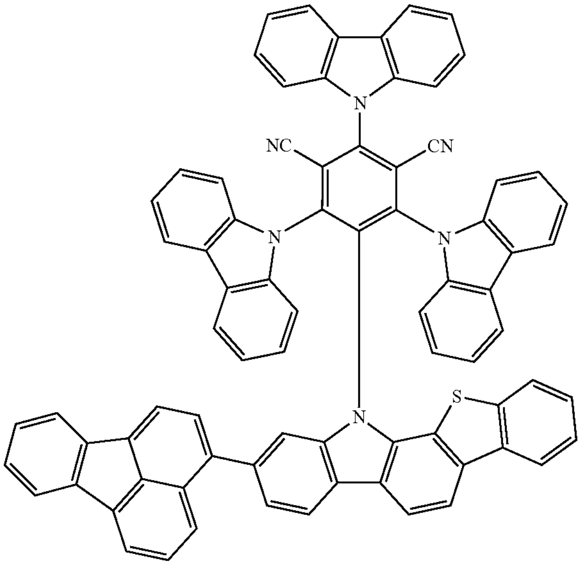
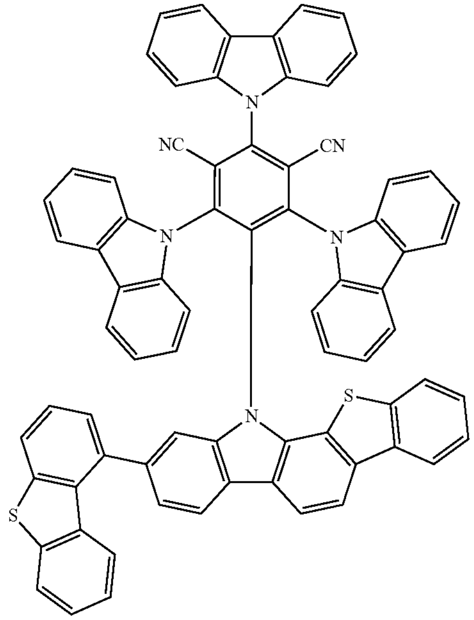
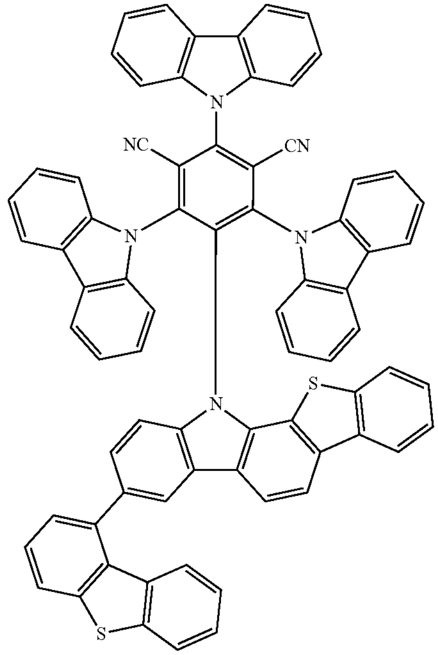

-continued
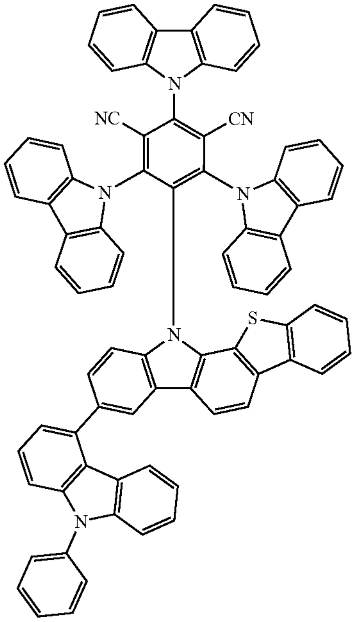
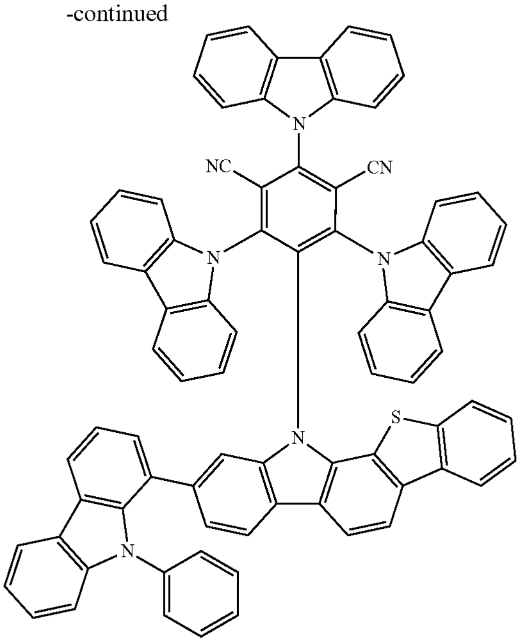
[Formula 57]
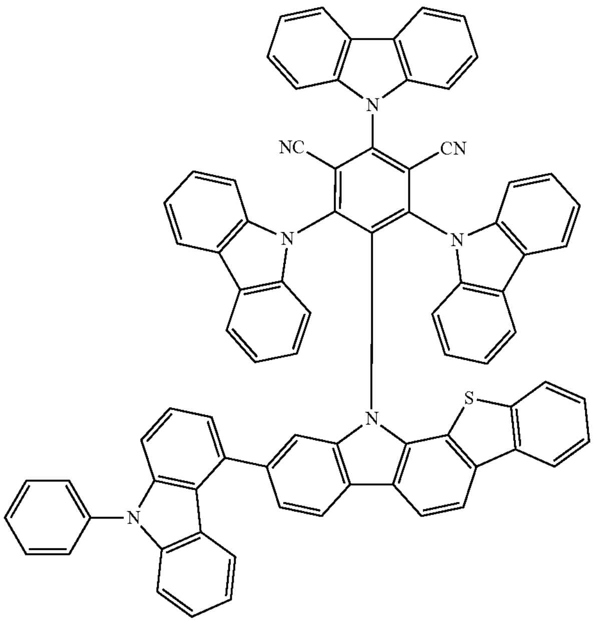
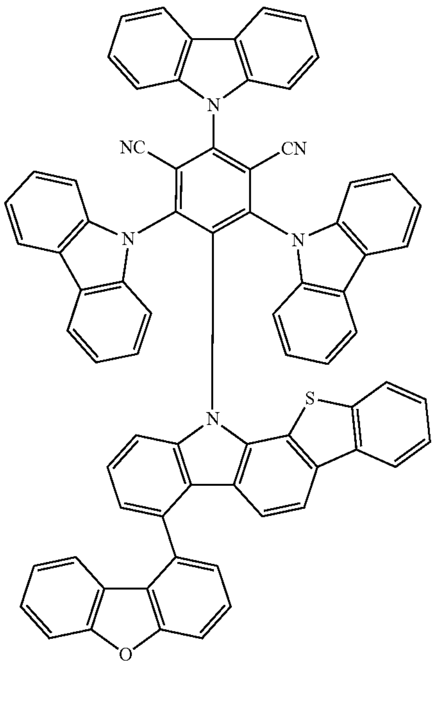

-continued
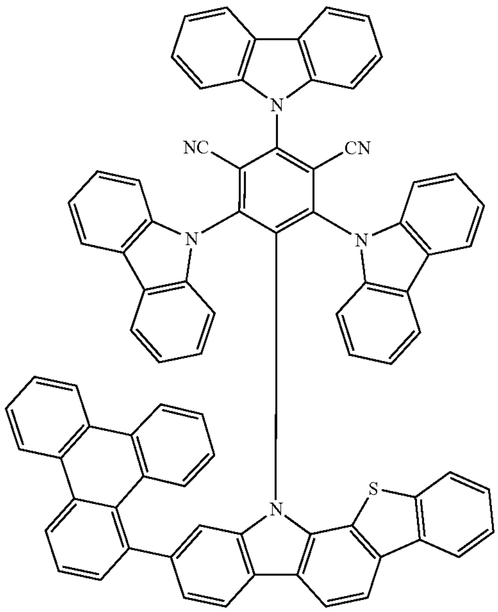
[Formula 58]
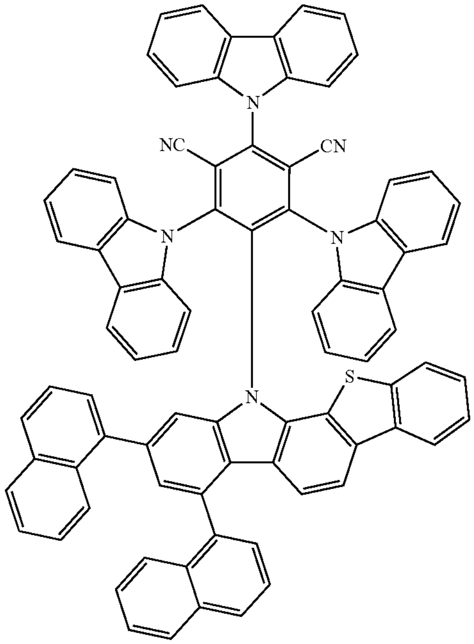
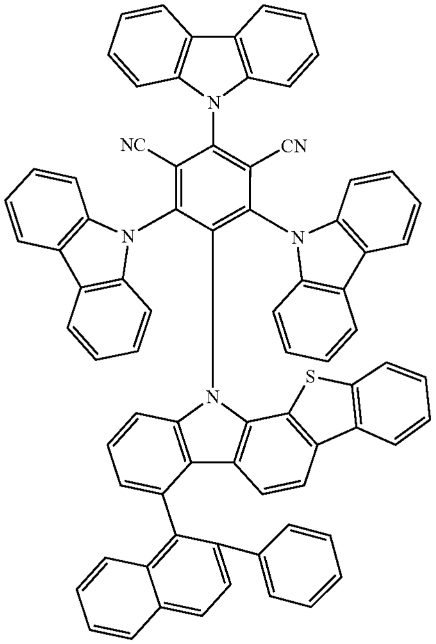

-continued
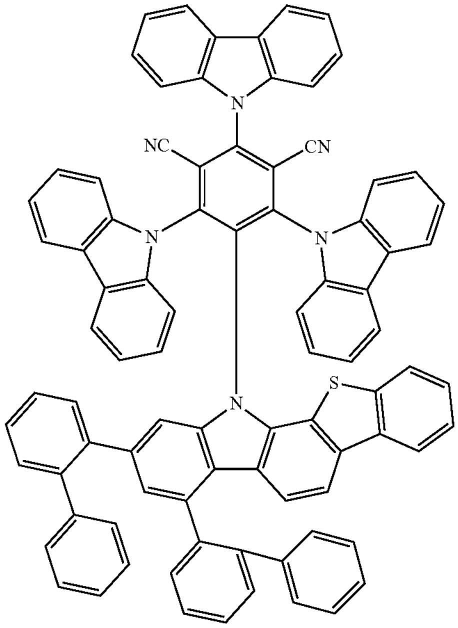
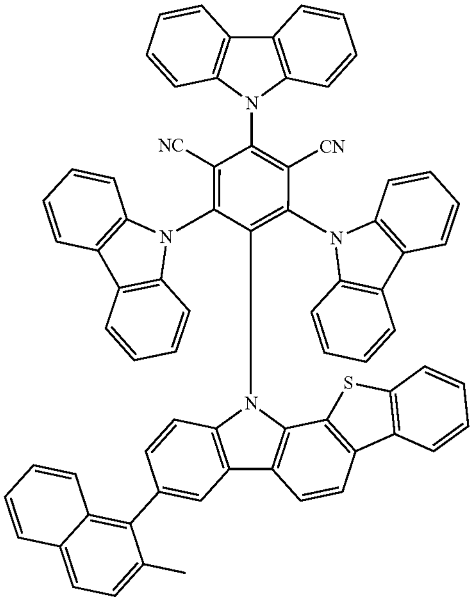
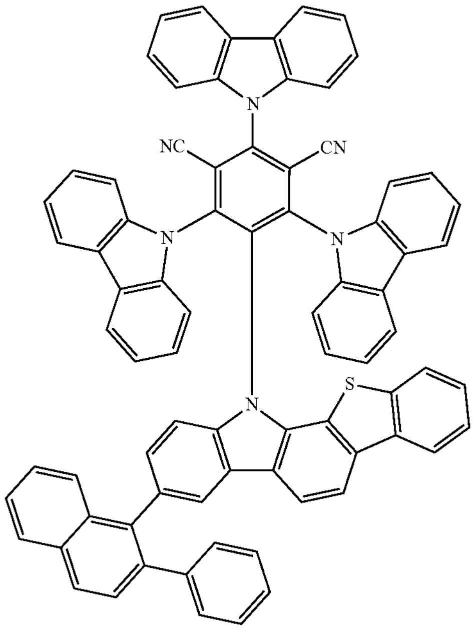
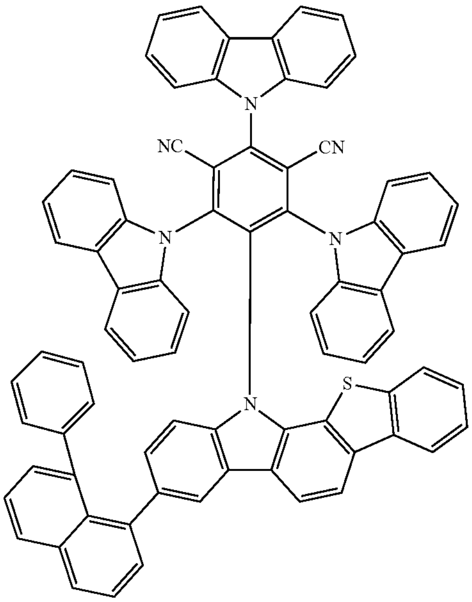

-continued
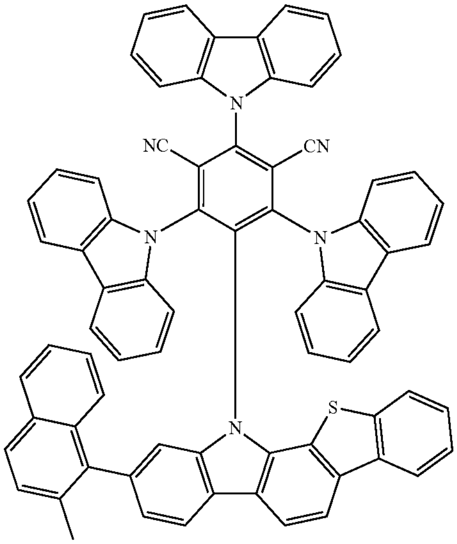
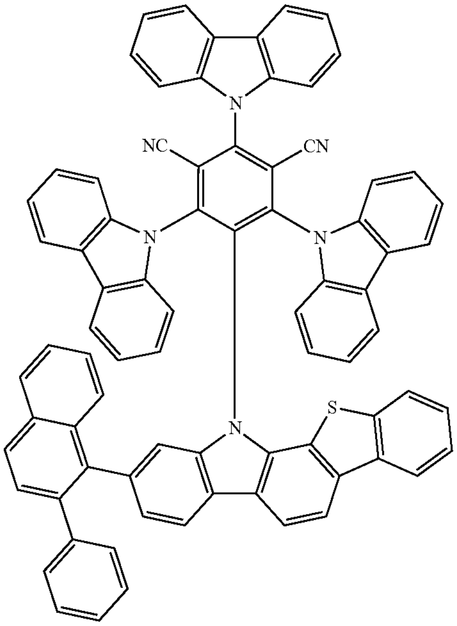
[Formula 59]
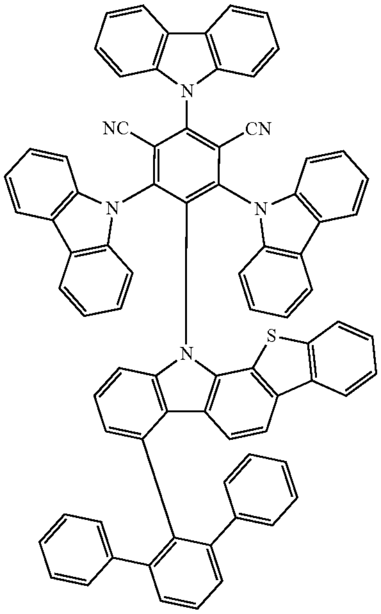
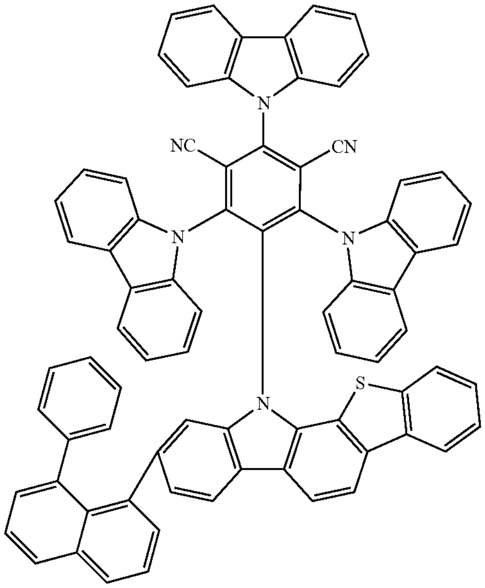

-continued
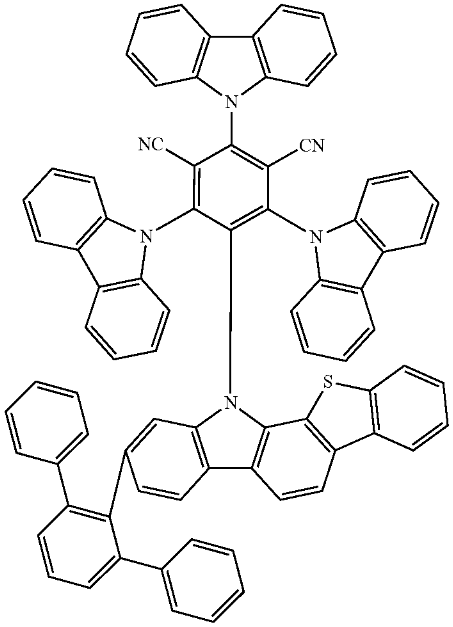
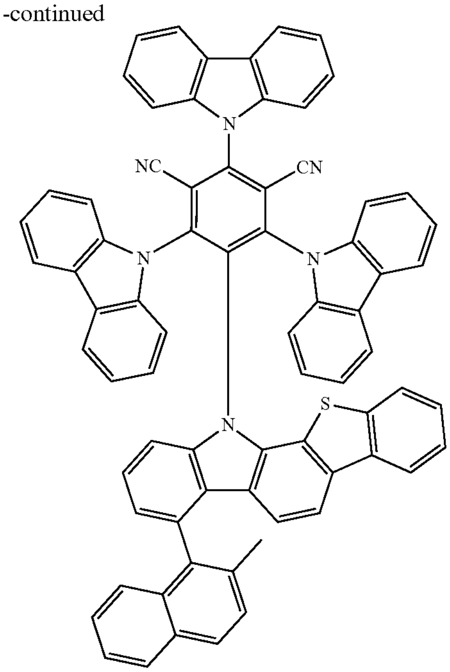
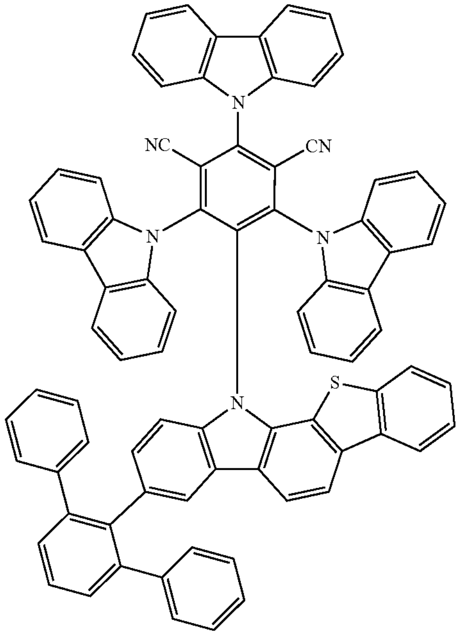
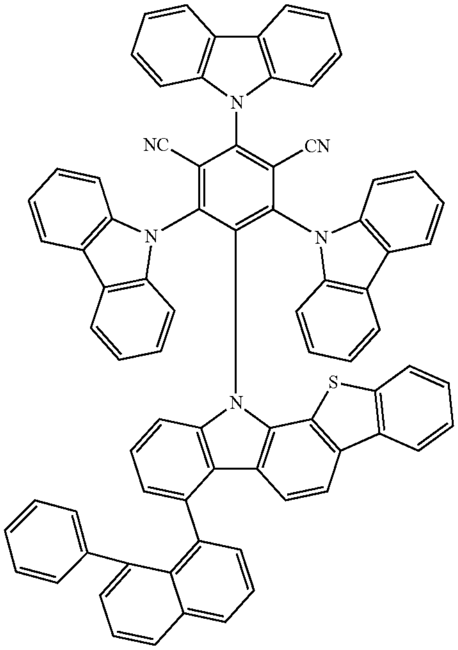

-continued
[Formula 60]
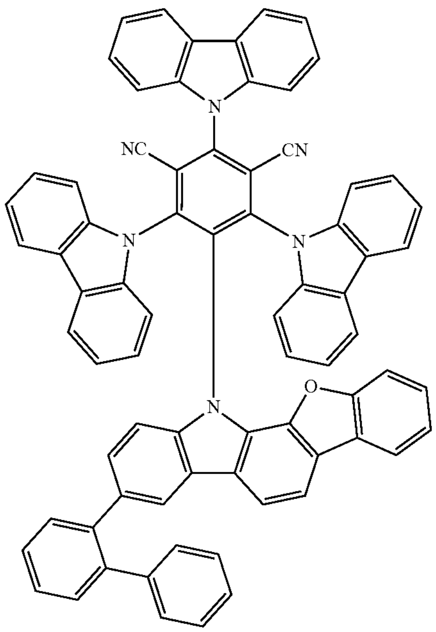
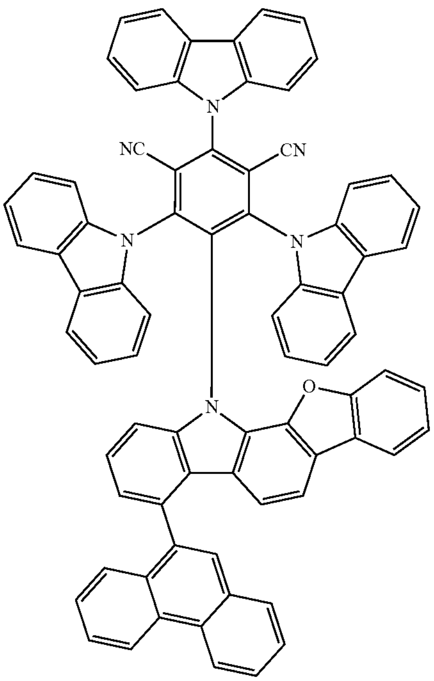
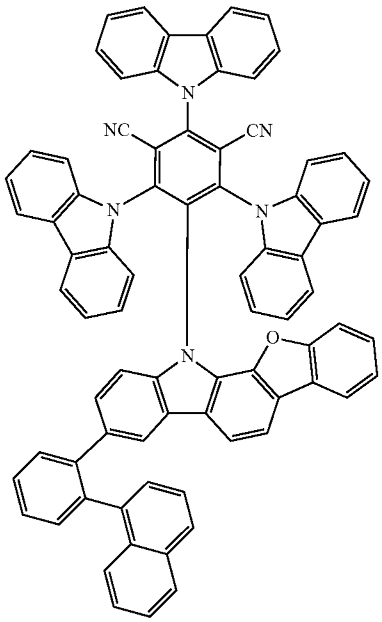
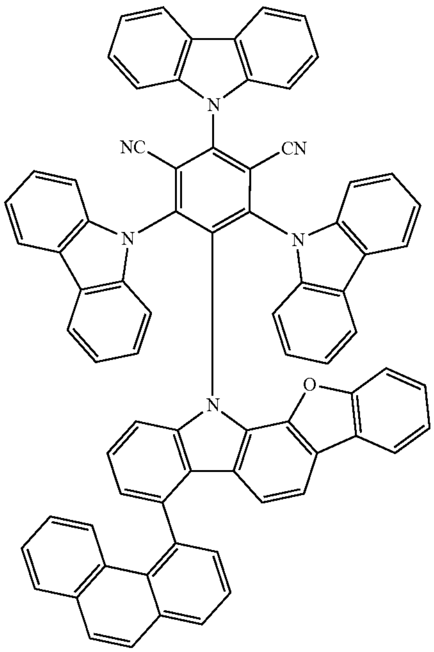

-continued
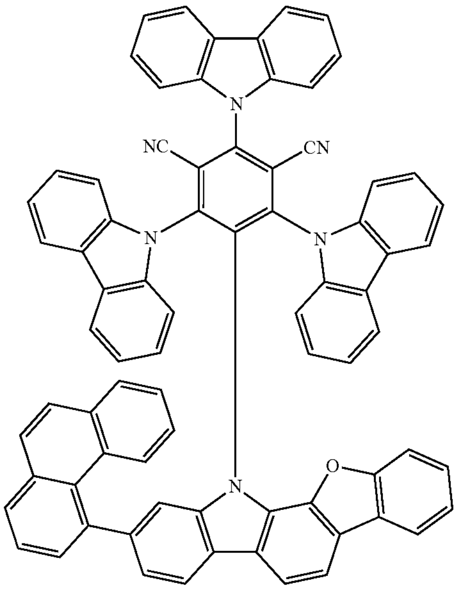
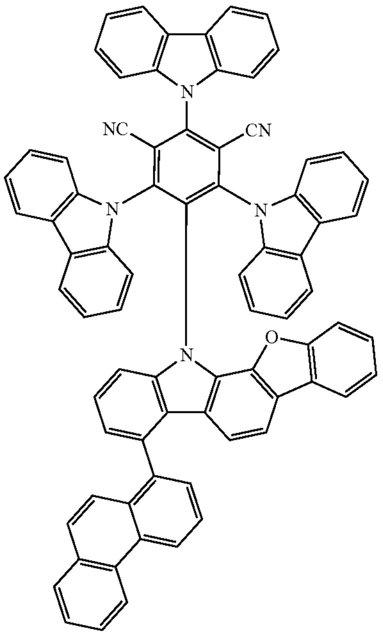
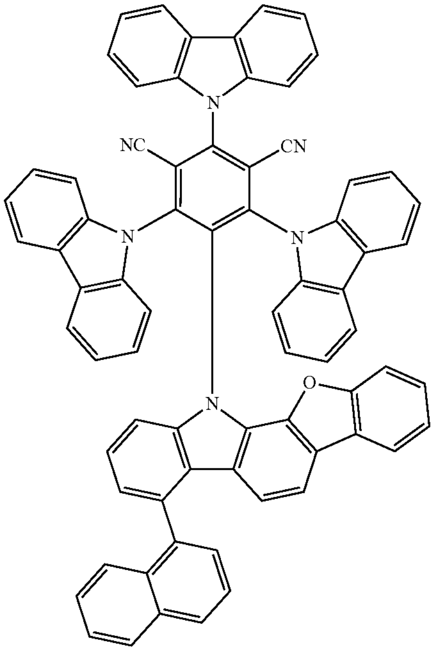
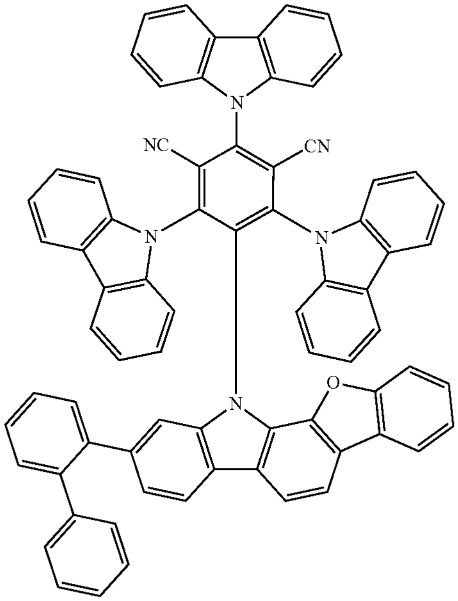

-continued
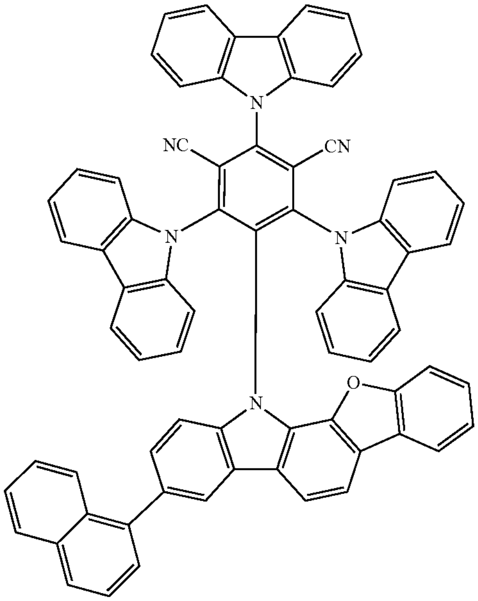
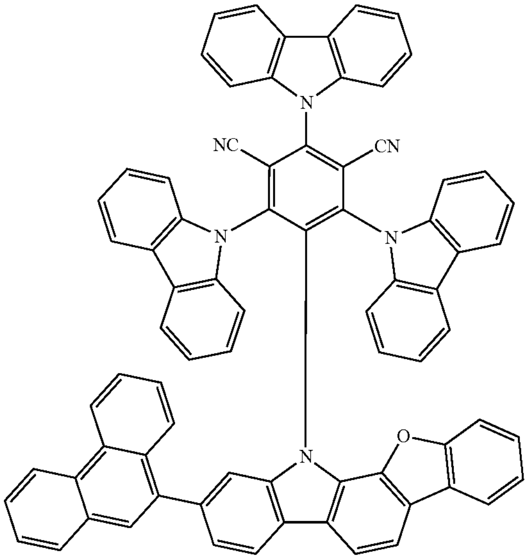
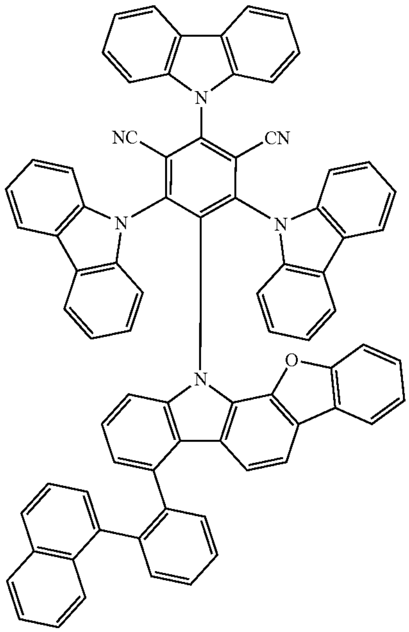
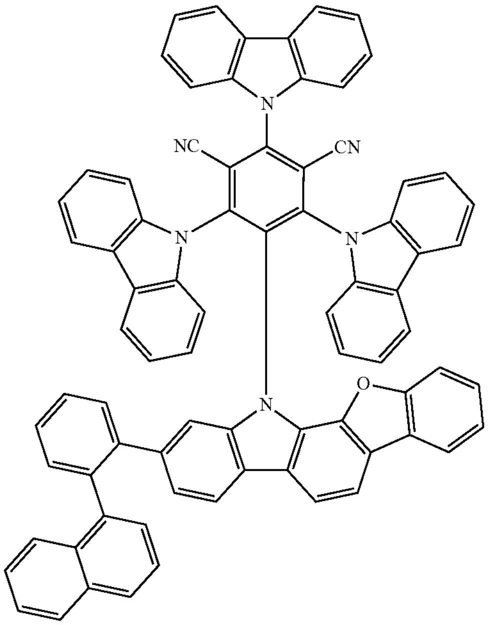

-continued
[Formula 61]
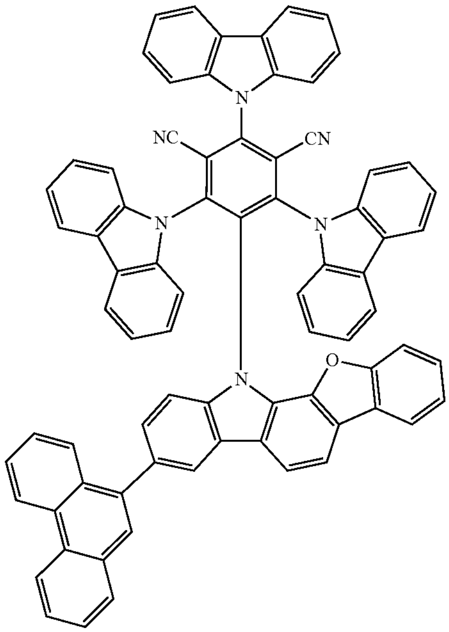
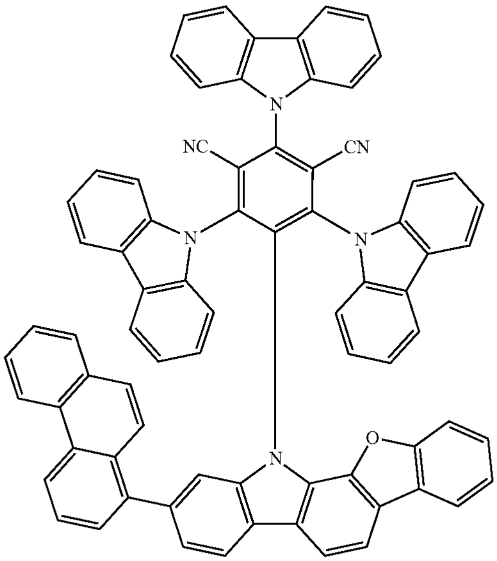
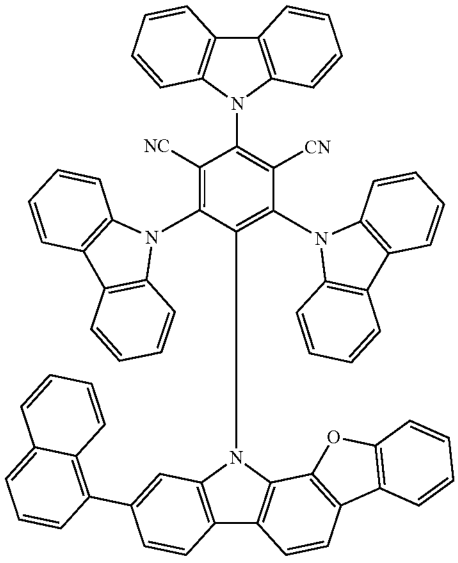
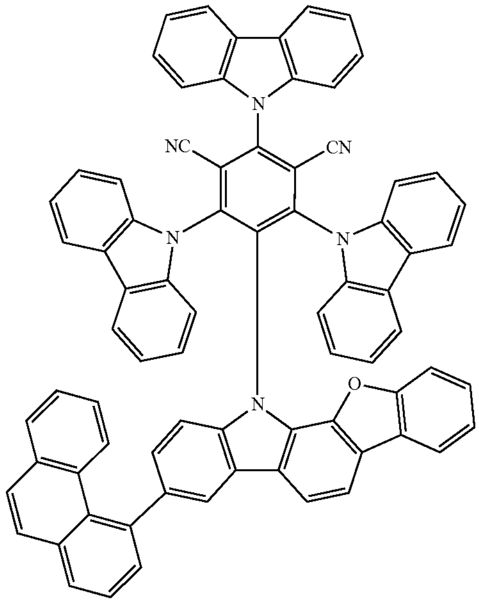

-continued
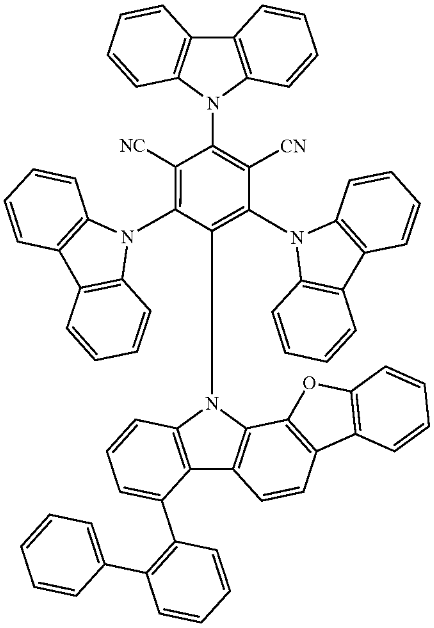
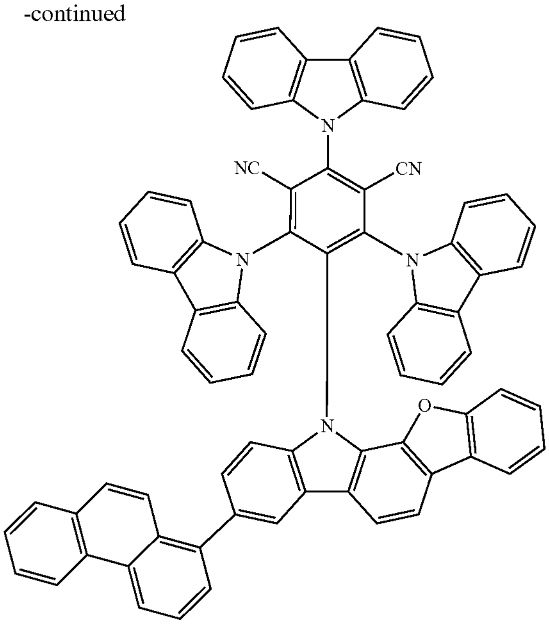
[Formula 62]
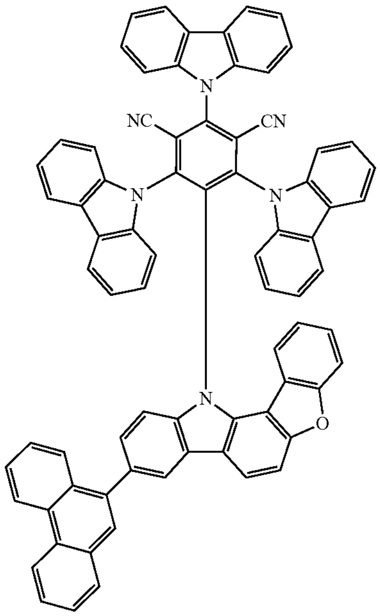
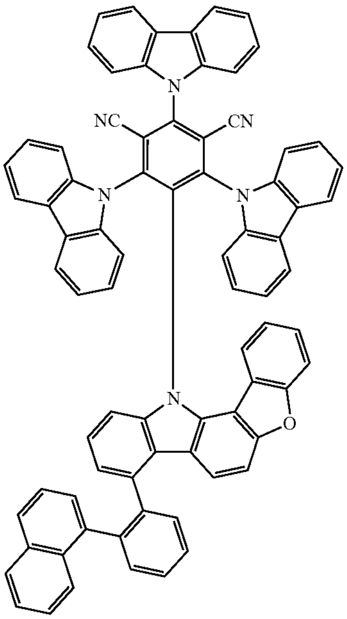
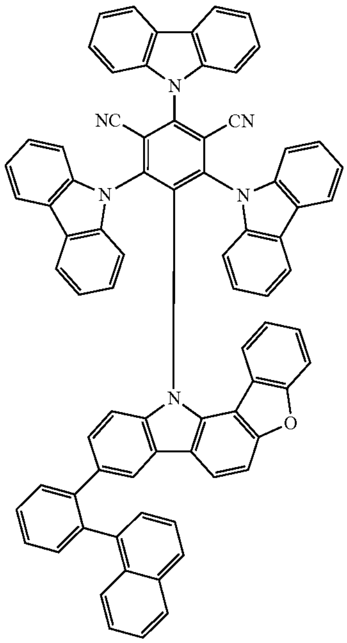

-continued
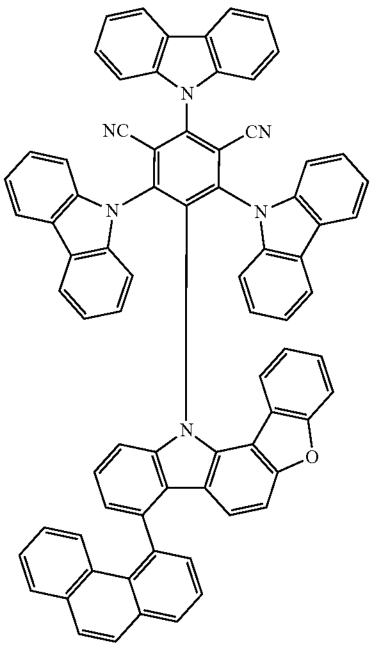
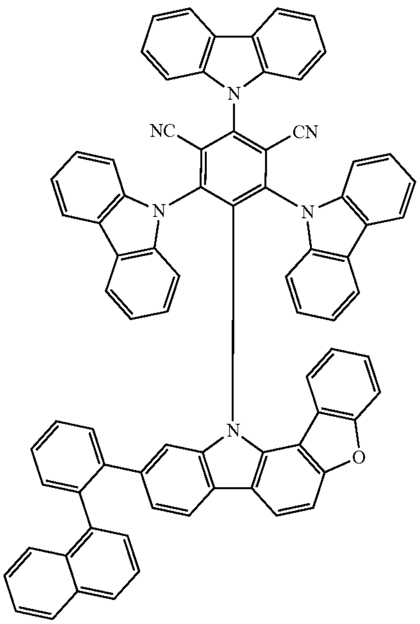
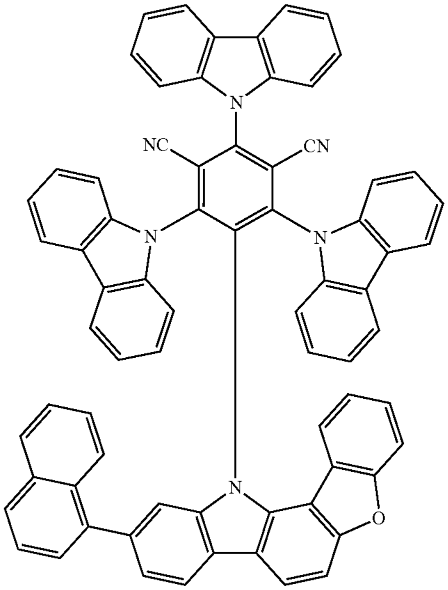
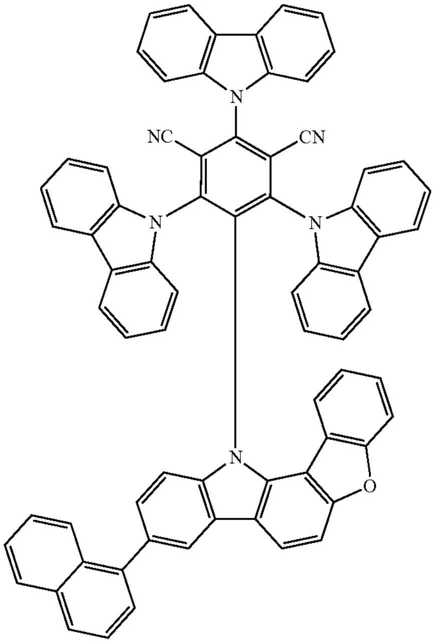

-continued
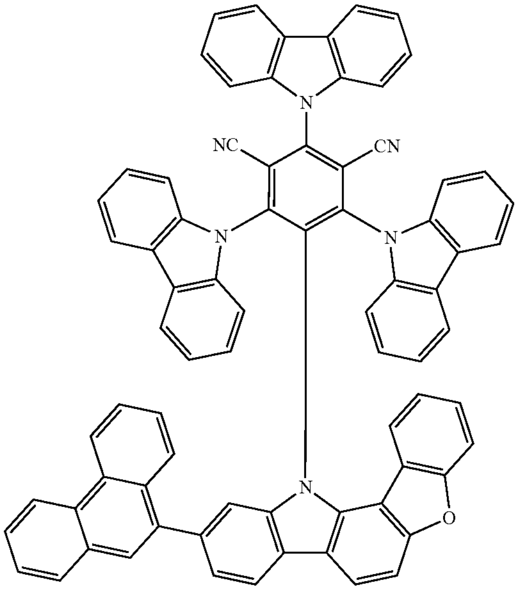
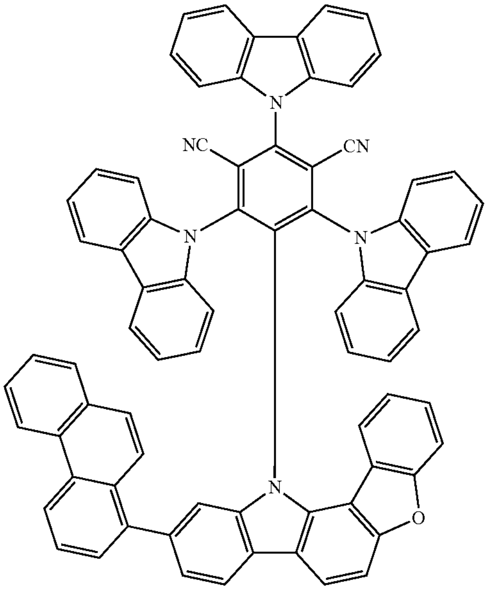
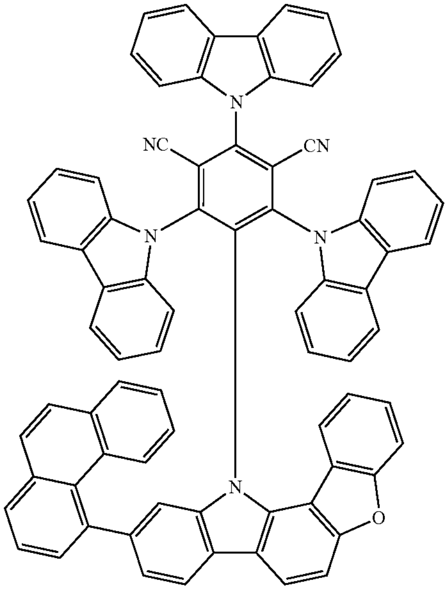
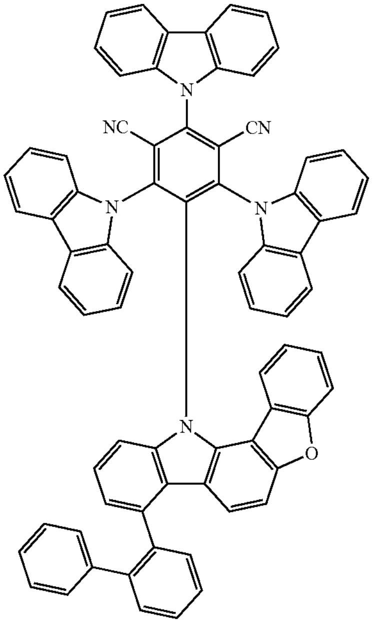

-continued
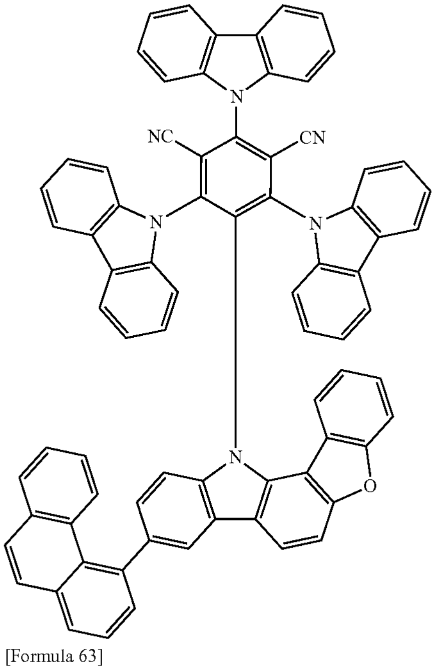
[Formula 63]
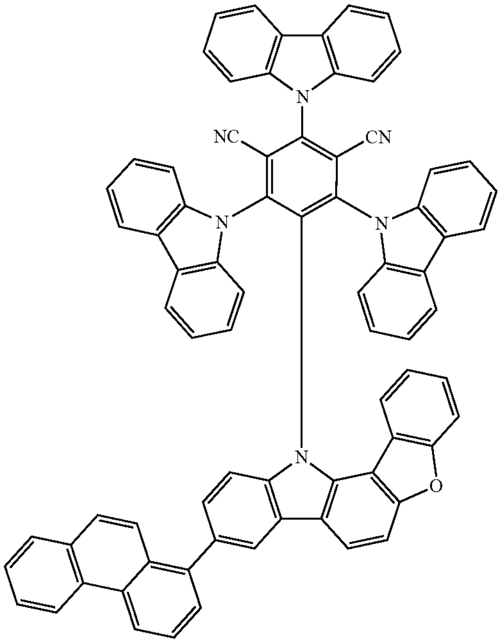
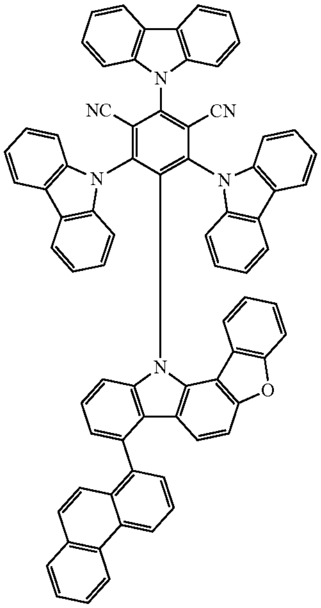

-continued
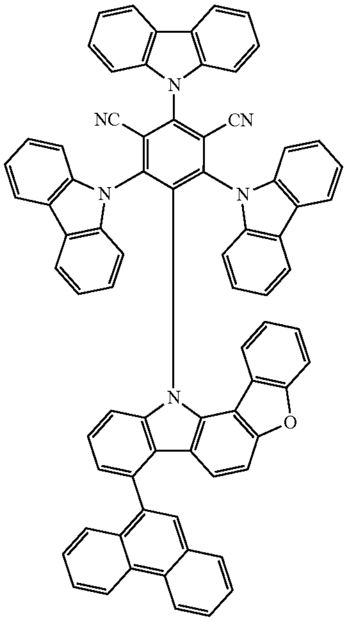
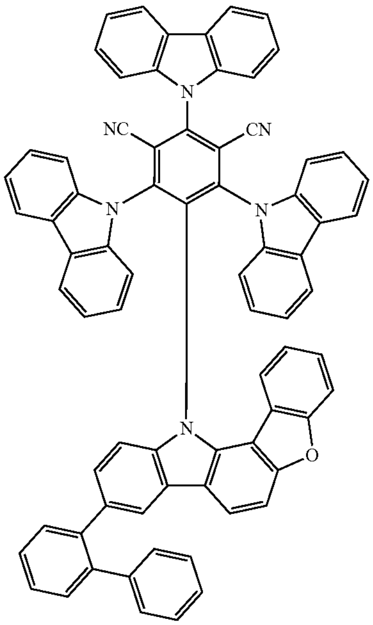
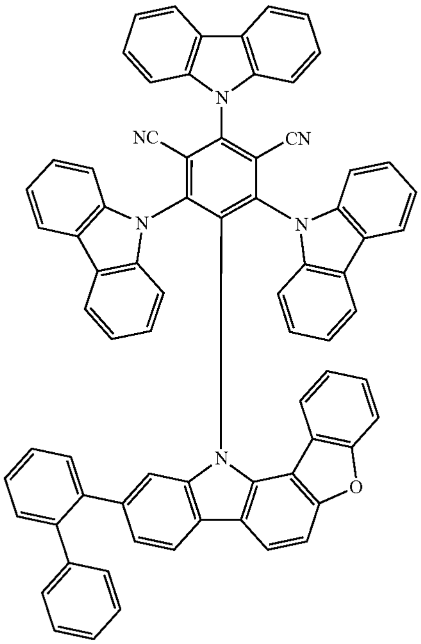
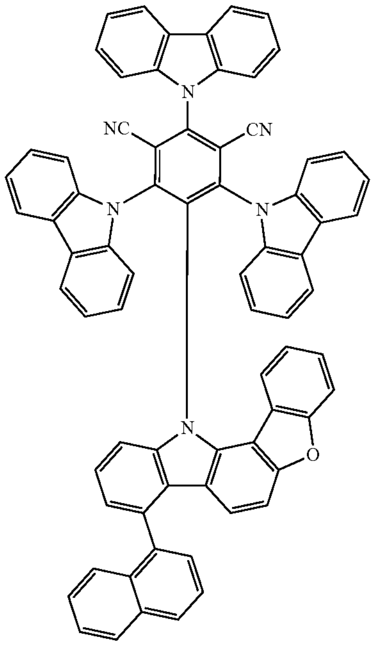

-continued
[Formula 64]
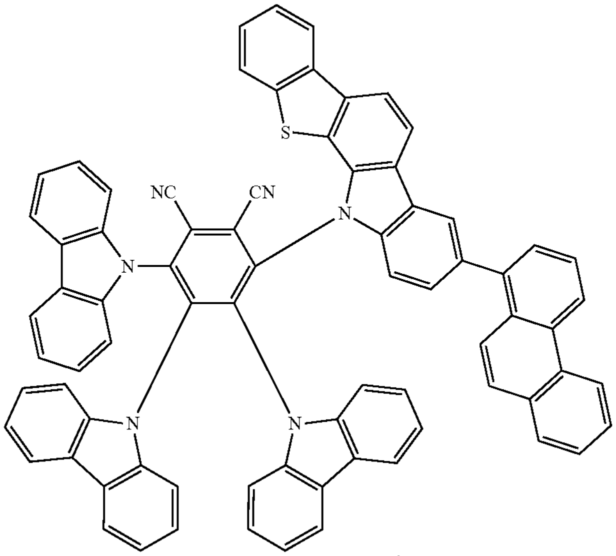
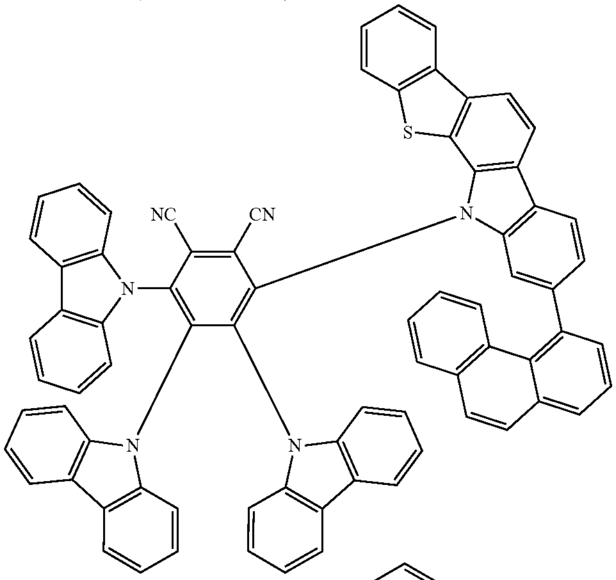
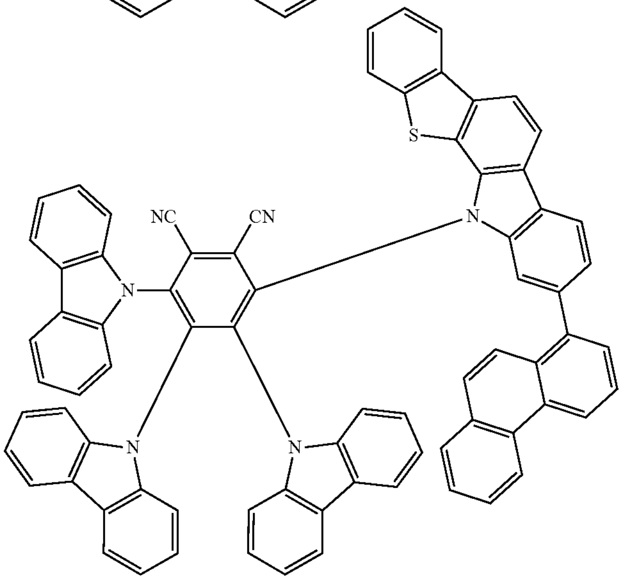

-continued
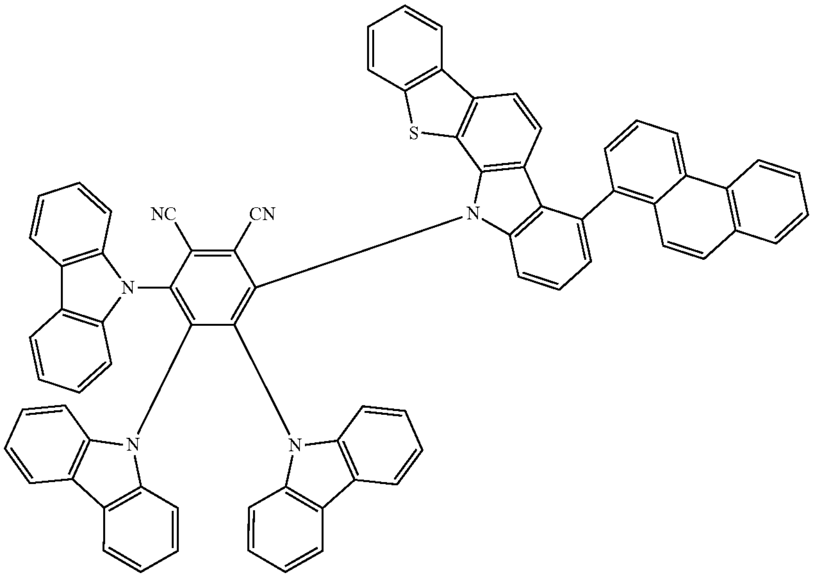
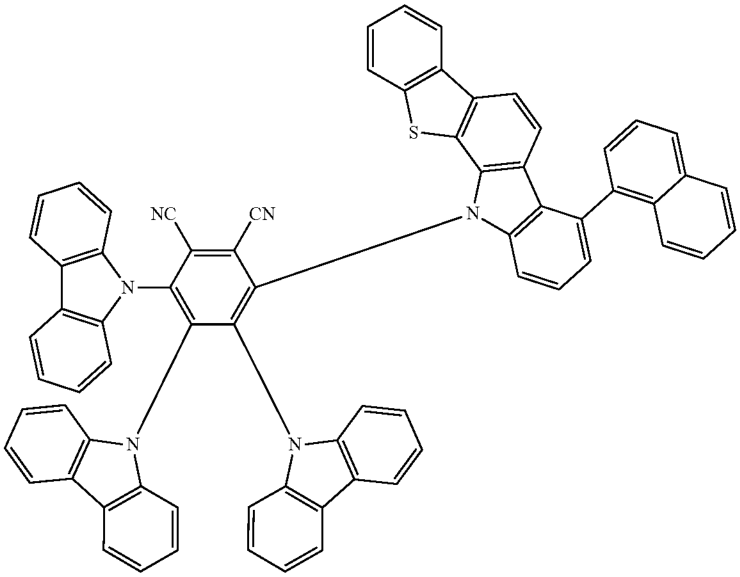
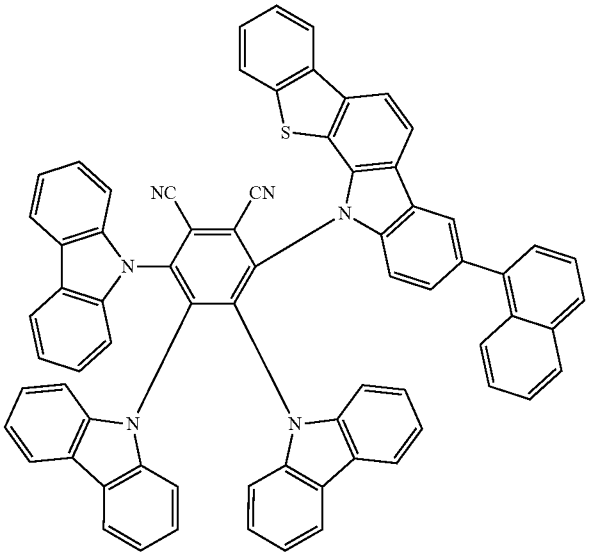

-continued
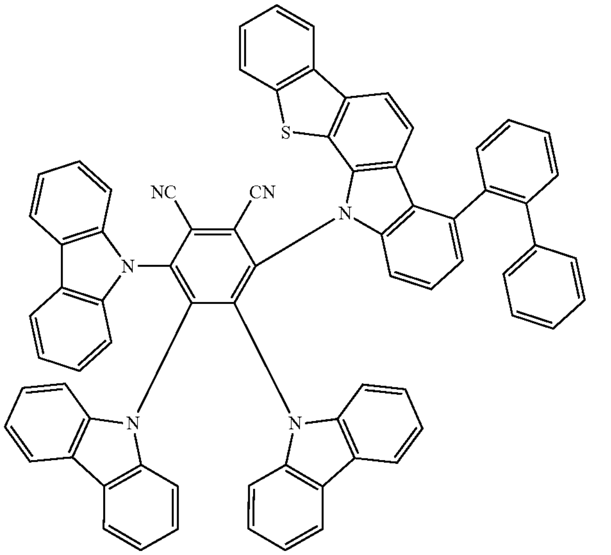
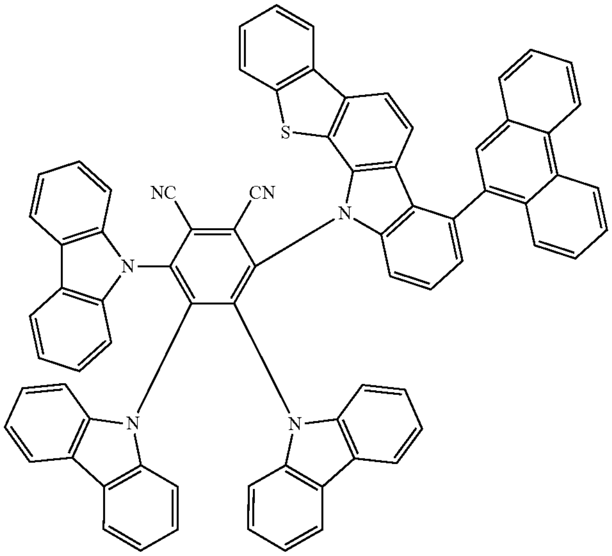
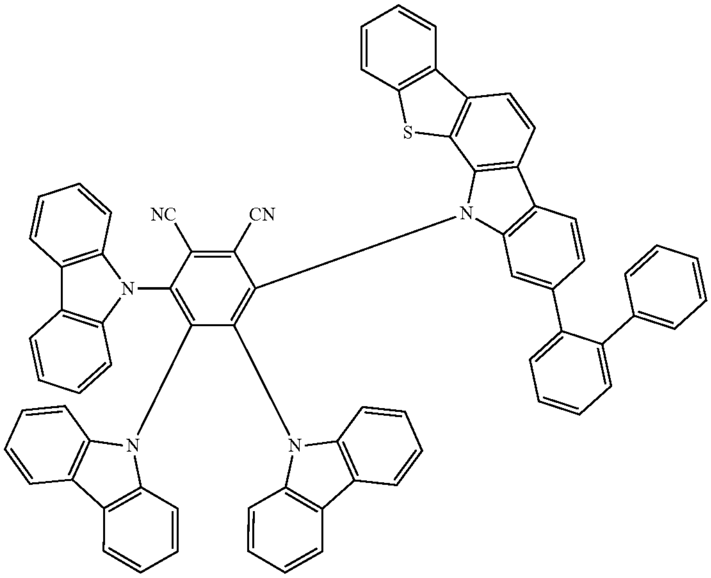

-continued
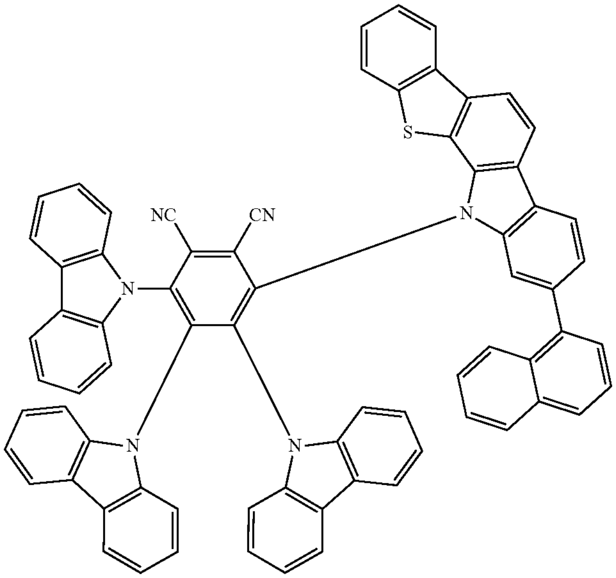
[Formula 65]
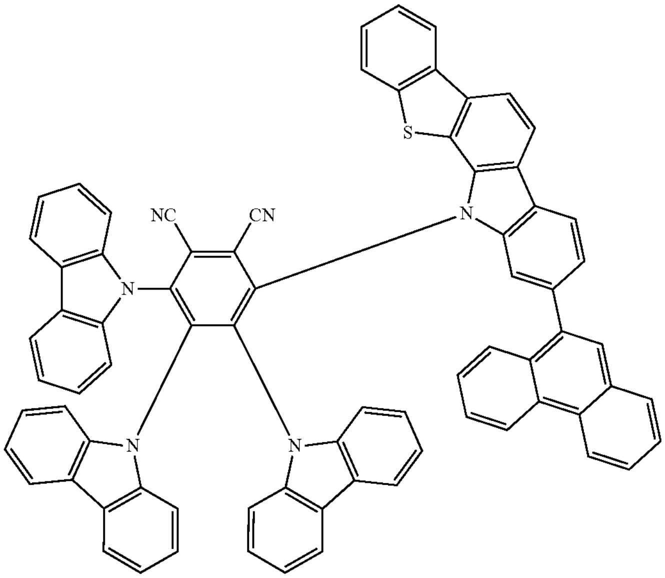

-continued
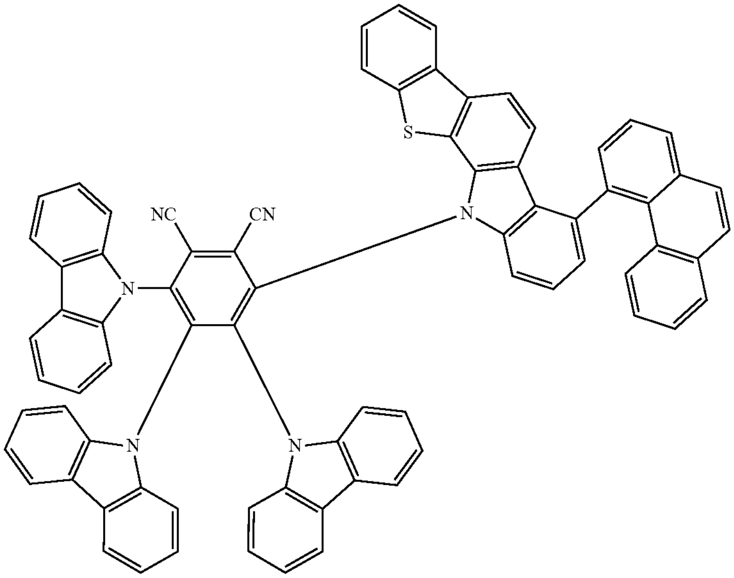
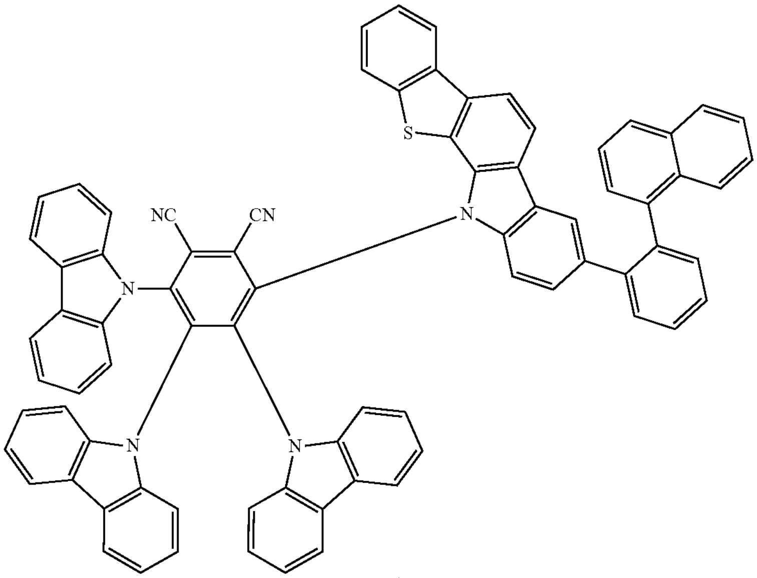
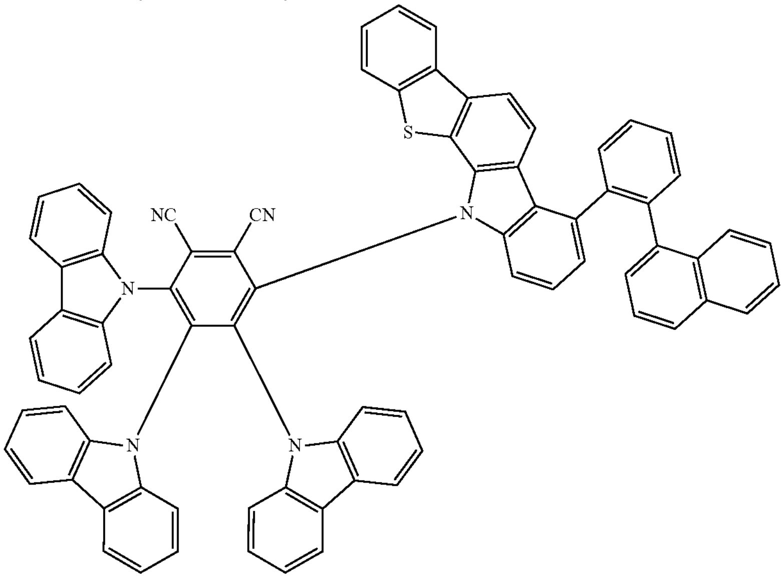

-continued
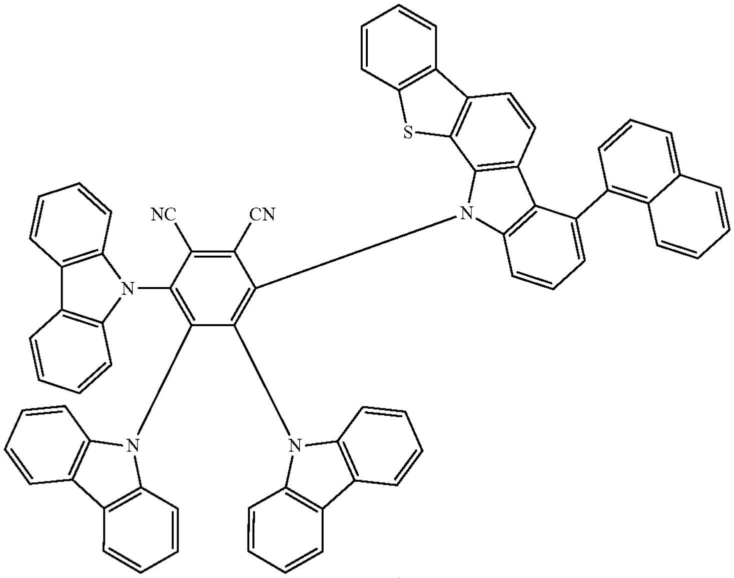
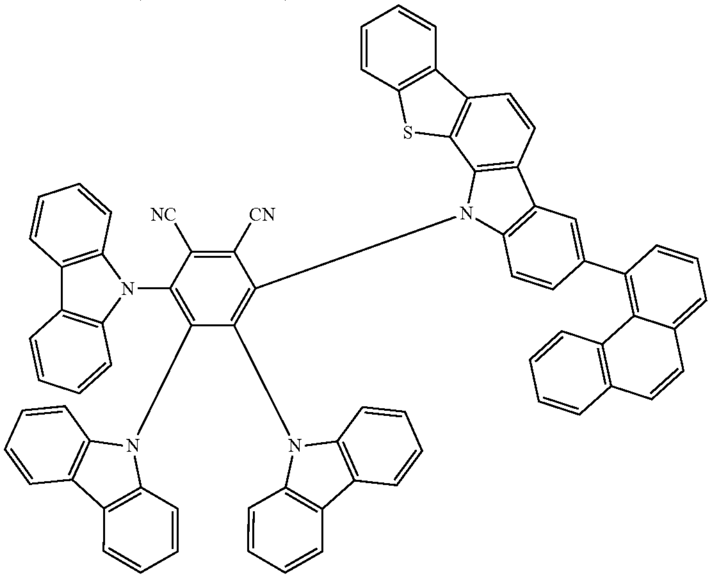
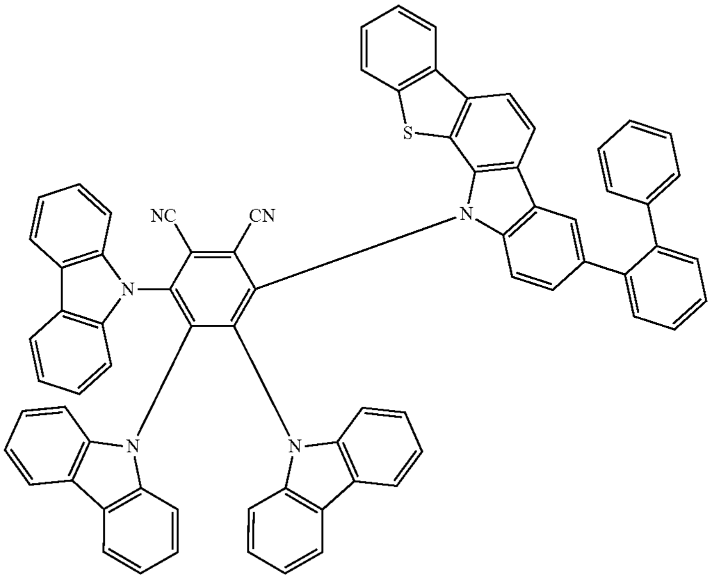

-continued
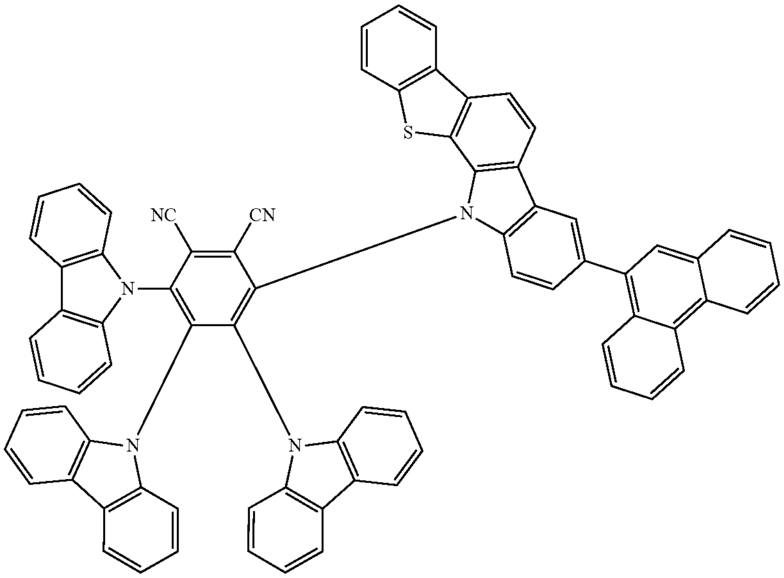
[Formula 66]
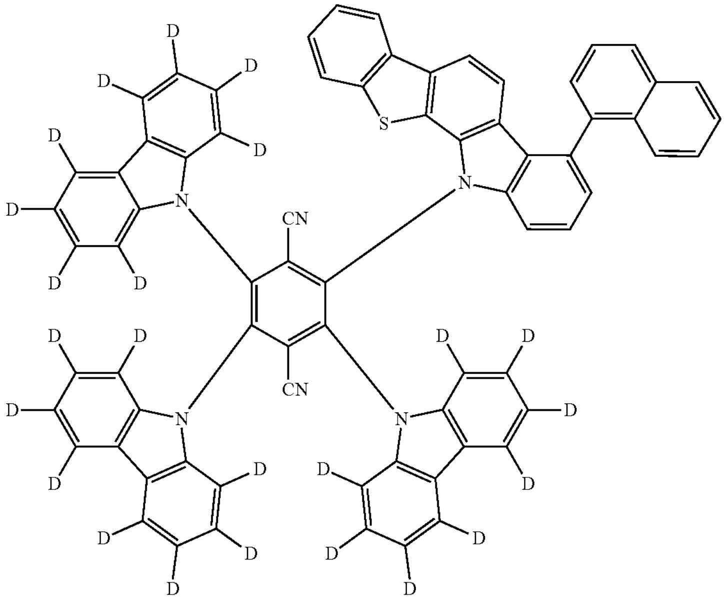

-continued
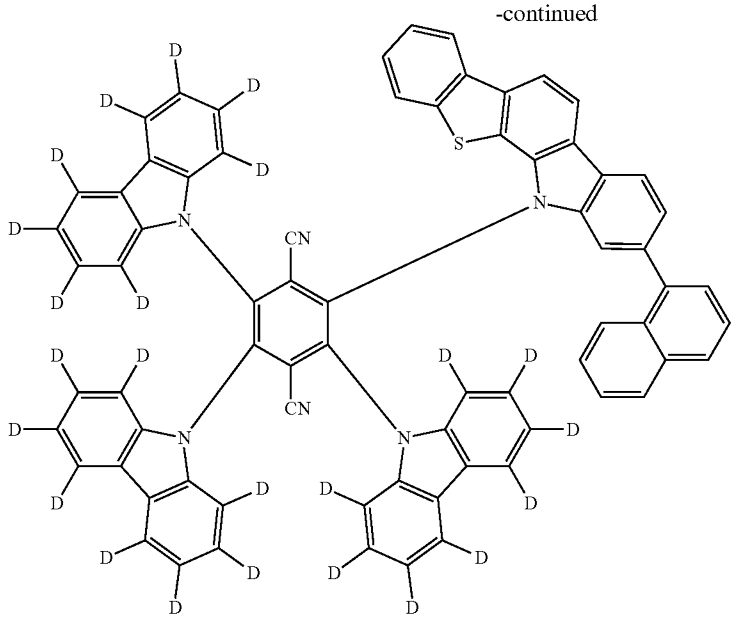
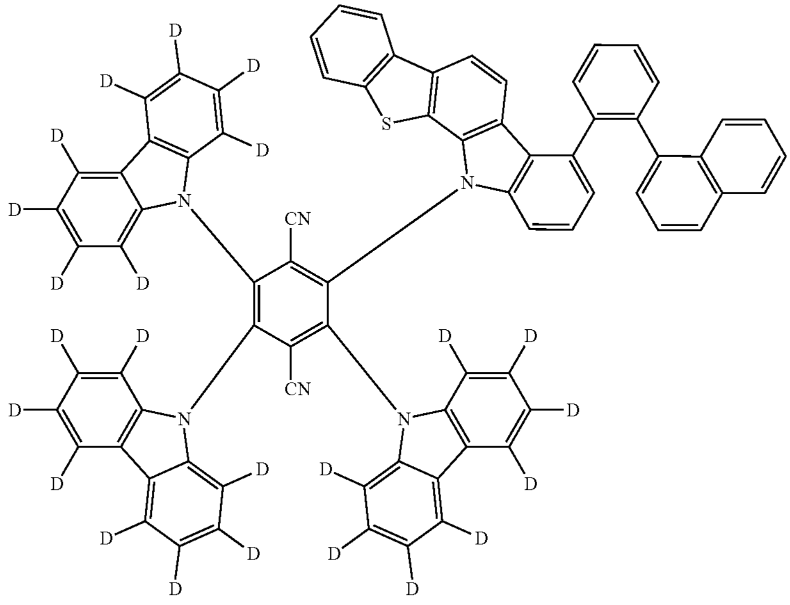

-continued
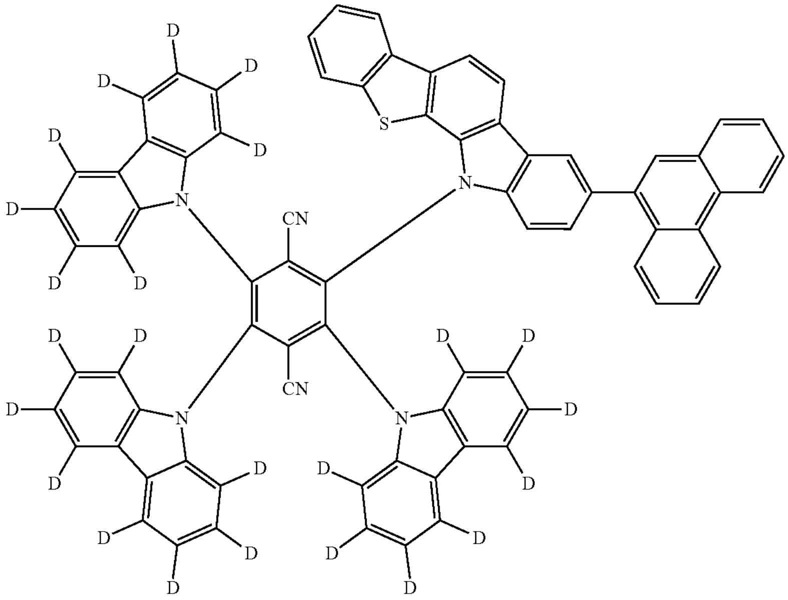
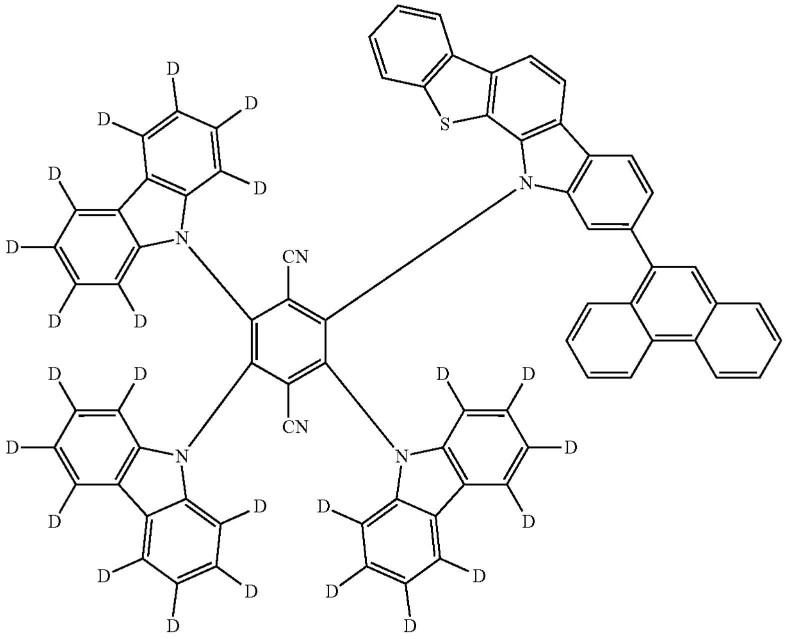

-continued
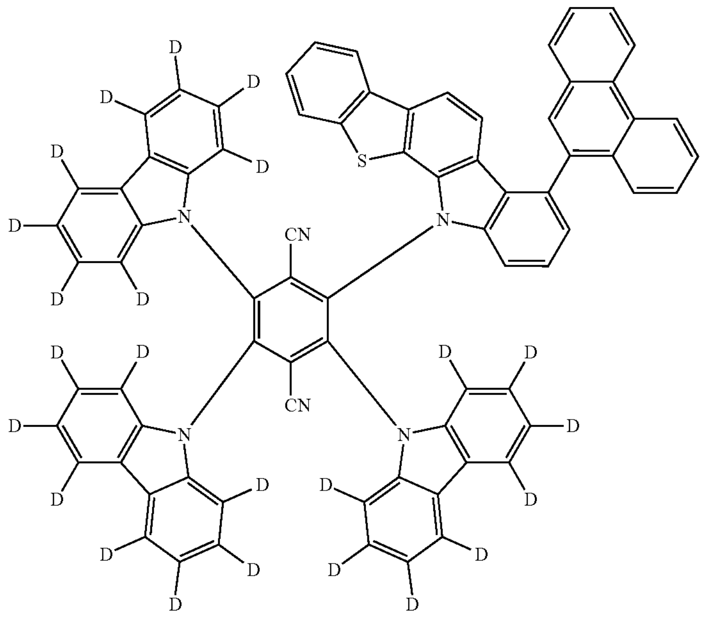
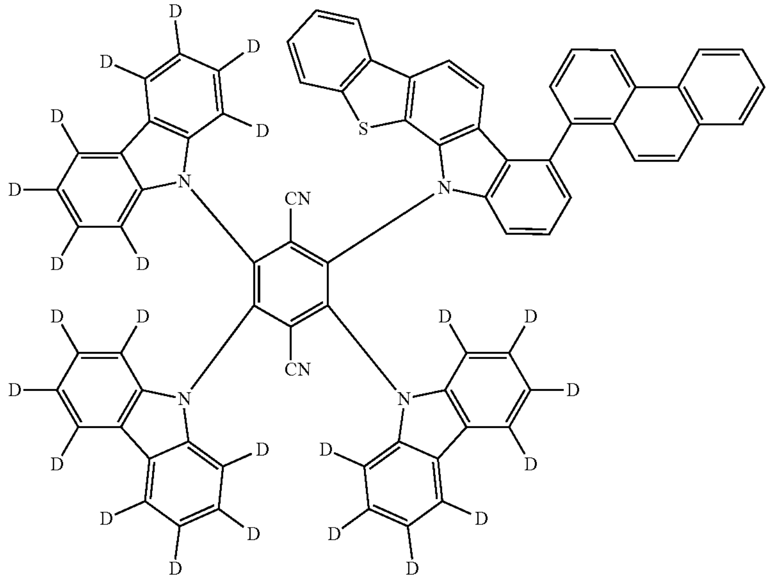

-continued
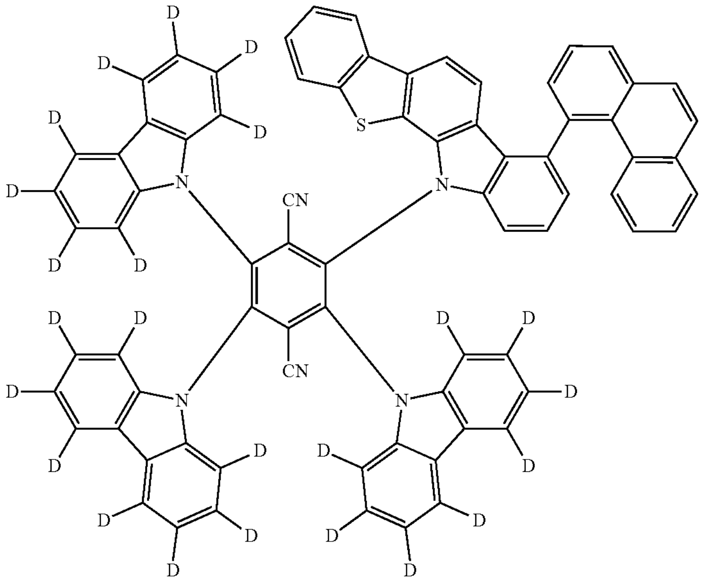
[Formula 67]
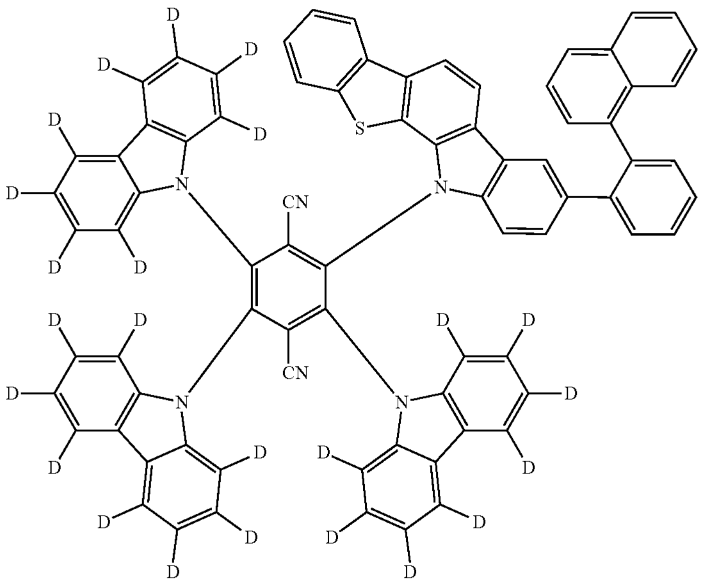

-continued
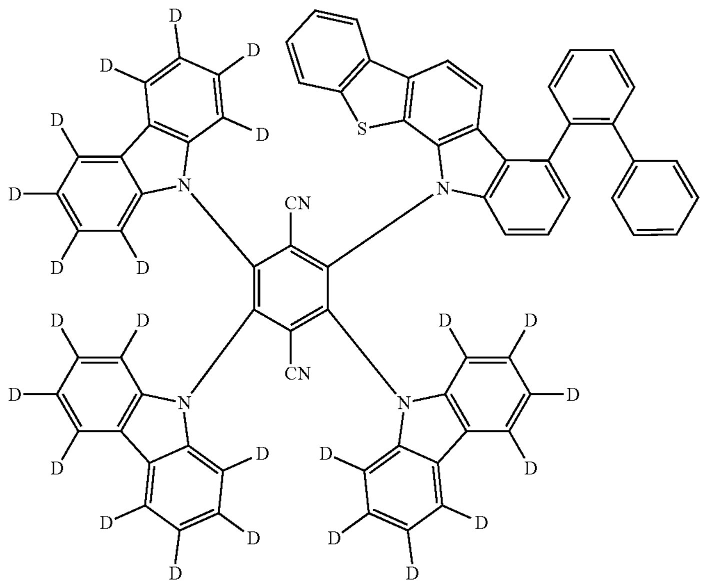
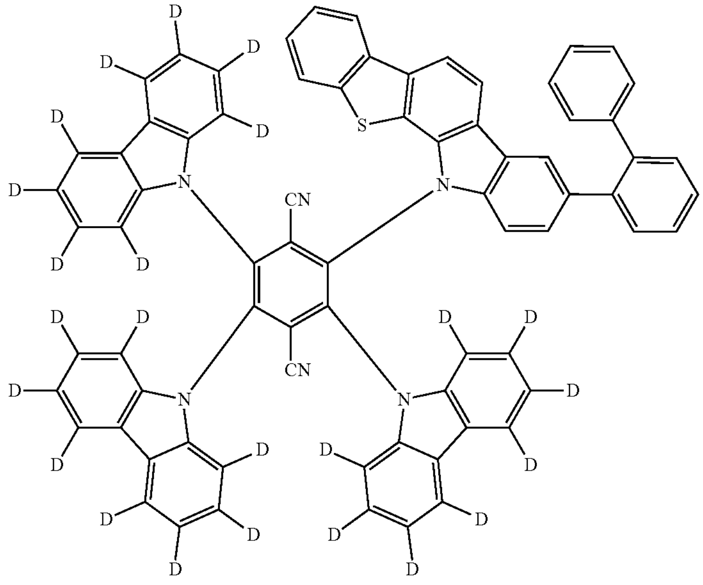

-continued
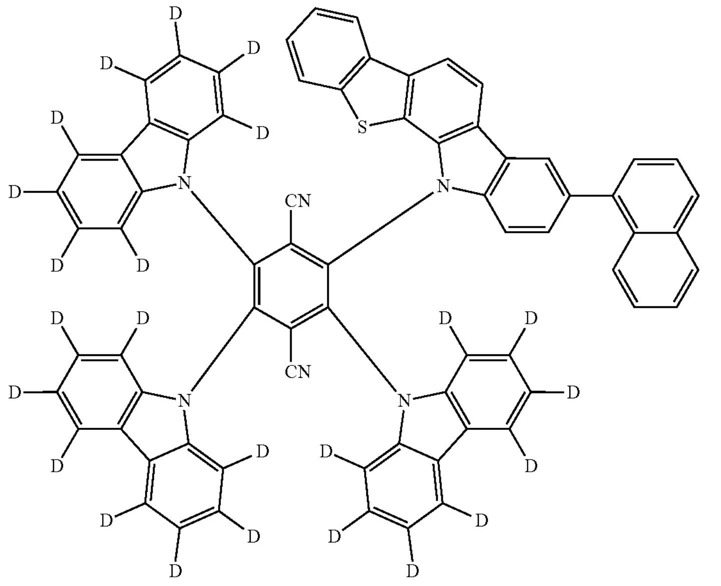
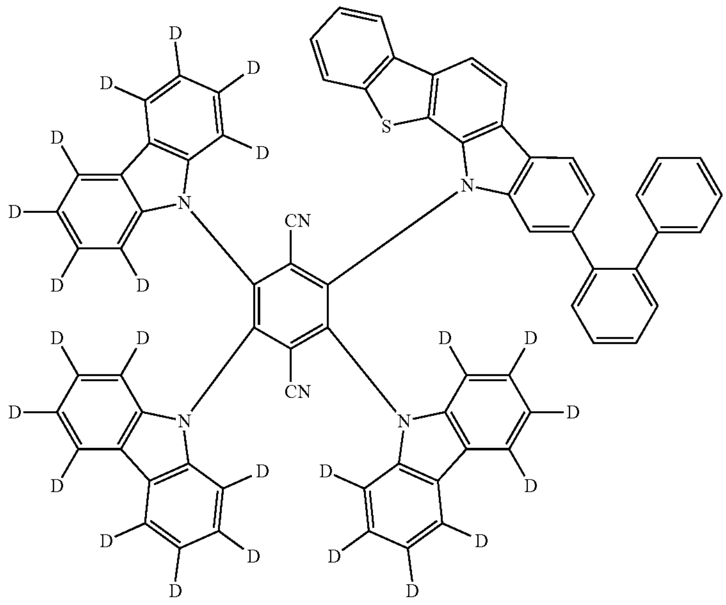

-continued
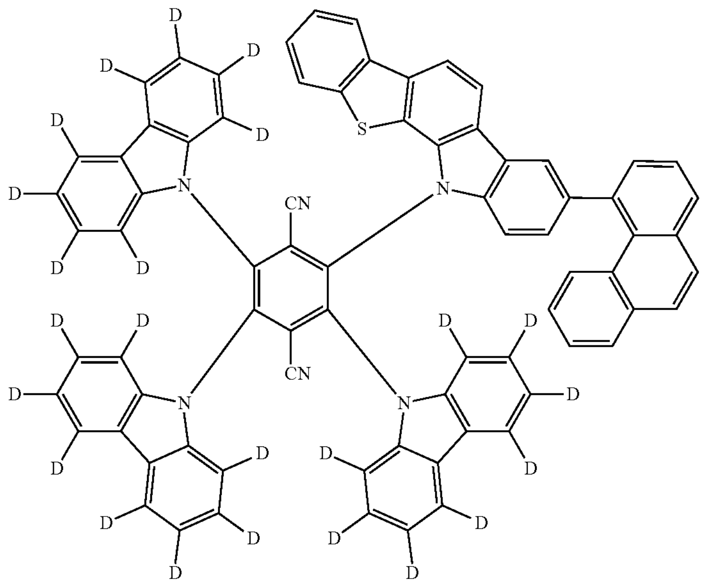
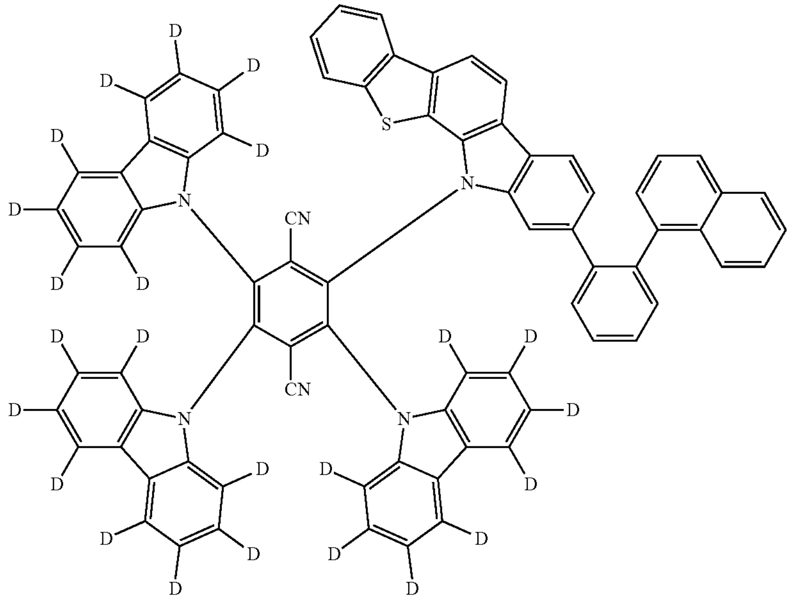

-continued
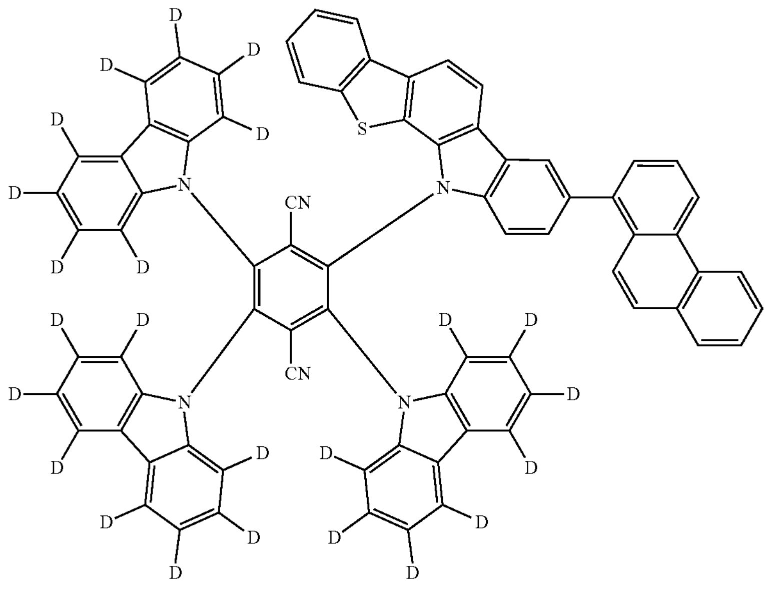
[Formula 68]
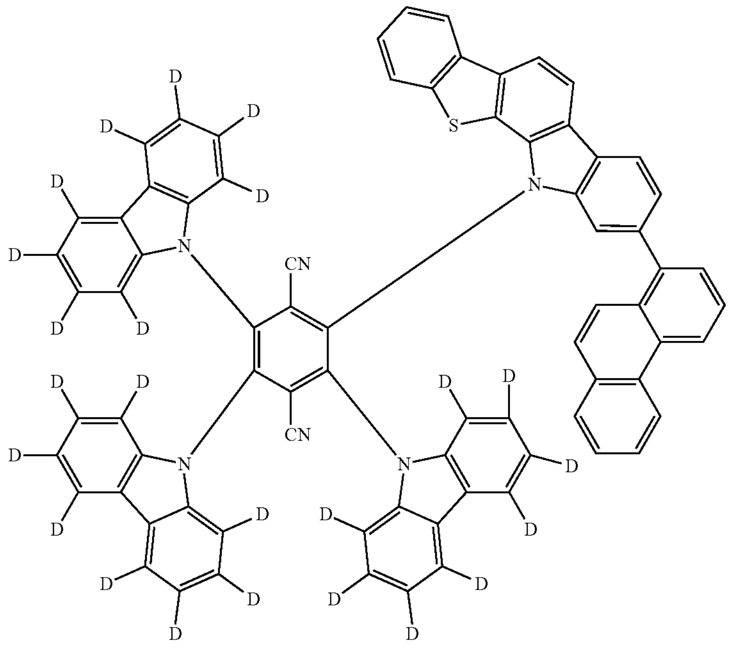

-continued
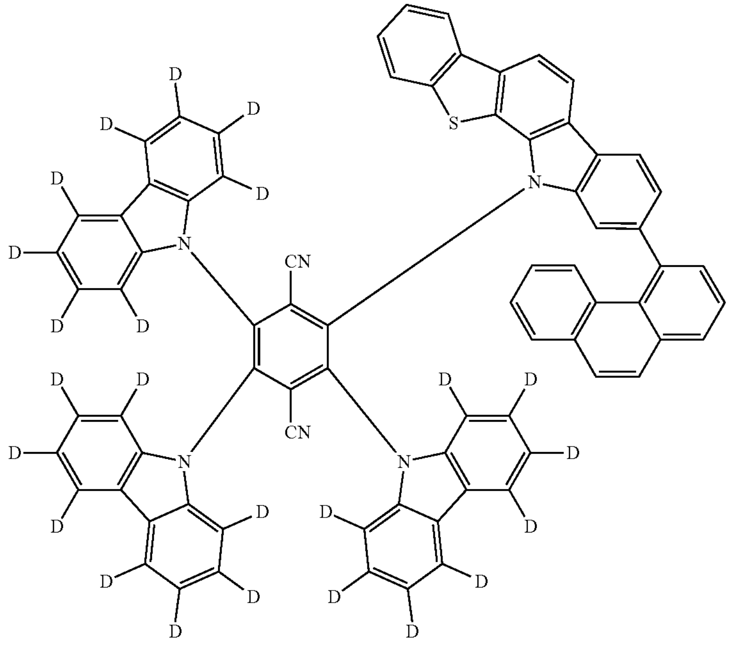
[Formula 69]
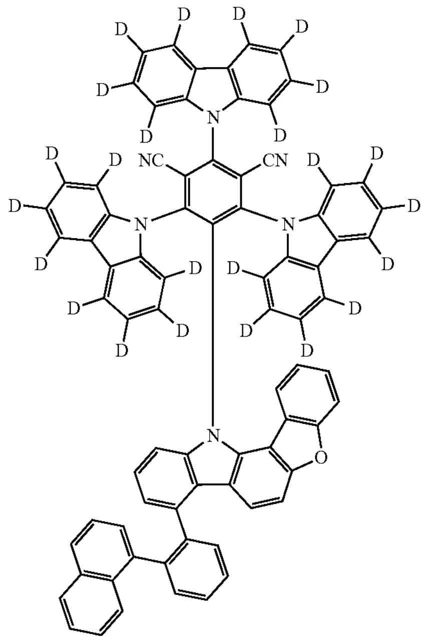
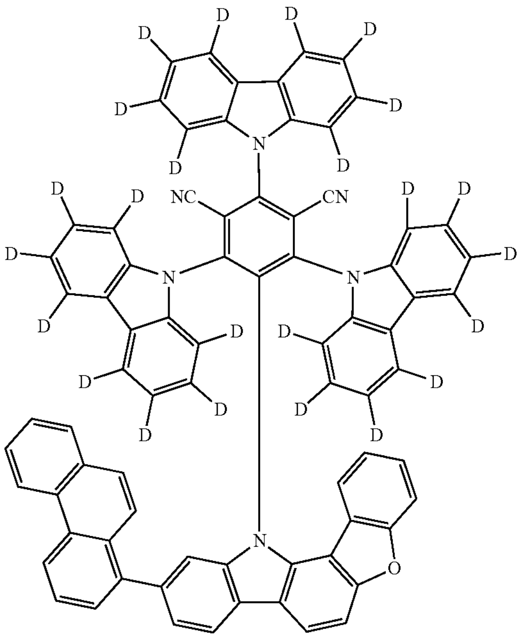

-continued
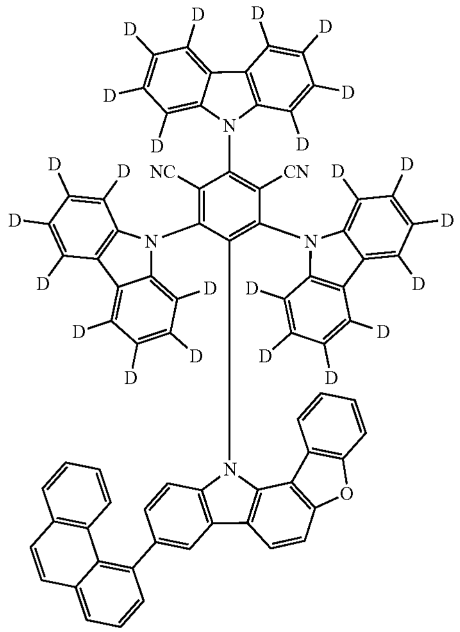
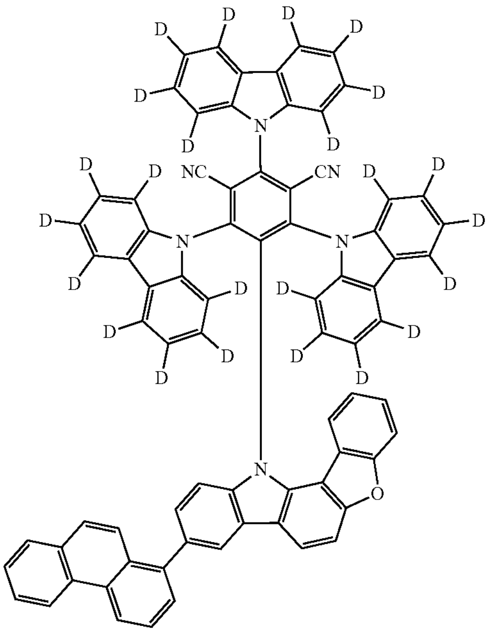
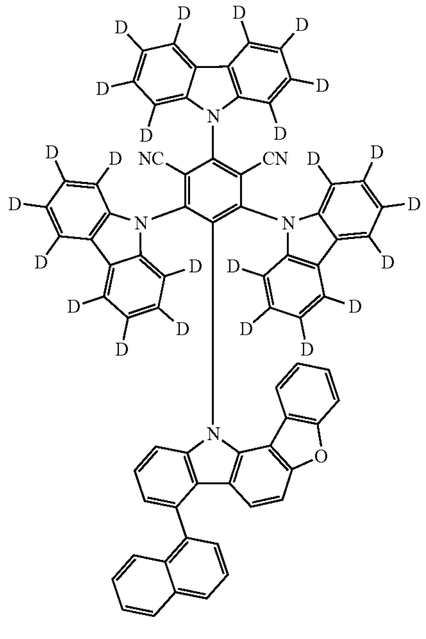
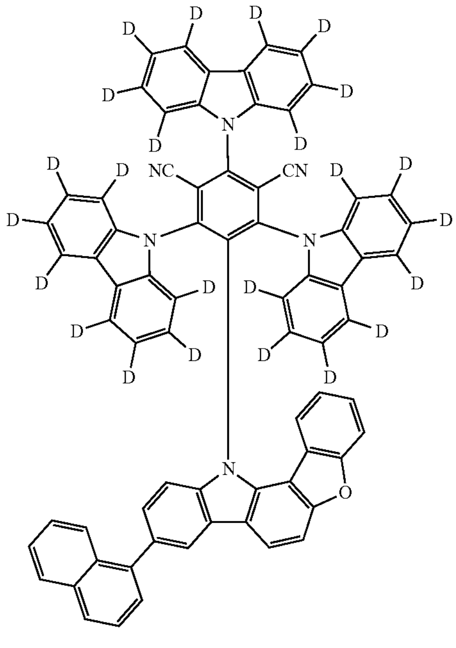

-continued
[Formula 70]
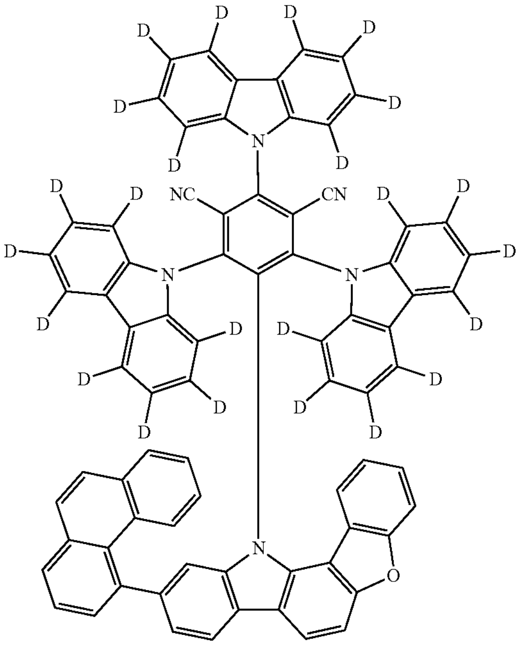
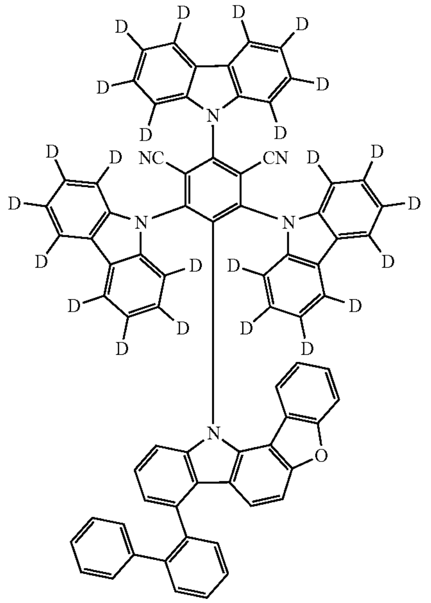
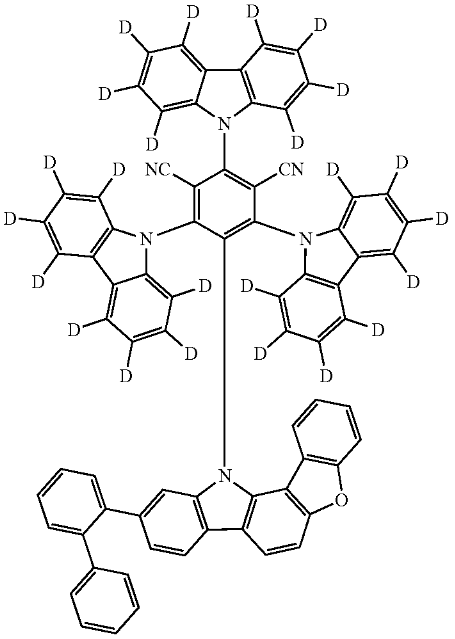
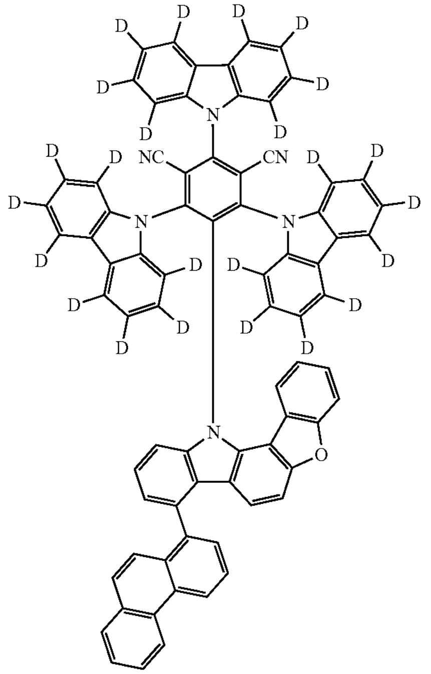

-continued
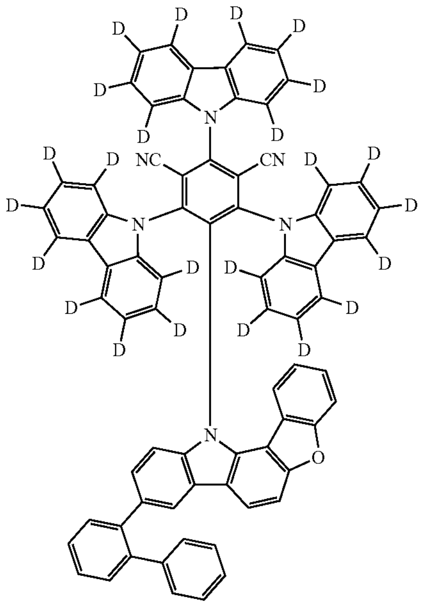
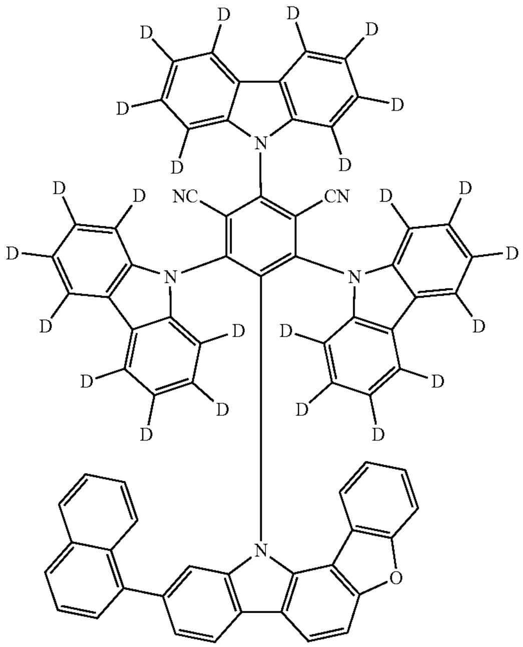
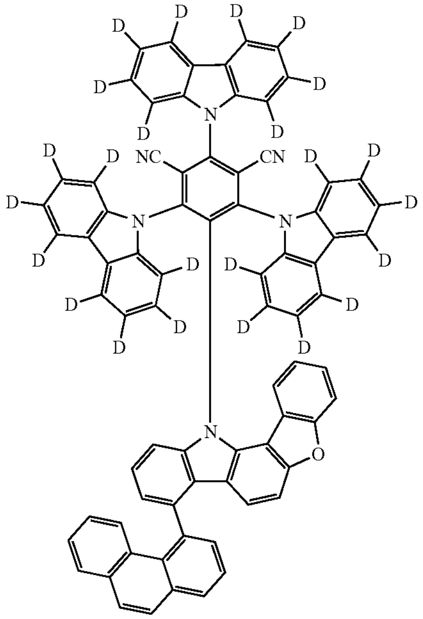
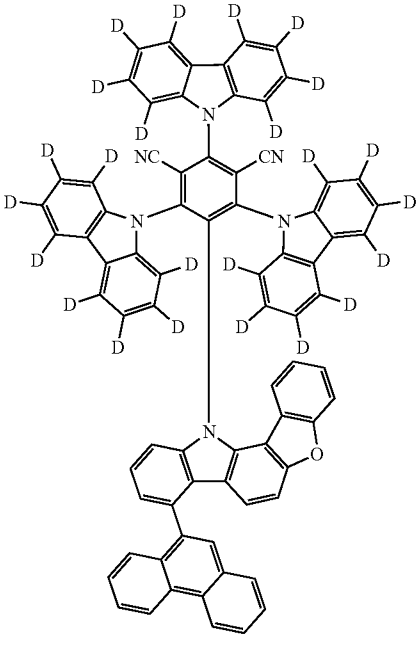

-continued
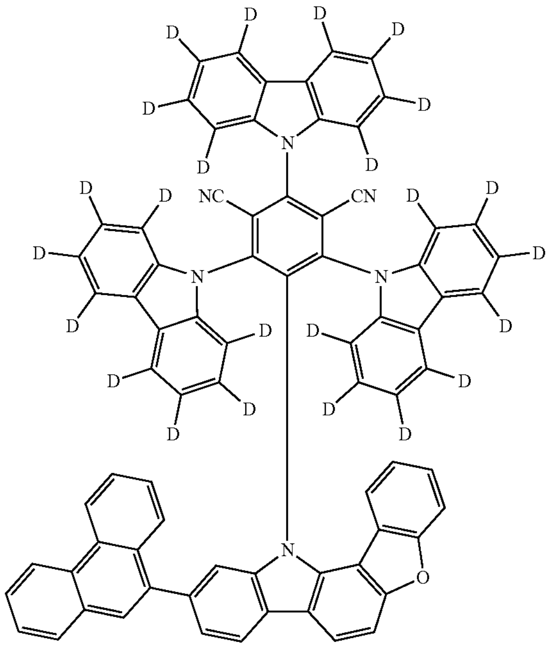
[Formula 71]
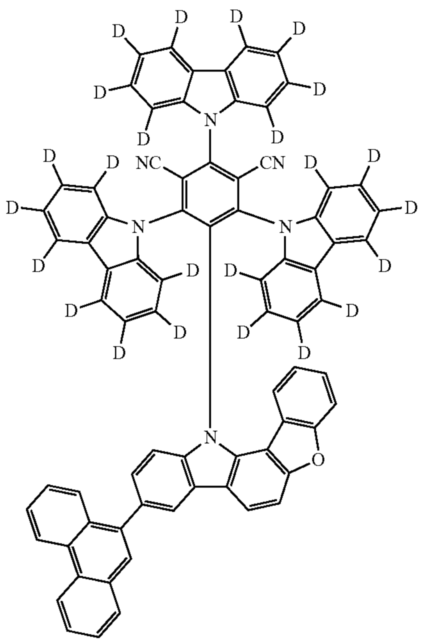
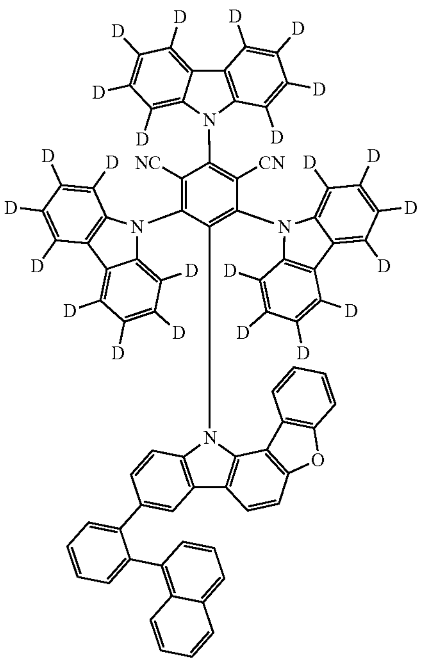

-continued
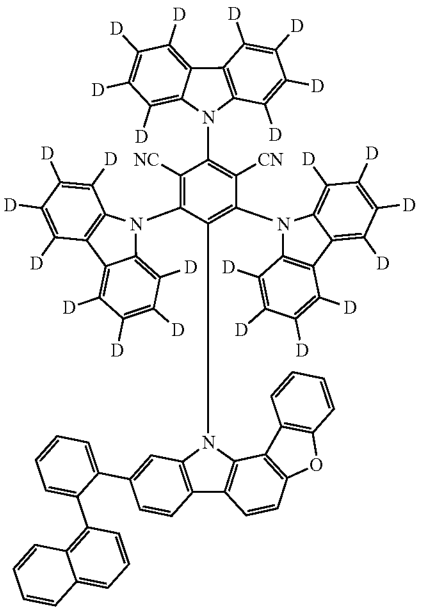
[Formula 72]
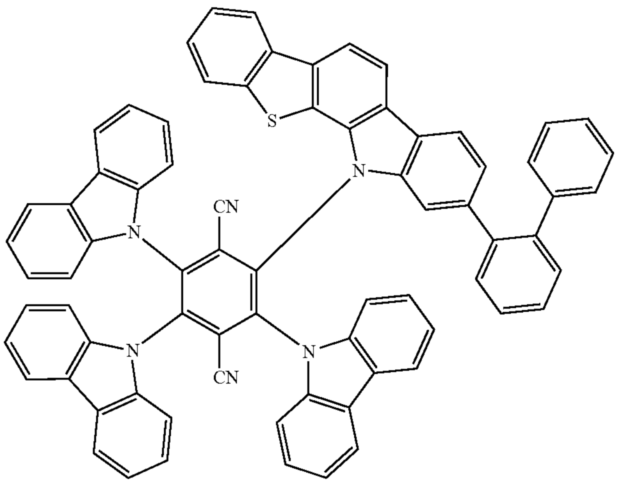
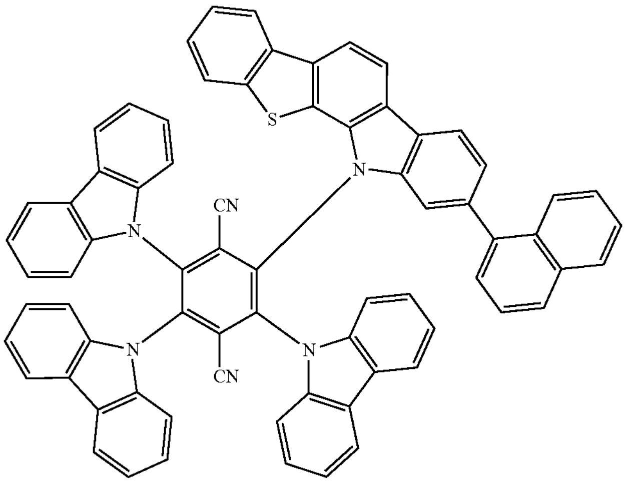

-continued
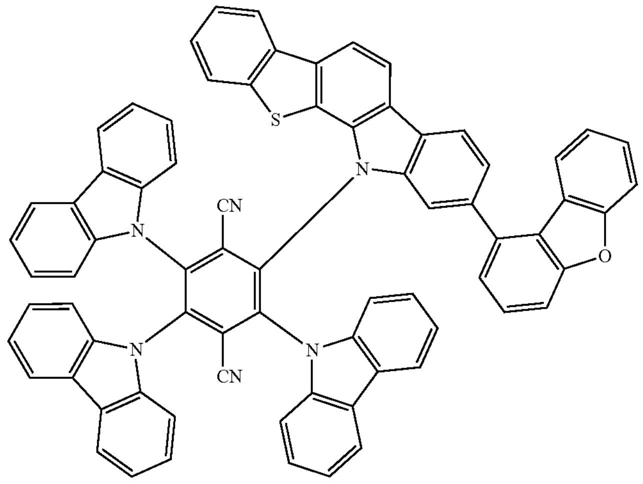
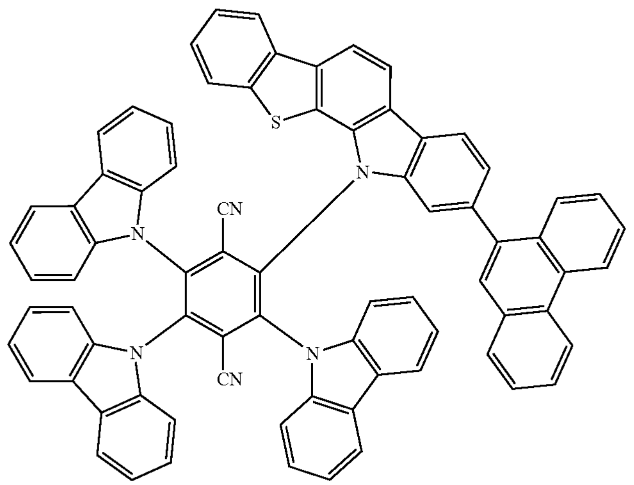
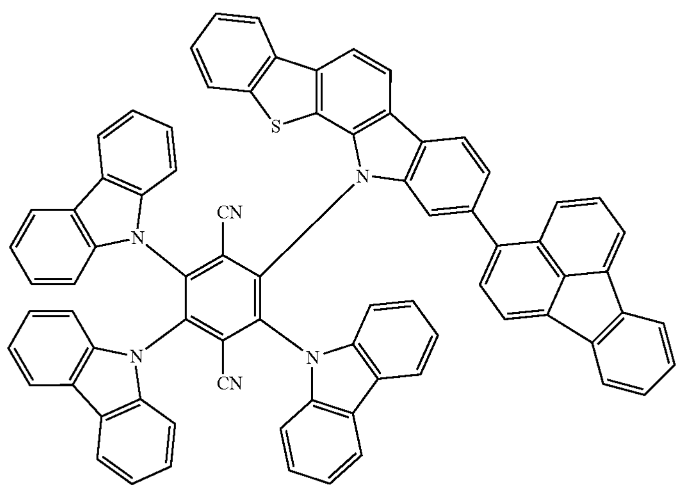

-continued
[Formula 73]
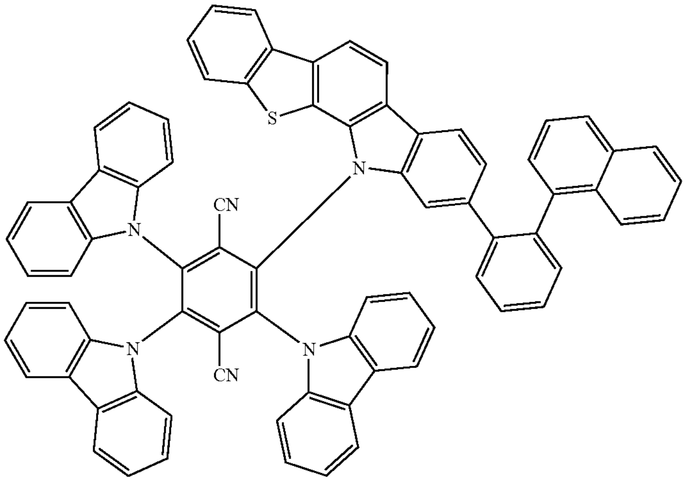
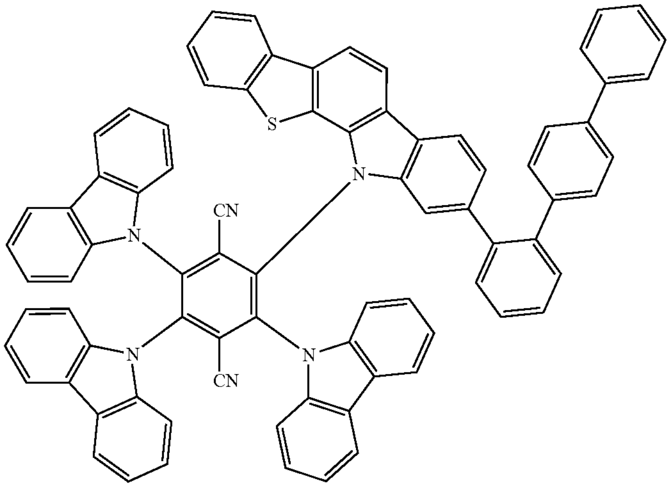
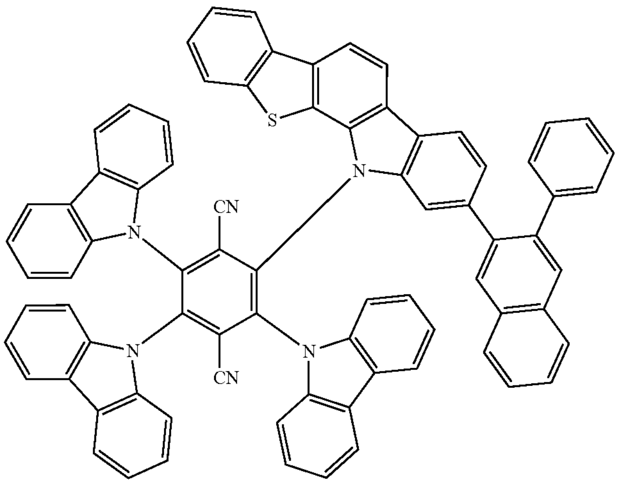

-continued
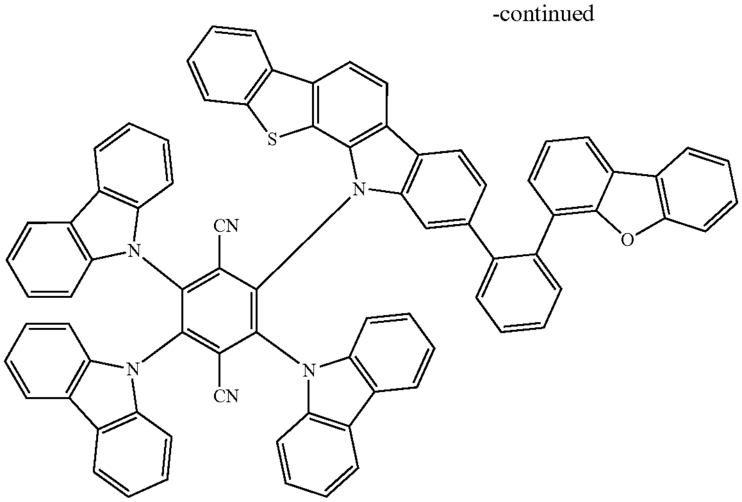
[Formula 74]
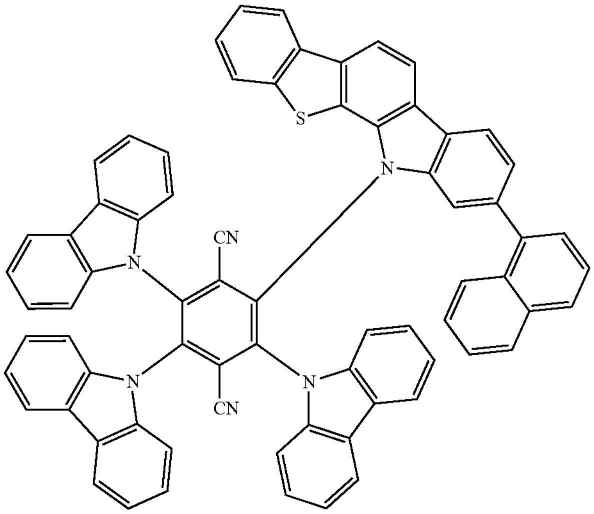
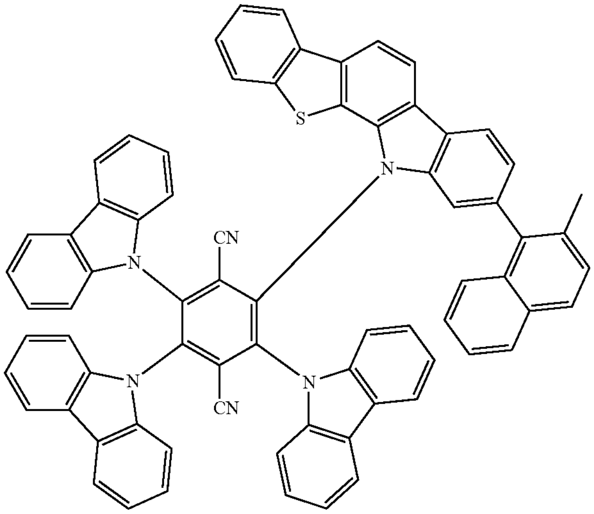

-continued
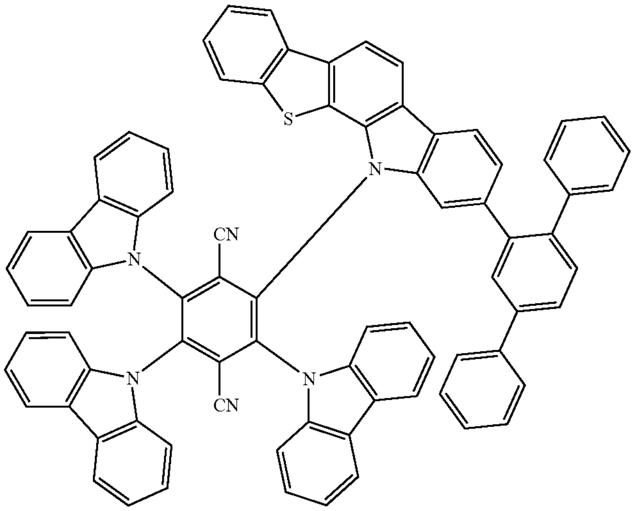
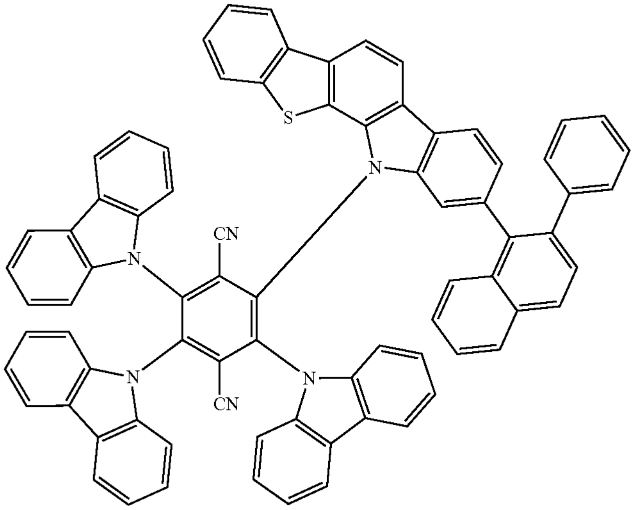
[Formula 75]
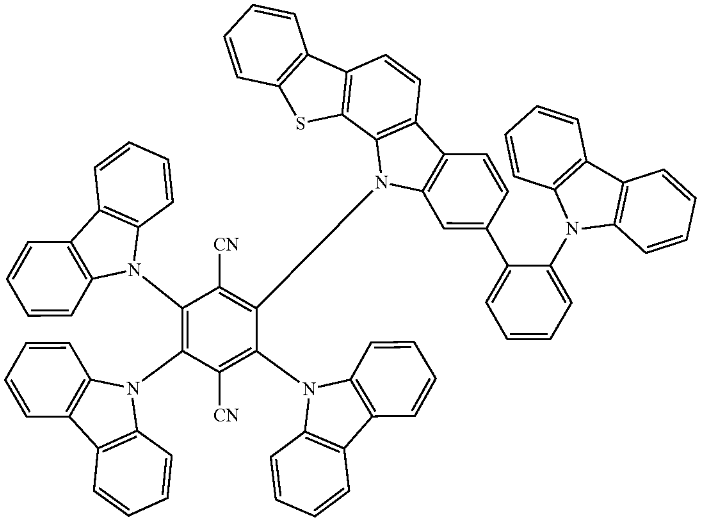

-continued
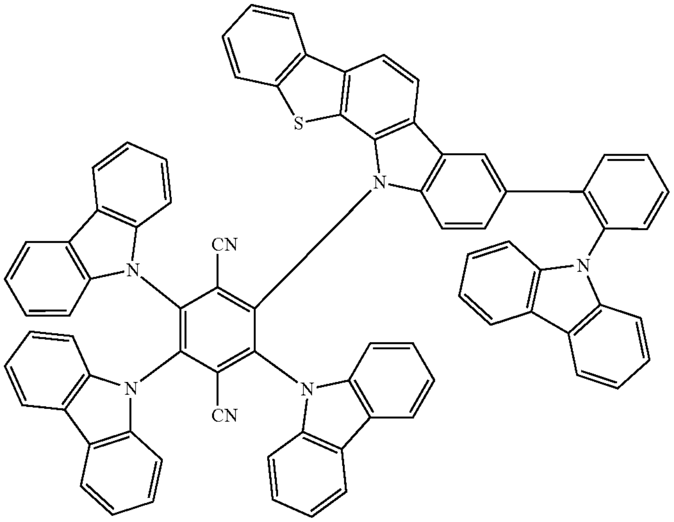
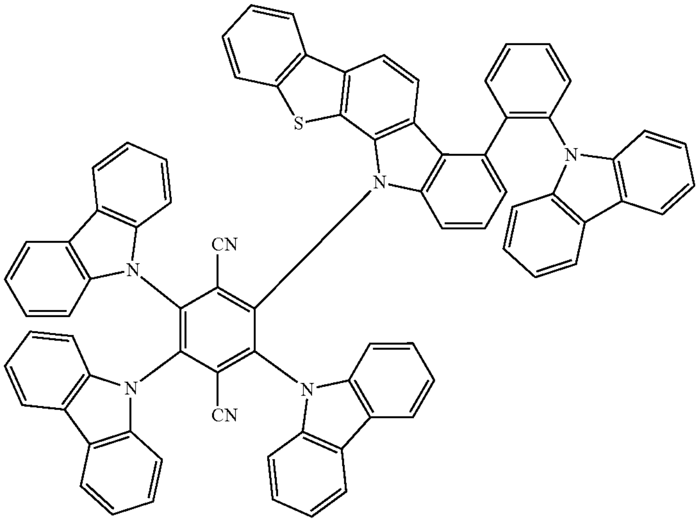
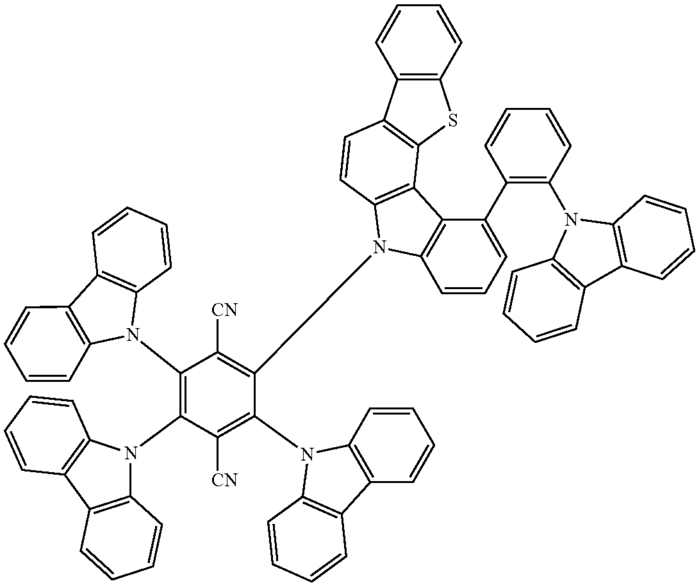

-continued
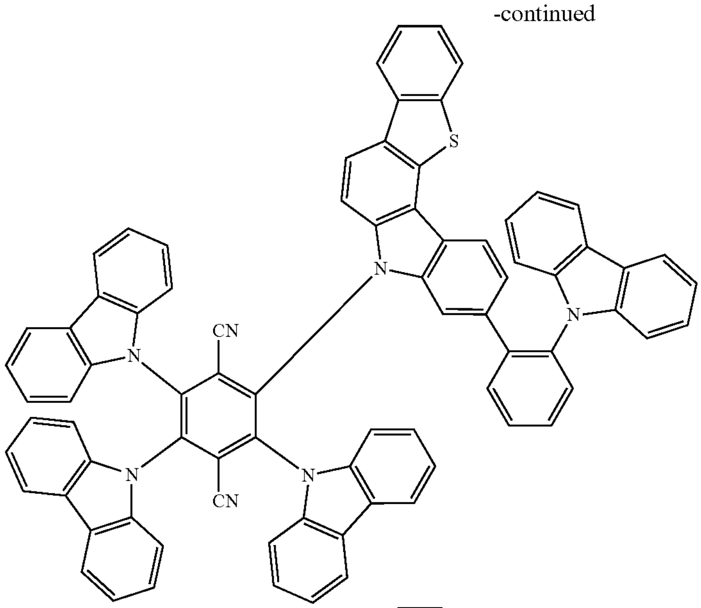
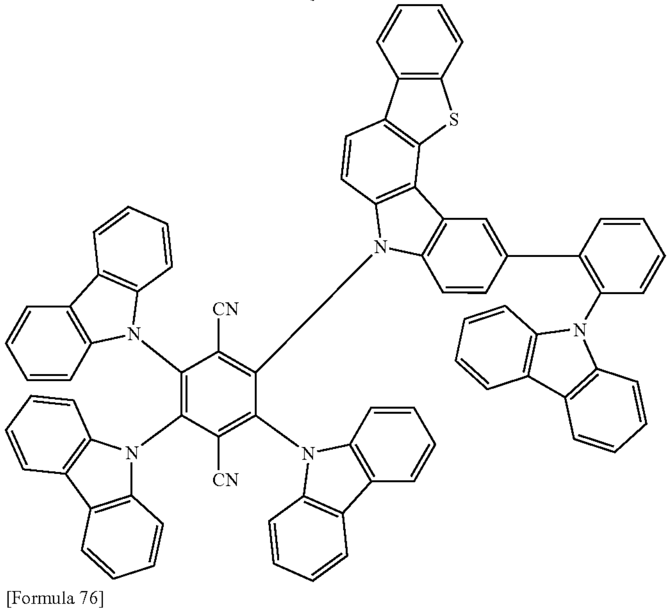
[Formula 76]
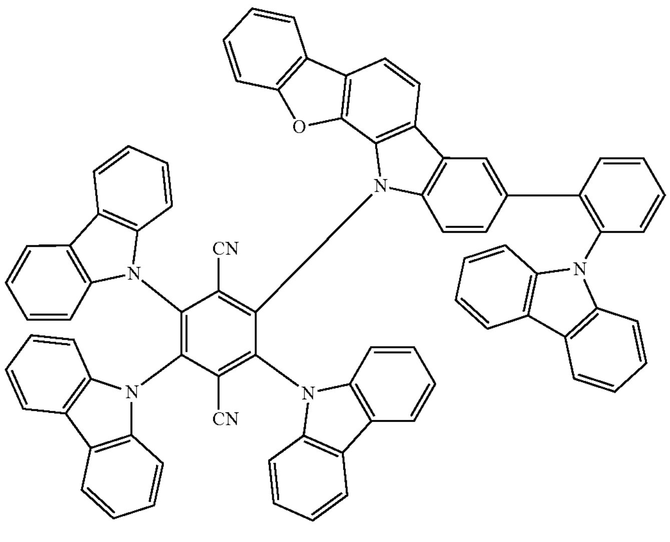

-continued
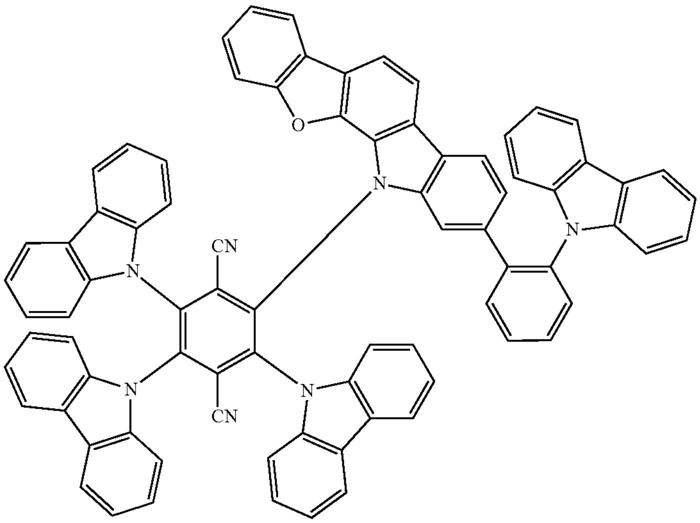
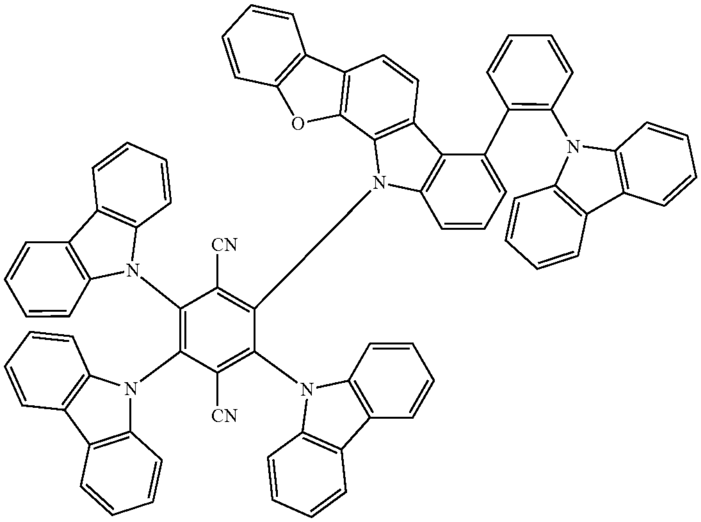
[Formula 77]
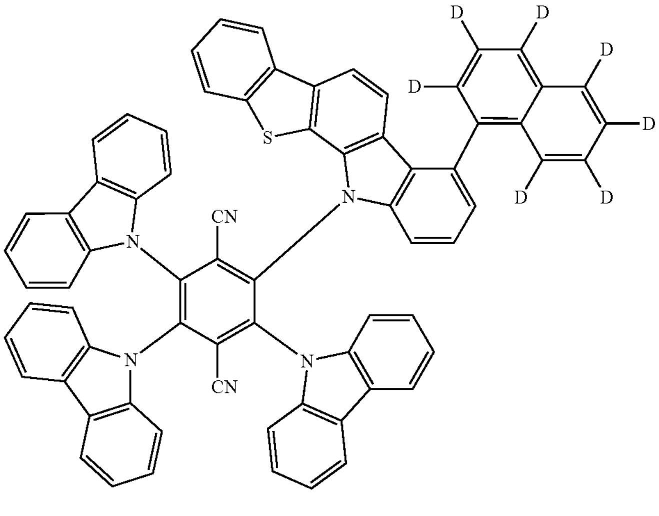

-continued
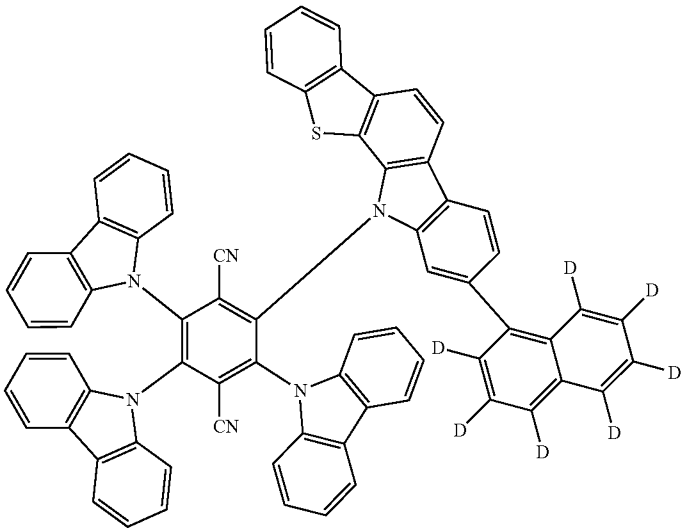
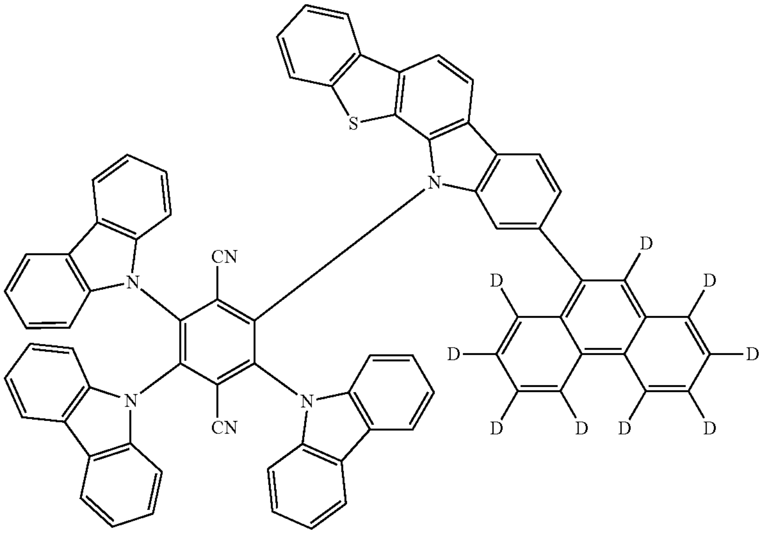
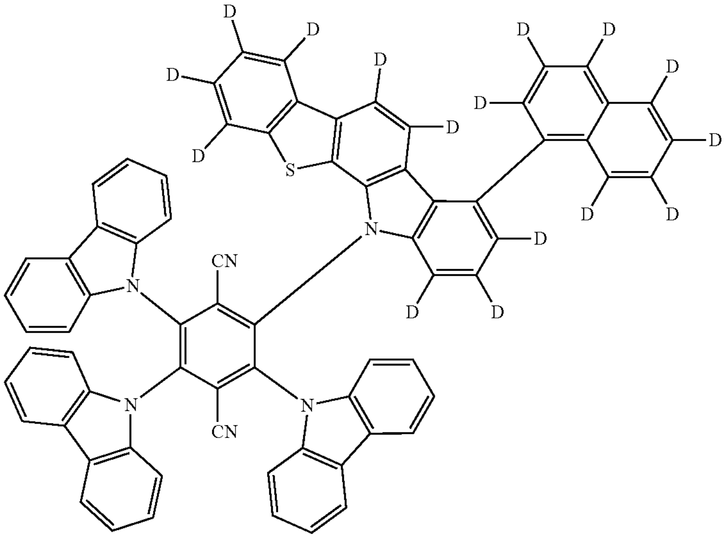

-continued
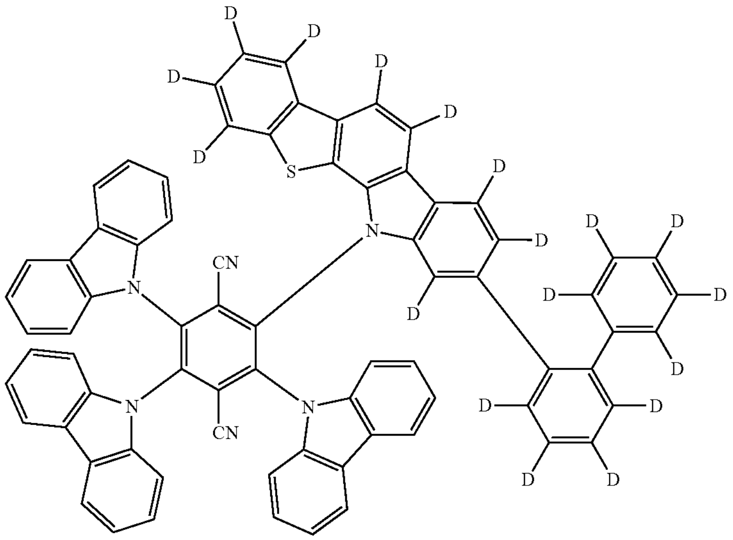
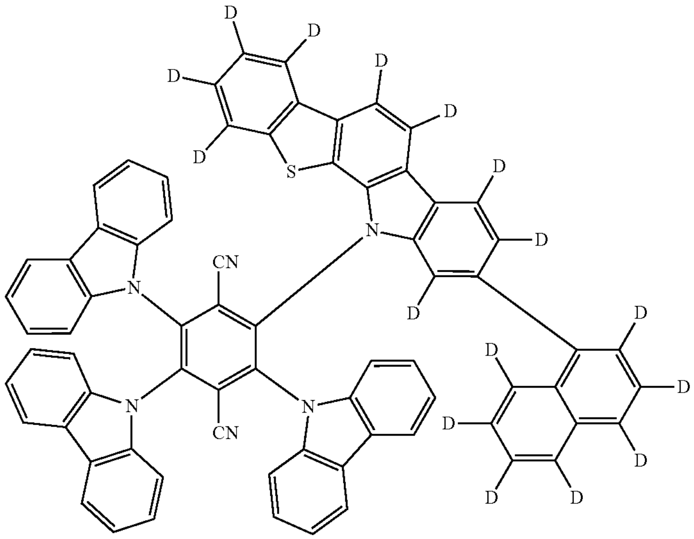
[Formula 78]
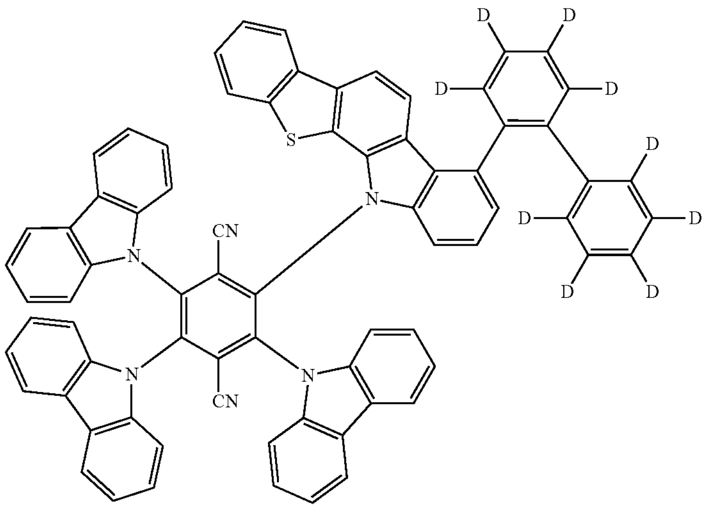

-continued
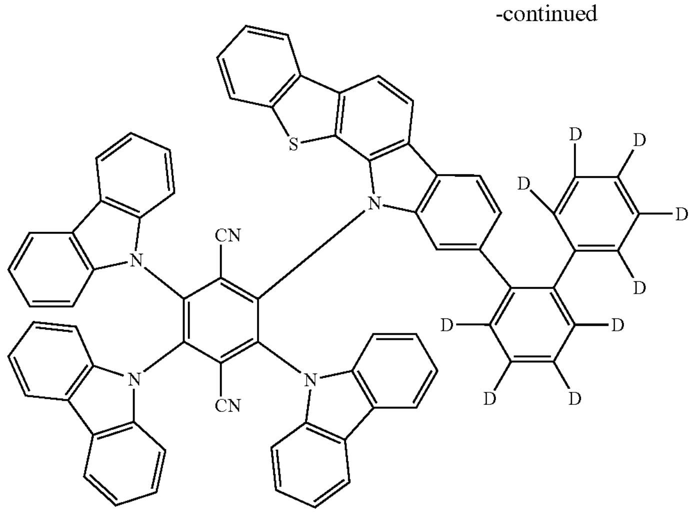
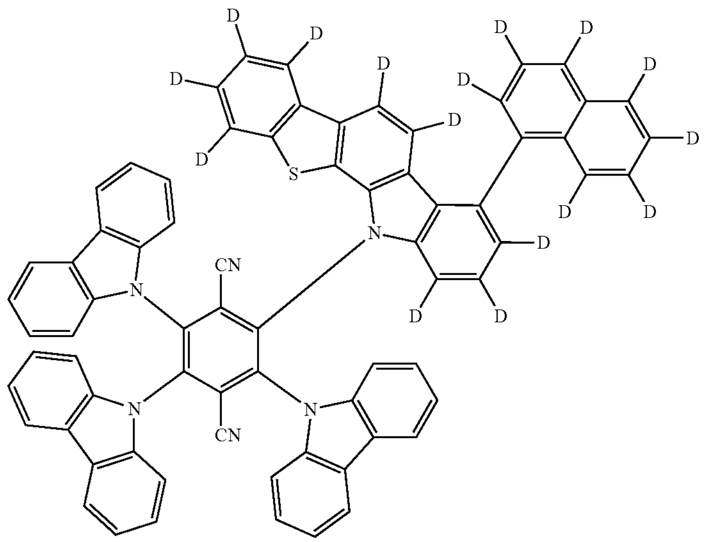
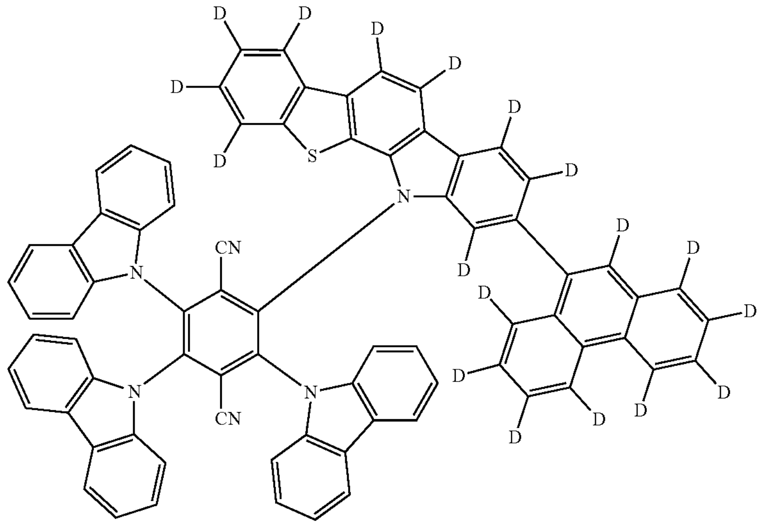

-continued
[Formula 79]
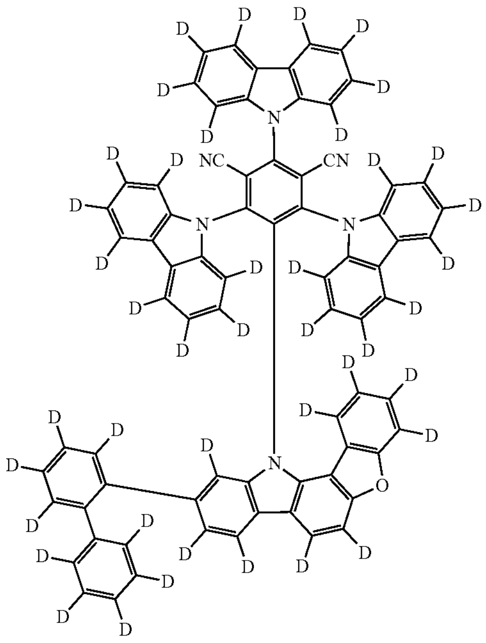
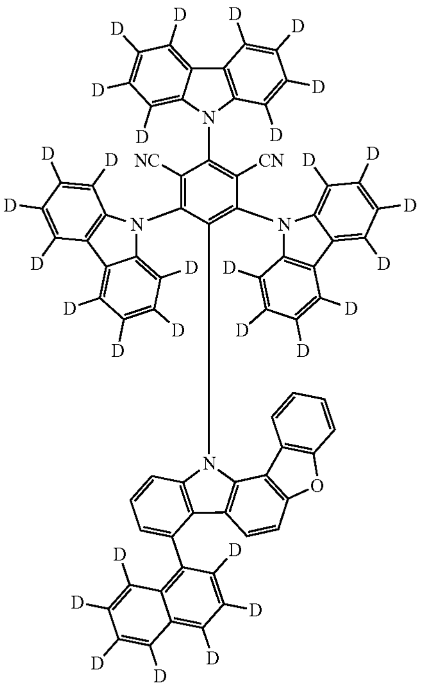
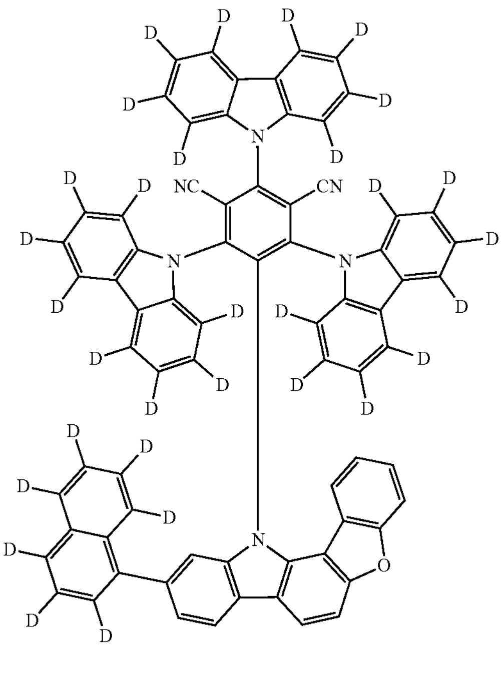
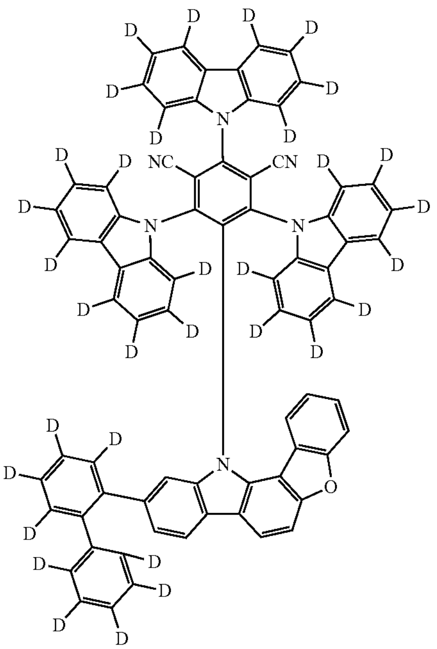

-continued
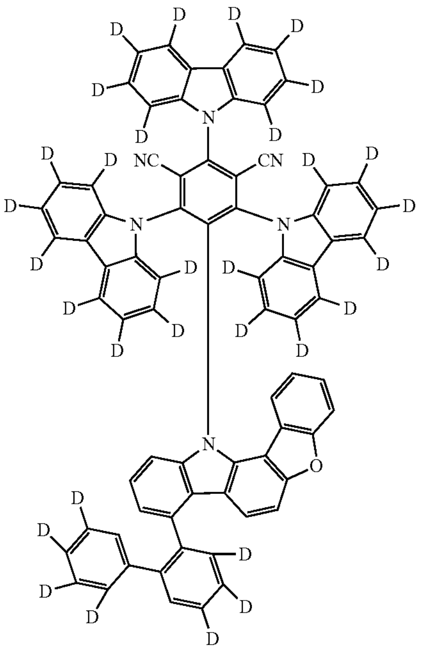
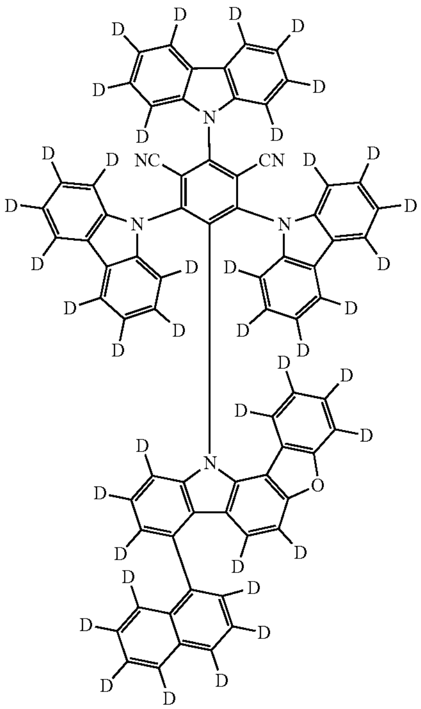
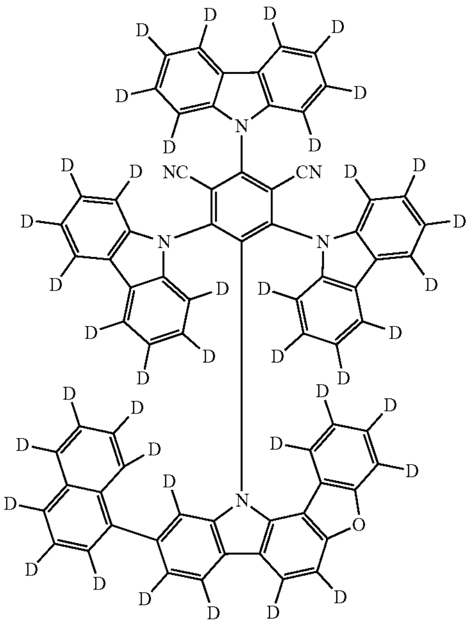
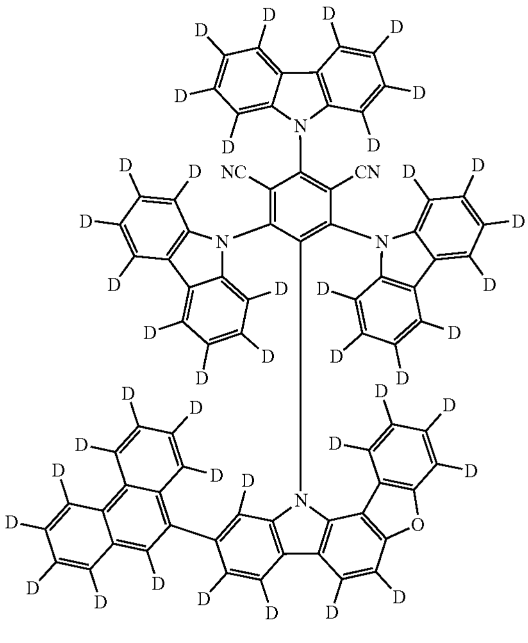

-continued
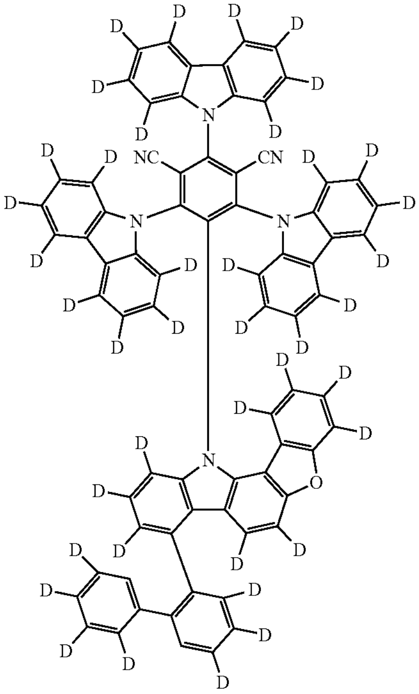
[Formula 80]
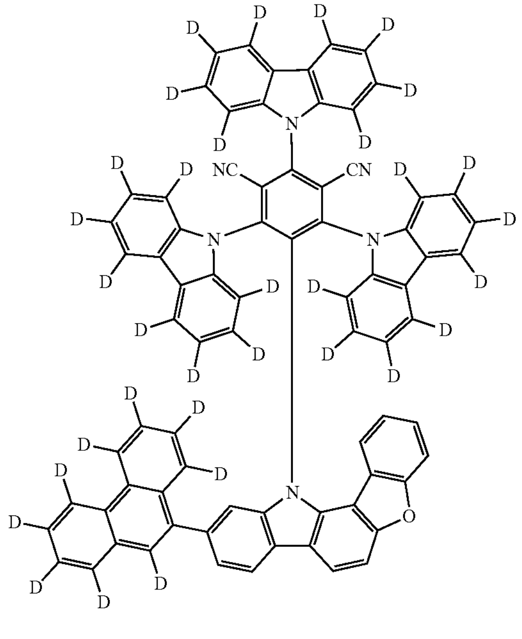
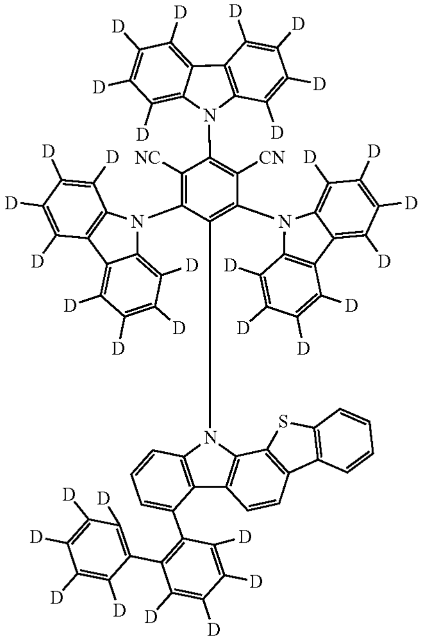

-continued

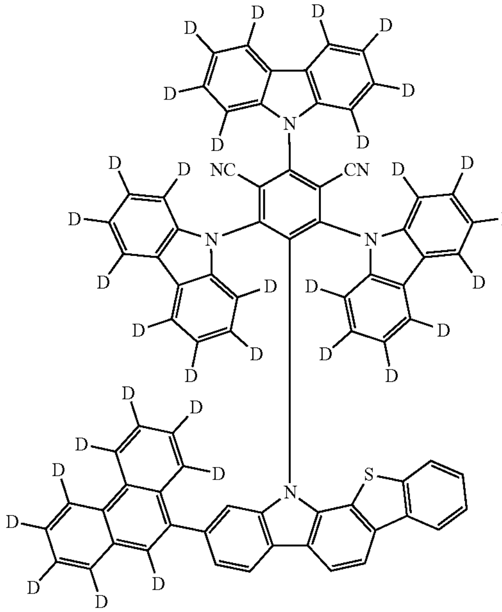

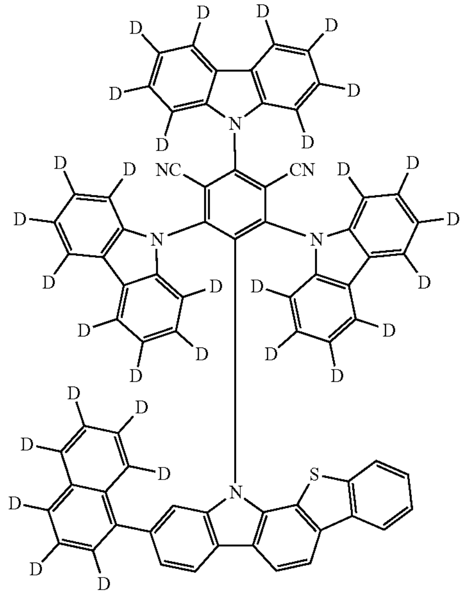

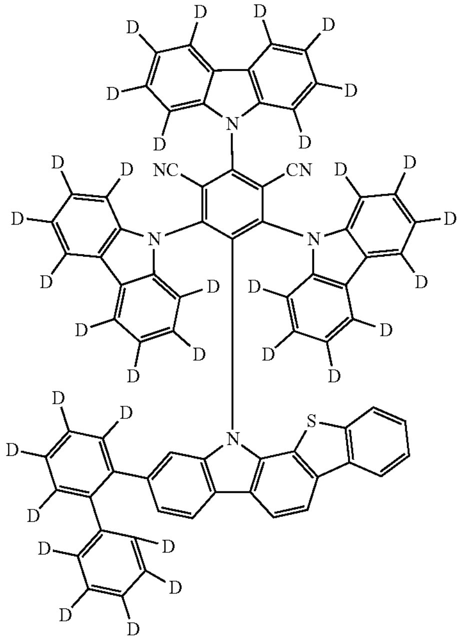

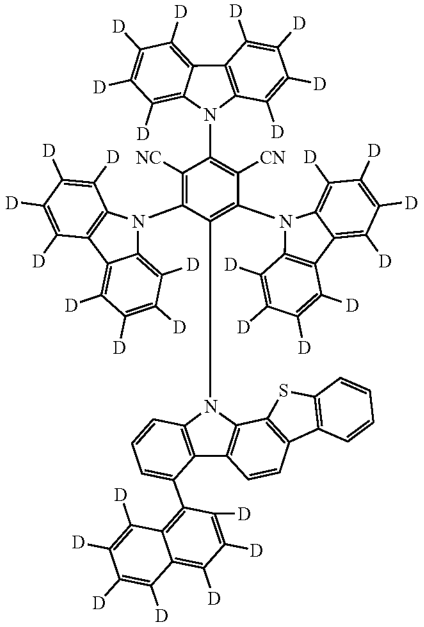

Second Exemplary Embodiment

Organic-EL-Device Material

An organic-EL-device material according to a second exemplary embodiment contains the compound according to the first exemplary embodiment (at least one of the compounds represented by the formulae (11) to (13).) As one example, the organic-EL-device material contains only the compound according to the first exemplary embodiment. As another example, the organic-EL-device material contains the compound according to the first exemplary embodiment and other compound(s) different from the compound according to the first exemplary embodiment.

In the organic-EL-device material of the present exemplary embodiment, the compound of the first exemplary embodiment is preferably a host material. In this arrangement, the organic-EL-device material optionally contains the compound according to the first exemplary embodiment as the host material and other compound(s) such as a dopant material.

In the organic-EL-device material of the present exemplary embodiment, the compound of the first exemplary embodiment is preferably a delayed fluorescent material.

The organic-EL-device material according to the second exemplary embodiment contains the compound (the compound of the first exemplary embodiment) capable of providing a high-performance organic electroluminescence device, especially the compound having high PLQY. Accordingly, the second exemplary embodiment can provide an organic-EL-device material capable of providing a high-performance organic electroluminescence device.

The organic-EL-device material according to the second exemplary embodiment may further contain a compound other than the compound according to the first exemplary embodiment. When organic-EL-device material according to the second exemplary embodiment contains the compound other than the compound according to the first exemplary embodiment, the compound in the second exemplary embodiment may be solid or liquid.

Third Exemplary Embodiment

Organic EL Device

An arrangement of an organic EL device according to a third exemplary embodiment will be described below.

The organic EL device includes an anode, a cathode, and an organic layer between the anode and the cathode. The organic layer typically includes a plurality of layers formed of an organic compound(s). The organic layer may further contain an inorganic compound. The organic EL device according to the present exemplary embodiment includes a first organic layer between the anode and the cathode. The first organic layer contains at least one compound (the compound represented by any one of formulae (11) to (13)) according to the first exemplary embodiment.

The first organic layer is, for instance, at least one layer selected from the group consisting of a hole injecting layer, a hole transporting layer, an emitting layer, an electron injecting layer, an electron transporting layer, a hole blocking layer and an electron blocking layer.

The first organic layer is preferably the emitting layer.

In the organic EL device of the present exemplary embodiment, the first organic layer is the emitting layer.

In the present exemplary embodiment, the organic layer may consist of the emitting layer as the first organic layer. Alternatively, the organic layer may further include, for instance, at least one layer selected from the group consisting of the hole injecting layer, the hole transporting layer, the electron injecting layer, the electron transporting layer, the hole blocking layer, and the electron blocking layer.

FIG. 1 schematically shows an exemplary structure of the organic EL device of the present exemplary embodiment.

An organic EL device 1 includes a light-transmissive substrate 2, an anode 3, a cathode 4, and an organic layer 10 provided between the anode 3 and the cathode 4. The organic layer 10 includes a hole injecting layer 6, a hole transporting layer 7, an emitting layer 5 (the first organic layer), an electron transporting layer 8, and an electron injecting layer 9, which are sequentially layered on the anode 3.

In the organic EL device 1 according to the present exemplary embodiment, the emitting layer 5 contains the first compound.

The first compound is the compound according to the first exemplary embodiment (at least one of the compounds represented by the formulae (11) to (13)).

It is preferable that the emitting layer 5 does not contain a phosphorescent material (dopant material).

It is preferable that the emitting layer 5 does not contain a heavy-metal complex and a phosphorescent rare-earth metal complex. Examples of the heavy-metal complex herein include iridium complex, osmium complex, and platinum complex.

It is also preferable that the emitting layer 5 does not contain a metal complex.

The emitting layer 5 of the organic EL device 1 of the present exemplary embodiment contains the first compound (the compound represented by any one of formulae (11) to (13)) and a second compound.

In this form, the first compound is preferably a host material (occasionally also referred to as a matrix material) and the second compound is preferably a dopant material (occasionally also referred to as a guest material, emitter or a luminescent material).

First Compound

The first compound is a compound according to the first exemplary embodiment.

The first compound is preferably a delayed fluorescent compound.

Delayed Fluorescence

Delayed fluorescence is explained in "Yuki Hando-tai no Debaisu Bussei (Device Physics of Organic Semiconductors)" (edited by ADACHI, Chihaya, published by Kodansha, on pages 261-268). This document describes that, if an energy difference $\Delta E_{13}$ of a fluorescent material between a singlet state and a triplet state is reducible, a reverse energy transfer from the triplet state to the singlet state, which usually occurs at a low transition probability, would occur at a high efficiency to express thermally activated delayed fluorescence (TADF). Further, a mechanism of generating delayed fluorescence is explained in FIG. 10.38 in the document. The first compound of the present exemplary embodiment is preferably a compound exhibiting thermally activated delayed fluorescence generated by such a mechanism.

In general, emission of delayed fluorescence can be confirmed by measuring the transient PL (Photo Luminescence).

The behavior of delayed fluorescence can also be analyzed based on the decay curve obtained from the transient PL measurement. The transient PL measurement is a method of irradiating a sample with a pulse laser to excite the sample, and measuring the decay behavior (transient characteristics) of PL emission after the irradiation is stopped. PL emission in TADF materials is classified into a light emission component from a singlet exciton generated by the first PL excitation and a light emission component from a singlet exciton generated via a triplet exciton. The lifetime of the singlet exciton generated by the first PL excitation is on the order of nanoseconds and is very short. Therefore, light emission from the singlet exciton rapidly attenuates after irradiation with the pulse laser.

On the other hand, the delayed fluorescence is gradually attenuated due to light emission from a singlet exciton generated via a triplet exciton having a long lifetime. As described above, there is a large temporal difference between the light emission from the singlet exciton generated by the first PL excitation and the light emission from the singlet exciton generated via the triplet exciton. Therefore, the luminous intensity derived from delayed fluorescence can be determined.

Figure 2:
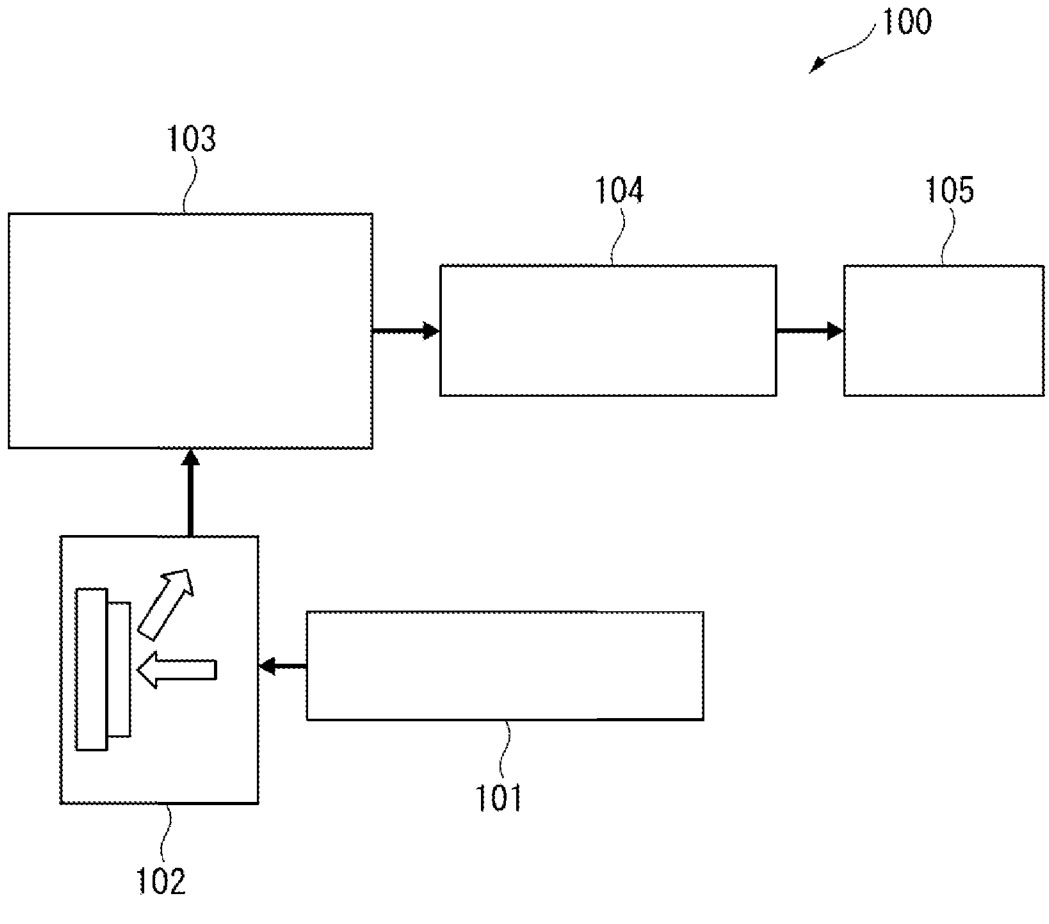

FIG. 2 shows a schematic diagram of an exemplary device for measuring the transient PL. An example of a method of measuring a transient PL using FIG. 2 and an example of behavior analysis of delayed fluorescence will be described.

A transient PL measuring device 100 in FIG. 2 includes: a pulse laser 101 capable of radiating a light having a predetermined wavelength; a sample chamber 102 configured to house a measurement sample; a spectrometer 103 configured to divide a light radiated from the measurement sample; a streak camera 104 configured to provide a two-dimensional image; and a personal computer 105 configured to import and analyze the two-dimensional image. A device for measuring the transient PL is not limited to the device shown in FIG. 2.

The sample housed in the sample chamber 102 is obtained by forming a thin film, in which a matrix material is doped with a doping material at a concentration of 12 mass %, on the quartz substrate.

The thin film sample housed in the sample chamber 102 is irradiated with the pulse laser from the pulse laser 101 to excite the doping material. Emission is extracted in a direction of 90 degrees with respect to a radiation direction of the excited light. The extracted emission is divided by the spectrometer 103 to form a two-dimensional image in the streak camera 104. As a result, the two-dimensional image is obtainable in which the ordinate axis represents a time, the abscissa axis represents a wavelength, and a bright spot represents a luminous intensity. When this two-dimensional image is taken out at a predetermined time axis, an emission spectrum in which the ordinate axis represents the luminous intensity and the abscissa axis represents the wavelength is obtainable. Moreover, when this two-dimensional image is taken out at the wavelength axis, a decay curve (transient PL) in which the ordinate axis represents a logarithm of the luminous intensity and the abscissa axis represents the time is obtainable.

For instance, a thin film sample A was prepared as described above from a reference compound H1 as the matrix material and a reference compound D1 as the doping material and was measured in terms of the transient PL.

[Formula 81]

(Reference Compound H1)

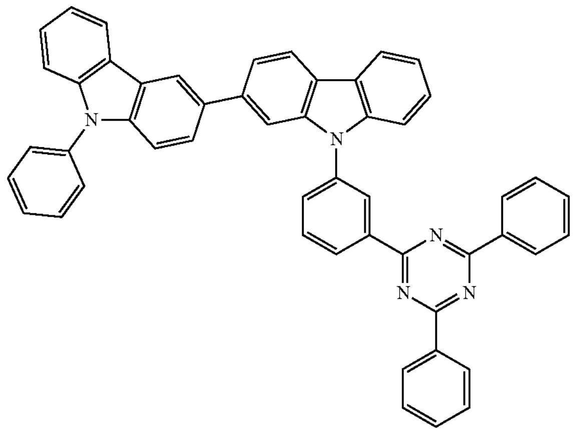

(Reference Compound D1)

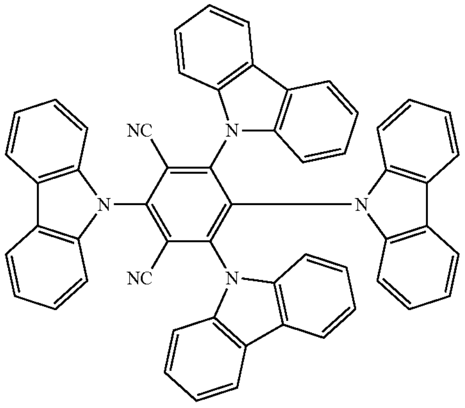

Herein, the decay curve was analyzed using the above-described thin film sample A and a thin film sample B. The thin film sample B was prepared in the same manner as described above from a reference compound H2 as the matrix material and the reference compound D1 as the doping material.

Figure 3:
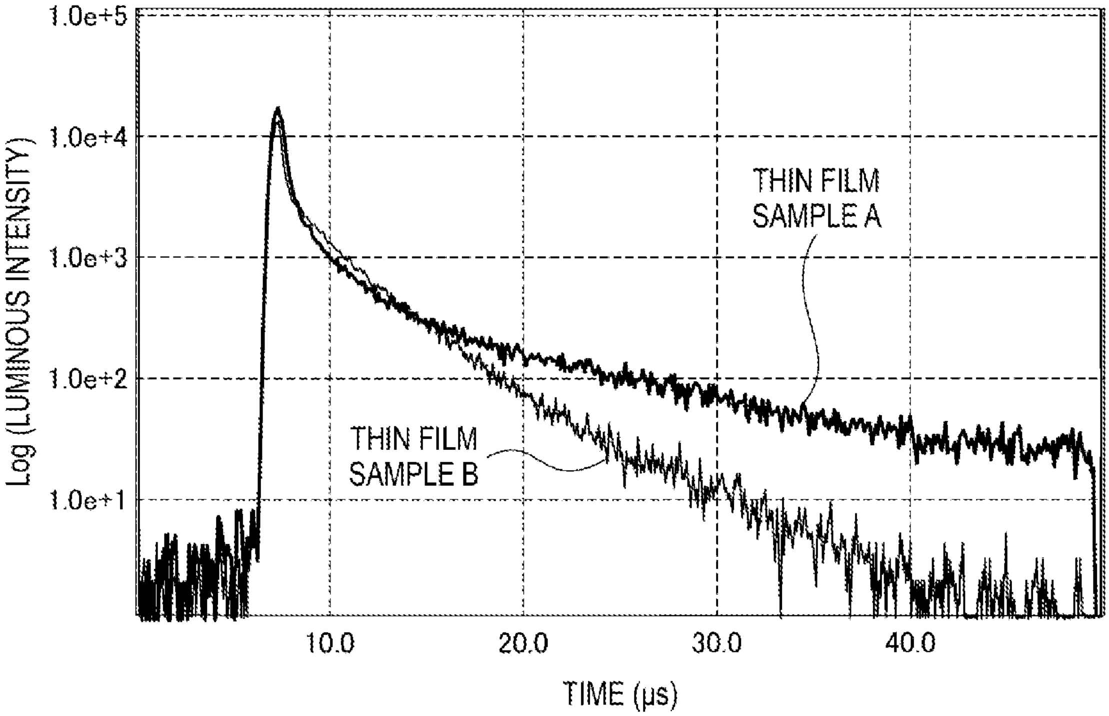
FIG. 3 shows an example of a decay curve of the transient PL.

FIG. 3 shows a decay curve obtained from the measured transitional PL of the thin film sample A and the thin film sample B.

[Formula 82]

(Reference Compound H2)

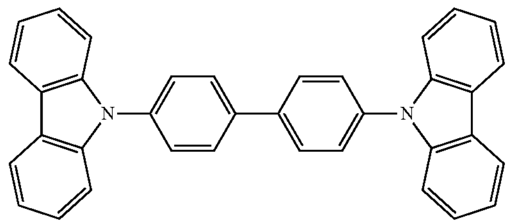

As described above, an emission decay curve in which the ordinate axis represents the luminous intensity and the abscissa axis represents the time can be obtained by the transient PL measurement. Based on the emission decay curve, a fluorescence intensity ratio between fluorescence emitted from a singlet state generated by photo-excitation and delayed fluorescence emitted from a singlet state generated by inverse energy transfer via a triplet state can be estimated. In a delayed fluorescent material, a ratio of the intensity of the slowly decaying delayed fluorescence to the intensity of the promptly decaying fluorescence is relatively large.

Specifically, Prompt emission and Delay emission are present as emission from the delayed fluorescent material. Prompt emission is observed promptly when the excited state is achieved by exciting the compound of the exemplary embodiment with a pulse beam (i.e., a beam emitted from a pulse laser) having a wavelength absorbable by the delayed fluorescent material. Delay emission is observed not promptly when the excited state is achieved but after the excited state is achieved.

An amount of Prompt emission, an amount of Delay emission and a ratio between the amounts thereof can be obtained according to the method as described in "Nature 492, 234-238, 2012" (Reference Document 1). The amount of Prompt emission and the amount of Delay emission may be calculated using a device different from one described in Reference Document 1 or one shown in FIG. 2.

Herein, a sample prepared by a method shown below is used for measuring delayed fluorescence of the first compound. For instance, the first compound is dissolved in toluene to prepare a dilute solution with an absorbance of 0.05 or less at the excitation wavelength to eliminate the contribution of self-absorption. In order to prevent quenching due to oxygen, the sample solution is frozen and degassed and then sealed in a cell with a lid under an argon atmosphere to obtain an oxygen-free sample solution saturated with argon.

The fluorescence spectrum of the sample solution is measured with a spectrofluorometer FP-8600 (manufactured by JASCO Corporation), and the fluorescence spectrum of a 9,10-diphenylanthracene ethanol solution is measured under the same conditions. Using the fluorescence area intensities of both spectra, the total fluorescence quantum yield is calculated by an equation (1) in Morris et al. J. Phys. Chem. 80 (1976) 969.

An amount of Prompt emission, an amount of Delay emission and a ratio between the amounts thereof can be obtained according to the method as described in "Nature 492, 234-238, 2012" (Reference Document 1). The amount of Prompt emission and the amount of Delay emission may be calculated using a device different from one described in Reference Document 1 or one shown in FIG. 2.

In the present exemplary embodiment, provided that an amount of Prompt emission of a measurement target compound (first compound) is denoted by $X_P$ and the amount of Delay emission is denoted by $X_D$, a value of $X_D/X_P$ is preferably 0.05 or more.

The amounts of Prompt emission and Delay emission and a ratio of the amounts thereof in compounds other than the first compound herein are measured in the same manner as those of the first compound.

Second Compound

The second compound of the present exemplary embodiment is preferably a fluorescent compound. The second compound may be a compound exhibiting thermally activated delayed fluorescence or a compound that does not exhibit thermally activated delayed fluorescence.

The second compound of the present exemplary embodiment is preferably a compound that does not exhibit thermally activated delayed fluorescence. The second compound of the present exemplary embodiment is not a phosphorescent metal complex. The second compound of the present exemplary embodiment is preferably not a heavy-metal complex. Further, the second compound of the present exemplary embodiment is preferably not a metal complex.

A fluorescent material is usable as the second compound in the present exemplary embodiment. Specific examples of the fluorescent material include a bisarylaminonaphthalene derivative, aryl-substituted naphthalene derivative, bisarylaminoanthracene derivative, aryl-substituted anthracene derivative, bisarylaminopyrene derivative, aryl-substituted pyrene derivative, bisarylamino chrysene derivative, aryl-substituted chrysene derivative, bisarylaminofluoranthene derivative, aryl-substituted fluoranthene derivative, indenoperylene derivative, acenaphthofluoranthene derivative, pyromethene boron complex compound, compound having a pyromethene skeleton, metal complex of the compound having a pyrromethene skeleton, diketopyrrolopyrrole derivative, perylene derivative, and naphthacene derivative.

Compound Represented by Formula (20)

The second compound in the present exemplary embodiment is also preferably represented by a formula (20) below.

[Formula 83]

(20)

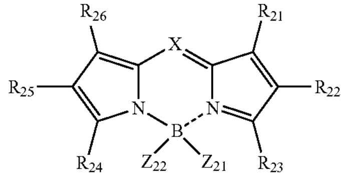

In the formula (20):

X is a nitrogen atom, or a carbon atom bonded to Y;

Y is a hydrogen atom or a substituent;

$R_{21}$ to $R_{26}$ are each independently a hydrogen atom or a substituent, or at least one combination of a combination of $R_{21}$ and $R_{22}$, a combination of $R_{22}$ and $R_{23}$, a combination of $R_{24}$ and $R_{25}$, or a combination of $R_{25}$ and $R_{26}$ are mutually bonded to form a ring;

Y and $R_{21}$ to $R_{26}$ serving as a substituent are each independently selected from the group consisting of a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, a substituted or unsubstituted alkylthio group having 1 to 30 carbon atoms, a substituted or unsubstituted aryloxy group having 6 to 30 ring carbon atoms, a substituted or unsubstituted arylthio group having 6 to 30 ring carbon atoms, a substituted or unsubstituted alkenyl group having 2 to 30 carbon atoms, a substituted or unsubstituted aralkyl group having 7 to 30 carbon atoms, a substituted or unsubstituted heteroaryl group having 5 to 30 ring atoms, a halogen atom, a carboxy group, a substituted or unsubstituted ester group, a substituted or unsubstituted carbamoyl group, a substituted or unsubstituted amino group, a nitro group, a cyano group, a substituted or unsubstituted silyl group, and a substituted or unsubstituted siloxanyl group;

$Z_{21}$ and $Z_{22}$ are each independently a substituent, or are mutually bonded to form a ring; and $Z_{21}$ and $Z_{22}$ serving as a substituent are each independently selected from the group consisting of a halogen atom, a substituted or unsubstituted alkyl group having 1 to 30 carbon atoms, a substituted or unsubstituted alkyl halide group having 1 to 30 carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, and a substituted or unsubstituted aryloxy group having 6 to 30 ring carbon atoms.

When the second compound is a fluorescent compound, the second compound preferably emits light whose maximum peak wavelength is in a range from 400 nm to 700 nm.

Herein, the maximum peak wavelength refers to a peak wavelength of a fluorescence spectrum exhibiting a maximum luminous intensity among fluorescence spectra measured in a toluene solution in which a measurement target compound is dissolved at a concentration ranging from $10^{-6}$ mol/l to $10^{-5}$ mol/l. A spectrophotofluorometer (F-7000 manufactured by Hitachi High-Tech Science Corporation) is used as a measurement device.

The second compound preferably exhibits red or green light emission.

Herein, the red emission refers to light emission whose maximum peak wavelength of fluorescence spectrum is in a range from 600 nm to 660 nm.

When the second compound is a red fluorescent compound, the maximum peak wavelength of the second compound is preferably in a range from 600 nm to 660 nm, more preferably in a range from 600 nm to 640 nm, further preferably in a range from 610 nm to 630 nm.

Herein, the green emission refers to light emission whose maximum peak wavelength of fluorescence spectrum is in a range from 500 nm to 560 nm.

When the second compound is a green fluorescent compound, the maximum peak wavelength of the second compound is preferably in a range from 500 nm to 560 nm, more preferably in a range from 500 nm to 540 nm, further preferably in a range from 510 nm to 540 nm.

Herein, the blue emission refers to light emission whose maximum peak wavelength of fluorescence spectrum is in a range from 430 nm to 480 nm.

When the second compound is a blue fluorescent compound, the maximum peak wavelength of the second compound is preferably in a range from 430 nm to 480 nm, more preferably in a range from 440 nm to 480 nm.

The maximum peak wavelength of the light emitted from the organic EL device is measured as follows.

Voltage is applied on the organic EL devices such that a current density becomes 10 mA/$cm^2$, where spectral radiance spectrum is measured by a spectroradiometer CS-2000 (manufactured by Konica Minolta, Inc.).

A peak wavelength of an emission spectrum, at which the luminous intensity of the obtained spectral radiance spectrum is at the maximum, is measured and defined as a maximum peak wavelength (unit: nm).

Manufacturing Method of Second Compound

The second compound can be manufactured by a known method.

Manufacturing Method of Second Compound

The second compound can be manufactured by a known method.

Specific Examples of Second Compound

Specific examples of the second compound (the compound represented by the formula (20)) of the present exemplary embodiment are shown below. It should however be noted that the invention is not limited to these specific examples of the compound.

A coordinate bond between a boron atom and a nitrogen atom in a pyrromethene skeleton is shown by various means such as a solid line, a broken line, an arrow, and omission. Herein, the coordinate bond is shown by a solid line or a broken line, or the illustration of the coordinate bond is omitted.

[Formula 84]

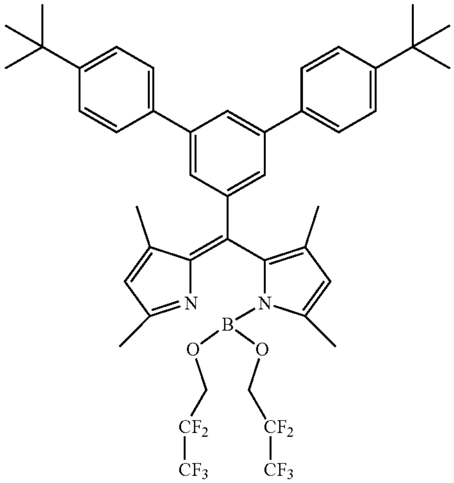

-continued

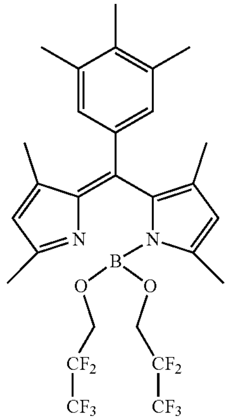

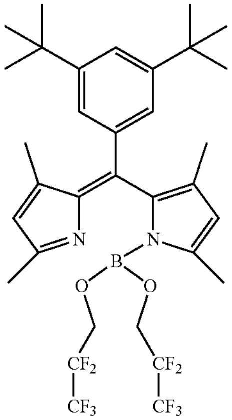

[Formula 85]

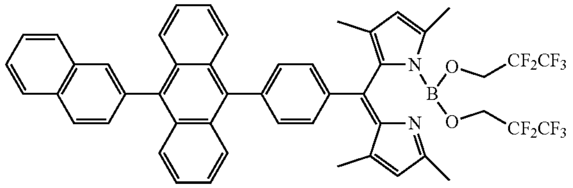

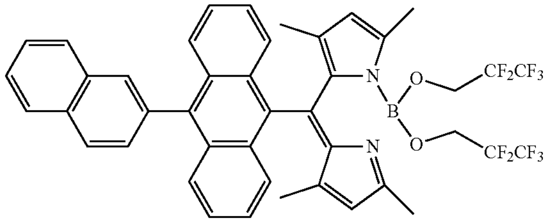

[Formula 86]

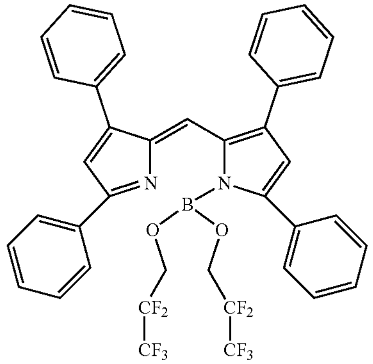

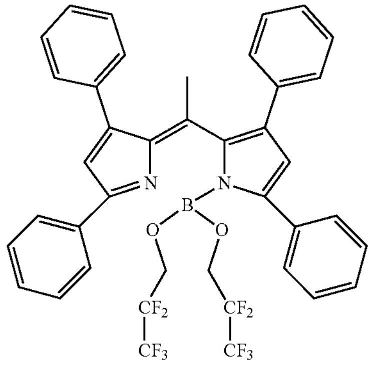

-continued
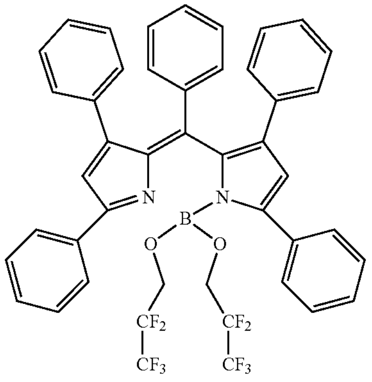
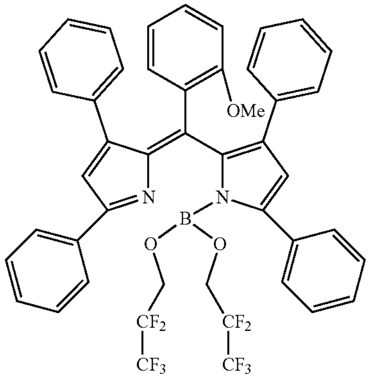
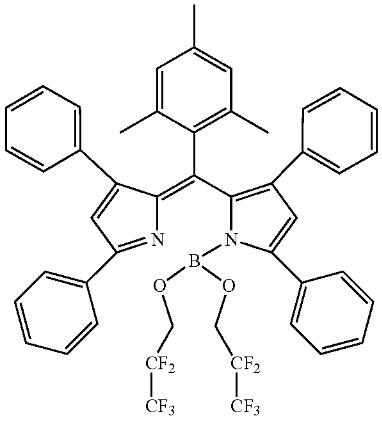
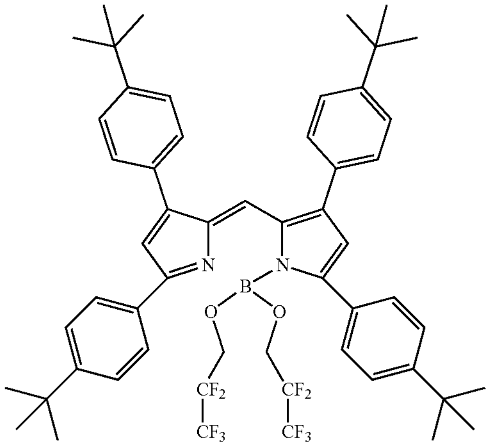
-continued
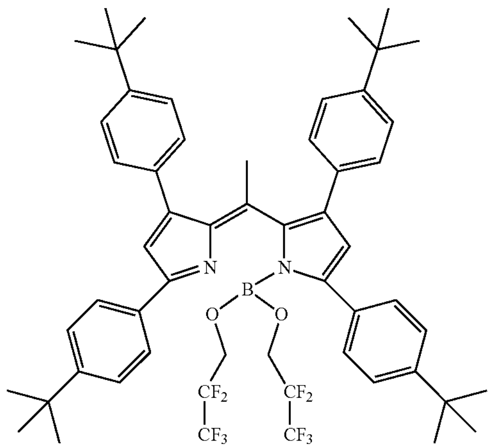
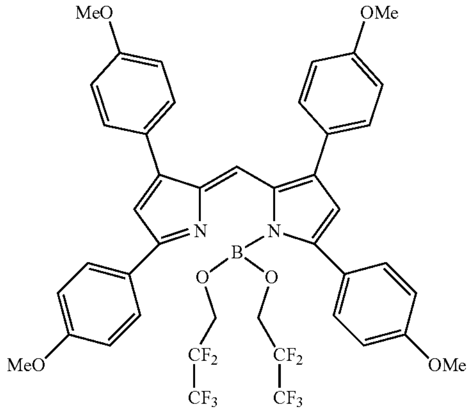
[Formula 87]
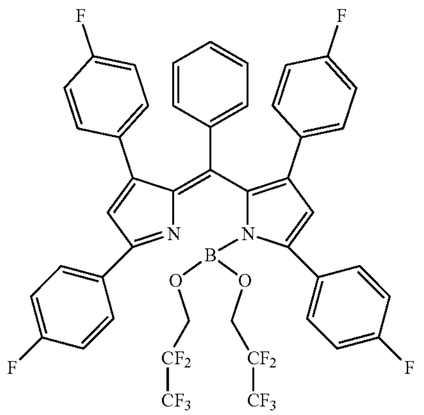
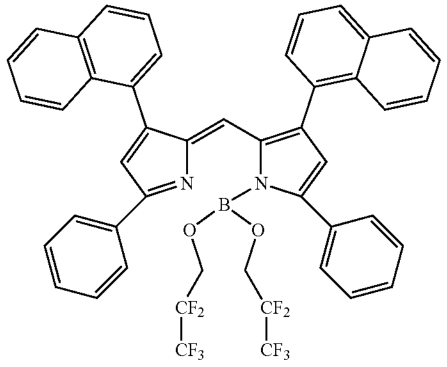

-continued
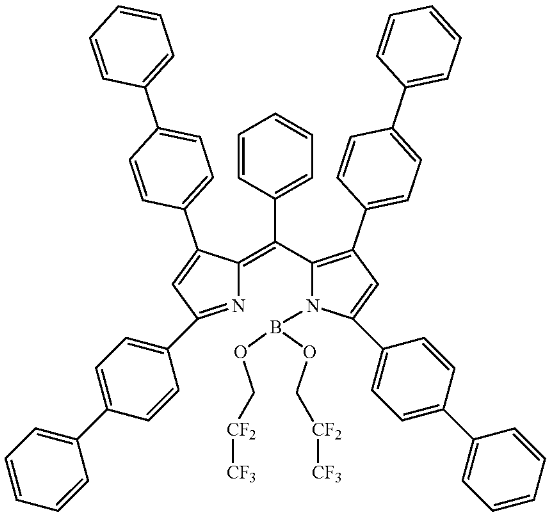
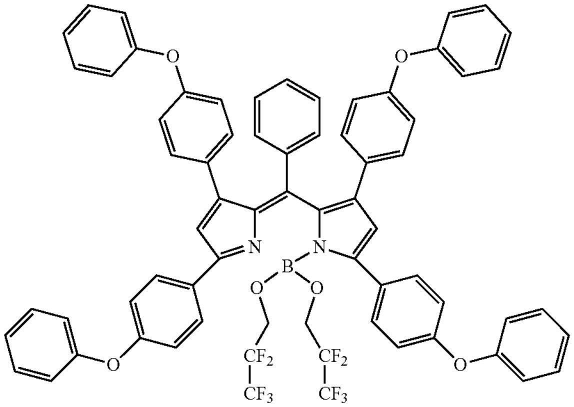
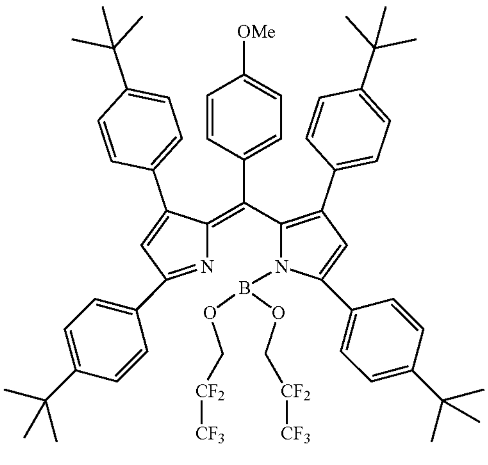
-continued
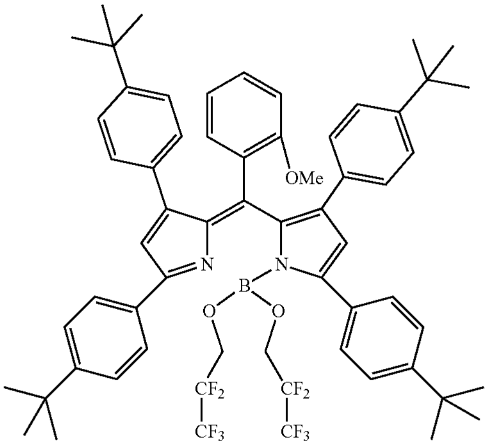
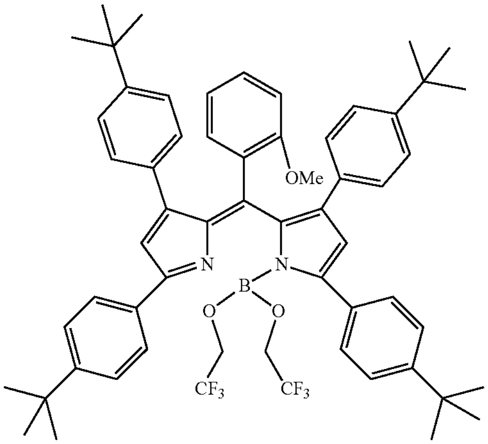
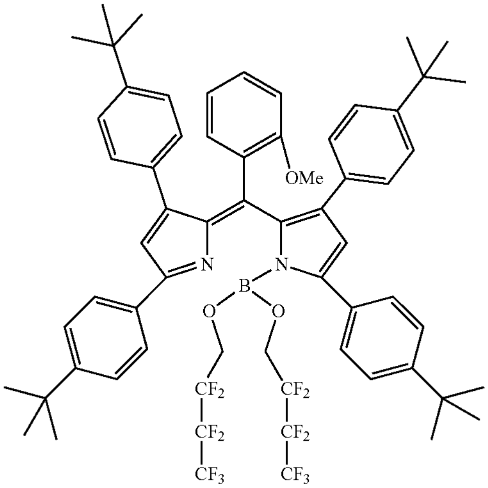

[Formula 88]
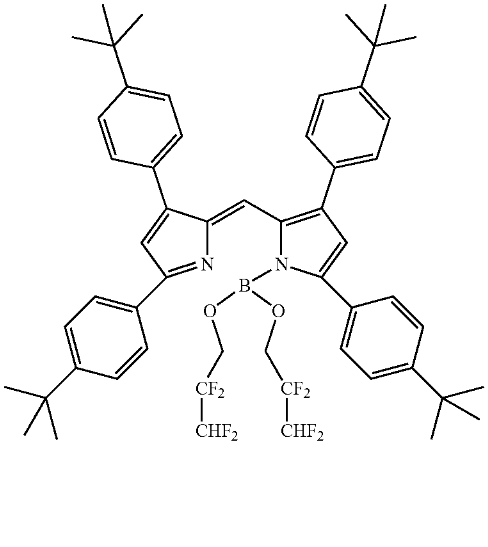
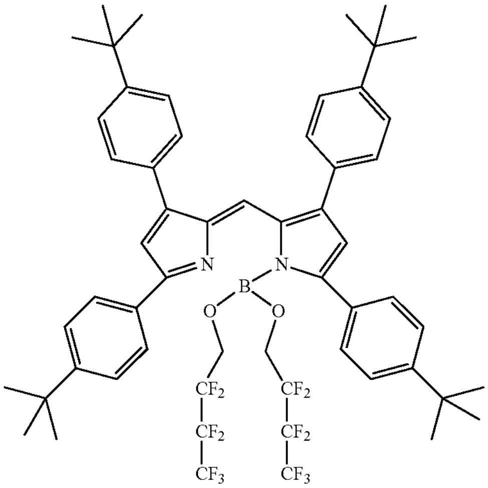
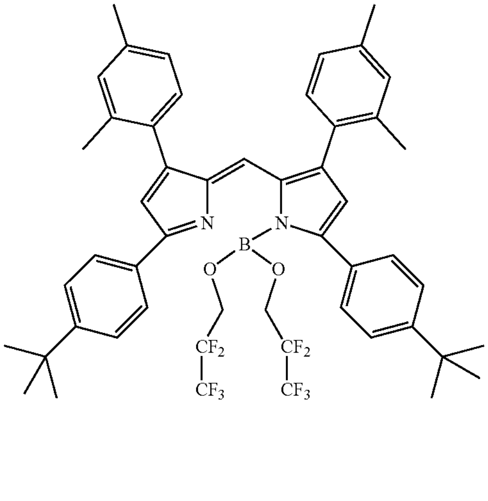
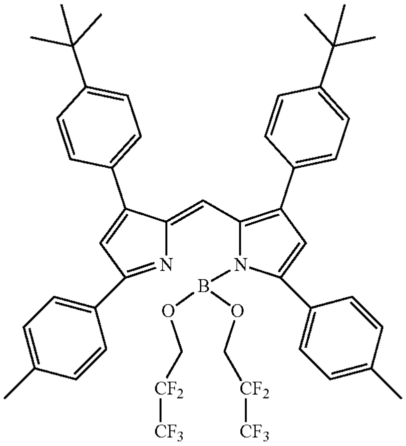
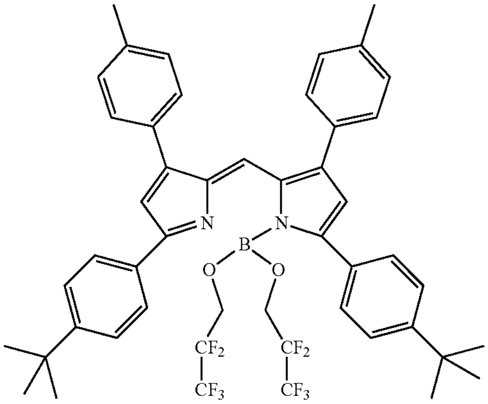
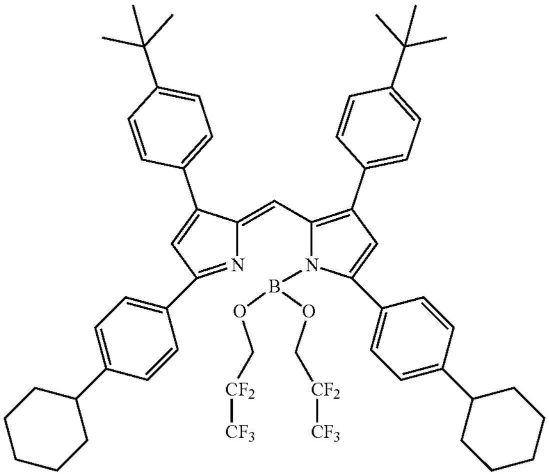

-continued
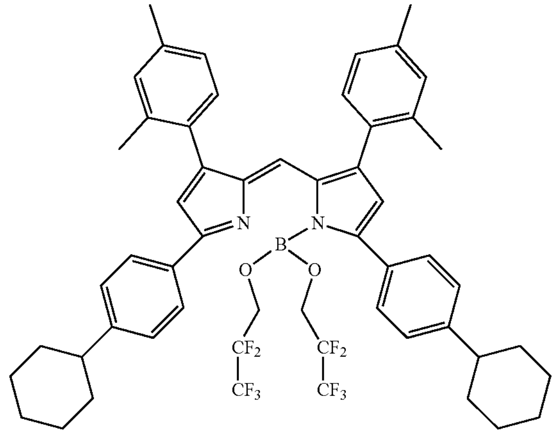
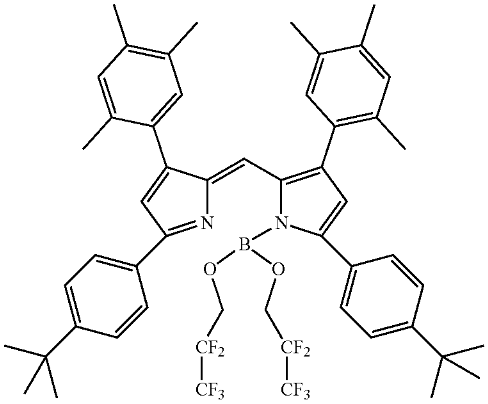
[Formula 89]
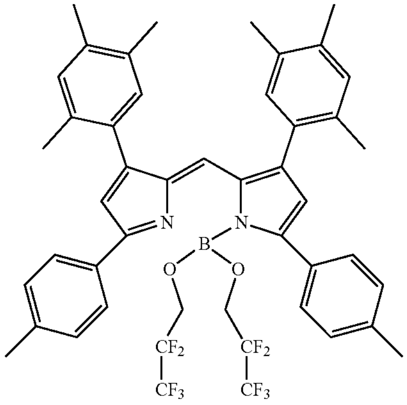
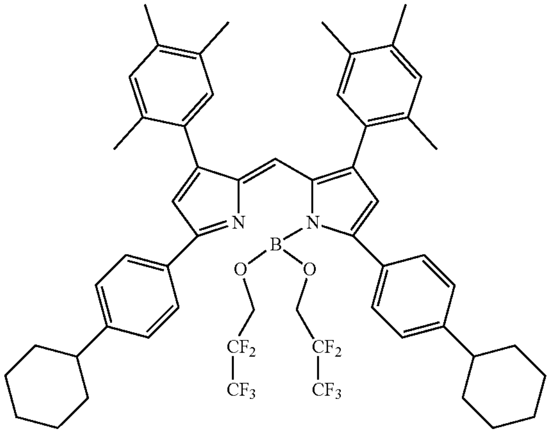
-continued
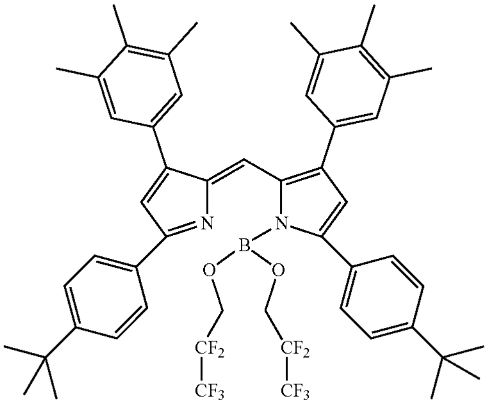
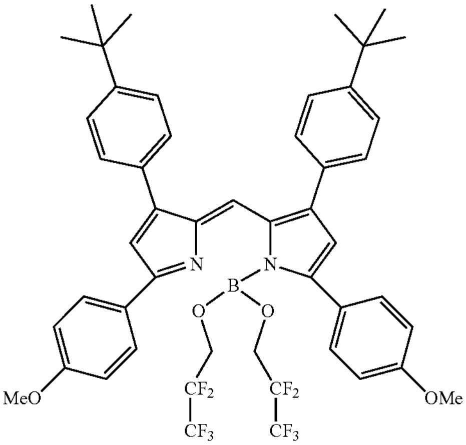
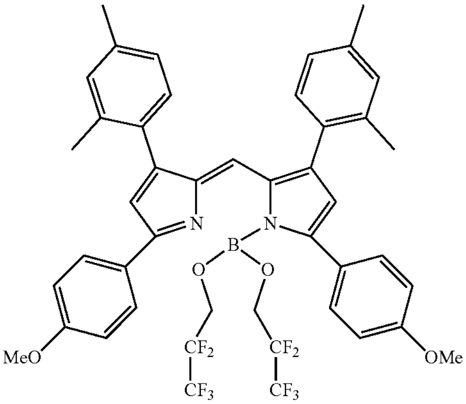
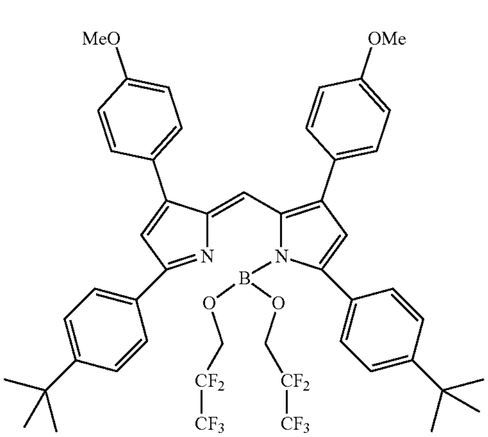

-continued
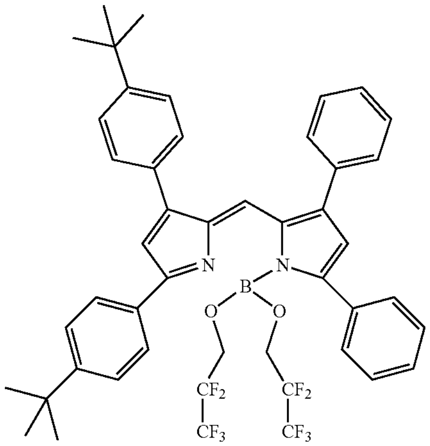
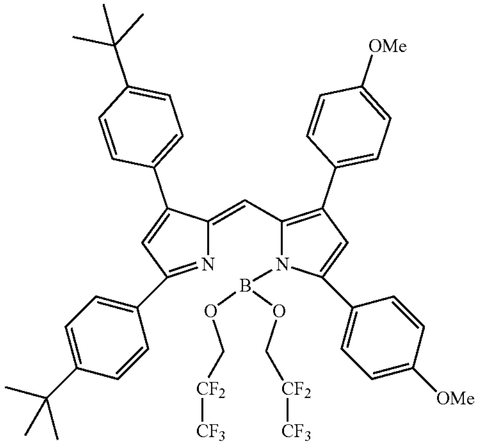
[Formula 90]
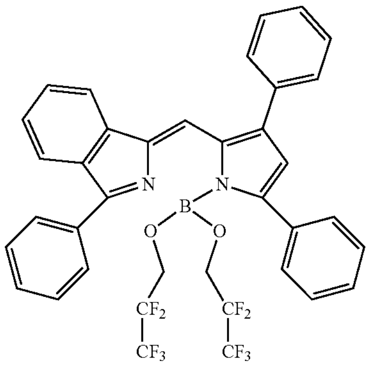
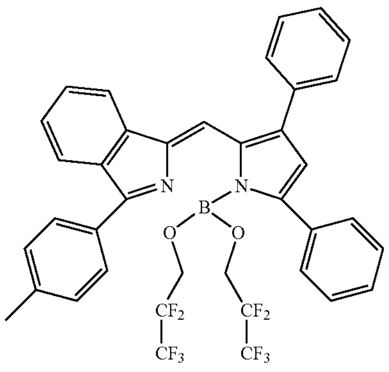
-continued
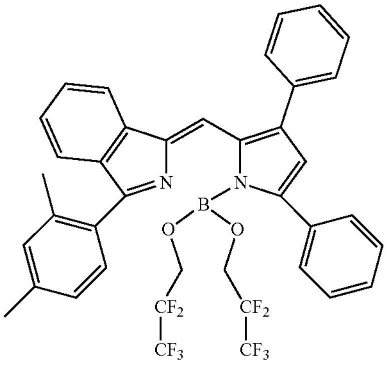
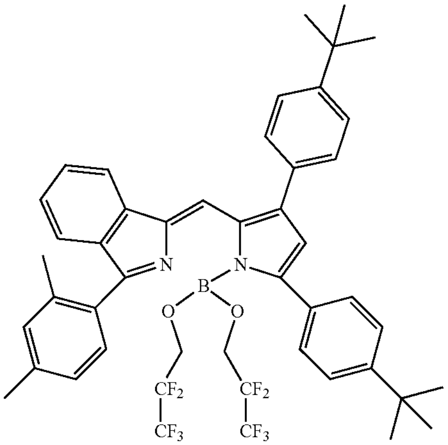
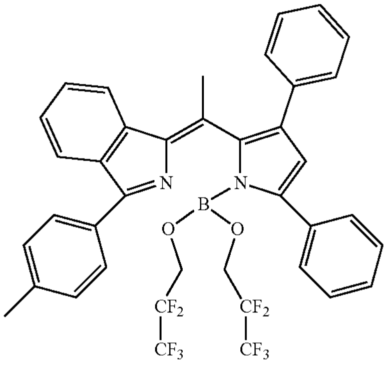
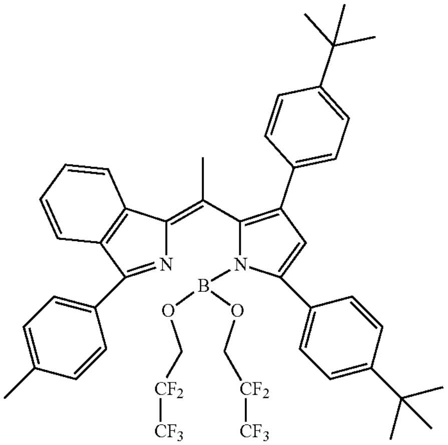

-continued
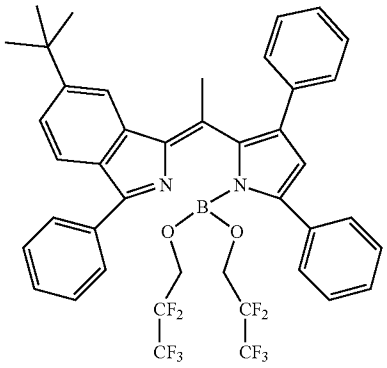
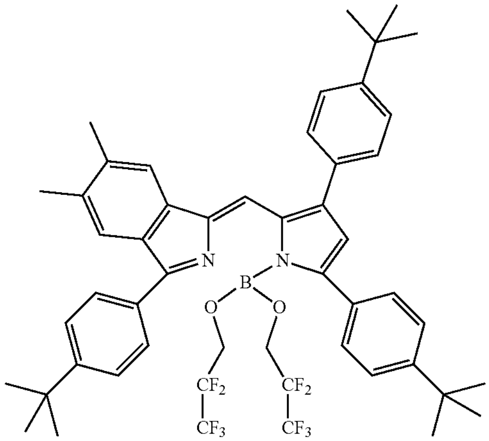
[Formula 91]
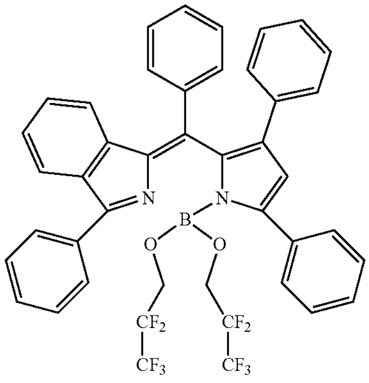
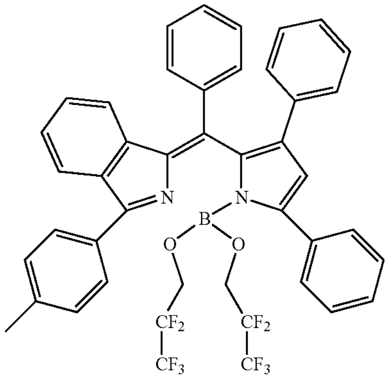
-continued
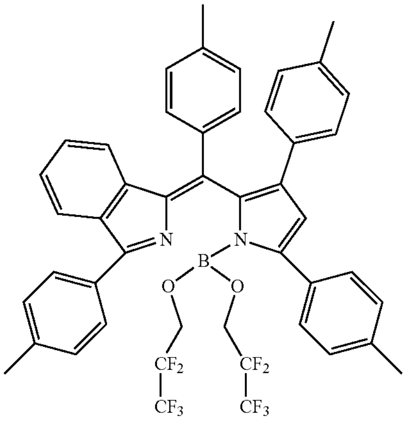
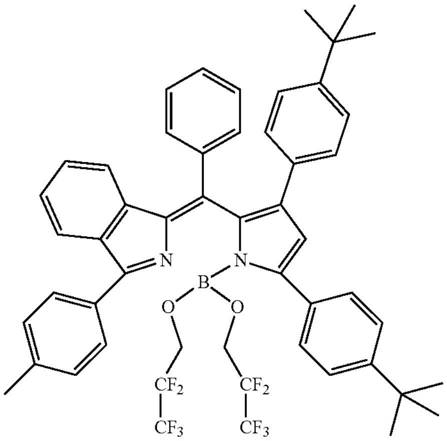
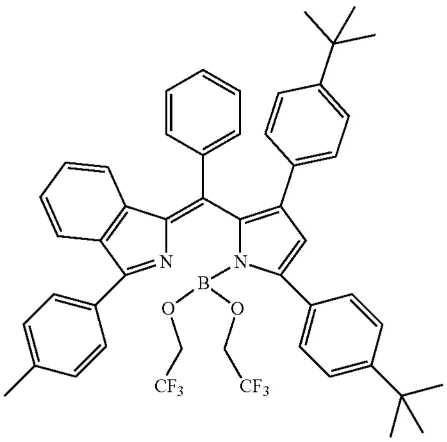

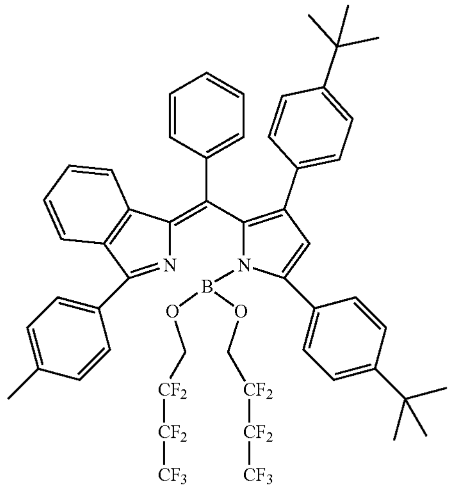
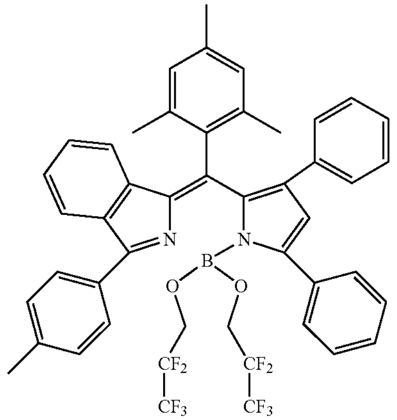
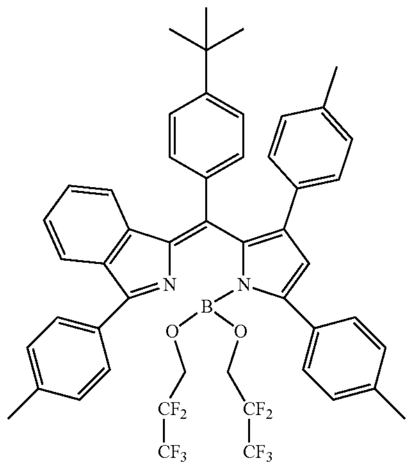
[Formula 92]
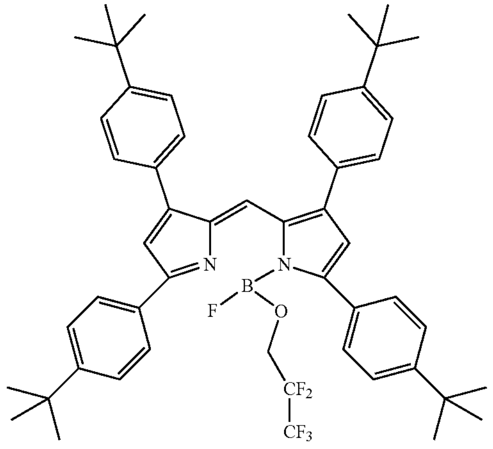
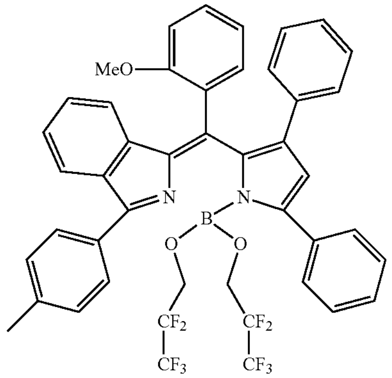
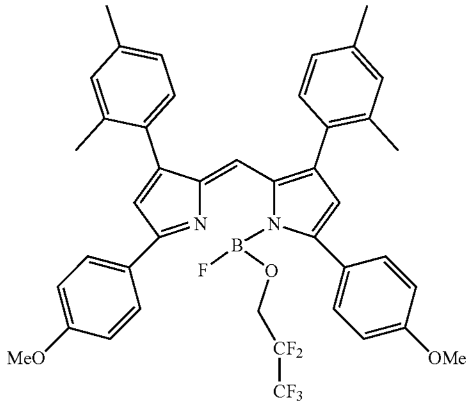
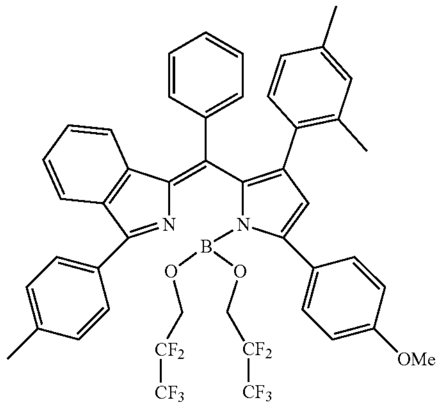

-continued
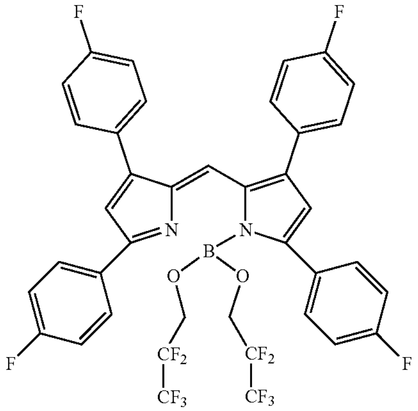
[Formula 93]
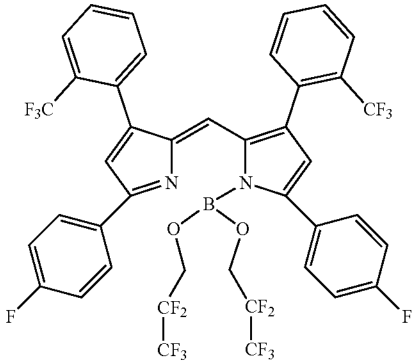
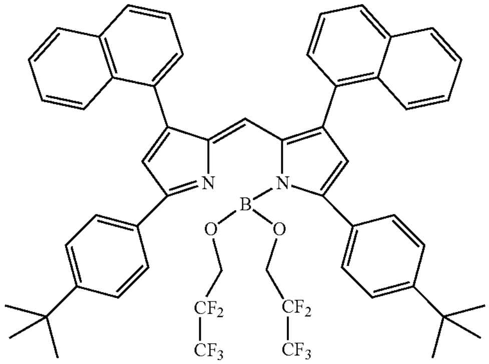
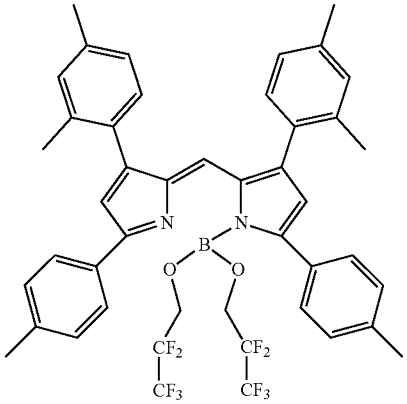
-continued
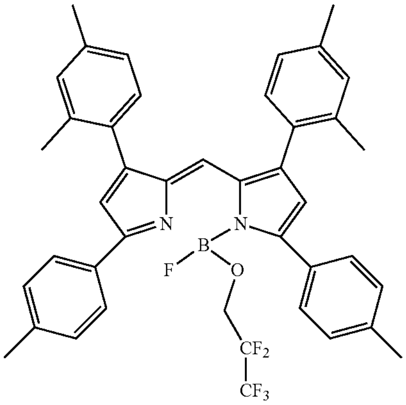
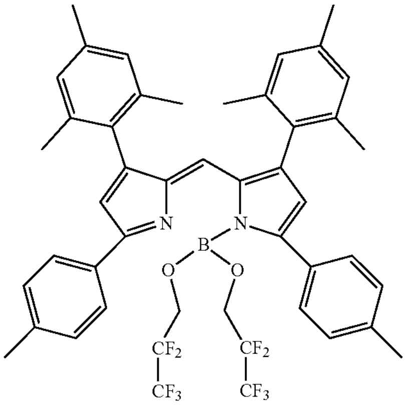
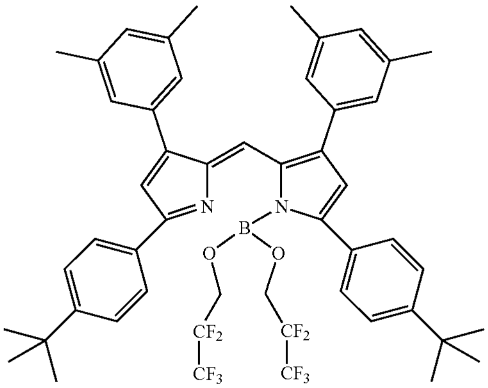
[Formula 94]
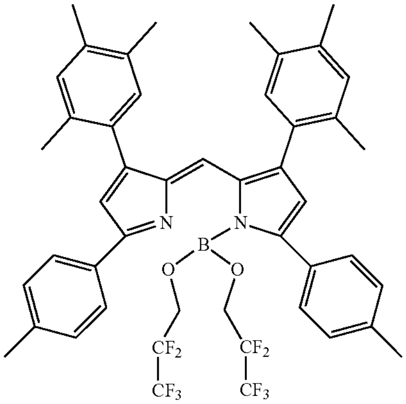

-continued
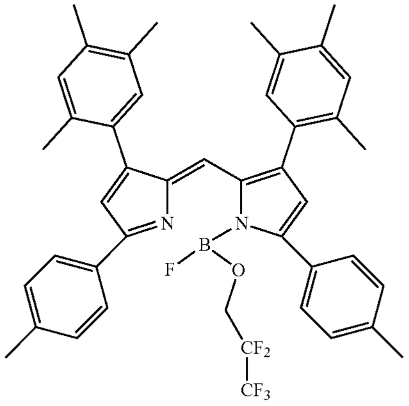
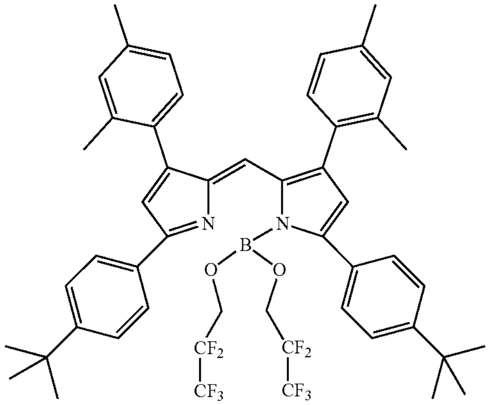
[Formula 95]
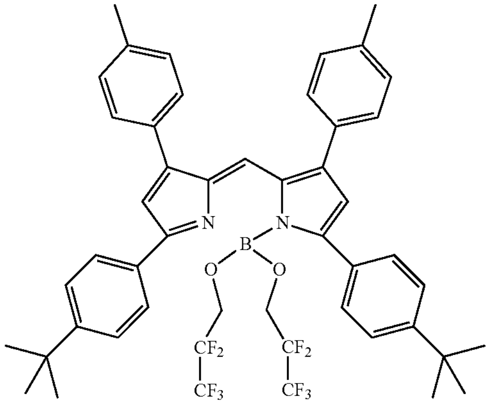
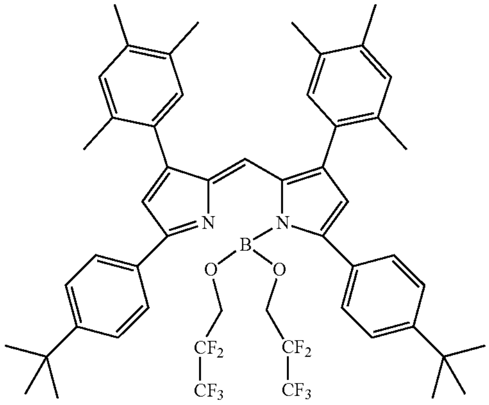
-continued
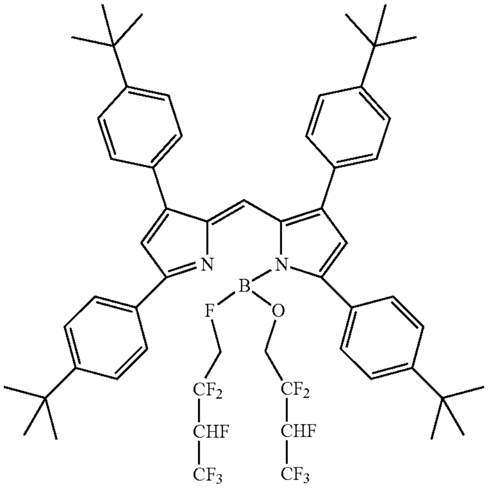
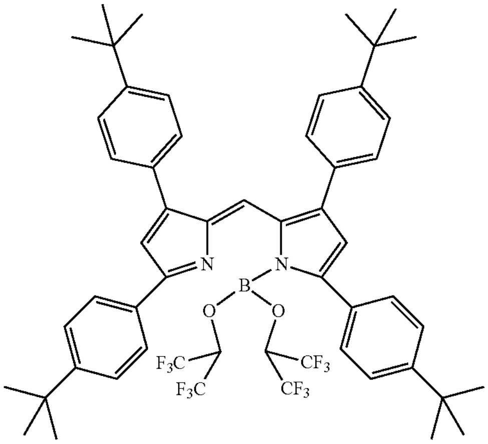
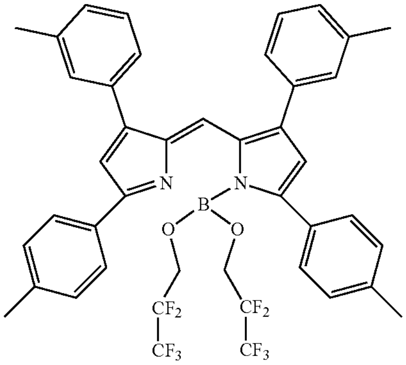

-continued
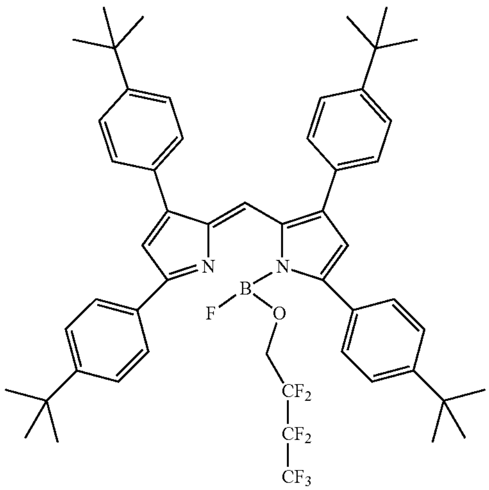
[Formula 96]
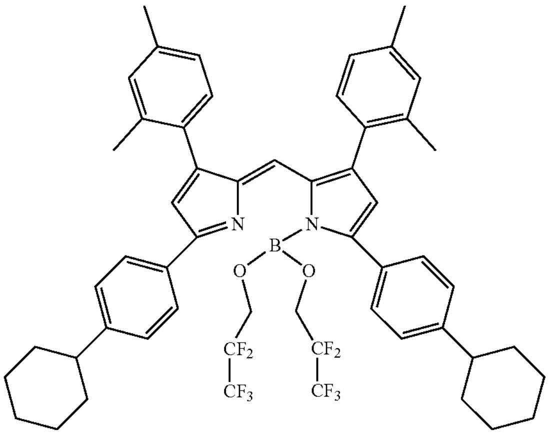
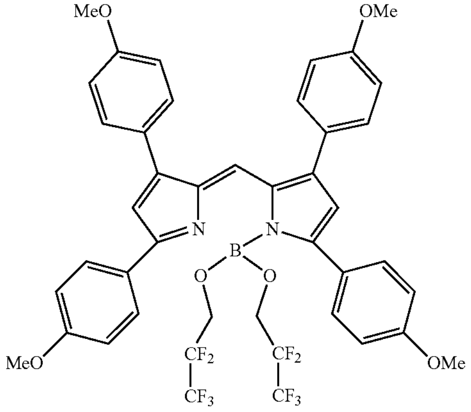
-continued
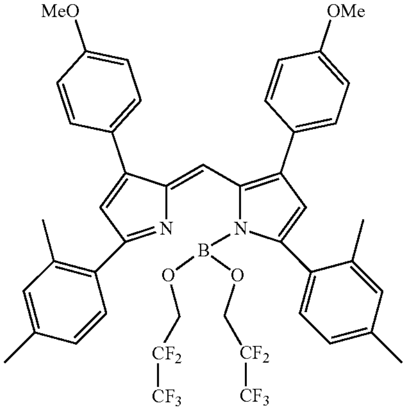
[Formula 97]
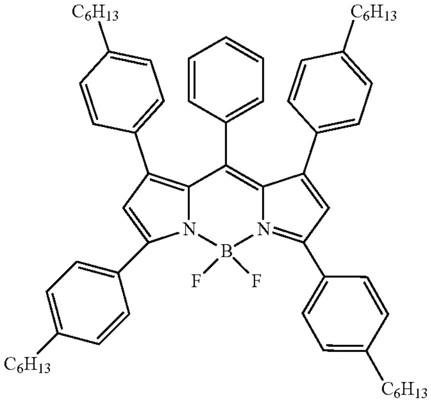
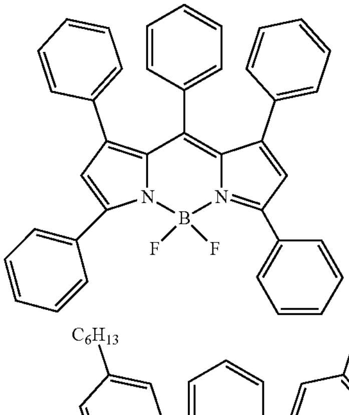
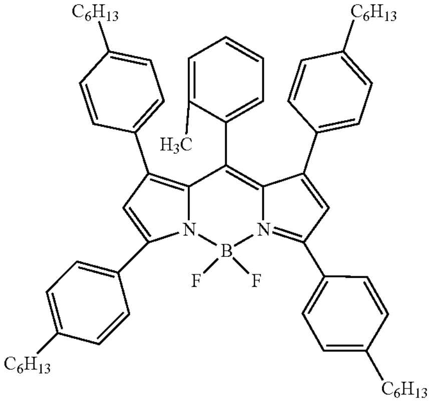

-continued
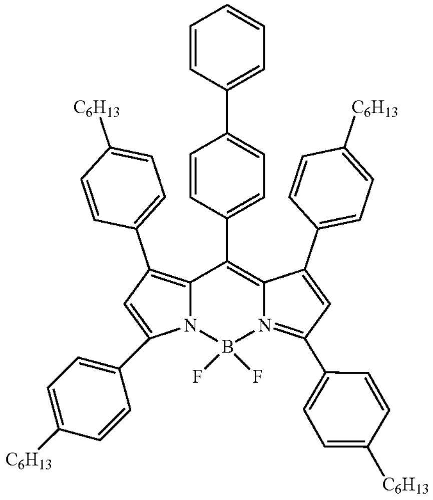
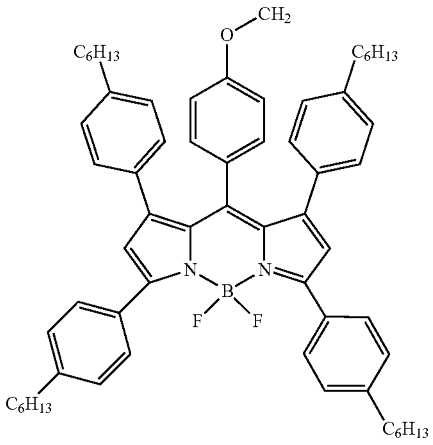
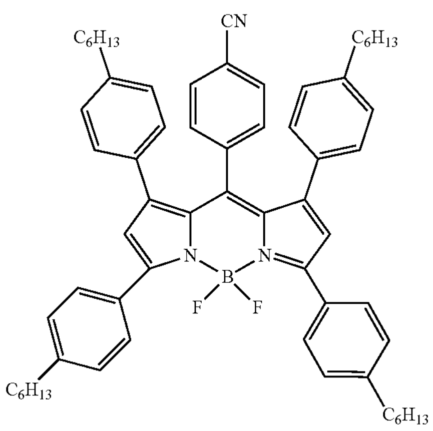
-continued
[Formula 98]
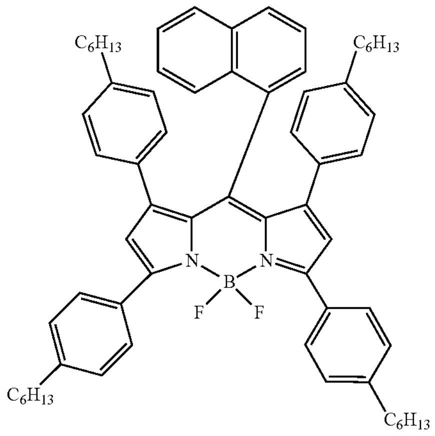
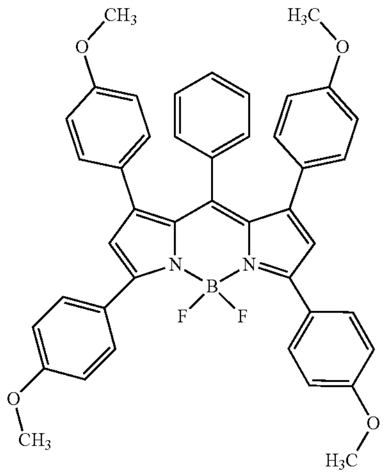
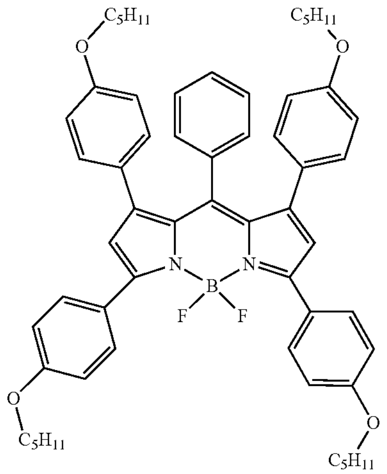

-continued
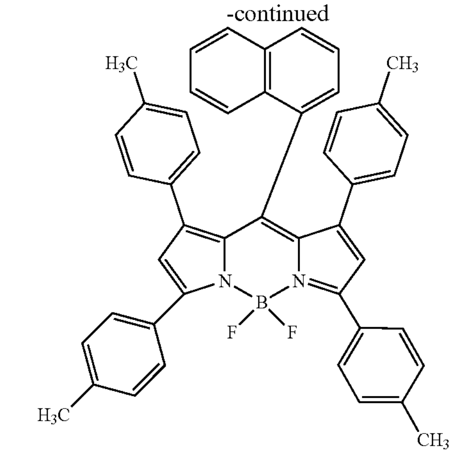
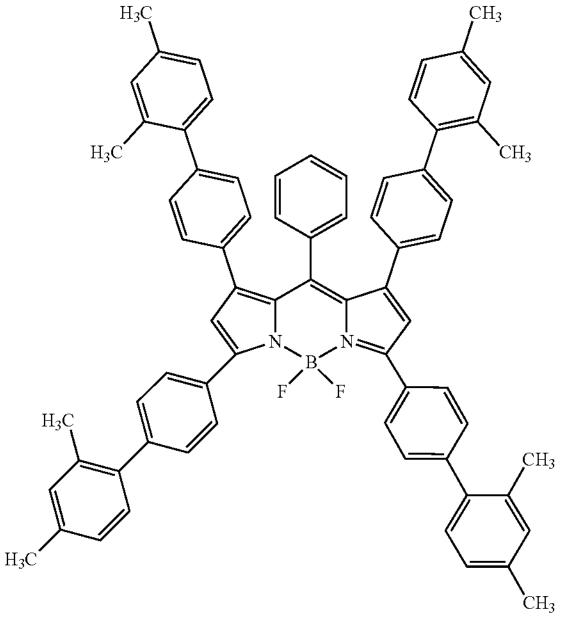
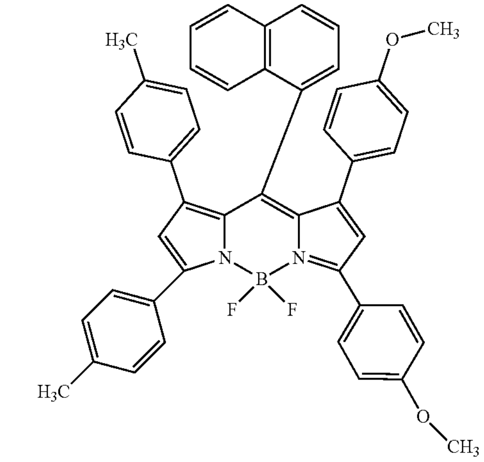
-continued
[Formula 99]
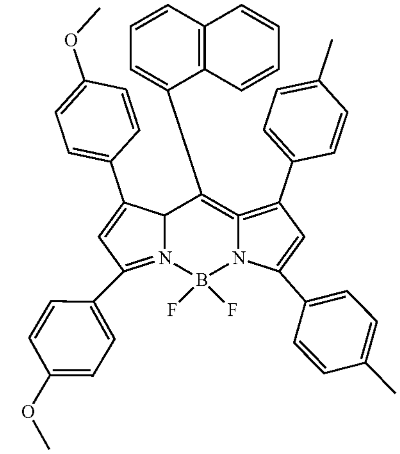
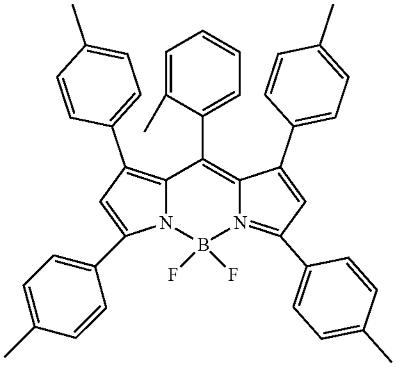
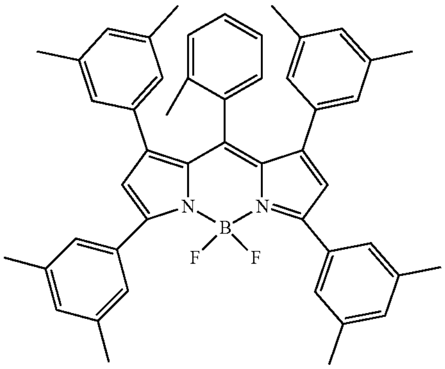
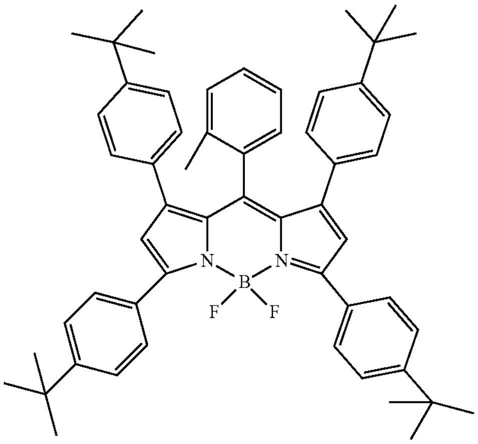

-continued
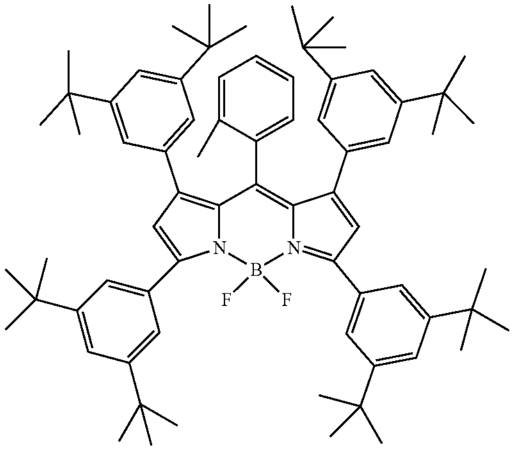
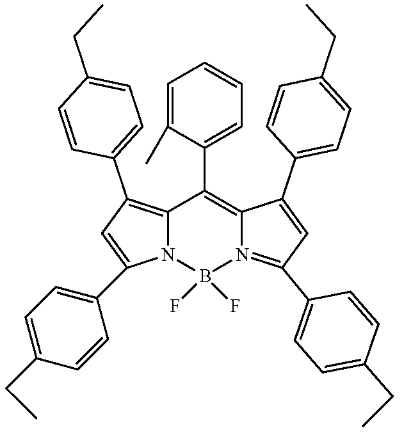
[Formula 100]
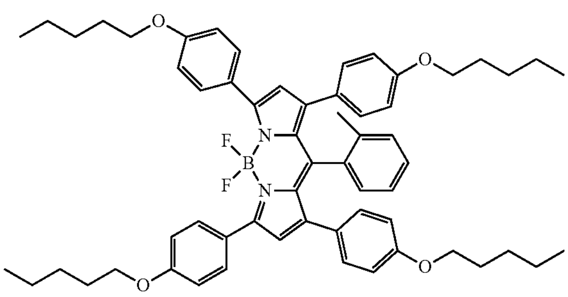
[Formula 101]
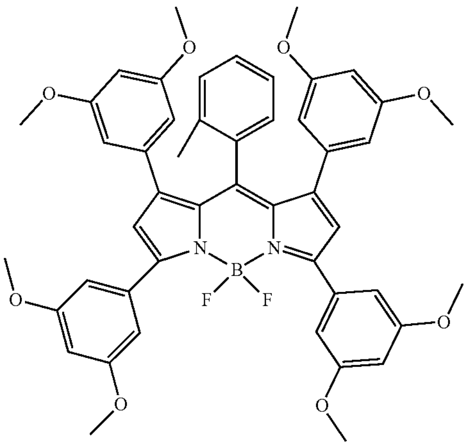
-continued
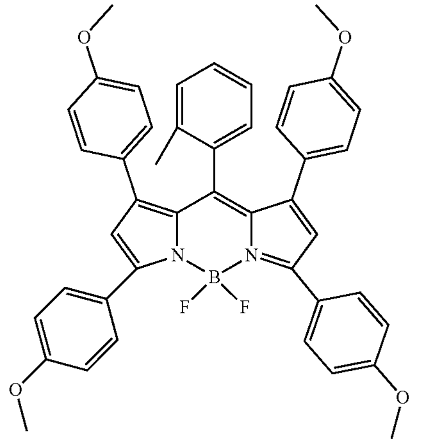
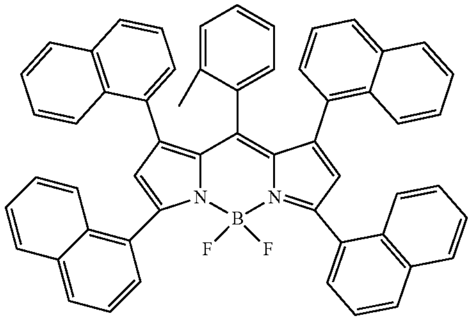
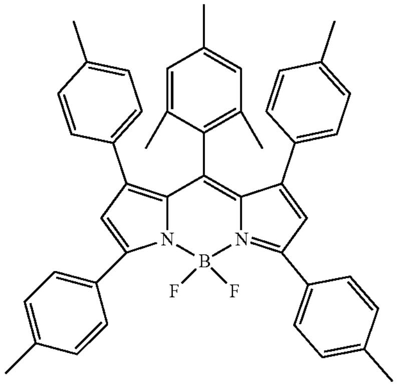
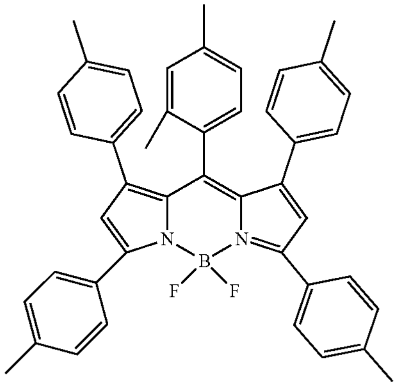

-continued
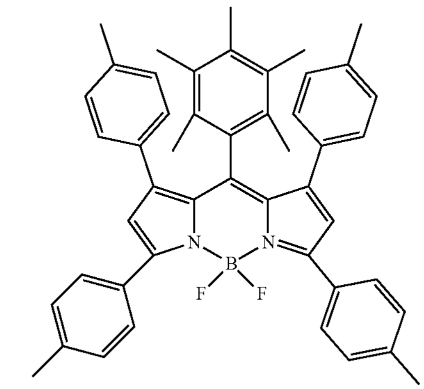
[Formula 102]
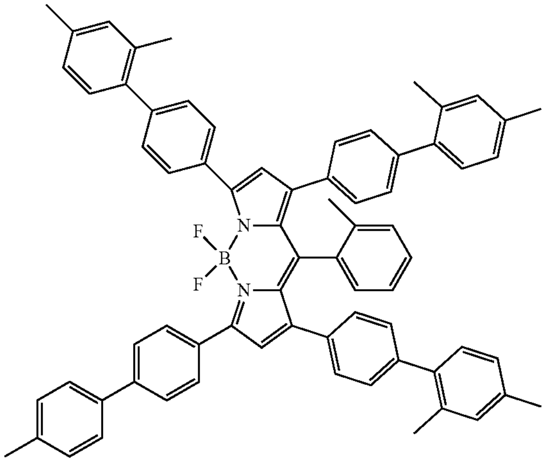
[Formula 103]
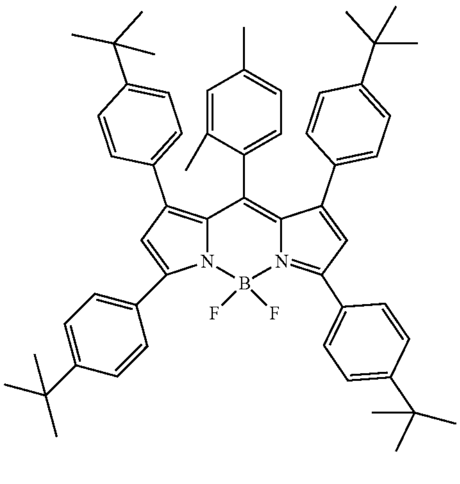
-continued
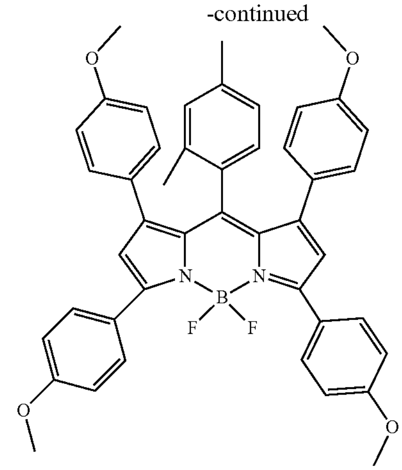
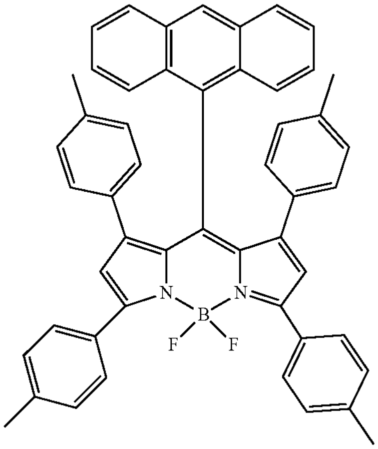
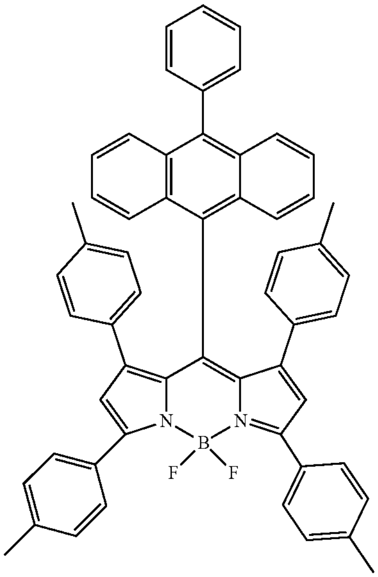

-continued
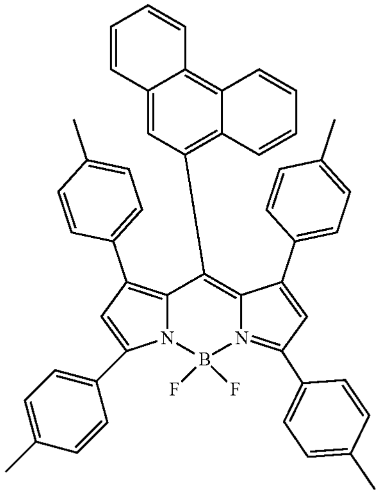
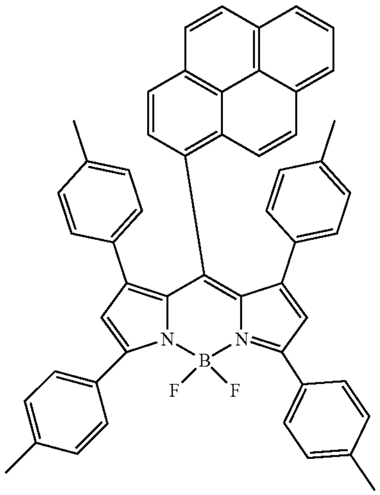
[Formula 104]
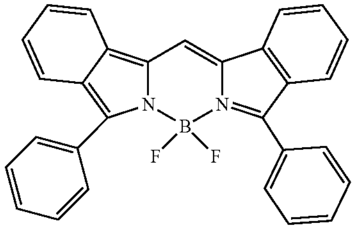
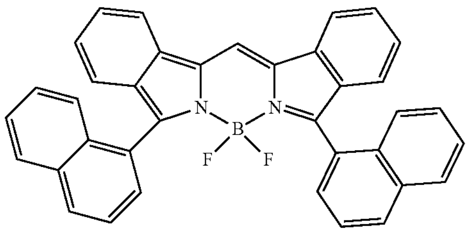
-continued
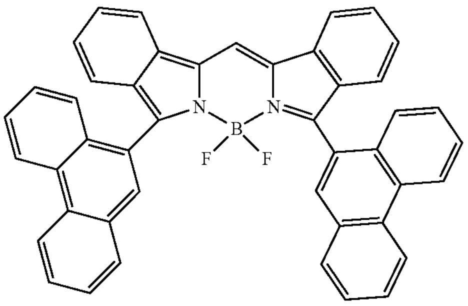
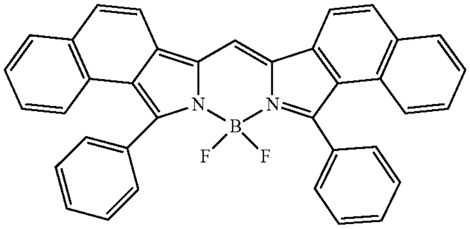
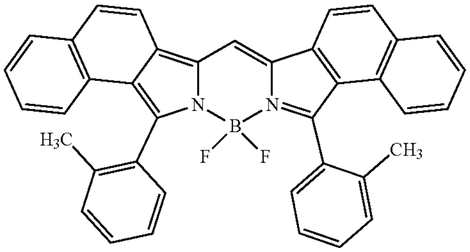
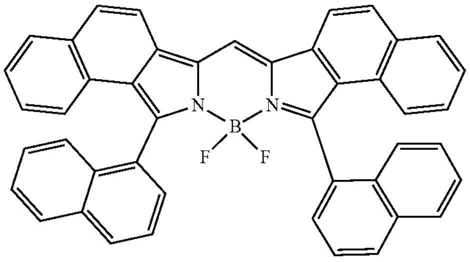
[Formula 105]
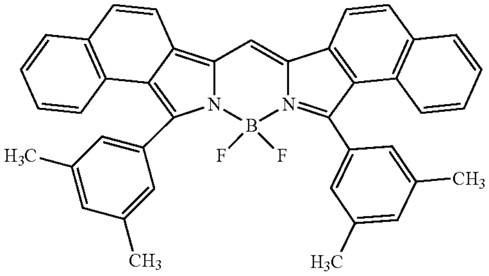
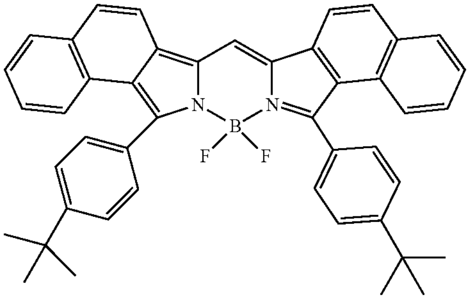

-continued

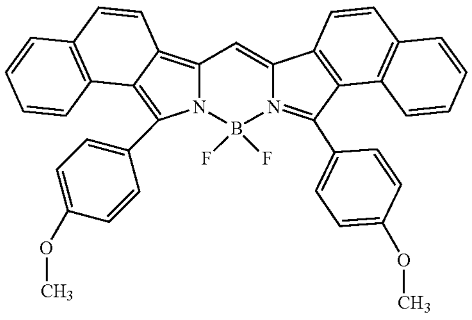

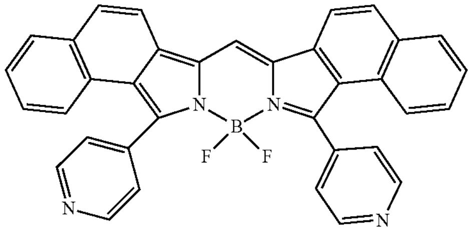

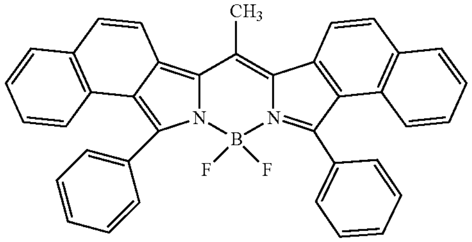

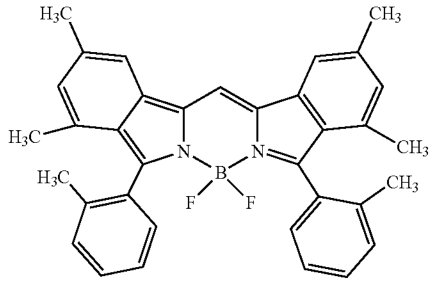

[Formula 106]

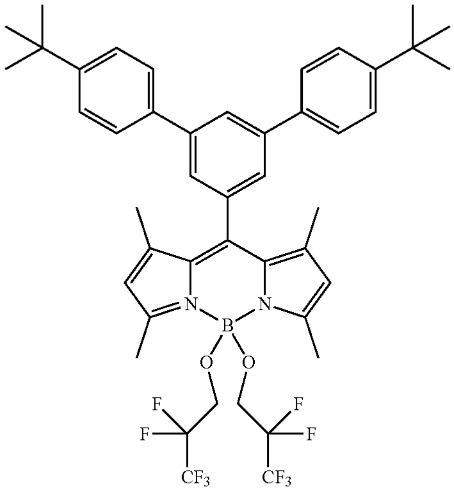

-continued

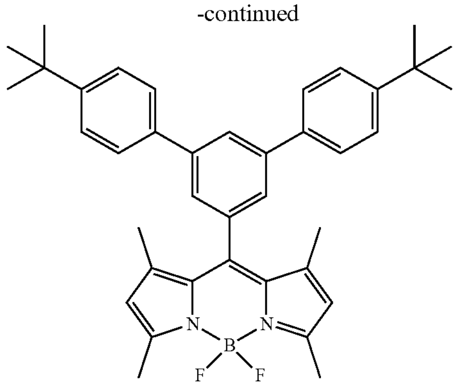

Relationship Between First Compound and Second Compound in Emitting Layer

In the organic EL device 1 of the present exemplary embodiment, a singlet energy $S_1$(Mat1) of the first compound and a singlet energy $S_1$(Mat2) of the second compound preferably satisfy a relationship of a numerical formula (Numerical Formula 1) below.

$$S_1(\text{Mat1})>S_1(\text{Mat2}) \quad \text{(Numerical Formula 1)}$$

An energy gap $T_{77K}$(Mat1) at 77K of the first compound is preferably larger than an energy gap $T_{77K}$(Mat2) at 77K of the second compound. In other words, a relationship of the following numerical formula (Numerical Formula 4) is preferably satisfied.

$$T_{77K}(\text{Mat1})>T_{77K}(\text{Mat2}) \quad \text{(Numerical Formula 4)}$$

When the organic EL device 1 of the present exemplary embodiment emits light, it is preferable that the second compound in the emitting layer 5 mainly emits light.

Relationship between Triplet Energy and Energy Gap at 77K Here, a relationship between a triplet energy and an energy gap at 77K will be described. In the present exemplary embodiment, the energy gap at 77K is different from a typical triplet energy in some aspects.

The triplet energy is measured as follows. First, a solution in which a compound (measurement target) is dissolved in an appropriate solvent is encapsulated in a quartz glass tube to prepare a sample. A phosphorescent spectrum (ordinate axis: phosphorescent luminous intensity, abscissa axis: wavelength) of the sample is measured at a low temperature (77K). A tangent is drawn to the rise of the phosphorescent spectrum close to the short-wavelength region. The triplet energy is calculated by a predetermined conversion equation based on a wavelength value at an intersection of the tangent and the abscissa axis.

Here, the thermally activated delayed fluorescent compound among the compounds of the present exemplary embodiment is preferably a compound having a small ΔST. When ΔST is small, intersystem crossing and inverse intersystem crossing are likely to occur even at a low temperature (77K), so that the singlet state and the triplet state coexist. As a result, the spectrum to be measured in the same manner as the above includes emission from both the singlet state and the triplet state. Although it is difficult to distinguish the emission from the singlet state from the emission from the triplet state, the value of the triplet energy is basically considered dominant.

Accordingly, in the present exemplary embodiment, the triplet energy is measured by the same method as a typical triplet energy T, but a value measured in the following manner is referred to as an energy gap $T_{77K}$ in order to differentiate the measured energy from the typical triplet energy in a strict meaning. The measurement target compound is dissolved in EPA (diethylether:isopentane:ethanol=5:5:2 in volume ratio) at a concentration of 10 μmol/L, and the obtained solution is encapsulated in a quartz cell to provide a measurement sample. A phosphorescent spectrum (ordinate axis: phosphorescent luminous intensity, abscissa axis: wavelength) of the sample is measured at a low temperature (77 K). A tangent is drawn to the rise of the phosphorescent spectrum close to the short-wavelength region. An energy amount is calculated by a conversion equation below based on a wavelength value λedge [nm] at an intersection of the tangent and the abscissa axis and is defined as an energy gap $T_{77K}$ at 77 K.

$$T_{77K}\,[\text{eV}]=1239.85/\lambda\text{edge} \quad \text{Conversion Equation (F1)}$$

The tangent to the rise of the phosphorescence spectrum close to the short-wavelength region is drawn as follows. While moving on a curve of the phosphorescence spectrum from the short-wavelength region to the local maximum value closest to the short-wavelength region among the local maximum values of the phosphorescence spectrum, a tangent is checked at each point on the curve toward the long-wavelength of the phosphorescence spectrum. An inclination of the tangent is increased along the rise of the curve (i.e., a value of the ordinate axis is increased). A tangent drawn at a point of the local maximum inclination (i.e., a tangent at an inflection point) is defined as the tangent to the rise of the phosphorescence spectrum close to the short-wavelength region.

A local maximum point where a peak intensity is 15% or less of the maximum peak intensity of the spectrum is not counted as the above-mentioned local maximum peak intensity closest to the short-wavelength region. The tangent drawn at a point that is closest to the local maximum peak intensity closest to the short-wavelength region and where the inclination of the curve is the local maximum is defined as a tangent to the rise of the phosphorescence spectrum close to the short-wavelength region.

For phosphorescence measurement, a spectrophotofluorometer body F-4500 (manufactured by Hitachi High-Technologies Corporation) is usable. Any device for phosphorescence measurement is usable. A combination of a cooling unit, a low temperature container, an excitation light source and a light-receiving unit may be used for phosphorescence measurement.

Singlet Energy $S_1$

A method of measuring a singlet energy $S_1$ with use of a solution (occasionally referred to as a solution method) is exemplified by a method below.

A toluene solution of a measurement target compound at a concentration of 10 μmol/L is prepared and put in a quartz cell. An absorption spectrum (ordinate axis: absorption intensity, abscissa axis: wavelength) of the thus-obtained sample is measured at a normal temperature (300 K). A tangent was drawn to the fall of the absorption spectrum close to the long-wavelength region, and a wavelength value λedge (nm) at an intersection of the tangent and the abscissa axis was assigned to a conversion equation (F2) below to calculate the singlet energy.

$$S_1\,[\text{eV}]=1239.85/\lambda\text{edge} \quad \text{Conversion Equation (F2)}$$

Any device for measuring absorption spectrum is usable. For instance, a spectrophotometer (U3310 manufactured by Hitachi, Ltd.) is usable.

The tangent to the fall of the absorption spectrum close to the long-wavelength region is drawn as follows. While moving on a curve of the absorption spectrum from the local maximum value closest to the long-wavelength region, among the local maximum values of the absorption spectrum, in a long-wavelength direction, a tangent at each point on the curve is checked. An inclination of the tangent is decreased and increased in a repeated manner as the curve falls (i.e., a value of the ordinate axis is decreased). A tangent drawn at a point where the inclination of the curve is the local minimum closest to the long-wavelength region (except when absorbance is 0.1 or less) is defined as the tangent to the fall of the absorption spectrum close to the long-wavelength region.

The local maximum absorbance of 0.2 or less is not counted as the above-mentioned local maximum absorbance closest to the long-wavelength region.

In the present exemplary embodiment, a difference ($S_1$-$T_{77K}$) between the singlet energy $S_1$ and the energy gap $T_{77K}$ at 77K is defined as ΔST.

In the present exemplary embodiment, a difference ΔST (Mat1) between the singlet energy $S_1$(Mat1) of the first compound and the energy gap $T_{77K}$(Mat1) at 77 [K] of the first compound is preferably less than 0.3 eV, more preferably less than 0.2 eV, further preferably less than 0.1 eV. In other words, ΔST(Mat1) preferably satisfies a relationship of one of numerical formulae (Numerical Formulae (1A) to Numerical Formulae (1C)) below.

$$\Delta ST(\text{Mat1})=S_1(\text{Mat1})-T_{77K}(\text{Mat1})<0.3\text{ eV} \quad \text{(Numerical Formula 1A)}$$

$$\Delta ST(\text{Mat1})=S_1(\text{Mat1})-T_{77K}(\text{Mat1})<0.2\text{ eV} \quad \text{(Numerical Formula 1B)}$$

$$\Delta ST(\text{Mat1})=S_1(\text{Mat1})-T_{77K}(\text{Mat1})<0.1\text{ eV} \quad \text{(Numerical Formula 1C)}$$

The organic EL device 1 of the present exemplary embodiment preferably emits red light or green light.

When the organic EL device 1 of the present exemplary embodiment emits green light, the maximum peak wavelength of the light emitted from the organic EL device 1 is preferably in a range from 500 nm to 560 nm.

When the organic EL device 1 of the present exemplary embodiment emits red light, the maximum peak wavelength of the light emitted from the organic EL device 1 is preferably in a range from 600 nm to 660 nm.

When the organic EL device 1 of the present exemplary embodiment emits blue light, the maximum peak wavelength of the light emitted from the organic EL device 1 is preferably in a range from 430 nm to 480 nm.

The maximum peak wavelength of the light emitted from the organic EL device is measured as follows.

Voltage is applied on the organic EL devices such that a current density becomes 10 mA/$cm^2$, where spectral radiance spectrum is measured by a spectroradiometer CS-2000 (manufactured by Konica Minolta, Inc.).

A peak wavelength of an emission spectrum, at which the luminous intensity of the obtained spectral radiance spectrum is at the maximum, is measured and defined as a maximum peak wavelength (unit: nm).

Film Thickness of Emitting Layer

A film thickness of the emitting layer 5 of the organic EL device 1 in the present exemplary embodiment is preferably in a range from 5 nm to 50 nm, more preferably in a range from 7 nm to 50 nm, most preferably in a range from 10 nm to 50 nm. When the film thickness of the emitting layer is 5 nm or more, the formation of the emitting layer and the adjustment of the chromaticity are easy. When the film thickness of the emitting layer is 50 nm or less, an increase in the drive voltage is likely to be reducible.

Content Ratios of Compounds in Emitting Layer

Content ratios of the first and second compounds in the emitting layer 5 preferably fall, for instance, within a range below.

The content ratio of the first compound is preferably in a range from 10 mass % to 80 mass %, more preferably in a range from 10 mass % to 60 mass %, further preferably in a range from 20 mass % to 60 mass %.

The content ratio of the second compound is preferably in a range from 0.01 mass % to 10 mass %, more preferably in a range from 0.01 mass % to 5 mass %, further preferably in a range from 0.01 mass % to 1 mass %.

It should be noted that the emitting layer 5 of the present exemplary embodiment may further contain material(s) other than the first and second compounds.

The emitting layer 5 may include a single type of the first compound or may include two or more types of the first compound. The emitting layer 5 may include a single type of the second compound or may include two or more types of the second compound.

TADF Mechanism

Figure 4:
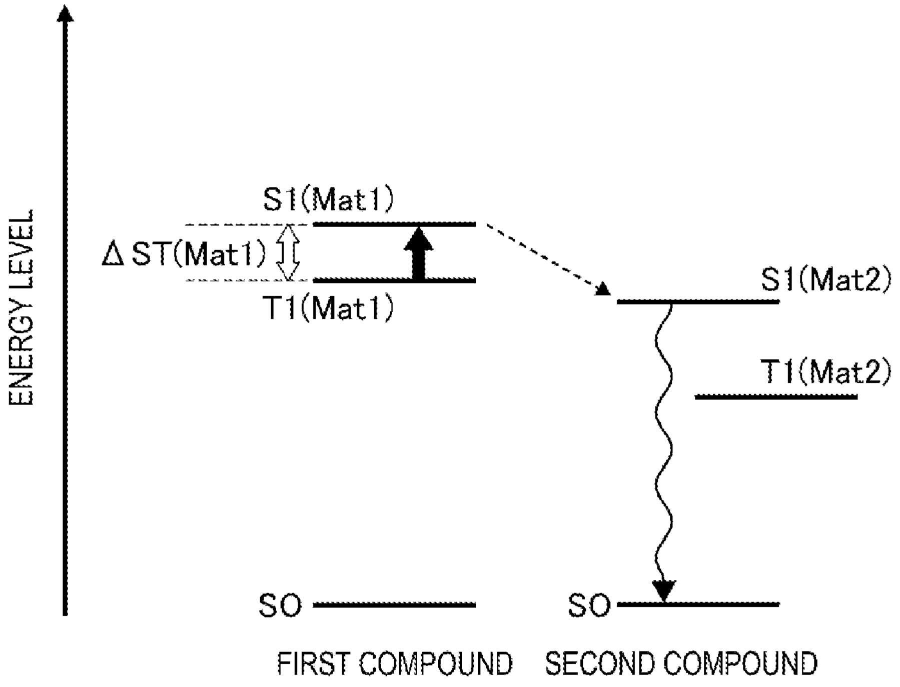
FIG. 4 shows a relationship in energy level and energy transfer between a first compound and a second compound in an emitting layer of an exemplary organic electroluminescence device according to the third exemplary embodiment of the invention.

FIG. 4 shows an example of a relationship between energy levels of the first compound and the second compound in the emitting layer. In FIG. 4, S0 represents a ground state. S1(Mat1) represents the lowest singlet state of the first compound. T1(Mat1) represents the lowest triplet state of the first compound. S1(Mat2) represents the lowest triplet state of the second compound. T1(Mat2) represents the lowest triplet state of the second compound.

A dashed arrow directed from S1(Mat1) to S1(Mat2) in FIG. 4 represents Förster energy transfer from the lowest singlet state of the first compound to the lowest singlet state of the second compound.

As shown in FIG. 4, when a compound having a small ΔST(Mat1) is used as the first compound, inverse intersystem crossing from the lowest triplet state T1(Mat1) to the lowest singlet state S1(Mat1) can be caused by a heat energy. Subsequently, Forster energy transfer from the lowest singlet state S1(Mat1) of the first compound the second compound occurs to generate the lowest singlet state S1(Mat2). Consequently, fluorescence from the lowest singlet state S1(Mat2) of the second compound can be observed. It is inferred that the internal quantum efficiency can be theoretically raised up to 100% also by using delayed fluorescence by the TADF mechanism.

The emitting layer 5 of the organic EL device 1 of the third exemplary embodiment contains the compound of the first exemplary embodiment as the first compound (the compound represented by any one of formulae (11) to (13)) and the second compound whose singlet energy is smaller than the singlet energy of the first compound.

The organic EL device according to the third exemplary embodiment contains the compound (the compound of the first exemplary embodiment) capable of providing a high-performance organic electroluminescence device, especially the compound having high PLQY. Accordingly, the third exemplary embodiment can provide a high-performance organic EL device.

The organic EL device 1 according to the third exemplary embodiment is applicable to an electronic device such as a display device and a light-emitting device.

An arrangement of the organic EL device 1 will be further described below. It should be noted that the reference numerals will be sometimes omitted below.

Substrate

The substrate is used as a support for the organic EL device. For instance, glass, quartz, plastics and the like are usable for the substrate. A flexible substrate is also usable. The flexible substrate is a bendable substrate, which is exemplified by a plastic substrate. Examples of the material for the plastic substrate include polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Metal, an alloy, an electrically conductive compound, a mixture thereof, or the like having a large work function (specifically, 4.0 eV or more) is preferably used as the anode formed on the substrate. Specific examples of the material include ITO (Indium Tin Oxide), indium oxide-tin oxide containing silicon or silicon oxide, indium oxide-zinc oxide, indium oxide containing tungsten oxide and zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), and nitrides of a metal material (e.g., titanium nitride) are usable.

The material is typically formed into a film by a sputtering method. For instance, the indium oxide-zinc oxide can be formed into a film by the sputtering method using a target in which zinc oxide in a range from 1 mass % to 10 mass % is added to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, the anode may be formed by a vacuum deposition method, a coating method, an inkjet method, a spin coating method or the like.

Among the organic layers formed on the anode, since the hole injecting layer adjacent to the anode is formed of a composite material into which holes are easily injectable irrespective of the work function of the anode, a material usable as an electrode material (e.g., metal, an alloy, an electroconductive compound, a mixture thereof, and the elements belonging to the group 1 or 2 of the periodic table) is also usable for the anode.

The elements belonging to the group 1 or 2 of the periodic table, which are a material having a small work function, specifically, an alkali metal such as lithium (Li) and cesium (Cs), an alkaline earth metal such as magnesium (Mg), calcium (Ca) and strontium (Sr), an alloy containing the alkali metal and the alkaline earth metal (e.g., MgAg, AlLi), a rare earth metal such as europium (Eu) and ytterbium (Yb), and an alloy containing the rare earth metal are usable for the anode. It should be noted that the vacuum deposition method and the sputtering method are usable for forming the anode using the alkali metal, alkaline earth metal and the alloy thereof. Further, when a silver paste is used for the anode, the coating method and the inkjet method are usable.

Cathode It is preferable to use metal, an alloy, an electroconductive compound, a mixture thereof, or the like having a small work function (specifically, 3.8 eV or less) for the cathode. Examples of materials for the cathode include elements belonging to the group 1 or 2 of the periodic table, specifically, an alkali metal such as lithium (Li) and cesium (Cs), an alkaline earth metal such as magnesium (Mg), calcium (Ca) and strontium (Sr), an alloy containing the alkali metal and the alkaline earth metal (e.g., MgAg, AlLi), a rare earth metal such as europium (Eu) and ytterbium (Yb), and an alloy containing the rare earth metal.

It should be noted that the vacuum deposition method and the sputtering method are usable for forming the cathode using the alkali metal, alkaline earth metal and the alloy thereof. Further, when a silver paste is used for the cathode, the coating method and the inkjet method are usable.

By providing the electron injecting layer, various conductive materials such as Al, Ag, ITO, graphene, and indium oxide-tin oxide containing silicon or silicon oxide may be used for forming the cathode regardless of the work function. The conductive materials can be formed into a film using the sputtering method, inkjet method, spin coating method and the like.

Hole Injecting Layer

The hole injecting layer is a layer containing a substance exhibiting a high hole injectability. Examples of the substance exhibiting a high hole injectability include molybdenum oxide, titanium oxide, vanadium oxide, rhenium oxide, ruthenium oxide, chrome oxide, zirconium oxide, hafnium oxide, tantalum oxide, silver oxide, tungsten oxide, and manganese oxide.

In addition, the examples of the highly hole-injectable substance include: an aromatic amine compound, which is a low-molecule organic compound, such that 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl(abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

In addition, a high polymer compound (e.g., oligomer, dendrimer and polymer) is usable as the substance exhibiting a high hole injectability. Examples of the high-molecule compound include poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide](abbreviation: PTPDMA), and poly[N,N'-bis(4-butylphenyl)-N,N'-bis(phenyl)benzidine] (abbreviation: Poly-TPD). Moreover, an acid-added high polymer compound such as poly(3,4-ethylenedioxythiophene)/poly(styrene sulfonic acid) (PEDOT/PSS) and polyaniline/poly(styrene sulfonic acid) (PAni/PSS) are also usable.

Hole Transporting Layer

The hole transporting layer is a layer containing a highly hole-transporting substance. An aromatic amine compound, carbazole derivative, anthracene derivative and the like are usable for the hole transporting layer. Specific examples of a material for the hole transporting layer include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluorene-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The above-described substances mostly have a hole mobility of $10^{-6}$ $cm^2/(V \cdot s)$ or more.

For the hole transporting layer, a carbazole derivative such as CBP, 9-[4-(N-carbazolyl)]phenyl-10-phenylanthracene (CzPA), and 9-phenyl-3-[4-(10-phenyl-9-anthryl)phenyl]-9H-carbazole (PCzPA) and an anthracene derivative such as t-BuDNA, DNA, and DPAnth may be used. A high polymer compound such as poly(N-vinylcarbazole) (abbreviation: PVK) and poly(4-vinyltriphenylamine) (abbreviation: PVTPA) is also usable.

However, in addition to the above substances, any substance exhibiting a higher hole transportability than an electron transportability may be used. It should be noted that the layer containing the substance exhibiting a high hole transportability may be not only a single layer but also a laminate of two or more layers formed of the above substance(s).

When the hole transporting layer includes two or more layers, one of the layers with a larger energy gap is preferably provided closer to the emitting layer. An example of the material with a larger energy gap is HT-2 used in later-described Examples.

Electron Transporting Layer

The electron transporting layer is a layer containing a highly electron-transporting substance. For the electron transporting layer, 1) a metal complex such as an aluminum complex, beryllium complex, and zinc complex, 2) a hetero aromatic compound such as imidazole derivative, benzimidazole derivative, azine derivative, carbazole derivative, and phenanthroline derivative, and 3) a high polymer compound are usable. Specifically, as a low-molecule organic compound, a metal complex such as Alq, tris(4-methyl-8-quinolinato)aluminum (abbreviation: $Almq_3$), bis(10-hydroxybenzo[h]quinolinato)beryllium (abbreviation: $BeBq_2$), BAlq, Znq, ZnPBO and ZnBTZ is usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) is usable. In the present exemplary embodiment, a benzimidazole compound is preferably usable. The above-described substances mostly have an electron mobility of $10^{-6}$ $cm^2/(V \cdot s)$ or more. It should be noted that any substance other than the above substance may be used for the electron transporting layer as long as the substance exhibits a higher electron transportability than the hole transportability. The electron transporting layer may be provided in the form of a single layer or a laminate of two or more layers of the above substance(s).

Further, a high polymer compound is usable for the electron transporting layer. For instance, poly[(9,9-dihexylfluorene-2,7-diyl)-co-(pyridine-3,5-diyl)](abbreviation: PF-Py), poly[(9,9-dioctylfluorene-2,7-diyl)-co-(2,2'-bipyridine-6,6'-diyl)](abbreviation: PF-BPy) and the like are usable.

Electron Injecting Layer

The electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride ($CaF_2$), and lithium oxide (LiOx). In addition, the alkali metal, alkaline earth metal or the compound thereof may be added to the substance exhibiting the electron transportability in use. Specifically, for instance, magnesium (Mg) added to Alq may be used. In this case, the electrons can be more efficiently injected from the cathode.

Alternatively, the electron injecting layer may be provided by a composite material in a form of a mixture of the organic compound and the electron donor. Such a composite material exhibits excellent electron injectability and electron transportability since electrons are generated in the organic compound by the electron donor. In this case, the organic compound is preferably a material excellent in transporting the generated electrons. Specifically, the above examples (e.g., the metal complex and the hetero aromatic compound) of the substance forming the electron transporting layer are usable. As the electron donor, any substance exhibiting electron donating property to the organic compound is usable. Specifically, the electron donor is preferably alkali metal, alkaline earth metal and rare earth metal such as lithium, cesium, magnesium, calcium, erbium and ytterbium. The electron donor is also preferably alkali metal oxide and alkaline earth metal oxide such as lithium oxide, calcium oxide, and barium oxide. Moreover, a Lewis base such as magnesium oxide is usable. Further, the organic compound such as tetrathiafulvalene (abbreviation: TTF) is usable.

Layer Formation Method

A method for forming each layer of the organic EL device in the present exemplary embodiment is subject to no limitation except for the above particular description. However, known methods of dry film-forming such as vacuum deposition, sputtering, plasma or ion plating and wet film-forming such as spin coating, dipping, flow coating or ink-jet are applicable.

Film Thickness

A thickness of each of the organic layers in the organic EL device according to the present exemplary embodiment is not limited except for the above particular description. In general, the thickness preferably ranges from several nanometers to 1 μm because excessively small film thickness is likely to cause defects (e.g. pin holes) and excessively large thickness leads to the necessity of applying high voltage and consequent reduction in efficiency.

Fourth Exemplary Embodiment

An arrangement of an organic EL device according to a fourth exemplary embodiment will be described below. In the description of the fourth exemplary embodiment, the same components as those in the third exemplary embodiment are denoted by the same reference signs and names to simplify or omit an explanation of the components. In the fourth exemplary embodiment, any materials and compounds that are not specified may be the same as those in the third exemplary embodiment.

The organic EL device according to the fourth exemplary embodiment is different from the organic EL device according to the third exemplary embodiment in that the emitting layer further includes a third compound. The rest of the arrangement of the organic EL device according to the fifth exemplary embodiment is the same as in the third exemplary embodiment.

Specifically, in the fourth exemplary embodiment, the emitting layer as a first organic layer contains the first compound, the second compound and the third compound.

In the fourth exemplary embodiment, the first compound is preferably a host material, the second compound is preferably a dopant material, and the third compound is preferably a host material. Occasionally, one of the first compound and the third compound is referred to as a first host material and the other thereof is referred to as a second host material.

Third Compound

The third compound may be a delayed fluorescent compound and a compound that does not exhibit delayed fluorescence.

The third compound is not particularly limited, but is preferably a compound other than an amine compound. Although the third compound may be a carbazole derivative, dibenzofuran derivative, or dibenzothiophene derivative, the third compound is not limited thereto.

It is also preferable that the third compound has at least one of a partial structure represented by a formula (31), a partial structure represented by a formula (32), a partial structure represented by a formula (33), or a partial structure represented by a formula (34) in one molecule.

[Formula 107]

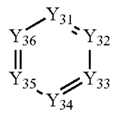
(31)

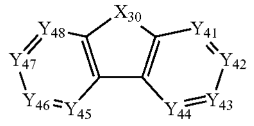
(32)

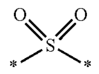
(33)

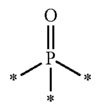
(34)

In the formula (31):

$Y_{31}$ to $Y_{36}$ each independently represent a nitrogen atom or a carbon atom bonded to another atom in the molecule of the third compound; and at least one of $Y_{31}$ to $Y_{36}$ is a carbon atom bonded to another atom in the molecule of the third compound.

In the formula (32):

$Y_{41}$ to $Y_{48}$ each independently represent a nitrogen atom or a carbon atom bonded to another atom in the molecule of the third compound;

at least one of $Y_{41}$ to $Y_{48}$ is a carbon atom bonded to another atom in the molecule of the third compound; and $X_{30}$ represents a nitrogen atom bonded to another atom in the molecule of the third compound, an oxygen atom, or a sulfur atom.

* in the formulae (33) to (34) each independently shows a bonding position with another atom or another structure in the molecule of the third compound.

In the formula (32), it is also preferable that at least two of $Y_{41}$ to $Y_{48}$ are carbon atoms bonded to other atoms in the molecule of the third compound to form a cyclic structure including the carbon atoms.

For instance, the partial structure represented by the formula (32) is preferably any one selected from the group consisting of partial structures represented by formulae (321), (322), (323), (324), (325) and (326).

[Formula 108]

(321)

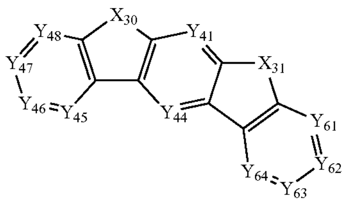

(322)

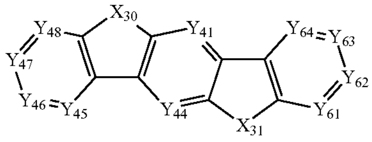

[Formula 109]

(323)

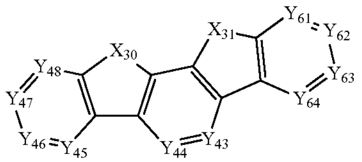

(324)

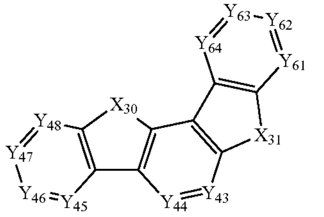

[Formula 110]

(325)

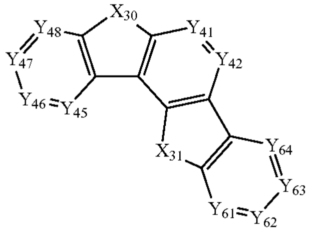

(326)

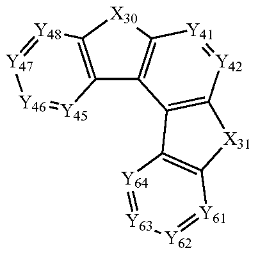

In the formulae (321) to (326):

$X_{30}$ each independently represents a nitrogen atom bonded to another atom in the molecule of the third compound, an oxygen atom, or a sulfur atom;

$Y_{41}$ to $Y_{43}$ each independently represent a nitrogen atom or a carbon atom bonded to another atom in the molecule of the third compound;

$X_{31}$ each independently represents a nitrogen atom bonded to another atom in the molecule of the third compound, an oxygen atom, a sulfur atom, or a carbon atom bonded to another atom in the molecule of the third compound; and $Y_{61}$ to $Y_{64}$ each independently represent a nitrogen atom or a carbon atom bonded to another atom in the molecule of the third compound.

In the present exemplary embodiments, the third compound preferably has the partial structure represented by the formula (323) among those represented by the formulae (323) to (326).

The partial structure represented by the formula (31) is preferably included in the third compound as at least one group selected from the group consisting of a group represented by a formula (33) and a group represented by a formula (34) below.

It is also preferable that the third compound has at least one of the partial structures represented by the formulae (33) and (34). Since bonding positions are situated in meta positions as shown in the partial structures represented by the formulae (33) and (34), an energy gap $T_{77K}$(Mat3) at 77 [K] of the second compound can be kept high.

[Formula 111]

(33)

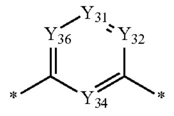

(34)

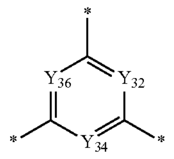

In the formula (33), $Y_{31}$, $Y_{32}$, $Y_{34}$ and $Y_{36}$ are each independently a nitrogen atom or $CR_{31}$.

In the formula (34), $Y_{32}$, $Y_{34}$ and $Y_{36}$ are each independently a nitrogen atom or $CR_{31}$.

In the formulae (33) and (34), $R_{31}$ is each independently a hydrogen atom or a substituent.

$R_{31}$ as a substituent is each independently selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a halogen atom, a cyano group, a nitro group, and a substituted or unsubstituted carboxy group.

The substituted or unsubstituted aryl group having 6 to 30 ring carbon atoms for $R_{31}$ is preferably a non-fused ring.

* in the formulae (33) and (34) each independently shows a bonding position with another atom or another structure in the molecule of the third compound.

In the formula (33), $Y_{31}$, $Y_{32}$, $Y_{34}$ and $Y_{36}$ are each independently preferably $CR_{31}$, in which a plurality of $R_{31}$ are the same or different.

In the formula (34), $Y_{32}$, $Y_{34}$ and $Y_{36}$ are each independently preferably $CR_{31}$, in which a plurality of $R_{31}$ are the same or different.

The substituted germanium group is preferably represented by —Ge($R_{301}$)$_3$. $R_{301}$ is each independently a substituent. The substituent $R_{301}$ is preferably a substituted or unsubstituted alkyl group having 1 to 30 carbon atoms or a substituted or unsubstituted aryl group having 6 to 30 ring carbon atoms. A plurality of $R_{301}$ are mutually the same or different.

The partial structure represented by the formula (32) is preferably included in the third compound as at least one group selected from the group consisting of groups represented by formulae (35) to (39) and a group represented by a formula (30a).

[Formula 112]

(35)

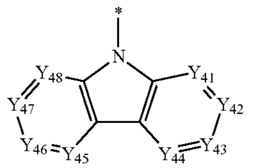

(36)

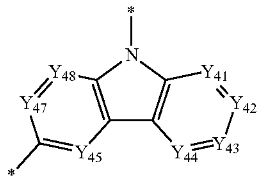

[Formula 113]

(37)

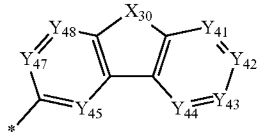

(38)

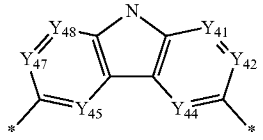

[Formula 114]

(39)

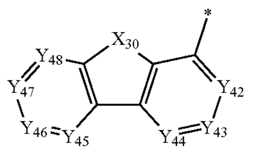

(30a)

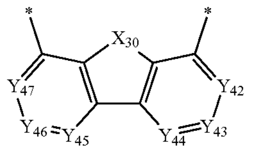

In the formula (35), $Y_{41}$ to $Y_{48}$ are each independently a nitrogen atom or $CR_{32}$.

In the formulae (36) and (37), $Y_{41}$ to $Y_{45}$, $Y_{47}$ and $Y_{48}$ are each independently a nitrogen atom or $CR_{32}$.

In the formula (38), $Y_{41}$, $Y_{42}$, $Y_{44}$, $Y_{45}$, $Y_{47}$ and $Y_{48}$ are each independently a nitrogen atom or $CR_{32}$.

In the formula (39), $Y_{42}$ to $Y_{48}$ are each independently a nitrogen atom or $CR_{32}$.

In the formula (30a), $Y_{42}$ to $Y_{47}$ are each independently a nitrogen atom or $CR_{32}$.

In the formulae (35) to (39) and (30a), $R_{32}$ is each independently a hydrogen atom or a substituent.

$R_{32}$ as a substituent is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a halogen atom, a cyano group, a nitro group, and a substituted or unsubstituted carboxy group.

A plurality of $R_{32}$ are the same or different.

In the formulae (37) to (39) and (30a), $X_{30}$ is $NR_{33}$, an oxygen atom or a sulfur atom.

$R_{33}$ is selected from the group consisting of a substituted or unsubstituted aryl group having 6 to 30 ring carbon atoms, a substituted or unsubstituted heteroaryl group having 5 to 30 ring atoms, a substituted or unsubstituted alkyl group having 1 to 30 carbon atoms, a substituted or unsubstituted fluoroalkyl group having 1 to 30 carbon atoms, a substituted or unsubstituted cycloalkyl group having 3 to 30 ring carbon atoms, a substituted or unsubstituted aralkyl group having 7 to 30 carbon atoms, a substituted or unsubstituted silyl group, a substituted germanium group, a substituted phosphine oxide group, a fluorine atom, a cyano group, a nitro group, and a substituted or unsubstituted carboxy group.

A plurality of $R_{33}$ are the same or different.

The substituted or unsubstituted aryl group having 6 to 30 ring carbon atoms for $R_{33}$ is preferably a non-fused ring.

* in the formulae (35) to (39) and (30a) each independently shows a bonding position with another atom or another structure in the molecule of the third compound.

In the formula (35), $Y_{41}$ to $Y_{48}$ are each independently preferably $CR_{32}$. In the formulae (36) and (37), $Y_{41}$ to $Y_{45}$, $Y_{47}$ and $Y_{48}$ are each independently preferably $CR_{32}$. In the formula (38), $Y_{41}$, $Y_{42}$, $Y_{44}$, $Y_{45}$, $Y_{47}$ and $Y_{48}$ are each independently preferably $CR_{32}$. In the formula (39), $Y_{42}$ to $Y_{48}$ are each independently preferably $CR_{32}$. In the formula (30a), $Y_{42}$ to $Y_{47}$ are each independently preferably $CR_{32}$. A plurality of $R_{32}$ are the same or different.

In the third compound, $X_{30}$ is preferably an oxygen atom or a sulfur atom, more preferably an oxygen atom.

In the third compound, $R_{31}$ and $R_{32}$ each independently represent a hydrogen atom or a substituent. $R_{31}$ and $R_{32}$ as a substituent are preferably each independently a group selected from the group consisting of a fluorine atom, a cyano group, a substituted or unsubstituted alkyl group having 1 to 30 carbon atoms, a substituted or unsubstituted aryl group having 6 to 30 ring carbon atoms, and a substituted or unsubstituted heteroaryl group having 5 to 30 ring atoms. $R_{31}$ and $R_{32}$ are more preferably a hydrogen atom, a cyano group, a substituted or unsubstituted aryl group having 6 to 30 ring carbon atoms, or a substituted or unsubsti tuted heteroaryl group having 5 to 30 ring atoms. When $R_{31}$ and $R_{32}$ as a substituent are each a substituted or unsubstituted aryl group having 6 to 30 ring carbon atoms, the aryl group is preferably a non-fused ring.

It is also preferable that the third compound is an aromatic hydrocarbon compound or an aromatic heterocyclic compound.

Manufacturing Method of Third Compound

The third compound can be manufactured by methods disclosed in International Publication No. WO2012/153780, International Publication No. WO2013/038650, and the like. Furthermore, the third compound can be manufactured, for instance, by application of known substitution reactions and/or materials depending on a target compound.

Examples of the substituent in the third compound are shown below, but the invention is not limited to these examples.

Specific examples of an aryl group (occasionally referred to as an aromatic hydrocarbon group) include a phenyl group, tolyl group, xylyl group, naphthyl group, phenanthryl group, pyrenyl group, chrysenyl group, benzo[c]phenanthryl group, benzo[g]chrysenyl group, benzoanthryl group, triphenylenyl group, fluorenyl group, 9,9-dimethylfluorenyl group, benzofluorenyl group, dibenzofluorenyl group, biphenyl group, terphenyl group, quarterphenyl group, fluoranthenyl group, among which a phenyl group, biphenyl group, terphenyl group, quarterphenyl group, naphthyl group, triphenylenyl group, fluorenyl group and the like are preferable.

Specific examples of the aryl group having a substituent include a tolyl group, xylyl group and 9,9-dimethylfluorenyl group.

As is understood from the specific examples, the aryl group includes both fused aryl group and non-fused aryl group.

Preferable examples of the aryl group include a phenyl group, biphenyl group, terphenyl group, quarterphenyl group, naphthyl group, triphenylenyl group and fluorenyl group.

Specific examples of the heteroaryl group (occasionally referred to as a heterocyclic group, heteroaromatic ring group or aromatic heterocyclic group) include a pyrrolyl group, pyrazolyl group, pyrazinyl group, pyrimidinyl group, pyridazynyl group, pyridyl group, triazinyl group, indolyl group, isoindolyl group, imidazolyl group, benzimidazolyl group, indazolyl group, imidazo[1,2-a]pyridinyl group, furyl group, benzofuranyl group, isobenzofuranyl group, dibenzofuranyl group, azadibenzofuranyl group, thiophenyl group, benzothienyl group, dibenzothienyl group, azadibenzothienyl group, quinolyl group, isoquinolyl group, quinoxalinyl group, quinazolinyl group, naphthyridinyl group, carbazolyl group, azacarbazolyl group, phenanthridinyl group, acridinyl group, phenanthrolinyl group, phenazinyl group, phenothiazinyl group, phenoxazinyl group, oxazolyl group, oxadiazolyl group, furazanyl group, benzoxazolyl group, thienyl group, thiazolyl group, thiadiazolyl group, benzothiazolyl group, triazolyl group and tetrazolyl group, among which a dibenzofuranyl group, dibenzothienyl group, carbazolyl group, pyridyl group, pyrimidinyl group, triazinyl group, azadibenzofuranyl group, azadibenzothienyl group and the like are preferable.

The heteroaryl group is preferably a dibenzofuranyl group, dibenzothienyl group, carbazolyl group, pyridyl group, pyrimidinyl group, triazinyl group, azadibenzofuranyl group or azadibenzothienyl group, and more preferably a dibenzofuranyl group, dibenzothienyl group, azadibenzofuranyl group and azadibenzothienyl group.

In the third compound, it is also preferable that the substituted silyl group is selected from the group consisting of a substituted or unsubstituted trialkylsilyl group, a substituted or unsubstituted arylalkylsilyl group, or a substituted or unsubstituted triarylsilyl group.

Specific examples of the substituted or unsubstituted trialkylsilyl group include trimethylsilyl group and triethylsilyl group.

Specific examples of the substituted or unsubstituted arylalkylsilyl group include diphenylmethylsilyl group, ditolylmethylsilyl group, and phenyldimethylsilyl group.

Specific examples of the substituted or unsubstituted triarylsilyl group include triphenylsilyl group and tritolylsilyl group.

In the third compound, it is also preferable that the substituted phosphine oxide group is a substituted or unsubstituted diaryl phosphine oxide group.

Specific examples of the substituted or unsubstituted diaryl phosphine oxide group include a diphenyl phosphine oxide group and ditolyl phosphine oxide group.

In the third compound, the substituted carboxy group is exemplified by a benzoyloxy group.

Specific examples of the third compound in the present exemplary embodiment are shown below. It should be noted that the third compound of the invention is not limited to these specific examples.

[Formula 115]

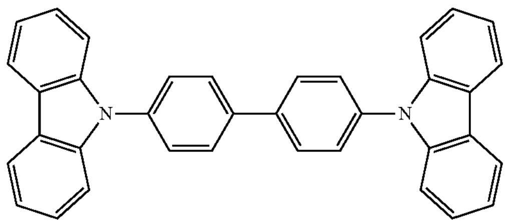

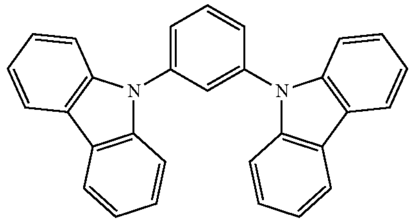

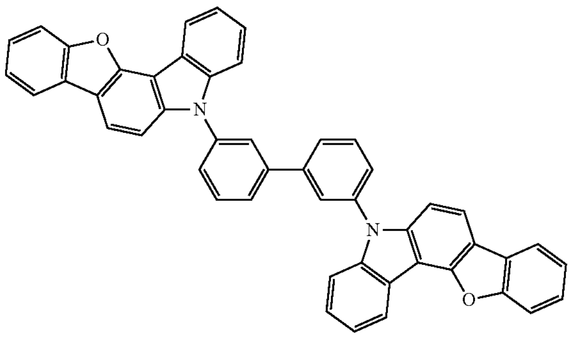

-continued

[Formula 116]

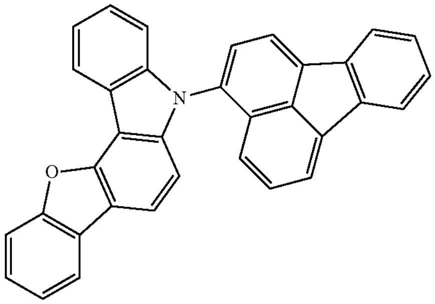

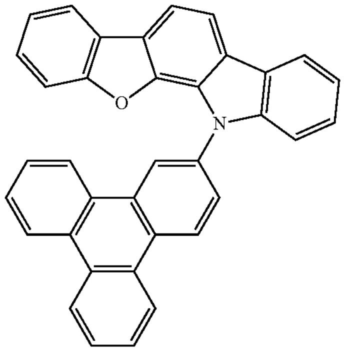

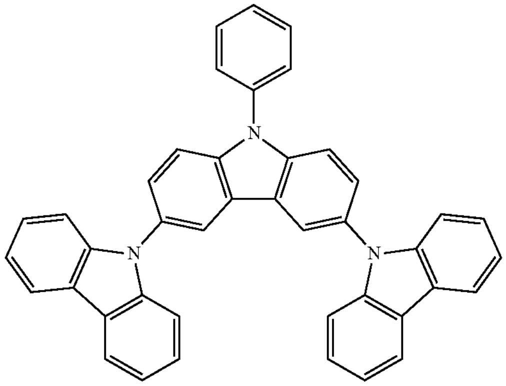

[Formula 117]

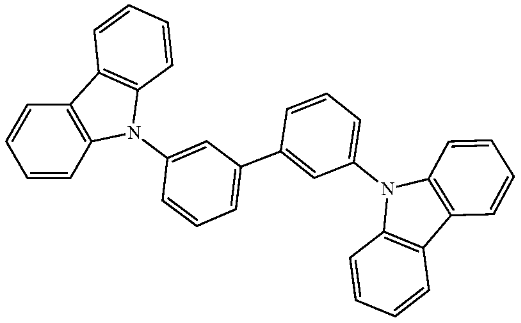

-continued

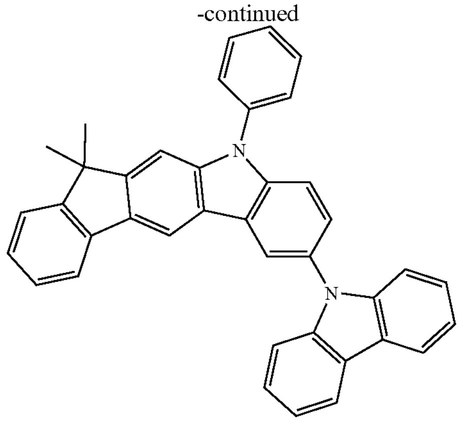

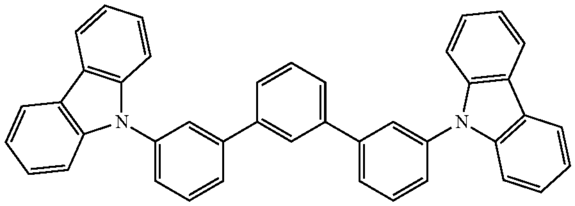

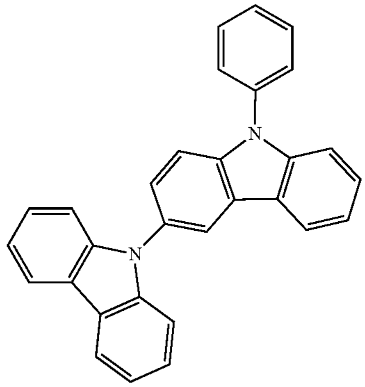

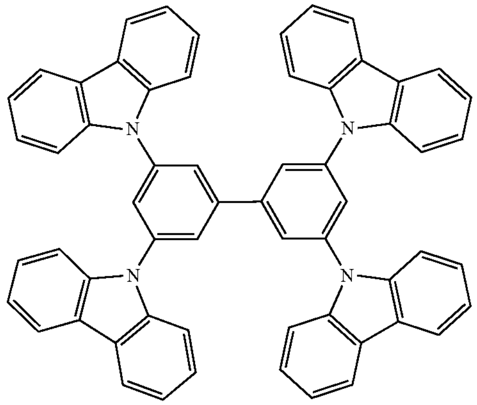

Relationship Between First Compound, Second Compound and Third Compound in Emitting Layer In the organic EL device of the present exemplary embodiment, the singlet energy $S_1$(Mat1) of the first compound and a singlet energy $S_1$(Mat3) of the third compound preferably satisfies a relationship of Numerical Formula 2 below.

$$S_1(\text{Mat3})>S_1(\text{Mat1}) \qquad \text{(Numerical Formula 2)}$$

The energy gap $T_{77K}$(Mat3) at 77K of the third compound is preferably larger than an energy gap $T_{77K}$(Mat1) at 77K of the first compound.

The energy gap $T_{77K}$(Mat3) at 77K of the third compound is preferably larger than the energy gap $T_{77K}$(Mat2) at 77K of the second compound The singlet energy $S_1$(Mat1) of the first compound, the singlet energy $S_1$(Mat2) of the second compound, the singlet energy $S_1$(Mat3) of the third compound preferably satisfy a relationship of Numerical Formula 2A.

$$S_1(\text{Mat3})>S_1(\text{Mat1})>S_1(\text{Mat2}) \quad \text{(Numerical Formula 2A)}$$

The energy gap $T_{77K}$(Mat1) at 77K of the first compound, the energy gap $T_{77K}$(Mat2) at 77K of the second compound, and the energy gap $T_{77K}$(Mat3) at 77K of the third compound preferably satisfy a relationship of Numerical Formula 2B.

$$T_{77K}(\text{Mat3})>T_{77K}(\text{Mat1})>T_{77K}(\text{Mat2}) \quad \text{(Numerical Formula 2B)}$$

When the organic EL device of the present exemplary embodiment emits light, it is preferable that the fluorescent compound in the emitting layer mainly emits light.

The organic EL device of the fourth exemplary embodiment preferably emits red light or green light in the same manner as the organic EL device of the third exemplary embodiment.

The maximum peak wavelength of light emitted from the organic EL device can be measured by the same method as that for the organic EL device of the third exemplary embodiment.

Content Ratios of Compounds in Emitting Layer

Content ratios of the first, second and third compounds in the emitting layer preferably fall, for instance, within a range below.

The content ratio of the first compound is preferably in a range from 10 mass % to 80 mass %, more preferably in a range from 10 mass % to 60 mass %, further preferably in a range from 20 mass % to 60 mass %.

The content ratio of the second compound is preferably in a range from 0.01 mass % to 10 mass %, more preferably in a range from 0.01 mass % to 5 mass %, further preferably in a range from 0.01 mass % to 1 mass %.

The content ratio of the third compound is preferably in a range from 10 mass % to 80 mass %.

An upper limit of the total of the respective content ratios of the first, second and third compounds in the emitting layer is 100 mass %. It should be noted that the emitting layer of the present exemplary embodiment may further contain material(s) other than the first, second and third compounds.

The emitting layer may include a single type of the first compound or may include two or more types of the first compound. The emitting layer may include a single of the second compound or may include two or more types of the second compound. The emitting layer may include a single of the third compound or may include two or more types of the third compound.

Figure 5:
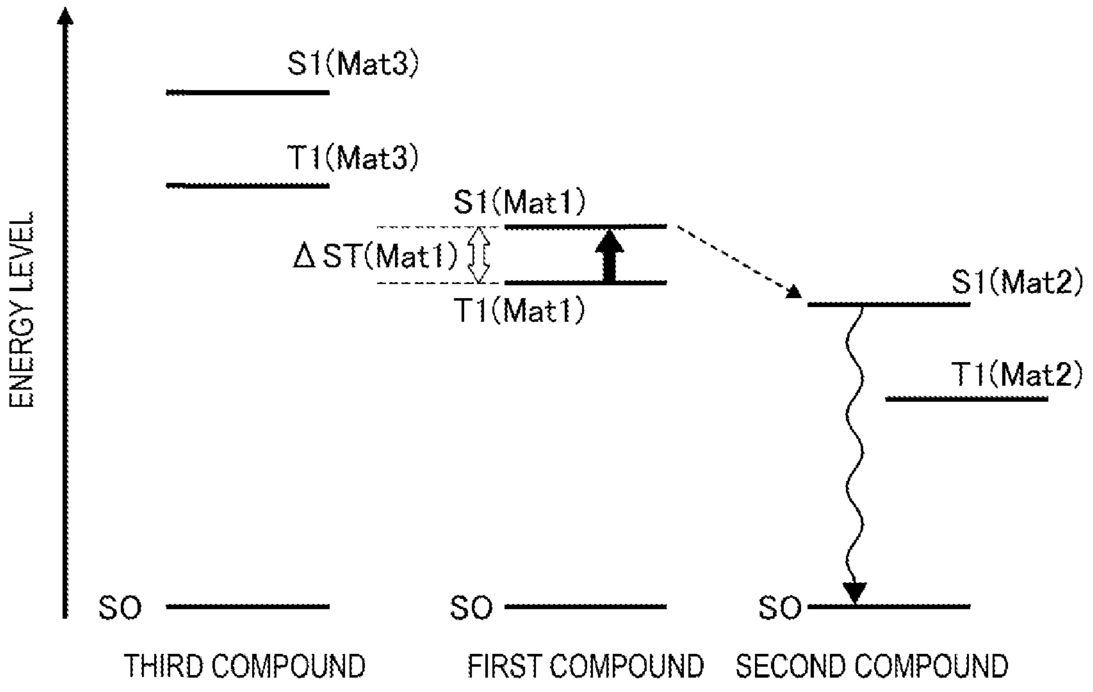
FIG. 5 shows a relationship in energy level and energy transfer between a first compound, a second compound and a third compound in an emitting layer of an exemplary organic electroluminescence device according to a fourth exemplary embodiment of the invention.

FIG. 5 shows an example of a relationship between energy levels of the first, second and third compounds in the emitting layer. In FIG. 5, S0 represents a ground state. S1(Mat1) represents the lowest singlet state of the first compound. T1(Mat1) represents the lowest triplet state of the first compound. S1(Mat2) represents the lowest singlet state of the second compound. T1(Mat2) represents the lowest triplet state of the second compound. S1(Mat3) represents the lowest singlet state of the third compound. T1(Mat3) represents the lowest triplet state of the third compound. A dashed arrow directed from 1(Mat1) to S1(Mat2) in FIG. 5 represents Förster energy transfer from the lowest singlet state of the first compound to the lowest singlet state of the second compound.

As shown in FIG. 5, when a compound having a small ΔST(Mat1) is used as the first compound, inverse intersystem crossing from the lowest triplet state T1(Mat1) to the lowest singlet state S1(Mat1) can be caused by a heat energy. Subsequently, Forster energy transfer from the lowest singlet state S1(Mat1) of the first compound the second compound occurs to generate the lowest singlet state S1(Mat2). Consequently, fluorescence from the lowest singlet state S1(Mat2) of the second compound can be observed. It is inferred that the internal quantum efficiency can be theoretically raised up to 100% also by using delayed fluorescence by the TADF mechanism.

The organic EL device 1 according to the fourth exemplary embodiment contains the first compound that is the compound according to the first exemplary embodiment (at least one of the compounds represented by the formulae (11) to (13)), the second compound having the singlet energy smaller than that of the first compound in the emitting layer 5, and the third compound having the singlet energy larger than that of the first compound.

The organic EL device according to the fourth exemplary embodiment contains the compound (the compound of the first exemplary embodiment) capable of providing a high-performance organic EL device. Accordingly, the fourth exemplary embodiment can provide a high-performance organic EL device.

The organic EL device according to the fourth exemplary embodiment is applicable to an electronic device such as a display device and a light-emitting device.

Fifth Exemplary Embodiment

An arrangement of an organic EL device according to a fifth exemplary embodiment will be described below. In the description of the fifth exemplary embodiment, the same components as those in the third and fourth exemplary embodiments are denoted by the same reference signs and names to simplify or omit an explanation of the components. In the fifth exemplary embodiment, any materials and compounds that are not specified may be the same as those in the third and fourth exemplary embodiments.

The organic EL device according to the fifth exemplary embodiment is different from the organic EL device according to the third exemplary embodiment in that the emitting layer further includes a fourth compound in place of the second compound. The rest of the arrangement of the organic EL device according to the fifth exemplary embodiment is the same as in the third exemplary embodiment.

In the fifth exemplary embodiment, the emitting layer contains the first compound and the fourth compound.

In the present exemplary embodiment, the first compound is preferably a dopant material (also referred to as a guest material, emitter or luminescent material), and the fourth compound is preferably a host material (also referred to as a matrix material).

The fourth compound may be a thermally activated delayed fluorescent compound or a compound exhibiting no thermally activated delayed fluorescence.

Although the fourth compound is not particularly limited, for instance, the third compound described in the fourth exemplary embodiment is usable as the fourth compound.

Relationship Between First Compound and Fourth Compound in Emitting Layer

In the organic EL device 1 of the present exemplary embodiment, a singlet energy $S_1$(Mat1) of the first compound and a singlet energy $S_1$(Mat4) of the fourth compound preferably satisfy a relationship of a numerical formula (Numerical Formula 3) below.

$$S_1(\text{Mat4}) > S_1(\text{Mat1}) \quad \text{(Numerical Formula 3)}$$

An energy gap $T_{77K}$(Mat4) at 77K of the fourth compound is preferably larger than the energy gap $T_{77K}$(Mat1) at 77K of the first compound. In other words, a relationship of the following numerical formula (Numerical Formula 5) is preferably satisfied.

$$T_{77K}(\text{Mat4}) > T_{77K}(\text{Mat1}) \quad \text{(Numerical Formula 5)}$$

When the organic EL device of the present exemplary embodiment emits light, it is preferable that the first compound in the emitting layer mainly emits light.

Content Ratios of Compounds in Emitting Layer

Content ratios of the first and fourth compounds in the emitting layer preferably fall, for instance, within a range below.

The content ratio of the first compound is preferably in a range from 10 mass % to 80 mass %, more preferably in a range from 10 mass % to 60 mass %, further preferably in a range from 20 mass % to 60 mass %.

The content ratio of the fourth compound is preferably in a range from 20 mass % to 90 mass %, more preferably in a range from 40 mass % to 90 mass %, further preferably in a range from 40 mass % to 80 mass %.

It should be noted that the emitting layer of the present exemplary embodiment may further contain material(s) other than the first and fourth compounds.

The emitting layer may include a single type of the first compound or may include two or more types of the first compound. The emitting layer may include a single type of the fourth compound or may include two or more types of the fourth compound.

Figure 6:
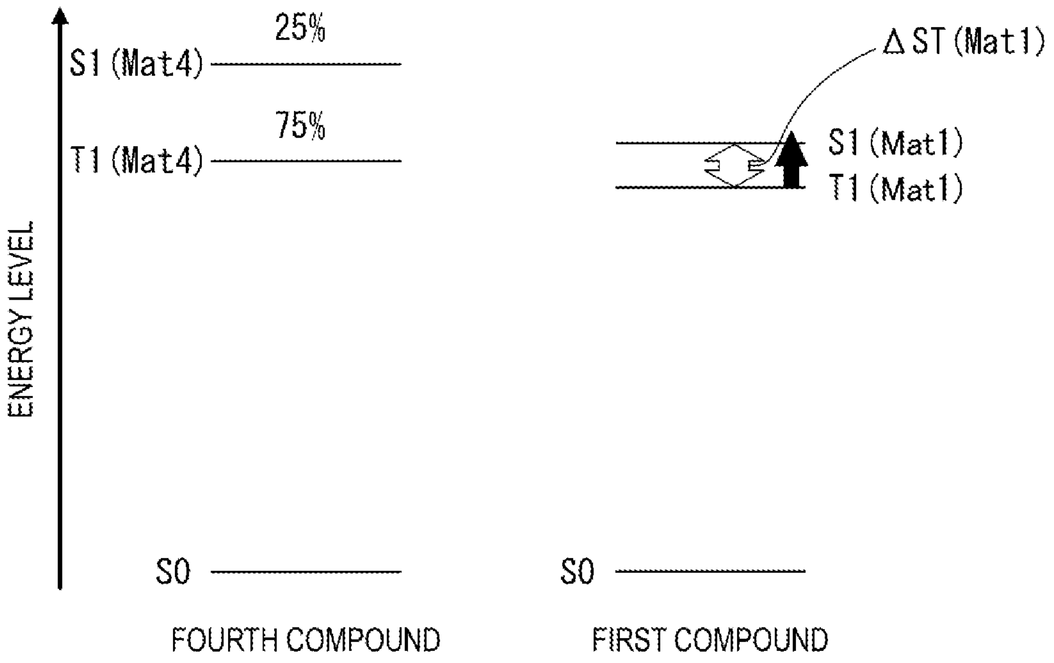
FIG. 6 shows a relationship in energy level and energy transfer between the first compound and a fourth compound in an emitting layer of an exemplary organic electroluminescence device according to a fifth exemplary embodiment of the invention.

FIG. 6 shows an example of a relationship between energy levels of the first and fourth compounds in the emitting layer. In FIG. 6, S0 represents a ground state. S1(Mat1) represents the lowest singlet state of the first compound. T1(Mat1) represents the lowest triplet state of the first compound. S1(Mat4) represents the lowest singlet state of the fourth compound. T1(Mat4) represents the lowest triplet state of the fourth compound. As shown in FIG. 6, when a material having a small ΔST(Mat1) is used as the first compound, inverse intersystem crossing can be caused by a heat energy from the lowest triplet state T1 to the lowest singlet state S1 in the first compound.

The inverse intersystem crossing caused in the first compound enables light emission from the lowest singlet state S1(Mat1) of the first compound can be observed when the emitting layer does not contain a fluorescent dopant with the lowest singlet state S1 smaller than the lowest singlet state S1(Mat1) of the first compound. It is inferred that the internal quantum efficiency can be theoretically raised up to 100% also by using delayed fluorescence by the TADF mechanism.

The organic EL device according to the fifth exemplary embodiment contains the first compound that is the compound according to the first exemplary embodiment (at least one of the compounds represented by the formulae (11) to (13)), and the fourth compound having the singlet energy larger than that of the first compound in the emitting layer.

The organic EL device according to the fifth exemplary embodiment contains the compound (the compound of the first exemplary embodiment) capable of providing a high-performance organic EL device, especially, the compound having a high PLQY in the first exemplary embodiment. Accordingly, the fifth exemplary embodiment can provide a high-performance organic EL device.

The organic EL device according to the fifth exemplary embodiment is applicable to an electronic device such as a display device and a light-emitting device.

Sixth Exemplary Embodiment

Compound

A compound of the sixth exemplary embodiment is a compound having a group represented by a formula (120C) below in place of a group represented by the formula (110) or (120) in the compound of the first exemplary embodiment (the compound represented by any one of formulae (11) to (13)). In other words, the compound of the sixth exemplary embodiment is different from the compound of the first exemplary embodiment.

Specifically, in the compound of the sixth exemplary embodiment, the requirement for the formulae (1-1) to (1-6) in the first exemplary embodiment that "$R_{101}$ to $R_{160}$ are each independently a hydrogen atom, a substituent, a group represented by the formula (110), or a group represented by the formula (120); and in at least one group $D_1$, at least one of $R_{101}$ to $R_{160}$ is a group represented by the formula (110) or a group represented by the formula (120)" is replaced by a requirement that "$R_{101}$ to $R_{160}$ are each independently a hydrogen atom, a substituent, or a group represented by a formula (120C) below, and in at least one group $D_1$, at least one of $R_{101}$ to $R_{160}$ is a group represented by the formula (120C)."

Accordingly, the "group represented by a formula (120C) below," which is different from the first exemplary embodiment, will be mainly described in the sixth exemplary embodiment, omitting or simplifying the description for the same components as those in the first exemplary embodiment.

[Formula 118]

(120C)

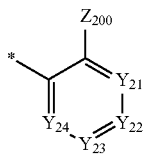

In the formula (120C):

$Z_{200}$ is a substituted or unsubstituted alkyl group having 2 to 30 carbon atoms, a substituted or unsubstituted alkyl halide group having 1 to 30 carbon atoms, or a substituted or unsubstituted trialkylsilyl group having 3 to 30 carbon atoms, and $Y_{21}$ to $Y_{24}$ each independently represent the same as $Y_{21}$ to $Y_{24}$ in the formula (120), none of at least one combination of adjacent two or more of a plurality of $R_{20A}$ being mutually bonded to form a ring, a plurality of $R_{20A}$ being mutually the same or different.

In the formula (120C), * represents a bonding position to a carbon atom of the six-membered ring in the formulae (1-1) to (1-6).

Preferable Forms of Compound of Sixth Exemplary Embodiment

Preferable forms of the compound of the sixth exemplary embodiment are the same as preferable forms of the compound of the first exemplary embodiment except that a group represented by the formula (120) in the compound of the first exemplary embodiment is replaced by a group represented by the formula (120C). Examples of the preferable forms are as follows.

In the compound of the sixth exemplary embodiment, it is preferable that, when three groups $D_1$ are selected as the groups for $R_1$ to $R_4$, all of the selected three groups $D_1$ are represented by one of the formulae (1-1) to (1-6) and are mutually identical groups including the substituent(s) thereof.

In the compound of the sixth exemplary embodiment, it is preferable that, when two groups $D_1$ are selected as the groups for $R_1$ to $R_4$, all of the selected two groups $D_1$ are represented by one of the formulae (1-1) to (1-6) and are mutually identical groups including the substituent(s) thereof.

In the compound of the sixth exemplary embodiment, it is preferable that, when two groups $D_2$ are selected as the groups for $R_1$ to $R_4$, all of the selected two groups $D_2$ are represented by one of the formulae (2-1) to (2-4) and are mutually identical groups including the substituent(s) thereof.

In the compound of the sixth exemplary embodiment, it is preferable that, when three groups $D_2$ are selected as the groups for $R_1$ to $R_4$, all of the selected three groups $D_2$ are represented by one of the formulae (2-1) to (2-4) and are mutually identical groups including the substituent(s) thereof.

In the compound according to the sixth exemplary embodiment, the group $D_2$ is preferably a group represented by the formula (2-1).

In the compound according to the sixth exemplary embodiment, the group $D_1$ is preferably a group represented by the formula (1-4) or (1-5).

In the compound of the sixth exemplary embodiment, it is preferable that, when one of $R_1$ to $R_4$ is the group $D_1$, only one of $R_{101}$ to $R_{160}$ in the group $D_1$ is a group represented by the formula (120C).

In the compound of the sixth exemplary embodiment, it is preferable that, when two of $R_1$ to $R_4$ are the group $D_1$, only one of $R_{101}$ to $R_{160}$ in the group $D_1$ is a group represented by the formula (120C).

In the compound of the sixth exemplary embodiment, it is preferable that, when three of $R_1$ to $R_4$ are the group $D_1$, only one of $R_{101}$ to $R_{160}$ in the group $D_1$ is a group represented by the formula (120C).

In the compound of the sixth exemplary embodiment, it is preferable that:

one of $R_{107}$ to $R_{110}$ in the formula (1-1) is a group represented by the formula (120C);

- one of $R_{116}$ to $R_{119}$ in the formula (1-2) is a group represented by the formula (120C);
- one of $R_{126}$ to $R_{129}$ in the formula (1-3) is a group represented by the formula (120C);
- one of $R_{135}$ to $R_{138}$ in the formula (1-4) is a group represented by the formula (120C);
- one of $R_{145}$ to $R_{148}$ in the formula (1-5) is a group represented by the formula (120C); or
- one of $R_{157}$ to $R_{160}$ in the formula (1-6) is a group represented by the formula (120C).

In the compound of the sixth exemplary embodiment, it is preferable that only one of $R_1$ to $R_4$ is the group $D_1$.

The compound of the sixth exemplary embodiment is preferably a compound represented by any one of formulae (1003A), (1007A), (1008A), (1012A), (1018A), and (1021A) below. It should however be noted that at least one of $R_{101}$ to $R_{160}$ in at least one of group $D_1$ in the formulae (1003A), (1007A), (1008A), (1012A), (1018A), and (1021A) is a group represented by the formula (120C).

In the compound of the sixth exemplary embodiment, it is preferable that only two of $R_1$ to $R_4$ are the groups $D_1$.

In the compound of the sixth exemplary embodiment, it is preferable that $Y_{21}$ to $Y_{24}$ in the formula (120C) are each $CR_{204}$.

In the compound of the sixth exemplary embodiment, $Z_{200}$ in the formula (120C) is preferably a substituted or unsubstituted ethyl group, substituted or unsubstituted n-propyl group, substituted or unsubstituted isopropyl group, substituted or unsubstituted n-butyl group, substituted or unsubstituted s-butyl group, substituted or unsubstituted isobutyl group, substituted or unsubstituted t-butyl group, substituted or unsubstituted n-pentyl group, substituted or unsubstituted n-hexyl group, substituted or unsubstituted n-heptyl group, substituted or unsubstituted n-octyl group, substituted or unsubstituted n-nonyl group, substituted or unsubstituted n-decyl group, substituted or unsubstituted n-undecyl group, substituted or unsubstituted n-dodecyl group, substituted or unsubstituted n-tridecyl group, substituted or unsubstituted n-tetradecyl group, substituted or unsubstituted n-pentadecyl group, substituted or unsubstituted n-hexadecyl group, substituted or unsubstituted n-heptadecyl group, substituted or unsubstituted n-octadecyl group, substituted or unsubstituted neopentyl group, substituted or unsubstituted amyl group, substituted or unsubstituted isoamyl group, substituted or unsubstituted 1-methylpentyl group, substituted or unsubstituted 2-methylpentyl group, substituted or unsubstituted 1-pentylhexyl group, substituted or unsubstituted 1-butylpentyl group, substituted or unsubstituted 1-heptyloctyl group, substituted or unsubstituted 3-methylpentyl group, fluoromethyl group, difluoromethyl group, trifluoromethyl group, fluoroethyl group, trifluoromethylethyl group, trifluoroethyl group, pentafluoroethyl group, substituted or unsubstituted trimethylsilyl group, substituted or unsubstituted triethylsilyl group, substituted or unsubstituted tri-n-butylsilyl group, substituted or unsubstituted tri-n-octylsilyl group, substituted or unsubstituted triisobutylsilyl group, substituted or unsubstituted dimethylethylsilyl group, substituted or unsubstituted dimethylisopropylsilyl group, substituted or unsubstituted dimethyl-n-propylsilyl group, substituted or unsubstituted dimethyl-n-butylsilyl group, substituted or unsubstituted dimethyl-t-butylsilyl group, substituted or unsubstituted diethylisopropylsilyl group, substituted or unsubstituted vinyldimethylsilyl group, substituted or unsubstituted propyldimethylsilyl group, or substituted or unsubstituted triisopropylsilyl group.

In the compound according to the sixth exemplary embodiment, $X_1$ to $X_6$ in the group $D_1$ are each preferably an oxygen atom.

In the compound according to the sixth exemplary embodiment, $X_1$ to $X_6$ in the group $D_1$ are each preferably a sulfur atom.

The compound of the sixth exemplary embodiment is preferably a compound represented by the formula (11).

The compound of the sixth exemplary embodiment is preferably a compound represented by the formula (12).

The compound of the sixth exemplary embodiment is preferably a compound represented by the formula (13).

In the compound of the sixth exemplary embodiment, it is preferable that $R_{101}$ to $R_{160}$, $R_{161}$ to $R_{168}$, $R_{171}$ to $R_{200}$, and $R_{204}$ are each independently a hydrogen atom, a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 30 carbon atoms, a substituted or unsubstituted alkylsilyl group having 3 to 6 carbon atoms, a substituted or unsubstituted alkoxy group having 1 to 6 carbon atoms, a substituted or unsubstituted aryloxy group having 6 to 14 ring carbon atoms, a group represented by —N(Rz)$_2$, a substituted or unsubstituted alkylthio group having 1 to 6 carbon atoms, or a substituted or unsubstituted arylthio group having 6 to 14 ring carbon atoms.

In the compound of the sixth exemplary embodiment, it is preferable that $R_{101}$ to $R_{160}$, $R_{161}$ to $R_{168}$, $R_{171}$ to $R_{200}$, and $R_{20A}$ are each independently a hydrogen atom, a halogen atom, an unsubstituted aryl group having 6 to 14 ring carbon atoms, an unsubstituted heterocyclic group having 5 to 14 ring atoms, an unsubstituted alkyl group having 1 to 6 carbon atoms, an unsubstituted alkyl halide group having 1 to 30 carbon atoms, an unsubstituted alkylsilyl group having 3 to 6 carbon atoms, an unsubstituted alkoxy group having 1 to 6 carbon atoms, an unsubstituted aryloxy group having 6 to 14 ring carbon atoms, an unsubstituted alkylamino group having 2 to 12 carbon atoms, an unsubstituted alkylthio group having 1 to 6 carbon atoms, or an unsubstituted arylthio group having 6 to 14 ring carbon atoms.

In the compound of the sixth exemplary embodiment, $R_{101}$ to $R_{160}$, $R_{161}$ to $R_{168}$, $R_{171}$ to $R_{200}$, and $R_{20A}$ are preferably each independently a hydrogen atom, an unsubstituted aryl group having 6 to 14 ring carbon atoms, an unsubstituted heterocyclic group having 5 to 14 ring atoms, or an unsubstituted alkyl group having 1 to 6 carbon atoms.

In the compound of the sixth exemplary embodiment, $R_{20A}$ is preferably a hydrogen atom.

In the compound of the sixth exemplary embodiment, it is also preferable that one or more hydrogen atoms in a molecule is a deuterium atom.

In the compound according to the sixth exemplary embodiment, it is also preferable that one or more $R_{101}$ to $R_{160}$ in the group $D_1$ are each a hydrogen atom and all of the hydrogen atom(s) are deuterium atoms.

In the compound according to the present exemplary embodiment, it is also preferable that one or more $R_{101}$ to $R_{160}$ in the group $D_1$ are each a hydrogen atom and all of the hydrogen atom(s) are protium atoms.

In the compound according to the sixth exemplary embodiment, it is also preferable that $R_{101}$ to $R_{160}$ in the group $D_1$ except for a group represented by the formula (120C) are hydrogen atom(s) and the hydrogen atom(s) are deuterium atoms.

In the compound of the sixth exemplary embodiment, it is preferable that, when at least one of $R_{101}$ to $R_{160}$ in the group $D_1$ are each a substituent (including a group represented by the formula (120C)) and the substituent has one or more hydrogen atoms, all of the hydrogen atom(s) are protium atoms, at least one of the hydrogen atom(s) is a deuterium atom, or all of the hydrogen atom(s) are deuterium atoms.

In the compound according to the sixth exemplary embodiment, it is also preferable that one or more $R_{161}$ to $R_{168}$ and $R_{171}$ to $R_{200}$ in the group $D_2$ are each a hydrogen atom and all of the hydrogen atom(s) are deuterium atoms.

In the compound of the sixth exemplary embodiment, it is also preferable that one or more $R_{161}$ to $R_{168}$ and $R_{171}$ to $R_{200}$ in the group $D_2$ are each a hydrogen atom and all of the hydrogen atom(s) are protium atoms.

In the compound of the sixth exemplary embodiment, it is also preferable that $R_{161}$ to $R_{168}$ and $R_{171}$ to $R_{200}$ in the group $D_2$ are hydrogen atoms and the hydrogen atoms are deuterium atoms.

In the compound of the sixth exemplary embodiment, it is preferable that, when at least one of $R_{161}$ to $R_{168}$ and $R_{171}$ to $R_{200}$ in the group $D_2$ is a substituent and the substituent has at least one hydrogen atom, all of the hydrogen atom(s) are protium atoms, at least one of the hydrogen atom(s) is a deuterium atom, or all of the hydrogen atom(s) are deuterium atoms.

In the compound of the sixth exemplary embodiment, it is preferable that $R_{101}$ to $R_{160}$ except for a group represented by the formula (120C) are hydrogen atom(s) and $R_{161}$ to $R_{168}$ and $R_{171}$ to $R_{200}$ are hydrogen atoms.

In the compound of the sixth exemplary embodiment, it is preferable that $R_{101}$ to $R_{160}$ except for a group represented by the formula (120C) are hydrogen atom(s), the hydrogen atom(s) are each a deuterium atom, $R_{161}$ to $R_{168}$ and $R_{171}$ to $R_{200}$ are hydrogen atoms, and the hydrogen atoms are deuterium atoms.

In the compound of the six exemplary embodiment, a substituent for a substituted or unsubstituted group each independently represents the same as a substituent for a substituted or unsubstituted group in the compound of the first exemplary embodiment.

Manufacturing Method of Compound of Sixth Exemplary Embodiment

The compound of the sixth exemplary embodiment can be manufactured according to known methods.

Specific Examples of Compound of Sixth Exemplary Embodiment

Specific examples of the compound of the sixth exemplary embodiment include compounds shown below. It should however be noted that the invention is not limited to the specific examples of the compound.

[Formula 119]

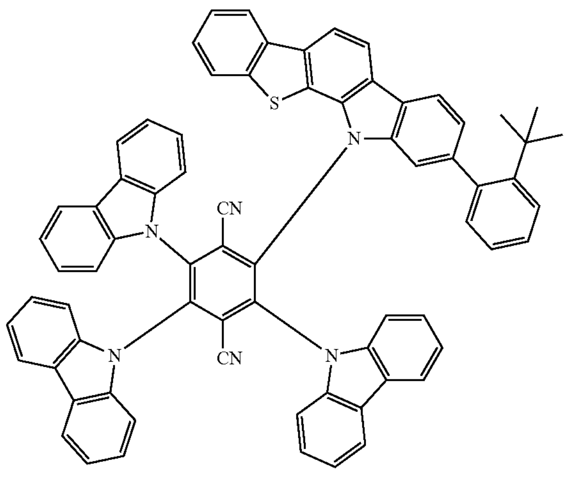

-continued
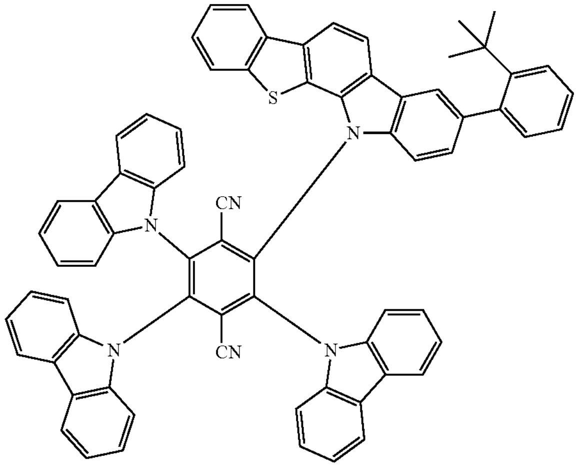
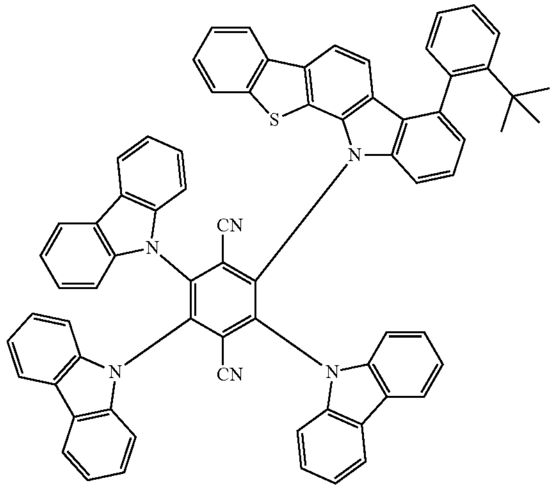
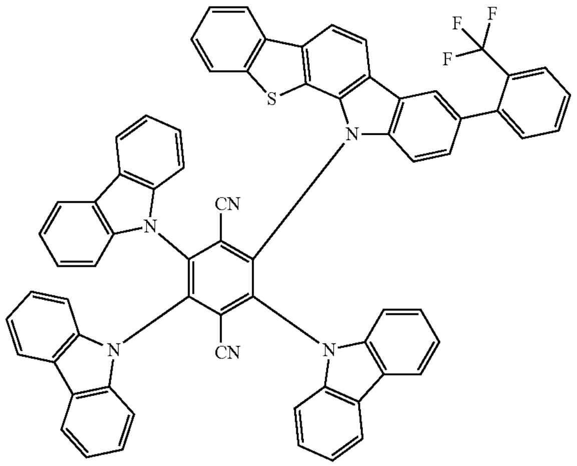
-continued
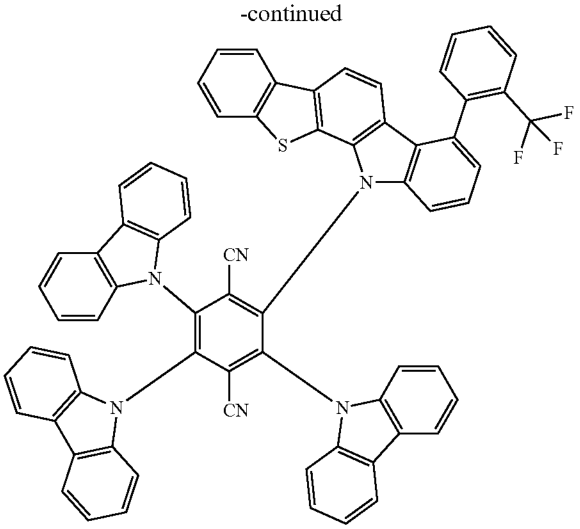
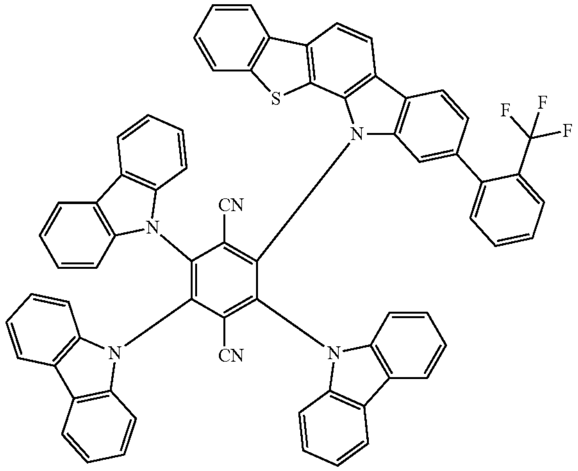
[Formula 120]
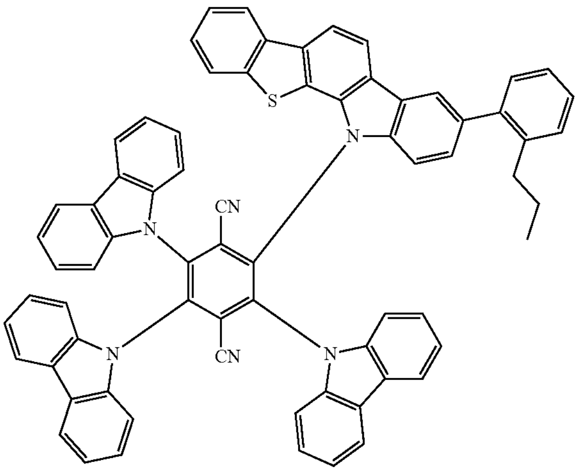

-continued
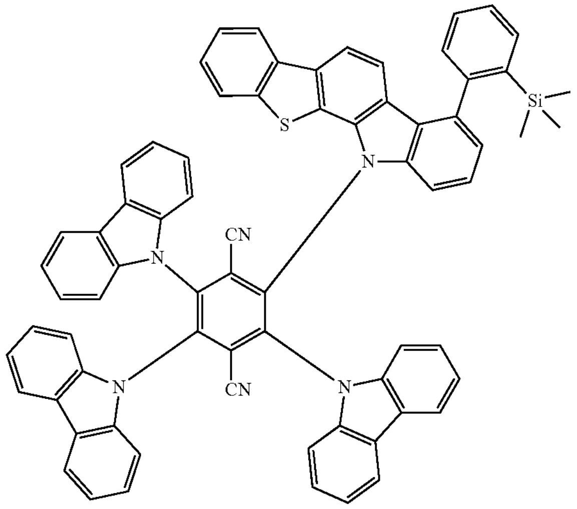
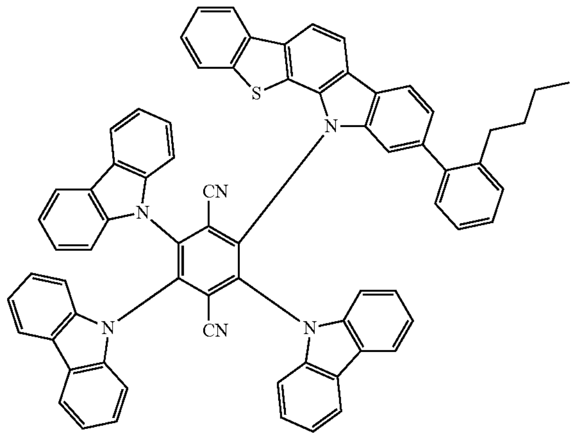
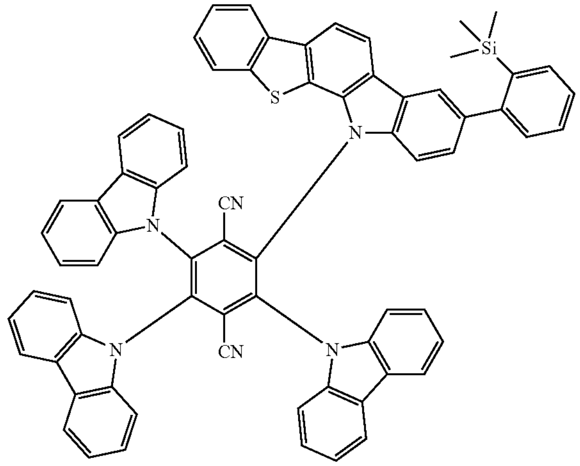
-continued
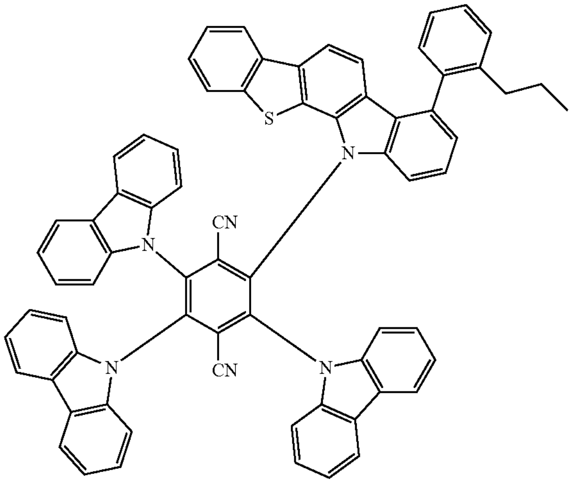
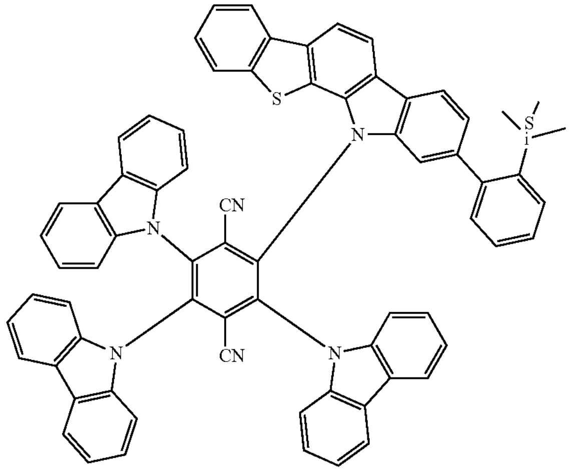
[Formula 121]
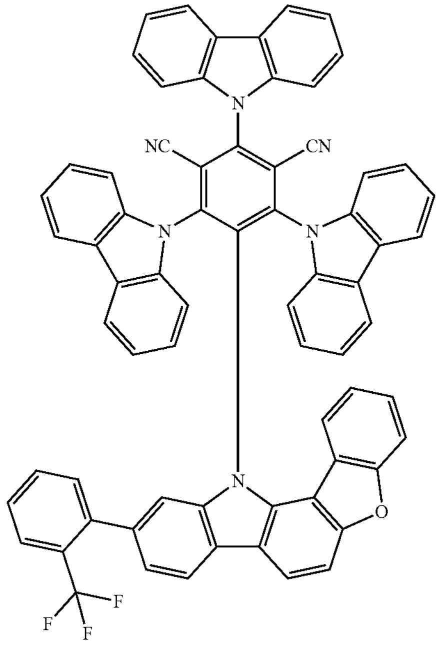

-continued
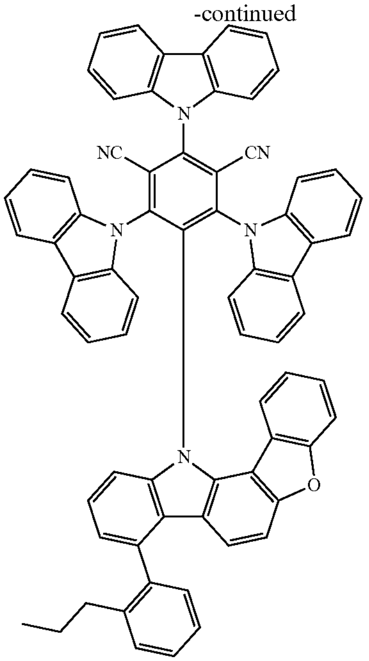
-continued
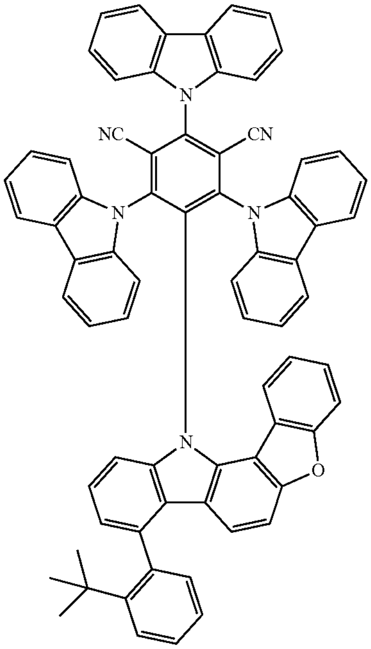
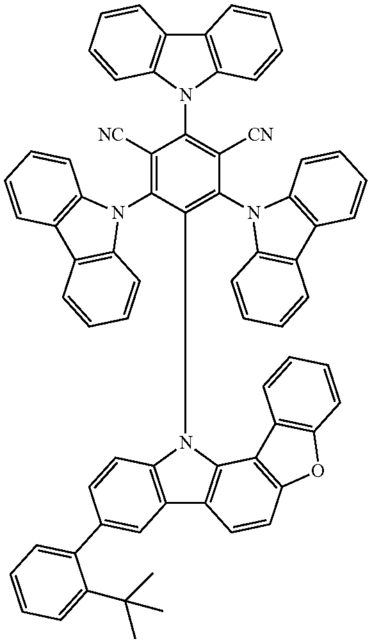
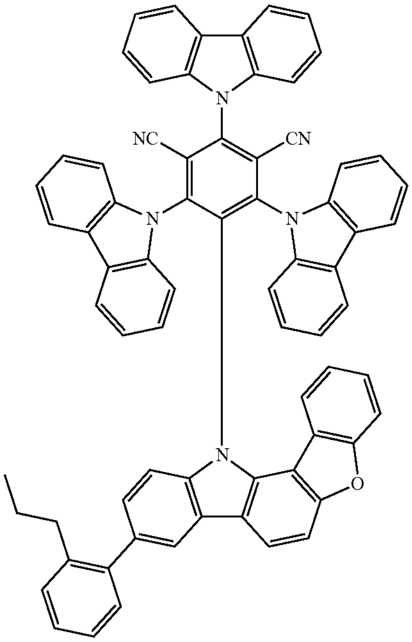

-continued
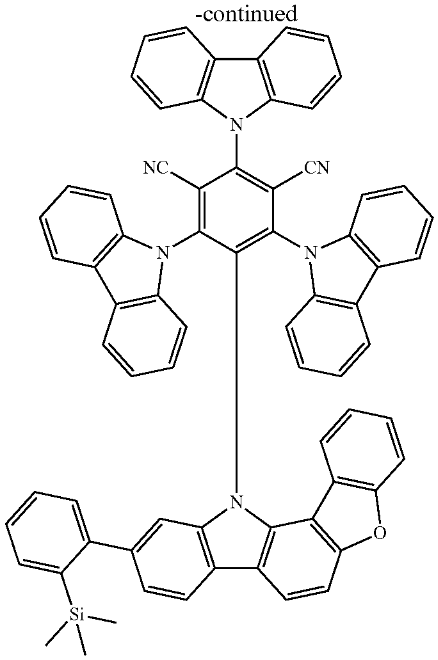
-continued
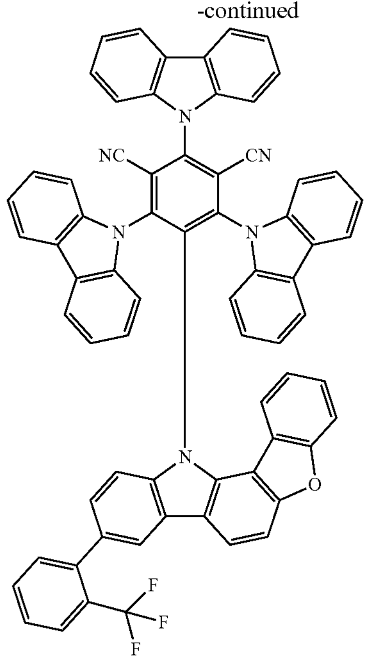
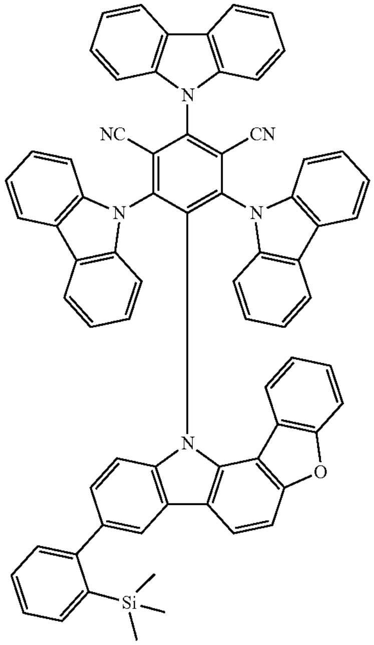
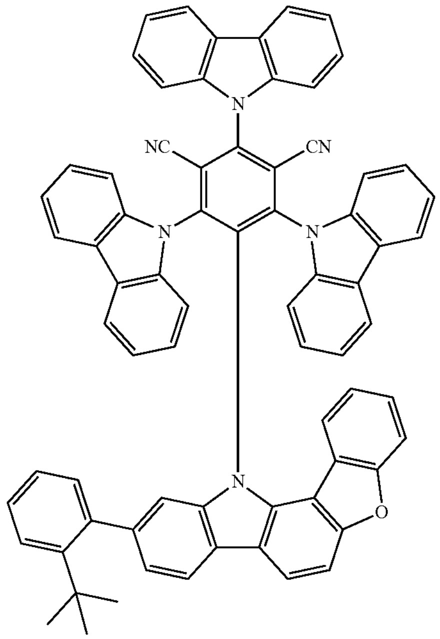

-continued

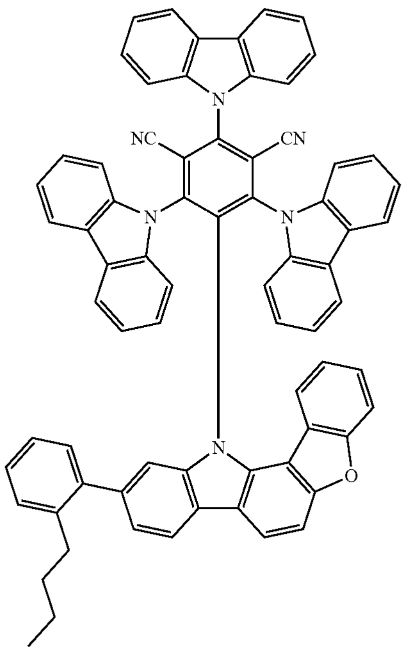

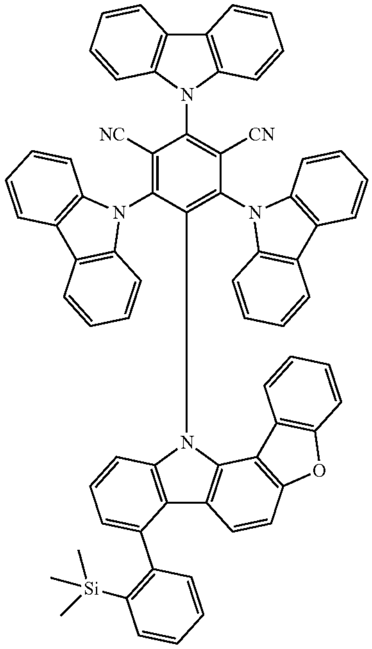

-continued

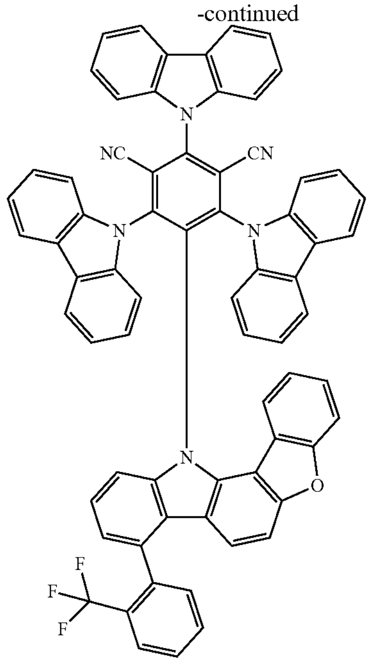

Seventh Exemplary Embodiment

Organic EL Device

An organic EL device according to an aspect of a seventh exemplary embodiment includes an anode, a cathode, and a first organic layer provided between the anode and the cathode, the first organic layer containing a first compound C, and the first compound C is the compound of the sixth exemplary embodiment.

In the organic EL device according to the above aspect of the seventh exemplary embodiment, the first compound in any one of the third exemplary embodiment, the fourth exemplary embodiment, and the fifth exemplary embodiment is replaced with the first compound C (the compound of the sixth exemplary embodiment). In other words, the organic EL device of the seventh exemplary embodiment is different from any of the organic electroluminescence devices of the third exemplary embodiment, the fourth exemplary embodiment, and the fifth exemplary embodiment.

Preferable Forms of Organic EL Device of Seventh Exemplary Embodiment

Preferable forms of the organic EL device of the seventh exemplary embodiment are the same as the preferable forms of the organic EL devices of the third exemplary embodiment, the fourth exemplary embodiment, and the fifth exemplary embodiment. Examples of the preferable forms are as follows.

The first organic layer of the organic EL device of the seventh exemplary embodiment is preferably the emitting layer.

In the organic EL device of the seventh exemplary embodiment, it is preferable that the first organic layer contains the first compound C (the compound of the sixth exemplary embodiment) and further a second compound, which is a fluorescent compound.

In the organic EL device of the seventh exemplary embodiment, a singlet energy $S_1$(Mat1') of the first compound C and a singlet energy $S_1$(Mat2) of the second compound preferably satisfy a relationship of a numerical formula (Numerical Formula 1') below.

$$S_1(\text{Mat1'})>S_1(\text{Mat2}) \quad \text{(Numerical Formula 1')}$$

In the organic EL device of the seventh exemplary embodiment, it is preferable that the first organic layer contains the first compound C (the compound of the sixth exemplary embodiment), the second compound, and further a third compound, and a singlet energy $S_1$(Mat1') of the first compound C and a singlet energy $S_1$(Mat3) of the third compound satisfy a relationship of a numerical formula (Numerical Formula 2') below.

$$S_1(\text{Mat3})>S_1(\text{Mat1'}) \quad \text{(Numerical Formula 2')}$$

In the organic EL device of the seventh exemplary embodiment, it is preferable that the first organic layer contains the first compound C (the compound of the sixth exemplary embodiment), the second compound, the third compound, and further a fourth compound, and a singlet energy $S_1$(Mat1') of the first compound C and a singlet energy $S_1$(Mat4) of the fourth compound satisfy a relationship of a numerical formula (Numerical Formula 3') below.

$$S_1(\text{Mat4})>S_1(\text{Mat1'}) \quad \text{(Numerical Formula 3')}$$

The first organic layer of the organic EL device of the seventh exemplary embodiment preferably does not contain metal complex.

It is preferable that the organic EL device of the seventh exemplary embodiment contains the first compound C (the compound of the sixth exemplary embodiment), the second compound, and a third compound, and the first compound C is a delayed fluorescent compound.

It should be noted that specific examples of the second, third and fourth compounds in the seventh exemplary embodiment are shown in the specific examples of the second, third and fourth compounds described in the third exemplary embodiment.

Eighth Exemplary Embodiment

Electronic Device

An electronic device according to the present exemplary embodiment is installed with any one of the organic EL devices according to the above exemplary embodiments. Examples of the electronic device include a display device and a light-emitting device. Examples of the display device include a display component (e.g., an organic EL panel module), TV, mobile phone, tablet and personal computer. Examples of the light-emitting unit include an illuminator and a vehicle light.

Modification of Embodiment(s)

The scope of the invention is not limited by the above-described exemplary embodiments but includes any modification and improvement as long as such modification and improvement are compatible with the invention.

For instance, the emitting layer is not limited to a single layer, but may be provided by laminating a plurality of emitting layers. When the organic EL device has a plurality of emitting layers, it is only required that at least one of the emitting layers satisfies the conditions described in the above exemplary embodiments. For instance, in some embodiments, the rest of the emitting layers is a fluorescent emitting layer or a phosphorescent emitting layer with use of emission caused by electron transfer from the triplet excited state directly to the ground state.

When the organic EL device includes a plurality of emitting layers, these emitting layers may be mutually adjacently provided, or may form a so-called tandem organic EL device, in which a plurality of emitting units are layered via an intermediate layer.

For instance, a blocking layer may be provided adjacent to at least one of a side of the emitting layer close to the anode or a side of the emitting layer close to the cathode. The blocking layer is preferably provided in contact with the emitting layer to block holes, electrons, excitons or combinations thereof.

For instance, when the blocking layer is provided in contact with the side of the emitting layer close to the cathode, the blocking layer permits transport of electrons and blocks holes from reaching a layer provided closer to the cathode (e.g., the electron transporting layer) beyond the blocking layer. When the organic EL device includes the electron transporting layer, the blocking layer is preferably disposed between the emitting layer and the electron transporting layer.

When the blocking layer is provided in contact with the side of the emitting layer close to the anode, the blocking layer permits transport of holes and blocks electrons from reaching a layer provided closer to the anode (e.g., the hole transporting layer) beyond the blocking layer. When the organic EL device includes the hole transporting layer, the blocking layer is preferably disposed between the emitting layer and the hole transporting layer.

Alternatively, the blocking layer may be provided adjacent to the emitting layer so that the excitation energy does not leak out from the emitting layer toward neighboring layer(s). The blocking layer blocks excitons generated in the emitting layer from being transferred to a layer(s) (e.g., the electron transporting layer and the hole transporting layer) closer to the electrode(s) beyond the blocking layer.

The emitting layer is preferably bonded with the blocking layer.

Specific structure, shape and the like of the components in the invention may be designed in any manner as long as an object of the invention can be achieved.

Herein, numerical ranges represented by "x to y" represents a range whose lower limit is the value (x) recited before "to" and whose upper limit is the value (y) recited after "to."

Herein, the phrase "Rx and Ry are mutually bonded to form a ring" means, for instance, that Rx and Ry include a carbon atom, a nitrogen atom, an oxygen atom, a sulfur atom or a silicon atom, the atom(s) contained in Rx (a carbon atom, a nitrogen atom, an oxygen atom, a sulfur atom or a silicon atom) and the atom(s) contained in Ry (a carbon atom, a nitrogen atom, an oxygen atom, a sulfur atom or a silicon atom) are bonded via a single bond(s), a double bond(s), a triple bond, and/or a divalent linking group(s) to form a ring having 5 or more ring atoms (specifically, a heterocycle or an aromatic hydrocarbon ring). x represents a number, a character or a combination of a number and a character. y represents a number, a character or a combination of a number and a character.

The divalent linking group is not limited. Examples of the divalent linking group include —O—, —CO—, $—CO_2—$, —S—, —SO—, $—SO_2—$, —NH—, —NRa—, and a group provided by a combination of two or more of these linking group.

Specific examples of the heterocyclic ring include a cyclic structure (heterocyclic ring) obtained by removing a bond from a "heteroaryl group $Sub_2$" exemplarily shown in the later-described "Description of Each Substituent in Formula." The heterocyclic ring may have a substituent.

Specific examples of the heterocyclic ring include cyclic structures (heterocyclic rings) obtained by removing a bond from an "aryl group $Sub_1$" exemplarily shown in the later-described "Description of Each Substituent in Formula." The aromatic hydrocarbon ring may have a substituent.

Examples of Ra include a substituted or unsubstituted alkyl group $Sub_3$ having 1 to 30 carbon atoms, a substituted or unsubstituted aryl group $Sub_1$ having 6 to 30 ring carbon atoms, and a substituted or unsubstituted heteroaryl group $Sub_2$ having 5 to 30 ring atoms, which are exemplarily shown in the later-described "Description of Each Substituent in Formula."

Rx and Ry are mutually bonded to form a ring, which means, for instance, that: an atom contained in $Rx_1$ and an atom contained in $Ry_1$ in a molecular structure represented by a formula (E1) below form a ring (cyclic structure) E represented by a formula (E2); an atom contained in $Rx_1$ and an atom contained in $Ry_1$ in a molecular structure represented by a formula (F1) below form a ring (cyclic structure) F represented by a formula (F2); an atom contained in $Rx_1$ and an atom contained in $Ry_1$ in a molecular structure represented by a formula (G1) below form a ring (cyclic structure) G represented by a formula (G2); an atom contained in $Rx_1$ and an atom contained in $Ry_1$ in a molecular structure represented by a formula (H1) below form a ring (cyclic structure) H represented by a formula (H2); and an atom contained in $Rx_1$ and an atom contained in $Ry_1$ in a molecular structure represented by a formula (I1) below form a ring (cyclic structure) I represented by a formula (I2).

In the formulae (E1) to (I1), * each independently represent a bonding position to another atom in a molecule. The two marks * in the formulae (E1), (F1), (G1), (H1) and (I1) correspond to two marks * in the formulae (E2), (F2), (G2), (H2) and (I2), respectively.

[Formula 122]

(E1)

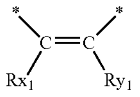

(F1)

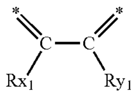

(G1)

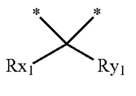

(H1)

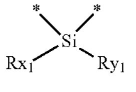

(I1)

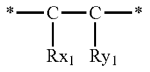

[Formula 123]

(E2)

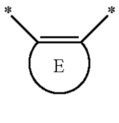

-continued (F2)

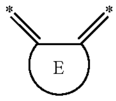

(G2)

(H2)

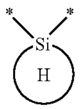

(I2)

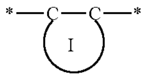

In the molecular structures represented by the formulae (E2) to (I2), E to I each represent a cyclic structure (the ring having 5 or more ring atoms). In the formulae (E2) to (I2), * each independently represent a bonding position to another atom in a molecule. The two marks * in the formula (E2) correspond to two marks * in the formula (E1). Similarly, two marks * in each of the formulae (F2) to (I2) correspond one-to-one to two marks * in in each of the formulae (F1) to (I1).

For instance, in the formula (E1), when $Rx_1$ and $Ry_1$ are mutually bonded to form the ring E in the formula (E2) and the ring E is an unsubstituted benzene ring, the molecular structure represented by the formula (E1) is a molecular structure represented by a formula (E3) below. Herein, two marks * in the formula (E3) each independently correspond to two marks * in the formula (E2) and the formula (E1).

For instance, in the formula (E1), when $Rx_1$ and $Ry_1$ are mutually bonded to form the ring E in the formula (E2) and the ring E is an unsubstituted pyrrole ring, the molecular structure represented by the formula (E1) is a molecular structure represented by a formula (E4) below. Herein, two marks * in the formula (E4) each independently correspond to two marks * in the formula (E2) and the formula (E1). In the formulae (E3) and (E4), * each independently represent a bonding position to another atom in a molecule.

[Formula 124]

(E3)

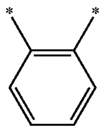

(E4)

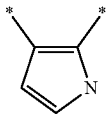

Herein, the ring carbon atoms refer to the number of carbon atoms among atoms forming a ring of a compound (e.g., a monocyclic compound, fused-ring compound, cross-linking compound, carbon ring compound, and heterocyclic compound) in which the atoms are bonded to each other to form the ring. When the ring is substituted by a substituent (s), carbon atom(s) contained in the substituent(s) is not counted in the ring carbon atoms. Unless specifically described, the same applies to the "ring carbon atoms" described later. For instance, a benzene ring has 6 ring carbon atoms, a naphthalene ring has 10 ring carbon atoms, a pyridinyl group has 5 ring carbon atoms, and a furanyl group has 4 ring carbon atoms. When a benzene ring and/or a naphthalene ring is substituted by a substituent (e.g., an alkyl group), the number of carbon atoms of the alkyl group is not counted in the number of the ring carbon atoms. When a fluorene ring is substituted by a substituent (e.g., a fluorene ring) (i.e., a spirofluorene ring is included), the number of carbon atoms of the fluorene ring as the substituent is not counted in the number of the ring carbon atoms of the fluorene ring.

Herein, the ring atoms refer to the number of atoms forming a ring of a compound (e.g., a monocyclic compound, fused-ring compound, crosslinking compound, carbon ring compound, and heterocyclic compound) in which the atoms are bonded to each other to form the ring (e.g., monocyclic ring, fused ring, ring assembly). Atom(s) not forming a ring and atom(s) included in a substituent when the ring is substituted by the substituent are not counted in the number of the ring atoms. Unless specifically described, the same applies to the "ring atoms" described later. For instance, a pyridine ring has six ring atoms, a quinazoline ring has ten ring atoms, and a furan ring has five ring atoms. A hydrogen atom(s) and/or an atom(s) of a substituent which are bonded to carbon atoms of a pyridine ring and/or quinazoline ring are not counted in the ring atoms. When a fluorene ring is substituted by a substituent (e.g., a fluorene ring) (i.e., a spirofluorene ring is included), the number of atoms of the fluorene ring as the substituent is not counted in the number of the ring atoms of the fluorene ring.

Description of Each Substituent in Formulae Herein

The aryl group (occasionally referred to as an aromatic hydrocarbon group) herein is exemplified by an aryl group $Sub_1$. The aryl group $Sub_1$ preferably has 6 to 30 ring carbon atoms, more preferably 6 to 20 ring carbon atoms, further preferably 6 to 14 ring carbon atoms, still further preferably 6 to 12 ring carbon atoms.

The aryl group $Sub_1$ herein is at least one group selected from the group consisting of a phenyl group, biphenyl group, terphenyl group, naphthyl group, anthryl group, phenanthryl group, fluorenyl group, pyrenyl group, chrysenyl group, fluoranthenyl group, benz[a]anthryl group, benzo[c]phenanthryl group, triphenylenyl group, benzo[k]fluoranthenyl group, benzo[g]chrysenyl group, benzo[b]triphenylenyl group, picenyl group, and perylenyl group.

Among the aryl group $Sub_1$, a phenyl group, biphenyl group, naphthyl group, phenanthryl group, terphenyl group and fluorenyl group are preferable. A carbon atom in a position 9 of each of 1-fluorenyl group, 2-fluorenyl group, 3-fluorenyl group and 4-fluorenyl group is preferably substituted by a substituted or unsubstituted alkyl group $Sub_3$ or a substituted or unsubstituted aryl group $Sub_1$ described later herein.

The heteroaryl group (occasionally referred to as a heterocyclic group, heteroaromatic cyclic group or aromatic heterocyclic group) herein is exemplified by a heterocyclic group $Sub_2$. The heterocyclic group $Sub_2$ is a group containing, as a hetero atom(s), at least one atom selected from the group consisting of nitrogen, sulfur, oxygen, silicon, selenium atom and germanium atom. The heterocyclic group $Sub_2$ preferably contains, as a hetero atom(s), at least one atom selected from the group consisting of nitrogen, sulfur and oxygen. The heterocyclic group $Sub_2$ preferably has 5 to 30 ring atoms, more preferably 5 to 20 ring atoms, further preferably 5 to 14 ring atoms.

The heterocyclic group $Sub_2$ herein are, for instance, at least one group selected from the group consisting of a pyridyl group, pyrimidinyl group, pyrazinyl group, pyridazinyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothienyl group, benzoxazolyl group, benzothiazolyl group, benzisoxazolyl group, benzisothiazolyl group, benzoxadiazolyl group, benzothiadiazolyl group, dibenzofuranyl group, dibenzothienyl group, piperidinyl group, pyrrolidinyl group, piperazinyl group, morpholyl group, phenazinyl group, phenothiazinyl group, and phenoxazinyl group.

Among the above heterocyclic group $Sub_2$, a 1-dibenzofuranyl group, 2-dibenzofuranyl group, 3-dibenzofuranyl group, 4-dibenzofuranyl group, 1-dibenzothienyl group, 2-dibenzothienyl group, 3-dibenzothienyl group, 4-dibenzothienyl group, 1-carbazolyl group, 2-carbazolyl group, 3-carbazolyl group, 4-carbazolyl group, and 9-carbazolyl group are further more preferable. A nitrogen atom in position 9 of 1-carbazolyl group, 2-carbazolyl group, 3-carbazolyl group and 4-carbazolyl group is preferably substituted by the substituted or unsubstituted aryl group $Sub_1$ or the substituted or unsubstituted heterocyclic group $Sub_2$ described herein.

Herein, the heterocyclic group $Sub_2$ may be a group derived from any one of moieties represented by formulae (XY-1) to (XY-18) below.

[Formula 125]

(XY-1)

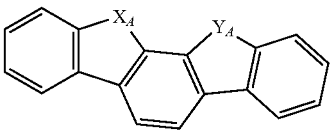

(XY-2)

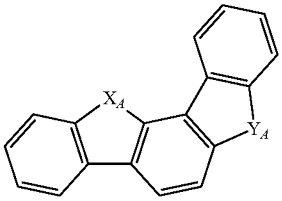

(XY-3)

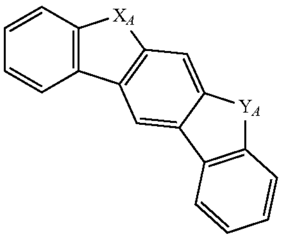

-continued (XY-4)

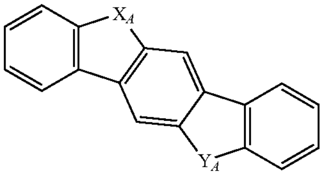

(XY-5)

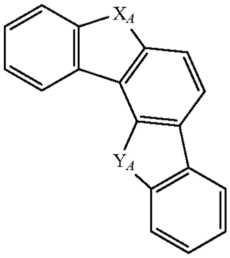

(XY-6)

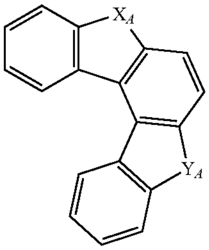

[Formula 126]

(XY-7)

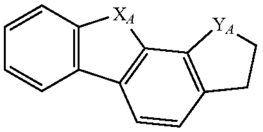

(XY-8)

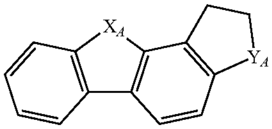

(XY-9)

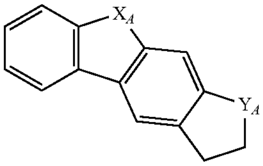

(XY-10)

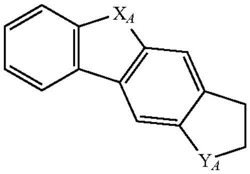

(XY-11)

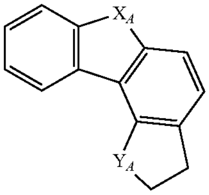

-continued (XY-12)

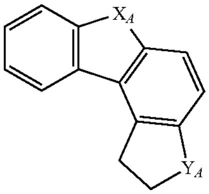

[Formula 127]

(XY-13)

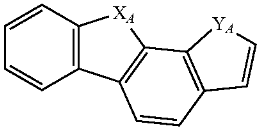

(XY-14)

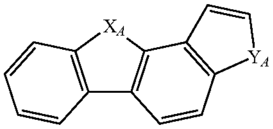

(XY-15)

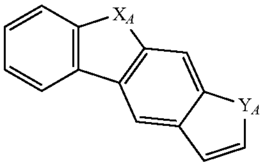

(XY-16)

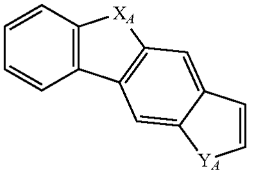

(XY-17)

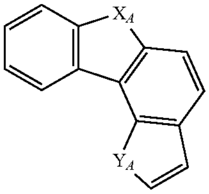

(XY-18)

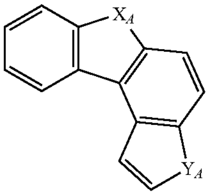

In the formulae (XY-1) to (XY-18), XA and YA each independently represent a hetero atom, and preferably represent an oxygen atom, sulfur atom, selenium atom, silicon atom or germanium atom. Each of the moieties represented by the respective formulae (XY-1) to (XY-18) has a bond at any position to provide a heterocyclic group. The heterocyclic group may be substituted.

Herein, the heterocyclic group $Sub_2$ may be a group represented by one of formulae (XY-19) to (XY-22) below. Moreover, the position of the bond may be changed as needed.

[Formula 128]

(XY-19)

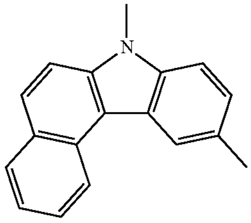

(XY-20)

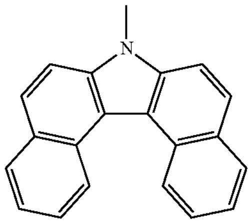

(XY-21)

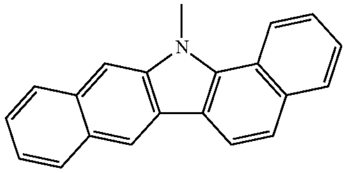

(XY-22)

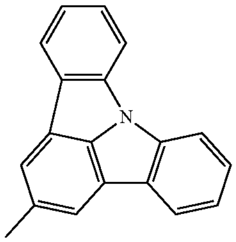

The alkyl group herein may be any one of a linear alkyl group, branched alkyl group and cyclic alkyl group.

The alkyl group herein is exemplified by an alkyl group $Sub_3$.

The linear alkyl group herein is exemplified by a linear alkyl group $Sub_{31}$.

The branched alkyl group herein is exemplified by a branched alkyl group $Sub_{32}$.

The cyclic alkyl group herein is exemplified by a cyclic alkyl group $Sub_{33}$ (also referred to as a cycloalkyl group $Sub_{33}$).

For instance, the alkyl group $Sub_3$ is at least one group selected from the group consisting of the linear alkyl group $Sub_{31}$, branched alkyl group $Sub_{32}$, and cyclic alkyl group $Sub_{33}$.

Herein, the linear alkyl group $Sub_{31}$ or branched alkyl group $Sub_{32}$ preferably has 1 to 30 carbon atoms, more preferably 1 to 20 carbon atoms, further preferably 1 to 10 carbon atoms, further more preferably 1 to 6 carbon atoms.

The cycloalkyl group $Sub_{33}$ preferably has 3 to 30 ring carbon atoms, more preferably 3 to 20 ring carbon atoms, further preferably 3 to 10 ring carbon atoms, still further preferably 5 to 8 ring carbon atoms.

The linear alkyl group $Sub_{31}$ or branched alkyl group $Sub_{32}$ is exemplified by at least one group selected from the group consisting of a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

The linear alkyl group $Sub_{31}$ or branched alkyl group $Sub_{32}$ is further more preferably a methyl group, ethyl group, propyl group, isopropyl group, n-butyl group, s-butyl group, isobutyl group, t-butyl group, n-pentyl group, n-hexyl group, amyl group, isoamyl group and neopentyl group.

The cycloalkyl group $Sub_{33}$ herein is exemplified by at least one group selected from the group consisting of a cyclopropyl group, cyclobutyl group, cyclopentyl group, cyclohexyl group, 4-methylcyclohexyl group, adamantyl group and norbornyl group. Among the cycloalkyl group $Sub_{33}$, a cyclopentyl group and a cyclohexyl group are still further preferable.

Herein, an alkyl halide group is exemplified by an alkyl halide group $Sub_4$. The alkyl halide group $Sub_4$ is provided by substituting the alkyl group $Sub_3$ with at least one halogen atom, preferably at least one fluorine atom.

Herein, the alkyl halide group $Sub_4$ is exemplified by at least one group selected from the group consisting of a fluoromethyl group, difluoromethyl group, trifluoromethyl group, fluoroethyl group, trifluoromethylethyl group, trifluoroethyl group, and pentafluoroethyl group.

Herein, a substituted silyl group is exemplified by a substituted silyl group $Sub_5$. The substituted silyl group $Sub_5$ is exemplified by at least one group selected from the group consisting of an alkylsilyl group $Sub_{51}$ and an arylsilyl group $Sub_{52}$.

Herein, the alkylsilyl group $Sub_{51}$ is exemplified by a trialkylsilyl group $Sub_{511}$ having the above-described alkyl group $Sub_3$.

The trialkylsilyl group $Sub_{511}$ is exemplified by at least one group selected from the group consisting of a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups $Sub_3$ in the trialkylsilyl group $Sub_{511}$ may be mutually the same or different.

Herein, the arylsilyl group $Sub_{52}$ is exemplified by at least one group selected from the group consisting of a dialkylarylsilyl group $Sub_{521}$, alkyldiarylsilyl group $Sub_{522}$ and triarylsilyl group $Sub_{523}$.

The dialkylarylsilyl group $Sub_{521}$ is exemplified by a dialkylarylsilyl group including two alkyl groups $Sub_3$ and one aryl group $Sub_1$. The dialkylarylsilyl group $Sub_{521}$ preferably has 8 to 30 carbon atoms.

The alkyldiarylsilyl group $Sub_{522}$ is exemplified by an alkyldiarylsilyl group including one alkyl group $Sub_3$ and two aryl groups $Sub_1$. The alkyldiarylsilyl group $Sub_{522}$ preferably has 13 to 30 carbon atoms.

The triarylsilyl group $Sub_{523}$ is exemplified by a triarylsilyl group including three aryl groups $Sub_1$. The triarylsilyl group $Sub_{523}$ preferably has 18 to 30 carbon atoms.

Herein, a substituted or unsubstituted alkyl sulfonyl group is exemplified by an alkyl sulfonyl group $Sub_6$. The alkyl sulfonyl group $Sub_6$ is represented by $-SO_2R_w$. $R_w$ in $-SO_2R_w$ represents a substituted or unsubstituted alkyl group $Sub_3$ described above.

Herein, an aralkyl group (occasionally referred to as an arylalkyl group) is exemplified by an aralkyl group $Sub_7$. An aryl group in the aralkyl group $Sub_7$ includes, for instance, at least one of the above-described aryl group $Sub_1$ or the above-described heteroaryl group $Sub_2$.

The aralkyl group $Sub_7$ herein is preferably a group having the aryl group $Sub_1$ and is represented by $-Z_3-Z_4$. $Z_3$ is exemplified by an alkylene group corresponding to the above alkyl group $Sub_3$. $Z_4$ is exemplified by the above aryl group $Sub_1$. In this aralkyl group $Sub_7$, an aryl moiety has 6 to 30 carbon atoms (preferably 6 to 20 carbon atoms, more preferably 6 to 12 carbon atoms) and an alkyl moiety has 1 to 30 carbon atoms (preferably 1 to 20 carbon atoms, more preferably 1 to 10 carbon atoms, further preferably 1 to 6 carbon atoms). The aralkyl group $Sub_7$ is exemplified by at least one group selected from the group consisting of a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, p-naphthylmethyl group, 1-β-naphthylethyl group, 2-β-naphthylethyl group, 1-β-naphthylisopropyl group, and 2-β-naphthylisopropyl group.

The alkoxy group herein is exemplified by an alkoxy group $Sub_8$. The alkoxy group $Sub_8$ is represented by $-OZ_1$. $Z_1$ is exemplified by the above alkyl group $Sub_3$. The alkoxy group $Sub_8$ preferably has 1 to 30 carbon atoms, more preferably 1 to 20 carbon atoms. The alkoxy group $Sub_8$ is exemplified by at least one group selected from the group consisting of a methoxy group, ethoxy group, propoxy group, butoxy group, pentyloxy group and hexyloxy group.

Herein, an alkoxy halide group is exemplified by an alkoxy halide group $Sub_9$. The alkoxy halide group $Sub_9$ is provided by substituting the alkoxy group $Sub_8$ with at least one halogen atom, preferably at least one fluorine atom.

Herein, an aryloxy group (occasionally referred to as an arylalkoxy group) is exemplified by an arylalkoxy group $Sub_{10}$. An aryl group in the arylalkoxy group $Sub_{10}$ includes at least one of the aryl group $Sub_1$ or the heteroaryl group $Sub_2$.

The arylalkoxy group $Sub_{10}$ herein is represented by $-OZ_2$. $Z_2$ is exemplified by the aryl group $Sub_1$ or the heteroaryl group $Sub_2$. The arylalkoxy group $Sub_{10}$ preferably has 6 to 30 ring carbon atoms, more preferably 6 to 20 ring carbon atoms. The arylalkoxy group $Sub_{10}$ is exemplified by a phenoxy group.

Herein, a substituted amino group is exemplified by a substituted amino group $Sub_{11}$. The substituted amino group $Sub_{11}$ is exemplified by at least one group selected from the group consisting of an arylamino group $Sub_{111}$ and an alkylamino group $Sub_{112}$.

The arylamino group $Sub_{111}$ is represented by $-NHR_{V1}$ or $-N(R_{V1})_2$. $R_{V1}$ is exemplified by the aryl group $Sub_1$. Two $R_{V1}$ in $-N(R_{V1})_2$ are mutually the same or different.

The alkylamino group $Sub_{112}$ is represented by $-NHR_{V2}$ or $-N(R_{V2})_2$. $R_{V2}$ is exemplified by the alkyl group $Sub_3$. Two $R_{V2}$ in $-N(R_{V2})_2$ are mutually the same or different.

Herein, the alkenyl group is exemplified by an alkenyl group $Sub_{12}$. The alkenyl group $Sub_{12}$, which is linear or branched, is exemplified by at least one group selected from the group consisting of a vinyl group, propenyl group, butenyl group, oleyl group, eicosapentaenyl group, docosahexaenyl group, styryl group, 2,2-diphenylvinyl group, 1,2,2-triphenylvinyl group, and 2-phenyl-2-propenyl group.

The alkynyl group herein is exemplified by an alkynyl group $Sub_{13}$. The alkynyl group $Sub_{13}$ may be linear or branched and is at least one group selected from the group consisting of an ethynyl group, a propynyl group and a 2-phenylethynyl group.

The alkylthio group herein is exemplified by an alkylthio group $Sub_{14}$.

The alkylthio group $Sub_{14}$ is represented by $-SR_{V3}$. $R_{V3}$ is exemplified by the alkyl group $Sub_3$. The alkylthio group $Sub_{14}$ preferably has 1 to 30 carbon atoms, more preferably 1 to 20 carbon atoms.

The arylthio group herein is exemplified by an arylthio group $Sub_{15}$.

The arylthio group $Sub_{15}$ is represented by $-SR_{V4}$. $R_{V4}$ is exemplified by the aryl group $Sub_1$. The arylthio group $Sub_{15}$ preferably has 6 to 30 ring carbon atoms, more preferably 6 to 20 ring carbon atoms.

Herein, examples of the halogen atom include a fluorine atom, a chlorine atom, a bromine atom and an iodine atom, among which a fluorine atom is preferable.

A substituted phosphino group herein is exemplified by a substituted phosphino group $Sub_{16}$. The substituted phosphino group $Sub_{16}$ is exemplified by a phenyl phosphanyl group.

An arylcarbonyl group herein is exemplified by an arylcarbonyl group $Sub_{17}$. The arylcarbonyl group $Sub_{17}$ is represented by $-COY'$. Y' is exemplified by the aryl group $Sub_1$. Herein, the arylcarbonyl group $Sub_{17}$ is exemplified by at least one group selected from the group consisting of a phenyl carbonyl group, diphenyl carbonyl group, naphthyl carbonyl group, and triphenyl carbonyl group.

An acyl group herein is exemplified by an acyl group $Sub_{13}$. The acyl group $Sub_{13}$ is represented by $-COR'$. R' is exemplified by the alkyl group $Sub_3$. The acyl group $Sub_{13}$ herein is exemplified by at least one group selected from the group consisting of an acetyl group and a propionyl group.

A substituted phosphoryl group herein is exemplified by a substituted phosphoryl group $Sub_{19}$. The substituted phosphoryl group $Sub_{19}$ is represented by a formula (P) below.

[Formula 129]

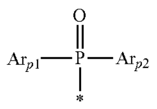

(P)

In the formula (P), $Ar_{P1}$ and $Ar_{P2}$ are any one substituent selected from the group consisting of the above alkyl group $Sub_3$ and the above aryl group $Sub_1$.

An ester group herein is exemplified by an ester group $Sub_{20}$. The ester group $Sub_{20}$ is exemplified by at least one group selected from the group consisting of an alkyl ester group and an aryl ester group.

An alkyl ester group herein is exemplified by an alkyl ester group $Sub_{201}$. The alkyl ester group $Sub_{201}$ is represented by $-C(=O)OR^E$. $R^E$ is exemplified by a substituted or unsubstituted alkyl group $Sub_3$ described above.

An aryl ester group herein is exemplified by an aryl ester group $Sub_{202}$. The aryl ester group $Sub_{202}$ is represented by $-C(=O)OR^{Ar}$. $R^{Ar}$ is exemplified by a substituted or unsubstituted aryl group $Sub_1$ described above.

A siloxanyl group herein is exemplified by a siloxanyl group $Sub_{21}$. The siloxanyl group $Sub_{21}$ is a silicon compound group through an ether bond. The siloxanyl group $Sub_{21}$ is exemplified by a trimethylsiloxanyl group.

A carbamoyl group herein is represented by —$CONH_2$.

A substituted carbamoyl group herein is exemplified by a carbamoyl group $Sub_{22}$. The carbamoyl group $Sub_{22}$ is represented by —CONH—$Ar^C$ or —CONH—$R^C$. $Ar^C$ is exemplified by at least one group selected from the group consisting of the above-described aryl group $Sub_1$ (preferably 6 to 10 ring carbon atoms) and the above-described heteroaryl group $Sub_2$ (preferably 5 to 14 ring atoms). $Ar^C$ may be a group formed by bonding the aryl group $Sub_1$ and the heteroaryl group $Sub_2$.

$R^C$ is exemplified by a substituted or unsubstituted alkyl group $Sub_3$ described above (preferably having 1 to 6 carbon atoms).

Herein, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a ring including a saturated ring, unsaturated ring, or aromatic ring.

Herein, a hydrogen atom includes isotope having different numbers of neutrons, specifically, protium, deuterium and tritium.

In chemical formulae herein, it is assumed that a hydrogen atom (i.e. protium, deuterium or tritium) is bonded to each of bondable positions that are not annexed with signs "R" or the like or "D" representing a deuterium.

Hereinafter, an alkyl group $Sub_3$ means at least one group of a linear alkyl group $Sub_{31}$, a branched alkyl group $Sub_{32}$, and a cyclic alkyl group $Sub_{33}$ described in "Description of Each Substituent."

Similarly, a substituted silyl group $Sub_5$ means at least one group of an alkylsilyl group $Sub_{51}$ and an arylsilyl group $Sub_{52}$.

Similarly, a substituted amino group $Sub_{11}$ means at least one group of an arylamino group $Sub_{111}$ and an alkylamino group $Sub_{112}$.

Herein, a substituent for a "substituted or unsubstituted" group is exemplified by a substituent $R_{F1}$. The substituent $R_{F1}$ is at least one group selected from the group consisting of an aryl group $Sub_1$, heteroaryl group $Sub_2$, alkyl group $Sub_3$, alkyl halide group $Sub_4$, substituted silyl group $Sub_5$, alkylsulfonyl group $Sub_6$, aralkyl group $Sub_7$, alkoxy group $Sub_8$, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, arylcarbonyl group $Sub_{17}$, acyl group $Sub_{13}$, substituted phosphoryl group $Sub_{19}$, ester group $Sub_{20}$, siloxanyl group $Sub_{21}$, carbamoyl group $Sub_{22}$, unsubstituted amino group, unsubstituted silyl group, halogen atom, cyano group, hydroxy group, nitro group, and carboxy group.

Herein, the substituent $R_{F1}$ for a "substituted or unsubstituted" group may be a diaryl boron group ($Ar_{B1}Ar_{B2}B$—) .$Ar_{B1}$ and $Ar_{B2}$ are exemplified by the above-described aryl group $Sub_1$. $Ar_{B1}$ and $Ar_{B2}$ in $Ar_{B1}Ar_{B2}B$— are the same or different.

Specific examples and preferable examples of the substituent $R_{F1}$ are the same as those of the substituents described in "Description of Each Substituent" (e.g., an aryl group $Sub_1$, heteroaryl group $Sub_2$, alkyl group $Sub_3$, alkyl halide group $Sub_4$, substituted silyl group $Sub_8$, alkylsulfonyl group $Sub_6$, aralkyl group $Sub_7$, alkoxy group $Sub_8$, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, arylcarbonyl group $Sub_{17}$, acyl group $Sub_{13}$, substituted phosphoryl group $Sub_{19}$, ester group $Sub_{20}$, siloxanyl group $Sub_{21}$, and carbamoyl group $Sub_{22}$).

The substituent $R_{F1}$ for a "substituted or unsubstituted" group may be further substituted by at least one group (hereinafter, also referred to as a substituent $R_{F2}$) selected from the group consisting of an aryl group $Sub_1$, heteroaryl group $Sub_2$, alkyl group $Sub_3$, alkyl halide group $Sub_4$, substituted silyl group $Sub_5$, alkylsulfonyl group $Sub_6$, aralkyl group $Sub_7$, alkoxy group $Sub_8$, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, arylcarbonyl group $Sub_{17}$, acyl group $Sub_{13}$, substituted phosphoryl group $Sub_{19}$, ester group $Sub_{20}$, siloxanyl group $Sub_{21}$, carbamoyl group $Sub_{22}$, unsubstituted amino group, unsubstituted silyl group, halogen atom, cyano group, hydroxy group, nitro group, and carboxy group. Moreover, a plurality of substituents $R_{F2}$ may be bonded to each other to form a ring.

"Unsubstituted" for a "substituted or unsubstituted" group means that a group is not substituted by the above-described substituent $R_{F1}$ but bonded with a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of the substituent $R_{F1}$ of the substituted ZZ group.

Herein, "XX to YY atoms" in the description of "substituted or unsubstituted ZZ group having XX to YY atoms" represent atoms of an unsubstituted ZZ group and do not include atoms of the substituent $R_{F1}$ of the substituted ZZ group.

The same description as the above applies to "substituted or unsubstituted" in compounds or moieties thereof described herein.

Herein, when the substituents are bonded to each other to form a ring, the ring is structured to be a saturated ring, an unsaturated ring, an aromatic hydrocarbon ring or a hetero ring.

Herein, examples of the aromatic hydrocarbon group in the linking group include a divalent or multivalent group obtained by eliminating one or more atoms from the above monovalent aryl group $Sub_1$.

Herein, examples of the heterocyclic group in the linking group include a divalent or multivalent group obtained by eliminating one or more atoms from the above monovalent heteroaryl group $Sub_2$.

EXAMPLES

Compounds

Structures of the compounds in Examples 1 to 3 are shown below. The compounds in Examples 1 to 3 were synthesized according to Synthesis Examples 1 to 3.

Compounds TADF1 and TADF3 were used for manufacturing organic EL devices of Example 1A and Example 2A, respectively.

[Formula 130]
TADF1
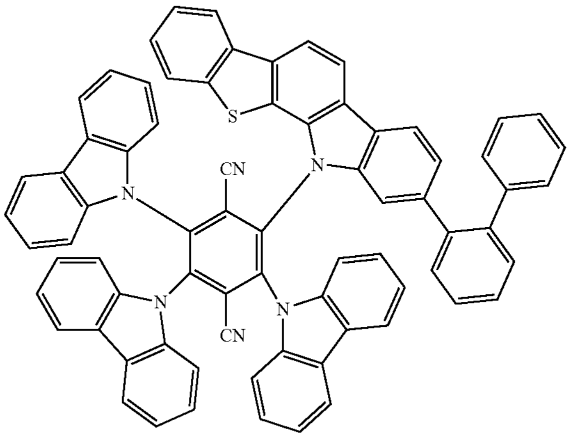
TADF2
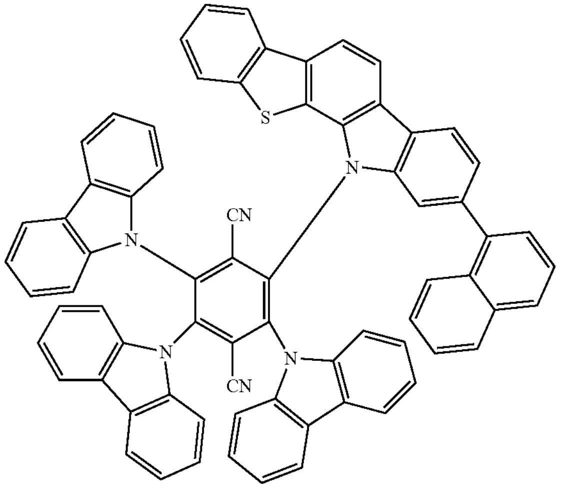
TADF3
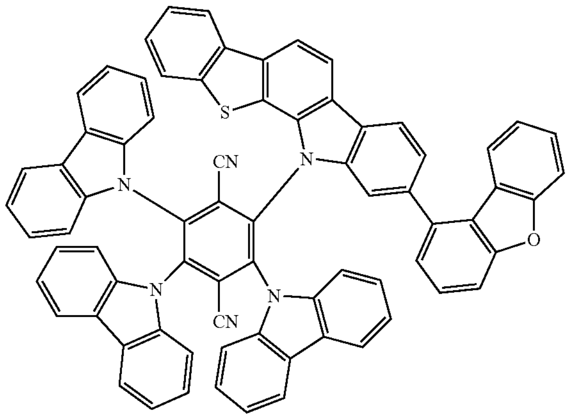
Structures of compounds synthesized according to Synthesis Examples 4 and 5 are shown below.
[Formula 131]
TADF4
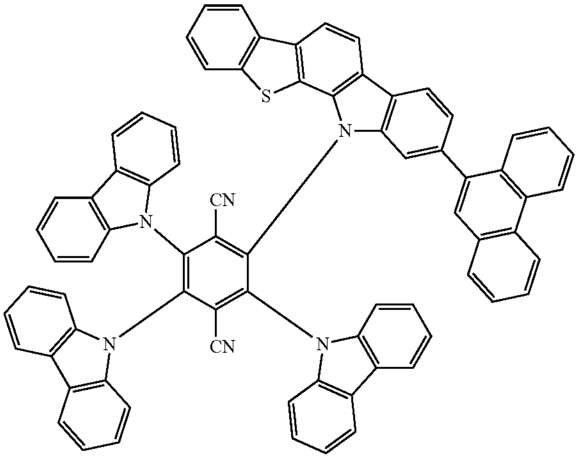
TADF5
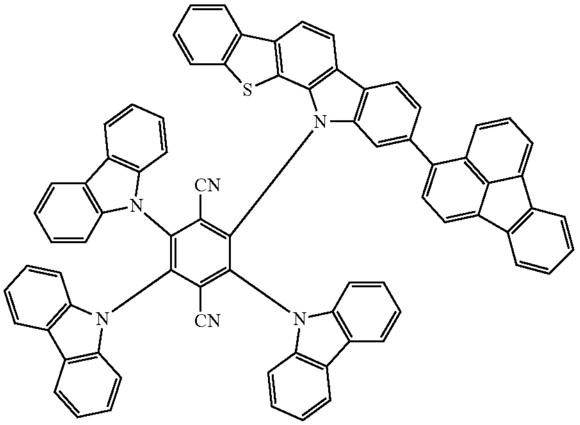
Structures of compounds according to Comparatives 1 to 6 are shown below. Compound Ref-3 was used for manufacturing an organic EL device of Comparative 1B.
[Formula 132]
Ref-1
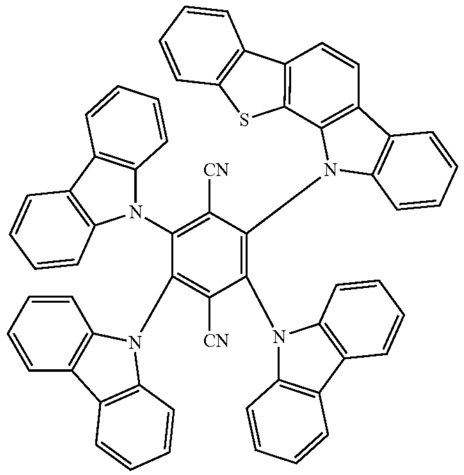

Ref-2
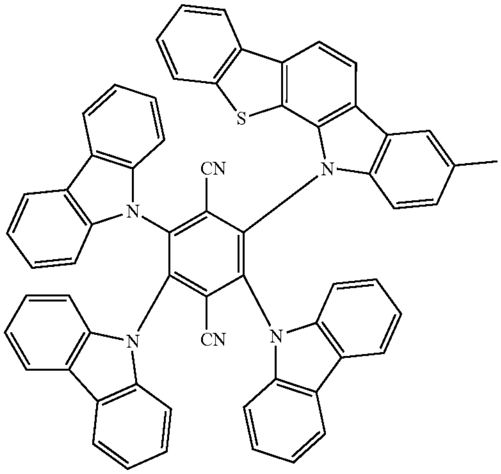
[Formula 133]
Ref-3
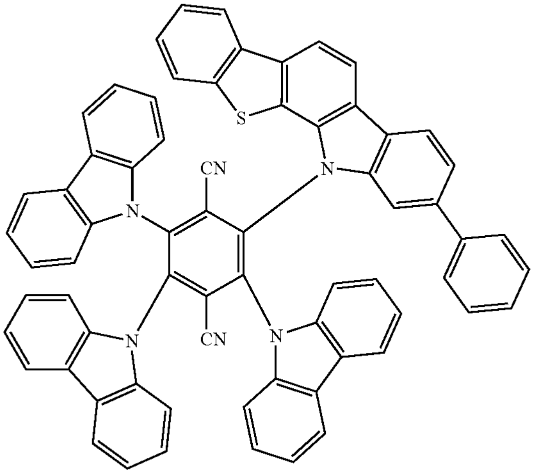
Ref-4
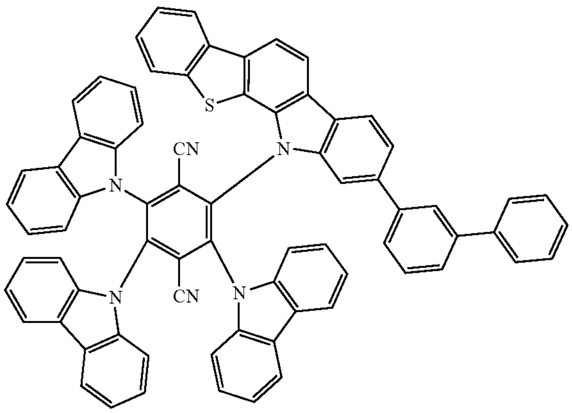
[Formula 134]
Ref-5
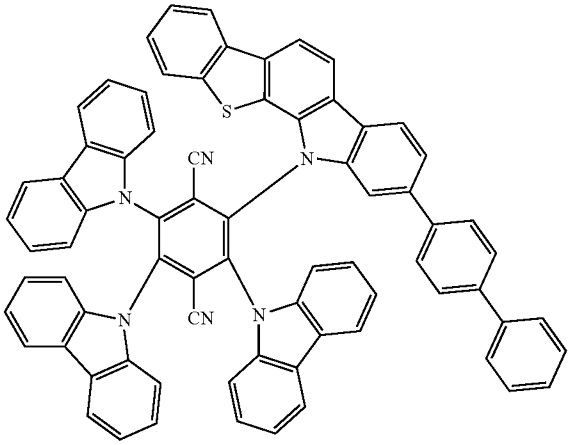
Ref-6
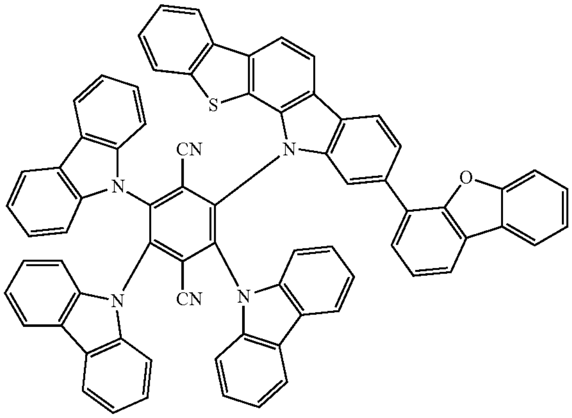
Other compounds used for manufacturing the organic EL devices in Examples 1A and 2A and Comparative 1B are shown below.
[Formula 135]
HA
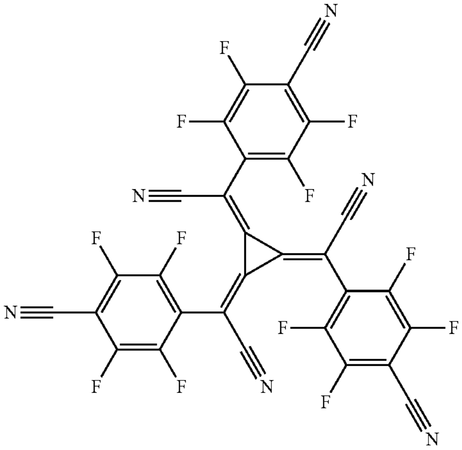

-continued

HT1

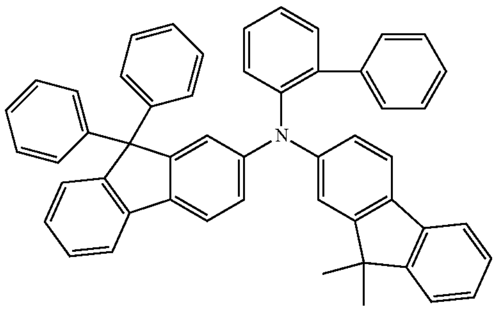

[Formula 136]

HT2

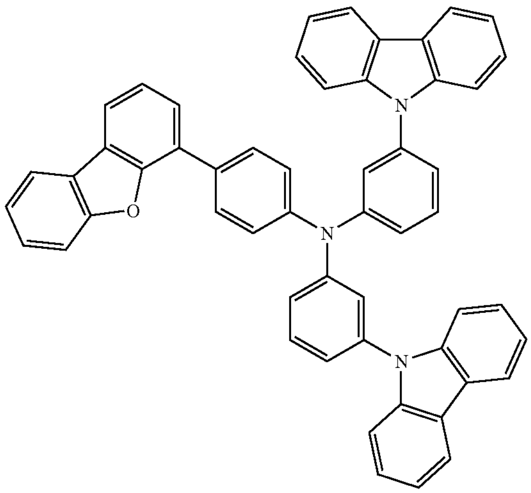

HOST

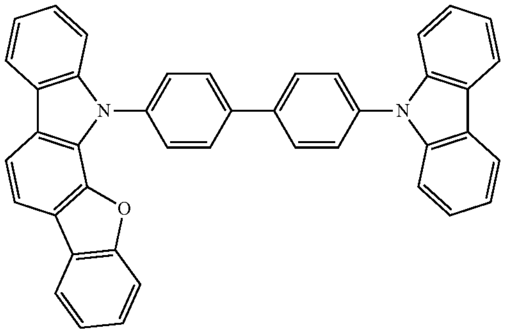

-continued

[Formula 137]

RD

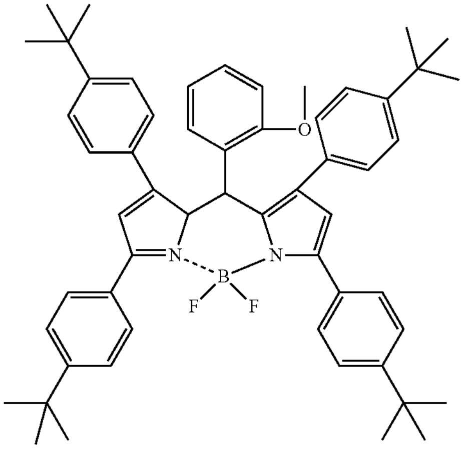

ET1

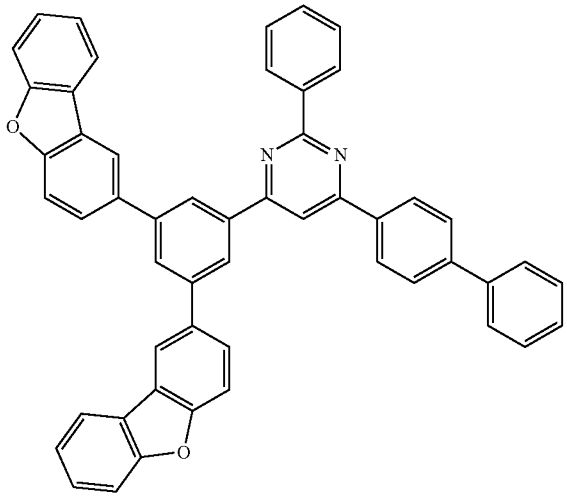

[Formula 138]

ET2

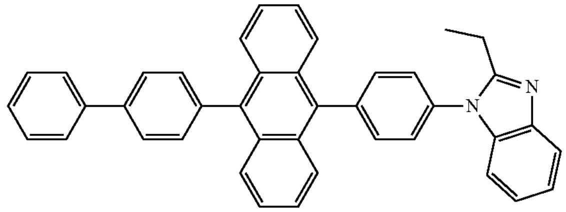

Manufacture of Organic EL Device

The organic EL devices were manufactured and evaluated as follows.

Example 1A

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for one minute. A film of ITO was 130 nm thick.

After the glass substrate having the transparent electrode line was cleaned, the glass substrate was mounted on a substrate holder of a vacuum deposition apparatus. Firstly, a compound HT1 and a compound HA were co-deposited on a surface of the glass substrate where the transparent electrode line was provided in a manner to cover the transparent electrode, thereby forming a 10-nm-thick hole injecting layer. The concentrations of the compound HT1 and the compound HA in the hole injecting layer were 97 mass % and 3 mass %, respectively.

Next, the compound HT1 was vapor-deposited on the hole injecting layer to form a 200-nm-thick first hole transporting layer.

Next, a compound HT2 was vapor-deposited on the first hole transporting layer to form a 10-nm-thick second hole transporting layer (sometimes referred to as an electron blocking layer).

Next, a compound TADF1 (the first compound), a compound RD (the second compound), and a compound HOST (the third compound) were co-deposited on the second hole transporting layer to form a 25-nm-thick emitting layer. The concentrations of the compound TADF1, the compound RD, and the compound HOST in the emitting layer were 25 mass %, 1 mass %, and 74 mass %, respectively.

Next, a compound ET1 was vapor-deposited on the emitting layer to form a 10-nm-thick first electron transporting layer (sometimes referred to as hole blocking layer).

Next, a compound ET2 was vapor-deposited on the first electron transporting layer to form a 30-nm-thick second electron transporting layer.

Then, lithium fluoride (LiF) was vapor-deposited on the second electron transporting layer to form a 1-nm-thick electron injectable electrode (cathode).

Subsequently, metal aluminum (Al) was vapor-deposited on the electron injectable electrode to form an 80-nm-thick metal Al cathode.

The device arrangement of the organic EL device in Example 1A is roughly shown as follows.

ITO(130)/HT1:HA(10, 97%:3%)/HT1(200)/HT2(10)/HOST:TADF1:RD(25, 74%:25%:1%)/ET1(10)/ET2(30)/LiF(1)/Al(80)

Numerals in parentheses represent a film thickness (unit: nm).

The numerals (97%:3%) represented by percentage in the same parentheses indicate a ratio (mass %) between the compound HT1 and the compound HA in the hole injecting layer, and the numerals (74%:25%:1%) represented by percentage in the same parentheses indicate a ratio (mass %) between the compound HOST, the compound TADF1, and the compound RD in the emitting layer.

Example 2A and Comparative 1B

The organic EL devices in Example 2A and Comparative 1B were manufactured in the same manner as in Example 1A except that the compound shown in Table 1 was used in place of the compound TADF1 in the emitting layer of Example 1A.

Evaluation of Organic EL Devices

The organic EL devices manufactured in Examples 1A and 2A and Comparative 1B were evaluated as follows. The results are shown in Table 1. It should be noted that the compound Ref-3 used in Comparative 11B, which is not representable by the formula of the first compound, is listed in the same column as the compound TADF1 of Example 1A for descriptive purpose.

External Quantum Efficiency EQE

Voltage was applied on the organic electroluminescence devices so that a current density was 0.1 mA/$cm^2$ or 10 mA/$cm^2$, where spectral radiance spectrum was measured by a spectroradiometer (CS-2000 manufactured by Konica Minolta, Inc.). The external quantum efficiency EQE (unit: %) was calculated based on the obtained spectral-radiance spectra, assuming that the spectra was provided under a Lambertian radiation.

The external quantum efficiency (EQE) (%) when the current density is 0.1 mA/$cm^2$ will be referred to as "low-current EQE (%)" hereinafter. The external quantum efficiency (EQE) (%) when the current density is 10 mA/$cm^2$ will be referred to as "high-current EQE (%)" hereinafter.

Using a formula (Numerical Formula 100) below, the "low-current EQE (%)" of each of Examples was calculated as "low-current EQE (%) (relative value: %)" relative to the "low-current EQE (%)" of Comparative 1B defined as 100.

Low-Current EQE (relative value: %) of Examples=(low-current EQE (%) of Examples/low-current EQE (%) of Comparative 1B)×100 (Numerical Formula 100)

Using a formula (Numerical Formula 101) below, the "high-current EQE (%)" of each of Examples was calculated as "high-current EQE (%) (relative value: %)" relative to the "high-current EQE (%)" of Comparative 1B defined as 100.

High-Current EQE (relative value:%) of Examples=(high-current EQE (%) of Examples/high-current EQE (%) of Comparative 1B)×100 (Numerical Formula 101)

Chromaticity CIEx, CIEy, and Maximum Peak Wavelength λp

Voltage was applied on each of the organic EL devices such that a current density was 10 mA/$cm^2$, where spectral radiance spectra were measured by a spectroradiometer CS-2000 (manufactured by Konica Minolta, Inc.). Chromaticity CIEx, chromaticity CIEy, and maximum peak wavelength λp (unit: nm) were calculated based on the obtained spectral-radiance spectra.

TABLE 1

| | Emitting Layer | | | Evaluation | | | | |
|---|---|---|---|---|---|---|---|---|
| | | | | EQE | | | | |
| | | | | Low-current | High-current | | | |
| | First Compound | Second Compound | Third Compound | (relative value: %) | (relative value: %) | CIEx | CIE y | λp [nm] |
| Ex. 1A | TADF1 | RD | HOST | 107 | 103 | 0.66 | 0.34 | 622 |
| Ex. 2A | TADF3 | RD | HOST | 102 | 106 | 0.66 | 0.34 | 622 |
| Comp. 1B | Ref-3 | RD | HOST | 100 | 100 | 0.67 | 0.33 | 623 |

The organic EL devices of Examples 1A and 2A exhibited improved external quantum efficiency (EQE) as compared with the organic EL device of Comparative 1B in both low-current application (when the current density was 0.1 mA/cm$^2$) and high-current application (when the current density was 10 mA/cm$^2$).

Evaluation of Compounds

Preparation of Toluene Solution

The compound TADF1 was dissolved in toluene so that the concentration became 5 μmol/L to prepare a toluene solution of the compound TADF1. Subsequently, the prepared solution was bubbled with nitrogen for five minutes and was hermetically sealed to prevent invasion of external air.

A toluene solution was prepared for each of the compounds TADF2 to TADF3 and Ref-1 to Ref-6 in the same manner as the compound TADF1. Subsequently, the prepared solution was bubbled with nitrogen for five minutes and was hermetically sealed to keep external air from being mixed.

Measurement of Fluorescence Quantum Yield (PLQY)

PLQY of the toluene solution of each of the prepared compounds TADF1 to TADF3 and Ref-1 to Ref-6 was measured using an absolute PL (photoluminescence) quantum yield measurement machine Quantaurus-QY (manufactured by Hamamatsu Photonics K.K.).

Measurement results are shown in Table 2.

Maximum Peak Wavelength of Compounds

A toluene solution of each of measurement target compounds at a concentration of 5 μmol/L was prepared and put in a quartz cell. A fluorescence spectrum (ordinate axis: fluorescence intensity, abscissa axis: wavelength) of each sample was measured at a normal temperature (300 K).

In Examples, the fluorescence spectrum was measured using a spectrophotometer (F-7000 manufactured by Hitachi, Ltd.). It should be noted that the fluorescence spectrum measuring device may be different from the above device. A peak wavelength of the fluorescence spectrum exhibiting the maximum luminous intensity was defined as the maximum peak wavelength.

Measurement results are shown in Table 2.

Thermally Activated Delayed Fluorescence

Delayed Fluorescence of Compound TADF1

Delayed fluorescence was checked by measuring transient PL using a device shown in FIG. 2. The compound TADF1 was dissolved in toluene to prepare a dilute solution with an absorbance of 0.05 or less at the excitation wavelength to eliminate the contribution of self-absorption. In order to prevent quenching due to oxygen, the sample solution was frozen and degassed and then sealed in a cell with a lid under an argon atmosphere to obtain an oxygen-free sample solution saturated with argon.

The fluorescence spectrum of the above sample solution was measured with a spectrofluorometer FP-8600 (manufactured by JASCO Corporation), and the fluorescence spectrum of a 9,10-diphenylanthracene ethanol solution was measured under the same conditions. Using fluorescence area intensities of both spectra, the total fluorescence quantum yield was calculated by an equation (1) in Morris et al. J. Phys. Chem. 80 (1976) 969.

Prompt emission was observed immediately when the excited state was achieved by exciting the compound TADF1 with a pulse beam (i.e., a beam emitted from a pulse laser) having a wavelength to be absorbed by the compound TADF1, and Delay emission was observed not immediately when the excited state was achieved but after the excited state was achieved. The delayed fluorescence in Examples means that an amount of Delay Emission is 5% or more with respect to an amount of Prompt Emission. Specifically, provided that the amount of Prompt emission is denoted by $X_P$ and the amount of Delay emission is denoted by $X_D$, the delayed fluorescence means that a value of $X_D/X_P$ is 0.05 or more.

An amount of Prompt emission, an amount of Delay emission and a ratio between the amounts thereof can be obtained according to the method as described in "Nature 492, 234-238, 2012" (Reference Document 1).

The amount of Prompt emission and the amount of Delay emission may be calculated using a device different from one described in Reference Document 1 or one shown in FIG. 2.

It was confirmed that the amount of Delay Emission was 5% or more with respect to the amount of Prompt Emission in the compound TADF1.

Specifically, it was found that a value of $X_D/X_P$ was 0.05 or more in the compound TADF1.

Delayed Fluorescence of Compounds TADF2 to 3 and Comparative Compounds Ref-1 to Ref-6

The delayed fluorescence of the compounds TADF2 to 3 and the comparative compounds Ref-1 to Ref-6 was measured in the same manner as the above except that the compounds TADF2 to 3 and the comparative compounds Ref-1 to Ref-6 were used in place of the compound TADF1.

The value of $X_D/X_P$ was 0.05 or more in all of the compounds TADF2 to 3 and the comparative compounds Ref-1 to Ref-6.

Singlet Energy $S_1$

The single energies $S_1$ of the compounds TADF2 to 3 and the comparative compounds Ref-1 to Ref-6 were measured by the above-described solution method. Measurement results are shown in Table 2.

ΔST

ΔST was calculated based on the measurement results of $T_{77K}$ of the compounds TADF2 to 3 and the comparative compounds Ref-1 to Ref-6 and the values of the above singlet energy $S_1$.

$T_{77K}$ of the compounds TADF2 to 3 and the comparative compounds Ref-1 to Ref-6 was measured by the measurement method of energy gap $T_{77K}$ described in the above "Relationship between Triplet Energy and Energy Gap at 77K."

Measurement results are shown in Table 2.

TABLE 2

| | Type | $S_1$ [eV] | ΔST [eV] | Main Peak Wavelength [nm] | PLQY |
|---|---|---|---|---|---|
| Ex. 1 | TADF1 | 2.34 | <0.01 | 539 | 0.48 |
| Ex. 2 | TADF2 | 2.34 | <0.01 | 538 | 0.48 |
| Ex. 3 | TADF3 | 2.34 | <0.01 | 538 | 0.58 |
| Comp. 1 | Ref-1 | 2.34 | <0.01 | 539 | 0.39 |
| Comp. 2 | Ref-2 | 2.32 | <0.01 | 545 | 0.27 |
| Comp. 3 | Ref-3 | 2.34 | <0.01 | 539 | 0.38 |
| Comp. 4 | Ref-4 | 2.34 | <0.01 | 540 | 0.40 |
| Comp. 5 | Ref-5 | 2.34 | <0.01 | 540 | 0.33 |
| Comp. 6 | Ref-6 | 2.34 | <0.01 | 541 | 0.39 |

Description about Table

"<0.01" indicates that the value is less than 0.01 eV.

As shown in Table 2, the compounds TADF1 to TADF3 in Examples 1 to 3 exhibited improved PLQY as compared with the comparative compounds Ref-1 to Ref-6.

The compounds TADF1 to TADF3 of Examples 1 to 3 are different from the compounds Ref-1 to Ref-6 in Comparatives 1 to 6 only in terms of the presence of a group represented by the formula (110) or (120). Accordingly, it can be understood that a group represented by the formula (110) or (120) improves PLQY.

Especially, by comparing Example 1 with Comparatives 4, 5, it is found that the compounds Ref-4 and Ref-5, which are represented by formulae similar to the formula (120) except for the difference in the bonding position of $Z_2$, are inferior to the compound TADF1 representable by the formula (120) in terms of PLQY.

Further, especially by comparing Example 3 with Comparative 6, it is found that, as compared with the compound TADF3 including a 1-dibenzofuranyl group in a form of a group represented by the formula (110), the compound Ref-6, which includes a 4-dibenzofuranyl group (i.e. the same dibenzofuranyl group but not representable by the formula (110)), is inferior in PLQY.

Synthesis of Compounds

Synthesis Example 1

A synthesis method of the compound TADF1 will be described below.

[Formula 139]

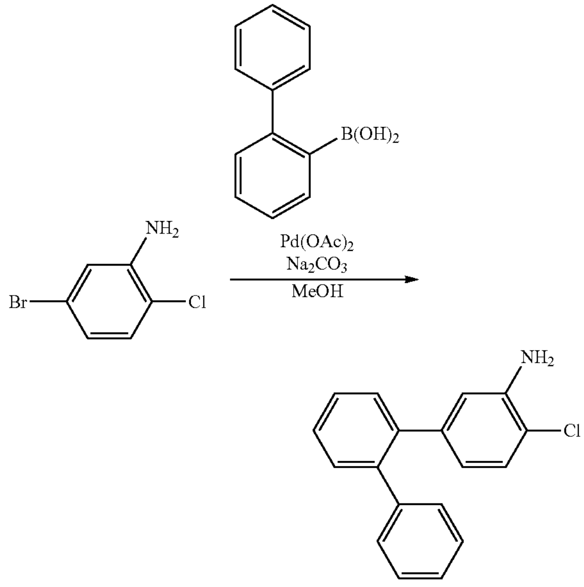

M-a

Under nitrogen atmosphere, 5-bromo-2-chloro-aniline (10 g, 49 mmol), 2-biphenyl boronate (9.7 g, 49 mmol), palladium acetate (0.11 g, 0.5 mmol), sodium carbonate (10 g, 98 mmol), and methanol (100 mL) were put into a 300-mL three-neck flask and were stirred at 80 degrees C. for six hours. Ion exchange water (100 mL) was added to the reaction mixture. Then, deposited solid was purified by silica-gel column chromatography to obtain a white solid (13.3 g). Through GC-MS (Gas Chromatograph Mass Spectrometer) analysis, the white solid was identified as a compound M-a (yield rate 97%).

[Formula 140]

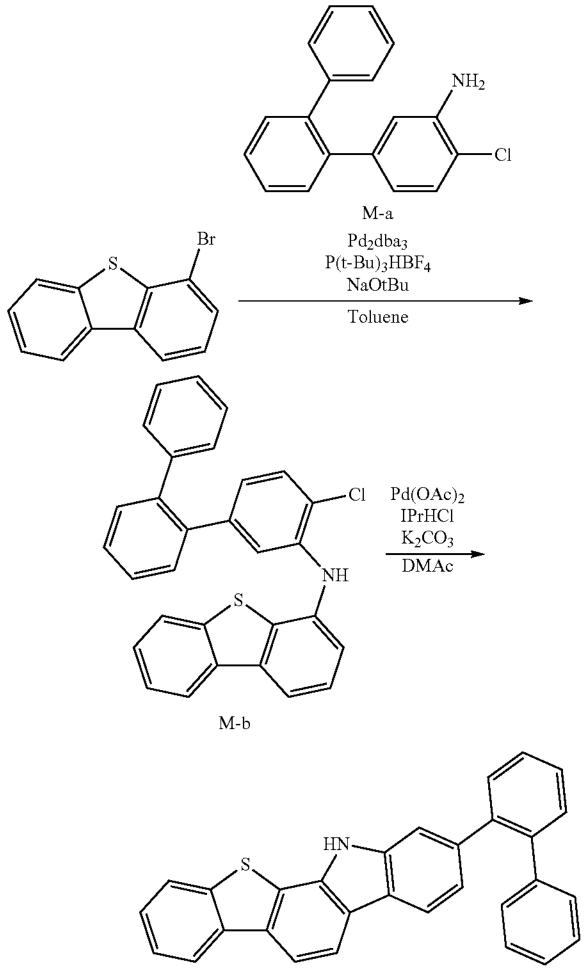

M-c

Under nitrogen atmosphere, 4-bromodibenzothiophene (10 g, 38 mmol), the compound M-a (11 g, 38 mmol), tris(dibenzylidene acetone)dipalladium(0) ($Pd_2dba_3$) (0.35 g, 0.38 mmol), tri-tert-butylphosphonium tetrafluoroborate ($P(t\text{-}Bu)_3HBF_4$) (0.44 g, 1.5 mmol), sodium tert-butoxide (NaOtBu) (5.5 g, 57 mmol), and toluene (120 mL), which were put into a 200-mL three-neck flask, were stirred at 60 degrees C. for four hours and then cooled to a room temperature (25 degrees C.). The reaction solution was purified by silica-gel column chromatography to obtain a white solid (16 g). Through GC-MS analysis, the white solid was identified as a compound M-b (yield rate 91%).

Under nitrogen atmosphere, the compound M-b (16 g, 35 mmol), 1,3-bis(2,6-diisopropylphenyl)imidazoriumchloride (IPrHCl) (0.30 g, 0.70 mmol), palladium(II) acetate (Pd $(OAc)_2$) (78 mg, 0.35 mmol), potassium carbonate (9.7 g, 70 mmol), and N,N-dimethylacetamide (DMAc) (100 mL) were put into a 200-mL three-neck flask, stirred at 160 degrees C. for three hours, and then cooled to a room temperature (25 degrees C.). The reaction solution was purified by silica-gel column chromatography to obtain a white solid (10.6 g). Through GC-MS analysis, the white solid was identified as a compound M-c (yield rate 72%).

[Formula 141]

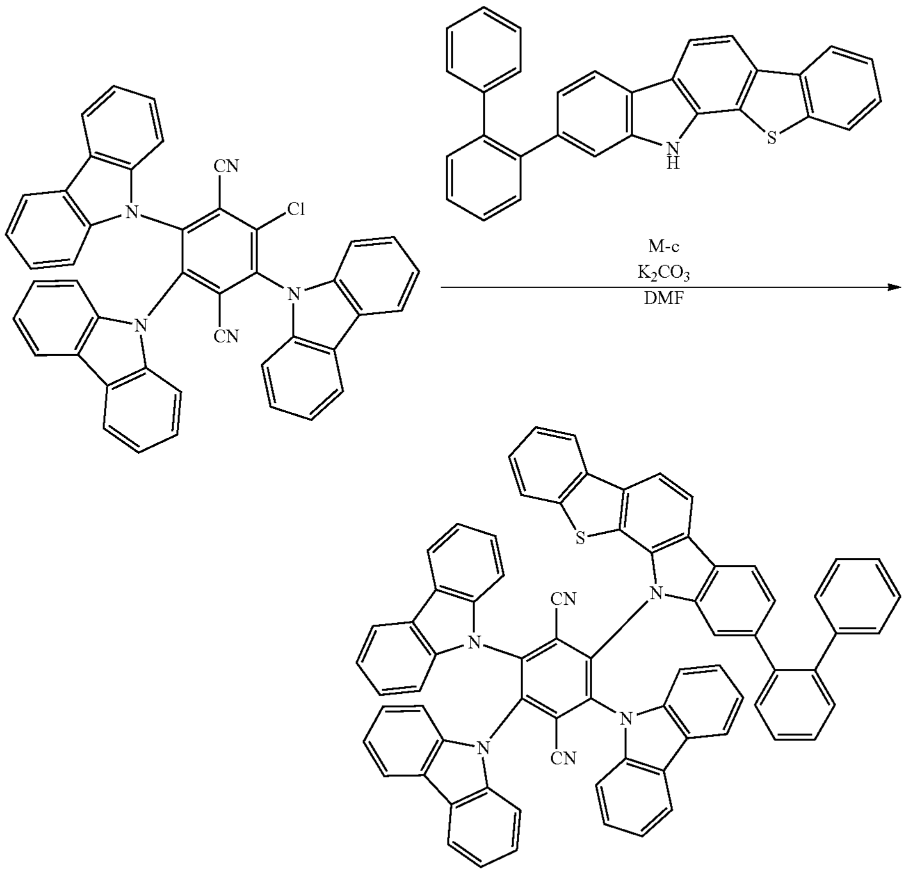

TADF1

Under nitrogen atmosphere, 1,4-benzene dicarbonitrile, 2,3,5-tri-9H-carbazole-9-yl-6-chloro (3.0 g, 4.6 mmol), the compound M-c (2.4 g, 5.5 mmol), potassium carbonate (1.1 g, 8.2 mmol), and DMF (20 mL) were put into a 50-mL three-neck flask and were stirred at 120 degrees C. for four hours. Saturated ammonium chloride aqueous solution (10 mL) was added to the reaction mixture. Then, deposited solid was purified by silica-gel column chromatography to obtain a red solid (4.2 g). Through ASAP-MS (Atmospheric Pressure Solid Analysis Probe Mass Spectrometry) analysis, the red solid was identified as TADF1 (yield rate 88%).

Synthesis Example 2

A synthesis method of the compound TADF2 will be described below.

[Formula 142]

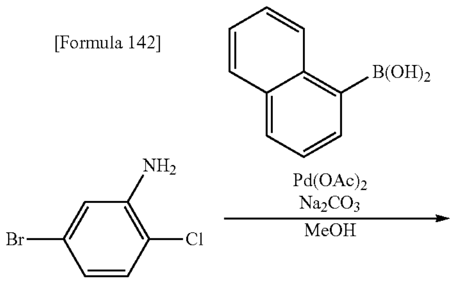

-continued

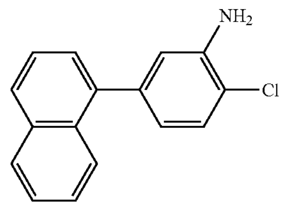

M-d

Under nitrogen atmosphere, 5-bromo-2-chloro-aniline (10 g, 49 mmol), 1-naphthyl boronate (8.4 g, 49 mmol), palladium acetate (0.11 g, 0.5 mmol), sodium carbonate (10 g, 98 mmol), and methanol (100 mL) were put into a 300-mL three-neck flask and were stirred at 80 degrees C. for six hours. Ion exchange water (100 mL) was added to the reaction mixture. Then, deposited solid was purified by silica-gel column chromatography to obtain a white solid (9.6 g). Through GC-MS analysis, the white solid was identified as a compound M-d (yield rate 77%).

[Formula 143]

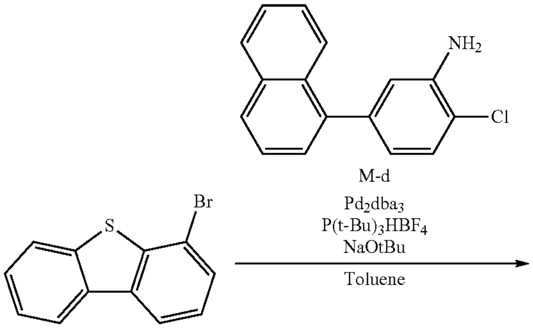

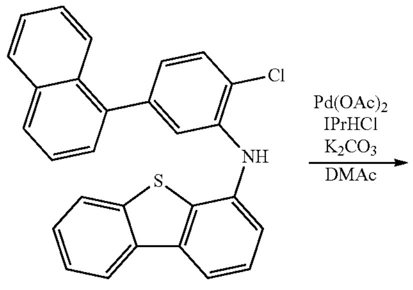

M-e

-continued

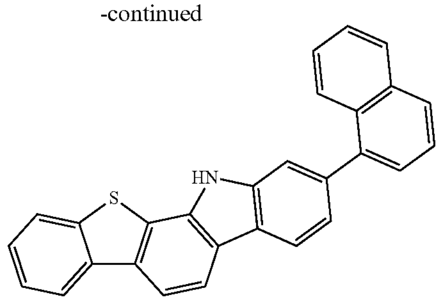

M-f

Under nitrogen atmosphere, 4-bromodibenzothiophene (9.2 g, 35 mmol), the compound M-d (9.6 g, 35 mmol), tris(dibenzylidene acetone)dipalladium(0) ($Pd_2dba_3$) (0.32 g, 0.35 mmol), tri-tert-butylphosphonium tetrafluoroborate ($P(t-Bu)_3HBF_4$) (0.41 g, 1.4 mmol), sodium tert-butoxide (NaOtBu) (5.0 g, 53 mmol), and toluene (100 mL) were put into a 200-mL three-neck flask, stirred at 60 degrees C. for four hours, and then cooled to a room temperature (25 degrees C.). The reaction solution was purified by silica-gel column chromatography to obtain a white solid (14 g). Through GC-MS analysis, the white solid was identified as a compound M-e (yield rate 94%).

Under nitrogen atmosphere, the compound M-e (14 g, 35 mmol), 1,3-bis(2,6-diisopropylphenyl)imidazoriumchloride (IPrHCl) (0.30 g, 0.70 mmol), palladium(II) acetate ($Pd(OAc)_2$) (78 mg, 0.35 mmol), potassium carbonate (9.7 g, 70 mmol), and N,N-dimethylacetamide (DMAc) (100 mL) were put into a 200-mL three-neck flask, stirred at 160 degrees C. for three hours, and then cooled to a room temperature (25 degrees C.). The reaction solution was purified by silica-gel column chromatography to obtain a white solid (11.2 g). Through GC-MS analysis, the white solid was identified as a compound M-f (yield rate 85%).

[Formula 144]

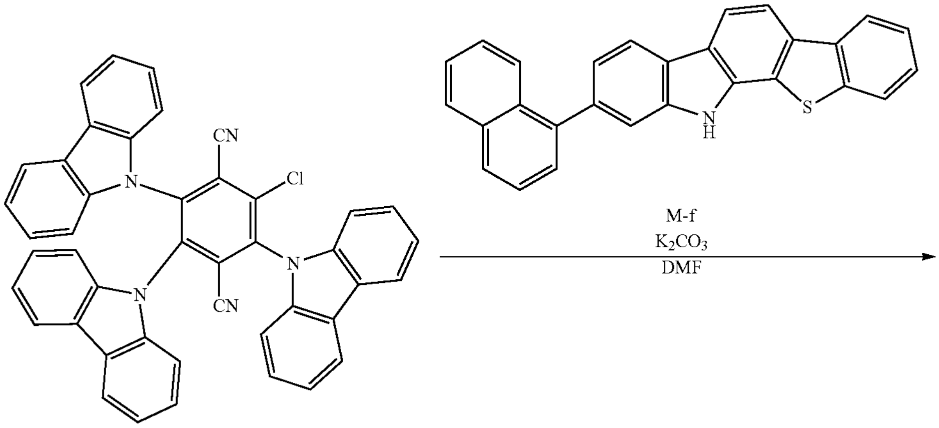

-continued

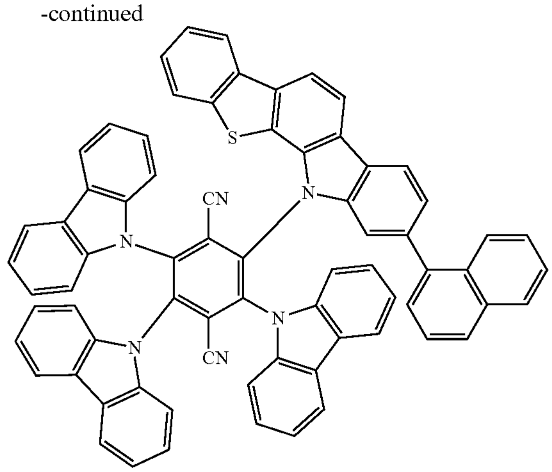

TADF2

Under nitrogen atmosphere, 1,4-benzene dicarbonitrile, 2,3,5-tri-9H-carbazole-9-yl-6-chloro-(3.0 g, 4.6 mmol), the compound M-f (2.4 g, 5.5 mmol), potassium carbonate (1.1 g, 8.2 mmol), and DMF (20 mL) were put into a 50-mL three-neck flask and were stirred at 120 degrees C. for four hours. Saturated ammonium chloride aqueous solution (10 mL) was added to the reaction mixture. Then, deposited solid was purified by silica-gel column chromatography to obtain a red solid (3.8 g). Through ASAP-MS analysis, the red solid was identified as TADF2 (yield rate 80%).

Synthesis Example 3

A synthesis method of the compound TADF3 will be described below.

[Formula 145]

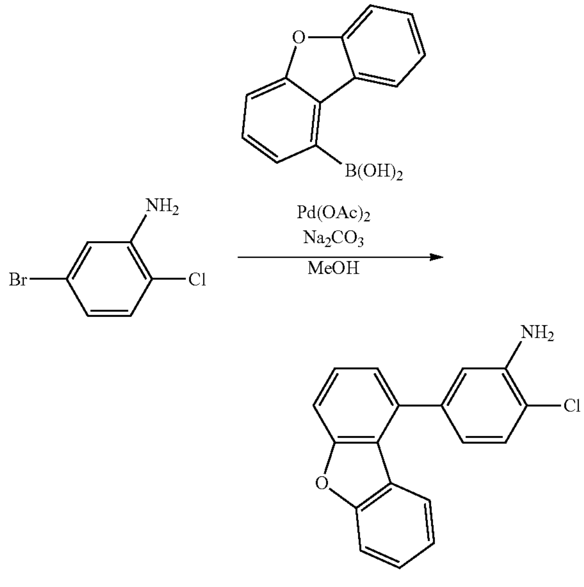

M-g

Under nitrogen atmosphere, 5-bromo-2-chloro-aniline (10 g, 49 mmol), 1-dibenzofuranyl boronate (10.4 g, 49 mmol), palladium acetate (0.11 g, 0.5 mmol), sodium carbonate (10 g, 98 mmol), and methanol (100 mL) were put into a 300-mL three-neck flask and stirred at 80 degrees C. for eight hours. Ion exchange water (100 mL) was added to the reaction mixture. Then, deposited solid was purified by silica-gel column chromatography to obtain a white solid (13.7 g). Through GC-MS analysis, the white solid was identified as a compound M-g (yield rate 95%).

[Formula 146]

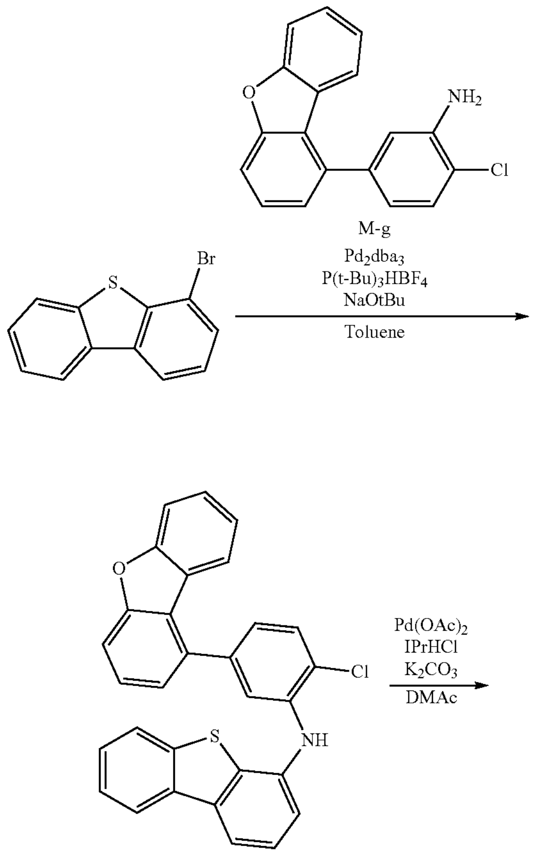

M-h

-continued

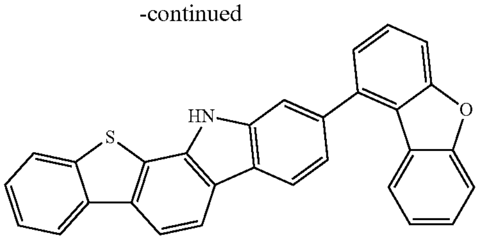

M-i

Under nitrogen atmosphere, 4-bromodibenzothiophene (10 g, 38 mmol), the compound M-g (11.2 g, 38 mmol), tris(dibenzylidene acetone)dipalladium(0) ($Pd_2dba_3$) (0.35 g, 0.38 mmol), tri-tert-butylphosphonium tetrafluoroborate ($P(t\text{-}Bu)_3HBF_4$) (0.44 g, 1.5 mmol), sodium tert-butoxide (NaOtBu) (5.5 g, 57 mmol), and toluene (120 mL) were put into a 200-mL three-neck flask, stirred at 60 degrees C. for four hours, and then cooled to a room temperature (25 degrees C.). The reaction solution was purified by silica-gel column chromatography to obtain a white solid (17.7 g). Through GC-MS analysis, the white solid was identified as a compound M-h (yield rate 98%).

Under nitrogen atmosphere, the compound M-h (17.7 g, 37.2 mmol), 1,3-bis(2,6-diisopropylphenyl)imidazoriumchloride (IPrHCl) (0.32 g, 0.74 mmol), palladium(II) acetate ($Pd(OAc)_2$) (84 mg, 0.37 mmol), potassium carbonate (10.2 g, 74 mmol), and N,N-dimethylacetamide (DMAc) (100 mL) were put into a 200-mL three-neck flask, stirred at 160 degrees C. for three hours, and then cooled to a room temperature (25 degrees C.). The reaction solution was purified by silica-gel column chromatography to obtain a white solid (14.4 g). Through GC-MS analysis, the white solid was identified as a compound M-i (yield rate 88%).

[Formula 147]

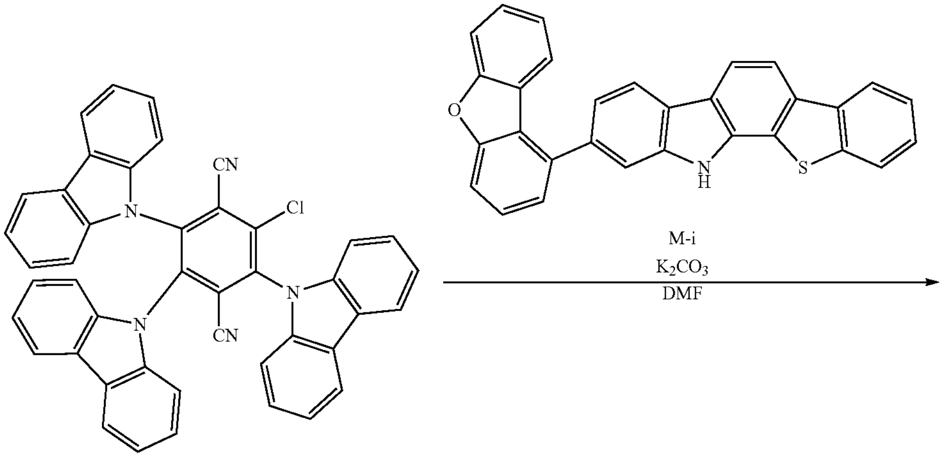

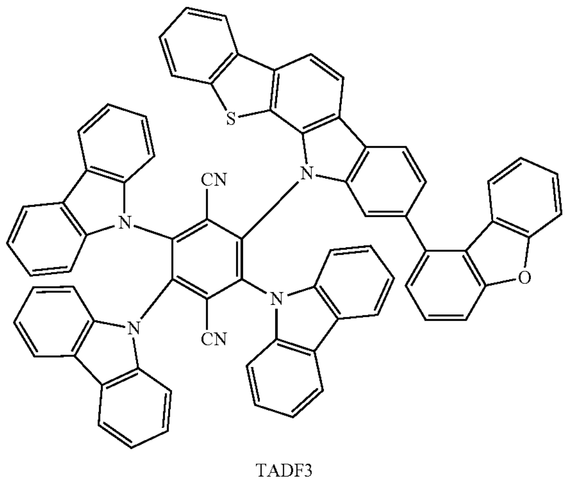

TADF3

Under nitrogen atmosphere, 1,4-benzene dicarbonitrile, 2,3,5-tri-9H-carbazole-9-yl-6-chloro-(3.0 g, 4.6 mmol), the compound M-i (2.4 g, 5.5 mmol), potassium carbonate (1.1 g, 8.2 mmol), and DMF (20 mL) were put into a 50-mL three-neck flask and stirred at 120 degrees C. for four hours. Saturated ammonium chloride aqueous solution (10 mL) was added to the reaction mixture. Then, deposited solid was purified by silica-gel column chromatography to obtain a red solid (3.5 g). Through ASAP-MS analysis, the red solid was identified as TADF3 (yield rate 71%).

Synthesis Example 4

A synthesis method of the compound TADF4 will be described below.

[Formula 148]

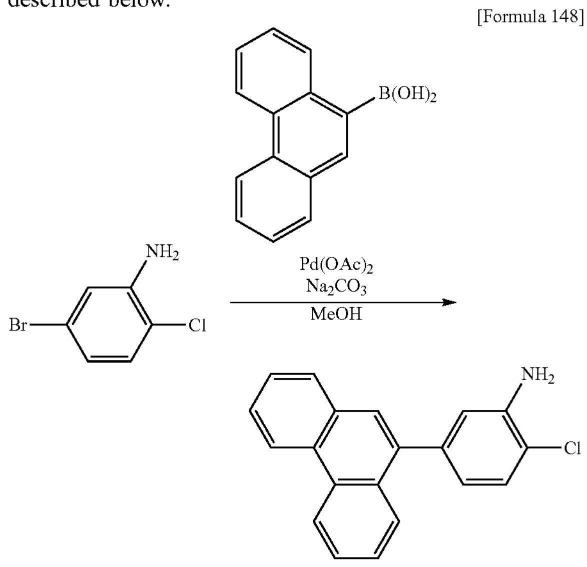

M-j

Under nitrogen atmosphere, 5-bromo-2-chloro-aniline (10 g, 49 mmol), 9-phenanthrenyl boronate (10.8 g, 49 mmol), palladium acetate (0.11 g, 0.5 mmol), sodium carbonate (10 g, 98 mmol), and methanol (100 mL) were put into a 300-mL three-neck flask and stirred at 80 degrees C. for six hours. Ion exchange water (100 mL) was added to the reaction mixture. Then, deposited solid was purified by silica-gel column chromatography to obtain a white solid (13.4 g). Through GC-MS analysis, the white solid was identified as a compound M-j (yield rate 90%).

[Formula 149]

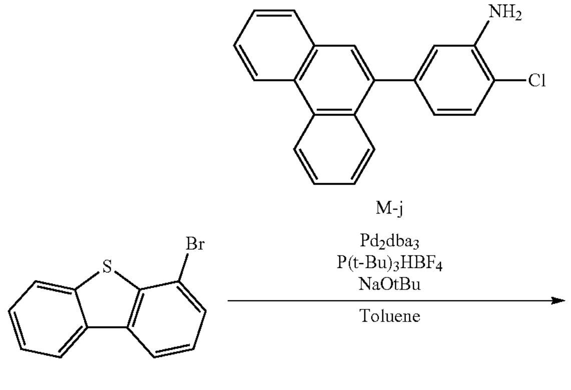

-continued

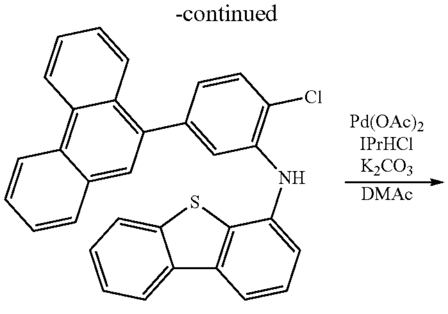

M-k

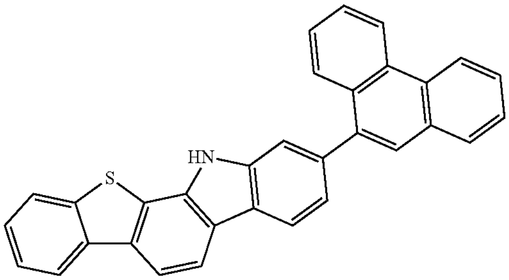

M-l

Under nitrogen atmosphere, 4-bromodibenzothiophene (10 g, 38 mmol), the compound M-j (11.6 g, 38 mmol), tris(dibenzylidene acetone)dipalladium(0) ($Pd_2dba_3$) (0.35 g, 0.38 mmol), tri-tert-butylphosphonium tetrafluoroborate ($P(t\text{-}Bu)_3HBF_4$) (0.44 g, 1.5 mmol), sodium tert-butoxide (NaOtBu) (5.5 g, 57 mmol), and toluene (120 mL) were put into a 200-mL three-neck flask, stirred at 60 degrees C. for four hours, and then cooled to a room temperature (25 degrees C.). The reaction solution was purified by silica-gel column chromatography to obtain a white solid (16.4 g). Through GC-MS analysis, the white solid was identified as a compound M-k (yield rate 89%).

Under nitrogen atmosphere, the compound M-k (16.4 g, 33.8 mmol), 1,3-bis(2,6-diisopropylphenyl)imidazoriumchloride (IPrHCl) (0.29 g, 0.68 mmol), palladium(II) acetate ($Pd(OAc)_2$) (77 mg, 0.34 mmol), potassium carbonate (9.4 g, 68 mmol), and N,N-dimethylacetamide (DMAc) (100 mL) were put into a 200-mL three-neck flask, stirred at 160 degrees C. for three hours, and then cooled to a room temperature (25 degrees C.). The reaction solution was purified by silica-gel column chromatography to obtain a white solid (10.5 g). Through GC-MS analysis, the white solid was identified as a compound M-l (yield rate 69%).

[Formula 150]

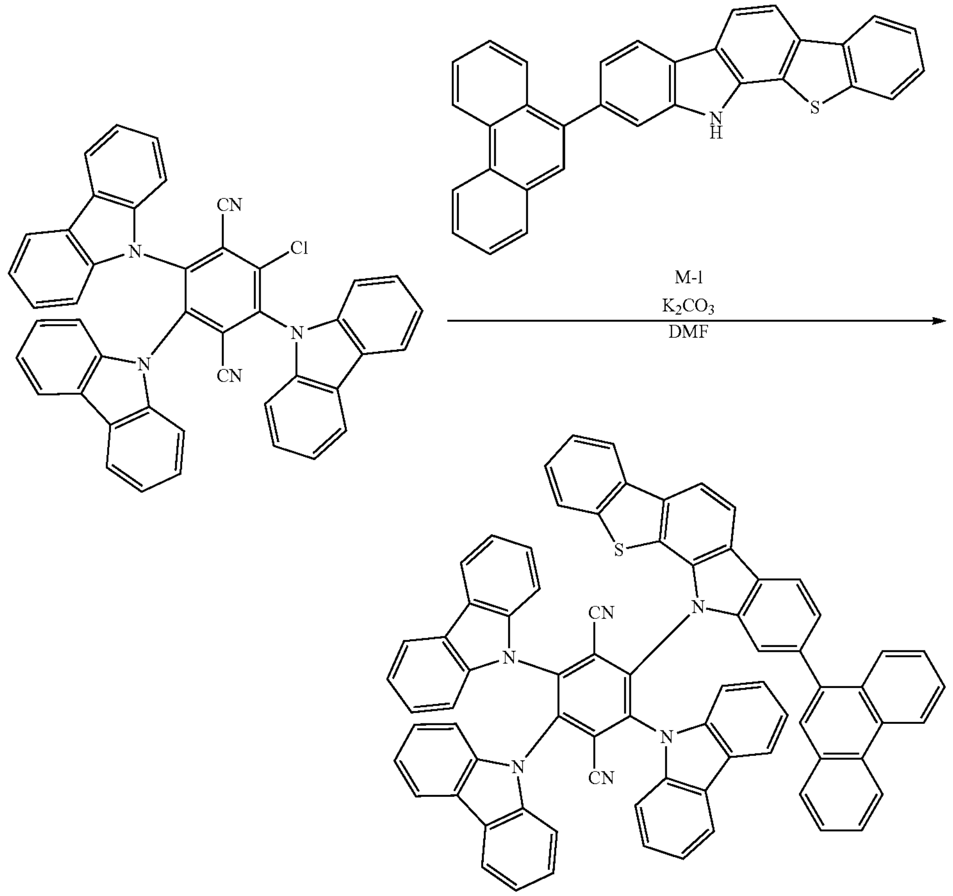

TADF4

Under nitrogen atmosphere, 1,4-benzene dicarbonitrile, 2,3,5-tri-9H-carbazole-9-yl-6-chloro-(3.0 g, 4.6 mmol), the compound M-l (2.5 g, 5.5 mmol), potassium carbonate (1.1 g, 8.2 mmol), and DMF (20 mL) were put into a 50-mL three-neck flask and stirred at 120 degrees C. for four hours. Saturated ammonium chloride aqueous solution (10 mL) was added to the reaction mixture. Then, deposited solid was purified by silica-gel column chromatography to obtain a red solid (4.1 g). Through ASAP-MS analysis, the red solid was identified as TADF4 (yield rate 84%).

Synthesis Example 5

A synthesis method of the compound TADF5 will be described below.

[Formula 151]

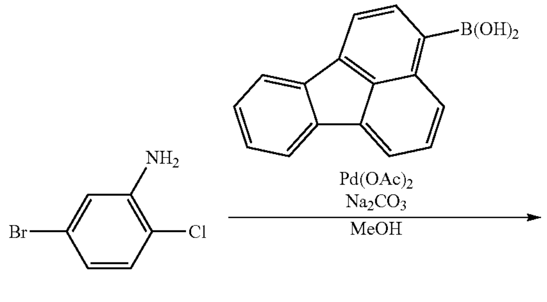

-continued

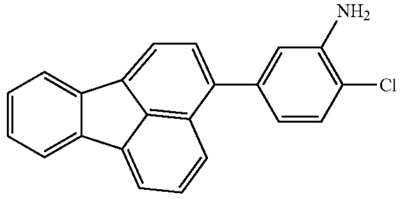

M-m

Under nitrogen atmosphere, 5-bromo-2-chloro-aniline (10 g, 49 mmol), 3-fluoranthene boronate (12 g, 49 mmol), palladium acetate (0.11 g, 0.5 mmol), sodium carbonate (10 g, 98 mmol), and methanol (100 mL) were put into a 300-mL three-neck flask and stirred at 80 degrees C. for six hours. Ion exchange water (100 mL) was added to the reaction mixture. Then, deposited solid was purified by silica-gel column chromatography to obtain a white solid (13.7 g). Through GC-MS analysis, the white solid was identified as a compound M-m (yield rate 85%).

[Formula 152]

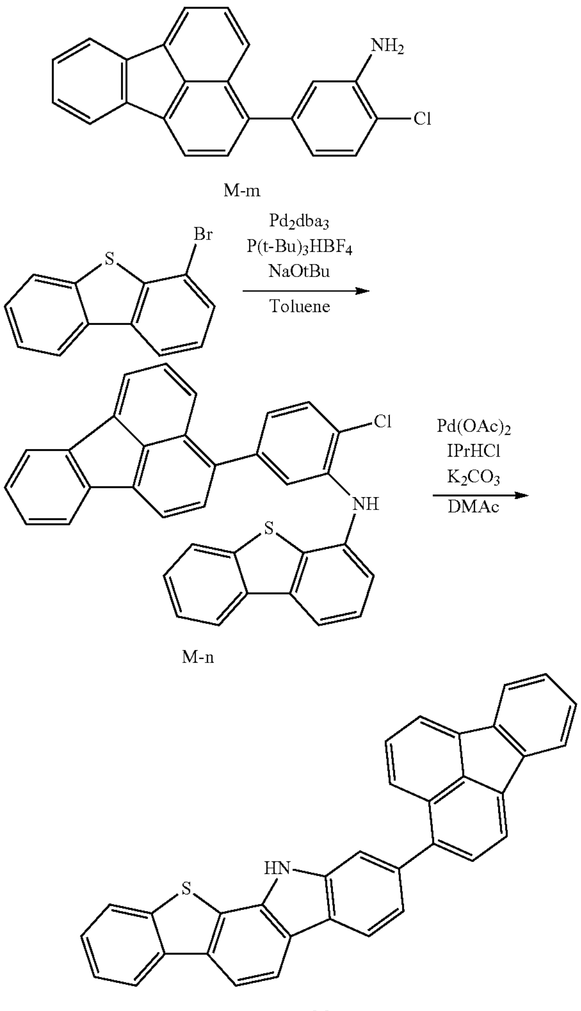

M-m

M-n

M-o

Under nitrogen atmosphere, 4-bromodibenzothiophene (10 g, 38 mmol), the compound M-m (12.5 g, 38 mmol), tris(dibenzylidene acetone)dipalladium(0) ($Pd_2dba_3$) (0.35 g, 0.38 mmol), tri-tert-butylphosphonium tetrafluoroborate ($P(t\text{-}Bu)_3HBF_4$) (0.44 g, 1.5 mmol), sodium tert-butoxide (NaOtBu) (5.5 g, 57 mmol), and toluene (120 mL), which were put into a 200-mL three-neck flask, were stirred at 60 degrees C. for four hours and then cooled to a room temperature (25 degrees C.). The reaction solution was purified by silica-gel column chromatography to obtain a yellow solid (16.9 g). Through GC-MS analysis, the yellow solid was identified as a compound M-n (yield rate 87%).

Under nitrogen atmosphere, the compound M-n (16.9 g, 33.1 mmol), 1,3-bis(2,6-diisopropylphenyl)imidazoriumchloride (IPrHCl) (0.28 g, 0.66 mmol), palladium(II) acetate ($Pd(OAc)_2$) (74 mg, 0.33 mmol), potassium carbonate (9.1 g, 66 mmol), and N,N-dimethylacetamide (DMAc) (100 mL) were put into a 200-mL three-neck flask, stirred at 160 degrees C. for three hours, and then cooled to a room temperature (25 degrees C.). The reaction solution was purified by silica-gel column chromatography to obtain a yellow solid (14.3 g). Through GC-MS analysis, the yellow solid was identified as a compound M-o (yield rate 91%).

[Formula 153]

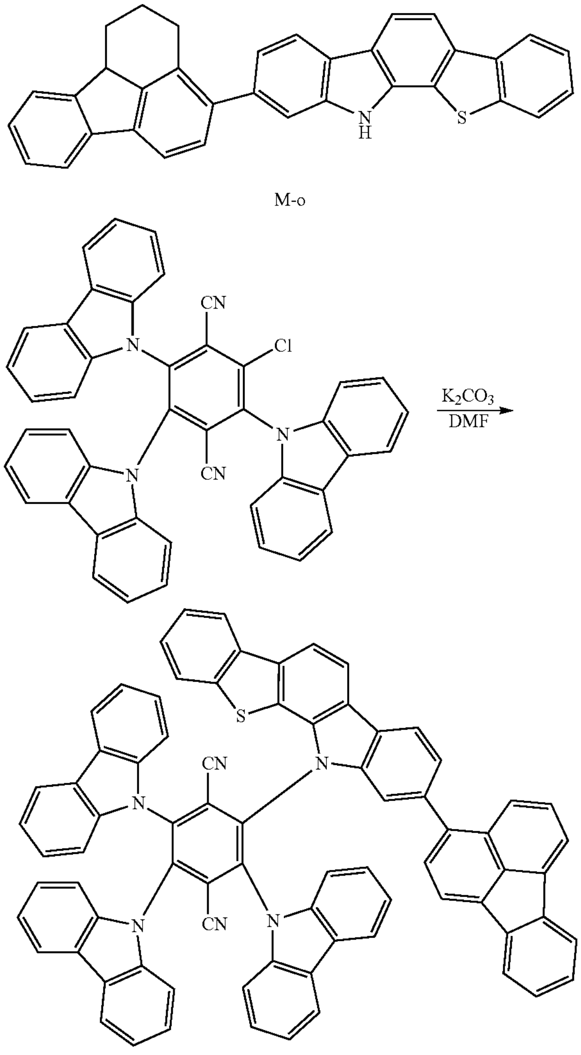

M-o

TADF5

Under nitrogen atmosphere, 1,4-benzene dicarbonitrile, 2,3,5-tri-9H-carbazole-9-yl-6-chloro (3.0 g, 4.6 mmol), the compound M-o (2.6 g, 5.5 mmol), potassium carbonate (1.1 g, 8.2 mmol), and DMF (20 mL) were put into a 50-mL three-neck flask and stirred at 120 degrees C. for four hours. Saturated ammonium chloride aqueous solution (10 mL) was added to the reaction mixture. Then, deposited solid was purified by silica-gel column chromatography to obtain a red solid (3.0 g). Through ASAP-MS analysis, the red solid was identified as TADF5 (yield rate 66%).

Comparative Synthesis Example 1

The comparative compound Ref-1 was synthesized according to synthesis example 21 disclosed in WO 2020/022378 A1.

Comparative Synthesis Example 2

The comparative compound Ref-2 was synthesized according to synthesis example 22 disclosed in WO 2020/022378 A1.

Comparative Synthesis Example 3

A synthesis method of a comparative compound Ref-3 will be described below.

[Formula 154]

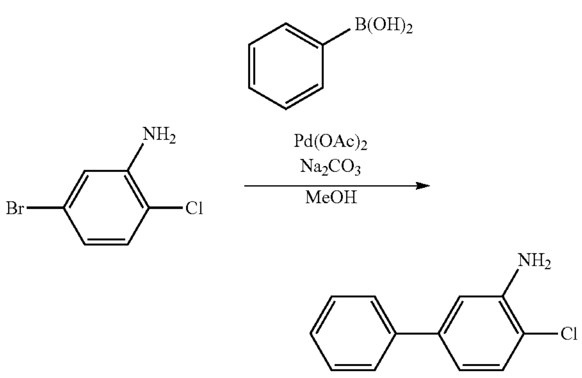

M-E1

Under nitrogen atmosphere, 5-bromo-2-chloro-aniline (50 g, 242 mmol), phenyl boronate (32.5 g, 266 mmol), palladium acetate (1.4 g, 6.2 mmol), sodium carbonate (50 g, 484 mmol), and methanol (250 mL) were put into a 500-mL three-neck flask and were stirred at 80 degrees C. for 6 hours. Ion exchange water (100 mL) was added to the reaction mixture. Then, deposited solid was purified by silica-gel column chromatography to obtain a white solid (39.5 g). Through GC-MS analysis, the white solid was identified as a compound M-E1 (yield rate 80%).

[Formula 155]

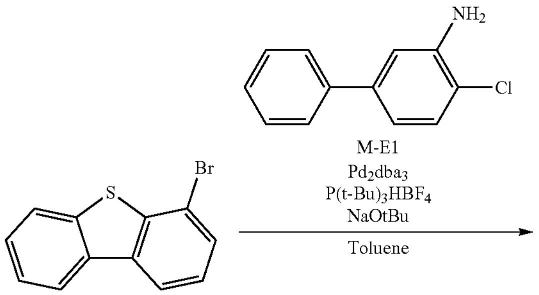

-continued

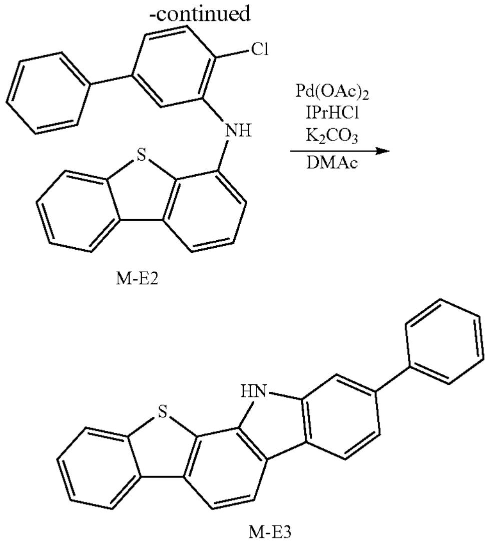

M-E2

M-E3

Under nitrogen atmosphere, 4-bromodibenzothiophene (12.9 g, 49.1 mmol), the compound M-E1 (10 g, 49.1 mmol), tris(dibenzylidene acetone)dipalladium(0) ($Pd_2dba_3$) (0.67 g, 0.74 mmol), tri-tert-butylphosphonium tetrafluoroborate ($P(t\text{-}Bu)_3HBF_4$) (0.85 g, 2.95 mmol), sodium tert-butoxide (NaOtBu) (7.1 g, 73.7 mmol), and toluene (130 mL), which were put into a 200-mL three-neck flask, were stirred at 60 degrees C. for seven hours and then cooled to a room temperature (25 degrees C.). The reaction solution was purified by silica-gel column chromatography to obtain a white solid (18 g). Through GC-MS analysis, the white solid was identified as a compound M-E2 (yield rate 93%).

Under nitrogen atmosphere, the compound M-E2 (10 g, 26 mmol), 1,3-bis(2,6-diisopropylphenyl)imidazoriumchloride (IPrHCl) (0.22 g, 0.52 mmol), palladium(II) acetate ($Pd(OAc)_2$) (58 mg, 0.26 mmol), potassium carbonate (7.1 g, 52 mmol), and N,N-dimethylacetamide (DMAc) of 90 mL, which were put into a 200-mL three-neck flask, were stirred at 160 degrees C. for three hours and were then cooled to a room temperature (25 degrees C.). The reaction solution was purified by silica-gel column chromatography to obtain a white solid (7.9 g). Through GC-MS analysis, the white solid was identified as a compound M-E3 (yield rate 87%).

[Formula 156]

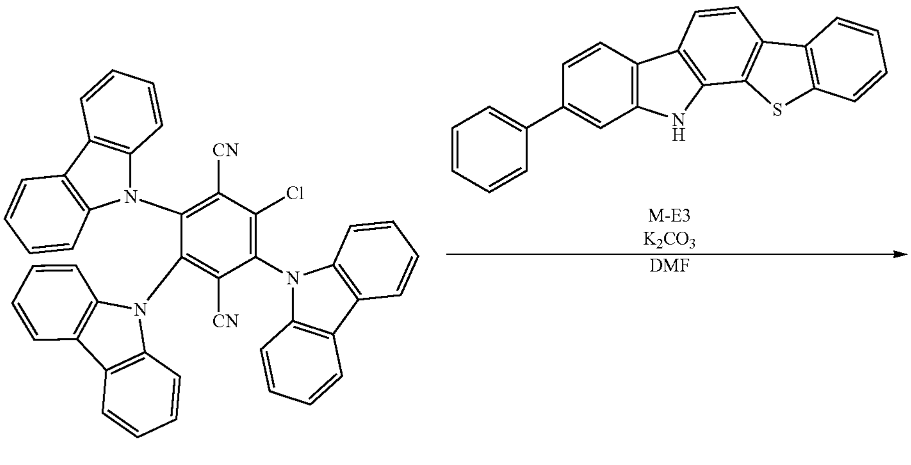

-continued

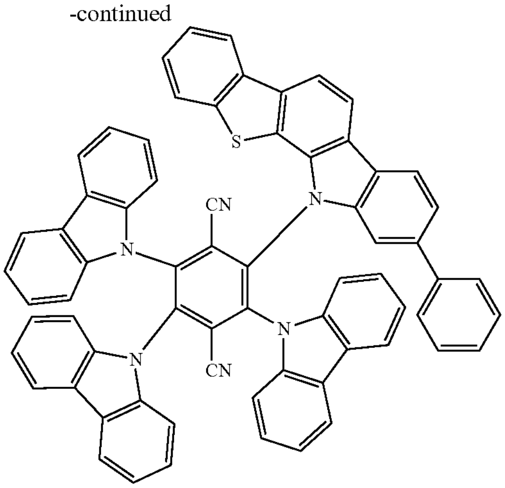

Ref-3

Under nitrogen atmosphere, 1,4-benzene dicarbonitrile, 2,3,5-tri-9H-carbazole-9-yl-6-chloro (3.0 g, 4.6 mmol), the compound M-E3 (1.9 g, 5.5 mmol), potassium carbonate (1.1 g, 8.2 mmol), and DMF (11 mL) were put into a 50-mL three-neck flask and were stirred at 120 degrees C. for four hours. Saturated ammonium chloride aqueous solution (10 mL) was added to the reaction mixture. Then, deposited solid was purified by silica-gel column chromatography to obtain a red solid (2.3 g). Through ASAP-MS analysis, the red solid was identified as Comparative Compound Ref-3 (yield rate 52%).

Comparative Synthesis Example 4

A synthesis method of a comparative compound Ref-4 will be described below.

[Formula 157]

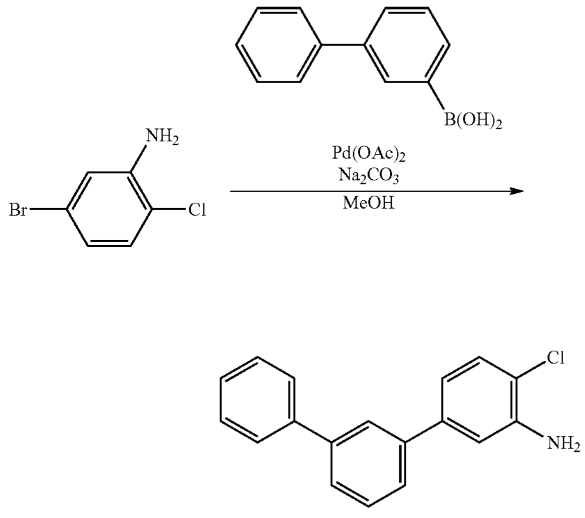

M-p

Under nitrogen atmosphere, 5-bromo-2-chloro-aniline (10 g, 49 mmol), 3-biphenyl boronate (9.7 g, 49 mmol), palladium acetate (0.11 g, 0.5 mmol), sodium carbonate (10 g, 98 mmol), and methanol (100 mL) were put into a 300-mL three-neck flask and stirred at 80 degrees C. for seven hours. Ion exchange water (100 mL) was added to the reaction mixture. Then, deposited solid was purified by silica-gel column chromatography to obtain a white solid (13.0 g). Through GC-MS analysis, the white solid was identified as a compound M-p (yield rate 95%).

[Formula 158]

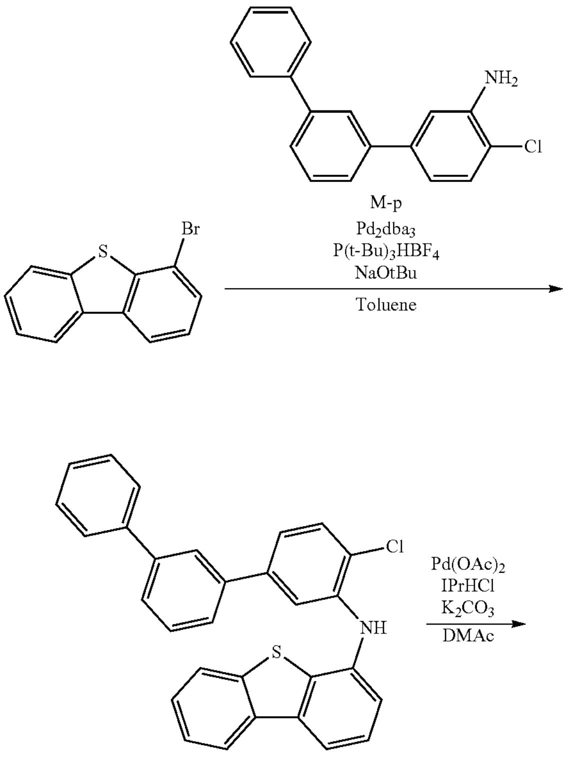

M-q

-continued

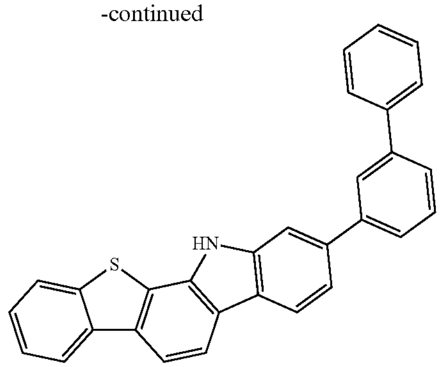

M-r

Under nitrogen atmosphere, 4-bromodibenzothiophene (10 g, 38 mmol), the compound M-p (11 g, 38 mmol), tris(dibenzylidene acetone)dipalladium(0) ($Pd_2dba_3$) (0.35 g, 0.38 mmol), tri-tert-butylphosphonium tetrafluoroborate ($P(t\text{-}Bu)_3HBF_4$) (0.44 g, 1.5 mmol), sodium tert-butoxide (NaOtBu) (5.5 g, 57 mmol), and toluene (120 mL) were put into a 200-mL three-neck flask, stirred at 60 degrees C. for four hours, and then cooled to a room temperature (25 degrees C.). The reaction solution was purified by silica-gel column chromatography to obtain a white solid (15.6 g). Through GC-MS analysis, the white solid was identified as a compound M-q (yield rate 89%).

Under nitrogen atmosphere, the compound M-q (15 g, 32 mmol), 1,3-bis(2,6-diisopropylphenyl)imidazoriumchloride (IPrHCl) (0.27 g, 0.64 mmol), palladium(II) acetate ($Pd(OAc)_2$) (72 mg, 0.32 mmol), potassium carbonate (8.8 g, 64 mmol), and N,N-dimethylacetamide (DMAc) (100 mL), which were put into a 200-mL three-neck flask, were stirred at 160 degrees C. for three hours and were then cooled to a room temperature (25 degrees C.). The reaction solution was purified by silica-gel column chromatography to obtain a white solid (12.8 g). Through GC-MS analysis, the white solid was identified as a compound M-r (yield rate 94%).

[Formula 159]

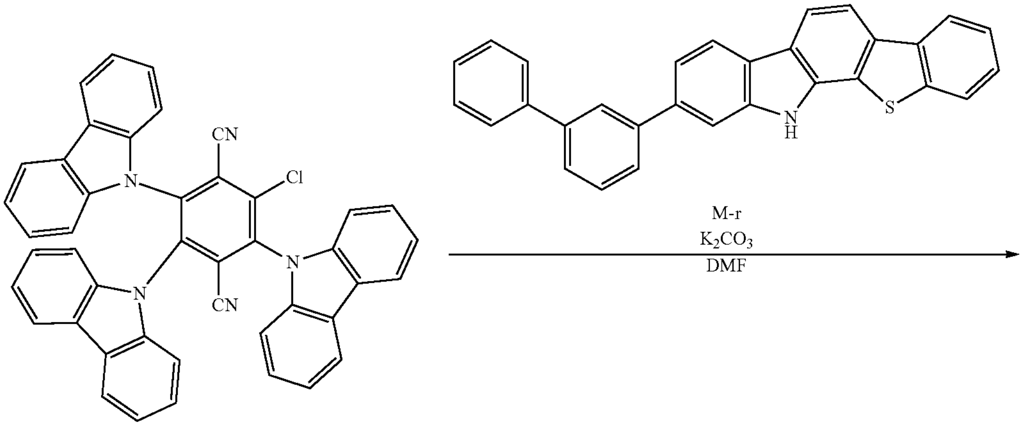

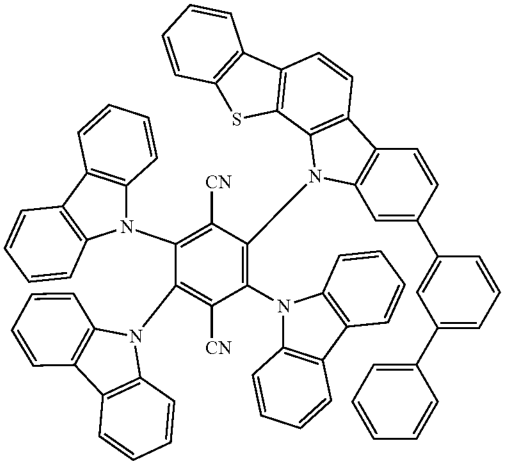

Ref-4

Under nitrogen atmosphere, 1,4-benzene dicarbonitrile, 2,3,5-tri-9H-carbazole-9-yl-6-chloro-(3.0 g, 4.6 mmol), the compound M-r (2.4 g, 5.5 mmol), potassium carbonate (1.1 g, 8.2 mmol), and DMF (20 mL) were put into a 50-mL three-neck flask and were stirred at 120 degrees C. for four hours. Saturated ammonium chloride aqueous solution (10 mL) was added to the reaction mixture. Then, deposited solid was purified by silica-gel column chromatography to obtain a red solid (3.7 g). Through ASAP-MS analysis, the red solid was identified as the comparative compound Ref-4 (yield rate 77%).

Comparative Synthesis Example 5

A synthesis method of a comparative compound Ref-5 will be described below.

[Formula 160]

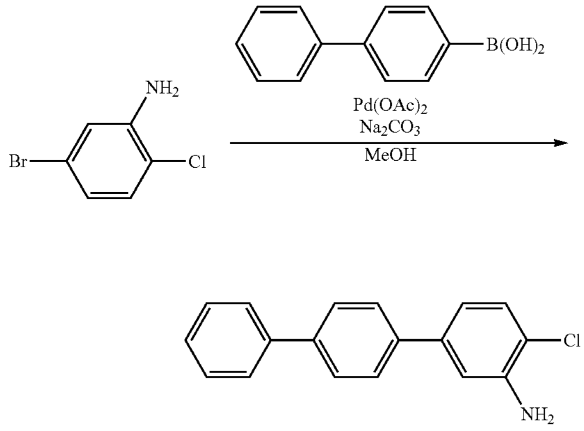

M-s

Under nitrogen atmosphere, 5-bromo-2-chloro-aniline (10 g, 49 mmol), 4-biphenyl boronate (9.7 g, 49 mmol), palladium acetate (0.11 g, 0.5 mmol), sodium carbonate (10 g, 98 mmol), and methanol (100 mL) were put into a 300-mL three-neck flask and were stirred at 80 degrees C. for seven hours. Ion exchange water (100 mL) was added to the reaction mixture. Then, deposited solid was purified by silica-gel column chromatography to obtain a white solid (12.3 g). Through GC-MS analysis, the white solid was identified as a compound M-s (yield rate 90%).

[Formula 161]

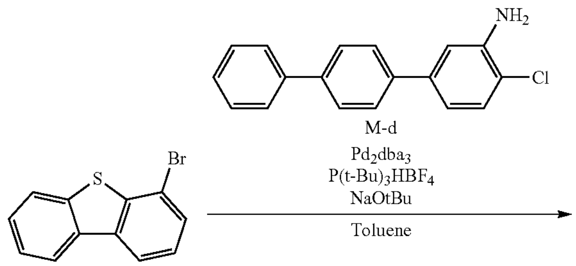

-continued

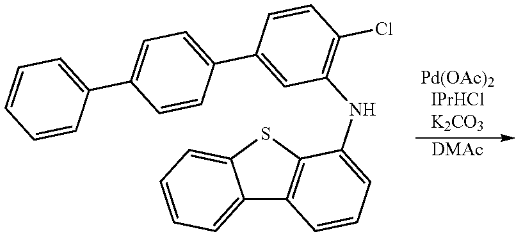

M-t

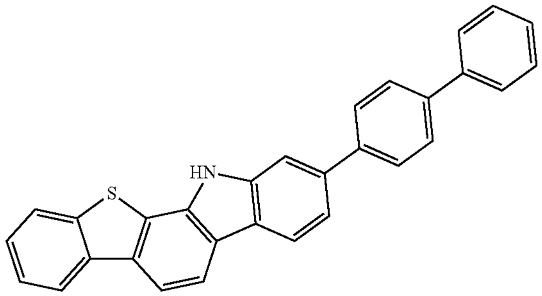

M-u

Under nitrogen atmosphere, 4-bromodibenzothiophene (10 g, 38 mmol), the compound M-s (11 g, 38 mmol), tris(dibenzylidene acetone)dipalladium(0) ($Pd_2dba_3$) (0.35 g, 0.38 mmol), tri-tert-butylphosphonium tetrafluoroborate ($P(t\text{-}Bu)_3HBF_4$) (0.44 g, 1.5 mmol), sodium tert-butoxide (NaOtBu) (5.5 g, 57 mmol), and toluene (120 mL), which were put into a 200-mL three-neck flask, were stirred at 60 degrees C. for four hours and then cooled to a room temperature (25 degrees C.). The reaction solution was purified by silica-gel column chromatography to obtain a white solid (12.4 g). Through GC-MS analysis, the white solid was identified as a compound M-t (yield rate 71%).

Under nitrogen atmosphere, the compound M-t (12 g, 26 mmol), 1,3-bis(2,6-diisopropylphenyl)imidazoriumchloride (IPrHCl) (0.22 g, 0.52 mmol), palladium(II) acetate ($Pd(OAc)_2$) (59 mg, 0.26 mmol), potassium carbonate (7.2 g, 52 mmol), and N,N-dimethylacetamide (DMAc) (100 mL), which were put into a 200-mL three-neck flask, were stirred at 160 degrees C. for three hours and were then cooled to a room temperature (25 degrees C.). The reaction solution was purified by silica-gel column chromatography to obtain a white solid (9.4 g). Through GC-MS analysis, the white solid was identified as a compound M-u (yield rate 85%).

[Formula 162]

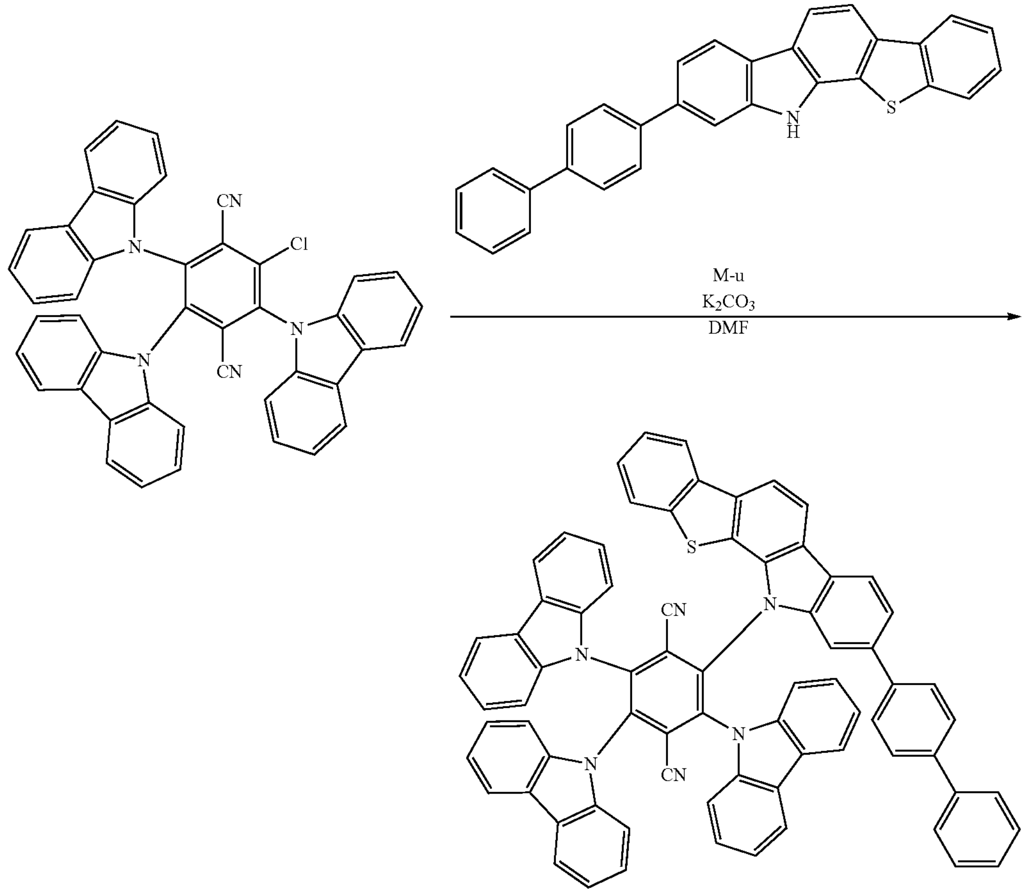

Ref-5

Under nitrogen atmosphere, 1,4-benzene dicarbonitrile, 2,3,5-tri-9H-carbazole-9-yl-6-chloro-(3.0 g, 4.6 mmol), the compound M-u (2.4 g, 5.5 mmol), potassium carbonate (1.1 g, 8.2 mmol), and DMF (20 mL) were put into a 50-mL three-neck flask and were stirred at 120 degrees C. for four hours. Saturated ammonium chloride aqueous solution (10 mL) was added to the reaction mixture. Then, deposited solid was purified by silica-gel column chromatography to obtain a red solid (2.6 g). Through ASAP-MS analysis, the red solid was identified as comparative compound Ref-5 (yield rate 55%).

Comparative Synthesis Example 6

A synthesis method of a comparative compound Ref-6 will be described below.

[Formula 163]

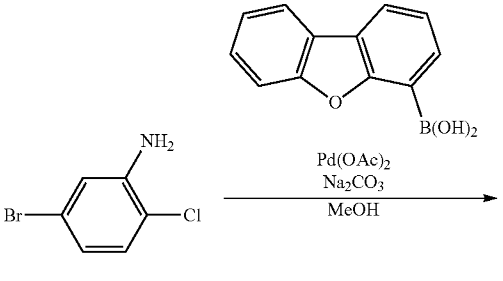

-continued

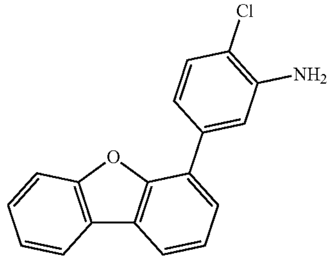

M-v

Under nitrogen atmosphere, 5-bromo-2-chloro-aniline (10 g, 49 mmol), 4-dibenzofuranyl boronate (10.4 g, 49 mmol), palladium acetate (0.11 g, 0.5 mmol), sodium carbonate (10 g, 98 mmol), and methanol (100 mL) were put into a 300-mL three-neck flask and stirred at 80 degrees C. for seven hours. Ion exchange water (100 mL) was added to the reaction mixture. Then, deposited solid was purified by silica-gel column chromatography to obtain a white solid (12.7 g). Through GC-MS analysis, the white solid was identified as a compound M-v (yield rate 88%).

[Formula 164]

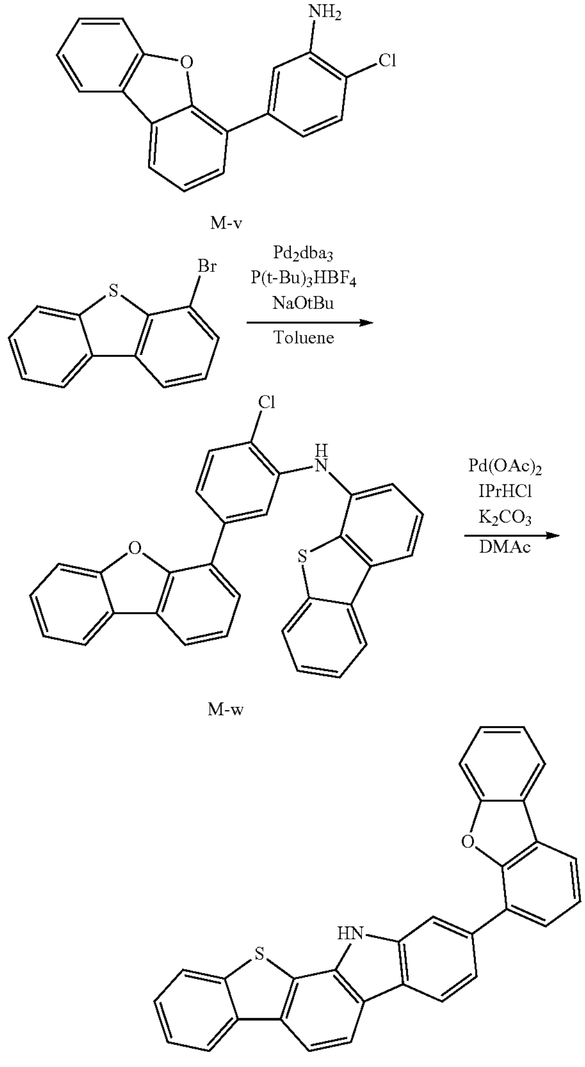

M-v

M-w

M-x

Under nitrogen atmosphere, 4-bromodibenzothiophene (10 g, 38 mmol), the compound M-v (11.2 g, 38 mmol), tris(dibenzylidene acetone)dipalladium(0) ($Pd_2dba_3$) (0.35 g, 0.38 mmol), tri-tert-butylphosphonium tetrafluoroborate ($P(t\text{-}Bu)_3HBF_4$) (0.44 g, 1.5 mmol), sodium tert-butoxide (NaOtBu) (5.5 g, 57 mmol), and toluene (120 mL) were put into a 200-mL three-neck flask, stirred at 60 degrees C. for seven hours, and then cooled to a room temperature (25 degrees C.). The reaction solution was purified by silica-gel column chromatography to obtain a white solid (13.2 g). Through GC-MS analysis, the white solid was identified as a compound M-w (yield rate 73%).

Under nitrogen atmosphere, the compound M-w (13 g, 27 mmol), 1,3-bis(2,6-diisopropylphenyl)imidazoriumchloride (IPrHCl) (0.23 g, 0.54 mmol), palladium(II) acetate ($Pd(OAc)_2$) (61 mg, 0.27 mmol), potassium carbonate (7.5 g, 54 mmol), and N,N-dimethylacetamide (DMAc) (100 mL) were put into a 200-mL three-neck flask, stirred at 160 degrees C. for three hours, and then cooled to a room temperature (25 degrees C.). The reaction solution was purified by silica-gel column chromatography to obtain a white solid (8.2 g). Through GC-MS analysis, the white solid was identified as a compound M-x (yield rate 69%).

[Formula 165]

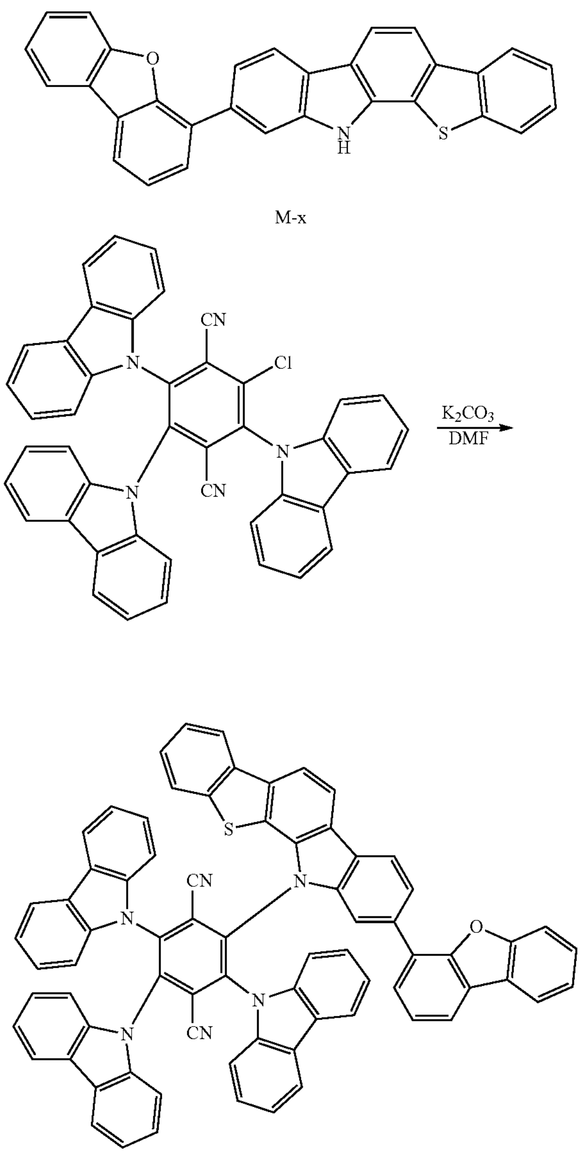

M-x

Ref-6

Under nitrogen atmosphere, 1,4-benzene dicarbonitrile, 2,3,5-tri-9H-carbazole-9-yl-6-chloro-(3.0 g, 4.6 mmol), the compound M-x (2.4 g, 5.5 mmol), potassium carbonate (1.1 g, 8.2 mmol), and DMF (20 mL) were put into a 50-mL three-neck flask and stirred at 120 degrees C. for four hours. Saturated ammonium chloride aqueous solution (10 mL) was added to the reaction mixture. Then, deposited solid was purified by silica-gel column chromatography to obtain a red solid (3.6 g). Through ASAP-MS analysis, the red solid was identified as the comparative compound Ref-6 (yield rate 74%).

The invention claimed is:

1. A compound represented by one of formulae (11) to (13) below, (11)

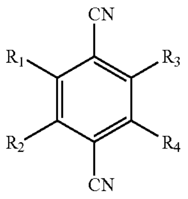

(12)

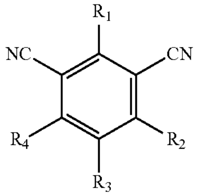

(13)

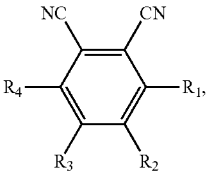

where $R_1$ to $R_4$ are each independently a group $D_1$ represented by one of formulae (1-1) to (1-6) below, or $D_2$ represented by one of formulae (2-1) to (2-4) below;

at least one of $R_1$ to $R_4$ is the group $D_1$;

at least one of $R_1$ to $R_4$ is the group $D_2$;

when a plurality of groups $D_1$ are present, the plurality of groups $D_1$ are mutually the same or different; and when a plurality of groups $D_2$ are present, the plurality of groups $D_2$ are mutually the same or different, (1-1)

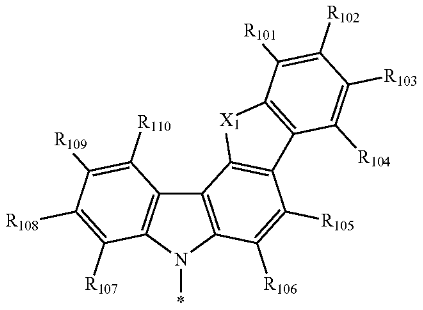

(1-2)

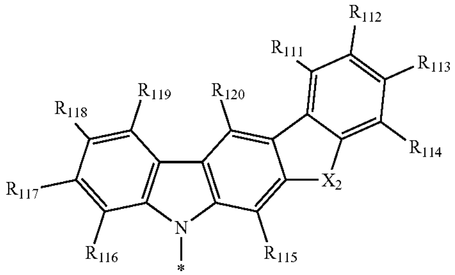

-continued (1-3)

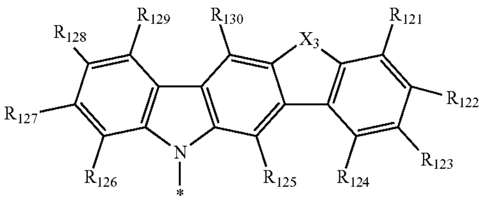

(1-4)

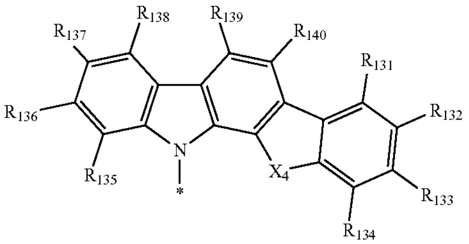

(1-5)

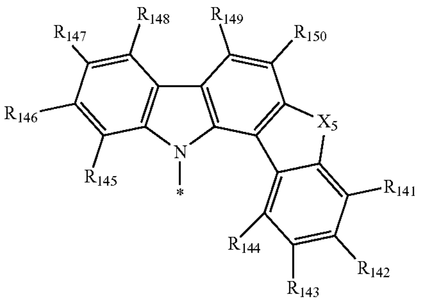

(1-6)

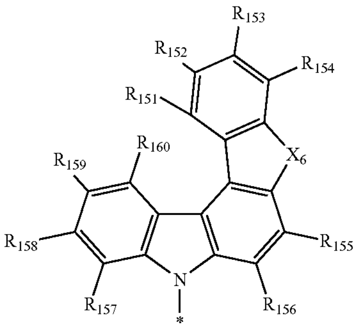

(110)

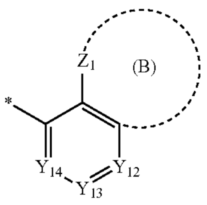

(120)

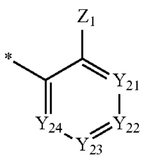

-continued (2-1)

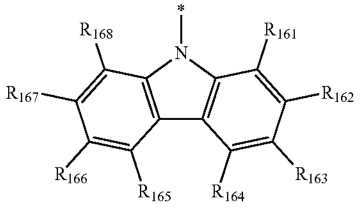

(2-2)

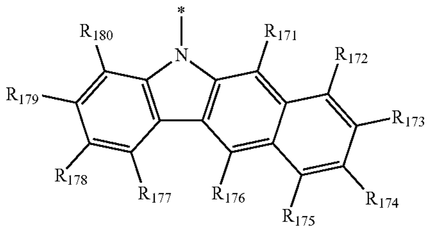

(2-3)

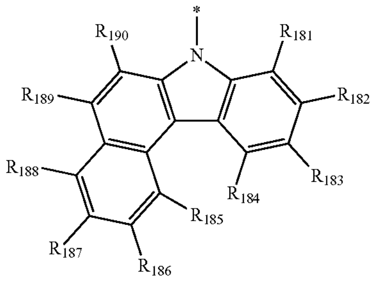

(2-4)

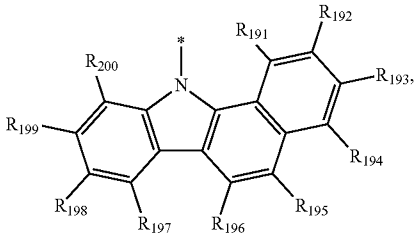

wherein in formulae (1-1) to (1-6);

$X_1$ to $X_6$ are each independently an oxygen atom or a sulfur atom;

$R_{101}$ to $R_{160}$ are each independently a hydrogen atom, a substituent, a group represented by the formula (110), or a group represented by the formula (120); and in at least one group $D_1$, at least one of $R_{101}$ to $R_{160}$ is a group represented by the formula (110) or a group represented by the formula (120), in the formula (110), $Z_1$ is an atom forming a ring (B) and is a carbon atom or a nitrogen atom, the ring (B) including $Z_1$ is a substituted or unsubstituted aromatic hydrocarbon ring having 6 to 30 ring carbon atoms or a substituted or unsubstituted heterocyclic ring having 5 to 30 ring carbon atoms;

$Y_{12}$ to $Y_{14}$ are each independently a nitrogen atom or $CR_{10A}$; and $R_{10A}$ is each independently a hydrogen atom or a substituent, at least one combination of adjacent two or more of a plurality of $R_{10A}$ are bonded to each other to form a ring, the ring (B) is bonded to one $R_{10A}$ adjacent to the ring (B) to form a ring, or the ring (B) is bonded to at least one combination of adjacent two or more of a plurality of $R_{10A}$, in the formula (120);

$Z_2$ is a substituted or unsubstituted aryl group having 6 to 30 ring carbon atoms or a substituted or unsubstituted heterocyclic group having 5 to 30 ring atoms;

$Y_{21}$ to $Y_{24}$ are each independently a nitrogen atom or $CR_{20A}$;

$R_{20A}$ each independently a hydrogen atom or a substituent, or at least one combination of adjacent two or more of a plurality of $R_{20A}$ are mutually bonded to form a ring;

a plurality of $R_{10A}$ are mutually the same or different; and a plurality of $R_{20A}$ are mutually the same or different, in the formulas (2-1) to (2-4), $R_{161}$ to $R_{168}$ and $R_{171}$ to $R_{200}$ are each independently a hydrogen atom or a substituent;

$R_{101}$ to $R_{160}$ as a substituent except for a group represented by the formula (110) and a group represented by the formula (120), $R_{10A}$ as a substituent in the formula (110), and $R_{20A}$ as a substituent in the formula (120) in the formulae (1-1) to (1-6), and $R_{161}$ to $R_{168}$ and $R_{171}$ to $R_{200}$ as a substituent in the formulae (2-1) to (2-4) are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, a group represented by $—N(Rz)_2$, a thiol group, a substituted or unsubstituted alkylthio group having 1 to 30 carbon atoms, a substituted or unsubstituted aralkyl group having 7 to 30 ring carbon atoms, a substituted germanium group, a substituted phosphine oxide group, a nitro group, a substituted boryl group, or a substituted or unsubstituted arylthio group having 6 to 30 ring carbon atoms;

Rz is a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms;

two Rz in $—N(Rz)_2$ are mutually the same or different;

in the formulae (1-1) to (1-6), * each independently represents a bonding position to a carbon atom of the six-membered ring in the formulae (11) to (13);

in the formula (110), * represents a bonding position to a carbon atom of the six-membered ring in the formulae (1-1) to (1-6);

in the formula (120), * represents a bonding position to a carbon atom of the six-membered ring in the formulae (1-1) to (1-6); and in the formulae (2-1) to (2-4), * each independently represents a bonding position to a carbon atom of the six-membered ring in the formulae (11) to (13).

2. The compound according to claim 1, wherein when three groups $D_1$ are selected as the groups for $R_1$ to $R_4$, all of the selected three groups $D_1$ are represented by one of the formulae (1-1) to (1-6) and are mutually identical groups including substituent(s) thereof, and when two groups $D_1$ are selected as the groups for $R_1$ to $R_4$, all of the selected two groups $D_1$ are represented by one of the formulae (1-1) to (1-6) and are mutually identical groups including substituent(s) thereof.

3. The compound according to claim 1, wherein when three groups $D_2$ are selected as the groups for $R_1$ to $R_4$, all of the selected three groups $D_2$ are represented by one of the formulae (2-1) to (2-4) and are mutually identical groups including substituent(s) thereof, and when two groups $D_2$ are selected as the groups for $R_1$ to $R_4$, all of the selected two groups $D_2$ are represented by one of the formulae (2-1) to (2-4) and are mutually identical groups including substituent(s) thereof.

4. The compound according to claim 1, wherein one of $R_{107}$ to $R_{110}$ in the formula (1-1) is a group represented by the formula (110) or a group represented by the formula (120), one of $R_{116}$ to $R_{119}$ in the formula (1-2) is a group represented by the formula (110) or a group represented by the formula (120), one of $R_{126}$ to $R_{129}$ in the formula (1-3) is a group represented by the formula (110) or a group represented by the formula (120), one of $R_{135}$ to $R_{138}$ in the formula (1-4) is a group represented by the formula (110) or a group represented by the formula (120), one of $R_{145}$ to $R_{148}$ in the formula (1-5) is a group represented by the formula (110) or a group represented by the formula (120), or one of $R_{157}$ to $R_{160}$ in the formula (1-6) is a group represented by the formula (110) or a group represented by the formula (120).

5. The compound according to claim 1, wherein the group $D_2$ is a group represented by the formula (2-1).

6. The compound according to claim 1, wherein only one of $R_1$ to $R_4$ is the group $D_1$.

7. The compound according to claim 1, wherein only two of $R_1$ to $R_4$ are the groups $D_1$.

8. The compound according to claim 1, wherein the compound is represented by any one of formulae (1003A), (1007A), (1008A), (1012A), (1018A), and (1021A) below, (1003A)

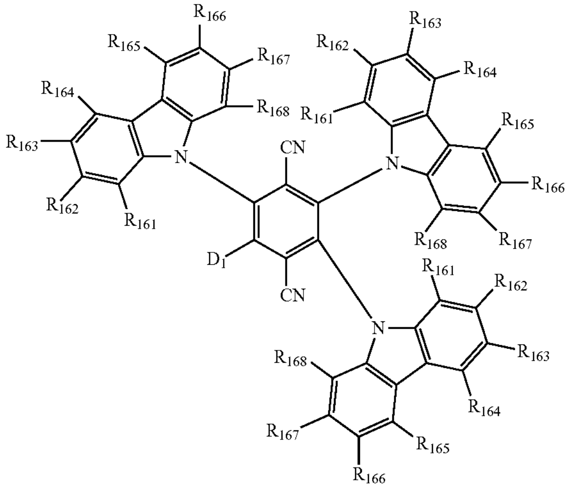

-continued (1007A)

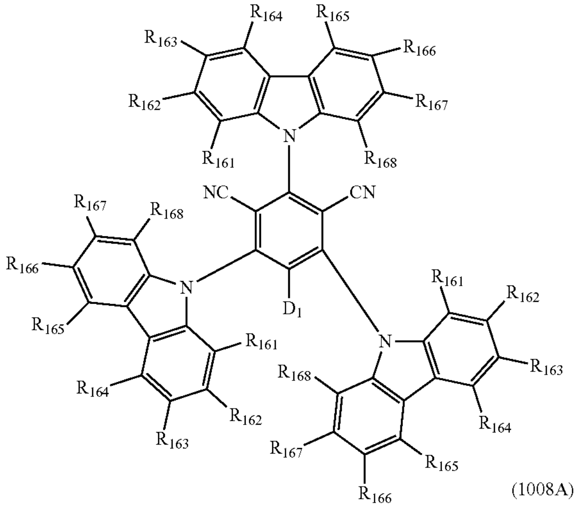

(1008A)

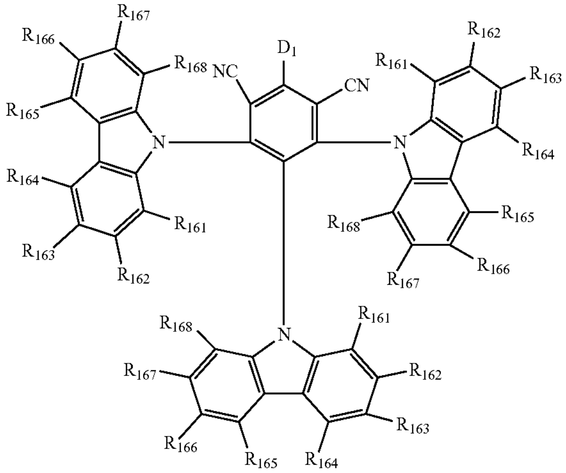

(1012A)

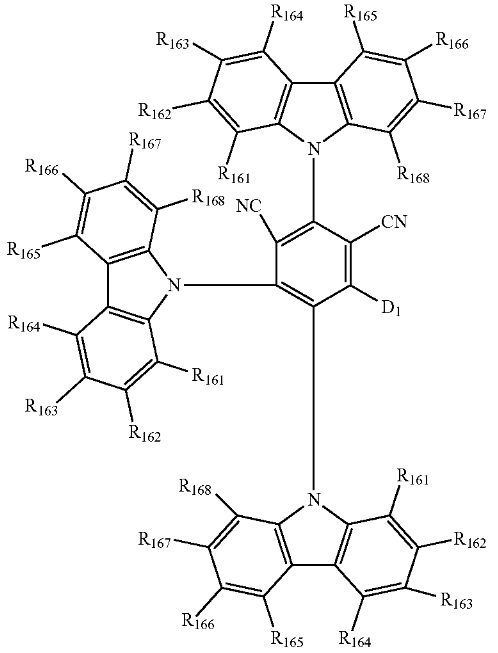

-continued (1018A)

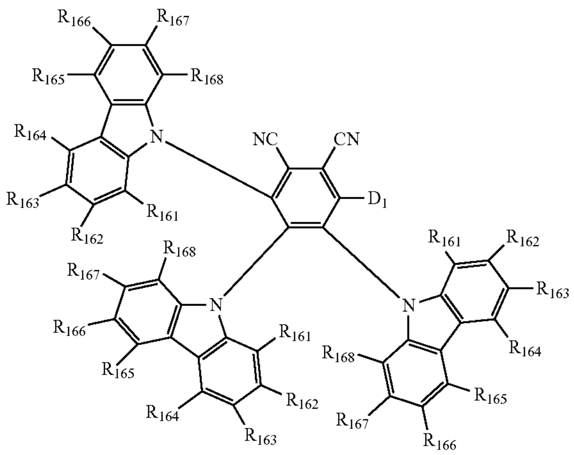

(1021A)

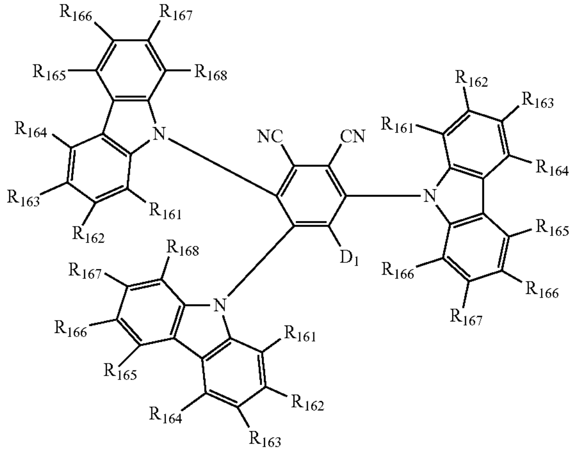

(1018A)

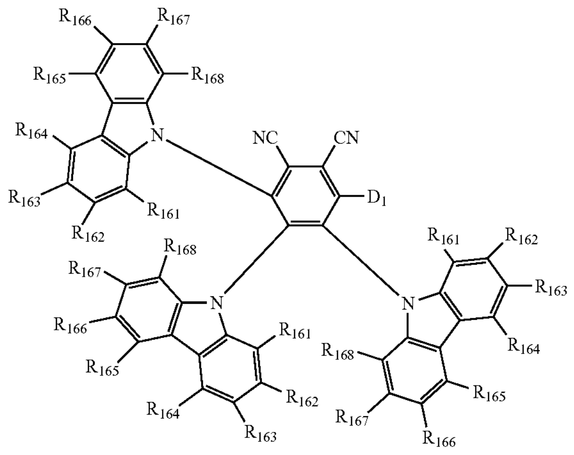

-continued (1021A)

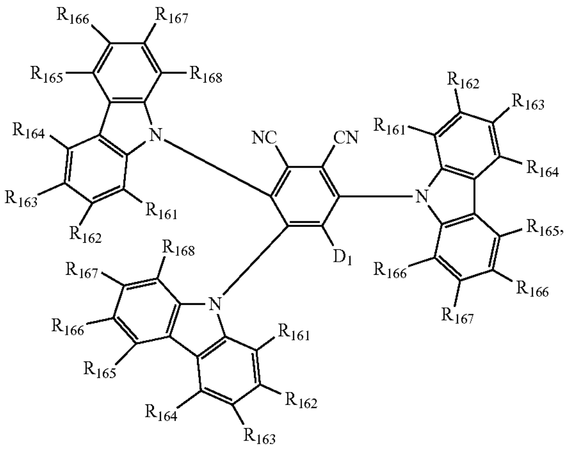

where: $D_1$ represents the same as the group $D_1$ represented by one of the formulae (1-1) to (1-6) and $R_{161}$ to $R_{168}$ each independently represent the same as $R_{161}$ to $R_{168}$ in the formula (2-1).

9. The compound according to claim 1, wherein the group $D_1$ is a group represented by the formula (1-4) or the formula (1-5).

10. The compound according to claim 1, wherein $R_{161}$ to $R_{168}$ and $R_{171}$ to $R_{200}$ in the group $D_2$ are each a hydrogen atom.

11. The compound according to claim 1, wherein when one of $R_1$ to $R_4$ is the group $D_1$, only one of $R_{101}$ to $R_{160}$ in the group $D_1$ is a group represented by the formula (110) or a group represented by the formula (120), when two of $R_1$ to $R_4$ are the groups $D_1$, only one of $R_{101}$ to $R_{160}$ in each of the groups $D_1$ is a group represented by the formula (110) or a group represented by the formula (120), and when three of $R_1$ to $R_4$ are the groups $D_1$, only one of $R_{101}$ to $R_{160}$ in each of the groups $D_1$ is a group represented by the formula (110) or a group represented by the formula (120).

12. The compound according to claim 1, wherein in at least one of the groups $D_1$, at least one of $R_{101}$ to $R_{160}$ is a group represented by the formula (110).

13. The compound according to claim 1, wherein when one of $R_1$ to $R_4$ is the group $D_1$, only one of $R_{101}$ to $R_{160}$ in the group $D_1$ is a group represented by the formula (110), when two of $R_1$ to $R_4$ are the groups $D_1$, only one of $R_{101}$ to $R_{160}$ in each of the groups $D_1$ is a group represented by the formula (110), and when three of $R_1$ to $R_4$ are the groups $D_1$, only one of $R_{101}$ to $R_{160}$ in each of the groups $D_1$ is a group represented by the formula (110).

14. The compound according to claim 1, wherein $Z_1$ in the formula (110) is a carbon atom.

15. The compound according to claim 1, wherein a group represented by the formula (110) is a group represented by any one of formulae (111) to (117) below, (111)

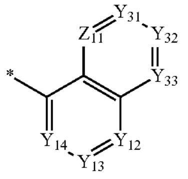

(112)

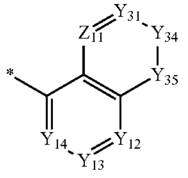

(113)

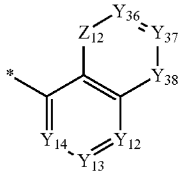

(114)

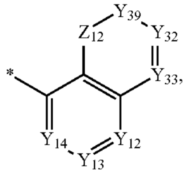

where in the formula (111):

$Y_{12}$ to $Y_{14}$ are each independently a nitrogen atom or $CR_{10A}$;

$Z_{11}$ and $Y_{31}$ to $Y_{33}$ are each independently a nitrogen atom or $CR_{30A}$;

$R_{10A}$ and $R_{30A}$ are each independently a hydrogen atom or a substituent, or at least one combination of adjacent two or more groups selected from the group consisting of one or more of $R_{30A}$ and one or more of $R_{10A}$ are mutually bonded to form a ring; and $R_{10A}$ as a substituent and $R_{30A}$ as a substituent each independently represent the same as $R_{10A}$ as a substituent in the formula (110), in the formula (112):

$Y_{12}$ to $Y_{14}$ are each independently a nitrogen atom or $CR_{10A}$;

$Z_{11}$ and $Y_{31}$ are each independently a nitrogen atom or $CR_{30A}$;

$Y_{34}$ and $Y_{35}$ are each independently $NR_{30B}$, an oxygen atom, a sulfur atom, or $CR_{30C}R_{30D}$;

$R_{10A}$, $R_{30A}$, $R_{30B}$, $R_{30C}$, and $R_{30D}$ are each independently a hydrogen atom or a substituent, or at least one combination of adjacent two or more groups selected from the group consisting of one or more of $R_{10A}$, one or more of $R_{30A}$, one or more of $R_{30B}$, one or more of $R_{30C}$, and one or more of $R_{30D}$ are mutually bonded to form a ring; and $R_{10A}$ as a substituent and $R_{30A}$, $R_{30B}$, $R_{30C}$, and $R_{30D}$ as substituents each independently represent the same as $R_{10A}$ as a substituent in the formula (110), in the formula (113):

$Y_{12}$ to $Y_{14}$ are each independently a nitrogen atom or $CR_{10A}$;

$Z_{12}$ is $NR_{30B}$ or $CR_{30C}R_{30D}$;

$Y_{38}$ is $NR_{30B}$, an oxygen atom, a sulfur atom, or $CR_{30C}R_{30D}$;

$Y_{36}$ and $Y_{37}$ are each independently a nitrogen atom or $CR_{30A}$;

$R_{10A}$, $R_{30A}$, $R_{30B}$, $R_{30C}$, and $R_{30D}$ are each independently a hydrogen atom or a substituent, or at least one combination of adjacent two or more groups selected from the group consisting of one or more of $R_{10A}$, one or more of $R_{30A}$, one or more of $R_{30B}$, one or more of $R_{30C}$, and one or more of $R_{30D}$ are mutually bonded to form a ring; and $R_{10A}$ as a substituent and $R_{30A}$, $R_{30B}$, $R_{30C}$, and $R_{30D}$ as substituents each independently represent the same as $R_{10A}$ as a substituent in the formula (110), in the formula (114):

$Y_{12}$ to $Y_{14}$ are each independently a nitrogen atom or $CR_{10A}$;

$Z_{12}$ is $NR_{30B}$ or $CR_{30C}R_{30D}$;

$Y_{39}$ is $NR_{30B}$, an oxygen atom, a sulfur atom, or $CR_{30C}R_{30D}$;

$Y_{32}$ and $Y_{33}$ are each independently a nitrogen atom or $CR_{30A}$;

$R_{10A}$, $R_{30A}$, $R_{30B}$, $R_{30C}$, and $R_{30D}$ are each independently a hydrogen atom or a substituent, or at least one combination of adjacent two or more groups selected from the group consisting of one or more of $R_{10A}$, one or more of $R_{30A}$, one or more of $R_{30B}$, one or more of $R_{30C}$, and one or more of $R_{30D}$ are mutually bonded to form a ring; and $R_{10A}$ as a substituent and $R_{30A}$, $R_{30B}$, $R_{30C}$, and $R_{30D}$ as substituents each independently represent the same as $R_{10A}$ as a substituent in the formula (110), (115)

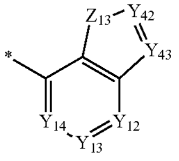

(116)

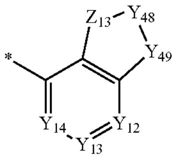

(117)

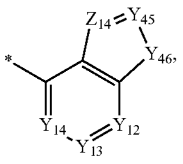

where in the formula (115):

$Y_{12}$ to $Y_{14}$ are each independently a nitrogen atom or $CR_{10A}$;

$Z_{13}$ is $NR_{30B}$ or $CR_{30C}R_{30D}$;

$Y_{42}$ and $Y_{43}$ are each independently a nitrogen atom or $CR_{30A}$;

$R_{10A}$, $R_{30A}$, $R_{30B}$, $R_{30C}$, and $R_{30D}$ are each independently a hydrogen atom or a substituent, or at least one combination of adjacent two or more groups selected from the group consisting of one or more of $R_{10A}$, one or more of $R_{30A}$, one or more of $R_{30B}$, one or more of $R_{30C}$, and one or more of $R_{30D}$ are mutually bonded to form a ring; and $R_{10A}$ as a substituent and $R_{30A}$, $R_{30B}$, $R_{30C}$, and $R_{30D}$ as substituents each independently represent the same as $R_{10A}$ as a substituent in the formula (110), in the formula (116):

$Y_{12}$ to $Y_{14}$ are each independently a nitrogen atom or $CR_{10A}$;

$Z_{13}$ is $NR_{30B}$ or $CR_{30C}R_{30D}$;

$Y_{48}$ and $Y_{49}$ are each independently $NR_{30B}$, an oxygen atom, a sulfur atom, or $CR_{30C}R_{30D}$;

$R_{10A}$, $R_{30B}$, $R_{30C}$, and $R_{30D}$ are each independently a hydrogen atom or a substituent, or at least one combination of adjacent two or more groups selected from the group consisting of one or more of $R_{10A}$, one or more of $R_{30B}$, one or more of $R_{30C}$, and one or more of $R_{30D}$ are mutually bonded to form a ring; and $R_{10A}$ as a substituent and $R_{30B}$, $R_{30C}$, and $R_{30D}$ as substituents each independently represent the same as $R_{10A}$ as a substituent in the formula (110), in the formula (117):

$Y_{12}$ to $Y_{14}$ are each independently a nitrogen atom or $CR_{10A}$;

$Z_{14}$ and $Y_{45}$ are each independently a nitrogen atom or $CR_{30A}$;

$Y_{46}$ is $NR_{30B}$, an oxygen atom, a sulfur atom, or $CR_{30C}R_{30D}$;

$R_{10A}$, $R_{30A}$, $R_{30B}$, $R_{30C}$, and $R_{30D}$ are each independently a hydrogen atom or a substituent, or at least one combination of adjacent two or more groups selected from the group consisting of one or more of $R_{10A}$, one or more of $R_{30A}$, one or more of $R_{30B}$, one or more of $R_{30C}$, and one or more of $R_{30D}$ are mutually bonded to form a ring; and $R_{10A}$ as a substituent and $R_{30A}$, $R_{30B}$, $R_{30C}$, and $R_{30D}$ as substituents each independently represent the same as $R_{10A}$ as a substituent in the formula (110), and where in the formulae (111) to (117), when a plurality of $R_{10A}$ are present, the plurality of $R_{10A}$ are mutually the same or different, when a plurality of $R_{30A}$ are present, the plurality of $R_{30A}$ are mutually the same or different, when a plurality of $R_{30B}$ are present, the plurality of $R_{30B}$ are mutually the same or different, when a plurality of $R_{30C}$ are present, the plurality of $R_{30C}$ are mutually the same or different, and when a plurality of $R_{30D}$ are present, the plurality of $R_{30D}$ are mutually the same or different.

16. The compound according to claim 1, wherein $Y_{12}$ to $Y_{14}$ in the formula (110) are $CR_{10A}$, and $Y_{21}$ to $Y_{24}$ in the formula (120) are $CR_{20A}$.

17. The compound according to claim 1, wherein a group represented by the formula (110) is a group represented by any one of formulae (b1) to (b14) below, (b1)

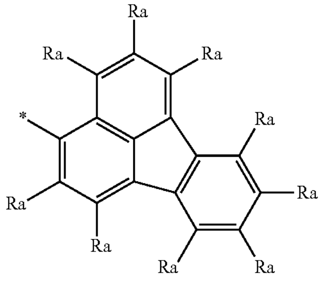

-continued (b2)

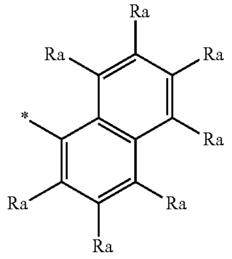

(b3)

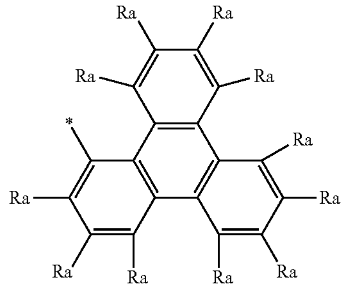

(b4)

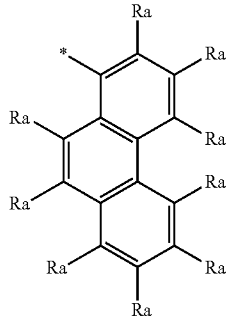

(b5)

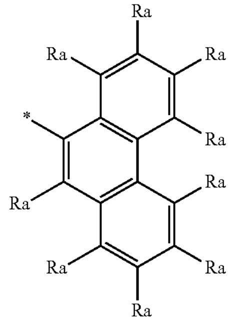

(b6)

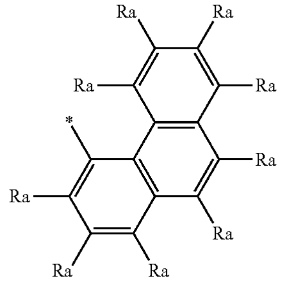

-continued

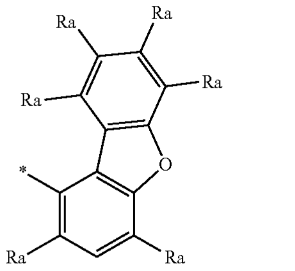

(b7)

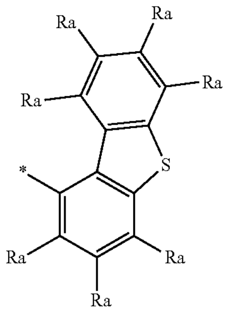

(b8)

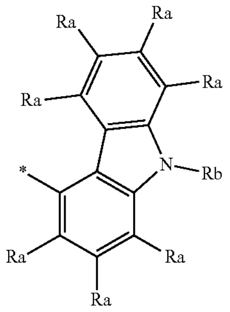

(b9)

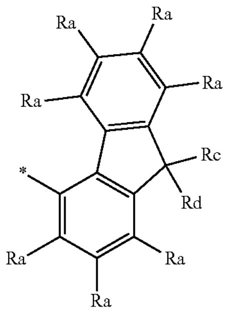

(b10)

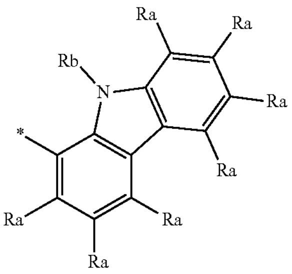

(b11)

-continued

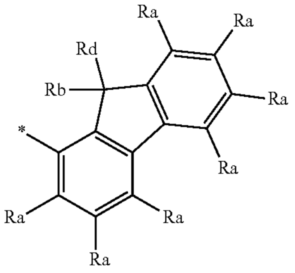

(b12)

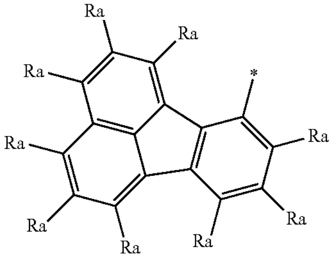

(b13)

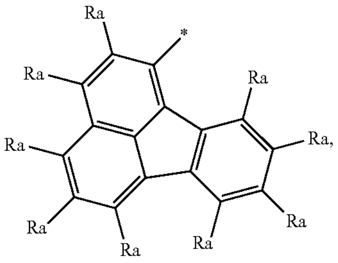

(b14)

where: Ra is a hydrogen atom or a substituent, or at least one combination of adjacent ones of Ra are mutually bonded to form a ring;

a plurality of Ra are mutually the same or different;

Rb is a hydrogen atom or a substituent;

Rc and Rd are each independently a hydrogen atom or a substituent, or a combination of Rc and Rd are mutually bonded to form a ring; and Ra, Rb, Rc, and Rd as substituents represent the same as $R_{104}$ as a substituent in the formula (110).

18. The compound according to claim 17, wherein at least one combination of adjacent ones of Ra are not mutually bonded to form a ring, and a combination of Rc and Rd are not mutually bonded to form a ring.

19. The compound according to claim 1, wherein a group represented by the formula (110) is a substituted or unsubstituted naphthyl group, a substituted or unsubstituted phenanthryl group, a substituted or unsubstituted chrysenyl group, a substituted or unsubstituted benzophenanthryl group, a substituted or unsubstituted benzochrysenyl group, a substituted or unsubstituted triphenylenyl group, a substituted or unsubstituted fluorenyl group, a substituted or unsubstituted benzofluorenyl group, a substituted or unsubstituted dibenzofluorenyl group, a substituted or unsubstituted fluoranthenyl group, a substituted or unsubstituted dibenzofuranyl group, a substituted or unsubstituted dibenzothienyl group, or a substituted or unsubstituted carbazolyl group.

20. The compound according to claim 1, wherein in at least one group $D_1$, at least one of $R_{101}$ to $R_{160}$ is a group represented by the formula (120).

21. The compound according to claim 20, wherein when one of $R_1$ to $R_4$ is the group $D_1$, only one of $R_{101}$ to $R_{160}$ in the group $D_1$ is a group represented by the formula (120), when two of $R_1$ to $R_4$ are the groups $D_1$, only one of $R_{101}$ to $R_{160}$ in each of the groups $D_1$ is a group represented by the formula (120), and when three of $R_1$ to $R_4$ are the groups $D_1$, only one of $R_{101}$ to $R_{160}$ in each of the groups $D_1$ is a group represented by the formula (120).

22. The compound according to claim 20, wherein $Z_2$ in the formula (120) is a substituted or unsubstituted phenyl group, a substituted or unsubstituted naphthyl group, a substituted or unsubstituted anthryl group, a substituted or unsubstituted phenanthryl group, a substituted or unsubstituted pyrenyl group, a substituted or unsubstituted chrysenyl group, a substituted or unsubstituted benzophenanthryl group, a substituted or unsubstituted benzochrysenyl group, a substituted or unsubstituted benzanthryl group, a substituted or unsubstituted triphenylenyl group, a substituted or unsubstituted fluorenyl group, a substituted or unsubstituted 9,9-dimethylfluorenyl group, a substituted or unsubstituted benzofluorenyl group, a substituted or unsubstituted dibenzofluorenyl group, a substituted or unsubstituted biphenyl group, a substituted or unsubstituted terphenyl group, a substituted or unsubstituted quarterphenyl group, a substituted or unsubstituted fluoranthenyl group, a substituted or unsubstituted dibenzofuranyl group, a substituted or unsubstituted dibenzothienyl group, a substituted or unsubstituted carbazolyl group, a substituted or unsubstituted pyridyl group, a substituted or unsubstituted pyrimidinyl group, or a substituted or unsubstituted triazinyl group.

23. The compound according to claim 20, wherein $Z_2$ in the formula (120) is a group represented by any one of formulae ($Z_{21}$) to ($Z_{31}$) below, (Z-21)

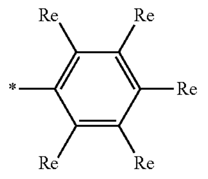

(Z-22)

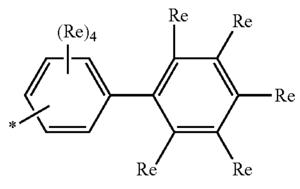

(Z-23)

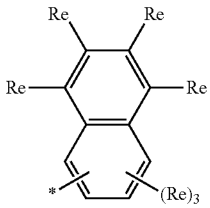

-continued (Z-24)

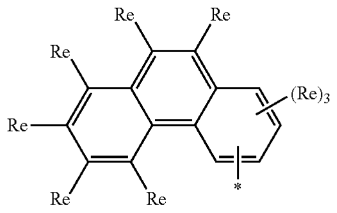

(Z-25)

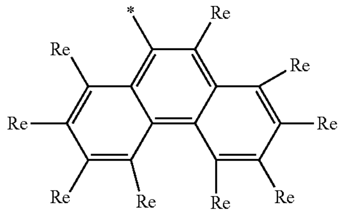

(Z-26)

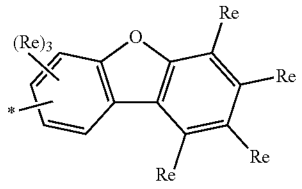

(Z-27)

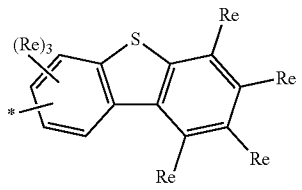

(Z-28)

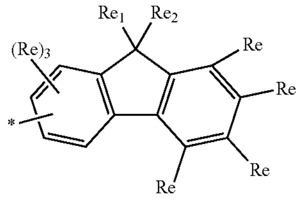

(Z-29)

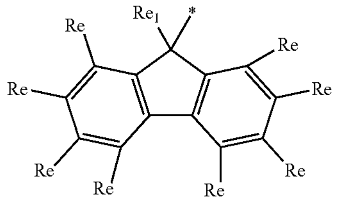

(Z-30)

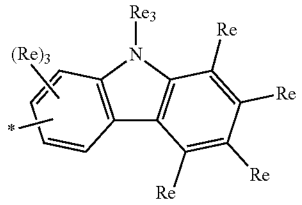

-continued (Z-31)

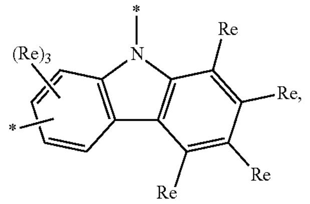

where: Re is a hydrogen atom or a substituent, or at least one combination of adjacent ones of Re are bonded to each other to form a ring, and a plurality of Re are mutually the same or different;

$Re_1$ and $Re_2$ are each independently a hydrogen atom or a substituent, or a combination of $Re_1$ and $Re_2$ are mutually bonded to form a ring;

$Re_3$ is a hydrogen atom or a substituent;

Re, $Re_1$, $Re_2$, and $Re_3$ as substituents each independently represent the same as $R_{20A}$ as a substituent in the formula (120); and

* represents a bonding position to a carbon atom of the six-membered ring in the formula (120).

24. The compound according to claim 20, wherein a group represented by the formula (120) is a group represented by any one of formulae (c1) to (c8) below, (c1)

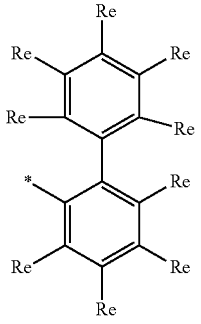

(c2)

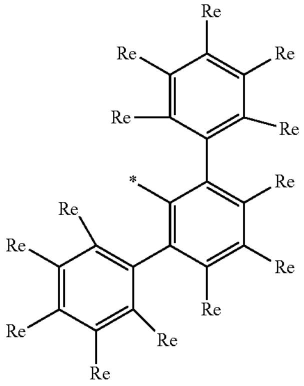

-continued (c3)

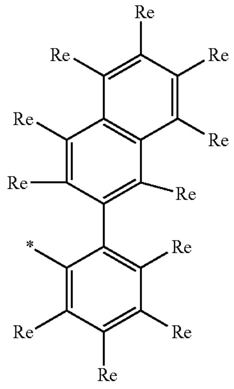

(c4)

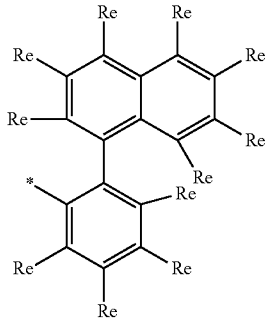

(c5)

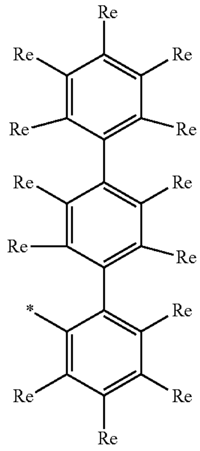

(c6)

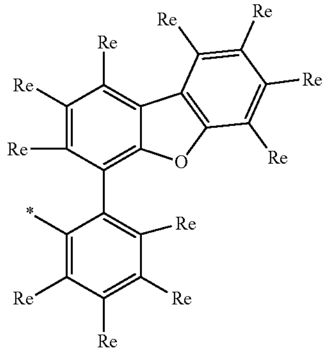

-continued (c7)

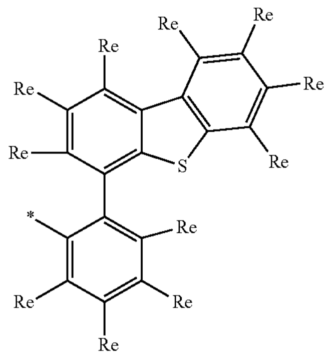

(c8)

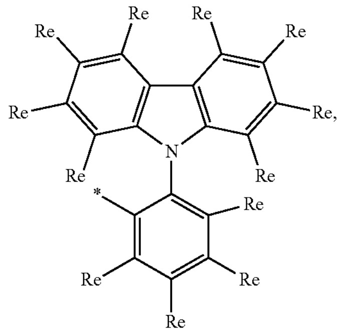

where: Re is a hydrogen atom or a substituent;

a plurality of Re are mutually the same or different; and

Re as a substituent represents the same as $R_{20A}$ as a substituent in the formula (120).

25. The compound according to claim 1, wherein $X_1$ to $X_6$ in the group $D_1$ are each an oxygen atom.

26. The compound according to claim 1, wherein $X_1$ to $X_6$ in the group $D_1$ are each a sulfur atom.

27. The compound according to claim 1, wherein the compound is a compound represented by the formula (11).

28. The compound according to claim 1, wherein the compound is a compound represented by the formula (12).

29. The compound according to claim 1, wherein the compound is a compound represented by the formula (13).

30. The compound according to claim 1, wherein $R_{101}$ to $R_{160}$, $R_{161}$ to $R_{168}$, $R_{171}$ to $R_{200}$, $R_{10A}$, and $R_{20A}$ are each independently a hydrogen atom, a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 30 carbon atoms, a substituted or unsubstituted alkylsilyl group having 3 to 6 carbon atoms, a substituted or unsubstituted alkoxy group having 1 to 6 carbon atoms, a substituted or unsubstituted aryloxy group having 6 to 14 ring carbon atoms, a group represented by —N(Rz)$_2$, a substituted or unsubstituted alkylthio group having 1 to 6 carbon atoms, or a substituted or unsubstituted arylthio group having 6 to 14 ring carbon atoms.

31. The compound according to claim 1, wherein $R_{101}$ to $R_{160}$, $R_{161}$ to $R_{168}$, $R_{171}$ to $R_{200}$, $R_{10A}$, and $R_{20A}$ are each independently a hydrogen atom, a halogen atom, an unsubstituted aryl group having 6 to 14 ring carbon atoms, an unsubstituted heterocyclic group having 5 to 14 ring atoms, an unsubstituted alkyl group having 1 to 6 carbon atoms, an unsubstituted alkyl halide group having 1 to 30 carbon atoms, an unsubstituted alkylsilyl group having 3 to 6 carbon atoms, an unsubstituted alkoxy group having 1 to 6 carbon atoms, an unsubstituted aryloxy group having 6 to 14 ring carbon atoms, or an unsubstituted alkylamino group having 2 to 12 carbon atoms, and an unsubstituted alkylthio group having 1 to 6 carbon atoms, or an unsubstituted arylthio group having 6 to 14 ring carbon atoms.

32. The compound according to claim 1, wherein $R_{101}$ to $R_{160}$, $R_{161}$ to $R_{168}$, $R_{171}$ to $R_{200}$, $R_{10A}$, and $R_{20A}$ are each independently a hydrogen atom, an unsubstituted aryl group having 6 to 14 ring carbon atoms, an unsubstituted heterocyclic group having 5 to 14 ring atoms, or an unsubstituted alkyl group having 1 to 6 carbon atoms.

33. The compound according to claim 1, wherein $R_{101}$ to $R_{160}$ except for a group represented by the formula (110) and a group represented by the formula (120) are each hydrogen atom, and $R_{161}$ to $R_{168}$ and $R_{171}$ to $R_{200}$ are each hydrogen atom.

34. The compound according to claim 1, wherein $R_{10A}$ and $R_{20A}$ are each hydrogen atom, the ring (B) is an unsubstituted aromatic hydrocarbon ring having 6 to 30 ring carbon atoms or an unsubstituted heterocyclic ring having 5 to 30 ring carbon atoms, and $Z_2$ is an unsubstituted aryl group having 6 to 30 ring carbon atoms or an unsubstituted heterocyclic group having 5 to 30 ring atoms.

35. An organic-electroluminescence-device material comprising the compound according to claim 1.

36. An organic electroluminescence device comprising:

an anode;

a cathode; and a first organic layer provided between the anode and the cathode, wherein the first organic layer comprises a first compound, and the first compound is the compound according to claim 1.

37. The organic electroluminescence device according to claim 36, wherein the first organic layer is an emitting layer.

38. The organic electroluminescence device according to claim 36, wherein the first organic layer comprises a second compound in addition to the first compound, and the second compound is a fluorescent compound.

39. The organic electroluminescence device according to claim 38, wherein a singlet energy $S_1$(Mat1) of the first compound and a singlet energy $S_1$(Mat2) of the second compound satisfy a relationship of a numerical formula (Numerical Formula 1) below, $$S_1(\mathrm{Mat1}) > S_1(\mathrm{Mat2}) \quad \text{(Numerical Formula 1).}$$

40. The organic electroluminescence device according to claim 38, wherein the first organic layer comprises a third compound in addition to the first compound and the second compound, and a singlet energy $S_1$(Mat1) of the first compound and a singlet energy $S_1$(Mat3) of the third compound satisfy a relationship of a numerical formula (Numerical Formula 2) below, $$S_1(\mathrm{Mat3}) > S_1(\mathrm{Mat1}) \quad \text{(Numerical Formula 2).}$$

41. The organic electroluminescence device according to claim 36, wherein the first organic layer comprises a fourth compound in addition to the first compound, and a singlet energy $S_1$(Mat1) of the first compound and a singlet energy $S_1$(Mat4) of the fourth compound satisfy a relationship of a numerical formula (Numerical Formula 3) below, $$S_1(\text{Mat4})>S_1(\text{Mat1}) \qquad \text{(Numerical Formula 3).}$$

42. The organic electroluminescence device according to claim 36, wherein the first organic layer does not comprise a metal complex.

43. The organic electroluminescence device according to claim 36, wherein the first compound is a delayed fluorescent compound.

44. An electronic device, comprising:

the organic electroluminescence device according to claim 36.

* * * * *